(12) United States Patent
Coburn et al.

(10) Patent No.: US 9,090,661 B2
(45) Date of Patent: Jul. 28, 2015

(54) INHIBITORS OF HEPATITIS C VIRUS REPLICATION

(71) Applicant: Merck Sharp & Dohme Corp., Rahway, NJ (US)

(72) Inventors: Craig A. Coburn, San Rafael, CA (US); John A. McCauley, Maple Glen, PA (US); Steven W. Ludmerer, North Wales, PA (US); Kun Liu, Boston, MA (US); Joseph P. Vacca, Telford, PA (US); Hao Wu, Shanghai (CN); Bin Hu, Shanghai (CN); Richard Soll, San Diego, CA (US); Fei Sun, Shanghai (CN); Xinghai Wang, Shanghai (CN); Man Yan, Shanghai (CN); Chengren Zhang, Shanghai (CN); Mingwei Zheng, Shanghai (CN); Bin Zhong, Shanghai (CN); Jian Zhu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/473,117

(22) Filed: Aug. 29, 2014

(65) Prior Publication Data
US 2014/0371138 A1 Dec. 18, 2014

Related U.S. Application Data

(62) Division of application No. 13/260,684, filed as application No. PCT/US2010/028653 on Mar. 25, 2010, now Pat. No. 8,871,759.

(60) Provisional application No. 61/247,318, filed on Sep. 30, 2009, provisional application No. 61/163,958, filed on Mar. 27, 2009.

(51) Int. Cl.
| | |
|---|---|
| *A61K 31/4178* | (2006.01) |
| *C07D 405/14* | (2006.01) |
| *C07K 5/08* | (2006.01) |
| *C07D 401/14* | (2006.01) |
| *C07D 403/12* | (2006.01) |
| *C07D 403/14* | (2006.01) |
| *C07D 405/12* | (2006.01) |
| *C07D 409/14* | (2006.01) |
| *C07D 413/14* | (2006.01) |
| *C07D 471/04* | (2006.01) |
| *C07D 487/04* | (2006.01) |
| *C07D 498/04* | (2006.01) |
| *C07D 498/10* | (2006.01) |
| *A61K 31/437* | (2006.01) |
| *A61K 38/05* | (2006.01) |
| *A61K 38/06* | (2006.01) |
| *A61K 45/06* | (2006.01) |
| *C07K 5/06* | (2006.01) |

(52) U.S. Cl.
CPC ............... *C07K 5/08* (2013.01); *A61K 31/437* (2013.01); *A61K 38/05* (2013.01); *A61K 38/06* (2013.01); *A61K 45/06* (2013.01); *C07D 401/14* (2013.01); *C07D 403/12* (2013.01); *C07D 403/14* (2013.01); *C07D 405/12* (2013.01); *C07D 405/14* (2013.01); *C07D 409/14* (2013.01); *C07D 413/14* (2013.01); *C07D 471/04* (2013.01); *C07D 487/04* (2013.01); *C07D 498/04* (2013.01); *C07D 498/10* (2013.01); *C07K 5/06* (2013.01)

(58) Field of Classification Search
USPC ............................. 514/397; 548/313.1, 311.4
See application file for complete search history.

(56) References Cited

U.S. PATENT DOCUMENTS

| | | | |
|---|---|---|---|
| 7,153,848 B2 | 12/2006 | Hudyma et al. | |
| 7,662,809 B2 | 2/2010 | Ercolani et al. | |
| 7,973,040 B2 | 7/2011 | Harper et al. | |
| 8,080,654 B2 | 12/2011 | Harper et al. | |
| 8,377,980 B2 | 2/2013 | Belema et al. | |
| 2006/0019974 A1 | 1/2006 | Mederski et al. | |

(Continued)

FOREIGN PATENT DOCUMENTS

| | | |
|---|---|---|
| CN | 101336248 A | 12/2008 |
| EP | 1719773 A1 | 11/2006 |

(Continued)

OTHER PUBLICATIONS

Wilson, et al., "Tunable DNA Photocleavage by an Acridine-Imidazole Conjugate", Inorganic Chemistry, 2005, vol. 44, No. 18, pp. 6159-6173.

(Continued)

*Primary Examiner* — Charanjit Aulakh
(74) *Attorney, Agent, or Firm* — Jeffrey P. Bergman; Laura M. Ginkel

(57) ABSTRACT

The present invention relates to compounds of formula (I) that are useful as hepatitis C virus (HCV) NS5A inhibitors, the synthesis of such compounds, and the use of such compounds for inhibiting HCV NS5A activity, for treating or preventing HCV infections and for inhibiting HCV viral replication and/or viral production in a cell-based system.

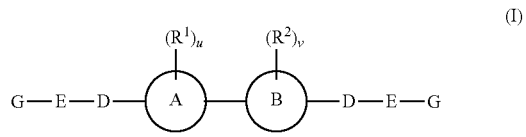

16 Claims, No Drawings

(56) References Cited

U.S. PATENT DOCUMENTS

| | | |
|---|---|---|
| 2006/0258682 A1 | 11/2006 | Liao et al. |
| 2007/0049593 A1 | 3/2007 | Oka et al. |
| 2007/0110708 A1 | 5/2007 | Miller et al. |
| 2007/0185175 A1 | 8/2007 | Liu et al. |
| 2008/0299075 A1 | 12/2008 | Bachand et al. |
| 2009/0004111 A1 | 1/2009 | Rice et al. |
| 2009/0042860 A1 | 2/2009 | Bergstrom et al. |
| 2010/0316607 A1 | 12/2010 | Or et al. |
| 2011/0104109 A1 | 5/2011 | Bennett et al. |
| 2011/0130361 A1 | 6/2011 | Grimm et al. |
| 2011/0223134 A1 | 9/2011 | Nair et al. |
| 2011/0224211 A1 | 9/2011 | Schmitz et al. |
| 2012/0040962 A1 | 2/2012 | Li et al. |
| 2012/0083483 A1 | 4/2012 | Coburn et al. |
| 2013/0156731 A1 | 6/2013 | Chen et al. |
| 2013/0164258 A1 | 6/2013 | Chen et al. |
| 2013/0280214 A1 | 10/2013 | Vacca et al. |
| 2014/0170111 A1 | 6/2014 | Coburn et al. |
| 2014/0199264 A1 | 7/2014 | Coburn et al. |
| 2014/0377223 A1 | 12/2014 | Kozlowski et al. |

FOREIGN PATENT DOCUMENTS

| | | |
|---|---|---|
| JP | 10101591 A1 | 4/1984 |
| WO | 2007009120 A2 | 1/2007 |
| WO | 2007084413 A2 | 7/2007 |
| WO | 2009023179 A2 | 2/2009 |
| WO | 2009102325 A1 | 8/2009 |
| WO | 2010041687 A1 | 4/2010 |
| WO | 2010065674 A1 | 6/2010 |
| WO | 2012040923 A1 | 4/2012 |
| WO | 2012050850 A1 | 4/2012 |
| WO | 20120401014 A1 | 4/2012 |
| WO | WO 2012/050850 A1 * | 4/2012 ........... A61K 31/675 |

OTHER PUBLICATIONS

Marsilje, T.H., et al., "Optimization of small molecule agonists of the thrombopoietin (Tpo) receptor derived from a benzo[a]carbazole hit scaffold", Bioorganic and Medicinal Chem. Lett., 2008, vol. 18, pp. 5255-5258.

CAR RN 1025830-17-4, STN Entry, Jun. 5, 2008.

CAPLUS Accession No. 1980:471599.

CAPLUS Accession No. 2009:295362 (JP2009-054809).

Alper, P.B., et al., "Discovery and biological evaluation of benzo[a]carbazole-based small molecule agonists of the thrombopoietin (Tpo) receptor", Bioorganic and Medicinal Chem. Lett., 2008, vol. 18, pp. 5255-5258.

CN1474815—English Abstract—Corresponding to US Application No. US2006/0019974.

* cited by examiner

INHIBITORS OF HEPATITIS C VIRUS REPLICATION

CROSS-REFERENCE TO RELATED APPLICATIONS

This application is a divisional of pending U.S. application Ser. No. 13/260,684, filed Dec. 19, 2011, which is the national stage application under 35 U.S.C. 371 of International Patent Application No. PCT/US2010/028653, filed Mar. 25, 2010, which claims priority to U.S. Provisional Application No. 61/163,958, filed Mar. 27, 2009 and U.S. Provisional Application No. 61/247,318, filed Sep. 30, 2009. Each of the aforementioned PCT and priority applications is incorporated by reference in its entirety.

FIELD OF THE INVENTION

The present disclosure relates to antiviral compounds that are useful as inhibitors of hepatitis C virus (HCV) replication. The compounds are expected to act on HCV NS5A (non-structural 5A) protein. Compositions comprising such compounds, the use of such compounds for treating HCV infection and/or reducing the likelihood or severity of symptoms of HCV infection, methods for inhibiting the function of the NS5A non-structural protein, and methods for inhibiting HCV viral replication and/or viral production are also provided.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside-analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

One identified target for therapeutic intervention is HCV NS5A non-structural protein, which is described, for example, in Seng-Lai Tan & Michael G. Katze, *How Hepatitis C Virus Counteracts the Interferon Response: The Jury Is Still Out on NS5A*, 284 VIROLOGY 1-12 (2001); and in Kyu-Jin Park et al., *Hepatitis C Virus NS5A Protein Modulates c-Jun N-terminal Kinase through Interaction with Tumor Necrosis Factor Receptor-associated Factor 2*, 278(33) J. BIO. CHEM. 30711 (2003). A non-structural protein, NS5A is an essential component for viral replication and assembly. Mutations in NS5A at or near known sites of phosphorylation can affect the ability for high-level replication in cell-culture systems, suggesting an important role for NS5A phosphorylation in viral replication efficiency. Inhibitors of the phosphorylation of NS5A can lead to reduced viral RNA replication.

NS5A is a zinc metalloprotein organized into three discreet domains. NS5A localizes to the membrane-associated site of RNA synthesis via an N-terminal amphipathic α-helix anchor. The crystal structure of domain I demonstrates that NS5A can exist as a dimer, with a large putative RNA binding groove located at the interface of the monomers. Timothy L. Tellinghuisen et al., *Structure of the zinc-binding domain of an essential component of the hepatitis C viral replicase*, 435(7040) NATURE 374 (2005). Robert A. Love et al., *Crystal Structure of a Novel Dimeric Form of NS5A Domain I Protein From Hepatitis C Virus*, 89(3) J. VIROLOGY 4395-403 (2009). The interaction of NS5A with RNA is thought to be critical for the function of this protein in RNA replication. No structural information has yet been obtained for domains II or III. Recent genetic mapping has shown that although some residues in domain II are essential for RNA replication, many portions of domain II and all of domain III are dispensable. Timothy L. Tellinghuisen et al., *Identification of Residues Required for RNA Replication in Domains II and III of the Hepatitis C Virus NS5A Protein*, J. VIROLOGY 1073 (2008). Mutations constructed within domain III result in virus that can maintain RNA replication but that produces lower titers of infectious virus in cell culture, demonstrating a second distinct role for NS5A after RNA replication has occurred. Timothy L. Tellinghuisen et al., *Regulation of Hepatitis C Virion Production via Phosphorylation of the NS5A Protein*, 4(3) PLOS PATHOGENS e1000032 (2008); Nicole Appel et al., *Mutational Analysis of Hepatitis C Virus Nonstructural Protein 5A: Potential Role of Differential Phosphorylation in RNA Replication and Identification of a Genetically Flexible Domain*, 79(5) J. VIROLOGY 3187 (2005). NS5A, unlike the other non-structural proteins, can be trans-complemented, consistent with functions outside of the viral replicase. The interaction of NS5A with numerous host-signaling pathways has been described (Michael J. Gale Jr. et al., *Evidence That Hepatitis C Virus Resistance to Interferon Is Mediated through Repression of the PKR Protein Kinase by the Nonstructural 5A Protein*, 230 VIROLOGY 217 (1997); Andrew Macdonald & Mark Harris, *Hepatitis C virus NS5A: tales of a promiscuous protein*, 85 J. GEN. VIROLOGY 2485 (2004).), suggesting this protein may modify the host cell environment to a state favorable for the virus, events that may require a form of NS5A dissociated from the replication complex.

There is a clear and long-felt need to develop effective therapeutics for treatment of HCV infection. Specifically, there is a need to develop compounds that are useful for treating HCV-infected patients and compounds that selectively inhibit HCV viral replication.

SUMMARY OF THE INVENTION

The present disclosure relates to novel compounds of formula (I) and/or pharmaceutically acceptable salts, hydrates, solvates, prodrugs or isomers thereof. These compounds are useful, either as compounds or their pharmaceutically acceptable salts (when appropriate), in the inhibition of HCV (hepatitis C virus) NS5A (non-structural 5A) protein, the prevention or treatment of one or more of the symptoms of HCV infection, the inhibition of HCV viral replication and/or HCV viral production, and/or as pharmaceutical composition ingredients. As pharmaceutical composition ingredients, these compounds, which includes reference to hydrates and solvates of such compounds, and their salts may be the primary active therapeutic agent, and, when appropriate, may be combined with other therapeutic agents including but not limited to other HCV antivirals, anti-infectives, immuno-modulators, antibiotics or vaccines.

More particularly, the present disclosure relates to a compound of formula (I):

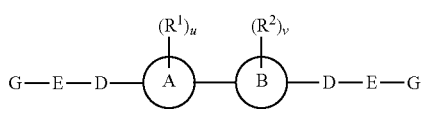

(I)

and/or a pharmaceutically acceptable salt thereof, wherein:

is chosen from the group consisting of 9-membered bicyclic aryl ring systems that contain from 0 to 4 heteroatoms independently chosen from the group consisting of N, O and S, and that are substituted on C or N atoms by u substituents $R^1$, each $R^1$ is independently chosen from the group consisting of hydrogen, halogen, —$OR^{3a}$, —CN, —$(CH_2)_{0-6}C(O)R^3$, —$CO_2R^{3a}$, —$C(O)N(R^{3a})_2$, —$SR^{3a}$, —$S(O)R^{3a}$, —$S(O_2)R^{3a}$, —$(CH_2)_{0-6}N(R^{3a})_2$, —$N(R^{3a})SO_2R^{3a}$, —$N(R^{3a})CO_2R^{3a}$, —$N(R^{3a})C(O)R^3$, —$N(R^{3a})COR^{3a}$, —$N(R^{3a})C(O)N(R^{3a})$, $C_{1-6}$alkyl, $C_{3-8}$carbocycle containing from 0 to 3 heteroatoms chosen from N, O and S, and phenyl, and the $C_{1-6}$alkyl, $C_{3-8}$carbocycle and phenyl are substituted by from 0 to 3 substituents independently chosen from the group consisting of hydrogen, halogen, —$OR^{3a}$, —CN, —$CO_2R^{3a}$, —$C(O)N(R^{3a})_2$, —$N(R^{3a})_2$, —$N(R^{3a})CO_2R^{3a}$, —$SR^{3a}$, —$S(O)R^{3a}$, —$S(O_2)R^{3a}$, —$N(R^{3a})SO_2R^{3a}$, —$N(R^{3a})CO_2R^{3a}$, —$N(R^{3a})C(O)N(R^{3a})$, $C_{1-6}$alkyl, —O—$C_{1-6}$alkyl, —S—$C_{1-6}$alkyl, and $C_{3-8}$cycloalkyl, u is from 0 to 4, each $R^3$ is independently chosen from the group consisting of hydrogen, $C_{1-6}$alkyl, —OH, —O—$C_{1-6}$alkyl and $C_{3-8}$cycloalkyl, and each $R^{3a}$ is independently chosen from the group consisting of hydrogen, $C_{1-6}$alkyl and $C_{3-8}$cycloalkyl;

is a group chosen from the group consisting of
(a) —C≡C— and
(b) aryl ring systems B' chosen from the group consisting of:
  (i) 5- to 7-membered monocyclic ring systems and
  (ii) 8- to 10-membered bicyclic ring systems,
  and the aryl ring systems B' containing from 0 to 4 heteroatoms independently chosen from the group consisting of N, O and S, and substituted on C or N atoms by v substituents $R^2$, each $R^2$ is independently chosen from the group consisting of hydrogen, halogen, —$OR^{4a}$, —CN, —$CO_2R^{4a}$, —$C(O)R^{4a}$, —$C(O)N(R^{4a})_2$, —$N(R^{4a})_2$, —$N(R^{4a})COR^4$, —$N(R^{4a})CO_2R^{4a}$, —$N(R^{4a})C(O)N(R^{4a})$, —$N(R^{4a})SO_2R^{4a}$, —$SR^{4a}$, —$S(O)R^{4a}$, —$S(O_2)R^{4a}$, $C_{1-6}$alkyl substituted by from 0 to 4 $R^4$ and $C_{3-8}$cycloalkyl substituted by from 0 to 4 $R^4$, v is from 0 to 4, each $R^4$ is independently chosen from the group consisting of hydrogen, —OH, $C_{1-6}$alkyl and $C_{3-8}$cycloalkyl;

each $R^{4a}$ is independently chosen from the group consisting of hydrogen, $C_{1-6}$alkyl and $C_{3-8}$cycloalkyl;

$R^1$ and $R^2$ may be taken together with

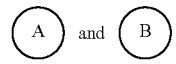

to form a 5- to 9-membered carbocyclic ring containing 1 or 2 heteroatoms independently chosen from the group consisting of N, O and S;

each D is a group independently chosen from the group consisting of:
(a) a single bond,
(b) —$C(O)N(R^5)$—,
(c) —$N(R^5)C(O)$—, and
(d) a 5- or 6-membered aryl ring system D' containing from 0 to 4 heteroatoms independently chosen from the group consisting of N, O and S, and substituted on C or N atoms by from 0 to 2 substituents $R^5$, each $R^5$ is independently chosen from the group consisting of hydrogen, halogen, —$OR^6$, —CN, —$CO_2R^6$, —$C(O)N(R^6)_2$, —$N(R^6)_2$, —$N(R^6)COR^6$, —$SR^6$, —$S(O)R^6$, —$S(O_2)R^6$, —$N(R^6)SO_2R^6$, —$NCO_2R^6$, —$NC(O)N(R^6)_2$, $C_{1-6}$alkyl substituted by from 0 to 3 $R^6$ and $C_{3-8}$cycloalkyl substituted by from 0 to 3 $R^6$, and each $R^6$ is independently chosen from the group consisting of hydrogen, $C_{1-6}$alkyl and $C_{3-8}$cycloalkyl;

each E is a group independently chosen from the group consisting of:
(a) a single bond,
(b) —$(C(R^7)_2)_{0-2}NR^7C(O)O_{0-1}$—, and
(c) a pyrrolidinyl derivative chosen from the group consisting of:

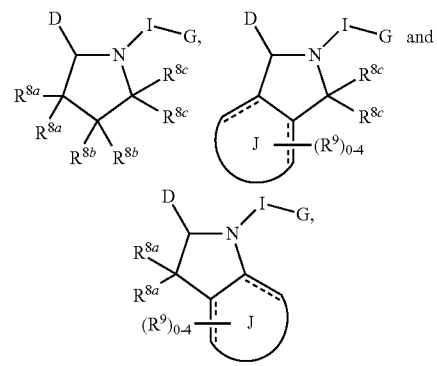

I is a bivalent group chosen from —C(O)—, —$CO_2$— and —$C(O)N(R^7)$—,

J is a fused ring system chosen from the group consisting of 3- to 7-membered carbocycles and 5- or 6-membered aryl rings containing from 0 to 4 heteroatoms independently chosen from the group consisting of N, O and S, and substituted on C or N atoms by substituents $R^9$, each $R^{8a}$ is independently chosen from the group consisting of hydrogen, halogen, —OH, —$OC_{1-6}$alkyl and $C_{1-6}$alkyl, or two $R^{8a}$ may be taken together to form oxo, each $R^{8b}$ is independently chosen from the group consisting of hydrogen, halogen, —OH, —OC$_{1-6}$alkyl and C$_{1-6}$alkyl, or two $R^{8b}$ may be taken together to form oxo, each $R^{8c}$ is independently chosen from the group consisting of hydrogen and C$_{1-6}$alkyl, or any two groups selected from $R^{8a}$, $R^{8b}$ and $R^{8c}$ may be taken together to form a spiro-bicyclic or bridged bicyclic ring;

each $R^9$ is independently chosen from the group consisting of hydrogen, halogen, C$_{1-6}$alkyl, —O—C$_{1-6}$alkyl, —S—C$_{1-6}$alkyl, —NH—C$_{1-6}$alkyl and —NHC(O)—C$_{1-6}$alkyl, each $R^7$ is independently chosen from the group consisting of hydrogen, C$_{1-6}$alkyl and phenyl, and the C$_{1-6}$alkyl and phenyl are substituted by from 0 to 3 substitutents independently chosen from the group consisting of hydrogen, halogen, C$_{1-6}$alkyl, —O—C$_{1-6}$alkyl and —S—C$_{1-6}$alkyl; and each G is independently chosen from the group consisting of:
(a) hydrogen,
(b) —OR$^{10a}$,
(c) —CN,
(d) —CO$_2$R$^{10a}$,
(e) —C(O)N(R$^{10}$)$_2$,
(f) —SR$^{10a}$,
(g) —S(O)R$^{10a}$,
(h) —S(O$_2$)R$^{10a}$,
(i) —N(R$^{10}$)$_2$,
(j) —N(R$^{10}$)SO$_2$R$^{10a}$,
(k) —NCO$_2$R$^{10a}$,
(l) —NC(O)N(R$^{10}$)$_2$,
(m) C$_{1-6}$alkyl having 0 to 4 substituents R$^{11}$,
  each R$^{11}$ is independently chosen from the group consisting of:
   (i) —OH,
   (ii) —N(R$^{10}$)$_2$,
   (iii) =NR$^{10}$,
   (iv) —O—C$_{1-6}$ alkyl,
   (v) —C(O)R$^{10}$,
   (vi) —S—C$_{1-6}$ alkyl,
   (vii) —SO$_2$—C$_{1-6}$ alkyl,
   (viii) 3- to 8-membered carbocycles containing from 0 to 3 heteroatoms independently chosen from the group consisting of N, O and S, and having from 0 to 3 substitutents R$^{12}$ on N or C atoms, and each R$^{12}$ is independently selected from the group consisting of hydrogen, halogen, C$_{1-6}$alkyl having from 0 to 3 substituents chosen from R$^{10}$, —O—C$_{1-6}$alkyl, —S—C$_{1-6}$alkyl, —OR$^{10a}$, —CN, —C(O)R$^{10}$, —CO$_2$R$^{10a}$, —C(O)N(R$^{10}$)$_2$, —SR$^{10a}$, —S(O)R$^{10a}$, —S(O$_2$)R$^{10a}$, —N(R$^{10}$)SO$_2$R$^{10a}$, —NCO$_2$R$^{10a}$, —NC(O)N(R$^{10}$)$_2$ and —N(R$^{10}$)$_2$, or two R$^{12}$ are taken together to form oxo, and
   (ix) 5- or 6-membered aryl containing from 0 to 3 heteroatoms independently chosen from the group consisting of N, O and S, and having from 0 to 3 substitutents R$^{13}$ on N or C atoms, and each R$^{13}$ is independently selected from the group consisting of hydrogen, halogen, C$_{1-6}$alkyl, —O—C$_{1-6}$alkyl and 3- to 8-membered carbocycles containing from 0 to 3 heteroatoms independently chosen from the group consisting of N, O and S,
(n) 3- to 8-membered carbocycles containing from 0 to 3 heteroatoms independently chosen from the group consisting of N, O and S, and having from 0 to 3 substitutents R$^{10}$ on N or C atoms; and
(o) aryl ring systems G' chosen from the group consisting of:
  (i) 5- to 7-membered monocyclic ring systems and
  (ii) 8- to 10-membered bicyclic ring systems,
  and the aryl ring systems G' containing from 0 to 4 heteroatoms independently chosen from the group consisting of N, O and S, and substituted on C or N atoms by 0 to 3 substitutents R$^{10}$;

each R$^{10}$ is independently chosen from the group consisting of
(i) hydrogen,
(ii) —CN,
(iii) C$_{1-6}$alkyl,
(iv) —O—C$_{0-6}$alkyl,
(v) —S—C$_{0-6}$alkyl,
(vi) C$_{1-6}$alkyl-O—R$^{14}$,
(vii) —C(O)R$^{14}$,
(viii) —CO$_2$R$^{14}$,
(ix) —SO$_2$R$^{14}$,
(x) —N(R$^{14}$)$_2$,
(xi) —N(R$^{14}$)SO$_2$R$^{14}$,
(xii) —NCO$_2$R$^{14}$,
(xiii) —NC(O)N(R$^{14}$)$_2$, and
(xiv) 3- to 8-membered carbocycles containing from 0 to 3 heteroatoms independently chosen from the group consisting of N, O and S,
or two R$^{10}$ may be taken together to form oxo;

each R$^{10a}$ is independently chosen from the group consisting of
(i) hydrogen,
(ii) —CN,
(iii) C$_{1-6}$alkyl,
(iv) C$_{1-6}$alkyl-O—R$^{14}$,
(v) —C(O)R$^{14}$,
(vi) —CO$_2$R$^{14}$,
(vii) —SO$_2$R$^{14}$,
(x) —N(R$^{14}$)$_2$,
(xi) —N(R$^{14}$)SO$_2$R$^{14}$,
(xii) —NCO$_2$R$^{14}$,
(xiii) —NC(O)N(R$^{14}$)$_2$, and
(xiv) 3- to 8-membered carbocycles containing from 0 to 3 heteroatoms independently chosen from the group consisting of N, O and S, and two R$^{10}$ or R$^{10a}$ groups can be taken together with the N to which they are attached to form a ring, which may be substituted by from 0 to 3 substituents R$^{14}$, and each R$^{14}$ is independently chosen from the group consisting of hydrogen, C$_{1-6}$alkyl, C$_{3-8}$cycloalkyl, —(CH$_2$)$_{0-3}$C$_{3-8}$cycloalkyl and phenyl.

The present invention also includes pharmaceutical compositions containing a compound of the present invention and methods of preparing such pharmaceutical compositions. The present invention further includes methods of treating or reducing the likelihood or severity of HCV infection, methods for inhibiting the function of the NS5A protein, and methods for inhibiting HCV viral replication and/or viral production.

Other embodiments, aspects and features of the present invention are either further described in or will be apparent from the ensuing description, examples and appended claims.

DETAILED DESCRIPTION OF THE INVENTION

The present invention includes compounds of formula (I) above, and pharmaceutically acceptable salts thereof. The compounds of formula (I) are HCV NS5A inhibitors.

A first embodiment of the invention relates to compounds having structural formula (I):

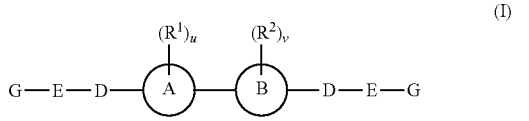

and/or a pharmaceutically acceptable salt thereof, wherein:

is chosen from the group consisting of 9-membered bicyclic aryl ring systems that contain from 0 to 4 heteroatoms independently chosen from the group consisting of N, O and S, and that are substituted on C or N atoms by u substituents $R^1$, each $R^1$ is independently chosen from the group consisting of hydrogen, halogen, —$OR^{3a}$, —CN, —C(O)$R^3$, —$CO_2R^{3a}$, —C(O)N($R^{3a}$)$_2$, —$SR^{3a}$, —S(O)$R^{3a}$, —S(O$_2$)$R^{3a}$, —(CH$_2$)$_{0-6}$N($R^{3a}$)$_2$, —N($R^{3a}$)SO$_2R^{3a}$, —N($R^{3a}$)CO$_2R^{3a}$, —N($R^{3a}$)C(O)$R^3$, —N($R^{3a}$)COR$^{3a}$, —N($R^{3a}$)C(O)N($R^{3a}$), $C_{1-6}$alkyl, $C_{3-8}$carbocycle containing from 0 to 3 heteroatoms chosen from N, O and S, and phenyl, and the $C_{1-6}$alkyl, $C_{3-8}$carbocycle and phenyl are substituted by from 0 to 3 substitutents independently chosen from the group consisting of hydrogen, halogen, —$OR^{3a}$, —CN, —$CO_2R^{3a}$, —C(O)N($R^{3a}$)$_2$, —N($R^{3a}$)$_2$, —N($R^{3a}$)CO$_2R^{3a}$, —$SR^{3a}$, —S(O)$R^{3a}$, —S(O$_2$)$R^{3a}$, —N($R^{3a}$)SO$_2R^{3a}$, —N($R^{3a}$)CO$_2R^{3a}$, —N($R^{3a}$)C(O)N($R^{3a}$), $C_{1-6}$alkyl, —O—$C_{1-6}$alkyl and —S—$C_{1-6}$alkyl, u is from 0 to 4, each $R^3$ is independently chosen from the group consisting of hydrogen, $C_{1-6}$alkyl, —OH, —O—$C_{1-6}$alkyl and $C_{3-8}$cycloalkyl, and each $R^{3a}$ is independently chosen from the group consisting of hydrogen, $C_{1-6}$alkyl and $C_{3-8}$cycloalkyl;

is a group chosen from the group consisting of
(a) —C≡C— and
(b) aryl ring systems B' chosen from the group consisting of:
  (i) 5- to 7-membered monocyclic ring systems and
  (ii) 8- to 10-membered bicyclic ring systems,
  and the aryl ring systems B' containing from 0 to 4 heteroatoms independently chosen from the group consisting of N, O and S, and substituted on C or N atoms by v substituents $R^2$, each $R^2$ is independently chosen from the group consisting of hydrogen, halogen, —$OR^{4a}$, —CN, —$CO_2R^{4a}$, —C(O)N($R^{4a}$)$_2$, —N($R^{4a}$)$_2$, —N($R^{4a}$)COR$^4$, —N($R^{4a}$)CO$_2R^{4a}$, —N($R^{4a}$)C(O)N($R^{4a}$), —N($R^{4a}$)SO$_2R^{4a}$, —$SR^{4a}$, —S(O)$R^{4a}$, —S(O$_2$)$R^{4a}$, $C_{1-6}$alkyl substituted by from 0 to 4 $R^4$ and $C_{3-8}$cycloalkyl substituted by from 0 to 4 $R^4$, v is from 0 to 4, each $R^4$ is independently chosen from the group consisting of hydrogen, —OH, $C_{1-6}$alkyl and $C_{3-8}$cycloalkyl;

each $R^{4a}$ is independently chosen from the group consisting of hydrogen, $C_{1-6}$alkyl and $C_{3-8}$cycloalkyl;

$R^1$ and $R^2$ may be taken together with

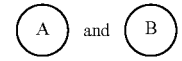

to form a 5- to 9-membered carbocyclic ring containing 1 or 2 heteroatoms independently chosen from the group consisting of N, O and S;

each D is a group independently chosen from the group consisting of:
(a) a single bond,
(b) —C(O)N($R^5$)—,
(c) —N($R^5$)C(O)—, and
(d) a 5- or 6-membered aryl ring system D' containing from 0 to 4 heteroatoms independently chosen from the group consisting of N, O and S, and substituted on C or N atoms by from 0 to 2 substituents $R^5$, each $R^5$ is independently chosen from the group consisting of hydrogen, halogen, —$OR^6$, —CN, —$CO_2R^6$, —C(O)N($R^6$)$_2$, —N($R^6$)$_2$, —N($R^6$)COR$^6$, —$SR^6$, —S(O)$R^6$, —S(O$_2$)$R^6$, —N($R^6$)SO$_2R^6$, —NCO$_2R^6$, —NC(O)N($R^6$)$_2$, $C_{1-6}$alkyl substituted by from 0 to 3 $R^6$ and $C_{3-8}$cycloalkyl substituted by from 0 to 3 $R^6$, and each $R^6$ is independently chosen from the group consisting of hydrogen, $C_{1-6}$alkyl and $C_{3-8}$cycloalkyl;

each E is a group independently chosen from the group consisting of:
(a) a single bond,
(b) —(C($R^7$)$_2$)$_{0-2}$NR$^7$C(O)O$_{0-1}$—, and
(c) a pyrrolidinyl derivative chosen from the group consisting of:

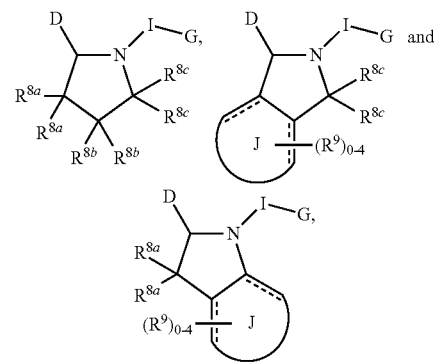

I is a bivalent group chosen from —C(O)—, —CO$_2$— and —C(O)N($R^7$)—,

J is a fused ring system chosen from the group consisting of 3- to 7-membered carbocycles and 5- or 6-membered aryl rings containing from 0 to 4 heteroatoms independently chosen from the group consisting of N, O and S, and substituted on C or N atoms by substituents $R^9$, each $R^{8a}$ is independently chosen from the group consisting of hydrogen, halogen, —OH, —OC$_{1-6}$alkyl and $C_{1-6}$alkyl, or two $R^{8a}$ may be taken together to form oxo, each $R^{8b}$ is independently chosen from the group consisting of hydrogen, halogen, —OH, —$OC_{1-6}$alkyl and $C_{1-6}$alkyl, or two $R^{8b}$ may be taken together to form oxo, each $R^{8c}$ is independently chosen from the group consisting of hydrogen and $C_{1-6}$alkyl, or any two groups selected from $R^{8a}$, $R^{8b}$ and $R^{8c}$ may be taken together to form a spiro-bicyclic or bridged bicyclic ring;

each $R^9$ is independently chosen from the group consisting of hydrogen, halogen, $C_{1-6}$alkyl, —O—$C_{1-6}$alkyl, —S—$C_{1-6}$alkyl, —NH—$C_{1-6}$alkyl and —NHC(O)—$C_{1-6}$alkyl, each $R^7$ is independently chosen from the group consisting of hydrogen, $C_{1-6}$alkyl and phenyl, and the $C_{1-6}$alkyl and phenyl are substituted by from 0 to 3 substitutents independently chosen from the group consisting of hydrogen, halogen, $C_{1-6}$alkyl, —O—$C_{1-6}$alkyl and —S—$C_{1-6}$alkyl; and each G is independently chosen from the group consisting of:
- (a) hydrogen,
- (b) —$OR^{10a}$,
- (c) —CN,
- (d) —$CO_2R^{10a}$,
- (e) —$C(O)N(R^{10})_2$,
- (f) —$SR^{10a}$,
- (g) —$S(O)R^{10a}$,
- (h) —$S(O_2)R^{10a}$,
- (i) —$N(R^{10})_2$,
- (j) —$N(R^{10})SO_2R^{10a}$,
- (k) —$NCO_2R^{10a}$,
- (l) —$NC(O)N(R^{10})_2$,
- (m) $C_{1-6}$alkyl having 0 to 4 substituents $R^{11}$,
  each $R^{11}$ is independently chosen from the group consisting of:
    - (i) —OH,
    - (ii) —$N(R^{10})_2$,
    - (iii) =$NR^{10}$,
    - (iv) —O—$C_{1-6}$ alkyl,
    - (v) —$C(O)R^{10}$,
    - (vi) —S—$C_{1-6}$ alkyl,
    - (vii) —$SO_2$—$C_{1-6}$ alkyl,
    - (viii) 3- to 8-membered carbocycles containing from 0 to 3 heteroatoms independently chosen from the group consisting of N, O and S, and having from 0 to 3 substitutents $R^{12}$ on N or C atoms, and each $R^{12}$ is independently selected from the group consisting of hydrogen, halogen, $C_{1-6}$alkyl having from 0 to 3 substituents chosen from $R^{10}$, —O—$C_{1-6}$alkyl, —S—$C_{1-6}$alkyl, —$OR^{10a}$, —CN, —$C(O)R^{10}$, —$CO_2R^{10a}$, —$C(O)N(R^{10})_2$, —$SR^{10a}$, —$S(O)R^{10a}$, —$S(O_2)R^{10a}$, —$N(R^{10})SO_2R^{10a}$, —$NCO_2R^{10a}$, —$NC(O)N(R^{10})_2$ and —$N(R^{10})_2$, or two $R^{12}$ are taken together to form oxo, and
    - (ix) 5- or 6-membered aryl containing from 0 to 3 heteroatoms independently chosen from the group consisting of N, O and S, and having from 0 to 3 substitutents $R^{13}$ on N or C atoms, and each $R^{13}$ is independently selected from the group consisting of hydrogen, halogen, $C_{1-6}$alkyl, —O—$C_{1-6}$alkyl and 3- to 8-membered carbocycles containing from 0 to 3 heteroatoms independently chosen from the group consisting of N, O and S,
- (n) 3- to 8-membered carbocycles containing from 0 to 3 heteroatoms independently chosen from the group consisting of N, O and S, and having from 0 to 3 substitutents $R^{10}$ on N or C atoms; and
- (o) aryl ring systems G' chosen from the group consisting of:
    - (i) 5- to 7-membered monocyclic ring systems and
    - (ii) 8- to 10-membered bicyclic ring systems,
  and the aryl ring systems G' containing from 0 to 4 heteroatoms independently chosen from the group consisting of N, O and S, and substituted on C or N atoms by 0 to 3 substitutents $R^{10}$;

each $R^{10}$ is independently chosen from the group consisting of
- (i) hydrogen,
- (ii) —CN,
- (iii) $C_{1-6}$alkyl,
- (iv) —O—$C_{0-6}$alkyl,
- (v) —S—$C_{0-6}$alkyl,
- (vi) $C_{1-6}$alkyl-O—$R^{14}$,
- (vii) —$C(O)R^{14}$,
- (viii) —$CO_2R^{14}$,
- (ix) —$SO_2R^{14}$,
- (x) —$N(R^{14})_2$,
- (xi) —$N(R^{14})SO_2R^{14}$,
- (xii) —$NCO_2R^{14}$,
- (xiii) —$NC(O)N(R^{14})_2$, and
- (xiv) 3- to 8-membered carbocycles containing from 0 to 3 heteroatoms independently chosen from the group consisting of N, O and S, or two $R^{10}$ may be taken together to form oxo;

each $R^{10a}$ is independently chosen from the group consisting of
- (i) hydrogen,
- (ii) —CN,
- (iii) $C_{1-6}$alkyl,
- (iv) $C_{1-6}$alkyl-O—$R^{14}$,
- (v) —$C(O)R^{14}$,
- (vi) —$CO_2R^{14}$,
- (vii) —$SO_2R^{14}$,
- (x) —$N(R^{14})_2$,
- (xi) —$N(R^{14})SO_2R^{14}$,
- (xii) —$NCO_2R^{14}$,
- (xiii) —$NC(O)N(R^{14})_2$, and
- (xiv) 3- to 8-membered carbocycles containing from 0 to 3 heteroatoms independently chosen from the group consisting of N, O and S, and two $R^{10}$ or $R^{10a}$ groups can be taken together with the N to which they are attached to form a ring, which may be substituted by from 0 to 3 substituents $R^{14}$, and each $R^{14}$ is independently chosen from the group consisting of hydrogen, $C_{1-6}$alkyl, $C_{3-8}$cycloalkyl, —$(CH_2)_{0-3}C_{3-8}$cycloalkyl and phenyl. In this embodiment, all other groups are as provided in the general formula above.

In a second embodiment of the invention,

is chosen from the group consisting of

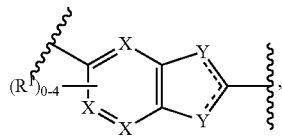

where each X is independently chosen from the group consisting of $CR^1$ and N,

is chosen from the group consisting of

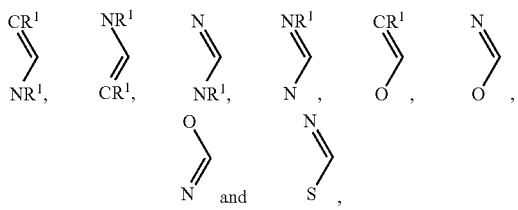

each $R^1$ is independently chosen from the group consisting of hydrogen, halogen, —$OR^{3a}$, —CN, —$C(O)R^3$, —$CO_2R^{3a}$, —$C(O)N(R^{3a})_2$, —$SR^{3a}$, —$S(O)R^{3a}$, —$S(O_2)R^{3a}$, —$(CH_2)_{0-6}N(R^{3a})_2$, —$N(R^{3a})SO_2R^{3a}$, —$N(R^{3a})CO_2R^{3a}$, —$N(R^{3a})C(O)R^3$, —$N(R^{3a})COR^{3a}$, —$N(R^{3a})C(O)N(R^{3a})$, $C_{1-6}$alkyl, $C_{3-8}$carbocycle containing from 0 to 3 heteroatoms chosen from N, O and S, and phenyl, and the $C_{1-6}$alkyl, $C_{3-8}$carbocycle and phenyl are substituted by from 0 to 3 substitutents independently chosen from the group consisting of hydrogen, halogen, —$OR^{3a}$, —CN, —$CO_2R^{3a}$, —$C(O)N(R^{3a})_2$, —$N(R^{3a})_2$, —$N(R^{3a})CO_2R^{3a}$, —$SR^{3a}$, —$S(O)R^{3a}$, —$S(O_2)R^{3a}$, —$N(R^{3a})SO_2R^{3a}$, —$N(R^{3a})CO_2R^3$, —$N(R^{3a})C(O)N(R^{3a})$, $C_{1-6}$alkyl, —O—$C_{1-6}$alkyl and —S—$C_{1-6}$alkyl, each $R^3$ is independently chosen from the group consisting of hydrogen, $C_{1-6}$alkyl, —OH, —O—$C_{1-6}$alkyl and $C_{3-8}$cycloalkyl, and each $R^{ia}$ is independently chosen from the group consisting of hydrogen, $C_{1-6}$alkyl and $C_{3-8}$cycloalkyl. In all aspects of this embodiment, all other groups are as provided in the general formula above or in the first embodiment above.

In a first aspect of the second embodiment of the invention,

Ⓐ is chosen from the group consisting of

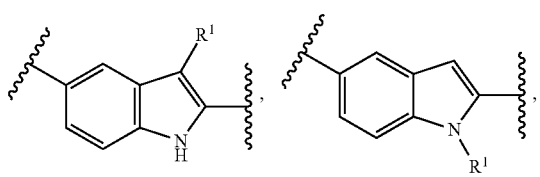

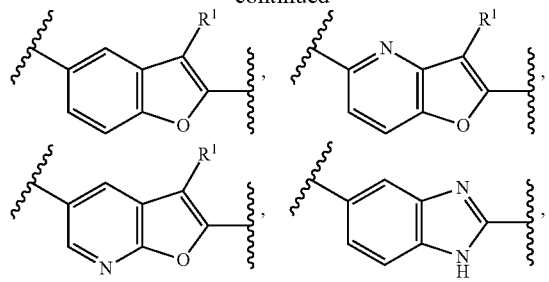

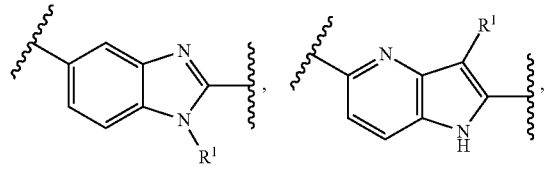

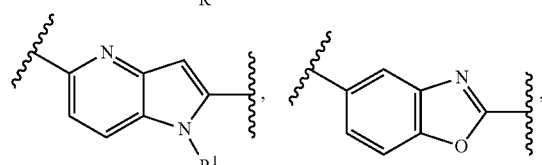

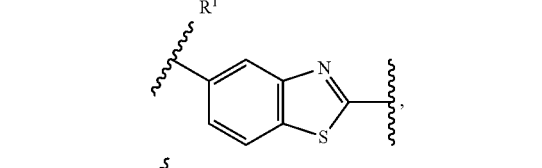

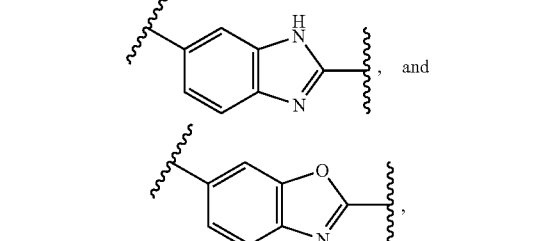

where

Ⓐ is substituted by from 0 to 3 additional $R^1$, which are as provided above.

In a second aspect of the second embodiment,

Ⓐ is chosen from the group consisting of

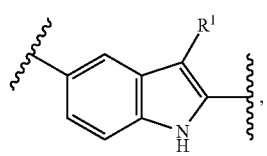

-continued

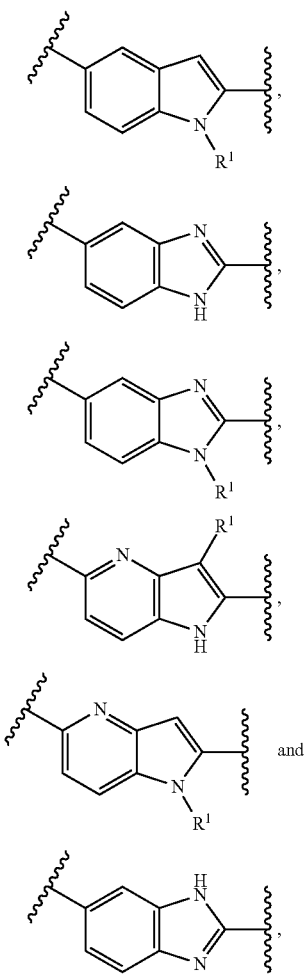

where

is substituted by from 0 to 3 additional R¹, which are as provided above. In preferred instances of this aspect,

is

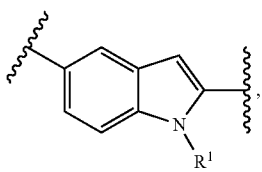

where

is substituted by from 0 to 3 additional R¹, which are as provided above.

In a third aspect of the second embodiment,

is chosen from the group consisting of

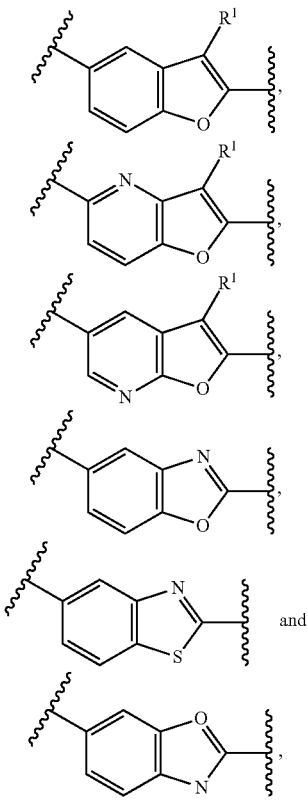

where

is substituted by from 0 to 3 additional R¹, which are as provided above. In preferred instances of this aspect,

is

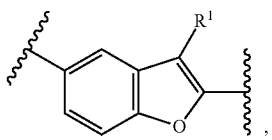

where

Ⓐ is substituted by from 0 to 3 additional R¹, which are as provided above.

In further aspects of the second embodiment, each R¹ is chosen from the group consisting of hydrogen, halogen, —CN and $C_{1-6}$alkyl. In particular, each R¹ is chosen from the group consisting of hydrogen, fluorine and —CN.

In a third embodiment of the invention,

Ⓑ is chosen from the group consisting of —C≡C—, phenyl, pyridinyl, pyrazinyl, pyrimidyl, 1,2,4-triazinyl, pyridazinyl, thiazyl and 9-membered bicyclic ring systems that contain from 1 to 3 heteroatoms independently chosen from the group consisting of N, O and S, v is from 0 to 4, each R² is independently chosen from the group consisting of hydrogen, halogen, —$OR^{4a}$, —CN, —$CO_2R^{4a}$, —$C(O)N(R^{4a})_2$, —$N(R^{4a})_2$, —$N(R^{4a})CO_2R^{4a}$, —$SR^{4a}$, —$S(O)R^{4a}$, —$S(O_2)R^{4a}$, —$N(R^{4a})SO_2R^{4a}$, —$N(R^{4a})CO_2R^{4a}$, —$N(R^{4a})C(O)N(R^{4a})$, $C_{1-6}$alkyl substituted by from 0 to 4 R⁴ and $C_{3-8}$cycloalkyl substituted by from 0 to 4 R⁴, each R⁴ is independently chosen from the group consisting of hydrogen, —OH, $C_{1-6}$alkyl and $C_{3-8}$cycloalkyl, and each $R^{4a}$ is independently chosen from the group consisting of hydrogen, $C_{1-6}$alkyl and $C_{3-8}$cycloalkyl. In particular aspects of this embodiment,

Ⓑ is phenyl, v is from 0 to 2, and each R² is independently chosen from the group consisting of fluorine, chlorine, —OH, —$CH_3$, —$OCH_3$ and —CN. In all aspects of this embodiment, all other groups are as provided in the general formula above and/or in the first or second embodiments.

In a fourth embodiment of the invention,

Ⓐ and Ⓑ, taken together with one substituent R¹ and one substituent R², are represented by a group chosen from the group consisting of:

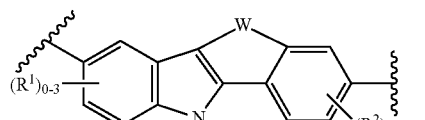

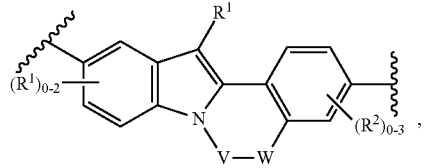

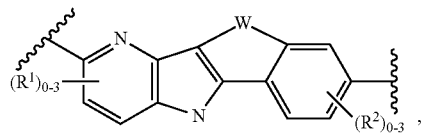

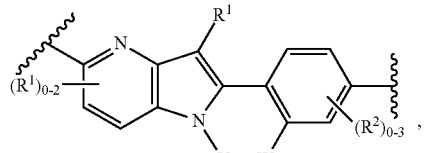

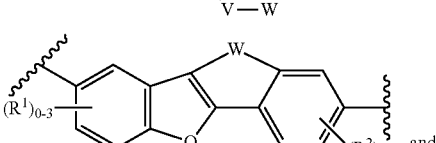

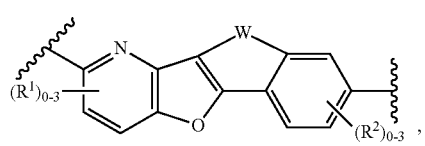

where W is chosen from the group consisting of —$(CH_2)_{1-3}$—, —$(CH_2)_{0-2}NH(CH_2)_{0-2}$—, —$(CH_2)_{0-2}N(C_{1-6}alkyl)(CH_2)_{0-2}$—, —$(CH_2)_{0-2}O(CH_2)_{0-2}$— and —$(CH_2)_{0-2}C(O)(CH_2)_{0-2}$—, where W is substituted by from 0 to 4 $R^w$, where each $R^w$ is independently selected from $C_{1-6}$alkyl and $C_{3-8}$cycloalkyl; and V is chosen from the group consisting of —C(O)— and —$CH_2$—, and where V is —$CH_2$—, V is substituted by from 0 to 2 $R^v$, where each $R^v$ is independently selected from the group consisting of $C_{1-6}$alkyl and $C_{3-8}$cycloalkyl. In a first aspect of this embodiment, Ⓐ and Ⓑ, taken together with one substituent R¹ and one substituent R², are represented by a group chosen from the group consisting of

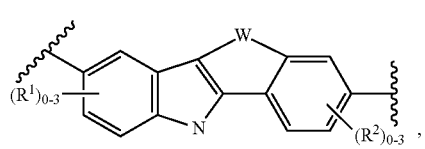

-continued

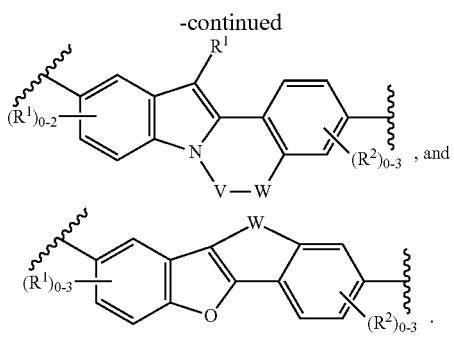

In particular instances of this embodiment, and of the first aspect of this embodiment, W is chosen from the group consisting of —CH$_2$—, —NH—, —N(C$_{1-6}$alkyl)-, —C(O)—, —CH$_2$NH—, —CH$_2$N(C$_{1-6}$alkyl)-, —CH$_2$CH$_2$—, —C(O)CH$_2$—, —CH$_2$C(O)—, —CH$_2$O—, —CH$_2$CH$_2$CH$_2$—, —C(O)CH$_2$CH$_2$—, —CH$_2$C(O)CH$_2$—, —CH$_2$OCH$_2$—, —CH$_2$CH$_2$C(O)—, —CH$_2$CH$_2$O—, —CH$_2$CH$_2$NH—, —CH$_2$CH$_2$N(C$_{1-6}$alkyl)-, —CH$_2$NHCH$_2$—, —CH$_2$N(C$_{1-6}$alkyl)CH$_2$—, —NHCH$_2$CH$_2$—, and —N(C$_{1-6}$alkyl)CH$_2$CH$_2$—. In all aspects of this embodiment, all other groups are as provided in the general formula above.

In a fifth embodiment of the invention, each D is independently chosen from the group consisting of a single bond, —C(O)N(R$^5$)—, —NR$^5$C(O)—,

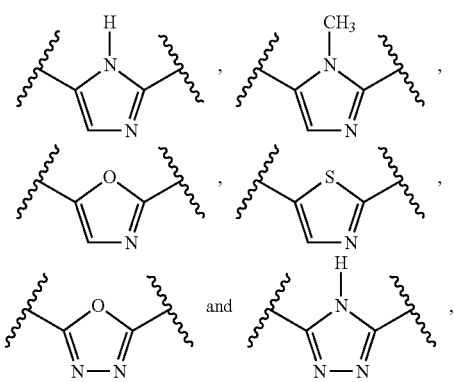

where R$^5$ is independently chosen from the group consisting of hydrogen, halogen —OR$^6$, —CN, —CO$_2$R$^6$, —C(O)N(R$^6$)$_2$, —N(R$^6$)$_2$, —N(R$^6$)COR$^6$, —SR$^6$, —S(O)R$^6$, —S(O$_2$)R$^6$, —N(R$^6$)SO$_2$R$^6$, —NCO$_2$R$^6$, —NC(O)N(R$^6$)$_2$, C$_{1-6}$alkyl substituted by from 0 to 3 substituents R$^6$ and C$_{3-8}$cycloalkyl substituted by from 0 to 3 substituents R$^6$, and each R$^6$ is independently chosen from the group consisting of hydrogen, C$_{1-6}$alkyl and C$_{3-8}$cycloalkyl. In particular aspects of this embodiment, each D is independently chosen from the group consisting of

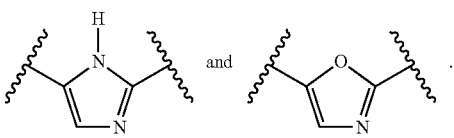 [SMILES: *c1cnc(*)[nH]1 ; *c1cnc(*)o1]

In this embodiment, all other groups are as provided in the general formula above and/or in the first through fourth embodiments.

In a sixth embodiment of the invention, each E is independently chosen from the group consisting of a single bond, —CH$_2$NHC(O)—, —CH$_2$N(CH$_3$)C(O)—, —C(CH$_3$)HNHC(O)—, —C(CH$_3$)HN(CH$_3$)C(O)—, —C(CH$_3$)$_2$NHC(O)—, —C(CH$_3$)$_2$N(CH$_3$)C(O)—, —CH$_2$NHC(O)O—, —CH$_2$N(CH$_3$)C(O)O—, —C(CH$_3$)HNHC(O)O—, —C(CH$_3$)HN(CH$_3$)C(O)O—, —C(CH$_3$)$_2$NHC(O)O—, —C(CH$_3$)$_2$N(CH$_3$)C(O)O—,

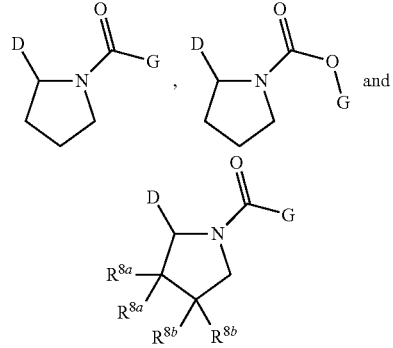

where one of R$^{8a}$ and R$^{8b}$ is —OH or fluorine. In a first aspect of this embodiment, each E is independently chosen from the group consisting of a single bond,

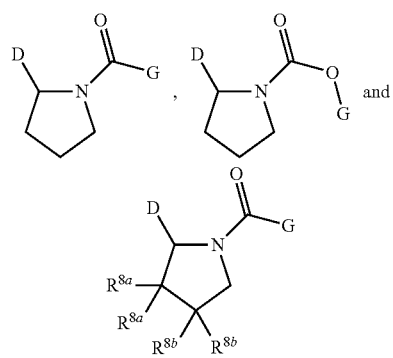

where one of R$^{8a}$ and R$^{8b}$ is —OH or fluorine. In all aspects of this embodiment, all other groups are as provided in the general formula above and/or in the first through fifth embodiments.

In some embodiments, adjacent D and E groups each may be selected to be a single bond. In such embodiments, D and E are combined to be one single bond, and all other groups are as provided in the general formula above and/or in the first, second, third and fourth embodiments. That is, where D is a single bond and the adjacent E is a single bond,

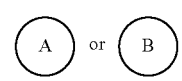

is connected directly to G by one single bond.

In a seventh embodiment of the invention, each G is independently chosen from the group consisting of:
(a) C$_{1-6}$alkyl having 0 to 4 substituents R$^{11}$,
(b) 3- to 8-membered carbocycles containing from 0 to 3 heteroatoms independently chosen from the group consisting of N, O and S, and having from 0 to 3 substitutents R$^{10}$ on N or C atoms; and (c) aryl ring systems G' chosen from the group consisting of:
  (i) 5- to 7-membered monocyclic ring systems and
  (ii) 8- to 10-membered bicyclic ring systems,
  and the aryl ring systems G' containing from 0 to 4 heteroatoms independently chosen from the group consisting of N, O and S, and substituted on C or N atoms by 0 to 3 substitutents $R^{10}$. In all aspects of the seventh embodiment, G is chosen such that stable compounds result. In all aspects of this seventh embodiment, all other groups are as provided in the general formula above and/or in the first through sixth embodiments.

In an eighth embodiment, each G is independently chosen from the group consisting of:
  (a) hydrogen,
  (b) —CN,
  (c) $C_{1-5}$alkyl having 1 to 3 substituents $R^{11}$,
  each $R^{11}$ is independently chosen from the group consisting of —OH, —NH₂, —NCH₃H, —N(CH₃)₂, —N(CH₂CH₃)₂, =NH, =NCH₃, —C(O)H, —C(O)OH, —C(O)CH₃, —C(O)OCH₃, —NHC(O)H, —NHC(O)OH, —NHC(O)CH₃, —NHC(O)OCH₃, cyclopropyl, cyclobutyl, cyclopentyl, cyclohexyl, pyranyl, pyrrolidinyl, piperidinyl, oxacyclopentyl, and oxacyclohexyl, phenyl, pyridinyl, pyrimidinyl and pyrrolyl, where
    the cyclopropyl, cyclobutyl, cyclopentyl, cyclohexyl, pyranyl, pyrrolidinyl, piperidinyl, oxacyclopentyl and oxacyclohexyl are substituted by from 0 to 2 substitutents $R^{12}$ on N or C atoms, and each $R^{12}$ is independently selected from the group consisting of hydrogen, halogen, carboxy, $C_{1-6}$alkyl, —O—$C_{1-6}$alkyl and —S—$C_{1-6}$alkyl; and
    the phenyl, pyridinyl, pyrimidinyl and pyrrolyl are substituted by from 0 to 3 substitutents $R^{13}$ on N or C atoms, and each $R^{13}$ is independently selected from the group consisting of hydrogen, halogen, $C_{1-6}$alkyl and 3- to 8-membered cycloalkyl containing from 0 to 3 heteroatoms independently chosen from the group consisting of N, O and S,
  (d) cyclopropyl, cyclobutyl, cyclopentyl, cyclohexyl, pyranyl, pyrrolidinyl, piperidinyl, oxacyclopentyl and oxacyclohexyl having from 0 to 3 substituents $R^{10}$ on N or C atoms, the $R^{10}$ independently selected from the group consisting of hydrogen, halogen, carboxy, $C_{1-6}$alkyl, —O—$C_{1-6}$alkyl, —S—$C_{1-6}$alkyl, phenyl and benzyl, and
  (e) aryl ring systems G' chosen from the group consisting of: phenyl, pyridinyl and 9-membered bicyclic ring systems containing from 0 to 2 heteroatoms independently chosen from the group consisting of N and O.

In a first aspect of the eighth embodiment, G is independently chosen from the group consisting of $C_{1-4}$alkyl having 1 to 2 substituents $R^{11}$, wherein each $R^{11}$ is independently chosen from the group consisting of —OH, —NH₂, —NCH₃H, —N(CH₃)₂, —N(CH₂CH₃)₂, —C(O)OCH₃, cyclopropyl, cyclobutyl, cyclopentyl, cyclohexyl, pyranyl, pyrrolidinyl, piperidinyl, oxacyclopentyl, oxacyclohexyl, phenyl, pyridinyl, pyrimidinyl and pyrrolyl. In all aspects of the eighth embodiment, G is chosen such that stable compounds result. In all aspects of this eighth embodiment, all other groups are as provided in the general formula above and/or in the first through sixth embodiments.

In a ninth embodiment of the invention,

is chosen from the group consisting of

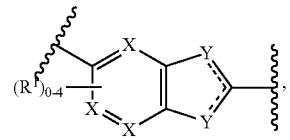

where
  each X is independently chosen from the group consisting of $CR^1$ and N,

is chosen from the group consisting of

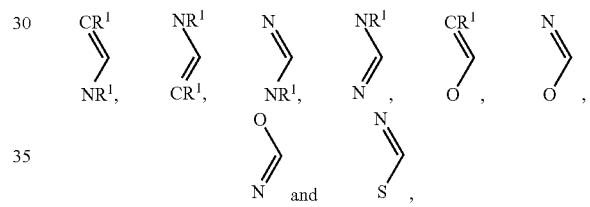

each $R^1$ is independently chosen from the group consisting of hydrogen, halogen, —$OR^{3a}$, —CN, —$C(O)R^3$, —$CO_2R^{3a}$, —$C(O)N(R^{3a})_2$, —$SR^{3a}$, —$S(O)R^{3a}$, —$S(O_2)R^{3a}$, —$(CH_2)_{0-6}N(R^{3a})_2$, —$N(R^{3a})SO_2R^{3a}$, —$N(R^{3a})CO_2R^{3a}$, —$N(R^{3a})C(O)R^3$, —$N(R^{3a})COR^{3a}$, —$N(R^{3a})C(O)N(R^{3a})$, $C_{1-6}$alkyl, $C_{3-8}$carbocycle containing from 0 to 3 heteroatoms chosen from N, O and S, and phenyl, and the $C_{1-6}$alkyl, $C_{3-8}$carbocycle and phenyl are substituted by from 0 to 3 substitutents independently chosen from the group consisting of hydrogen, halogen, —$OR^{3a}$, —CN, —$CO_2R^{3a}$, —$C(O)N(R^{3a})_2$, —$N(R^{3a})_2$, —$N(R^{3a})CO_2R^{3a}$, —$SR^{3a}$, —$S(O)R^{3a}$, —$S(O_2)R^{3a}$, —$N(R^{3a})SO_2R^{3a}$, —$N(R^{3a})CO_2R^3$, —$N(R^{3a})C(O)N(R^{3a})$, $C_{1-6}$alkyl, —O—$C_{1-6}$alkyl and —S—$C_{1-6}$alkyl,
  each $R^3$ is independently chosen from the group consisting of hydrogen, $C_{1-6}$alkyl, —OH, —O—$C_{1-6}$alkyl and $C_{3-8}$cycloalkyl, and
  each $R^{3a}$ is independently chosen from the group consisting of hydrogen, $C_{1-6}$alkyl and $C_{3-8}$cycloalkyl;

is chosen from the group consisting of —C≡C—, phenyl, pyridinyl, pyrazinyl, pyrimidyl, 1,2,4-triazinyl, pyridazinyl, thiazyl and 9-membered bicyclic ring systems that contain from 1 to 3 heteroatoms independently chosen from the group consisting of N, O and S, v is from 0 to 4, each $R^2$ is independently chosen from the group consisting of hydrogen, halogen, —$OR^{4a}$, —CN, —$CO_2R^{4a}$, —C(O)N($R^{4a}$)$_2$, —N($R^{4a}$)$_2$, —N($R^{4a}$)$CO_2R^{4a}$, —$SR^{4a}$, —$S(O)R^{4a}$, —$S(O_2)R^{4a}$, —N($R^{4a}$)$SO_2R^{4a}$, —N($R^{4a}$)$CO_2R^{4a}$, —N($R^{4a}$)C(O)N($R^{4a}$), $C_{1-6}$alkyl substituted by from 0 to 4 $R^4$ and $C_{3-8}$cycloalkyl substituted by from 0 to 4 $R^4$, each $R^4$ is independently chosen from the group consisting of hydrogen, —OH, $C_{1-6}$alkyl and $C_{3-8}$cycloalkyl, and each $R^{4a}$ is independently chosen from the group consisting of hydrogen, $C_{1-6}$alkyl and $C_{3-8}$cycloalkyl;

wherein each D is independently chosen from the group consisting of a single bond, —C(O)N($R^5$)—, —$NR^5$C(O)—,

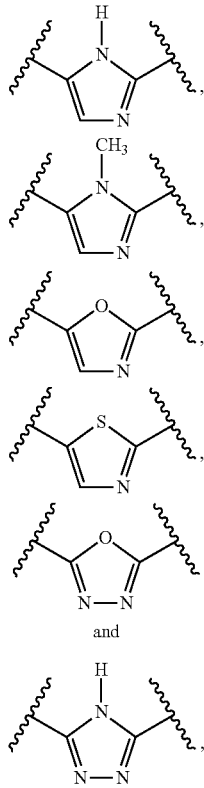

where $R^5$ is independently chosen from the group consisting of hydrogen, halogen —$OR^6$, —CN, —$CO_2R^6$, —C(O)N($R^6$)$_2$, —N($R^6$)$_2$, —N($R^6$)$COR^6$, —$SR^6$, —$S(O)R^6$, —$S(O_2)R^6$, —N($R^6$)$SO_2R^6$, —$NCO_2R^6$, —NC(O)N($R^6$)$_2$, $C_{1-6}$alkyl substituted by from 0 to 3 substituents $R^6$ and $C_{3-8}$cycloalkyl substituted by from 0 to 3 substituents $R^6$, and each $R^6$ is independently chosen from the group consisting of hydrogen, $C_{1-6}$alkyl and $C_{3-8}$cycloalkyl;

wherein each E is independently chosen from the group consisting of a single bond, —$CH_2NHC(O)$—, —$CH_2N(CH_3)C(O)$—, —$C(CH_3)HNHC(O)$—, —$C(CH_3)HN(CH_3)C(O)$—, —$C(CH_3)_2NHC(O)$—, —$C(CH_3)_2N(CH_3)C(O)$—, —$CH_2NHC(O)O$—, —$CH_2N(CH_3)C(O)O$—, —$C(CH_3)HNHC(O)O$—, —$C(CH_3)HN(CH_3)C(O)O$—, —$C(CH_3)_2NHC(O)O$—, —$C(CH_3)_2N(CH_3)C(O)O$—,

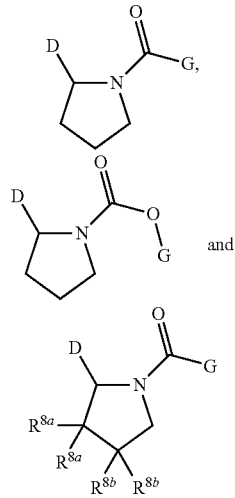

where one of $R^{8a}$ and $R^{8b}$ is —OH or fluorine;

wherein each G is independently chosen from the group consisting of (a) hydrogen, (b) —CN, (c) $C_{1-5}$alkyl having 1 to 3 substituents $R^{11}$, each $R^{11}$ is independently chosen from the group consisting of —OH, —$NH_2$, —$NCH_3H$, —N($CH_3$)$_2$, —N($CH_2CH_3$)$_2$, =NH, =$NCH_3$, —C(O)H, —C(O)OH, —C(O)$CH_3$, —C(O)$OCH_3$, —NHC(O)H, —NHC(O)OH, —NHC(O)$CH_3$, —NHC(O)$OCH_3$, cyclopropyl, cyclobutyl, cyclopentyl, cyclohexyl, pyranyl, pyrrolidinyl, piperidinyl, oxacyclopentyl, and oxacyclohexyl, phenyl, pyridinyl, pyrimidinyl and pyrrolyl, where the cyclopropyl, cyclobutyl, cyclopentyl, cyclohexyl, pyranyl, pyrrolidinyl, piperidinyl, oxacyclopentyl and oxacyclohexyl are substituted by from 0 to 2 substitutents $R^{12}$ on N or C atoms, and each $R^{12}$ is independently selected from the group consisting of hydrogen, halogen, carboxy, $C_{1-6}$alkyl, —O—$C_{1-6}$alkyl and —S—$C_{1-6}$alkyl; and the phenyl, pyridinyl, pyrimidinyl and pyrrolyl are substituted by from 0 to 3 substitutents $R^{13}$ on N or C atoms, and each $R^{13}$ is independently selected from the group consisting of hydrogen, halogen, $C_{1-6}$alkyl and 3- to 8-membered cycloalkyl containing from 0 to 3 heteroatoms independently chosen from the group consisting of N, O and S, (d) cyclopropyl, cyclobutyl, cyclopentyl, cyclohexyl, pyranyl, pyrrolidinyl, piperidinyl, oxacyclopentyl and oxacyclohexyl having from 0 to 3 substitutents $R^{10}$ on N or C atoms, the $R^{10}$ independently selected from the group consisting of hydrogen, halogen, carboxy, $C_{1-6}$alkyl, —O—$C_{1-6}$alkyl, —S—$C_{1-6}$alkyl, phenyl and benzyl, and (e) aryl ring systems G' chosen from the group consisting of: phenyl, pyridinyl and 9-membered bicyclic ring systems containing from 0 to 2 heteroatoms independently chosen from the group consisting of N and O. In all aspects of this embodiment, all other groups are as provided in the general formula above.

In a tenth embodiment of the invention,

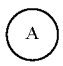

is chosen from the group consisting of

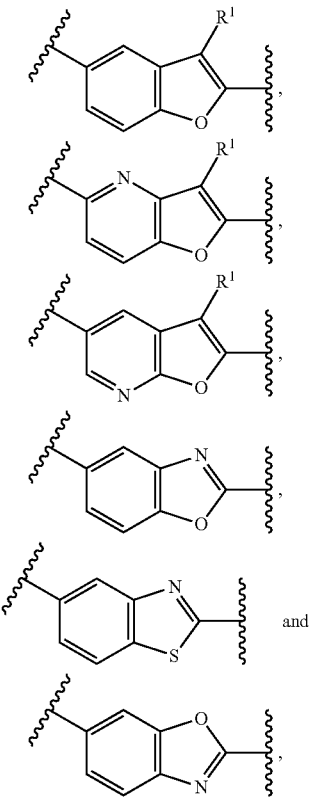

where

is substituted by from 0 to 3 additional R¹;

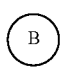

is phenyl; v is from 0 to 2; each $R^2$ is independently chosen from the group consisting of fluorine, chlorine, —OH, —CH₃, —OCH₃ and —CN; each D is independently chosen from the group consisting of

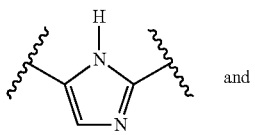

and

-continued

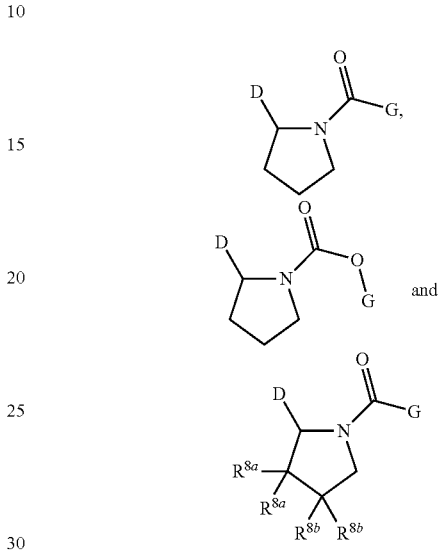

each E is independently chosen from the group consisting of a single bond,

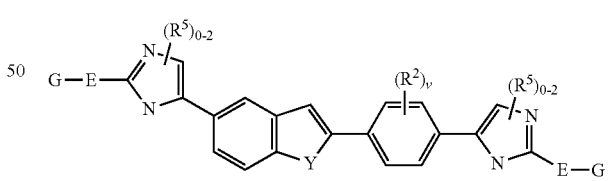

where one of $R^{8a}$ and $R^{8b}$ is —OH or fluorine; and each G is independently chosen from the group consisting of $C_{1-4}$alkyl having 1 to 2 substituents $R^{11}$, wherein each $R^{11}$ is independently chosen from the group consisting of —OH, —NH₂, —NCH₃H, —N(CH₃)₂, —N(CH₂CH₃)₂, —C(O)OCH₃, cyclopropyl, cyclobutyl, cyclopentyl, cyclohexyl, pyranyl, pyrrolidinyl, piperidinyl, oxacyclopentyl, oxacyclohexyl, phenyl, pyridinyl, pyrimidinyl and pyrrolyl. In all aspects of this embodiment, all other groups are as provided in the general formula above or in the eighth embodiment.

In an eleventh embodiment of the invention, the compound having structural formula (I) is a compound having structural formula (Ia):

(Ia)

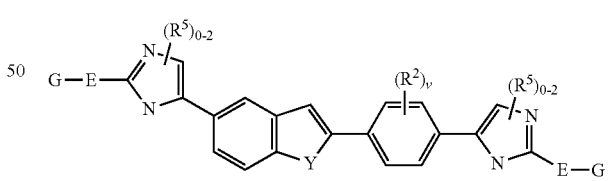

or a pharmaceutically acceptable salt thereof, wherein

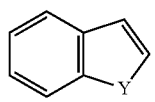

is substituted by u substituents $R^1$, and Y is selected from the group consisting of O and $NR^1$. In all aspects of this embodiment, all other groups are as provided in the general formula above or in any one of the first through tenth embodiments.

In a twelfth embodiment of the invention, the compound having structural formula (Ia) is a compound having structural formula (Ib):

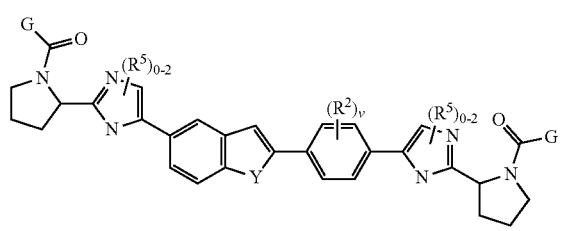

or a pharmaceutically acceptable salt thereof, wherein

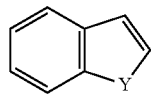

is substituted by u substituents R¹, and Y is selected from the group consisting of O and NR¹. In particular aspects of this embodiment,

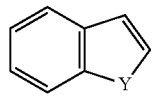

is substituted by u substituents R¹, Y is O, and both instances of G are

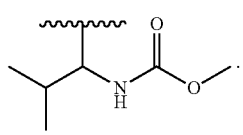 [SMILES: *C(NC(=O)OC)C(C)C]

In all aspects of this embodiment, all other groups are as provided in the general formula above or in the eleventh embodiment.

In a thirteenth embodiment of the invention, the compound having structural formula (Ia) is a compound having structural formula (Ib):

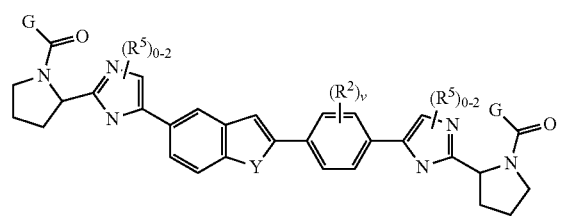

or a pharmaceutically acceptable salt thereof, wherein said

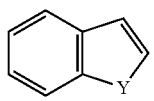

is substituted by u substituents R¹, and said

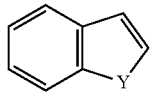

and said

taken together with one substituent R¹ and one substituent R², are represented by a group chosen from the group consisting of

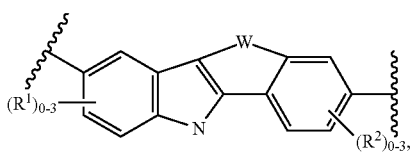

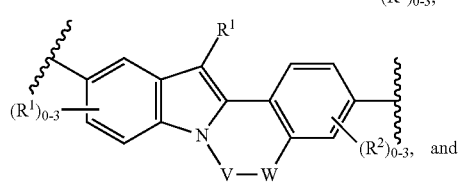

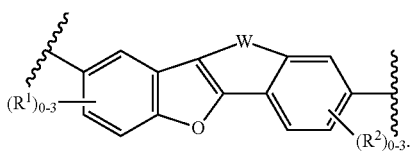

In particular aspects of this embodiment,

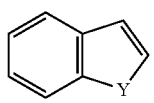

and said

taken together with one substituent $R^1$ and one substituent $R^2$, are represented by

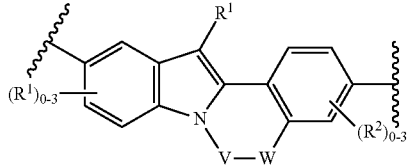

wherein V is —CH$_2$—, W is —(CH$_2$)$_{0-2}$O(CH$_2$)$_{0-2}$—, $R^1$ is fluorine, and both instances of G are

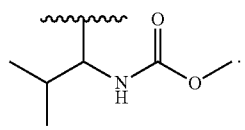 [SMILES: *C(NC(=O)OC)C(C)C]

In all aspects of this embodiment, all other groups are as provided in the general formula above or in the eleventh embodiment.

In a fourteenth embodiment of the invention,

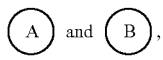

taken together with one substituent $R^1$ and one substituent $R^2$, are represented by a group chosen from the group consisting of:

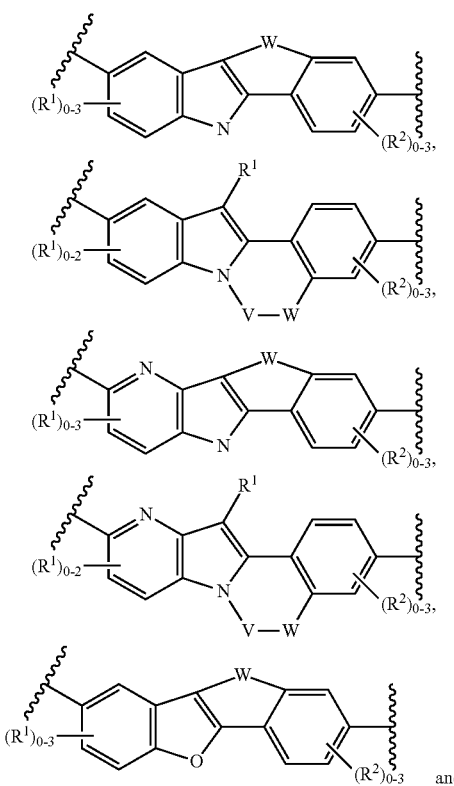

-continued

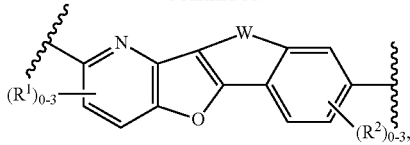

where
W is chosen from the group consisting of —(CH$_2$)$_{1-3}$—, —(CH$_2$)$_{0-2}$NH(CH$_2$)$_{0-2}$—, —(CH$_2$)$_{0-2}$N(C$_{1-6}$alkyl)(CH$_2$)$_{0-2}$—, —(CH$_2$)$_{0-2}$O(CH$_2$)$_{0-2}$— and —(CH$_2$)$_{0-2}$C(O)(CH$_2$)$_{0-2}$—, where W is substituted by from 0 to 4 R$^w$, where each R$^w$ is independently selected from C$_{1-6}$alkyl and C$_{3-8}$cycloalkyl; and V is chosen from the group consisting of —C(O)— and —CH$_2$—, and where V is —CH$_2$—, V is substituted by from 0 to 2 R$^v$, where each R$^v$ is independently selected from the group consisting of C$_{1-6}$alkyl and C$_{3-8}$cycloalkyl;

each $R^1$ is independently chosen from the group consisting of hydrogen, halogen, —OR$^3$, —CN, —C(O)R$^3$, —CO$_2$R$^3$, —C(O)N(R$^{3a}$)$_2$, —SR$^3$, —S(O)R$^3$, —S(O$_2$)R$^3$, —N(R$^{3a}$)$_2$, —(CH$_2$)$_{0-6}$N(R$^{3a}$)$_2$, —N(R$^{3a}$)SO$_2$R$^3$, —N(R$^{3a}$)CO$_2$R$^3$, —N(R$^{3a}$)COR$^3$, —N(R$^{3a}$)C(O)N(R$^{3a}$), C$_{1-6}$alkyl, C$_{3-8}$carbocycle containing from 0 to 3 heteroatoms chosen from N, O and S, and phenyl, and the C$_{1-6}$alkyl, C$_{3-8}$carbocycle and phenyl are substituted by from 0 to 3 substitutents independently chosen from the group consisting of hydrogen, halogen, —OR$^{3a}$, —CN, —CO$_2$R$^{3a}$, —C(O)N(R$^{3a}$)$_2$, —N(R$^{3a}$)$_2$, —N(R$^{3a}$)CO$_2$R$^{3a}$, —SR$^{3a}$, —S(O)R$^{3a}$, —S(O$_2$)R$^{3a}$, —N(R$^{3a}$)SO$_2$R$^{3a}$, —N(R$^{3a}$)CO$_2$R$^{3a}$, —N(R$^{3a}$)C(O)N(R$^{3a}$), C$_{1-6}$ alkyl, —O—C$_{1-6}$alkyl and —S—C$_{1-6}$alkyl, each $R^3$ is independently chosen from the group consisting of hydrogen, C$_{1-6}$alkyl, —OH, —O—C$_{1-6}$alkyl and C$_{3-8}$cycloalkyl, and each $R^{3a}$ is independently chosen from the group consisting of hydrogen, C$_{1-6}$alkyl and C$_{3-8}$cycloalkyl;

each $R^2$ is independently chosen from the group consisting of hydrogen, halogen, —OR$^{4a}$, —CN, —CO$_2$R$^{4a}$, —C(O)N(R$^{4a}$)$_2$, —N(R$^{4a}$)$_2$, —N(R$^{4a}$)CO$_2$R$^{4a}$, —SR$^{4a}$, —S(O)R$^{4a}$, —S(O$_2$)R$^{4a}$, —N(R$^{4a}$)SO$_2$R$^{4a}$, —N(R$^{4a}$)CO$_2$R$^{4a}$, —N(R$^{4a}$)C(O)N(R$^{4a}$), C$_{1-6}$alkyl substituted by from 0 to 4 R$^4$ and C$_{3-8}$cycloalkyl substituted by from 0 to 4 R$^4$, each $R^4$ is independently chosen from the group consisting of hydrogen, —OH, C$_{1-6}$alkyl and C$_{3-8}$cycloalkyl, and each $R^{4a}$ is independently chosen from the group consisting of hydrogen, C$_{1-6}$alkyl and C$_{3-8}$cycloalkyl;

wherein each D is independently chosen from the group consisting of a single bond, —C(O)N(R$^5$)—, —NR$^5$C(O)—,

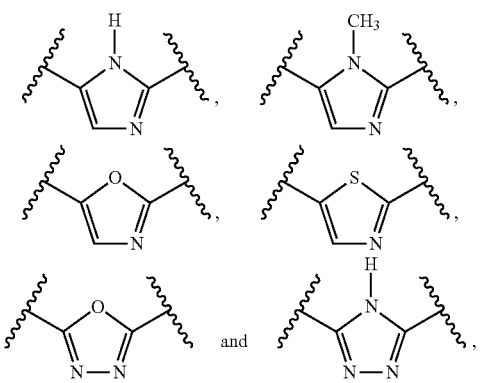

where
R$^5$ is independently chosen from the group consisting of hydrogen, halogen —OR$^6$, —CN, —CO$_2$R$^6$, —C(O)N(R$^6$)$_2$, —N(R$^6$)$_2$, —N(R$^6$)COR$^6$, —SR$^6$, —S(O)R$^6$, —S(O$_2$)R$^6$, —N(R$^6$)SO$_2$R$^6$, —NCO$_2$R$^6$, —NC(O)N(R$^6$)$_2$, C$_{1-6}$alkyl substituted by from 0 to 3 substituents R$^6$ and C$_{3-8}$cycloalkyl substituted by from 0 to 3 substituents R$^6$, and each R$^6$ is independently chosen from the group consisting of hydrogen, C$_{1-6}$alkyl and C$_{3-8}$cycloalkyl;

wherein each E is independently chosen from the group consisting of a single bond, —CH$_2$NHC(O)—, —CH$_2$N(CH$_3$)C(O)—, —C(CH$_3$)HNHC(O)—, —C(CH$_3$)HN(CH$_3$)C(O)—, —C(CH$_3$)$_2$NHC(O)—, —C(CH$_3$)$_2$N(CH$_3$)C(O)—, —CH$_2$NHC(O)O—, —CH$_2$N(CH$_3$)C(O)O—, —C(CH$_3$)HNHC(O)O—, —C(CH$_3$)HN(CH$_3$)C(O)O—, —C(CH$_3$)$_2$NHC(O)O—, —C(CH$_3$)$_2$N(CH$_3$)C(O)O—,

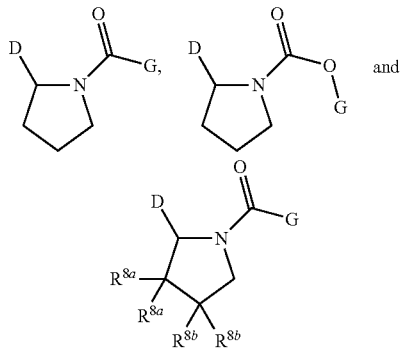

where one of R$^{8a}$ and R$^{8b}$ is —OH or fluorine;

wherein each G is independently chosen from the group consisting of
(a) hydrogen,
(b) —CN,
(c) C$_{1-5}$alkyl having 1 to 3 substituents R$^{11}$,
each R$^{11}$ is independently chosen from the group consisting of —OH, —NH$_2$, —NCH$_3$H, —N(CH$_3$)$_2$, —N(CH$_2$CH$_3$)$_2$, =NH, =NCH$_3$, —C(O)H, —C(O)OH, —C(O)CH$_3$, —C(O)OCH$_3$, —NHC(O)H, —NHC(O)OH, —NHC(O)CH$_3$, —NHC(O)OCH$_3$, cyclopropyl, cyclobutyl, cyclopentyl, cyclohexyl, pyranyl, pyrrolidinyl, piperidinyl, oxacyclopentyl, and oxacyclohexyl, phenyl, pyridinyl, pyrimidinyl and pyrrolyl, where
the cyclopropyl, cyclobutyl, cyclopentyl, cyclohexyl, pyranyl, pyrrolidinyl, piperidinyl, oxacyclopentyl and oxacyclohexyl are substituted by from 0 to 2 substitutents R$^{12}$ on N or C atoms, and each R$^{12}$ is independently selected from the group consisting of hydrogen, halogen, carboxy, C$_{1-6}$alkyl, —O—C$_{1-6}$alkyl and —S—C$_{1-6}$alkyl; and
the phenyl, pyridinyl, pyrimidinyl and pyrrolyl are substituted by from 0 to 3 substituents R$^{13}$ on N or C atoms, and each R$^{13}$ is independently selected from the group consisting of hydrogen, halogen, C$_{1-6}$alkyl and 3- to 8-membered cycloalkyl containing from 0 to 3 heteroatoms independently chosen from the group consisting of N, O and S,
(d) cyclopropyl, cyclobutyl, cyclopentyl, cyclohexyl, pyranyl, pyrrolidinyl, piperidinyl, oxacyclopentyl and oxacyclohexyl having from 0 to 3 substitutents R$^{10}$ on N or C atoms, the R$^{10}$ independently selected from the group consisting of hydrogen, halogen, carboxy, C$_{1-6}$alkyl, —O—C$_{1-6}$alkyl, —S—C$_{1-6}$alkyl, phenyl and benzyl, and
(e) aryl ring systems G' chosen from the group consisting of: phenyl, pyridinyl and 9-membered bicyclic ring systems containing from 0 to 2 heteroatoms independently chosen from the group consisting of N and O. In all aspects of this embodiment, all other groups are as provided in the general formula above.

In another embodiment of the invention, the compound of the invention is selected from the exemplary species depicted in Examples 1 through 215 shown below, or pharmaceutically acceptable salts thereof.

In another embodiment of the invention, for the compounds of formula (I), variables

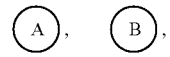

D, E, G, R$^1$, R$^2$, u, v, R$^3$, R$^{3a}$, R$^4$, R$^{4a}$, R$^5$, R$^6$, R$^7$, I, J, R$^{8a}$, R$^{8b}$, R$^{8c}$, R$^9$, R$^{10}$, R$^{10a}$, R$^{11}$, R$^{12}$, R$^{13}$, R$^{14}$, W, R$^w$, V and R$^v$, are selected independently from each other.

Other embodiments of the present invention include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a compound of formula (I) and (ii) a second therapeutic agent selected from the group consisting of HCV antiviral agents, immunomodulators, and anti-infective agents; wherein the compound of formula (I) and the second therapeutic agent are each employed in an amount that renders the combination effective for inhibiting HCV NS5A activity, or for treating HCV infection and/or reducing the likelihood or severity of symptoms of HCV infection, or for inhibiting HCV viral replication and/or HCV viral production in a cell-based system.

(e) The combination of (d), wherein the HCV antiviral agent is an antiviral selected from the group consisting of HCV protease inhibitors and HCV NS5B polymerase inhibitors.

(f) A method of inhibiting HCV NS5A activity in a subject in need thereof, which comprises administering to the subject an effective amount of a compound of formula (I).

(g) A method of treating HCV infection and/or reducing the likelihood or severity of symptoms of HCV infection in a subject in need thereof, which comprises administering to the subject an effective amount of a compound of formula (I).

(h) The method of (g), wherein the compound of formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV viral replication and/or HCV viral production in a cell-based system, which comprises administering to the subject an effective amount of a compound of formula (I).

(k) The method of (j), wherein the compound of formula (I) is administered in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of HCV protease inhibitors and HCV NS5B polymerase inhibitors.

(m) A method of inhibiting HCV NS5A activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

(o) A method of inhibiting HCV viral replication and/or HCV viral production in a cell-based system, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (o) above are understood to include all embodiments of the compounds and/or salts, including such embodiments as result from combinations of embodiments.

The present invention also includes a compound of the present invention for use (i) in, (ii) as a medicament for, or (iii) in the preparation of a medicament for: (a) inhibiting HCV NS5A activity, or (b) treating HCV infection and/or reducing the likelihood or severity of symptoms of HCV infection, or (c) inhibiting HCV viral replication and/or HCV viral production in a cell-based system, or (d) use in medicine. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(o) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt, or may be present in the form of a solvate or hydrate as appropriate.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and tert-butyl, n- and isopropyl, ethyl and methyl. As another example, "$C_{1-4}$ alkyl" refers to n-, iso-, sec- and tert-butyl, n- and isopropyl, ethyl and methyl. Where indicated, "$C_0$" refers to hydrogen; thus, for example, "$C_{0-6}$ alkyl" (or "$C_0$-$C_6$ alkyl") refers to all of the hexyl alkyl and pentyl alkyl isomers as well as n-, iso-, sec- and tert-butyl, n- and isopropyl, ethyl, methyl and hydrogen. Alkyl groups may be substituted as indicated.

The term "halogenated" refers to a group or molecule in which a hydrogen atom has been replaced by a halogen. Similarly, the term "haloalkyl" refers to a halogenated alkyl group. The term "halogen" (or "halo") refers to atoms of fluorine, chlorine, bromine and iodine (alternatively referred to as fluoro, chloro, bromo, and iodo), preferably fluorine.

The term "alkoxy" refers to an "alkyl-O—" group, where alkyl is as defined above. Alkoxy groups may be substituted as indicated.

The term "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group, where cycloalkyl is as defined above. Cycloalkyl groups may be substituted as indicated.

The term "aryl" (or "aryl ring system") refers to aromatic mono- and poly-carbocyclic or heterocyclic ring systems wherein the individual carbocyclic rings in the polyring systems are fused or attached to each other via a single bond. As used herein, the term aryl includes aromatic mono- and poly-carbocyclic ring systems that include from 0 to 4 heteroatoms (non-carbon atoms) that are independently chosen from N, O and S. Suitable aryl groups include phenyl, naphthyl, biphenylenyl, pyridinyl, pyrimidinyl and pyrrolyl, as well as those discussed below. Aryl groups may be substituted as indicated. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "carbocycle" (and variations thereof such as "carbocyclic") as used herein, unless otherwise indicated, refers to (i) a $C_5$ to $C_7$ monocyclic, saturated or unsaturated ring, or (ii) a $C_8$ to $C_{10}$ bicyclic saturated or unsaturated ring system. Each ring in (ii) is either independent of, or fused to, the other ring, and each ring is saturated or unsaturated. Carbocycle groups may be substituted as indicated. When the carbocycles contain one or more heteroatoms independently chosen from N, O and S, the carbocycles may also be referred to as "heterocycles," as defined below. The carbocycle may be attached to the rest of the molecule at any carbon or nitrogen atom that results in a stable compound. The fused bicyclic carbocycles are a subset of the carbocycles; i.e., the term "fused bicyclic carbocycle" generally refers to a $C_8$ to $C_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. Carbocycle ring systems may include, where appropriate, an indication of the variable to which a particular ring atom is attached. Unless otherwise indicated, substituents to the ring systems can be attached to any ring atom, provided that such attachment results in formation of a stable ring system.

Unless indicated otherwise, the term "heterocycle" (and variations thereof such as "heterocyclic" or "heterocyclyl") broadly refers to (i) a stable 5- to 7-membered, saturated or unsaturated monocyclic ring, or (ii) a stable 8- to 10-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results. Representative examples include pyranyl, piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl). Unless expressly stated to the contrary, the term "heteroaryl ring system" refers to aryl ring systems, as defined above, that include from 1 to 4 heteroatoms (non-carbon atoms) that are independently chosen from N, O and S. In the case of substituted heteraromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl. Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl and benzo-1,3-dioxolyl.

Unless otherwise specifically noted as only "substituted", alkyl, cycloalkyl, and aryl groups are not substituted. If substituted, preferred substituents are selected from the group that includes, but is not limited to, halo, $C_1$-$C_{20}$ alkyl, —$CF_3$, —$NH_2$, —$N(C_1$-$C_6$ alkyl$)_2$, —$NO_2$, oxo, —CN, —$N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_1$-$C_6$ alkyl)OC(O) NH—, aryl, aralkyl, heteroaryl, heterocycloalkyl, halo-aryl, halo-aralkyl, halo-heterocycle and halo-heterocycloalkyl.

Unless expressly stated to the contrary, all ranges cited herein are inclusive. For example, a heteroaryl ring described as containing from "0 to 3 heteroatoms" means the ring can contain 0, 1, 2, or 3 heteroatoms. It is also to be understood that any range cited herein includes within its scope all of the sub-ranges within that range. The oxidized forms of the heteroatoms N and S are also included within the scope of the present invention.

When any variable (for example, $R^1$ or $R^3$) occurs more than one time in any constituent or in formula (I) or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom provided such substitution is chemically allowed and results in a stable compound. A "stable" compound is a compound that can be prepared and isolated and that has a structure and properties that remain or can be caused to remain essentially unchanged for a period of time sufficient to allow use of the compound for the purposes described herein (e.g., therapeutic or prophylactic administration to a subject).

As used herein, the term "compound" is intended to encompass chemical agents described by generic formula (I) in all forms, including hydrates and solvates of such chemical agents.

In the compounds of generic formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula (I). For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula (I) can be prepared without undue experimentation by conventional techniques well known to those skilled in the art or by processes analogous to those described in the Schemes and Examples herein using appropriate isotopically-enriched reagents and/or intermediates.

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula (I) is a reference to the compound per se, or to any one of its tautomers per se, or to mixtures of two or more tautomers.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product that results, directly or indirectly, from combining the specified ingredients.

By "pharmaceutically acceptable" is meant that the ingredients of the pharmaceutical composition must be compatible with each other and not deleterious to the recipient thereof.

The terms "subject" (alternatively referred to herein as "patient") as used herein, refer to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5A and thereby elicit the response being sought (i.e., an "inhibition effective amount"). When the active compound (i.e., active ingredient) is administered as the salt, references to the amount of active ingredient are to the free acid or free base form of the compound.

It is understood that claimed compounds cause inhibition in replicon assay testing. Thus, compounds described herein are useful for inhibiting HCV replication, specifically the NS5A protein. Compounds described herein have different uses, including the prevention or treatment of one or more of the symptoms of HCV infection, the inhibition of HCV viral replication and/or HCV viral production, and/or as pharmaceutical composition ingredients.

The compounds of this invention are useful in the preparation and execution of screening assays for antiviral compounds. For example, the compounds of this invention are useful for identifying resistant HCV replicon cell lines harboring mutations within NS5A, which are excellent screening tools for more powerful antiviral compounds. Furthermore, the compounds of this invention are useful in establishing or determining the binding site of other antivirals to the HCV replicase.

For the purposes of inhibiting HCV NS5A protein, treating HCV infection and/or reducing the likelihood or severity of symptoms of HCV infection and inhibiting HCV viral replication and/or HCV viral production, the compounds of the present invention, optionally in the form of a salt or a hydrate, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, $18^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV replicon activity, inhibiting HCV viral replication and/or HCV viral production, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. The combination of peginterferon-α and ribaviron represents the current Standard of Care for HCV treatment. The combination of one or more compounds of the present invention with the Standard of Care for HCV treatment, pegylated-interferon and ribaviron is specifically contemplated as being encompassed by the present invention. Interferon-α includes, but is not limited to, recombinant interferon-α2a (such as ROFERON interferon), pegylated interferon-α2a (PEGASYS), interferon-α2b (such as INTRON-A interferon), pegylated interferon-α2b (PEGINTRON), a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in International Patent Application Publication WO 01/60379. In accordance with the method of the present invention, the individual components of the combination can be administered separately at different times during the course of therapy or concurrently in divided or single combination forms.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as those disclosed in International Patent Application Publications WO 97/41211, WO 01/00622 and WO 00/25780; or mycophenolate mofetil. See Anthony C. Allison and Elsie M. Eugui, *Immunosuppressive and Other Anti-Rheumatic Activities of Mychophenolate Mofetil*, 44 (SUPPL.) AGENTS ACTION 165 (1993).

For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in Rogers E. Harry-O'Kuru et al., *A Short, Flexible Route to 2'-C-Branched Ribonucleosides*, 62 J. ORG. CHEM. 1754-59 (1997); Michael S. Wolfe and Rogers E. Harry-O'Kuru, *A Consise Synthesis of 2'-C-Methylribonucleosides*, 36 TET. LETT. 7611-14 (1995); U.S. Pat. No. 3,480,613; and International Patent Application Publications WO 01/90121, WO 01/92282, WO 02/32920, WO 04/002999, WO 04/003000 and WO 04/002422; the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Exemplary substrate and non-substrate based inhibitors of HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116, WO 02/48172, WO 2008/057208 and WO 2008/057209, in British Patent No. GB 2 337 262, and in U.S. Pat. Nos. 6,323,180, 7,470,664, and 7,012,066 and in Ashok Arasappan et al., *Discovery of Narlaprevir (SCH 900518): A Potent, Second Generation HCV NS3 Serine Protease Inhibitor*, ACS MED. CHEM. LETT. DOI: 10.1021/m19000276 (Feb. 15, 2010).

The compounds of the present invention may also be combined for the treatment of HCV infection with nucleosides having anti-HCV properties, such as those disclosed in International Patent Application Publications WO 02/51425, WO 01/79246, WO 02/32920, WO 02/48165 and WO 2005/003147 (including R1656, (2'R)-2'-deoxy-2'-fluoro-2'-C-methylcytidine, shown as compounds 3-6 on page 77); WO 01/68663; WO 99/43691; WO 02/18404 and WO 2006/021341, and U.S. Patent Application Publication US 2005/0038240, including 4'-azido nucleosides such as R1626, 4'-azidocytidine; U.S. Patent Application Publications US 2002/0019363, US 2003/0236216, US 2004/0006007, US 2004/0063658 and US 2004/0110717; U.S. Pat. Nos. 7,105,499, 7,125,855, 7,202,224; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. Nos. 6,777,392, 7,105,499, 7,125,855, 7,202,224 and U.S. Patent Application Publications US 2004/0067901 and US 2004/0110717; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, nucleoside HCV NS5B polymerase inhibitors that are used in combination with the present HCV inhibitors are selected from the following compounds: 4-amino-7-(2-C-methyl-β-D-arabinofuranosyl)-7H-pyrrolo [2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]

pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in U.S. Patent Application Publications US 2006/0100262 and US 2009-0048239; International Patent Application Publications WO 01/77091, WO 01/47883, WO 02/04425, WO 02/06246, WO 02/20497, WO 2005/016927 (in particular JTK003), WO 2004/041201, WO 2006/066079, WO 2006/066080, WO 2008/075103, WO 2009/010783 and WO 2009/010785; the content of each is incorporated herein by reference in its entirety.

In one embodiment, non-nucleoside HCV NS5B polymerase inhibitors that are used in combination with the present HCV NS5A inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The HCV replicons and NS5A inhibitory activity of the present compounds may be tested using assays known in the art. HCV inhibitors, such as those described in the Examples herein have activities in genotype 1b, 2a and 1a replicon assays of from about 1 pM to about 1 µM. The assay is performed by incubating a replicon harboring cell-line in the presence of inhibitor for a set period of time and measuring the effect of the inhibitor on HCV replicon replication either directly by quantifying replicon RNA level, or indirectly by measuring enzymatic activity of a co-encoded reporter enzyme such as luciferase or β-lactamase. By performing a series of such measurements at different inhibitor concentrations, the effective inhibitory concentration of the inhibitor ($EC_{50}$ or $EC_{90}$) is determined. See Jan M. Vrolijk et al., *A replicons-based bioassay for the measurement of interferons in patients with chronic hepatitis C,* 110 J. VIROLOGICAL METHODS 201 (2003). Such assays may also be run in an automated format for high through-put screening. See Paul Zuck et al., *A cell-based β-lactamase reporter gene assay for the identification of inhibitors of hepatitis C virus replication,* 334 ANALYTICAL BIOCHEMISTRY 344 (2004).

The present invention also includes processes for making compounds of formula (I). The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

General Schemes

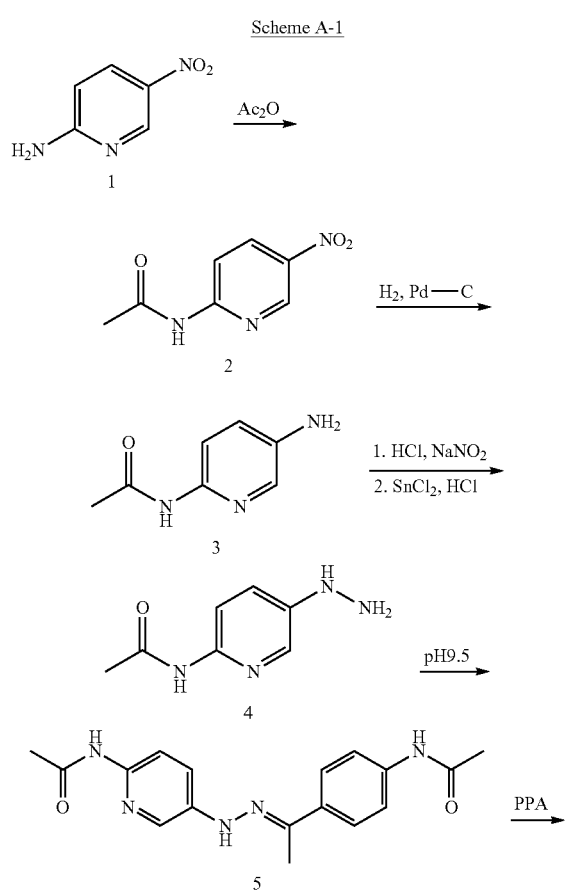

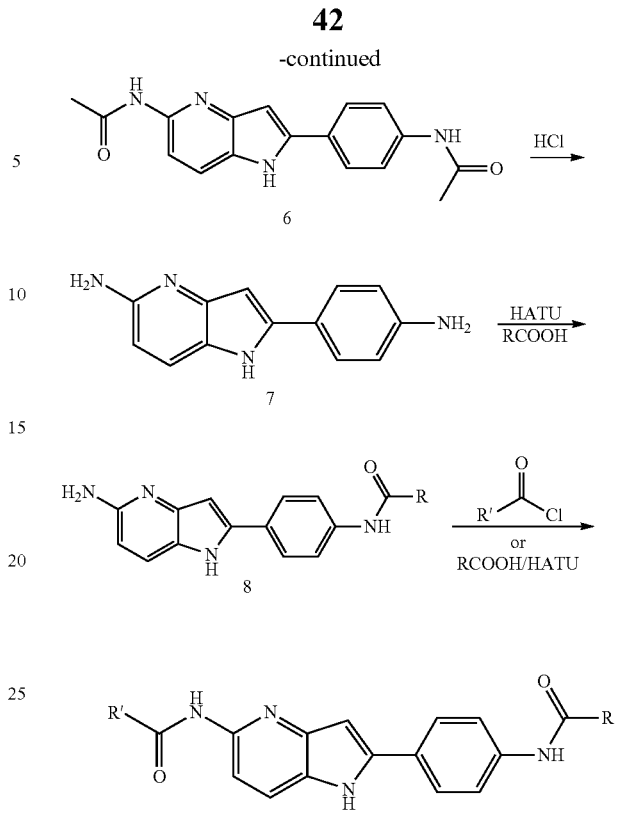

The synthesis of analogs containing the 4-azaindole core can be accomplished starting from a suitably protected 2-amino-5-nitropyridine 2, which can then be reduced by catalytic hydrogenation in order to convert the resulting free amino group to its hydrazine by the action of $NaNO_2$ and $SnCl_2$. The resulting pyridylhydrazine can be condensed with a ketone then subjected to Fisher indole cyclization conditions to afford the indole 6. Acidic deprotection of the acetyl groups can be accomplished by using a strong acid to liberate the diamine, which can be selectively coupled on the more reactive aniline nitrogen using standard coupling agents, such as HATU. The aminopyridine group can then be acylated with a reagent, such as acetyl chloride or a carboxylic acid, in the presence of an amide bond-forming reagent.

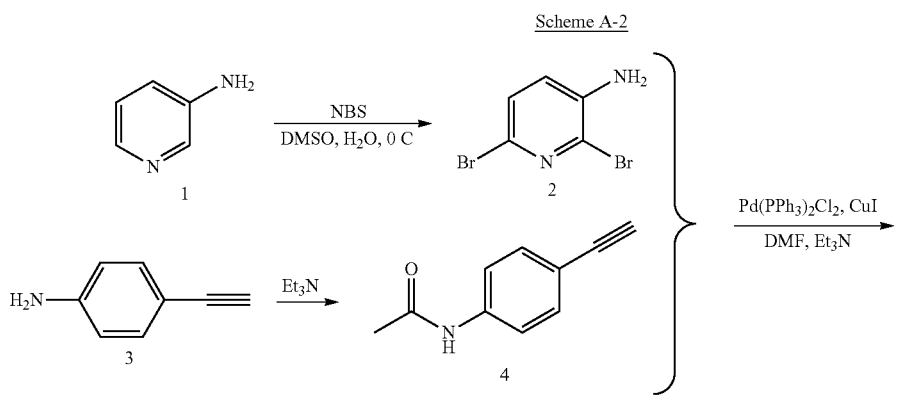

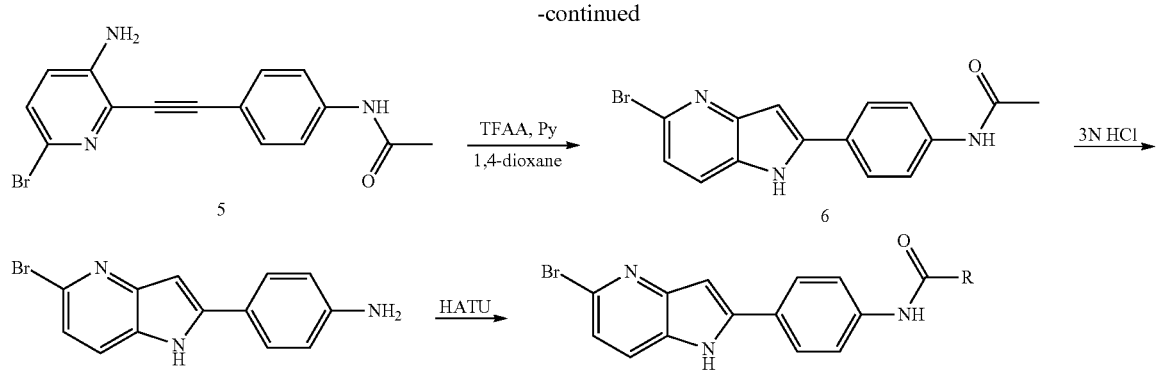

2-Bromo-3-aminopyridines can be coupled to a terminally substituted alkyne using standard Sonagashira coupling procedures to give intermediates 5, which can undergo TFAA-mediated cyclization to provide the 4-azaindole compounds 6. Protecting groups can be removed with a strong acid, such as aqueous HCl, and the resulting amine can be acylated using an appropriately substituted carboxylic acid and an amide bond forming reagent, such as HATU.

Scheme B

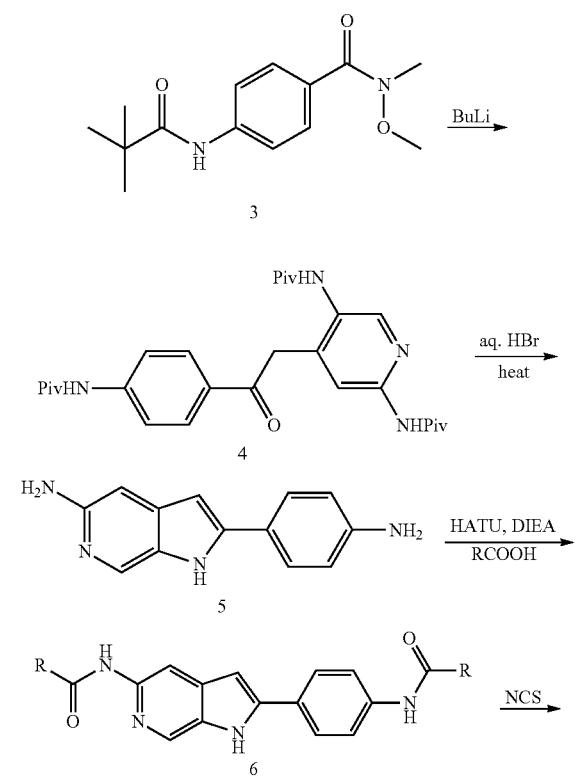

-continued

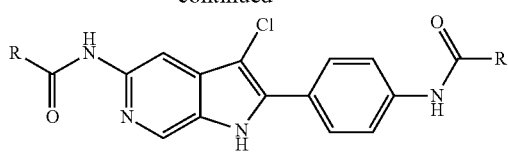

The synthesis of scaffolds B containing a 6-azaindole core can be accomplished by the metallation of the 4-methylpyridine analog 2 with a strong base, such as BuLi, and quenching the resulting anion with the acylating agent, such as 3. Intermediate 4 can be globally deprotected by the action of a strong acid, such as HBr, to give the diamino azaindole structure 5. Both amino groups can be acylated using an appropriately substituted carboxylic acid and an amide bond forming reagent, such as HATU. Compounds 6 can be further functionalized at the C-3 indole position with electrophiles, such as NCS.

Scheme C

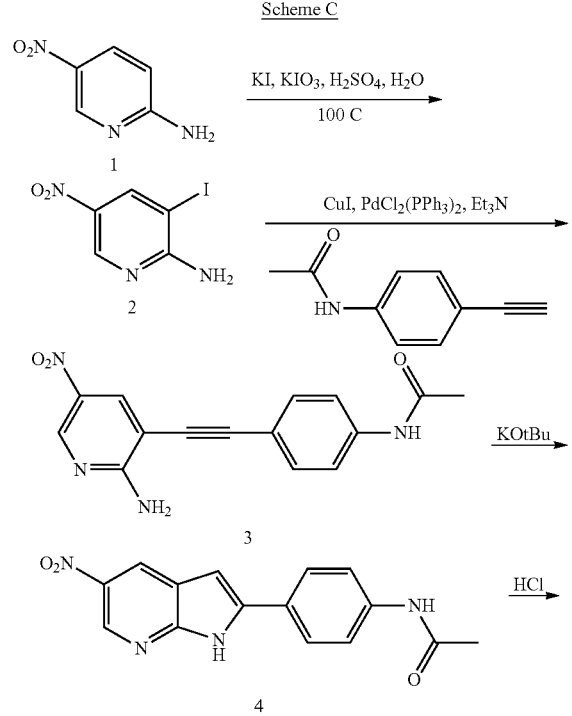

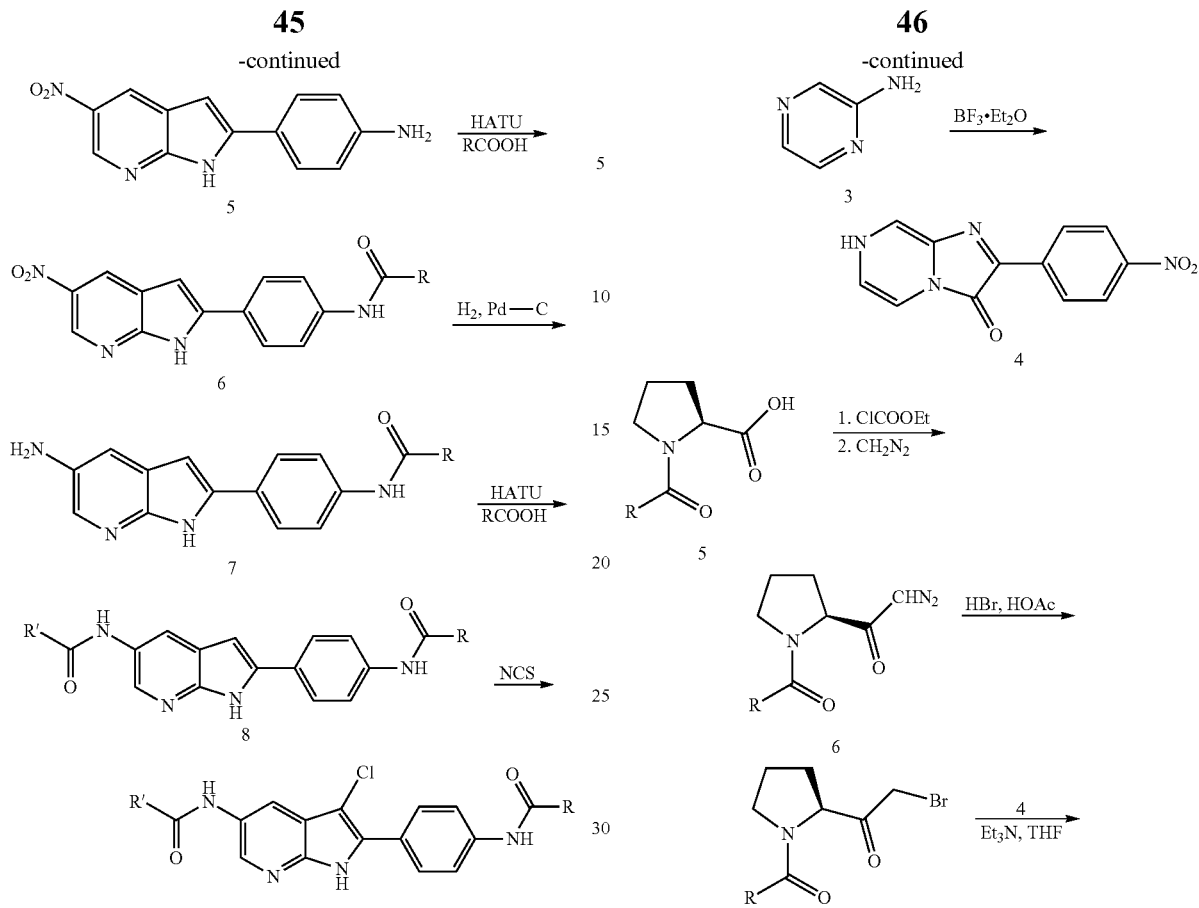

Iodo aminopyridines 2 can be coupled to a terminally substituted alkyne using standard Sonagashira coupling procedures to give intermediates 5, which can undergo a base-mediated cyclization using a reagent, such as KOtBu, to provide the 7-azaindole compounds 4. Protecting groups can be removed with a strong acid, such as aqueous HCl, and the resulting amine can be acylated using an appropriately substituted carboxylic acid and an amide bond forming reagent, such as HATU. Compounds 6 can then be reduced using hydrogen and a catalyst then coupled a second time with a carboxylic acid and HATU to provide 8. Treatment of 8 with an electrophilic agent, such as NCS, provides the desired compounds.

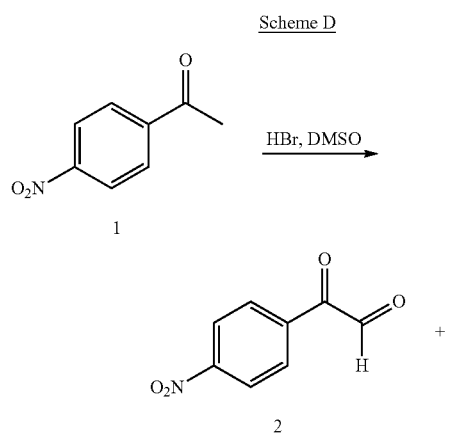

Scheme D

Compounds in the D series can be synthesized by reacting dicarbonyl intermediate 2 with a 2-aminopyrimidine derivative in the presence of a Lewis acid, such as boron trifluoride etherate. The resulting heterocycle can be alkylated with a bromoketone analog of an amino acid, such as proline, in the presence of a tertiary amine base. The nitro group can be reduced, and the resulting aniline can be acylated using an appropriately substituted carboxylic acid and an amide bond forming reagent, such as HATU, to give the final products.

Scheme E-1
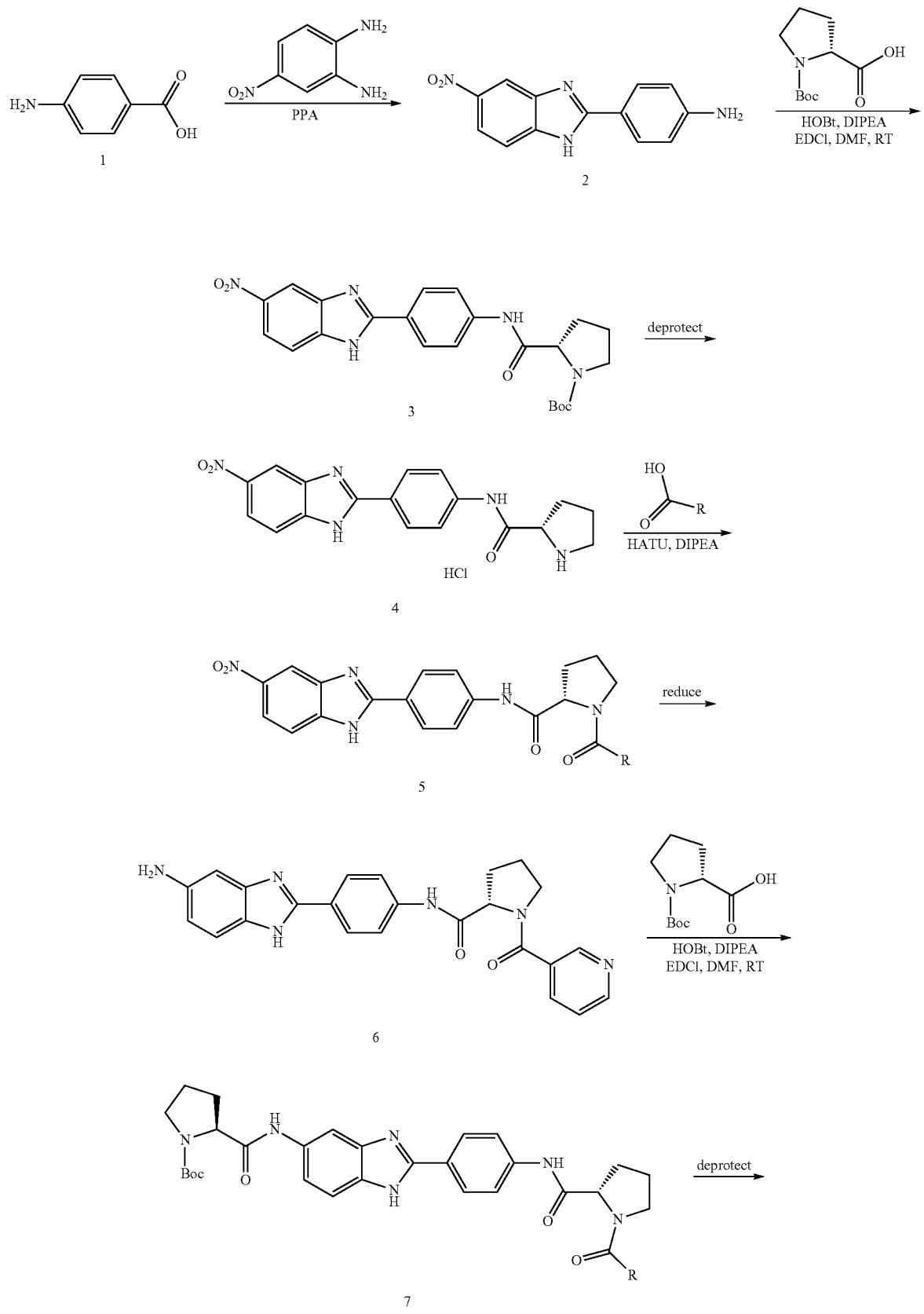

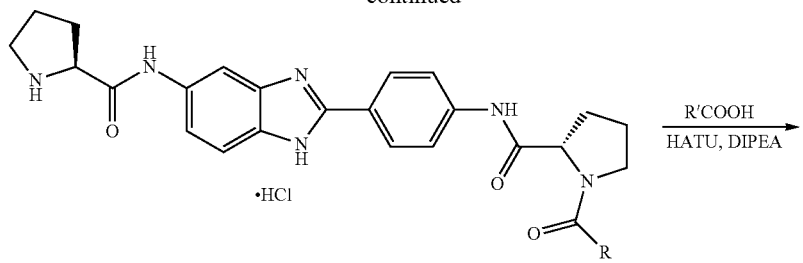

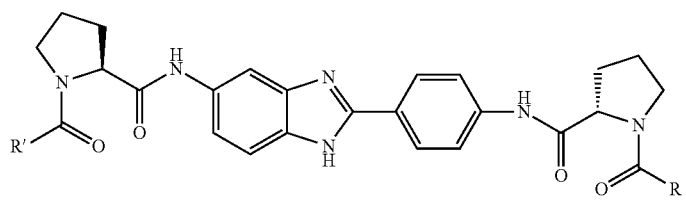

Scaffold E-1 can be prepared by the condensing a benzoic acid derivative, such as 1, with a phenylenediamine counterpart 2 in the presence of a dehydrating agent, such as polyphosphoric acid. The resulting aniline can be acylated using an appropriately substituted carboxylic acid, such as N-Boc-L-proline, and an amide bond-forming reagent, such as HATU, and can then be subjected to acidic conditions to remove the Boc group. Compounds 4 can be coupled again with an appropriately substituted carboxylic acid and an amide bond-forming reagent, such as HATU. The nitro group in 5 can be reduced under catalytic hydrogenating conditions, and the resulting aniline can be further coupled with various amines to give the target compounds.

Scheme E-2

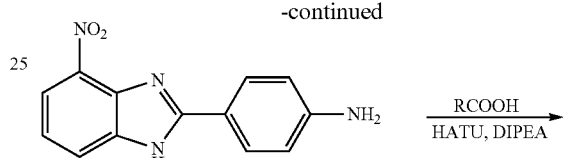

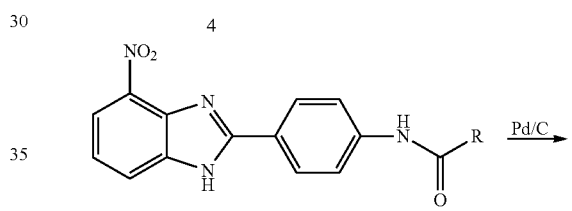

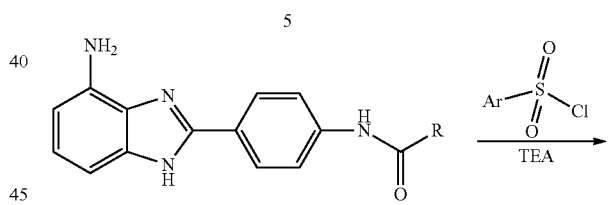

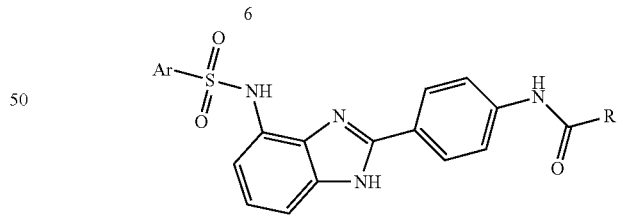

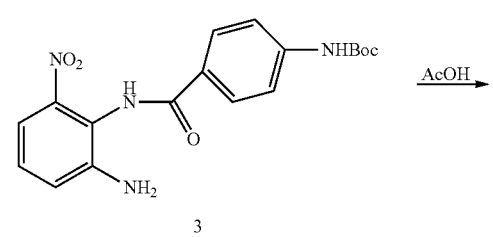

Scaffold E-2 can be prepared by the reacted with a benzoic acid derivative with a phenylenediamine analog and an amide bond-forming reagent, such as HATU, to give amides 3, which can be cyclodehydrated by heating with a reagent, such as HOAc. The resulting aniline can be acylated using an appropriately substituted carboxylic acid and an amide bond-forming reagent, such as HATU, to give intermediates 5. The nitro group can be reduced under catalytic hydrogenating conditions, and the resulting aniline can be sulfonylated with an appropriately substituted sulfonyl chloride and a tertiary amine base to give the targets.

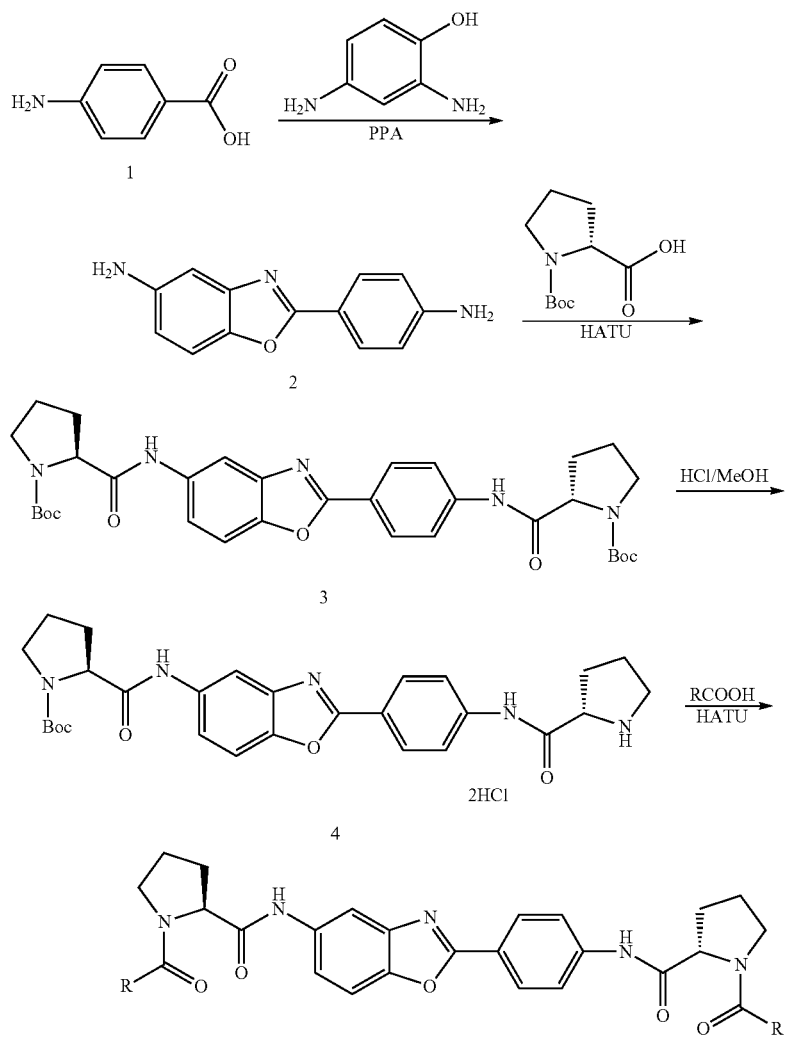

Scaffold F can be prepared by the condensing a benzoic acid derivative, such as 1, with an amino phenol counterpart 2 in the presence of a dehydrating agent, such as polyphosphoric acid. The resulting aniline can be acylated using an appropriately substituted carboxylic acid, such as N-Boc-L-proline, and an amide bond-forming reagent, such as HATU, and can then be subjected to acidic conditions to remove the Boc group. Compounds 4 can be coupled again with an appropriately substituted carboxylic acid and an amide bond-forming reagent, such as HATU.

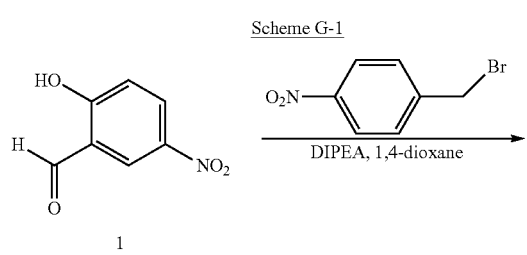

-continued

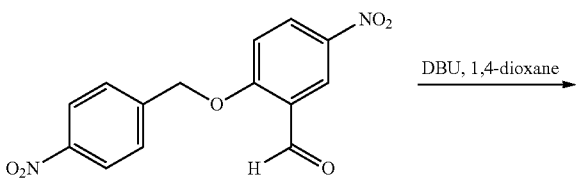

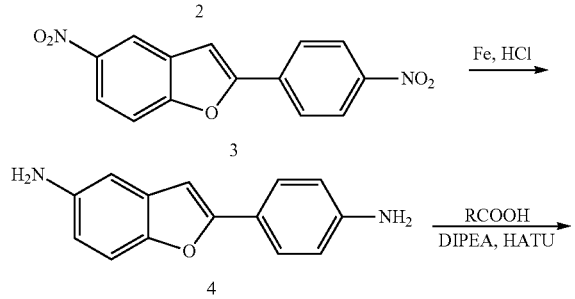

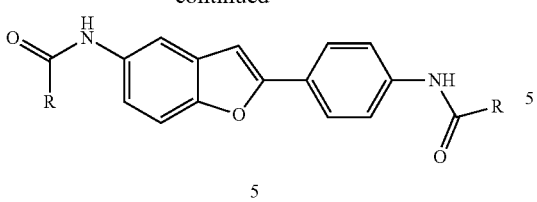

Compounds having the benzofuran structure G can be prepared by reacting an appropriately substituted salicylaldehyde with a benzyl halide, such as 4-nitrobenzyl bromide, in the presence of a tertiary amine base to give ethers 2. The benzylic ethers can be treated with a base, such as DBU, and heated to elevated temperatures to effect cyclization to the benzofurans 3. The nitro groups in 3 can be reduced under catalytic hydrogenating conditions, and the resulting anilines can be coupled with various carboxylic acids to give the target compounds G-1.

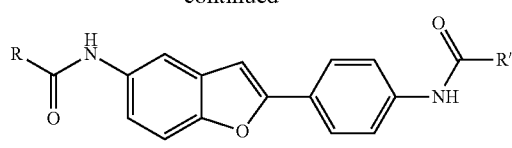

For differentially substituted compounds (R, R') having the benzofuran structure G, the synthesis can be modified by reacting an appropriately substituted bromo salicylaldehyde with a benzyl halide, such as 4-nitrobenzyl bromide, in the presence of a tertiary amine base to give ethers 2. The benzylic ethers can be treated with a base, such as DBU, and heated to elevated temperatures to effect cyclization to the benzofurans 3. The aryl bromide can be converted to the aryl amine by reaction with LHMDS and a palladium catalyst to provide 4, which can be coupled to an appropriately substituted carboxylic acid to give 5. The nitro group in 5 can be reduced under catalytic hydrogenating conditions, and the resulting aniline can be coupled with a second carboxylic acid analog to give the target compounds G-2.

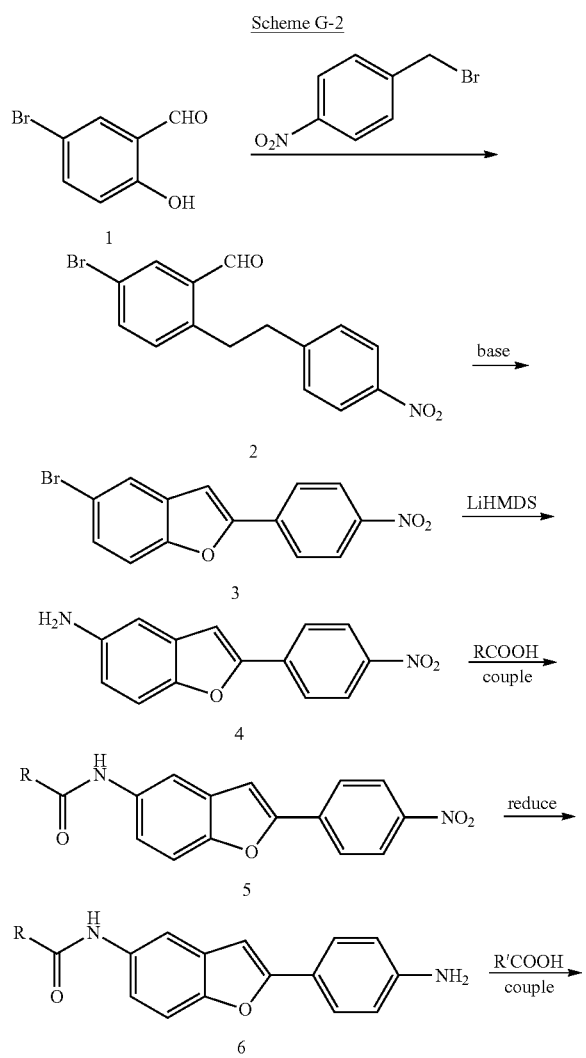

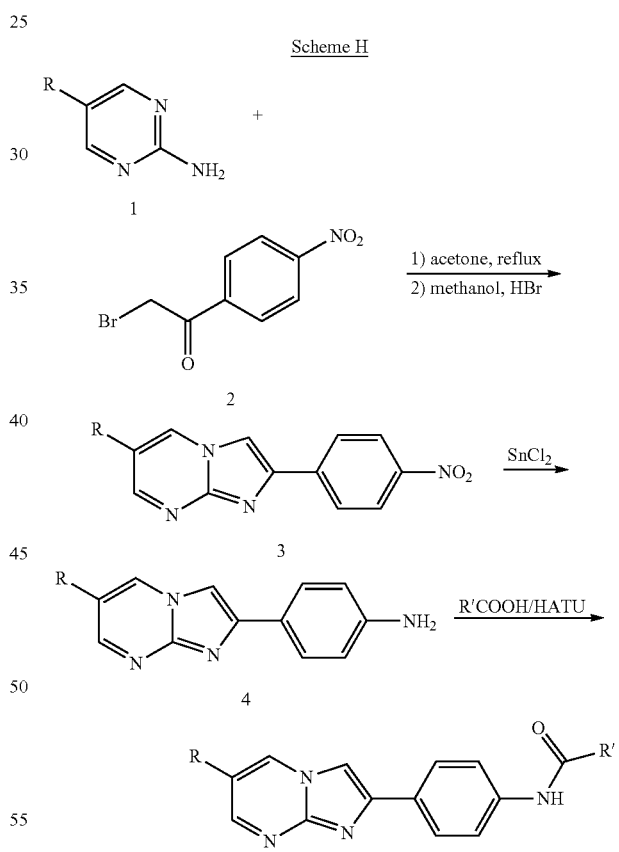

Appropriately substituted aminopyrimidines can be cyclodehydrated after acylation with an appropriately substituted ketone, such as 4'-nitro-2-bromobenzophenone, by heating in a solvent, such as MeOH, and an acid source, such as HBr. The resulting heterocyclic nitro compound can be converted to the aromatic amine by reduction with a reagent, such as $SnCl_2$. The final compounds H can be obtained by reacting 4 with an appropriately substituted carboxylic acid and an amide bond-forming reagent such as HATU.

Scheme I

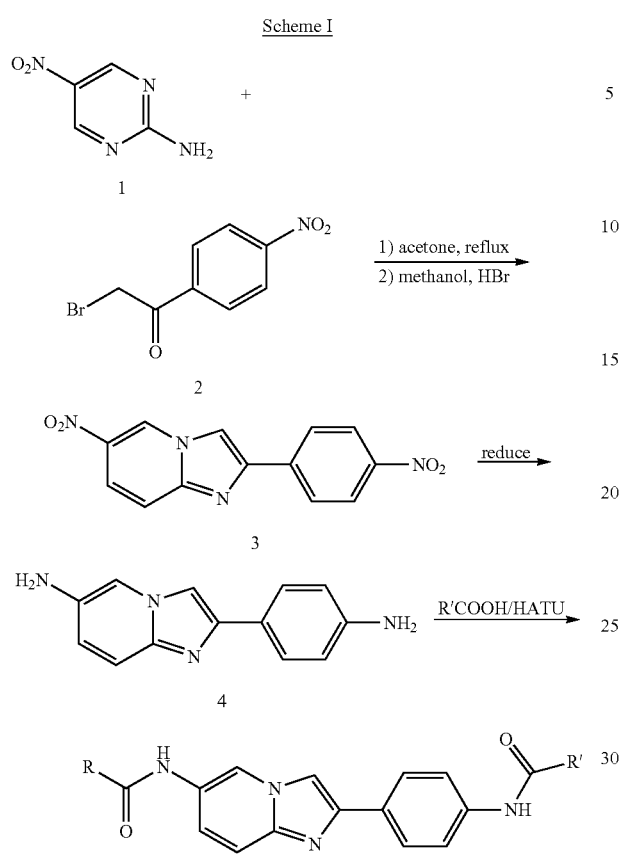

Compounds in scheme I can be prepared by reacting the appropriately substituted aminopyridine with 4'-nitro-2-bromobenzophenone by heating in a solvent, such as acetone, then effecting a cyclodehydration reaction using methanol and an acid source, such as HBr. The resulting heterocyclic nitro compound 3 can be converted to the aromatic amine by reduction with a reagent such as $SnCl_2$. The final compounds can be obtained by reacting 4 with an appropriately substituted carboxylic acid and an amide bond-forming reagent, such as HATU.

Scheme J

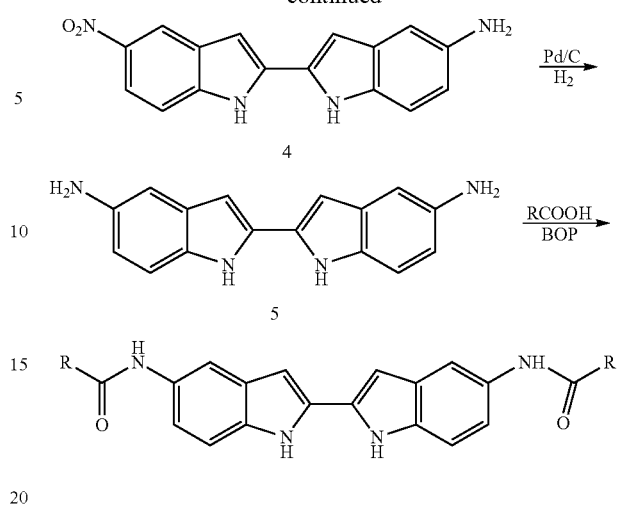

Compounds in scheme J can be prepared by coupling indole boronic acids with an appropriately substituted 2-bromoindole, such as 2, under standard Suzuki conditions. The protecting groups can be removed with HCl, and the nitro group in 4 can be reduced under catalytic hydrogenation conditions. The penultimate diamine can be coupled with an appropriately substituted carboxylic acid and an amide bond-forming reagent, such as BOP, reagent to give compounds with the targeted central scaffold.

Scheme K-1

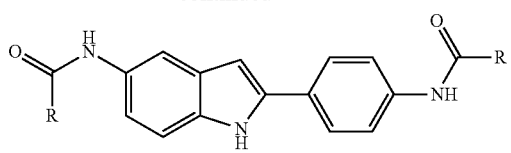

The synthesis of compounds with the indole core scaffold K can be prepared using standard Fisher indole synthesis protocol starting for an aryl hydrazine and a ketone such as 2. Conversion of the aryl bromide to the aryl amine 4 could be effected by the Pd-catalyzed reaction with LHMDS. The nitro group could be reduced and the diamine can be coupled with an appropriately substituted carboxylic acid and an amide bond-forming reagent, such as HATU, to give compounds with the targeted scaffold.

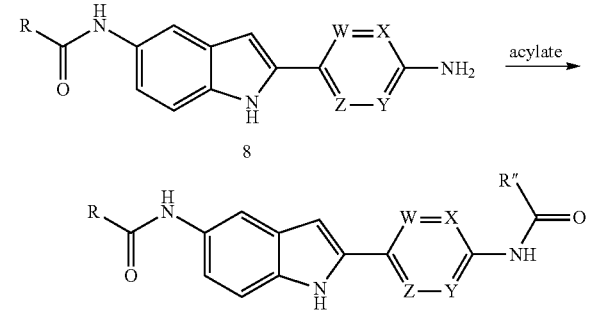

In an alternative procedure indoles K can be prepared starting from a suitably protected and substituted aminoindole 3. Lithiation and quenching with a boronate ester affords key intermediate 4, which can be coupled to an appropriately substituted aryl or heteroaryl halide to provide targets 5. The Boc groups can be removed with acid, and the resulting aniline can be coupled with an appropriately substituted carboxylic acid and an amide bond-forming reagent, such as HATU. The nitro group in 7 can be reduced and coupled in a second amide coupling reaction to give the desired compounds.

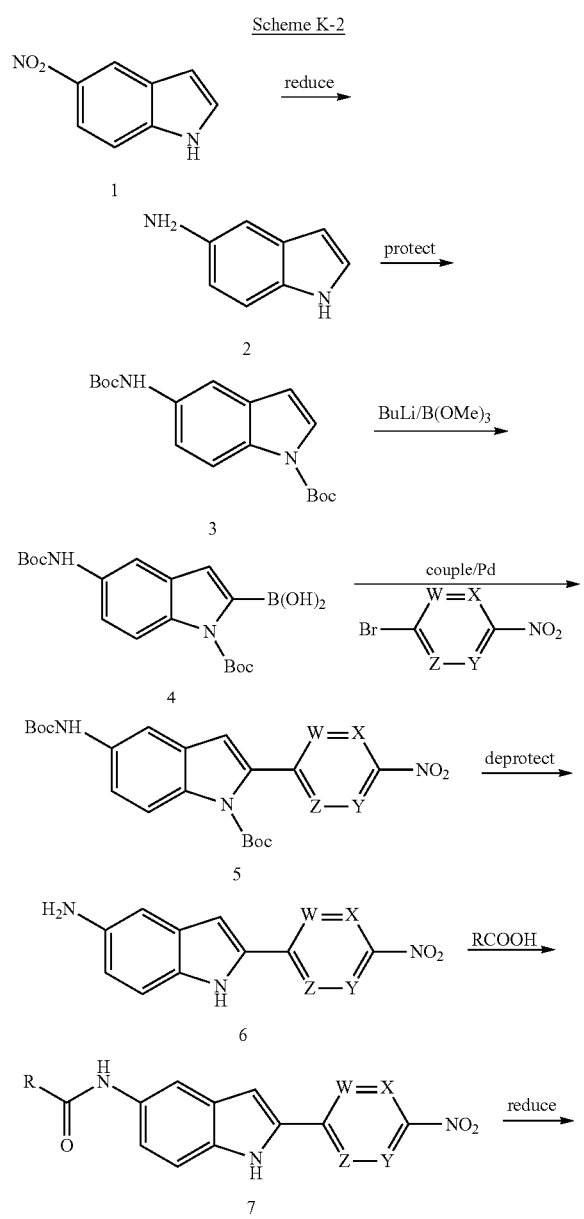

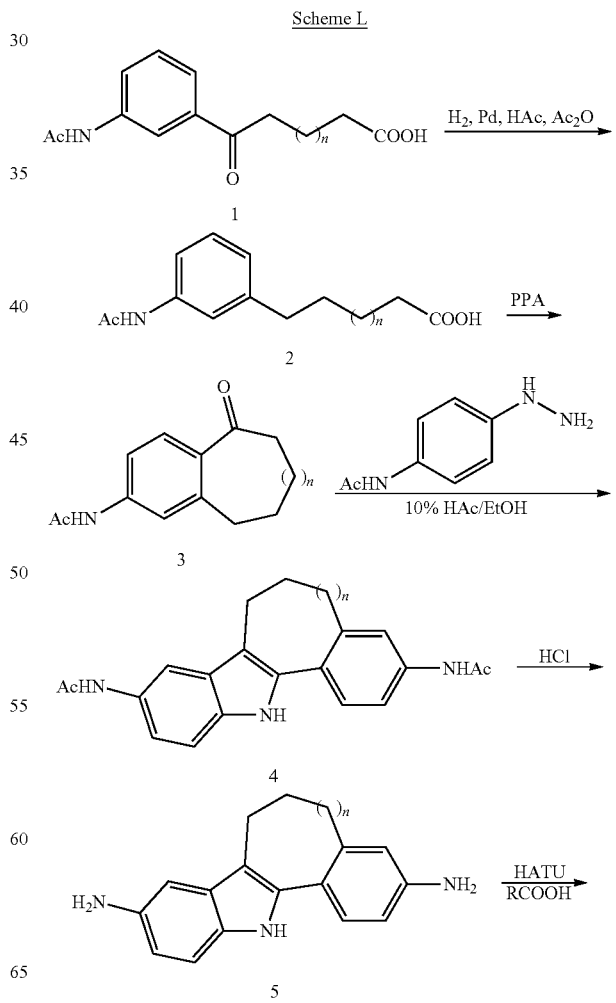

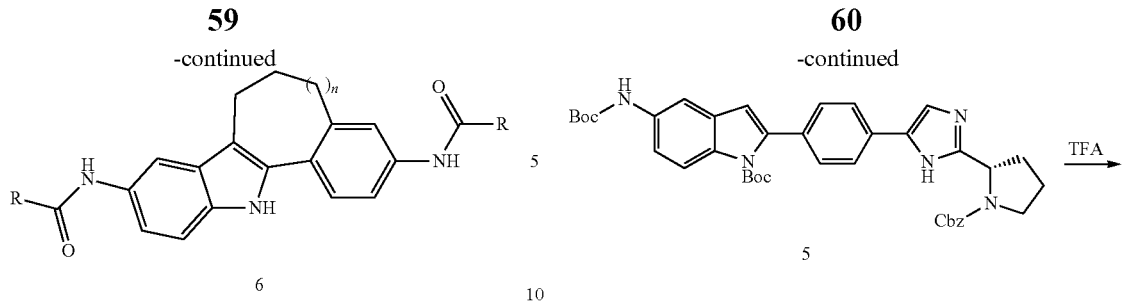

Tetracyclic indole scaffold L can be prepared as outline in the scheme above. Cyclization of a carboxylic acid derivative 2 with PPA can provide the ketones 3, which can participate in a Fischer indole reaction with an appropriately substituted phenylhydrazine to give 4. The acetamide groups can be deprotected under acidic conditions and the resulting aryl amines can be coupled with an appropriately substituted carboxylic acid and an amide bond-forming reagent, such as HATU, to give compounds with the targeted scaffold.

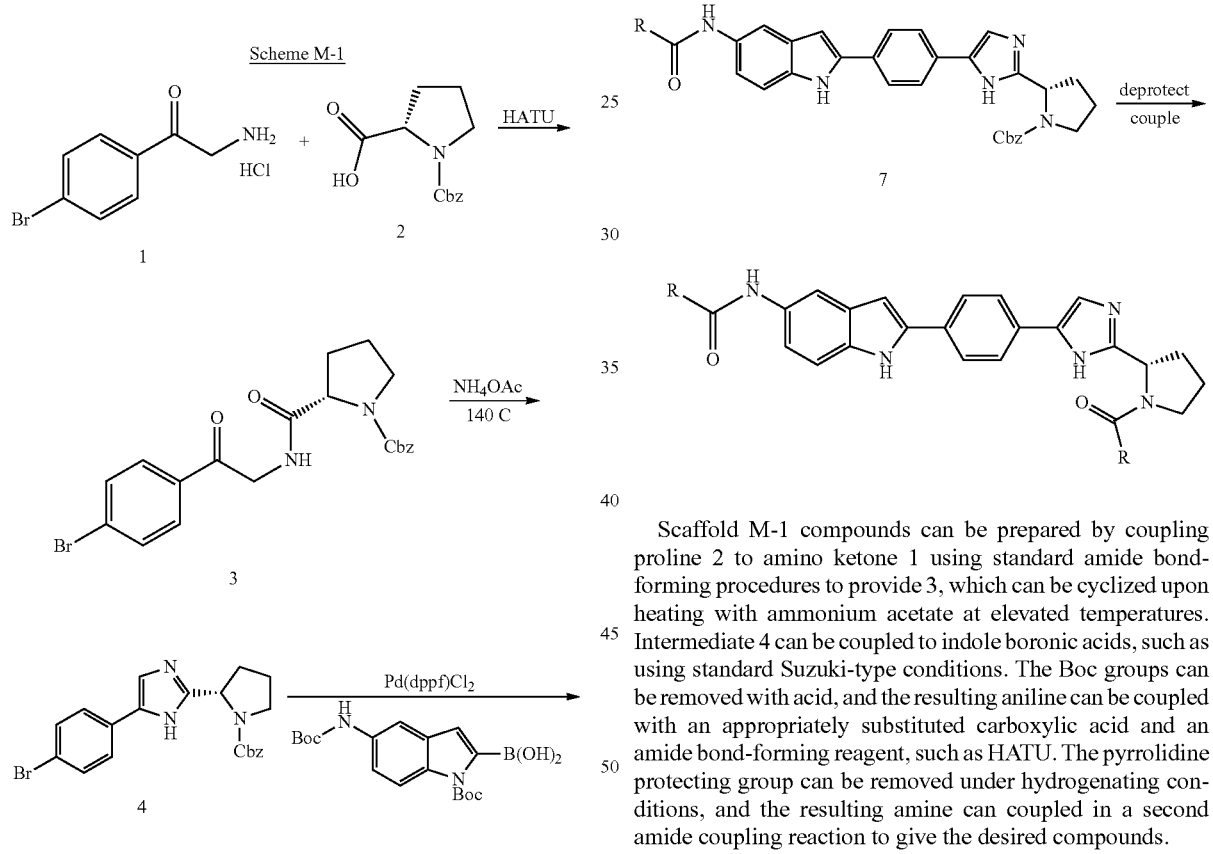

Scaffold M-1 compounds can be prepared by coupling proline 2 to amino ketone 1 using standard amide bond-forming procedures to provide 3, which can be cyclized upon heating with ammonium acetate at elevated temperatures. Intermediate 4 can be coupled to indole boronic acids, such as using standard Suzuki-type conditions. The Boc groups can be removed with acid, and the resulting aniline can be coupled with an appropriately substituted carboxylic acid and an amide bond-forming reagent, such as HATU. The pyrrolidine protecting group can be removed under hydrogenating conditions, and the resulting amine can coupled in a second amide coupling reaction to give the desired compounds.

Scheme M-2

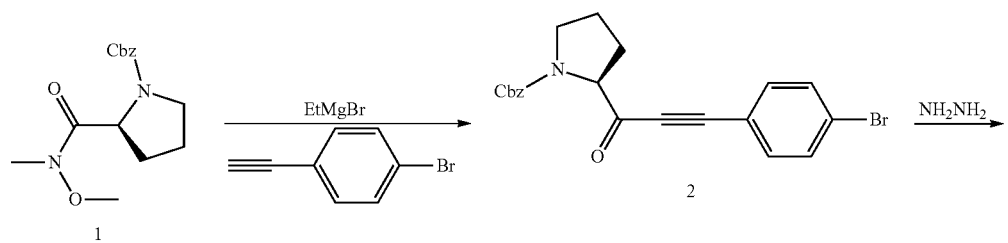

-continued

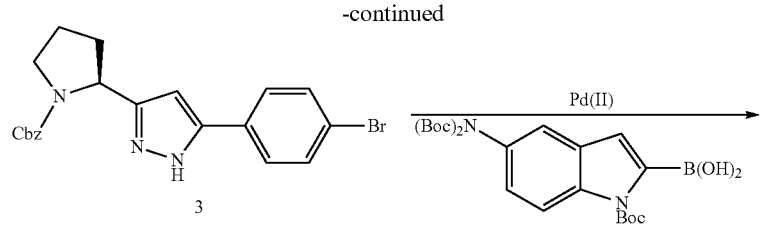
3

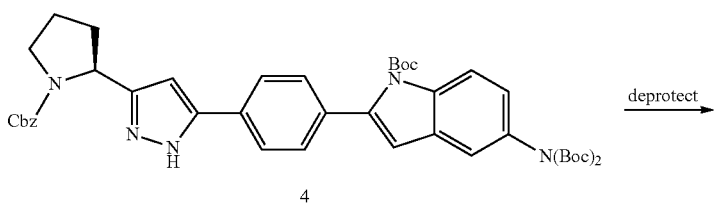
4

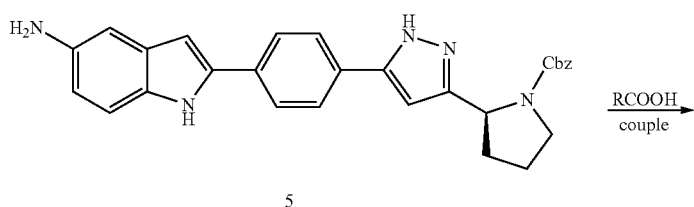
5

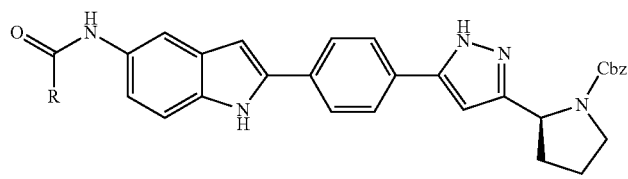
6

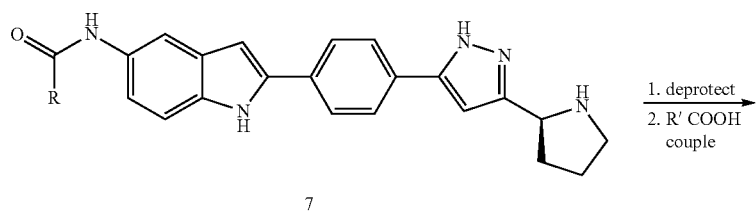
7

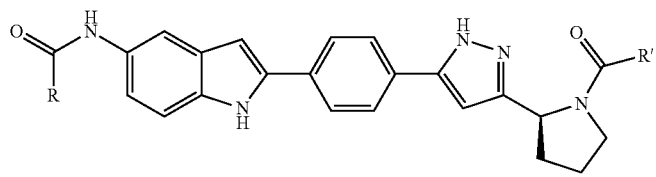

Scaffold M-2 compounds can be prepared by reacting proline 1 with an anion of 4-ethynylbenzene to give intermediate ketone 2, which can be cyclized with hydrazine. Intermediate 3 can be coupled to indole boronic acids, such as using standard Suzuki-type conditions. The Boc groups can be removed with acid and the resulting aniline can be coupled with an appropriately substituted carboxylic acid, and an amide bond-forming reagent such as HATU. The pyrrolidine protecting group can be removed under hydrogenating conditions, and the resulting amine can coupled in a second amide coupling reaction to give the desired compounds.

Scheme M-3

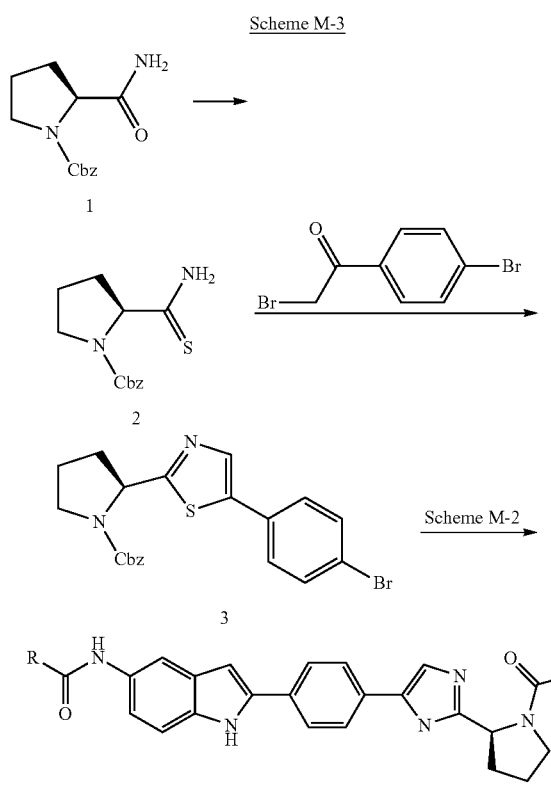

Thiazole analogs of scaffold M can be prepared from the cyclocondensation reaction of Z-proline thioamide 2 with an alpha-bromoacetophenone. Products 3 can be processed to the final compounds using methodology similar to that described in scheme M-2.

Scheme M-4 ketone 1 with an aromatic amidine derivative. Products 3 can be processed to the final compounds using methodology similar to that described in scheme M-2.

Scheme M-5

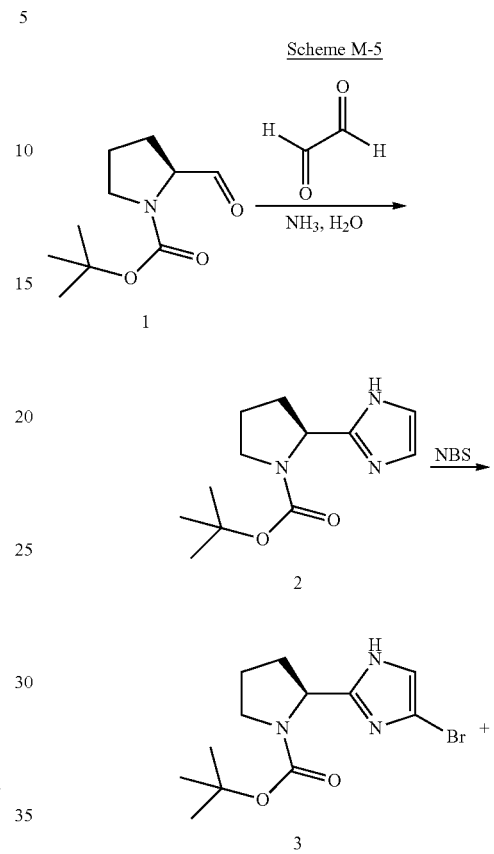

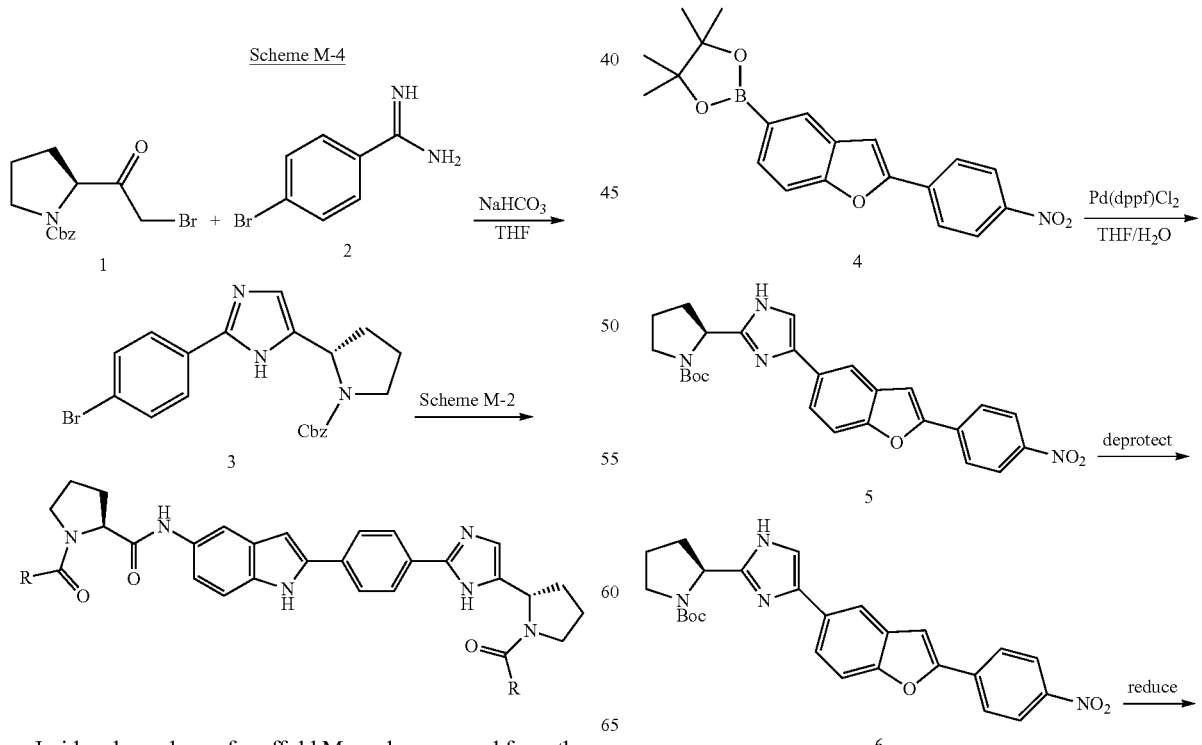

Imidazole analogs of scaffold M can be prepared from the cyclocondensation reaction of Z-proline bromomethyl

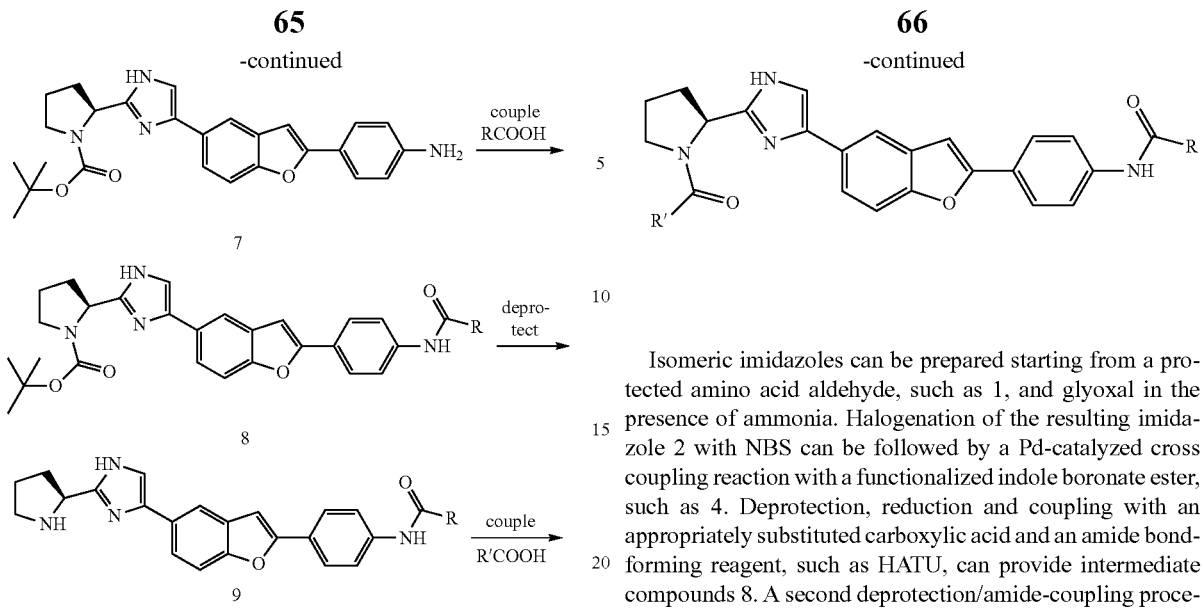

Isomeric imidazoles can be prepared starting from a protected amino acid aldehyde, such as 1, and glyoxal in the presence of ammonia. Halogenation of the resulting imidazole 2 with NBS can be followed by a Pd-catalyzed cross coupling reaction with a functionalized indole boronate ester, such as 4. Deprotection, reduction and coupling with an appropriately substituted carboxylic acid and an amide bond-forming reagent, such as HATU, can provide intermediate compounds 8. A second deprotection/amide-coupling procedure can provide the targeted M-5 scaffold.

Scheme M-6

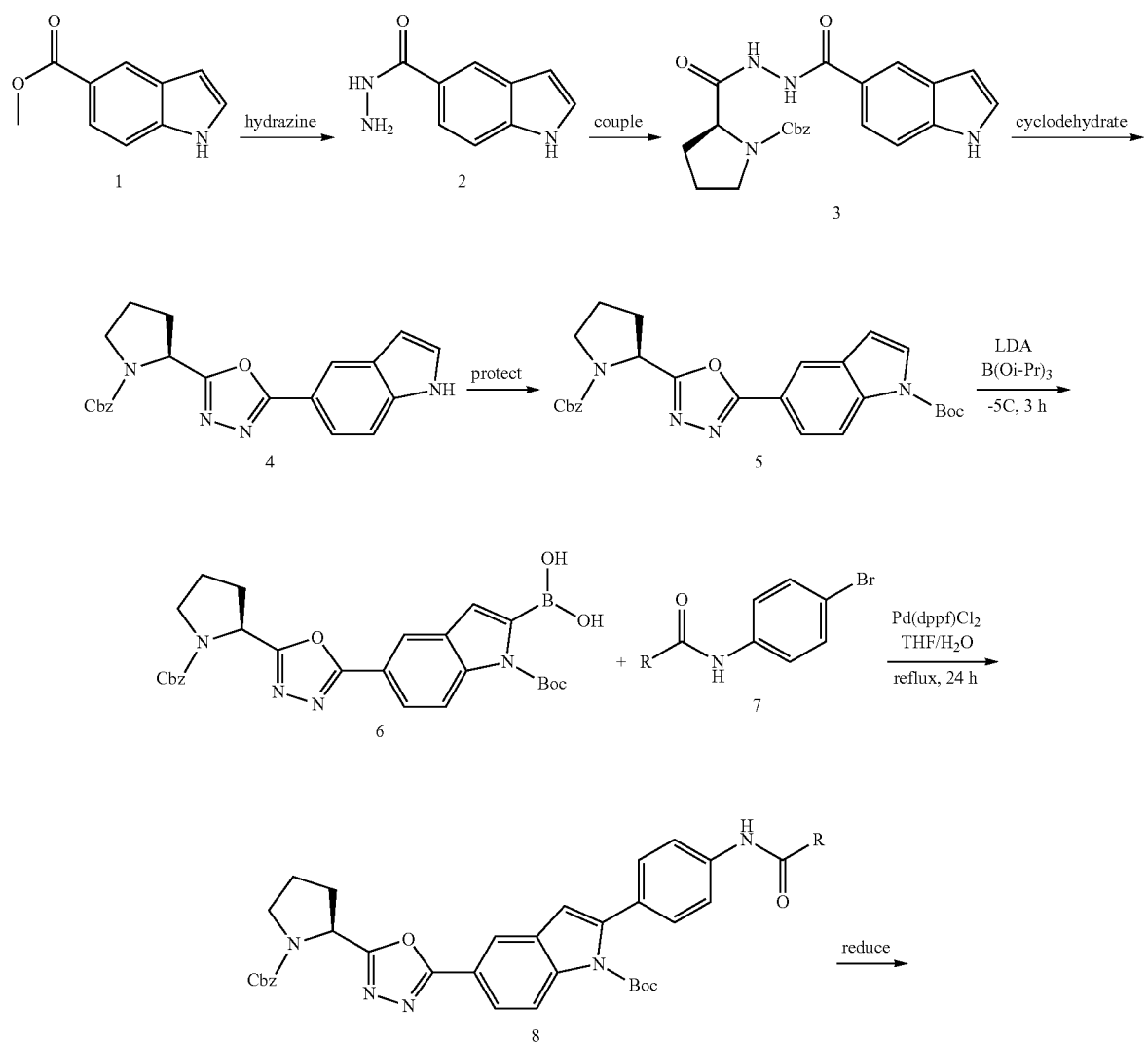

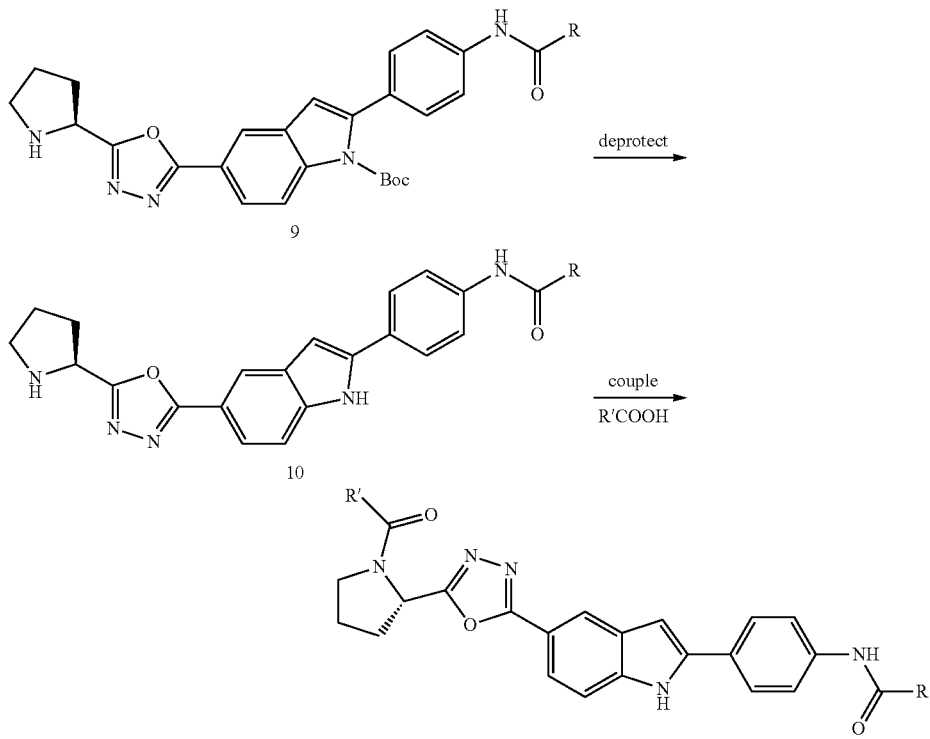

Oxadiazole compounds can be prepared starting from indole hydrazide 2 and coupling to an amino acid, such as Z-proline. Cyclodehydration of intermediate 3 can be effected with a reagent, such as TPP/iodine, to give the desired oxadiazole, which can be protected on the indole nitrogen with Boc anhydride. Introduction of the boronic acid functional group activates compound 6 for coupling with a substituted aryl halide 7 to give intermediate 8. Removal of the cbz and Boc groups afford the penultimate structure 10, which can be coupled with an appropriately substituted carboxylic acid and an amide bond-forming reagent to give the targets M-6.

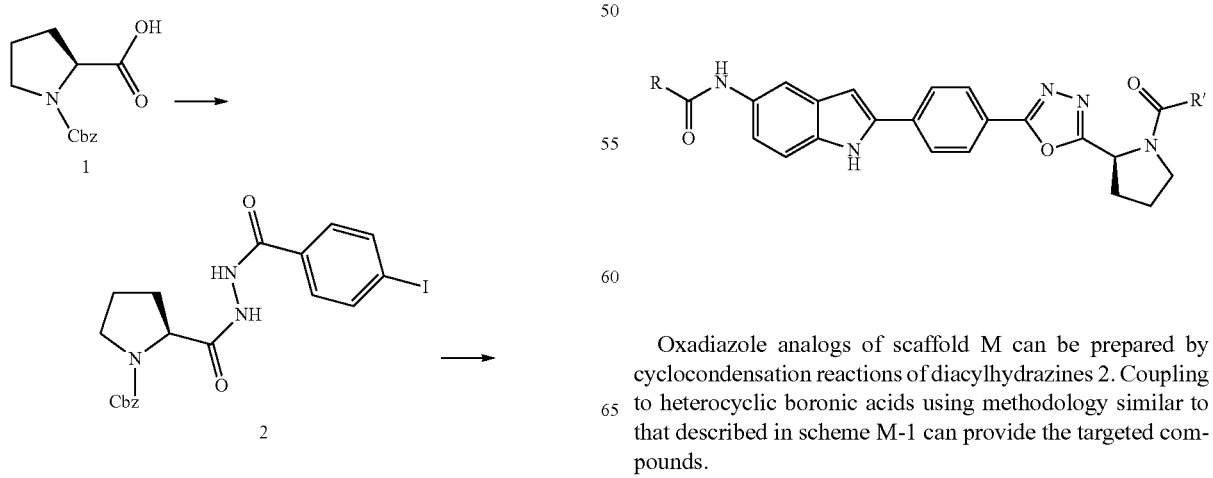

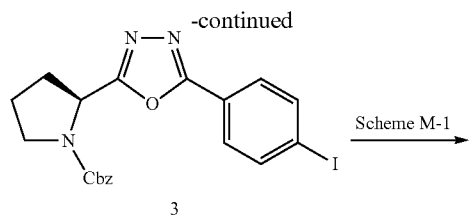

Oxadiazole analogs of scaffold M can be prepared by cyclocondensation reactions of diacylhydrazines 2. Coupling to heterocyclic boronic acids using methodology similar to that described in scheme M-1 can provide the targeted compounds.

Scheme M-8
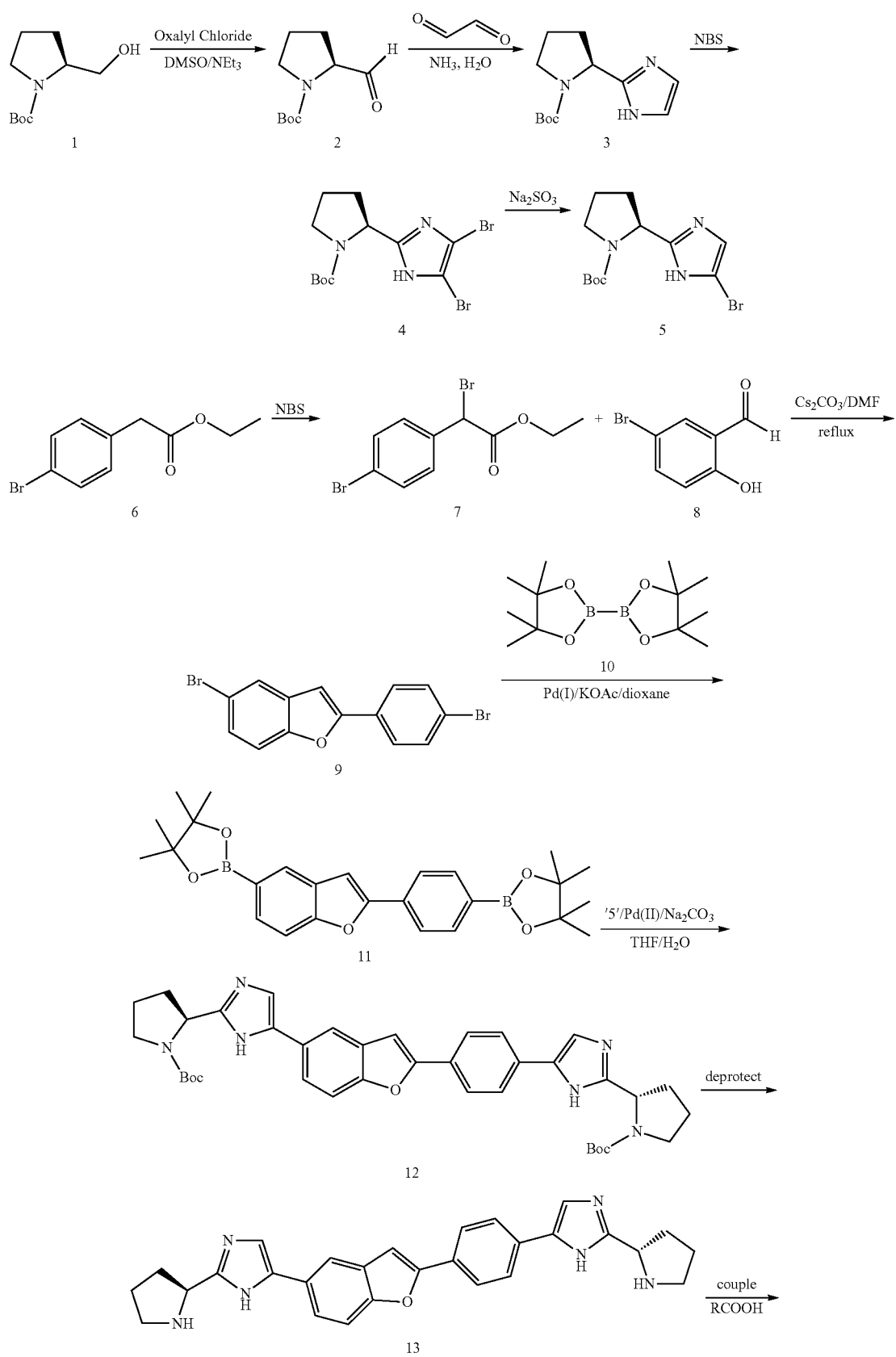

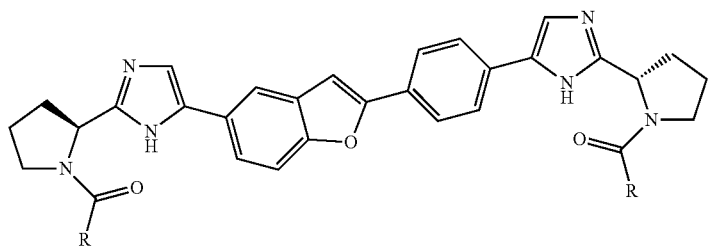

Double imidazole containing benzofuran compounds can be prepared starting from a protected amino acid aldehyde, such as 2, and glyoxal in the presence of ammonia. Halogenation of the resulting imidazole 3 with NBS can ultimately provide intermediate 5, which can be coupled to a functionalized boronate ester, such as 11, to provide 12. Deprotection and coupling with an appropriately substituted carboxylic acid and an amide bond-forming reagent, such as HATU, can provide the targeted M-8 scaffold.

An alternative synthesis of benzofurans can be realized starting from benzofuran 1, which can be converted to boronate ester 2, which can then coupled to an appropriately substituted aryl halide to afford 5. Intermediate 5 can subsequently be converted to a functionalized boronate ester and converted to the final products in a manner similar to that described in Scheme M-8.

Scheme M-9

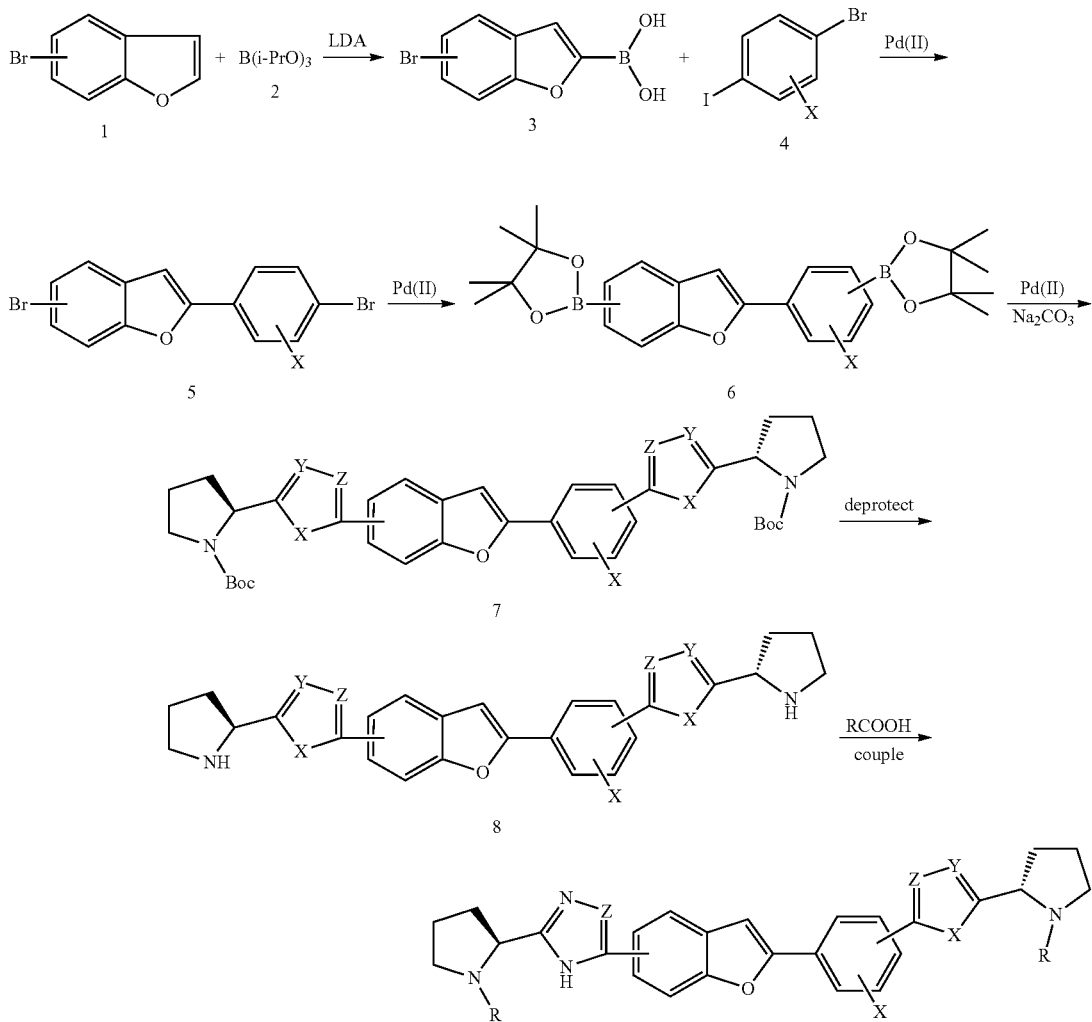

Scheme M-10

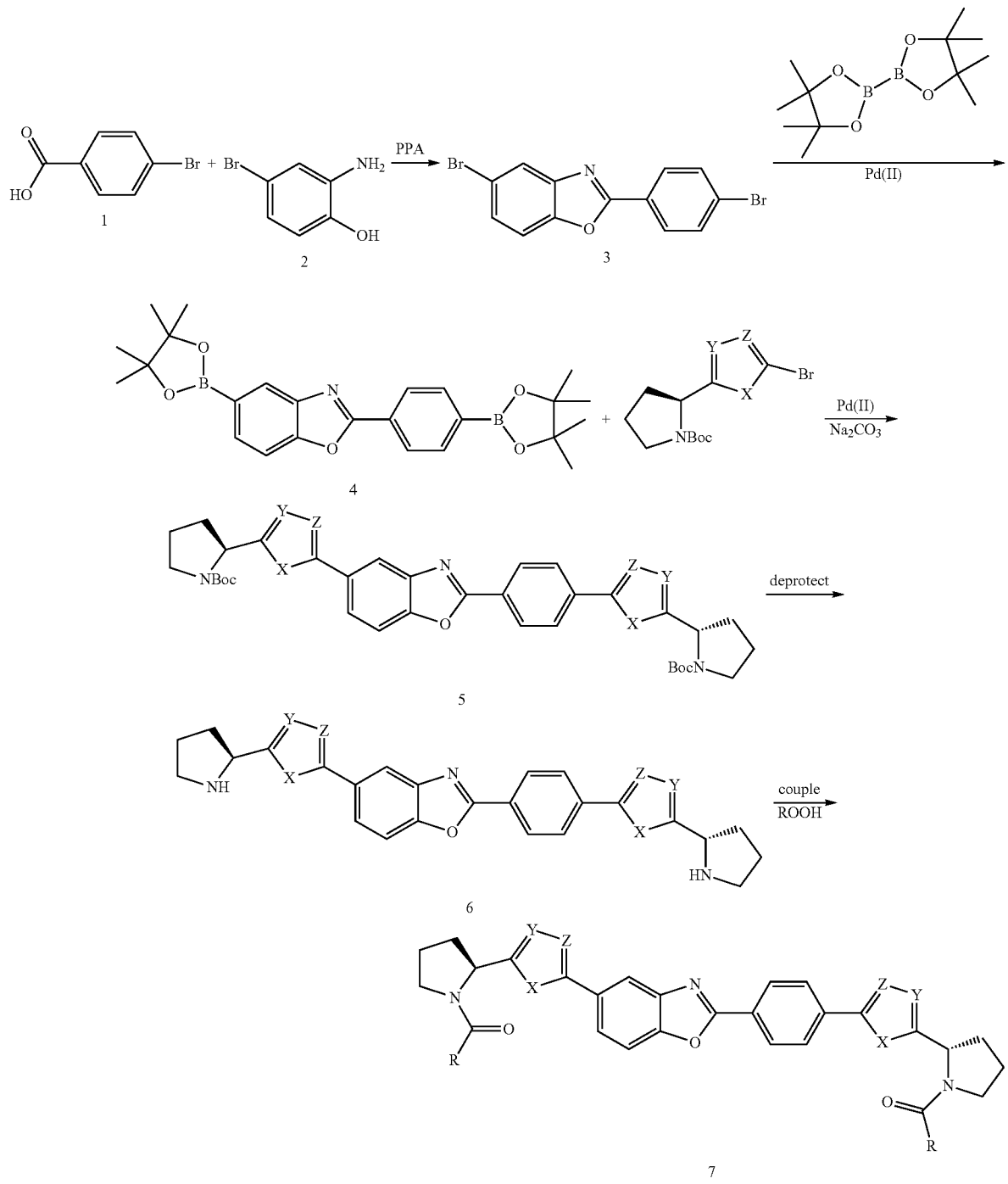

Benzoxazoles 3 can be prepared starting from a suitable substituted benzoic acid and an aminophenol, such as 2, in the presence of polyphosphoric acid. Such products can be converted to the corresponding boronate esters using standard procedures. Intermediates 4 can subsequently be coupled to a heterocyclic halide in the presence of a Pd(II) catalyst to provide compounds 5. Deprotection and coupling with an appropriately substituted carboxylic acid and an amide bond-forming reagent, such as HATU, can provide the targeted M-10 scaffold.

Scheme N-1

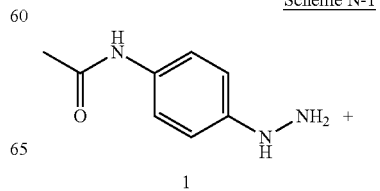

1

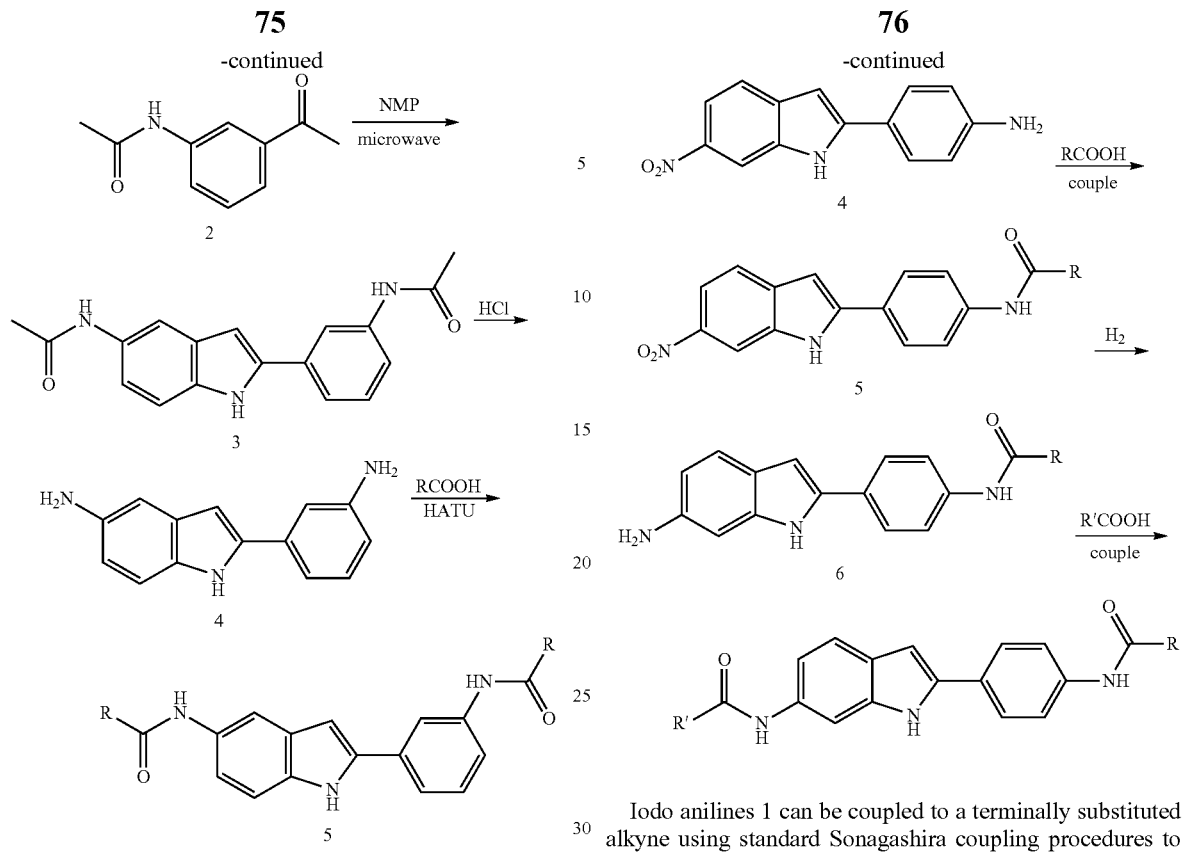

The compounds in scheme N-1 can be prepared by heating hydrazines 1 with ketones 2 in a microwave reactor in a polar aprotic solvent, such as NMP. The indole acetamides 3 can be deprotected with strong acid, such as HCl. The resulting aryl amines can be coupled with an appropriately substituted carboxylic acid, and an amide bond-forming reagent, such as HATU, to give compounds of the targeted scaffold.

Iodo anilines 1 can be coupled to a terminally substituted alkyne using standard Sonagashira coupling procedures to give intermediates 2, which can undergo cyclization using a reagent, such as indium bromide, to provide the indole compounds 3. Protecting groups can be removed with a strong acid, such as aqueous HCl, and the resulting amine can be acylated using an appropriately substituted carboxylic acid and an amide bond-forming reagent, such as HATU. Compounds 5 can then be reduced using hydrogen and a catalyst, then coupled a second time with a carboxylic acid and HATU to provide the desired compounds.

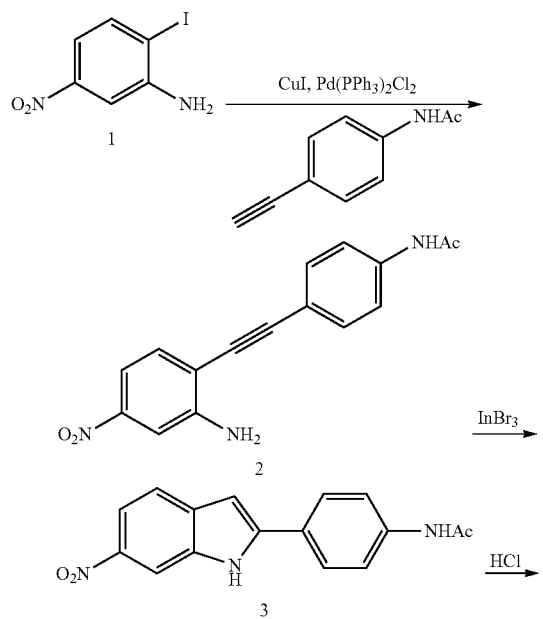

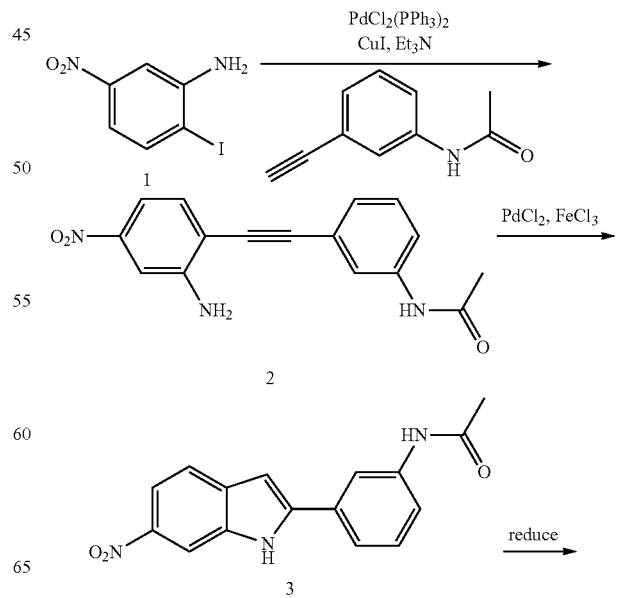

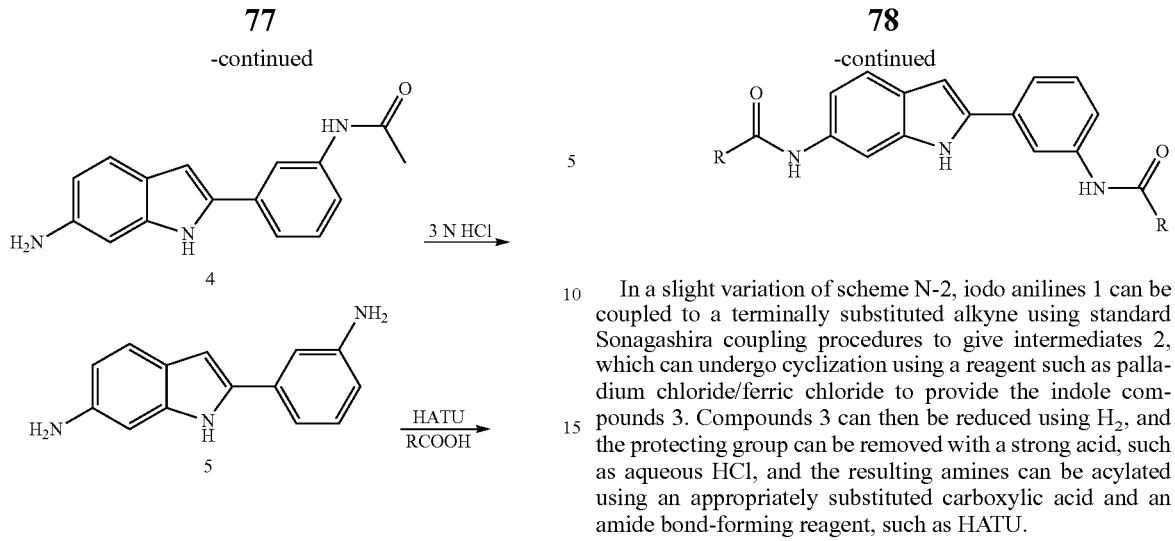

In a slight variation of scheme N-2, iodo anilines 1 can be coupled to a terminally substituted alkyne using standard Sonagashira coupling procedures to give intermediates 2, which can undergo cyclization using a reagent such as palladium chloride/ferric chloride to provide the indole compounds 3. Compounds 3 can then be reduced using $H_2$, and the protecting group can be removed with a strong acid, such as aqueous HCl, and the resulting amines can be acylated using an appropriately substituted carboxylic acid and an amide bond-forming reagent, such as HATU.

Scheme O

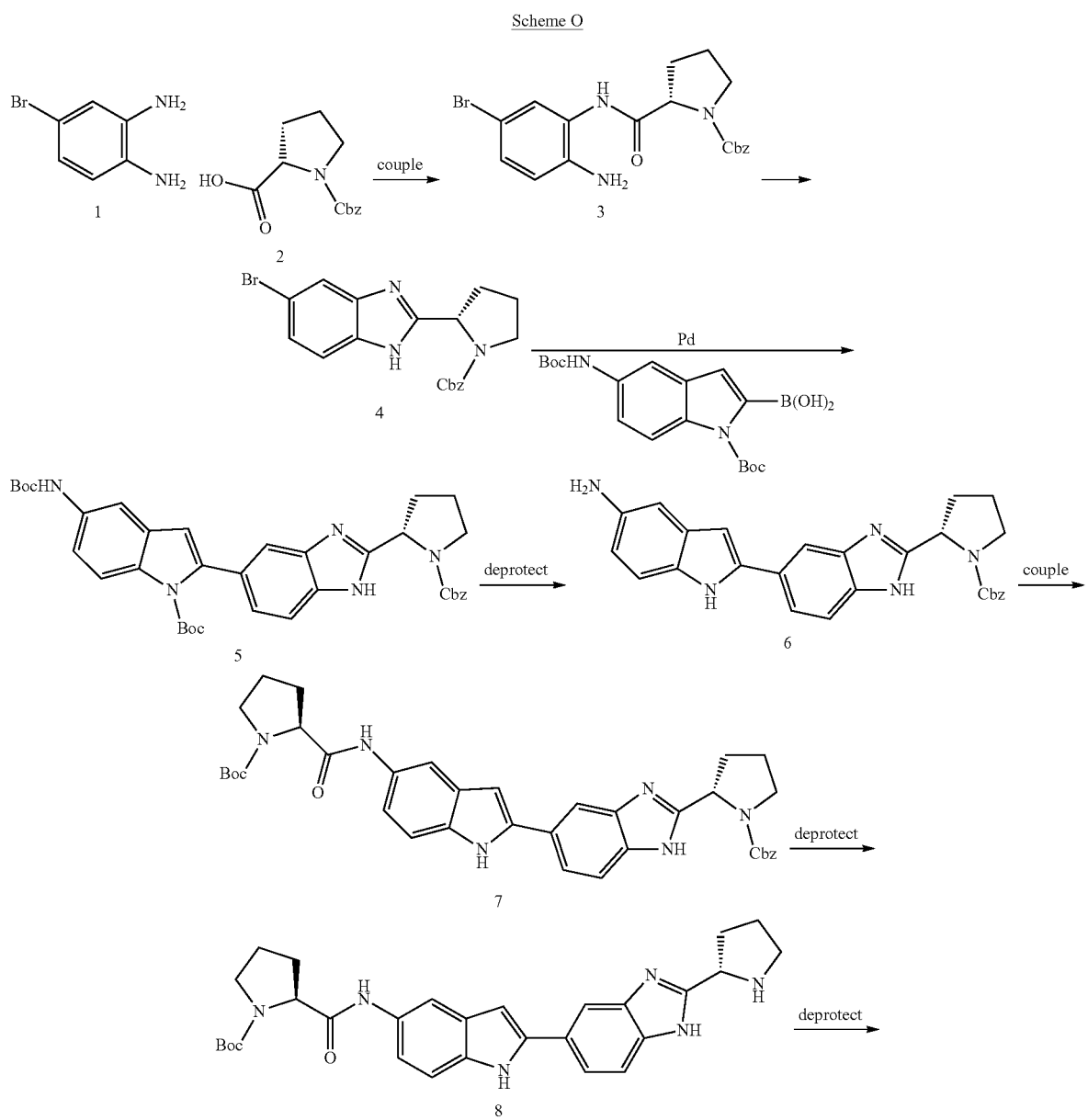

-continued

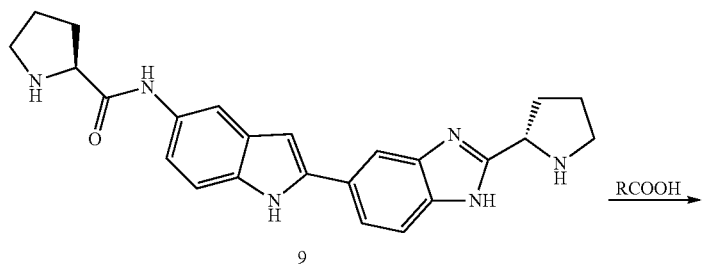
9
→ RCOOH

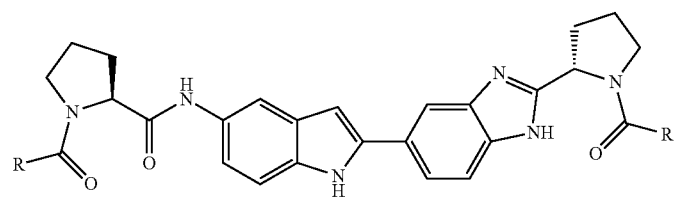

Scaffold O can be prepared by reacting a protected proline compound (such as Cbz) with a phenylenediamine analog and an amide bond-forming reagent, such as HATU, to give amides 3, which can be cyclodehydrated by heating with a reagent, such as HOAc. The resulting benzimidazole can be coupled to an indole boronic acid derivative using standard Suzuki conditions to provide 5. Removal of the Boc groups with acid provides 7, which can be acylated using an appropriately substituted carboxylic acid, such as Boc-L-proline, and an amide bond-forming reagent, such as HATU, to give intermediates 7. The Cbz group can be reduced under catalytic hydrogenating conditions, and the Boc group can be deprotected with acid to provide penultimate compounds 9. Amide bond formation between 9 and carboxylic acids afford the targeted compounds.

Scheme P-1

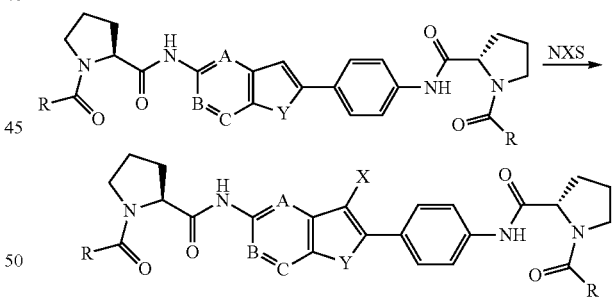

Heterocycles can be halogenated at C-3 by the action of electrophilic agents, such as N-halosuccinimides, to provide targets P-1.

Scheme P-2

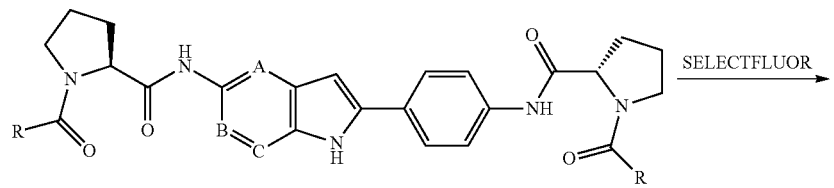

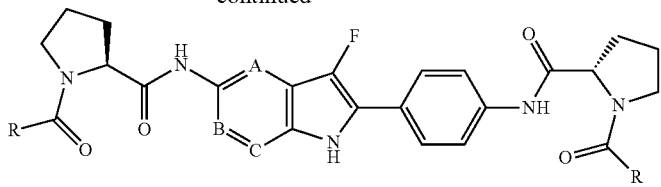

Heterocycles can be fluorinated at C-3 by the action of electrophilic fluorinating agents, such as SELECTFLUOR, to provide targets P-1.

Scheme P-3

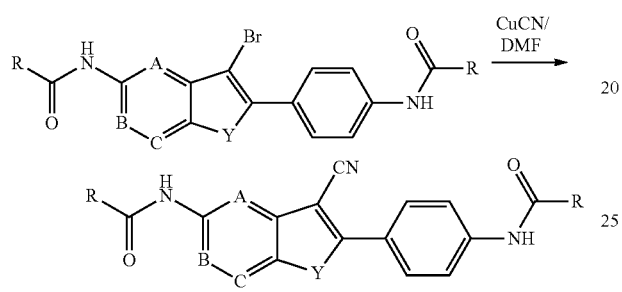

C-3 halogenated compounds can be converted to the corresponding cyano analogs by cyanating agents, such as CuCN.

Scheme P-4

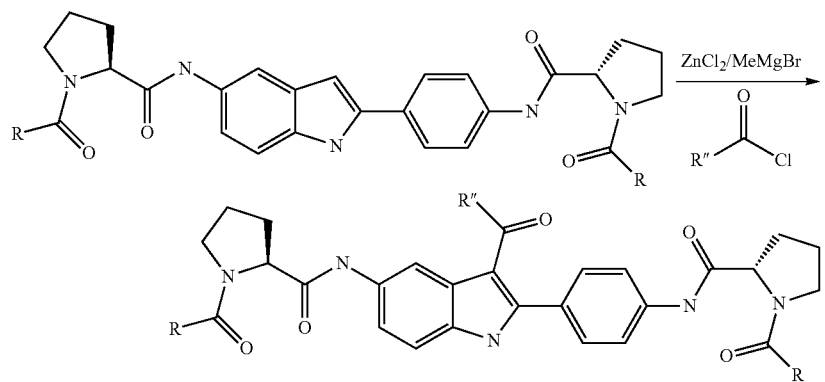

The compounds in scheme P-4 can be functionalized by the acylating indoles with Grignard reagents and zinc chloride.

Scheme P-5

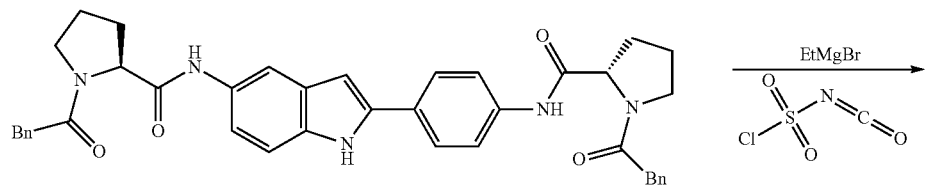

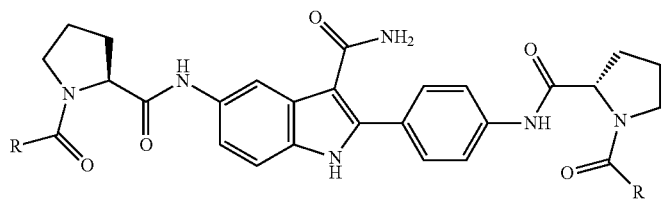

R = H

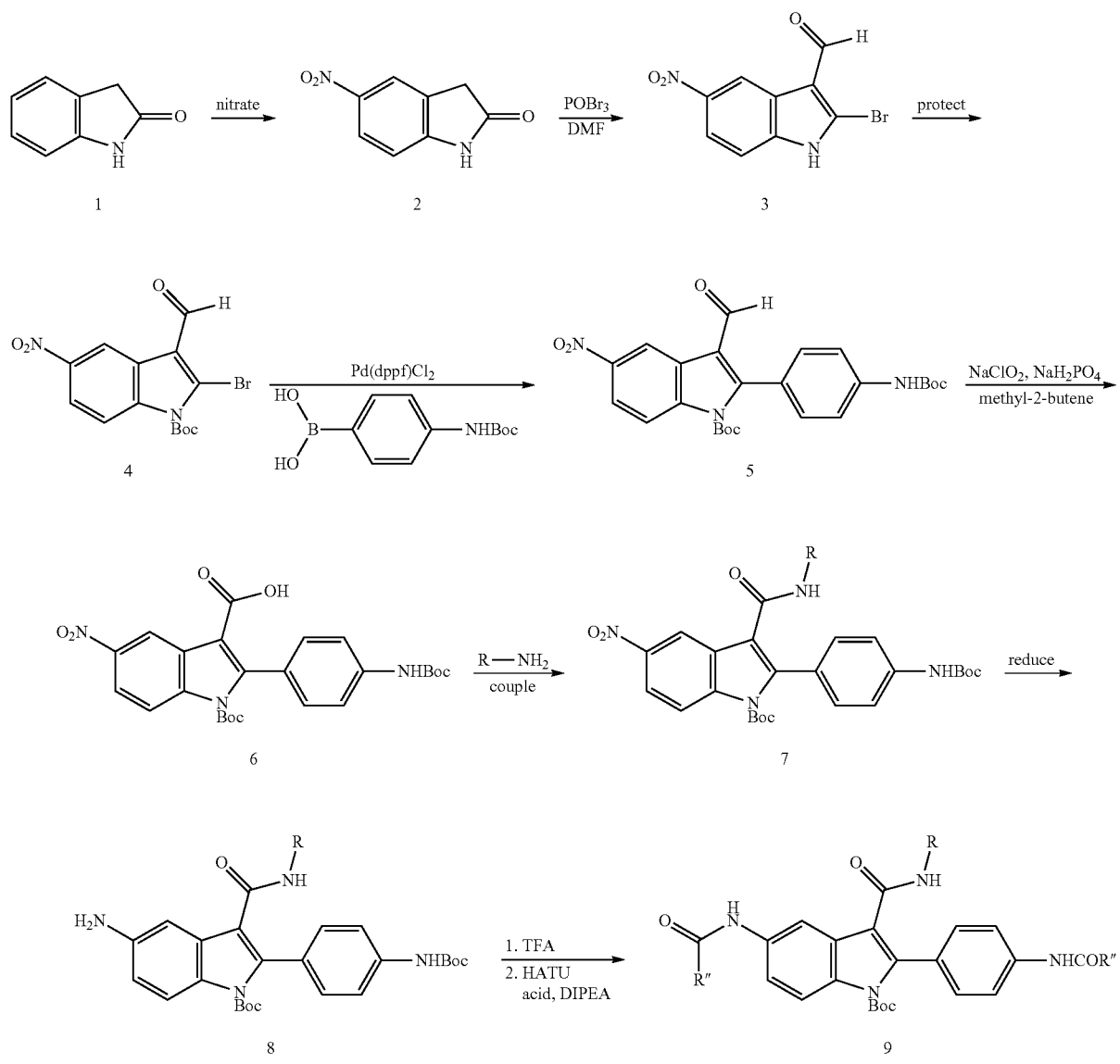

R > H

The compounds in scheme P-5 can be functionalized by deprotonating the indoles with a base such as ethylmagnesium bromide and treating the resulting intermediate with chlorosulfonyl isocyanate. Alternatively, the indoles 3 can be prepared using Vilsmeier-Haack conditions, which can subsequently be protected and coupled under Suzuki conditions to give intermediates 5. The aldehydes can be oxidized using standard methodology for carboxylic acid formation. Indole carboxylic acids 6 can be coupled to amines using a reagent, such as HATU, to give 7, which can be further functionalized by reduction of the nitro group, deprotection of the Boc group and coupling of the anilines to an appropriately substituted carboxylic acid and an amide bond-forming reagent, such as HATU.

Scheme P-6

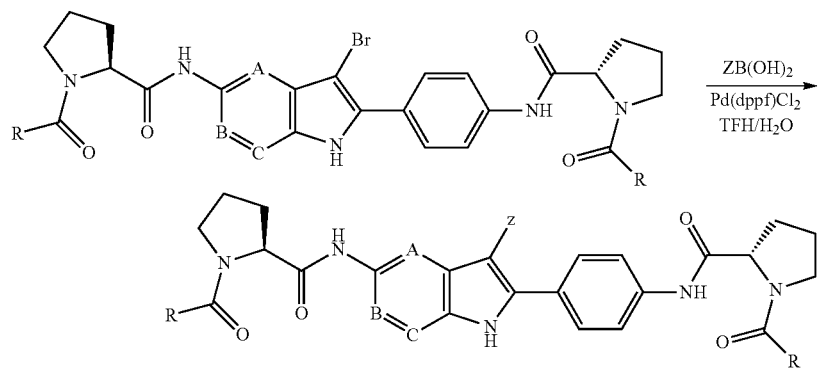

C-3 halogenated compounds can be coupled to a variety of alkyl and aryl boronic acids using standard Suzuki conditions.

Scheme Q

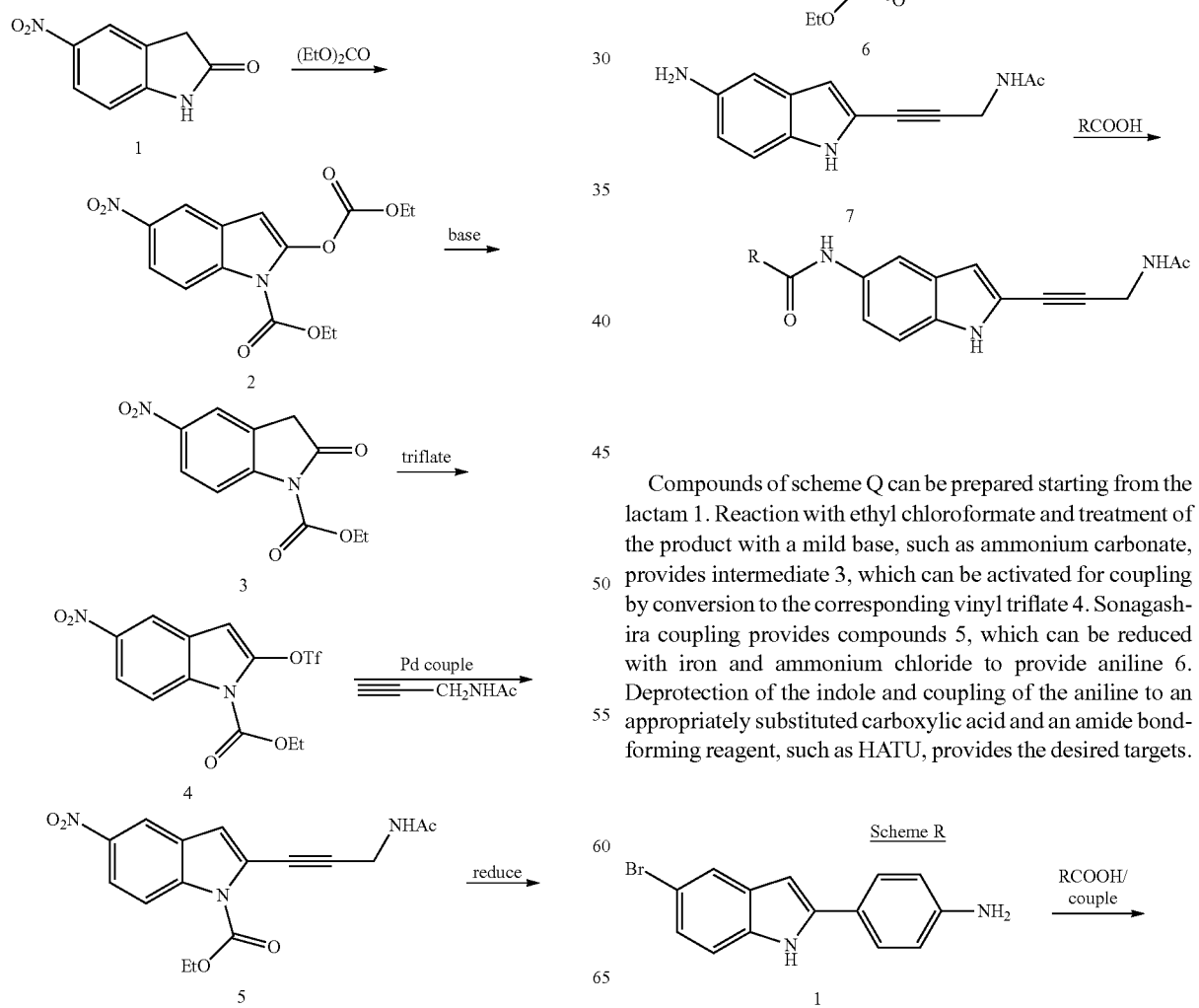

Compounds of scheme Q can be prepared starting from the lactam 1. Reaction with ethyl chloroformate and treatment of the product with a mild base, such as ammonium carbonate, provides intermediate 3, which can be activated for coupling by conversion to the corresponding vinyl triflate 4. Sonagashira coupling provides compounds 5, which can be reduced with iron and ammonium chloride to provide aniline 6. Deprotection of the indole and coupling of the aniline to an appropriately substituted carboxylic acid and an amide bond-forming reagent, such as HATU, provides the desired targets.

Scheme R

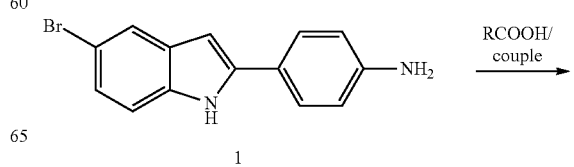

87

-continued

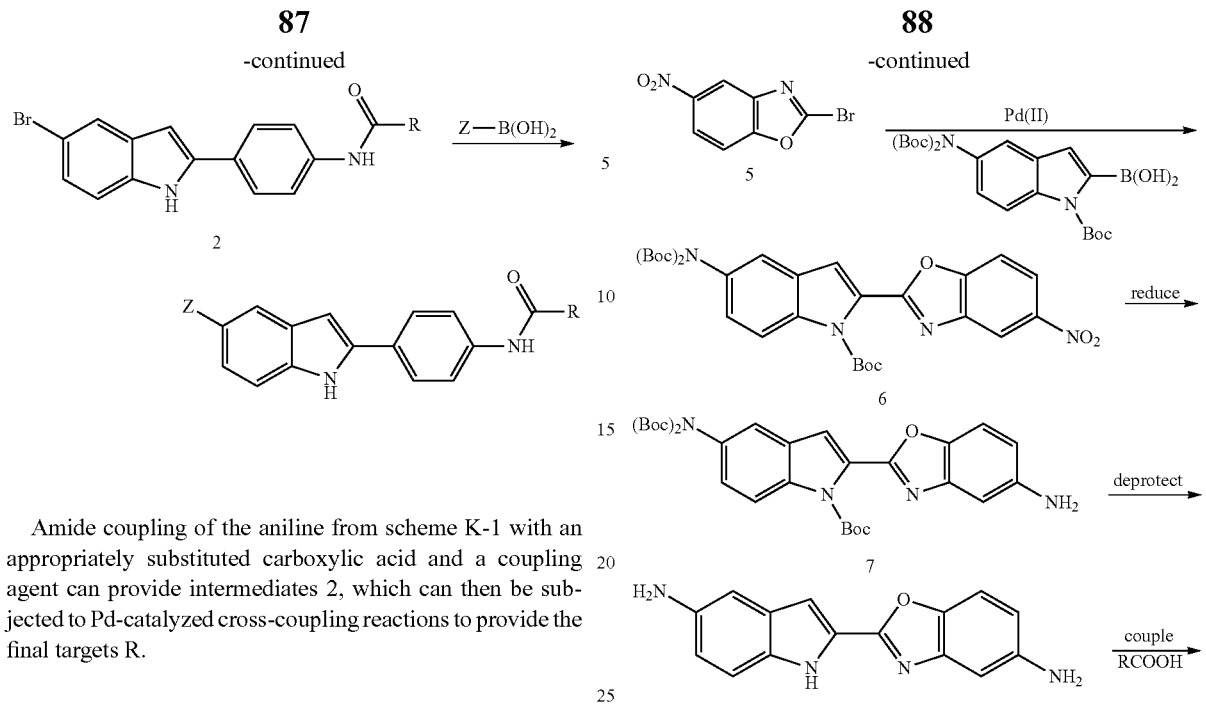

Amide coupling of the aniline from scheme K-1 with an appropriately substituted carboxylic acid and a coupling agent can provide intermediates 2, which can then be subjected to Pd-catalyzed cross-coupling reactions to provide the final targets R.

Scheme S

88

-continued

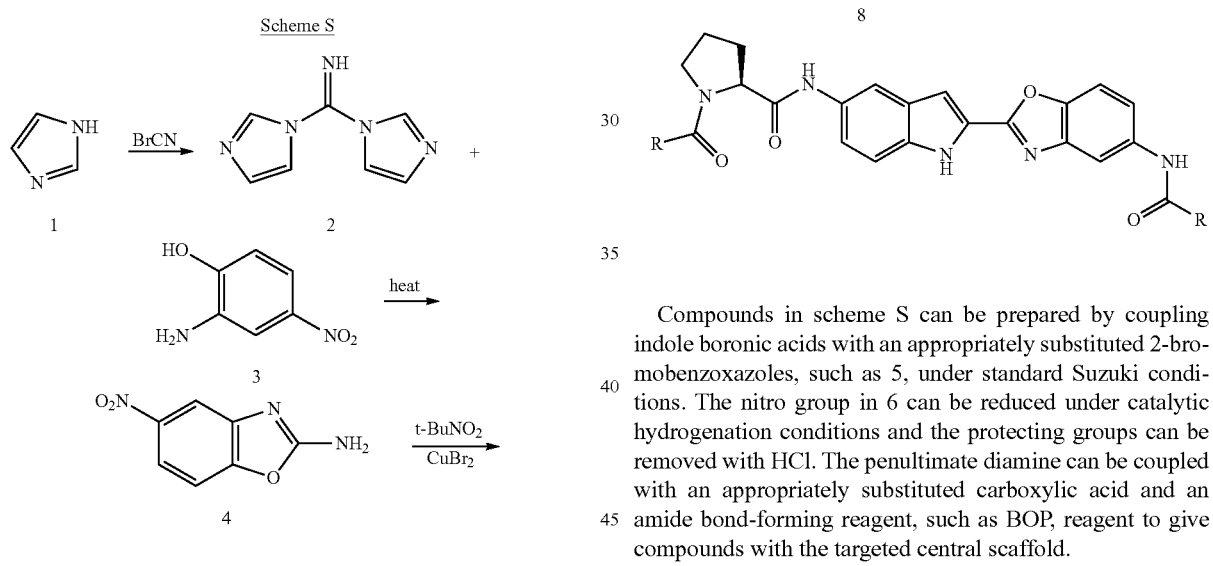

Compounds in scheme S can be prepared by coupling indole boronic acids with an appropriately substituted 2-bromobenzoxazoles, such as 5, under standard Suzuki conditions. The nitro group in 6 can be reduced under catalytic hydrogenation conditions and the protecting groups can be removed with HCl. The penultimate diamine can be coupled with an appropriately substituted carboxylic acid and an amide bond-forming reagent, such as BOP, reagent to give compounds with the targeted central scaffold.

Scheme T

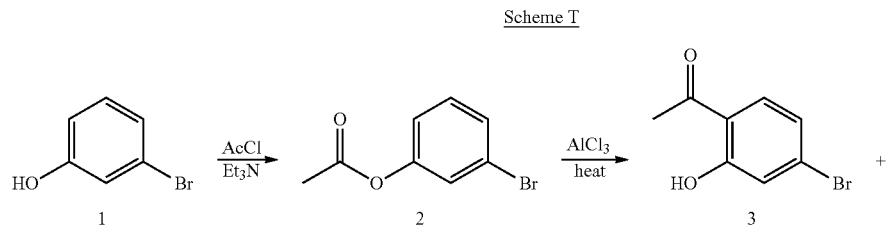

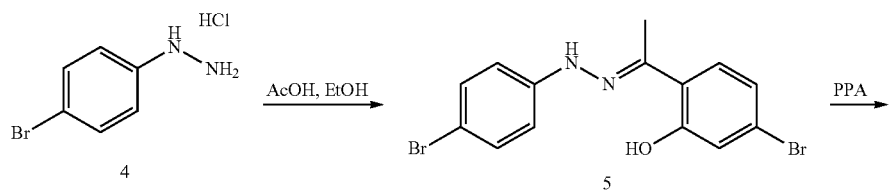

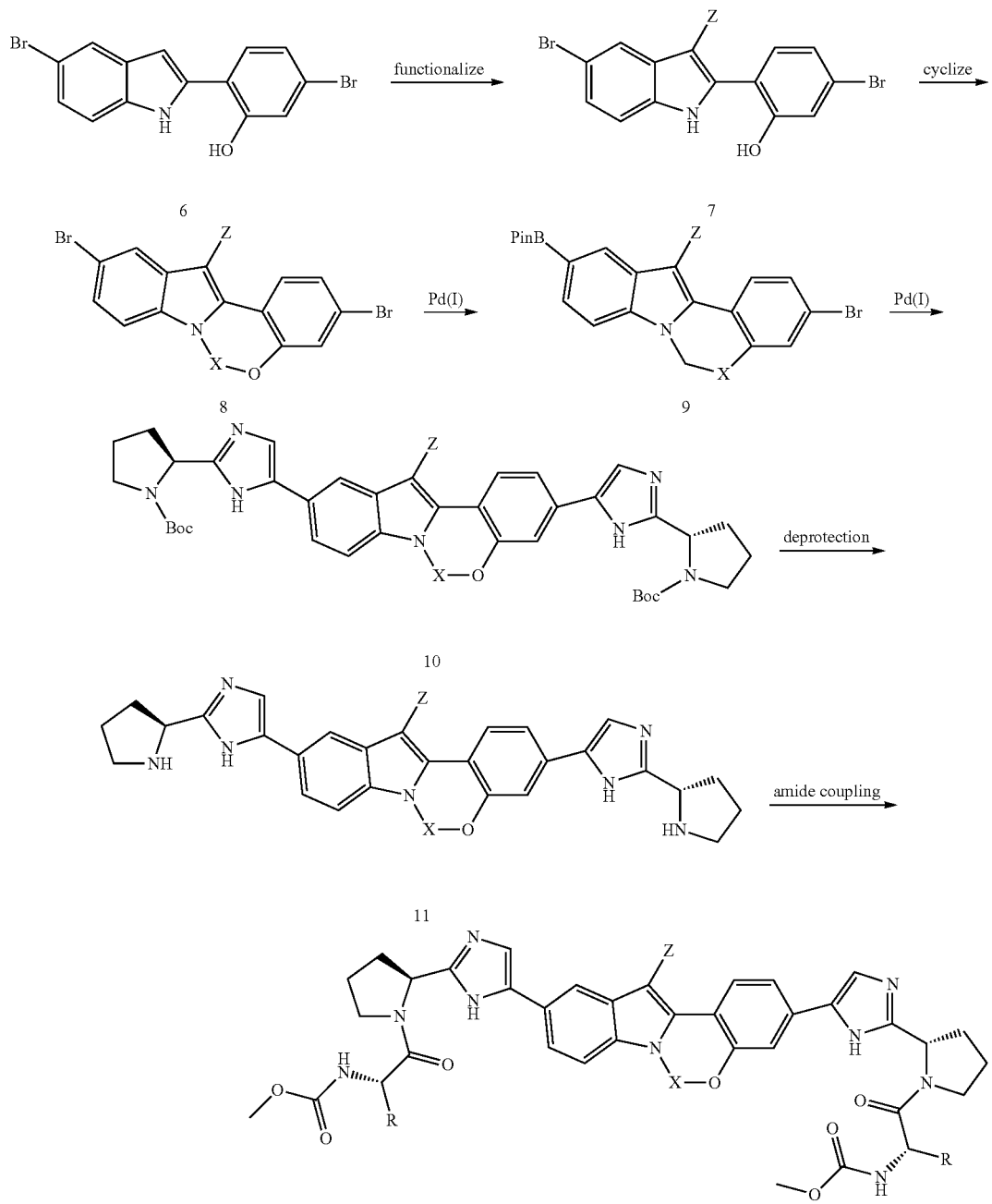

Compounds in scheme T can be prepared by starting from a suitably substituted phenol 3 and a hydrazine reagent, such as 4, using established Fisher indole conditions. The indole 3 position can then be functionalized or the indole NH can be cyclized onto the C-2 aromatic ring using standard conditions to give tetracycles 8, which can subsequently be converted to the corresponding boronate esters using standard procedures. Intermediates 9 can then be coupled to a heterocyclic halide in the presence of a Pd(II) catalyst to provide compounds 10. Deprotection and coupling with an appropriately substituted carboxylic acid and an amide bond-forming reagent, such as HATU, can provide the targeted T scaffold.

The following examples serve only to illustrate the invention and its practice. The examples are not to be construed as limitations on the scope or spirit of the invention.

LIST OF ABBREVIATIONS

Ac$_2$O Acetic anhydride
B(OiPr)$_3$, (iPrO)$_3$B Triisopropyl borate
B(OMe)$_3$ Trimethyl borate
BF$_3$ Boron trifluoride
BOC, Boc, boc tert-Butyloxycarbonyl
BOP Benzotriazole-1-yl-oxy-tris-(dimethylamino)-phosphonium hexafluorophosphate BrCN Cyanogen bromide
BuLi, n-BuLi Butyl lithium
CBZ, Cbz, cbz Benzyloxycarbonyl
CDCl$_3$ Deuterio-trichloromethane
CH$_3$CN, MeCN Acetonitrile
Cs$_2$CO$_3$ Cesium carbonate
CuBr$_2$ Copper(II) bromide
CuCN Copper(I) cyanide
CuI Copper iodide
DBU 1,8-Diazabicyclo[5.4.0]undec-7-ene
DCE Dichloroethane
DCM, CH$_2$Cl$_2$ Dichloromethane
DIPEA, DIEA Diisopropylethylamine
DMAP 4-Dimethylamino pyridine
DMF Dimethylformamide
DMSO Dimethyl sulfoxide
DPPF, Dppf, dppf 1,1'-bis(Diphenylphosphino)ferrocene
EDC, EDCI N-(3-Dimethylaminopropyl)-N'-ethylcarbodiimide
Et$_2$O Diethyl ether
Et$_3$N, TEA Triethylamine
EtMgBr Bromo(ethyl)magnesium or ethyl magnesium bromide
EtOAc Ethyl acetate
EtOH Ethanol
FeCl$_3$ Ferric chloride or Iron(III) chloride
H$_2$ Hydrogen or hydrogen atmosphere
H$_2$O Water
H$_2$SO$_4$ Sulfuric acid
HATU O-(7-Azabenzotriazol-1-yl)-N,N,N',N'-tetramethyluronium hexafluorophosphate
HBr Hydrobromic acid
HCl Hydrochloric acid
HNO$_3$ Nitric Acid
HOAc, HAc Acetic acid
HOBT, HOBt 1-Hydroxy benzotriazole
HPLC High performance liquid chromatography
InBr$_3$ Indium tribromide
iPr$_2$NH Diisopropylamine
K$_2$CO$_3$ Potassium carbonate
KI Potassium iodide
KIO$_3$ Potassium iodate
KOAc, AcOK Potassium acetate
KOH Potassium hydroxide
LDA Lithium diisopropylamide
LHMDS, LiHMDS Lithium hexamethyldisilamide
MeMgBr Bromo(methyl)magnesium or methyl magnesium bromide
MeOD Methan($^2$H)ol
MeOH, CH$_3$OH Methanol
MgSO$_4$ Magnesium sulfate
MOC, Moc Methoxy carbonyl
MS Mass spectroscopy
N$_2$ Nitrogen or nitrogen atmosphere
Na$_2$CO$_3$ Sodium carbonate
Na$_2$SO$_4$ Sodium sulfate (anhydrous)
NaClO$_2$ Sodium perchlorate
NaH$_2$PO$_4$ Dihydrogen sodium phosphate
NaHCO$_3$ Sodium hydrogen carbonate (sodium bicarbonate)
NaNO$_2$ Sodium nitrite
NaOH Sodium hydroxide
NBS N-bromosuccinimide
NCS N-chlorosuccinimide
NH$_4$OAc Ammonium acetate
NMM N-methylmorpholine
NMR, $^1$H-NMR Proton nuclear magnetic resonance spectroscopy
NXS N-halosuccinimide
P$_2$O$_5$, P$_4$O$_{10}$ Phosphorus pentoxide
Pd Palladium
Pd(dppf)Cl$_2$ Dichloro(1,1'-bis(Diphenylphosphino)ferrocene) palladium(II)
Pd(II) Palladium(II)
Pd(PPh$_3$)$_2$Cl$_2$, PdCl$_2$(PPh$_3$)$_2$ Dichlorobis(triphenylphosphine)palladium(II)
Pd(PPh$_3$)$_4$ Tetrakis(triphenylphosphine)palladium(0)
Pd/C, Pd—C Palladium on carbon
Pd$_2$(dba)$_3$ Tris(dibenzylidene acetone)dipalladium(0)
PdCl$_2$ Palladium(II) chloride
PE Petroleum ether
Phg Phenylglycine
PhCH$_3$, PhMe Toluene
Piv Pivaloyl
PivCl Pivaloyl chloride
POBr$_3$ Phosphorus oxybromide
PPA Polyphosphoric acid
PPH$_3$, TPP Triphenylphosphine
Pro Proline
Proc iso-Propylcarbamate
P$^t$Bu$_3$ Tri-tert-butyl phosphine
Py Pyradine
PyBOP (Benzotriazole-1-yl-oxy)-tripyrrolidinophosphonium hexafluorophosphate
RPLC Reverse phase liquid chromatography
RT, rt, r.t. Room temperature, approximately 25° C.
SiO$_2$ Silica or silica gel
SnCl$_2$ Stannous chloride or Tin(II) chloride
SOCl$_2$ Thionyl chloride
STP Standard temperature and pressure
t-BuLi tert-Butyl lithium
t-BuNO$_2$ tert-Butyl nitrate
t-BuOH tert-Butanol
t-BuOK, KOt-Bu Potassium tert-butoxide
TFA Trifluoroacetic acid
TFAA Trifluoroacetic anhydride
THF Tetrahydrofuran
TLC Thin layer chromatography
ZnCl$_2$ Zinc chloride

EXAMPLES

Example 1

N-{4-[5-(acetylamino)-1H-pyrrolo[3,2-b]pyridin-2-yl]phenyl}-1-(phenylacetyl)-L-prolinamide

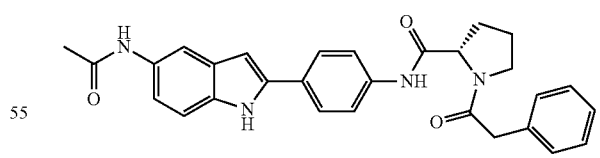

Step 1

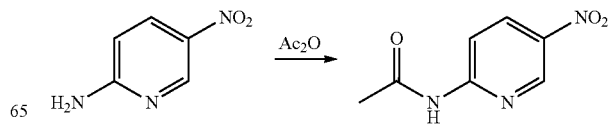

To a suspension of 2-amino-5-nitropyridine (25.0 g, 0.18 mol) and 0.5 g of DMAP in 200 mL of pyridine, Ac$_2$O (37 g, 0.36 mol) was added drop wise at 0° C. The mixture was stirred at RT for 5 hours. The volatile was removed in vacuo. The residue was washed with EtOAc to yield an off-white solid (28 g, 86%). MS (ESI) m/e (M+H$^+$): 182.

Step 2

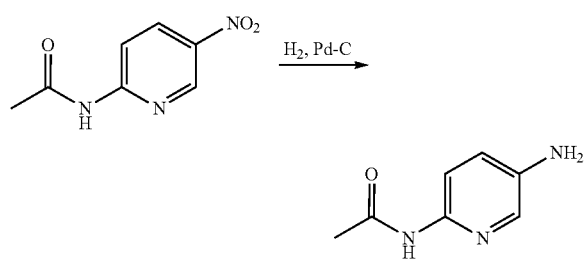

A heterogeneous mixture of 2-acetamido-5-nitropyridine (28 g, 0.15 mol) and 10% Pd/C (2.8 g) in 300 mL of MeOH was stirred in 50 psi of H$_2$ for 6 hours. The mixture was filtered through CELITE, and concentrated in vacuo to yield a solid (20.5 g). MS (ESI) m/e (M+H$^+$): 152.

Step 3

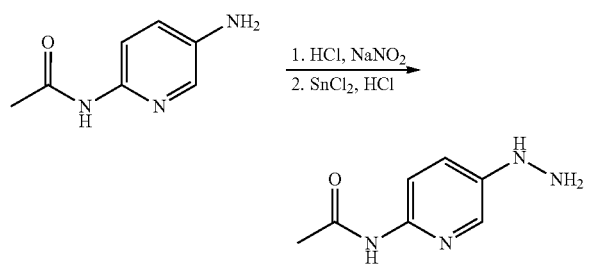

NaNO$_2$ (5.4 g, 78.2 mmol) was added slowly to a solution of 2-acetamido-5-aminopyridine (9.0 g, 60 mmol) in 6 M aqueous HCl (300 mL) at 0° C. and was stirred for 45 minutes. A solution of SnCl$_2$ (40.5 g, 180 mmol) in 15 mL of 6 M aqueous HCl was added, and the reaction mixture was allowed to warm to RT slowly while stirring for 16 hours. The reaction mixture was basified with 40 percent aqueous KOH, extracted with EtOAc (3×), and the organic layers are combined, dried over Na$_2$SO$_4$ and concentrated in vacuo to give the desired compound (3.2 g). MS (ESI) m/e (M+H$^+$): 167.

Step 4

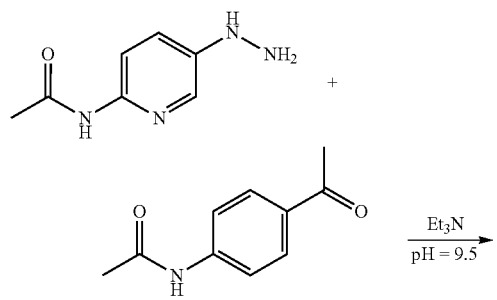

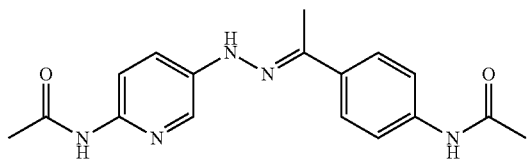

A suspension of the product from step 3 (3.32 g, 20 mmol) and N-(4-acetylphenyl)acetamide (3.54 g, 20 mmol) in 8 mL of EtOH was diluted with TEA to adjust the pH to about 9.5. The resulting reaction mixture was refluxed for 3 hours. The solvent was removed in vacuo, and the resulting residue was treated with 5% aqueous citric acid to form a precipitate. The precipitate was filtrated, washed with water and dried in vacuo (3.2 g). MS (ESI) m/e (M+H$^+$): 326.

Step 5

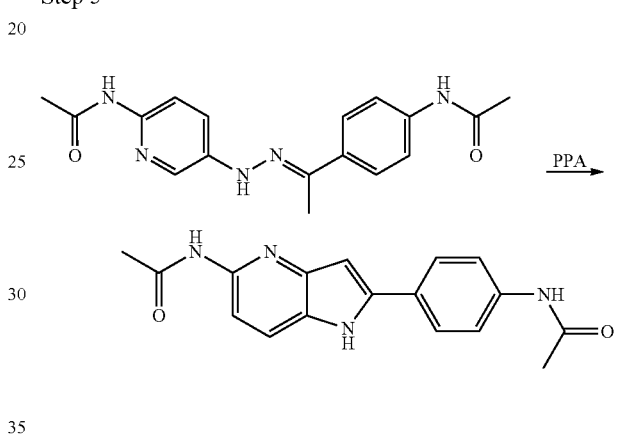

A mixture of the product from step 4 above (0.6 g, 1.8 mmol) and PPA (5 mL) was heated to 90° C. for 75 minutes under N$_2$. After cooling to RT, the reaction mixture was poured to an ice water, neutralized with solid NaOH, while maintaining the temperature of the mixture at or below RT. A solution of iso-propanol and DCM (1:3) was added to exact the organic. The combine organic phase was washed with brine, dried over Na$_2$SO$_4$ and concentrated in vacuo. The residue was purified by preparative HPLC to yield a solid (280 mg). MS (ESI) m/e (M+H$^+$): 309.

Step 6

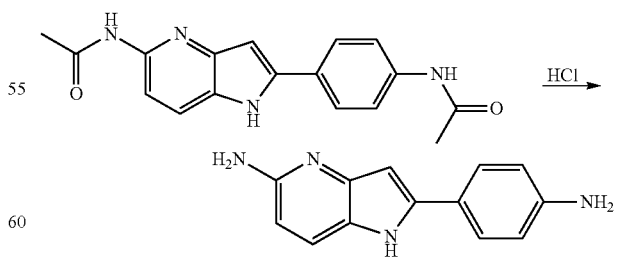

A mixture of the 4-azaindole (280 mg, 0.9 mmol) in 10 mL of 3 N HCl was refluxed for 2 hours. The solvent was removed in vacuo. The residue was purified by HPLC to yield a solid (120 mg). MS (ESI) m/e (M+H$^+$): 225.

Step 7

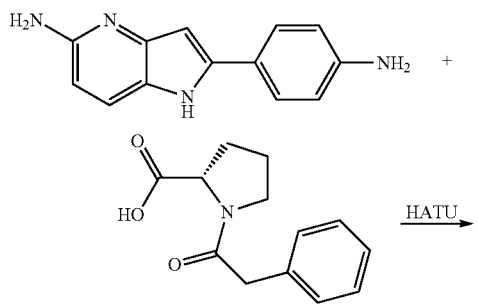

To a suspension of the product from step 6 (23 mg, 0.1 mmol), acid (23 mg, 0.1 mmol) and DIPEA (20 mg, 0.15 mmol) in 1 mL of CH₃CN was added HATU (42 mg, 0.12 mmol). The resulting mixture was stirred at RT overnight. After reaction completed, the mixture was purified by pre-HPLC (10 mg). MS (ESI) m/e (M+H$^+$): 440.

Step 8

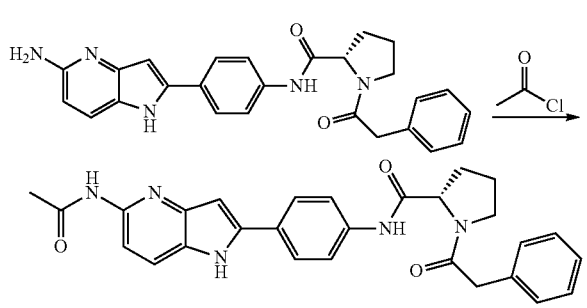

A mixture of product from step 7 (10 mg, 0.023 mmol) and TEA (3 g, 0.03 mmol) in CH₃CN (100 mL) was stirred at 0° C. Acetyl chloride (2 mg, 0.023 mmol) was added dropwise, and the resulting mixture was stirred at RT for 0.5 hour. The solvent was evaporated in vacuo, and the residue was purified by preparative HPLC to afford the desired product (5 mg). MS (ESI) m/e (M+H$^+$): 482. $^1$H NMR (MeOD): δ 8.25 (d, J=8.4 Hz, 1H), 7.74~7.89 (m, 4H), 7.26~7.32 (m, 5H), 7.00~7.02 (m, 2H), 4.63~4.64 (m, 1H), 3.72~3.84 (m, 4H), 2.18~2.33 (m, 2H), 2.07~2.10 (m, 5H).

Examples 2-3

The compounds of Examples 2 and 3 were prepared in a similar manner starting from intermediate 7 in step 6.

| Example | Structure | MW | Name |
|---|---|---|---|
| 2 | 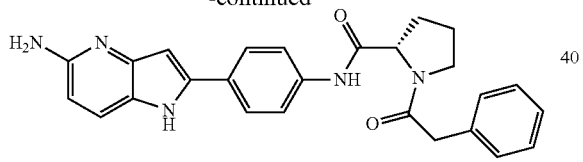 | 654.776 | (2S)-1-(phenylacetyl)-N-{2-[4-({[(2S)-1-(phenylacetyl)pyrrolidin-2-yl]carbonyl}amino)phenyl]-1H-pyrrolo[3,2-b]pyridin-5-yl}pyrrolidine-2-carboxamide |
| 3 | 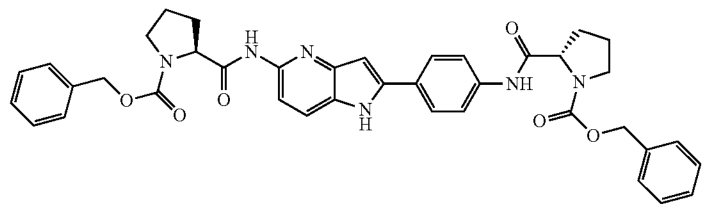 [SMILES: O=C(Nc1ccc(-c2cc3nc(NC(=O)[C@@H]4CCCN4C(=O)OCc4ccccc4)ccc3[nH]2)cc1)[C@@H]1CCCN1C(=O)OCc1ccccc1] | 686.774 | benzyl (2S)-2-[(2-{4-[({(2S)-1-[(benzyloxy)carbonyl]pyrrolidin-2-yl}carbonyl)amino]phenyl}-1H-pyrrolo[3,2-b]pyridin-5-yl)carbamoyl]pyrrolidine-1-carboxylate |

Example 4 tert-butyl {(1S)-2-[(2S)-2-{[4-(5-bromo-1H-pyrrolo[3,2-b]pyridin-2-yl)phenyl]carbamoyl}pyrrolidin-1-yl]-2-oxo-1-phenylethyl}carbamate

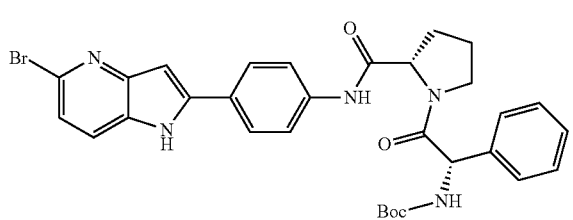 [SMILES: CC(C)(C)OC(=O)N[C@H](C(=O)N1CCC[C@H]1C(=O)Nc1ccc(-c2cc3nc(Br)ccc3[nH]2)cc1)c1ccccc1]

Step 1

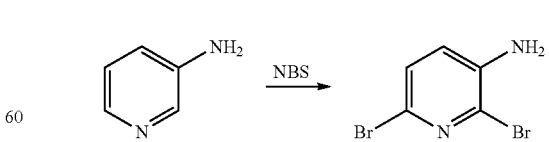

NBS (14.9 g, 84 mmol) was added portion wise to a solution of compound 3-aminopyridine (14.9 g, 84 mmol) in DMSO (80 mL) and water (20 mL) at 0° C., and the reaction was stirred at RT for 3 hours. The mixture was poured into ice-water (250 mL) and stirred for 30 minutes. The precipitate was collected and dried to yield a solid (7.0 g). MS (ESI) m/e (M+H⁺): 250. ¹H NMR (DMSO): δ 7.28 (d, J=7.6 Hz, 1H), 7.03 (d, J=7.6 Hz, 1H), 5.69 (s, 2H).

Step 2

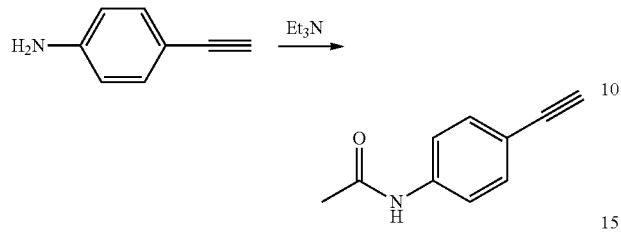

4-Ethynylacetanilide was prepared using the similar method shown in Example 1, step 1. MS (ESI) m/e (M+H⁺): 160.

Step 3

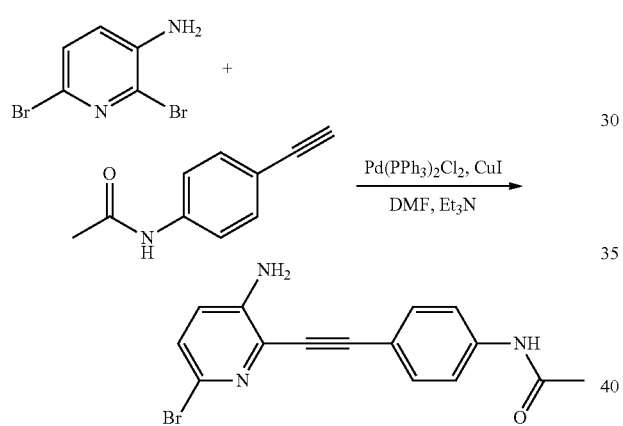

To a solution of 3-amino-2,6-dibromopyridine (9.41 g, 37.5 mmol), 4-ethynylacetanilide (4.77 g, 30 mmol) and Pd(PPh₃)₂Cl₂ (1.31 g, 1.9 mmol) in a mixture of 150 mL of Et₃N and 50 mL of DMF was added CuI (0.71 g, 0.4 mmol) under N₂. The resulting mixture was stirred at RT overnight. The solvent was removed, and the residue was purified by chromatography (8.5 g). MS (ESI) m/e (M+H⁺): 331. ¹HNMR (DMSO): δ 7.59 (d, J=8.8 Hz, 2H), 7.54 (d, J=8.4 Hz, 2H), 7.21 (d, J=8.8 Hz, 2H), 7.07 (d, J=8.4 Hz, 2H), 2.12 (s, 3H).

Step 4

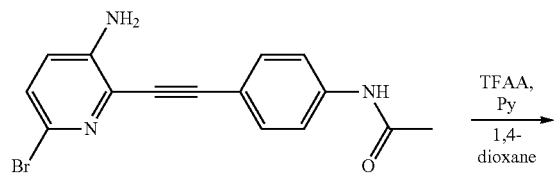

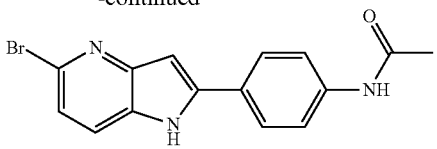

To a 0° C. solution of the product from step 3 (8.5 g, 25.7 mmol) and pyridine (4.0 g, 51.4 mmol) in 50 mL of 1,4-dioxane was added TFAA (10.8 g, 51.4 mmol). The resulting mixture was then heated to 100° C. overnight. The mixture was cooled and poured into 200 mL of water, and the precipitate was filtered and washed by water then dried to give a solid (1.3 g). MS (ESI) m/e (M+H⁺): 331.

Step 5

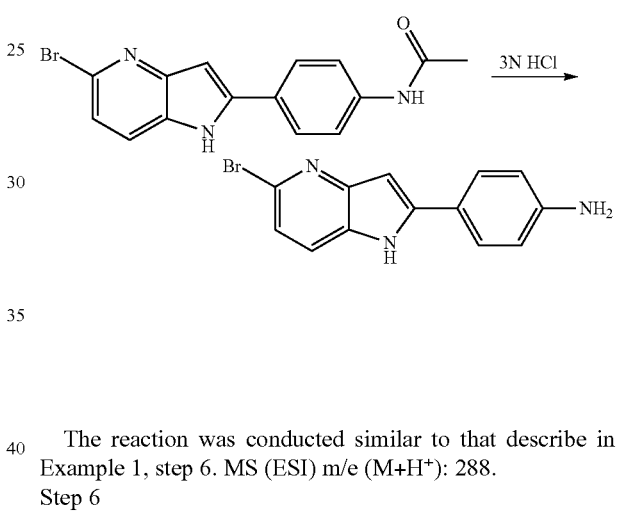

The reaction was conducted similar to that describe in Example 1, step 6. MS (ESI) m/e (M+H⁺): 288.

Step 6

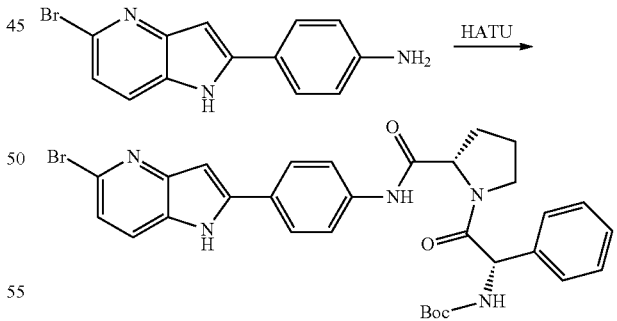

To a suspension of the product from step 5 (0.1 mmol), N-Boc-L-Phg-L-Pro-OH (0.1 mmol) and DIPEA (20 mg, 0.15 mmol) in 1 mL of CH₃CN was added HATU (42 mg, 0.12 mmol). The resulting mixture was stirred at RT overnight, concentrated and purified by RPLC to give the desired compound. MS (ESI) m/e (M+H⁺): 619. ¹H NMR (MeOD 400) δ: 7.85~7.77 (m, 5 H), 7.43~7.36 (m, 6 H), 6.89 (s, 1 H), 5.50 (s, 1H), 4.54 (d, J=8.0 Hz 1H), 3.93 (t, 1 H), 2.10~1.87 (m, 4 H) 1.41 (s, 9 H).

Example 5

(2S)—N-{3-chloro-2-[4-({[(2S)-1-(phenylacetyl)pyrrolidin-2-yl]carbonyl}amino)phenyl]-1H-pyrrolo[2,3-c]pyridin-5-yl}-1-(phenylacetyl)pyrrolidine-2-carboxamide

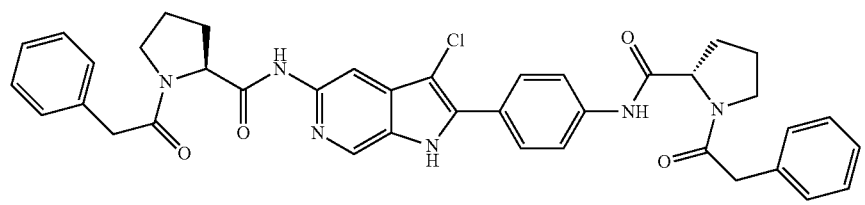 [SMILES: O=C(Nc1ccc(-c2[nH]c3cnc(NC(=O)[C@@H]4CCCN4C(=O)Cc4ccccc4)cc3c2Cl)cc1)[C@@H]1CCCN1C(=O)Cc1ccccc1]

Step 1

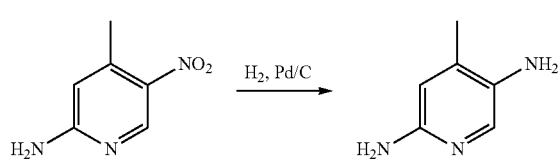

A heterogeneous mixture of 2-amino-4-methyl-5-nitropyridine (4.15 g, 27 mmol) and 10% Pd/C (0.4 g) in 50 mL of THF was stirred in 50 psi of $H_2$ for 3 hours. The mixture was filtered through CELITE and concentrated to yield a yellow solid (3.20 g). MS (ESI) m/e (M+H$^+$): 124. $^1$H NMR (DMSO): δ 7.38 (s, 1 H), 6.16 (s, 1 H), 4.84 (s, 2 H), 4.06 (s, 2 H), 1.96 (s, 3 H).

Step 2

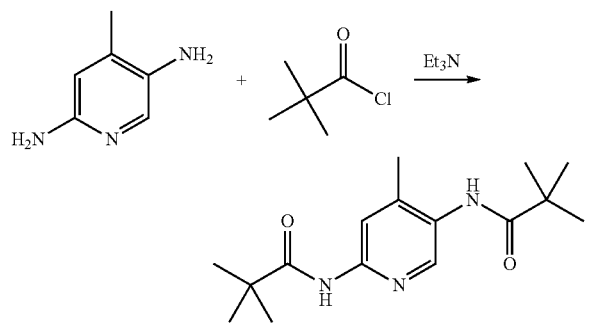

A mixture of diamine from step 1 (3.20 g, 26 mmol), TEA (5.25 g, 52 mmol) and a catalytic amount of DMAP in THF (100 mL) was stirred at 5-10° C., then treated with pivaloyl chloride (3.74 g, 31 mmol). The resulting mixture was stirred at RT for 5 hours, diluted with a 5% solution of citric acid, and extracted with EtOAc. The combined organic extracts were sequentially washed with water and brine, dried, filtered, and the filtrate was concentrated in vacuo to yield a residue. The residue was purified by column chromatography on silica gel to afford 7.4 g of the desired compound. MS (ESI) m/e (M+H$^+$): 292. $^1$H NMR (CDCl$_3$): δ 8.77 (s, 1 H), 8.47 (s, 1 H), 8.20 (s, 1 H), 7.15 (s, 1 H), 2.24 (s, 3 H), 1.30~1.32 (m, 18 H).

Step 3

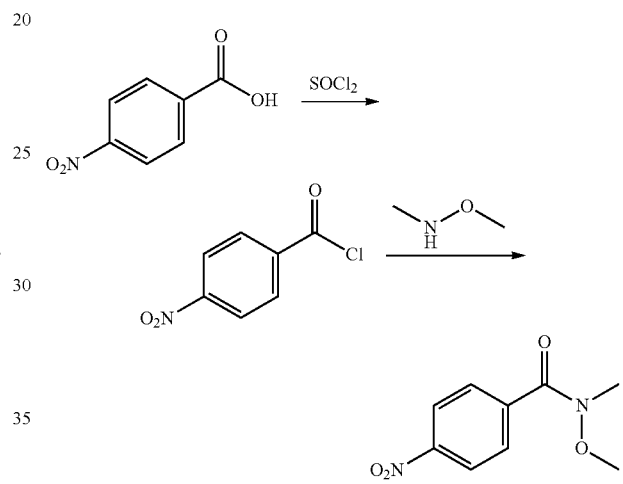

To a cooled solution of 4-nitrobenzoic acid (12 g, 72 mmol) in 50 mL of PhMe was added 20 mL of SOCl$_2$ drop wise. After the addition, the suspension was heated to reflux for 4 hours. The solvent was removed, and the residue was azeotroped with 50 mL of PhMe to afford 14.5 g of crude acid chloride. To a solution of TEA (101 g, 100 mmol), a catalytic amount of DMAP and N,O-dimethylhydroxylamine (5.3 g, 87 mmol) in 100 mL of DCM was added drop wise 14.5 g of the freshly prepared acid chloride in 100 mL of DCM. The resulting mixture was stirred at RT for 5 hours, then diluted with a 5% solution of citric acid, and extracted with DCM. The combined organic extracts were sequentially washed with water and brine, dried and filtered, and the filtrate was concentrated to yield a residue. The residue was purified by column chromatography on silica gel to afford 7.0 g of the Weinreb amide. MS (ESI) m/e (M+H$^+$): 211. $^1$H NMR (CDCl$_3$): δ 8.25 (d, J=8.8 Hz, 2 H), 7.82 (d, J=9.6 Hz, 2 H), 3.52 (s, 3 H), 3.82 (s, 3 H).

Step 4

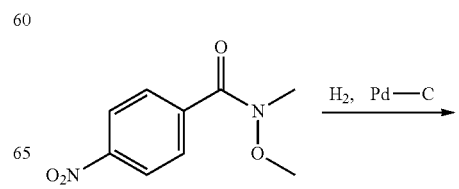

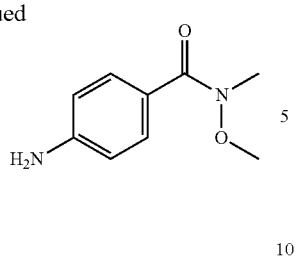

A heterogeneous mixture of the nitro compound above and 10% Pd/C in THF was stirred at STP with a balloon of H₂ for 3 hours. The mixture was filtered through CELITE, and concentrated to yield a yellow solid MS (ESI) m/e (M+H⁺): 181.
Step 5

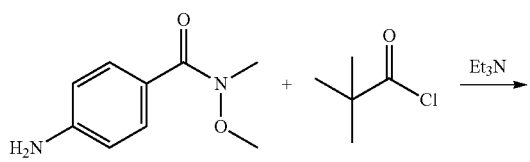

The product from step 4 was pivaloylated using conditions described in step 2. MS (ESI) m/e (M+H⁺): 265. ¹H NMR (CDCl₃): δ 7.66 (d, J=8.4 Hz, 2 H), 7.56 (d, J=8.8 Hz, 2 H), 3.51 (s, 3 H), 3.32 (s, 3 H).
Step 6

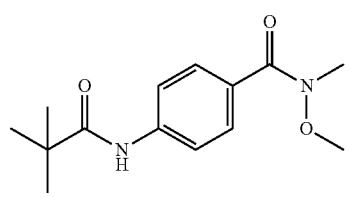

A solution of compound isolated from step 2 above (2.2 g, 7.5 mmol) in 15 mL of THF was cooled to below −40° C. t-BuLi in hexane (15 mL, 2.5 M, 37.5 mmol) was added dropwise, and the resulting solution was stirred at −40° C. for 1 hour. A solution of compound from step 5 (2.2 g, 8.25 mmol) in 10 mL of THF was added drop wise, and the resulting solution was continued to stir at this temperature for 30 minutes before being warmed to RT and stirred for 30 minutes again. An aqueous 5% citric acid solution was added to quench the reaction, which was extracted with DCM (×3), and the combined organic layers were washed with water and brine, dried over Na₂SO₄ and concentrated in vacuo. The residue was purified by preparative HPLC to yield a solid (0.4 g). MS (ESI) m/e (M+H⁺): 495. ¹H NMR (CDCl₃): δ 8.85 (s, 1 H), 8.68 (s, 1 H), 8.26 (s, 1 H), 8.03-8.05 (m, 3 H), 7.21 (d, J=8.8 Hz, 2 H), 7.53 (s, 1 H), 4.20 (s, 2 H), 1.33-1.29 (m, 27 H).
Step 7

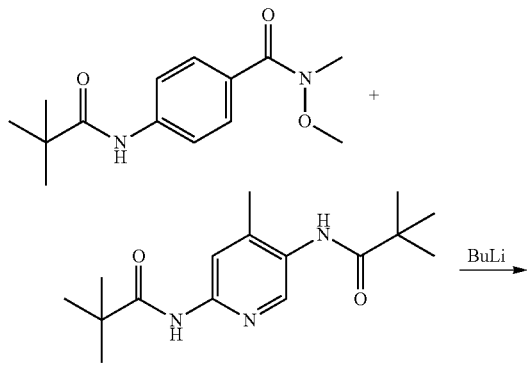

A solution of the product from step 6 (400 mg, 0.8 mmol) in 33% aqueous HBr (15 mL) was refluxed overnight. After cooling, the mixture was concentrated in vacuo. The residue was purified by preparative HPLC to give a solid (120 mg). MS (ESI) m/e (M+H⁺): 225. ¹H NMR (MeOD): δ 8.04 (s, 1 H), 7.78 (d, 2 H), 7.04 (d, 2 H), 6.86 (s, 1 H), 6.71 (s, 1 H).

Step 8

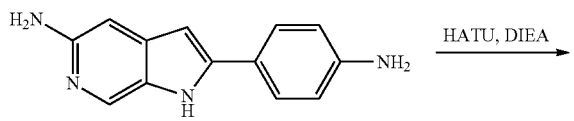

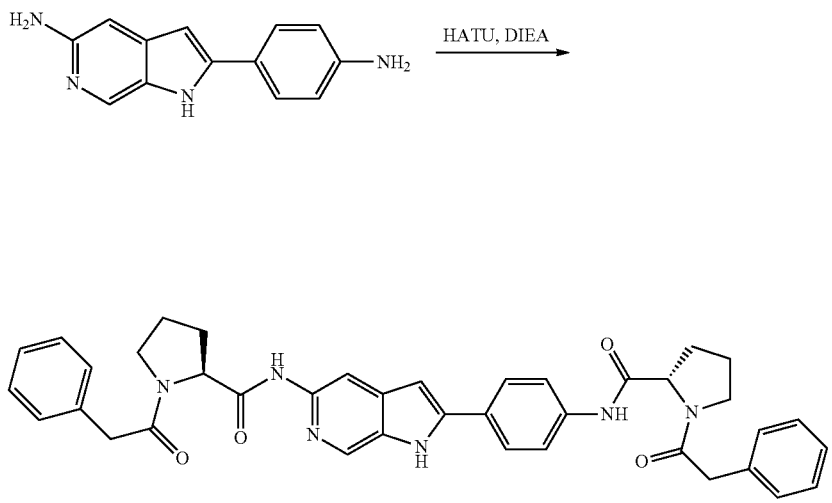

The product from step 7 was coupled to 2 equivalents of N-phenylacetyl-L-proline using 2 equivalents of HATU and DIEA in a manner similar to that shown in Example 1. MS (ESI) m/e (M+H$^+$): 687. $^1$H NMR (MeOD): δ 8.49~8.57 (m, 1 H), 7.38~7.45 (m, 2 H), 7.72 ~7.80 (m, 2 H), 5.15~5.20 (m, 4 H), 4.42~4.50 (m, 2 H), 3.57~2.59 (m, 4 H), 2.31~2.42 (m, 4 H), 1.89~2.15 (m, 6 H).

Step 9

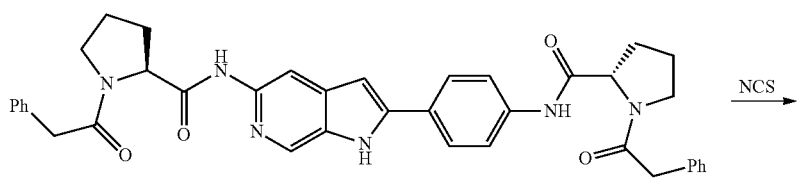

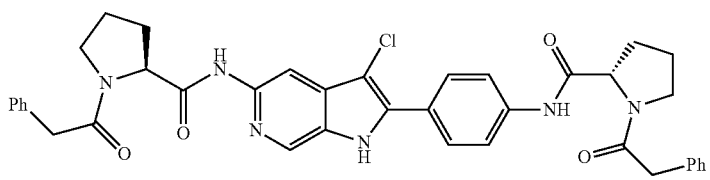

To a solution of product from step 8 (15 mg, 0.02 mmol) in 2 mL of dry THF was added NCS (2 mg, 0.015 mmol). The resulting mixture was stirred at RT for 30 minutes. The solvent was evaporated, and the residue was purified by prep HPLC to give 5 mg of the desired product. MS (ESI) m/e (M+H$^+$): 689. $^1$H NMR (MeOD): δ 8.53 (s, 1 H), 7.91 (d, J=9.2 Hz, 2 H), 7.77 (d, J=8.8 Hz, 2 H), 7.49 (s, 1 H), 7.20~7.23 (m, 10 H), 4.53~4.59 (m, 2 H), 3.64~3.79 (m, 8 H), 1.98~2.25 (m, 8 H).

Example 6

(2S)—N-{3-chloro-2-[4-({[(2S)-1-(phenylacetyl)pyrrolidin-2-yl]carbonyl}amino)phenyl]-1H-pyrrolo[2,3-b]pyridin-5-yl}-1-(phenylacetyl)pyrrolidine-2-carboxamide

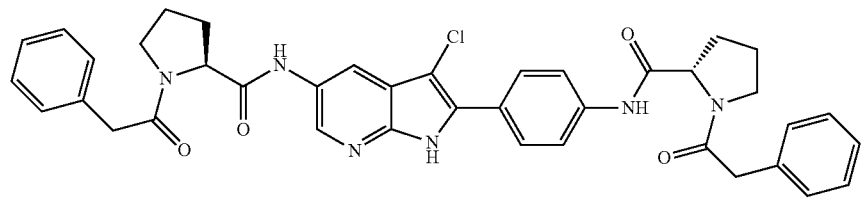 [SMILES: O=C(Nc1ccc(-c2[nH]c3ncc(NC(=O)[C@@H]4CCCN4C(=O)Cc4ccccc4)cc3c2Cl)cc1)[C@@H]1CCCN1C(=O)Cc1ccccc1]

Step 1

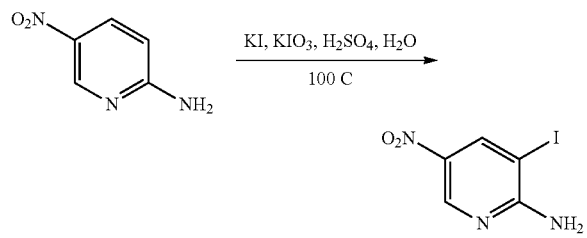

2-Amino-5-nitropyridine (7.00 g, 50.0 mmol) was dissolved in H$_2$SO$_4$ (2 M, 100 mL). Potassium iodate (4.28 g, 20 mmol) was added portion at RT with stirring. The solution was heated to 100° C. under reflux. Potassium iodide (8.00 g, 48.2 mmol) was added drop wise over 1 hour as a solution in water (20 mL). A brown solution resulted, with solid iodine collecting in the reflux condenser. Heating at reflux was continued for 30 minutes, and the mixture was cooled to RT. The mixture was adjusted to pH 7 with the careful addition of solid NaHCO$_3$. The mixture was diluted with water (200 mL) and CH$_2$Cl$_2$ (250 mL) was added. Solid sodium thiosulfate was added with vigorous stirring until the iodine coloration had been disappeared. A significant amount of yellowish solid remained out of solution, which was collected by filtration, washed with water and dried to give a yellow solid (10.5 g). The CH$_2$Cl$_2$ fraction was filtered through a silicone-treated filter paper and evaporated to give a yellow solid (2.4 g). The solids were combined to give the desired iodopyridine (12.7 g). MS (ESI) m/e (M+H$^+$): 266. $^1$H NMR (DMSO): δ 8.89 (s, 1 H), 8.62 (s, 1 H), 7.75 (bs, 1 H).

Step 2

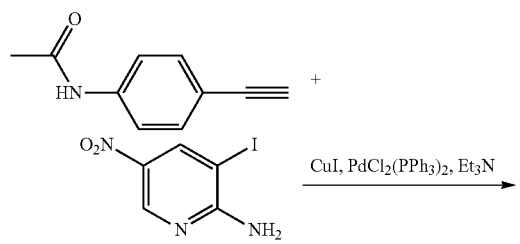

-continued

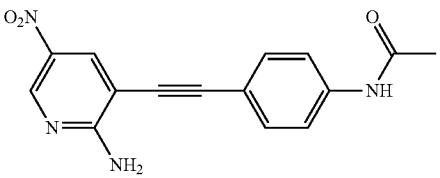

A solution of the iodide (1.05 g, 4.8 mmol), 4-ethynylacetanilide (636 mg, 4.0 mmol) and Pd(PPh$_3$)$_2$Cl$_2$ (76 mg, 0.4 mmol) in 10 mL of Et$_3$N and 5 mL of DMF was stirred at RT over 17 hours under N$_2$. The solvent was removed, and the residue was purified by column chromatography to give the product (0.9 g). MS (ESI) m/e (M+H$^+$): 297. $^1$H NMR (DMSO): δ 10.11 (s, 1H), 8.80 (s, 1H), 8.22 (s, 1H), 7.59 (s, 1H), 2.01 (s, 3H).

Step 3

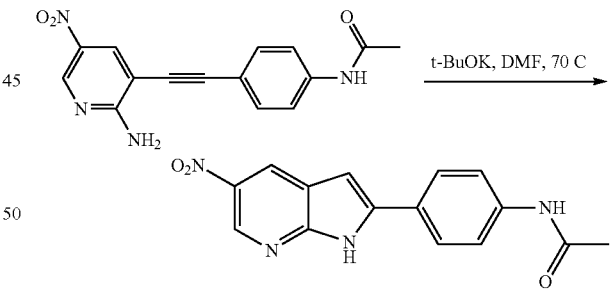

To a solution of the product from step 2 (730 mg, 2.5 mmol) in 3 mL of THF and 6 mL of DMF was added t-BuOK (580 mg, 5.25 mmol). The resulting mixture was heated to 70° C. for 6 hours. The solvent was removed and 10 mL of DCM, 5 mL of water was added, and the resulting precipitate was filtered to give the desired product as a yellow solid (680 mg). MS (ESI) m/e (M+H$^+$): 297. $^1$H NMR (DMSO): δ 10.11 (s, 1 H), 8.96 (s, 1 H), 8.65 (s, 1 H), 7.88 (d, J=8.8 Hz, 2 H), 7.63 (d, J=8.8 Hz, 2 H), 6.98 (s, 1 H), 2.02 (s, 3 H).

Step 4

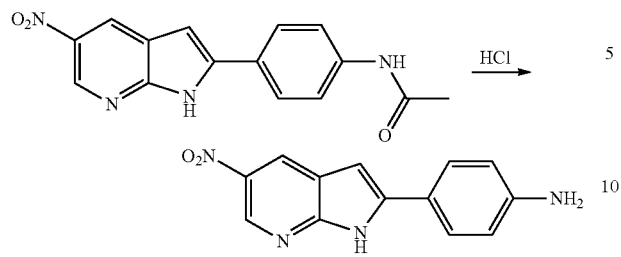

The synthetic method for the removal of the acetyl group was the same as used in Example 1, step 6. MS (ESI) m/e (M+H$^+$): 285.

Step 5

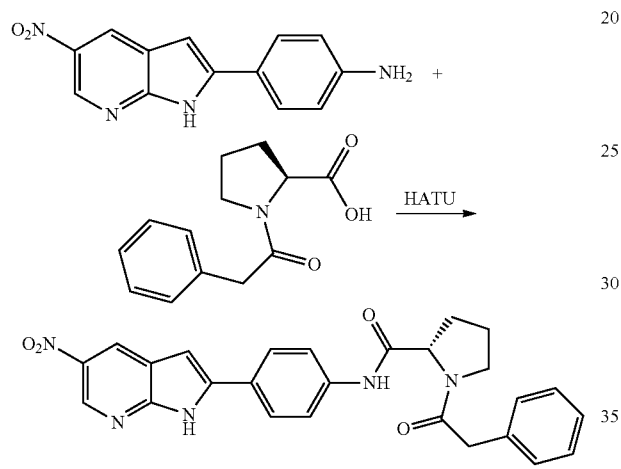

The synthetic method used for the coupling of the proline analog to the aniline prepared in step 4 was the same as used in Example 1, step 7. MS (ESI) m/e (M+H$^+$): 470.

Step 6

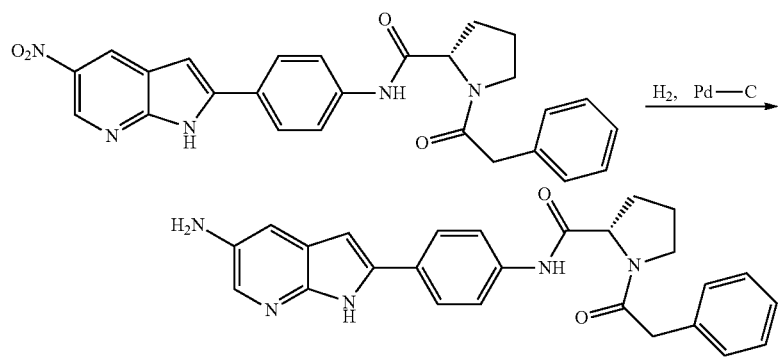

A heterogeneous mixture of product from step 6 (20 mg, 0.04 mmol) and 10% Pd/C in 5 mL of MeOH was stirred in 10 psi of H$_2$ for 3 hours. The mixture was filtered through CELITE, and concentrated in vacuo to yield a yellow solid (17 g). MS (ESI) m/e (M+H$^+$): 440.

Step 7

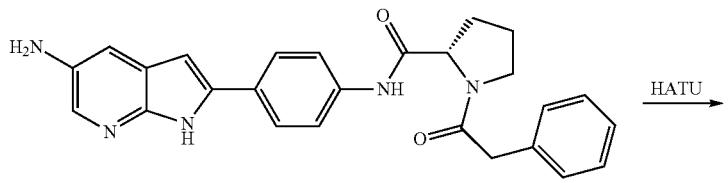

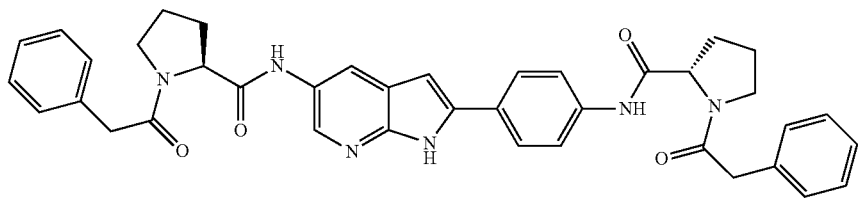

The product from step 6 was coupled to 1 equivalent of N-phenylacetyl-L-proline using 1 equivalent of HATU and DIEA in a manner similar to that shown in Example 1. MS (ESI) m/e (M+H$^+$): 655. $^1$H NMR (MeOD): δ 8.26 (s, 1 H), 8.19 (s, 1 H), 7.30~7.51 (m, 3 H), 7.18~7.27 (m, 1 H), 6.65 (s, 1 H), 4.51~4.56 (m, 2 H), 3.61~3.76 (m, 8 H), 1.95~2.15 (m, 8 H).

Step 8

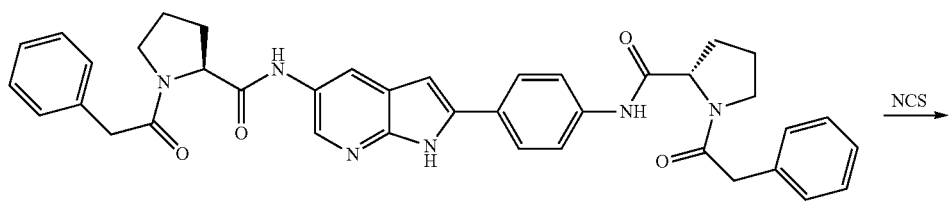

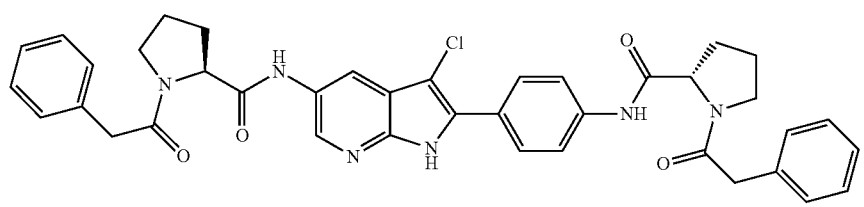

To a solution of product from step 7 (30 mg, 0.04 mmol) in 4 mL of dry THF was added NCS (4 mg, 0.03 mmol). The resulting mixture was stirred at RT for 30 minutes. The solvent was evaporated, and the residue was purified by prep HPLC to give the desired product. MS (ESI) m/e (M+H$^+$): 690. $^1$H NMR (MeOD): δ 8.29 (s, 1 H), 8.20 (s, 1 H), 7.81~7.84 (m, 2 H), 7.66~7.69 (m, 2 H), 7.18~7.29 (m, 10 H), 4.52~4.55 (m, 2 H), 3.62~3.78 (m, 8 H), 1.90~2.29 (m, 8 H).

Example 7

N-[4-(3-oxo-7-{2-oxo-2-[(2S)-1-(phenylacetyl)pyrrolidin-2-yl]ethyl}-3,7-dihydroimidazo[1,2-a]pyrazin-2-yl)phenyl]-1-(phenylacetyl)-L-prolinamide

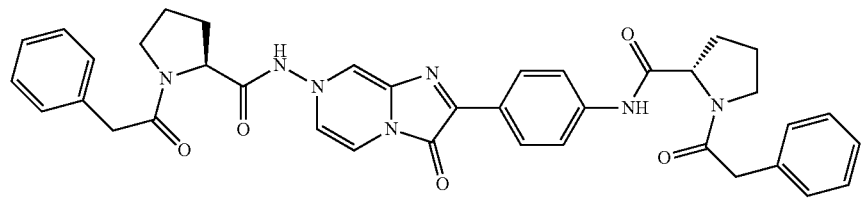 [SMILES: O=C(Nc1ccc(-c2nc3cn(NC(=O)[C@@H]4CCCN4C(=O)Cc4ccccc4)ccn-3c2=O)cc1)[C@@H]1CCCN1C(=O)Cc1ccccc1]

Step 1

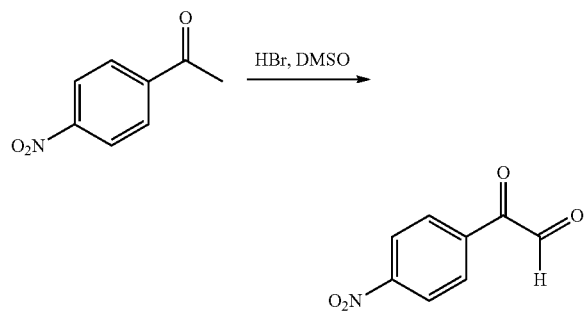

To a stirred solution of 4-nitroacetophenone (20 g, 121 mmol) in 100 ml of DMSO was added slowly 42 ml of 48% aqueous HBr (363 mmol). The solution was stirred in an open flask at 55° C. and the reaction was followed by TLC. When the starting material was consumed, the solution was poured into ice. The solid products were filtered, washed with water, and dried under vacuum at RT over $P_2O_5$.

Step 2

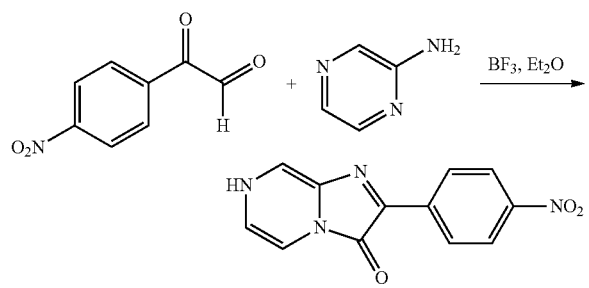

Arylglyoxal hydrate (5 g, 27.8 mmol) was added in one portion over a slurry of the heterocyclic amine (2.773 g, 29.2 mmol) in methylene chloride (10 ml). The resulting suspension was treated with 1 drop of freshly distilled $BF_3.Et_2O$ and stirred until most of the amine was consumed. The reaction products were isolated as hydrates by filtration of the thick, intensely colored reaction mixture. The residue obtained by concentration is allowed to cool, filtered with suction, washed twice with diethyl ether and dried under reduced pressure to give the desired product (4 g). MS (ESI) m/e (M+H$^+$): 256.

Step 3

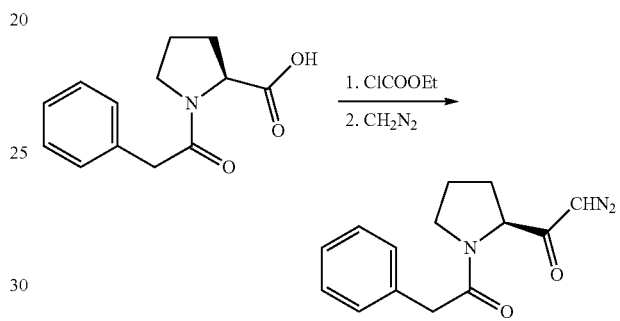

The N-protected proline (10 g, 42.8 mmol) in dry ether (60 ml) and THF (60 ml) was stirred under argon at −25° C. TEA (42.8 mol, 4.08 ml) and ethyl chloroformate (42.8 mmol, 2.6 4.14 ml) were added to this solution. The solution was stirred for further 30 minutes, the temperature then allowed to reach −10° C., and the diazomethane solution in ether (2-3 equivalents) was added drop wise. The suspension was stirred for an additional 3 hours and allowed to reach ambient temperature. The triethylamine hydrochloride was then filtered off, and the filtrate was evaporated to half of its original volume. The resulting solution was washed with saturated aqueous $NaHCO_3$ (50 ml) and brine (50 ml). The organic layer was dried and evaporated to give a crude product, which was used without further purification. MS (ESI) m/e (M+H$^+$): 258.

Step 4

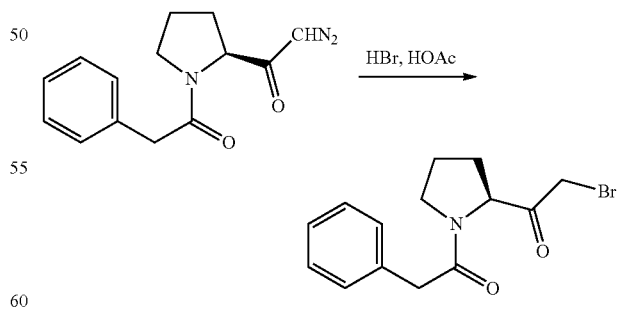

To a solution of a-diazoketone (2 g, 7.78 mmol) in glacial HOAc (25 ml) was treated with 48% HBr (2.8 ml) drop wise with stirring. After stirring for 1 hour, the reaction mixture was extracted with DCM and washed with water. Evaporation of the solvent and crystallization from ether-pet ether gave the pure product. MS (ESI) m/e (M+H$^+$): 310.

Step 5

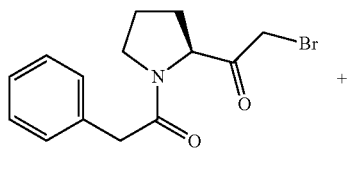
+
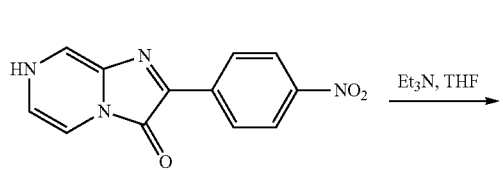

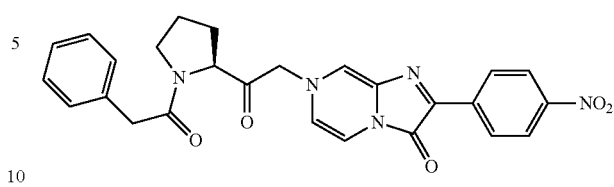

The product from step 4 (420 mg, 1.35 mmol) and the heterocycle from step 2 (347 mg, 1.35 mmol) in THF (2 ml) were stirred at RT overnight with Et$_3$N (0.3 mL). When the reaction was completed, the mixture was concentrated, and the residue was purified by RPLC to give the product (300 mg). MS (ESI) m/e (M+H$^+$): 486.

Step 6

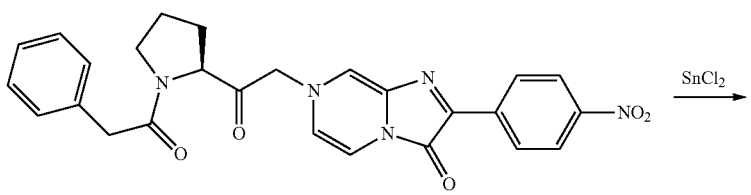

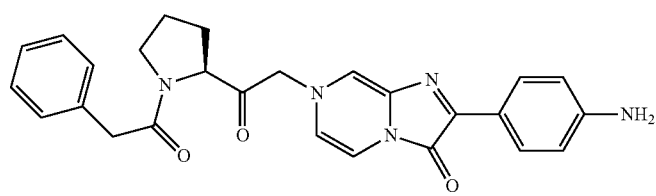

A solution of the product from step 5 (180 mg, 0.371 mmol) in absolute EtOH (3 ml) was added to stannous chloride dihydrate (418.6 mg, 1.85 mmol), and the mixture was stirred at 70° C. for 2 hours. The reaction mixture was cooled to RT and poured into ice/water (50 ml), and the pH was made strongly alkaline by the addition of saturated NaOH (100 ml) before being extracted with EtOAc (2×). The organic phase was combined and washed with brine, dried by MgSO$_4$, filtered, and concentrated to yield the crude product (150 mg). MS (ESI) m/z: (M+H$^+$) 456.

Step 7

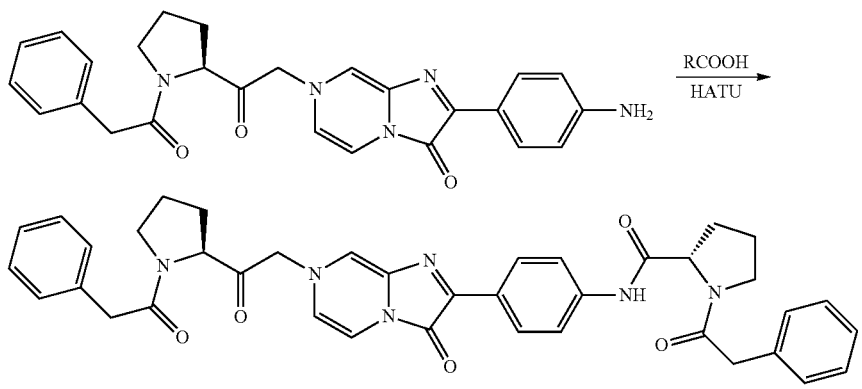

The mixture of the product from step 6 (30 mg, 0.066 mmol), N-phenylacetyl-L-proline (46.08 mg, 0.197 mmol), DIPEA (50.1 mg, 0.197 mmol) in CH$_3$CN (2 mL) was stirred at RT for 5 minutes, then HATU (74.86 mg, 0.197 mmol) was added into the mixture. The mixture was stirred at RT overnight, concentrated, and the residue was purified by RPLC to give the desired compound (20 mg). $^1$H NMR (DMSO) δ: 9.26 (s, 1H), 8.84-8.86 (m, 2H), 7.79-8.03 (m, 4H), 7.11-7.31 (m, 12H), 4.41~4.63 (m, 2H), 3.52~3.80 (m, 12H), 2.26~2.12 (m, 2H), 1.87~1.75 (m, 6H).

Example 8

(2S)-1-(cyclobutylcarbonyl)-N-{2-[4-({[(2S)-1-(pyridin-3-ylcarbonyl)pyrrolidin-2-yl]carbonyl}amino)phenyl]-1H-benzimidazol-5-yl}pyrrolidine-2-carboxamide

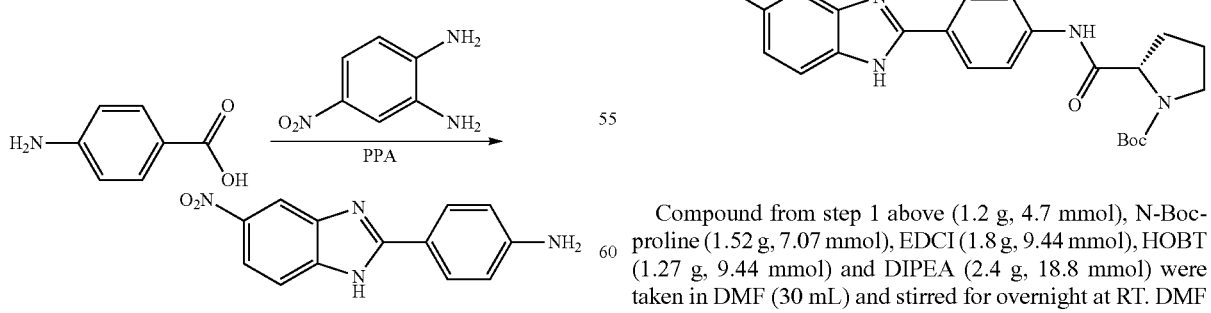

Step 1

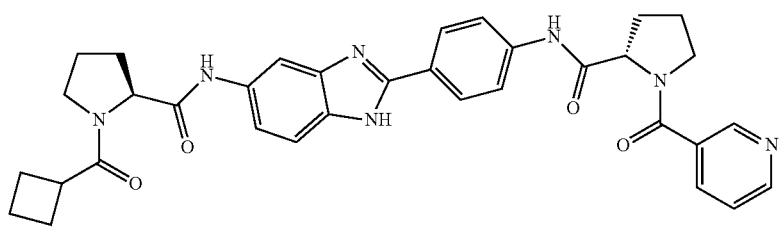 [SMILES: O=C(Nc1ccc(-c2nc3cc(NC(=O)[C@@H]4CCCN4C(=O)C4CCC4)ccc3[nH]2)cc1)[C@@H]1CCCN1C(=O)c1cccnc1]

p-Aminobenzoic acid (0.200 g, 1.45 mmol) and nitrophenylene diamine (0.221 g, 1.45 mmol) were added into PPA (30 mL). The mixture was stirred at 210° C. for 20 minutes. Then, it was poured into ice water and extracted with DCM. The organic layer was washed with brine, dried (NaSO$_4$), filtered and concentrated to afford 200 mg of the desired compound. MS m/z: 255 (M+1).

Step 2

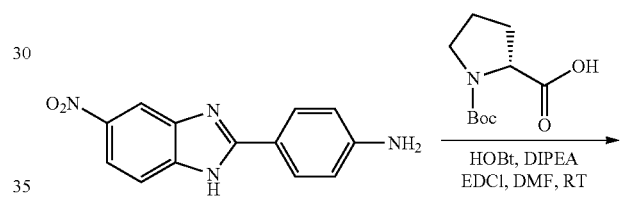

-continued

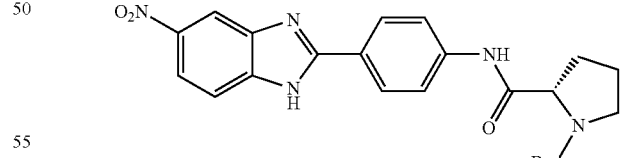

Compound from step 1 above (1.2 g, 4.7 mmol), N-Boc-proline (1.52 g, 7.07 mmol), EDCI (1.8 g, 9.44 mmol), HOBT (1.27 g, 9.44 mmol) and DIPEA (2.4 g, 18.8 mmol) were taken in DMF (30 mL) and stirred for overnight at RT. DMF was removed under reduced pressure, and the residue was extracted with DCM/water. The organic layer was washed with brine, dried (NaSO$_4$), concentrated and purified by column (DCM: MeOH/100:1) to afford 1.2 g of the desired compound. $^1$H NMR (MeOD) δ 8.49 (s, 1H), 8.28-8.19 (m, 3H), 7.79-7.76 (d, J=4.4 Hz, 2H), 7.72-7.65 (m, 1H), 4.41-4.29 (t, J=8.8 Hz, 1H), 3.59-3.51 (m, 2H), 2.18-1.95 (m, 4H), 1.49 (s, 9H).

Step 3

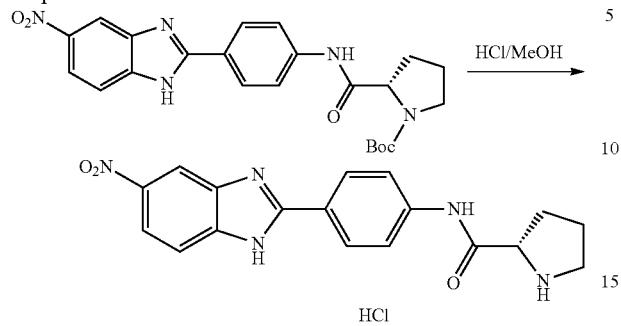

Compound from step 2 (0.600 g, 1.06 mmol) was stirred in MeOH/HCl (10 mL) for 1 hour at RT, and solvent was removed under reduced pressure. The resulting compound was dried at high vacuum to afford 370 mg of desired compound.

Step 4

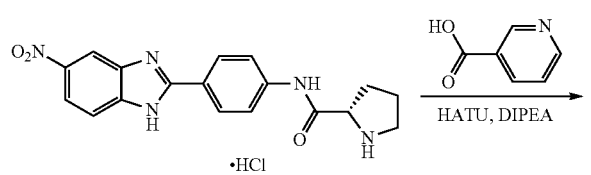

The product from step 3 (0.370 g, 1.052 mmol), pyridine-3-carboxylic acid (0.157 g, 1.27 mmol), HATU (1.2 g, 3.18 mmol) and DIPEA (0.814 g, 6.36 mmol) were taken in DMF (10 mL) and stirred for overnight at RT. DMF was removed under reduced pressure, and the residue was extracted with DCM/water. The organic layer was washed with brine, dried (NaSO$_4$), concentrated and purified by column (DCM: MeOH/100:1) to afford 300 mg of desired compound. $^1$H NMR (MeOD) δ ppm: 0.883 (s, 1H), 0.87-0.85 (d, J=4.4 Hz, 1H), 8.49 (s, 1H), 8.21-8.18 (m, 1H), 8.17-8.10 (m, 3H), 7.98-7.95 (d, J=8.8 Hz, 2H), 7.73-7.68 (m, 1H), 7.60-7.51 (m, 1H), 4.79-4.76 (t, J=6 Hz, 1H), 3.77-3.73 (m, 2H), 3.27-3.19 (m, 2H), 2.19-2.12 (m, 2H).

Step 5

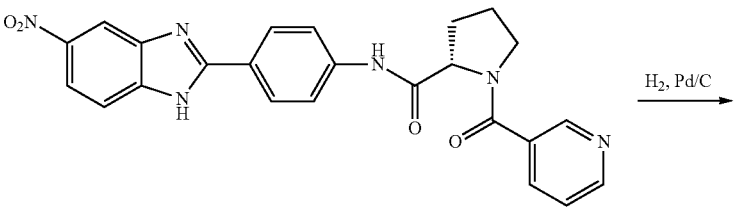

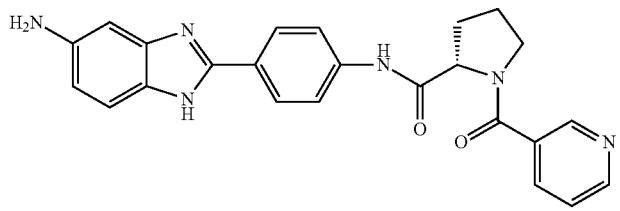

The product from step 4 (0.300 g, 0.657 mmol) was taken in MeOH (10 mL) and Pd/C (0.07 g) was added under N$_2$. The reaction was stirred for overnight at RT under H$_2$. The Pd/C was filtered through C<small>ELITE</small>, and the filtrate was concentrated under reduced pressure to afford 234 mg of desired compound.

Step 6

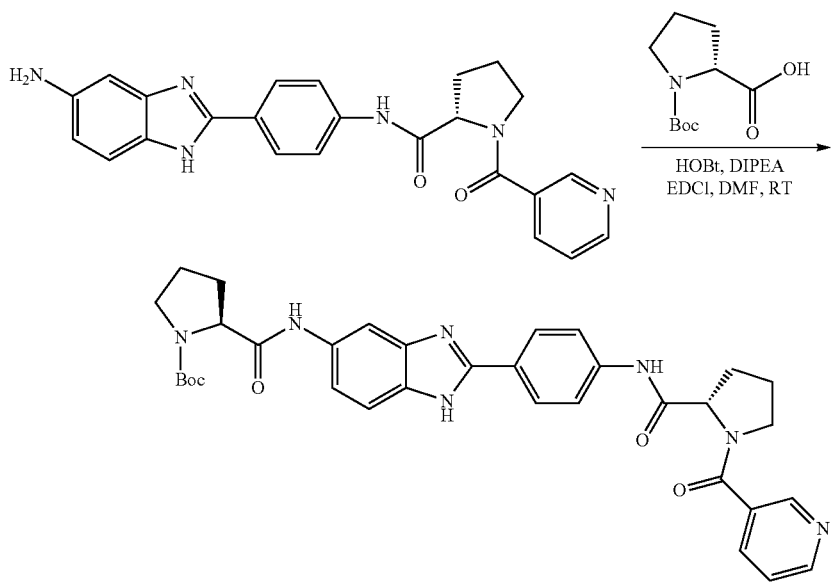

The product from step 5 (0.370 g, crude), N-Boc-proline (0.157 g, 1.27 mmol), HATU (1.2 g, 3.18 mmol) and DIPEA (0.814 g, 6.36 mmol) were taken in DMF (10 mL) and stirred for overnight at RT. DMF was removed under reduced pressure, and the residue was extracted with DCM/water. The organic layer was washed with brine, dried (NaSO$_4$), concentrated and purified by column (DCM: MeOH/100:1) to afford 300 mg of targeted compound.

Step 7

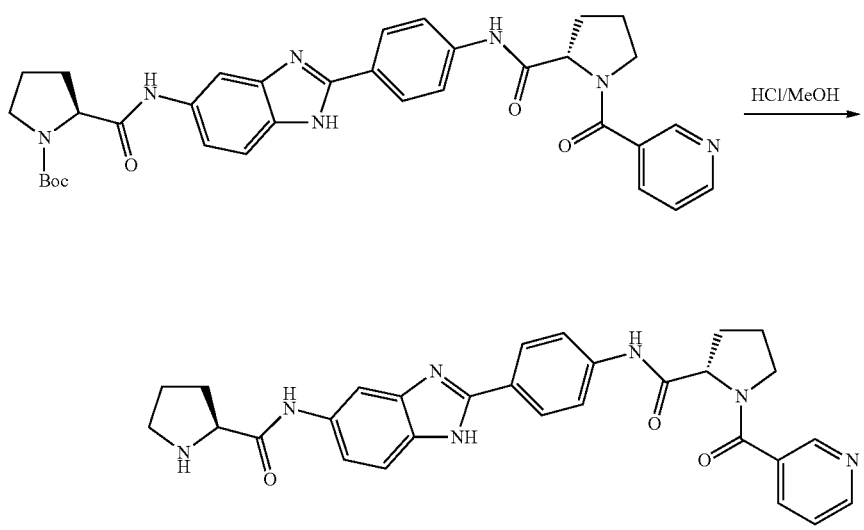

The product from step 6 (0.600 g, 1.06 mmol) was stirred in MeOH/HCl (15 mL) for 1 hour at RT, and the solvent was removed under reduced pressure. The compound was dried at high vacuum to afford 370 mg of desired compound. $^1$H NMR (MeOD) δ: 9.39 (s, 1H), 9.18-8.82 (m, 2H), 8.39-8.38 (m, 1H), 8.32-8.22 (m, 1H), 8.21-8.10 (m, 2H), 8.09-7.98 (m, 2H), 7.86-7.72 (m, 1H), 7.71-7.65 (m, 1H), 4.87-4.84 (t, J=8.8 Hz, 2H), 3.51-3.34 (m, 8H), 2.49-2.38 (m, 4H).

Step 8

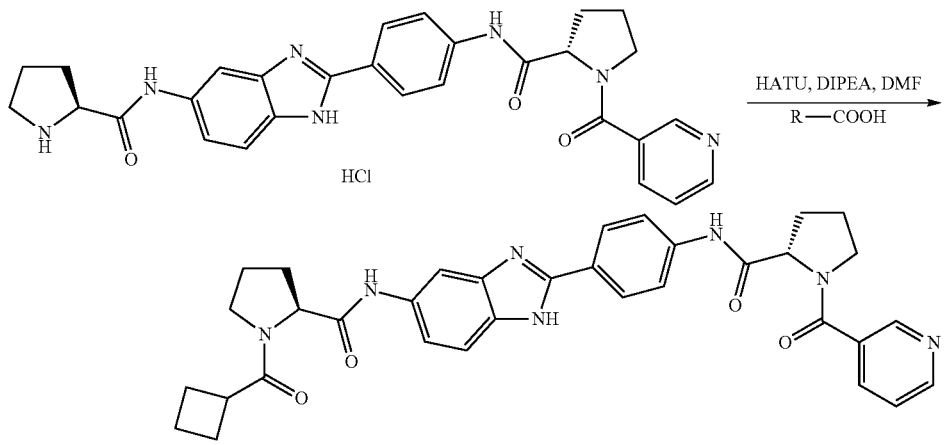

The product from step 7 (0.100 g, 0.191 mmol), cyclobutanecarboxylic acid (0.018 mg, 0.183 mmol), HATU (0.116 g, 0.305 mmol) and DIPEA (0.059 g, 0.416 mmol) were taken in DMF (5 mL) and stirred for overnight at RT. DMF was removed under reduced pressure, and the residue was extracted with DCM/water. The organic layer was washed with brine, dried (NaSO$_4$) and concentrated. The residue was purified by HPLC purification to afford 12 mg of the final product. $^1$H NMR (MeOD) δ: 8.91 (s, 1H), 8.75 (s, 1H), 8.41 (s, 1H), 8.25 (s, 1H), 7.96-7.95 (d, J=5.2 Hz, 4H), 7.73-7.67 (d, J=3.2 Hz, 2H), 7.52-7.51 (d, J=3.2 Hz, 1H), 4.54-4.82 (t, J=3.6 Hz, 2H), 3.63-3.46 (m, 4H), 2.48-2.46 (t, J=2 Hz, 1H), 2.34-2.29 (m, 6H), 2.18-2.10 (m, 4H), 2.08-2.02 (m, 4H).

Examples 9-15

Compounds of Examples 9-15 were prepared in a similar manner to Example 8.

| Example | Structure | MW | Name |
|---|---|---|---|
| 9 | 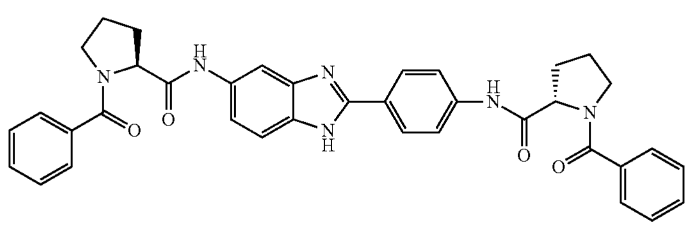 [SMILES: O=C(Nc1ccc(-c2nc3cc(NC(=O)[C@@H]4CCCN4C(=O)c4ccccc4)ccc3[nH]2)cc1)[C@@H]1CCCN1C(=O)c1ccccc1] | 626.721 | (2S)-1-(phenylcarbonyl)-N-{4-[5-({[(2S)-1-(phenylcarbonyl)pyrrolidin-2-yl]carbonyl}amino)-1H-benzimidazol-2-yl]phenyl}pyrrolidine-2-carboxamide |
| 10 | 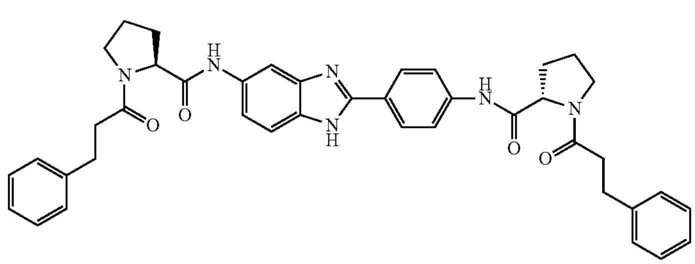 [SMILES: O=C(Nc1ccc(-c2nc3cc(NC(=O)[C@@H]4CCCN4C(=O)CCc4ccccc4)ccc3[nH]2)cc1)[C@@H]1CCCN1C(=O)CCc1ccccc1] | 682.83 | (2S)-1-[(4Z,5Z)-4-ethylidenehept-5-enoyl]-N-{2-[4-({[(2S)-1-(3-phenylpropanoyl)pyrrolidin-2-yl]carbonyl}amino)phenyl]-1H-benzimidazol-5-yl}pyrrolidine-2-carboxamide |
| 11 | 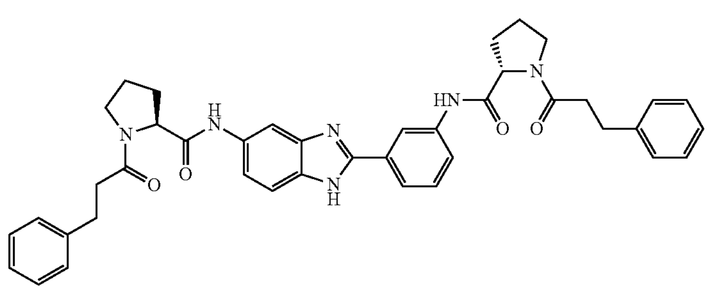 [SMILES: O=C(Nc1cccc(-c2nc3cc(NC(=O)[C@@H]4CCCN4C(=O)CCc4ccccc4)ccc3[nH]2)c1)[C@@H]1CCCN1C(=O)CCc1ccccc1] | 682.83 | (2S)-1-[(4Z,5Z)-4-ethylidenehept-5-enoyl]-N-{2-[3-({[(2S)-1-(3-phenylpropanoyl)pyrrolidin-2-yl]carbonyl}amino)phenyl]-1H-benzimidazol-5-yl}pyrrolidine-2-carboxamide |

| Example | Structure | MW | Name |
|---|---|---|---|
| 12 | 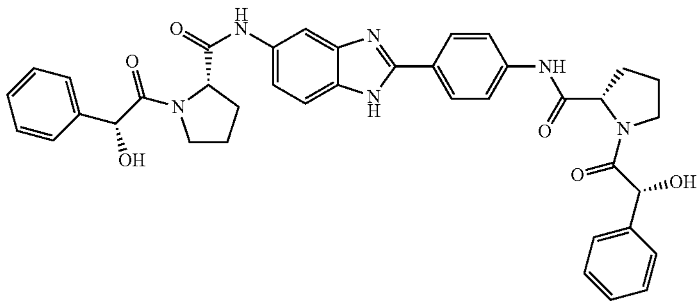 [SMILES: O=C(Nc1ccc(-c2nc3cc(NC(=O)[C@@H]4CCCN4C(=O)[C@H](O)c4ccccc4)ccc3[nH]2)cc1)[C@@H]1CCCN1C(=O)[C@H](O)c1ccccc1] | 686.774 | (2S)-1-[(2R)-2-hydroxy-2-phenylacetyl]-N-(4-{5-[({(2S)-1-[(2R)-2-hydroxy-2-phenylacetyl]pyrrolidin-2-yl}carbonyl)amino]-1H-benzimidazol-2-yl}phenyl)pyrrolidine-2-carboxamide |
| 13 | 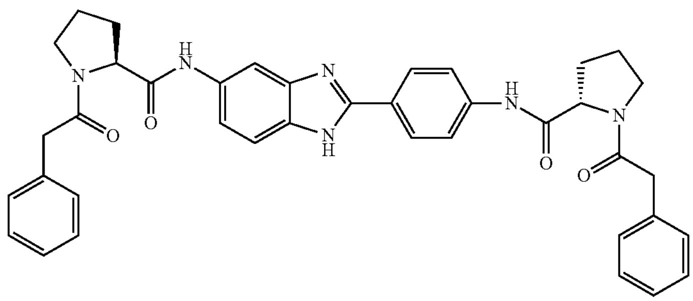 [SMILES: O=C(Nc1ccc(-c2nc3cc(NC(=O)[C@@H]4CCCN4C(=O)Cc4ccccc4)ccc3[nH]2)cc1)[C@@H]1CCCN1C(=O)Cc1ccccc1] | 654.776 | (2S)-1-(phenylacetyl)-N-{4-[5-({[(2S)-1-(phenylacetyl)pyrrolidin-2-yl]carbonyl}amino)-1H-benzimidazol-2-yl]phenyl}pyrrolidine-2-carboxamide |
| 14 | 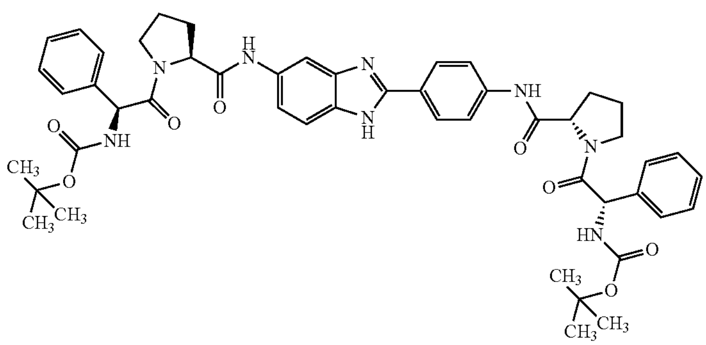 [SMILES: CC(C)(C)OC(=O)N[C@H](C(=O)N1CCC[C@H]1C(=O)Nc1ccc(-c2nc3cc(NC(=O)[C@@H]4CCCN4C(=O)[C@@H](NC(=O)OC(C)(C)C)c4ccccc4)ccc3[nH]2)cc1)c1ccccc1] | 885.041 | tert-butyl {(1S)-2-[(2S)-2-({4-[5-({[(2S)-1-{(2S)-2-[(tert-butoxycarbonyl)amino]-2-phenylacetyl}pyrrolidin-2-yl]carbonyl}amino)-1H-benzimidazol-2-yl]phenyl}carbamoyl)pyrrolidin-1-yl]-2-oxo-1-phenylethyl}carbamate |
| 15 | 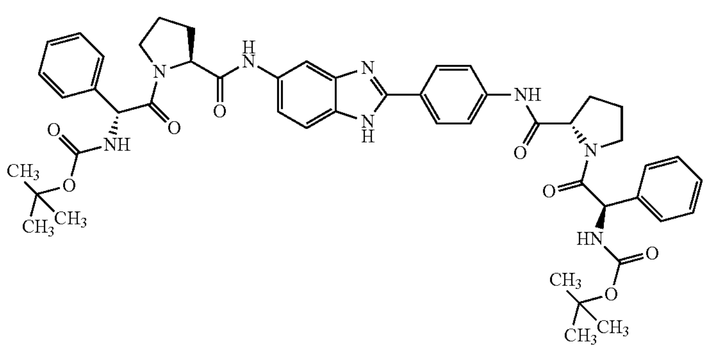 [SMILES: CC(C)(C)OC(=O)N[C@@H](C(=O)N1CCC[C@H]1C(=O)Nc1ccc(-c2nc3cc(NC(=O)[C@@H]4CCCN4C(=O)[C@H](NC(=O)OC(C)(C)C)c4ccccc4)ccc3[nH]2)cc1)c1ccccc1] | 885.041 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-1H-benzimidazol-2-yl]phenyl}carbamoyl)pyrrolidin-1-yl]-2-oxo-1-phenylethyl}carbamate |

Example 16

Benzyl (2S)-2-{[4-(4-{[(4-methylphenyl)sulfonyl]amino}-1H-benzimidazol-2-yl)phenyl]carbamoyl}pyrrolidine-1-carboxylate

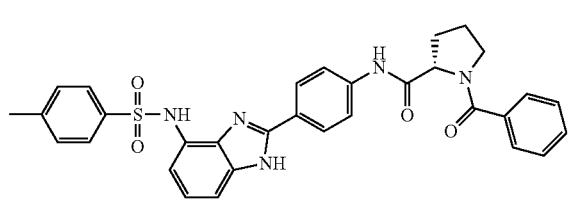 [SMILES: Cc1ccc(S(=O)(=O)Nc2cccc3[nH]c(-c4ccc(NC(=O)[C@@H]5CCCN5C(=O)c5ccccc5)cc4)nc23)cc1]

Step 1

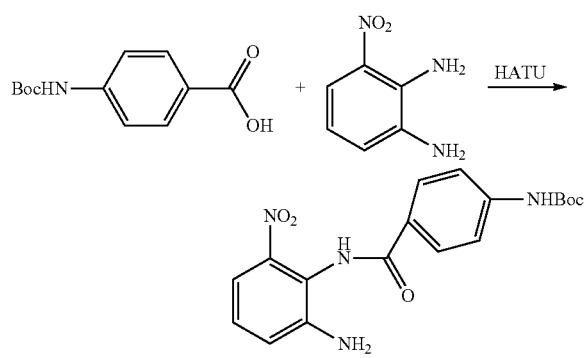

To a solution of N-Boc-p-aminobenzoic acid (1.86 g, 7.84 mmol) in DMF, 3-nitrophenylenediamine (1.0 g, 6.536 mmol), HOBt (0.875 g, 6.536 mmol) and EDCI (2.5 g, 9.804 mmol) were added, and reaction was stirred for overnight at RT. The excess of solvent was removed under reduced pressure, and the residue was diluted with DCM. The organic layer was washed with brine, dried (NaSO$_4$), filtered, concentrated and purified by column to obtain 400 mg of compound. MS m/z: 273 (M+1).

Step 2

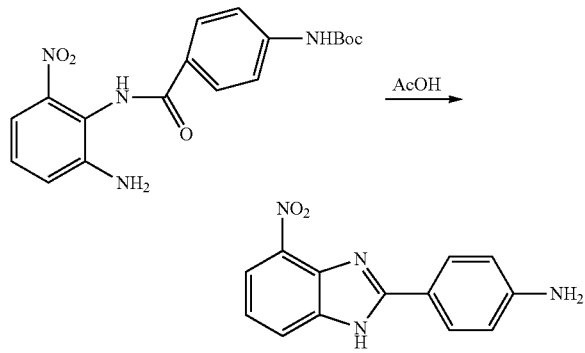

The compound from step 1 above (0.600 g, 1.611 mmol) and KOAc (0.158 g, 1.609 mmol) were taken in HOAc (9.3 mL). The reaction was stirred at 120° C. for overnight, cooled to RT and poured into ice-water. The aqueous layer was extracted with DCM. The organic layer was washed with brine, dried (NaSO$_4$), filtered and concentrated to obtain 120 mg of the desired compound. MS m/z: 255 (M+1). $^1$H NMR (DMSO) δ: 11.44 (s, 1H), 8.95-9.01 (m, 2H), 8.81-8.83 (d, J=8.0 Hz, 2H), 8.22-8.27 (m, 1H), 8.22-8.27 (m, 2H), 4.97 (s, 2H).

Step 3

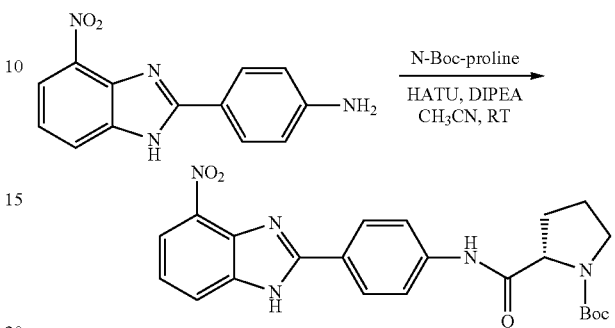

To a solution of the aniline (0.200 g, 0.787 mmol) in DMF, N-Boc-proline (0.186 g, 0.865 mmol), DIPEA (0.302 g, 2.361 mmol) and HATU (0.329 g, 0.865 mmol) were added. The reaction was stirred for overnight. The excess of solvent was removed under reduced pressure, and the residue was diluted with DCM. The organic layer was washed with brine, dried (NaSO$_4$), filtered, concentrated and purified by column to obtain 150 mg of the desired. MS m/z: 452 (M+1). $^1$H NMR (MeOD) δ: 8.70-8.73 (m, 2H), 8.40-8.42 (d, J=8 Hz, 2H), 7.87-7.89 (d, J=8 Hz, 1H), 7.50-7.53 (m, 2H), 6.78-6.80 (d, J=8 Hz, 1H), 3.83 (s, 1H), 3.69-3.76 (m, 2H), 3.56-3.60 (m, 4H), 1.37-1.43 (m, 9H).

Step 4

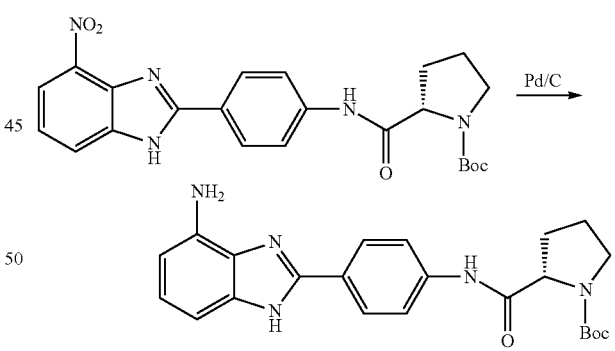

To a solution of compound from step 3 above (0.200 g, 0.443 mmol), Pd/C (10 mg) was added under argon, and the reaction was stirred for 2 hours in H$_2$. The Pd/C was filtered and washed with MeOH for several times. The solvent was evaporated to obtain 180 mg of desired compound. MS m/z: 422 (M+1). $^1$H NMR (MeOD) δ: 9.51 (s, 1H), 7.95-8.20 (m, 1H), 7.58-7.60 (m, 1H), 7.19-7.48 (m, 2H), 6.78-6.87 (m, 2H), 6.38 (s, 1H), 4.25-4.42 (m, 1H), 3.34-3.67 (m, 2H), 1.79-2.20 (m, 4H), 1.17-1.41 (m, 9H).

Step 5

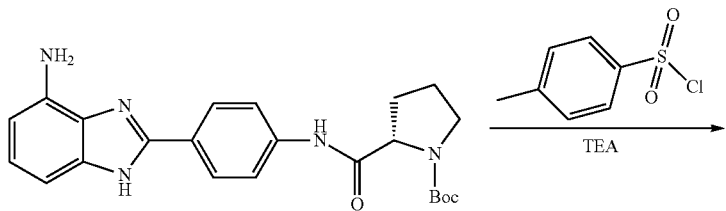

To a solution of the compound from step 4 above (0.196 g, 0.465 mmol) in THF, TEA (0.070 g, 0.693 mmol) and 4-methylbenzene-1-sulfonyl chloride (0.088 g, 0.461 mmol) were added drop wise at 0° C. The reaction was stirred for overnight, and the solvent was removed under reduced pressure. The residue was diluted with DCM and washed with brine. The organic layer was dried ($NaSO_4$), filtered and concentrated. The residue was purified by preparative TLC to afford 110 mg of desired compound. MS m/z: 576 (M+1). $^1$H NMR (MeOD) δ: 7.98-8.00 (d, J=8.0 Hz, 2H), 7.78-7.80 (d, J=8.0 Hz, 2H), 7.66-7.68 (d, J=8.0 Hz, 2H), 7.26-7.28 (m, 11H), 7.19-7.21 (d, J=8.0 Hz, 2H), 7.07-7.09 (m, 2H), 4.36-4.38 (m, 1H), 3.55-3.58 (m, 2H), 2.32-2.35 (m, 4H), 1.89-2.11 (m, 3H), 1.50 (s, 9H).

Step 6

The product from step 5 above (0.180 g, 0.312 mmol) was stirred in MeOH/HCl (5.0 mL) for 1 hour at RT. The solvent was removed under reduced pressure and dried at high vacuum. It was used directly without any further purification. The residue was taken in DMF, benzoic acid (0.042 g, 0.344 mmol), DIPEA (0.320 g, 2.504 mmol) and HATU (0.143 g, 0.375 mmol) were added. The reaction was stirred for overnight at RT. The excess of solvent was removed under reduced pressure, and the residue was diluted with DCM. The organic layer was washed with brine, dried ($NaSO_4$), filtered, concentrated and purified by column to afford 40 mg of the final compound. MS m/z: 580 (M+1). $^1$H NMR (MeOD) δ: 7.92-7.94 (d, J=8.8 Hz, 2H), 7.23-7.68 (m, 14H), 6.81-6.83 (d, J=10 Hz, 1H), 5.21 (s, 2H), 4.65-4.79 (m, 1H), 3.52-3.89 (m, 2H), 2.47-2.58 (m, 1H), 2.43 (s, 3H), 1.93-2.23 (m, 3H).

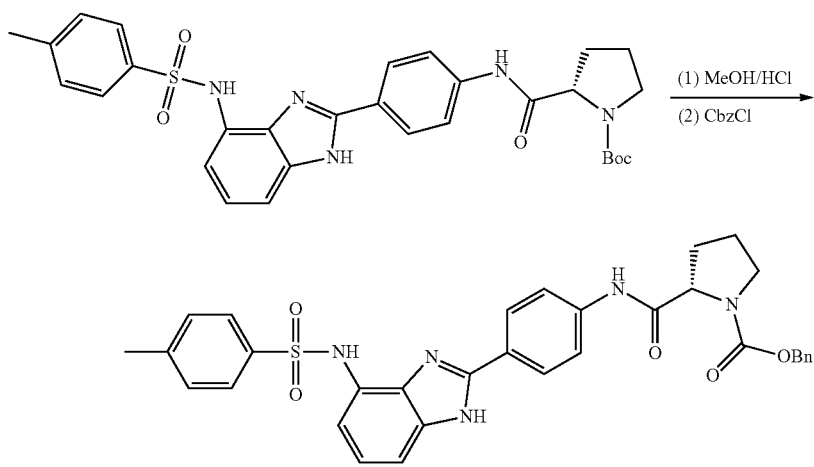

Example 17

(2S)-1-(3-phenylpropanoyl)-N-{4-[5-({[(2S)-1-(3-phenylpropanoyl)pyrrolidin-2-yl]carbonyl}amino)-1,3-benzoxazol-2-yl]phenyl}pyrrolidine-2-carboxamide

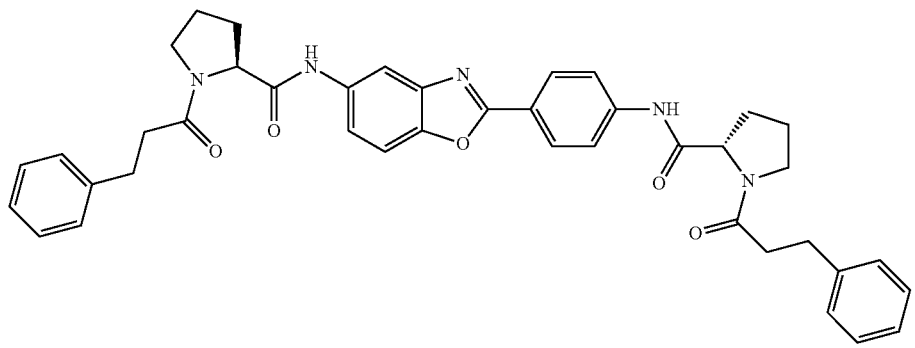 [SMILES: O=C(Nc1ccc(-c2nc3cc(NC(=O)[C@@H]4CCCN4C(=O)CCc4ccccc4)ccc3o2)cc1)[C@@H]1CCCN1C(=O)CCc1ccccc1]

Step 1

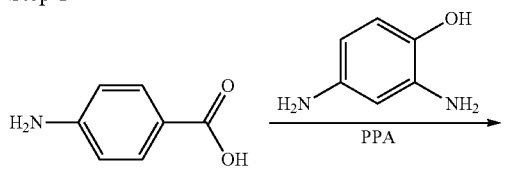

p-Aminobenzoic acid (1.37 g, 10 mmol) and 2,4-diaminophenol (1.24 g, 10 mmol) were combined under argon and treated with 12 mL of PPA. The resulting solution was heated at 200° C. for 30 minutes. The black solution was poured onto ice, and the resulting yellow solid was collected (1.12 g). $^1$H-NMR (DMSO) δ: 10.2-10.5 (s, 2H), 8.10-8.20 (m, 4H), 7.10-7.80 (m, 3H). MS m/z: 226 (M+1).

Step 2

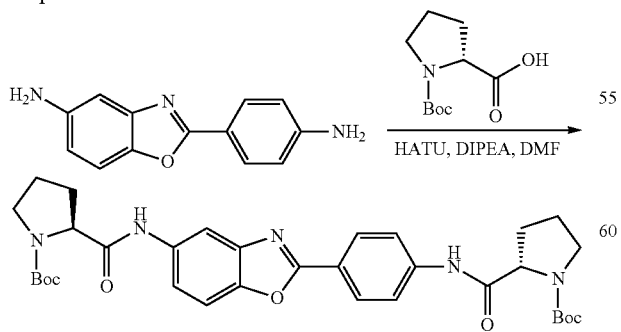

The product from step 1 above (0.100 g, 0.236 mmol), N-Boc-proline (0.098 g, 0.355 mmol), HATU (0.135 g, 0.355 mmol), TEA (0.100 g, 0.944 mmol) were taken in DCM (10 mL) and stirred overnight at RT. The reaction was diluted with DCM, and the organic layer was washed with water, brine, dried (NaSO$_4$), concentrated and purified by preparative TLC to afford 100 mg of desired compound. MS m/z: 620 (M+1).

Step 3

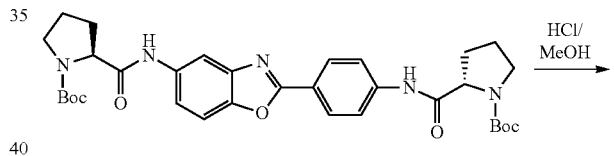

The product from step 2 above (0.100 g, 0.161 mmol) was stirred in MeOH/HCl (3.0 mL) for 1 hour at RT, and the solvent was removed under reduced pressure. The compound was dried at high vacuum to afford 80 mg of the desired compound. MS m/z: 420 (M+1).

Step 4

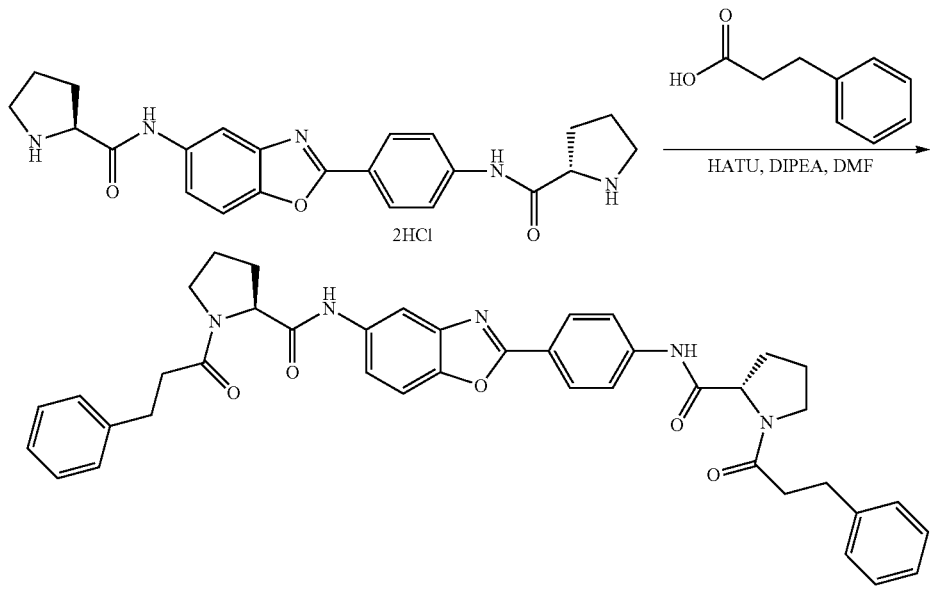

Compound from step 3 (0.080 g, 0.191 mmol), 3-phenyl-propanoic acid (0.086 g, 0.574 mmol), HATU (0.218 g, 0.574 mmol), DIPEA (0.146 g, 1.146 mmol) were taken in DMF (3 mL) and stirred for overnight at RT. DMF was removed under reduced pressure, and the residue was extracted with DCM/water. The organic layer was washed with brine, dried (NaSO$_4$) and concentrated. The residue was purified by HPLC purification to afford 108 mg of target. $^1$H NMR (DMSO) δ: 10.2-10.5 (s, 2H), 8.10-8.20 (m, 3H), 7.10-7.80 (m, 14H), 4.37-4.55 (m, 2H), 3.32-3.58 (m, 4H), 2.67-2.85 (m, 7H), 1.80-2.4 (m, 9H).

Example 18

(2S)-1-(3-phenylpropanoyl)-N-{4-[5-({[(2S)-1-(3-phenylpropanoyl)pyrrolidin-2-yl]carbonyl}amino)-1-benzofuran-2-yl]phenyl}pyrrolidine-2-carboxamide

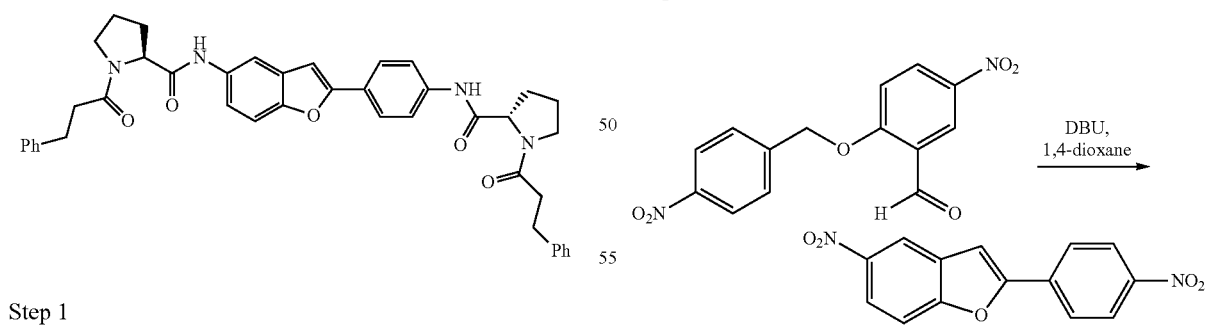

Step 1

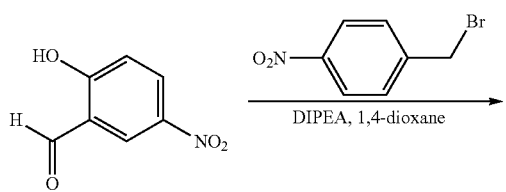

-continued

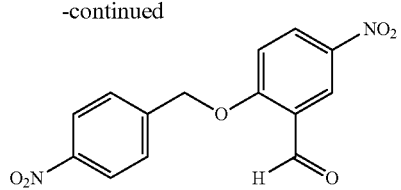

To a solution of 5-nitrosalicylaldehyde (1.0 g, 5.90 mmol) in 1,4-dioxane (10 mL), p-nitrobenzyl bromide (1.33 g, 6.15 mmol) and DIPEA (1.25 g, 9.70 mmol) were added, and the reaction was refluxed at 100° C. for 2 hours. The reaction was cooled, and the solids were filtered, washed with EtOH and dried with high vacuum to afford the desired compound. MS m/z: 303 (M+1).

Step 2

To a solution of the target compound from step 1 (1.5 g, 4.96 mmol) in 1,4-dioxane (5 mL), DBU (0.9 g, 6.45 mmol) was added. The reaction was heated to 100° C. for 3 hours, then cooled to RT, and the resulting solid was filtered off and sufficiently washed with EtOH to afford 927 mg of the desired compound. $^1$H NMR (MeOD) δ: 8.66 (s, 1H), 8.37-8.39 (d, J=8.0 Hz, 2H), 8.30-8.32 (d, J=8.0 Hz, 1H), 8.18-8.21 (d, J=12 Hz, 2H), 7.78-7.80 (d, J=8.0 Hz, 1H), 7.70 (s, 1H).

Step 3

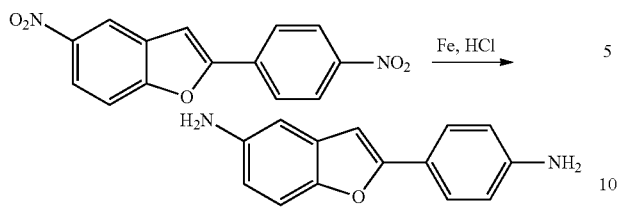

To a solution of the product from step 2 above (0.050 g, 0.176 mmol) in 1,4-dioxane (1.8 mL), water (1.8 mL), Fe (0.054 g) and HCl (1.1 μL) were added. The reaction was heated to 110° C. for 3 hours. Then, the solid was filtered, and the organic layer was concentrated to afford 40 mg of the desired compound. $^1$H NMR (MeOD) δ: 8.01-8.05 (m, 2H), 7.90-7.96 (m, 1H), 7.79 (s, 1H), 7.46-7.51 (m, 1H), 7.34 (s, 1H), 7.17-7.21 (m, 2H). MS m/z: 225 (M+1).

To a solution of the product from step 3 above (0.020 g, 0.089 mmol) in DCM (10 mL) N-Boc-proline (0.042 g, 0.196 mmol) and DIPEA (0.035 g, 0.267 mmol) were added. The reaction was stirred at RT for 5 minutes and then HATU (0.101 g, 0.267 mmol) was added. The reaction was stirred overnight and poured into brine and extracted with EtOAc. The organic layer was dried (Na$_2$SO$_4$), filtered and concentrated to afford 30 mg of the desired compound. MS m/z: 619 (M+1).

Step 5

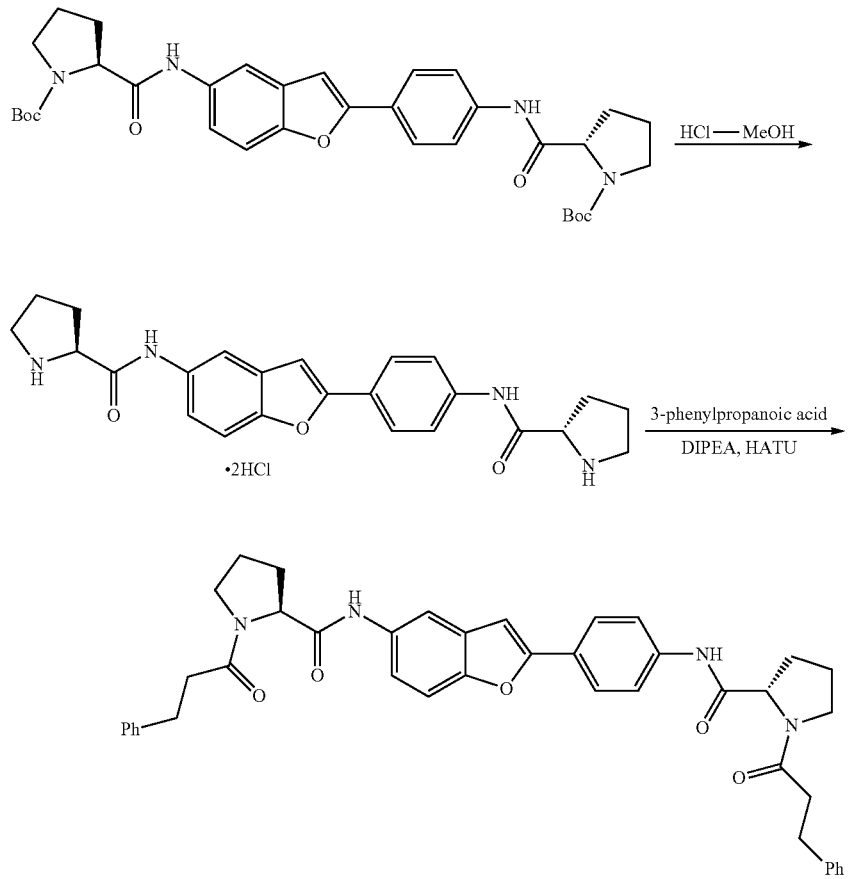

Step 4

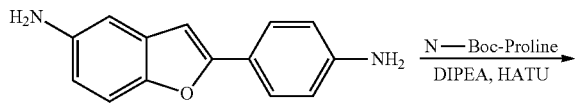

The product from step 4 (0.70 g, 1.13 mmol) was stirred in MeOH/HCl (20 mL) for 1 hour. The solvent was removed at high vacuum to afford the desired proline compound, which was used directly to the next step without further purification. 3-Phenylpropanoic acid (0.428 g, 2.85 mmol) were taken in DCM (30 mL) was reacted with the proline compound (0.500 g, 0.96 mmol) and DIPEA (0.9 g, 7.1 mmol). The reaction was stirred at RT for 5 minutes, and then HATU (1.0 g, 2.85 mmol) was added. The reaction was stirred overnight and poured into brine and extracted with EtOAc. The organic layer was dried (Na₂SO₄), concentrated and purified by HPLC to afford 30 mg of the desired compound. ¹H NMR (CDCl₃) δ: 9.85-9.87 (d, J=8.0 Hz, 2H), 7.86 (s, 1H), 7.42-7.44 (d, J=8.8 Hz, 2H), 7.46-7.48 (d, J=8.8 Hz, 2H), 7.03-7.31 (m, 9H), 6.90-6.99 (d, J=3.6 Hz, 1H), 6.58 (s, 1H), 4.71-4.82 (m, 2H), 3.62-3.71 (m, 2H), 3.43-3.50 (m, 2H), 2.95-3.05 (m, 4H), 2.63-2.88 (m, 4H), 2.21-2.43 (m, 4H), 1.87-2.14 (m, 4H). MS m/z: 683 (M+1).

Example 19

N-{2-[4-(acetylamino)phenyl]-1-benzofuran-5-yl}-1-{(2R)-2-[(tert-butoxycarbonyl)amino]-2-phenylacetyl}-L-prolinamide

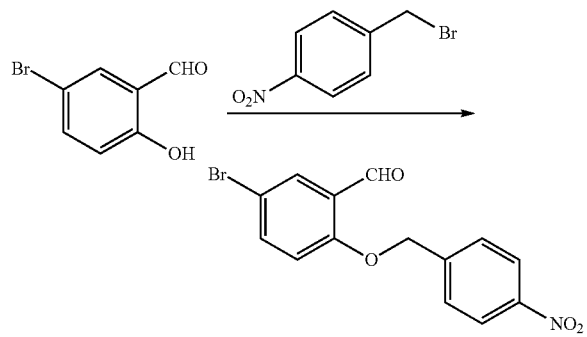

Step 1

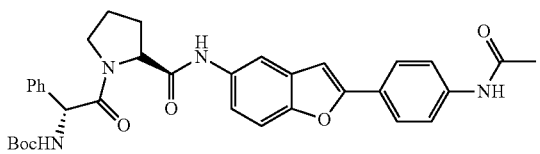

K₂CO₃ (68 g, 0.497 mol) was added to a solution of bromosalicylaldehyde (50 g, 0.248 mol) in DMF (300 ml). The resulting solution was stirred at RT for 1 hour, then to it was added compound 4-nitrobenzyl bromide (54 g, 0.25 mol). The reaction mixture was stirred for 30 minutes, filtered, and the filtrate was poured into water and extracted with EtOAc (3×). The combined organic layers were dried and concentrated. The product was recrystallized from dioxane to afford a white solid (50 g). ¹H NMR (CDCl₃) δ: 10.43 (s, 1H), 8.24 (d, J=4H), 7.51-7.58 (m, 2H), 7.37-7.42 (m, 4H), 7.31-7.36 (m, 6H), 5.52 (s, 1H), 4.57 (s, 2H), 3.90 (s, 2H), 3.34 (s, 2H), 2.06-2.15 (m, 6H), 1.86-1.88 (m, 1H), 1.41 (d, 18H).

Step 2

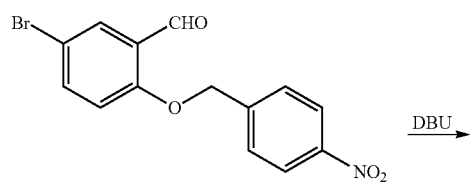

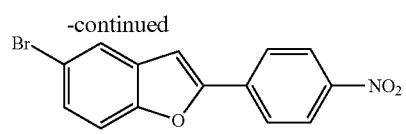

DBU (9 ml, 61.58 mmol) was added to a solution of the product from step 1 (10 g, 29.85 mmol) in dioxane (70 ml). The resulting solution was heated to reflux for 1 hour, cooled and filtered. The filter cake was washed with EtOAc and dried in air to afford a yellow solid (6.5 g).

Step 3

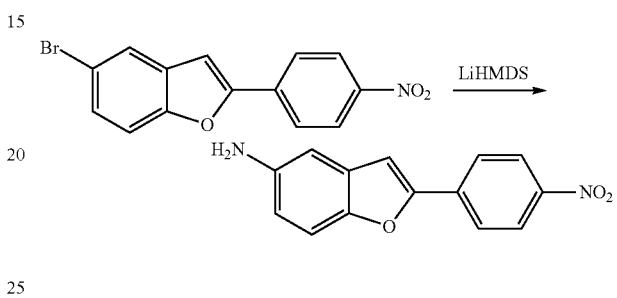

P$^t$Bu₃ (1.93 ml, 0.32 mmol) was added to a solution of the product from step 2 (2 g, 6.3 mmol) and Pd₂(dba)₃ (0.29 g, 0.32 mmol) in THF (100 ml) under N₂. Then a solution of LiHMDS (18.9 ml, 18.9 mmol) was added dropwise. The resulting solution was heated to reflux for 3 hours and then cooled to RT. The reaction mixture was adjusted to pH=1 using 1M HCl, then stirred for 0.5 hour. The reaction mixture was basified to pH=8-9 using aq. saturated NaHCO₃, and extracted with EtOAc (3×). The combined organic layers were dried and concentrated. The residue was recrystallized from MeOH to afford the product as brown solid.

Step 4

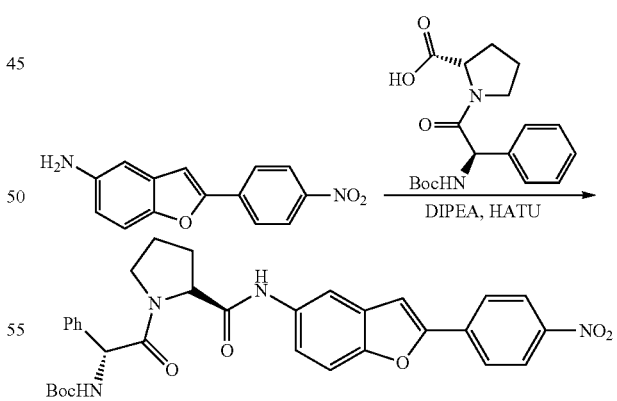

The mixture of the product from step 3 (500 mg, 2 mmol), R-Boc-Phg-L-Pro-OH (660 mg, 2.16 mmol), NMM (400 mg, 4 mmol) and DMF (30 ml) was stirred at RT for 30 minutes, then to it was added HATU (1.13 g, 3 mmol). The resulting mixture was stirred at RT overnight. The reaction mixture was diluted with water and filtered. The cake was washed with water and dried; the solid was used next step without purification.

Step 5

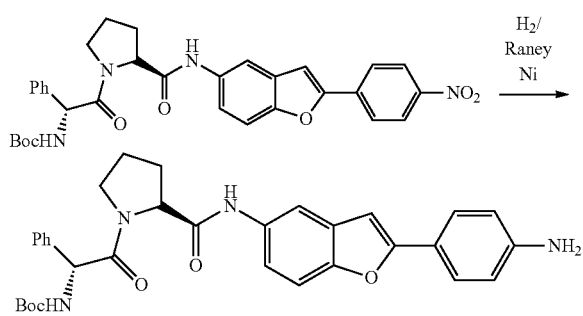

The product from step 4 (0.4 g, 1.3 mmol) in THF (10 ml) was hydrogenated using Raney Ni (0.2 mg) as the catalyst. After being stirred under H₂ atmosphere at RT overnight, the reaction slurry was filtered through CELITE, and the filtrate was concentrated under reduced pressure to afford 0.33 g of the desired compound.

Step 6

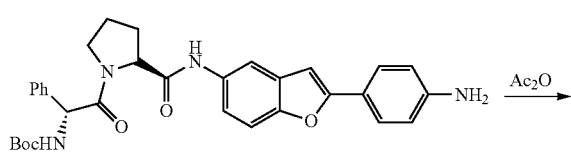

-continued

Ac₂O (18 mg, 0.18 mmol) was added to a solution of the aniline from step 5 (50 mg, 0.09 mmol) in THF (2 ml) at RT. The resulting solution was stirred at RT overnight, concentrated, and the residue was purified by RPLC to afford the desired product. $^1$H NMR (acetone-d6) δ: 7.95 (s, 1 H, NH), 7.65-7.74 (m, 7 H, ArH), 7.40-7.43 (m, 3 H, ArH), 7.30-7.34 (m, 2 H, ArH), 7.01 (s, 1 H, ArH), 5.64 (s, 1 H, CH), 4.56-4.59 (m, 1 H, CH), 3.93-.3.99 (m, 1 H, CH₂), 3.27-3.42 (m, 2 H, CH₂), 3.02-3.17 (m, 3H, CH₂), 1.98 (s, 3 H, CH₃), 1.98-1.95 (m, 4 H, CH₂), 1.22 (t, J=7.2 Hz, 6 H, CH₃).

Examples 20-36

Compounds of Examples 20-36 were prepared in a similar manner as described in either Example 18 or Example 19.

| Example | Structure | MW | Name |
|---|---|---|---|
| 20 | 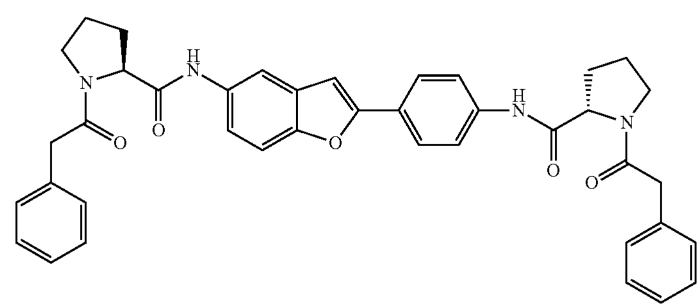 [SMILES: O=C(Nc1ccc(-c2cc3cc(NC(=O)[C@@H]4CCCN4C(=O)Cc4ccccc4)ccc3o2)cc1)[C@@H]1CCCN1C(=O)Cc1ccccc1] | 654.773 | (2S)-1-(phenylacetyl)-N-{4-[5-({[(2S)-1-(phenylacetyl)pyrrolidin-2-yl]carbonyl}amino)-1-benzofuran-2-yl]phenyl}pyrrolidine-2-carboxamide |
| 21 | 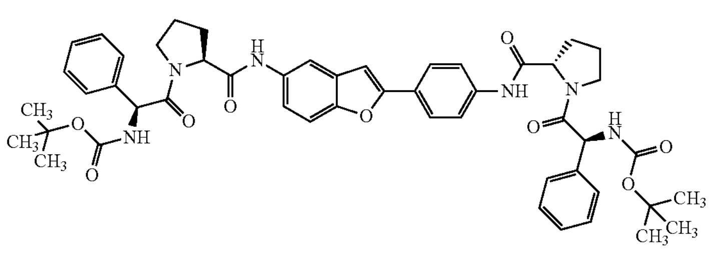 [SMILES: CC(C)(C)OC(=O)N[C@H](C(=O)N1CCC[C@H]1C(=O)Nc1ccc(-c2cc3cc(NC(=O)[C@@H]4CCCN4C(=O)[C@@H](NC(=O)OC(C)(C)C)c4ccccc4)ccc3o2)cc1)c1ccccc1] | 885.039 | tert-butyl {(1S)-2-[(2S)-2-({4-[5-({[(2S)-1-{(2S)-2-[(tert-butoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate |
| 22 | 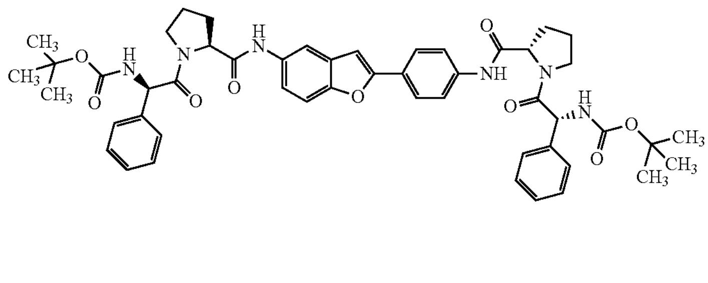 [SMILES: CC(C)(C)OC(=O)N[C@@H](C(=O)N1CCC[C@H]1C(=O)Nc1ccc(-c2cc3cc(NC(=O)[C@@H]4CCCN4C(=O)[C@H](NC(=O)OC(C)(C)C)c4ccccc4)ccc3o2)cc1)c1ccccc1] | 885.039 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate |

-continued

| Example | Structure | MW | Name |
|---|---|---|---|
| 23 | 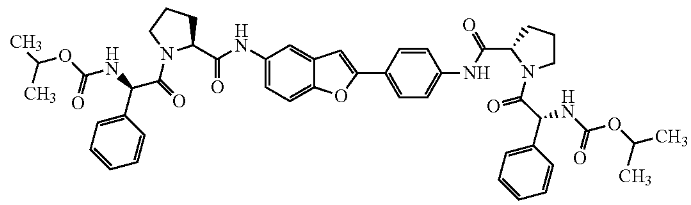 [SMILES: CC(C)OC(=O)N[C@@H](C(=O)N1CCC[C@H]1C(=O)Nc1ccc(-c2cc3cc(NC(=O)[C@@H]4CCCN4C(=O)[C@H](NC(=O)OC(C)C)c4ccccc4)ccc3o2)cc1)c1ccccc1] | 856.984 | propan-2-yl [(1R)-2-oxo-1-phenyl-2-{(2S)-2-[(4-{5-[({(2S)-1-[(2R)-2-phenyl-2-{[(propan-2-yloxy)carbonyl]amino}acetyl]pyrrolidin-2-yl}carbonyl)amino]-1-benzofuran-2-yl}phenyl)carbamoyl]pyrrolidin-1-yl}ethyl]carbamate |
| 24 | 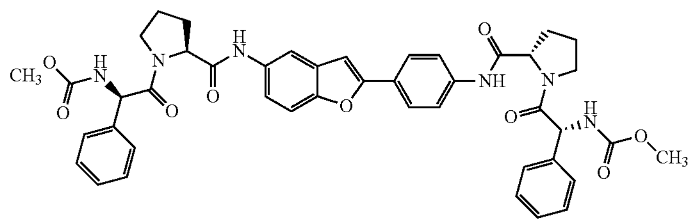 | 800.876 | methyl {(1R)-2-[(2S)-2-({4-[5-({[(2S)-1-{(2R)-2-[(methoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate |
| 25 | 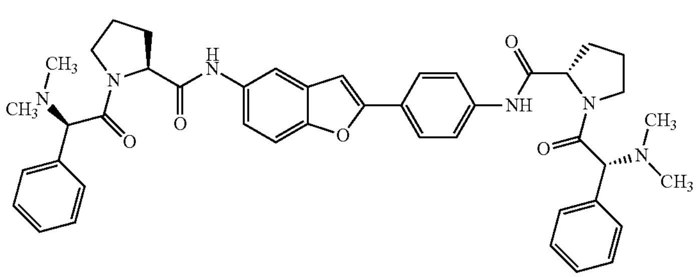 | 740.91 | (2S)-1-[(2R)-2-(dimethylamino)-2-phenylacetyl]-N-(4-{5-[({(2S)-1-[(2R)-2-(dimethylamino)-2-phenylacetyl]pyrrolidin-2-yl}carbonyl)amino]-1-benzofuran-2-yl}phenyl)pyrrolidine-2-carboxamide |
| 26 | 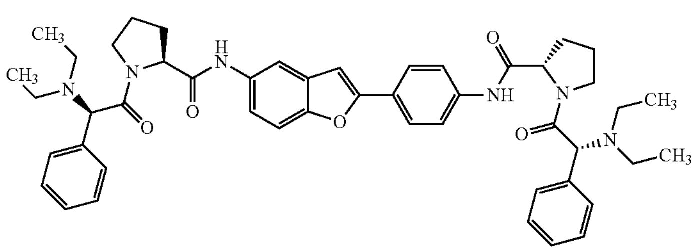 [SMILES: CCN(CC)[C@@H](C(=O)N1CCC[C@H]1C(=O)Nc1ccc(-c2cc3cc(NC(=O)[C@@H]4CCCN4C(=O)[C@@H](c4ccccc4)N(CC)CC)ccc3o2)cc1)c1ccccc1] | 797.019 | (2S)-1-[(2R)-2-(diethylamino)-2-phenylacetyl]-N-(4-{5-[({(2S)-1-[(2R)-2-(diethylamino)-2-phenylacetyl]pyrrolidin-2-yl}carbonyl)amino]-1-benzofuran-2-yl}phenyl)pyrrolidine-2-carboxamide |
| 27 | 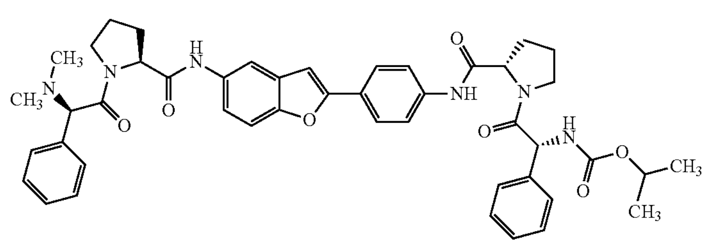 | 798.947 | propan-2-yl [(1R)-2-{(2S)-2-[(4-{5-[({(2S)-1-[(2R)-2-(dimethylamino)-2-phenylacetyl]pyrrolidin-2-yl}carbonyl)amino]-1-benzofuran-2-yl}phenyl)carbamoyl]pyrrolidin-1-yl}-2-oxo-1-phenylethyl]carbamate |
| 28 | 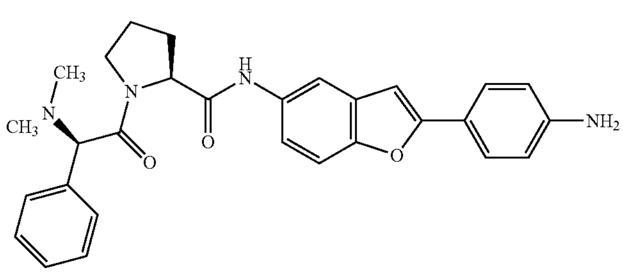 | 482.587 | N-[2-(4-aminophenyl)-1-benzofuran-5-yl]-1-[(2R)-2-(dimethylamino)-2-phenylacetyl]-L-prolinamide |

-continued

| Example | Structure | MW | Name |
|---|---|---|---|
| 29 | 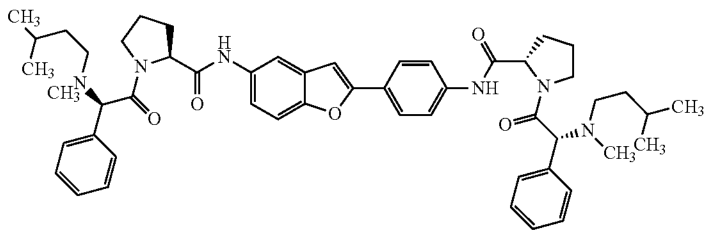 | 853.127 | (2S)-1-{(2R)-2-[methyl(3-methylbutyl)amino]-2-phenylacetyl}-N-{4-[5-({[(2S)-1-{(2R)-2-[methyl(3-methylbutyl)amino]-2-phenylacetyl}pyrrolidin-2-yl]carbonyl}amino)-1-benzofuran-2-yl]phenyl}pyrrolidine-2-carboxamide |
| 30 | 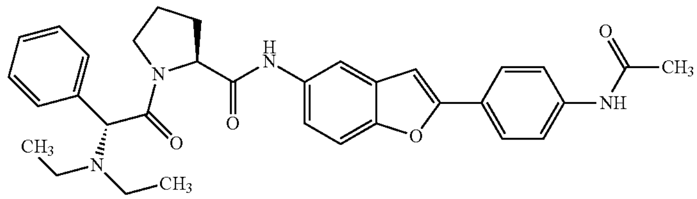 [SMILES: CCN(CC)[C@@H](C(=O)N1CCC[C@H]1C(=O)Nc1ccc2oc(-c3ccc(NC(C)=O)cc3)cc2c1)c1ccccc1] | 552.679 | N-{2-[4-(acetylamino)phenyl]-1-benzofuran-5-yl}-1-[(2R)-2-(diethylamino)-2-phenylacetyl]-L-prolinamide |
| 31 | 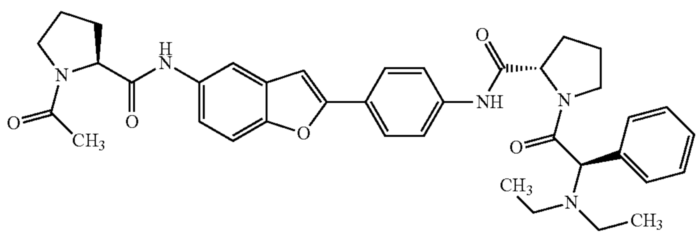 [SMILES: CCN(CC)[C@@H](C(=O)N1CCC[C@H]1C(=O)Nc1ccc(-c2cc3cc(NC(=O)[C@@H]4CCCN4C(C)=O)ccc3o2)cc1)c1ccccc1] | 649.797 | (2S)-1-acetyl-N-(2-{4-[({(2S)-1-[(2R)-2-(diethylamino)-2-phenylacetyl]pyrrolidin-2-yl}carbonyl)amino]phenyl}-1-benzofuran-5-yl)pyrrolidine-2-carboxamide |
| 32 | 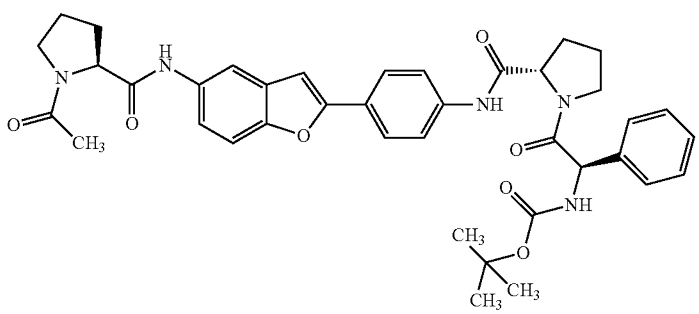 [SMILES: CC(=O)N1CCC[C@H]1C(=O)Nc1ccc2oc(-c3ccc(NC(=O)[C@@H]4CCCN4C(=O)[C@H](NC(=O)OC(C)(C)C)c4ccccc4)cc3)cc2c1] | 693.807 | tert-butyl {(1R)-2-[(2S)-2-({4-[5-({[(2S)-1-acetylpyrrolidin-2-yl]carbonyl}amino)-1-benzofuran-2-yl]phenyl}carbamoyl)pyrrolidin-1-yl]-2-oxo-1-phenylethyl}carbamate |
| 33 | 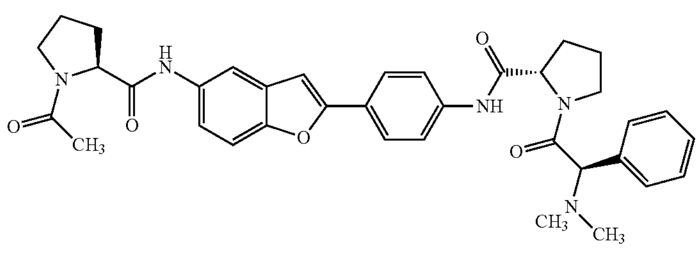 | 621.743 | (2S)-1-acetyl-N-(2-{4-[({(2S)-1-[(2R)-2-(dimethylamino)-2-phenylacetyl]pyrrolidin-2-yl}carbonyl)amino]phenyl}-1-benzofuran-5-yl)pyrrolidine-2-carboxamide |
| 34 | 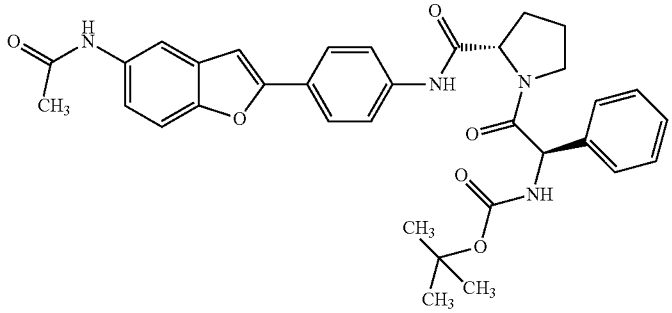 [SMILES: CC(=O)Nc1ccc2oc(-c3ccc(NC(=O)[C@@H]4CCCN4C(=O)[C@H](NC(=O)OC(C)(C)C)c4ccccc4)cc3)cc2c1] | 596.689 | N-{4-[5-(acetylamino)-1-benzofuran-2-yl]phenyl}-1-{(2R)-2-[(tert-butoxycarbonyl)amino]-2-phenylacetyl}-L-prolinamide |

| Example | Structure | MW | Name |
|---|---|---|---|
| 35 | 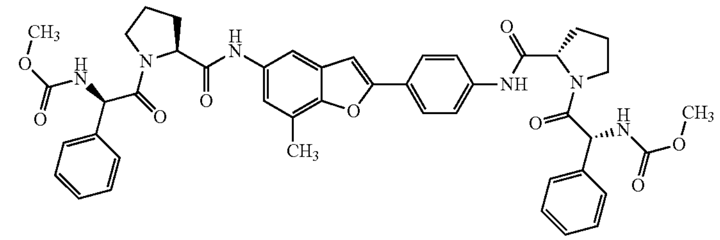 [SMILES: COC(=O)N[C@@H](C(=O)N1CCC[C@H]1C(=O)Nc1ccc(-c2cc3cc(NC(=O)[C@@H]4CCCN4C(=O)[C@H](NC(=O)OC)c4ccccc4)cc(C)c3o2)cc1)c1ccccc1] | 814.903 | methyl {(1R)-2-[(2S)-2-({4-[5-({[(2S)-1-{(2R)-2-[(methoxycarbonyl)amino]-2-phenylacetyl}pyrrolidin-2-yl]carbonyl}amino)-7-methyl-1-benzofuran-2-yl]phenyl}carbamoyl)pyrrolidin-1-yl]-2-oxo-1-phenylethyl}carbamate |
| 36 | 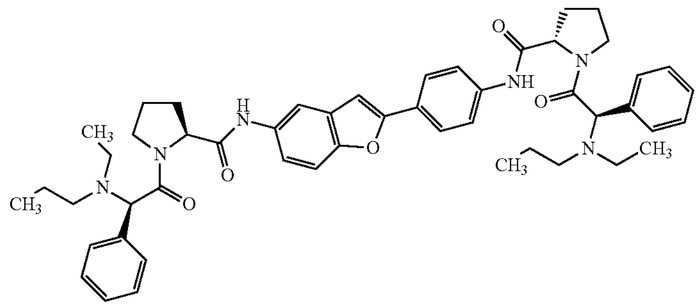 [SMILES: CCCN(CC)[C@@H](C(=O)N1CCC[C@H]1C(=O)Nc1ccc(-c2cc3cc(NC(=O)[C@@H]4CCCN4C(=O)[C@@H](c4ccccc4)N(CC)CCC)ccc3o2)cc1)c1ccccc1] | 825.073 | (2S)-1-{(2R)-2-[ethyl(propyl)amino]-2-phenylacetyl}-N-{4-[5-({[(2S)-1-{(2R)-2-[ethyl(propyl)amino]-2-phenylacetyl}pyrrolidin-2-yl]carbonyl}amino)-1-benzofuran-2-yl]phenyl}pyrrolidine-2-carboxamide |

Example 37

(2S)-1-(phenylacetyl)-N-{4-[6-({[(2S)-1-(phenylacetyl)pyrrolidin-2-yl]carbonyl}amino)imidazo[1,2-a]pyrimidin-2-yl]phenyl}pyrrolidine-2-carboxamide

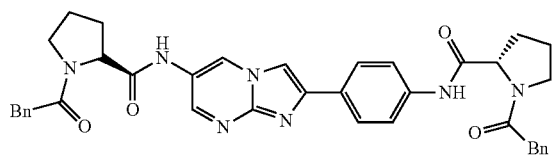

Step 1

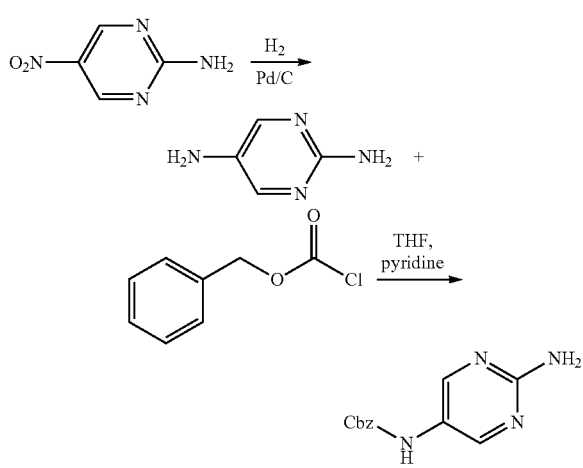

A suspension of pyrimidine (280 mg, 2 mmol), Pd/C (15 mg, 0.1 mmol) in 40 mL EtOH was hydrogenated under 30 psi for 1 hour. The mixture was then filtered, and the filtrate was then concentrated to give the product (200 mg). The residue was dissolved in 20 ml THF and CbzCl (375 mg, 2.19 mmol) and pyridine (1 ml) were added. The mixture was stirred at RT for 1 hour, then the mixture was concentrated in vacuo, and the residue was extracted with EtOAc (2×), washed with H$_2$O (30 mL) and brine (30 mL), dried over anhydrous NaSO$_4$, concentrated in vacuo to give the desired compound as white powder (330 mg). MS (ESI) m/e (M+H$^+$): 245.

Step 2

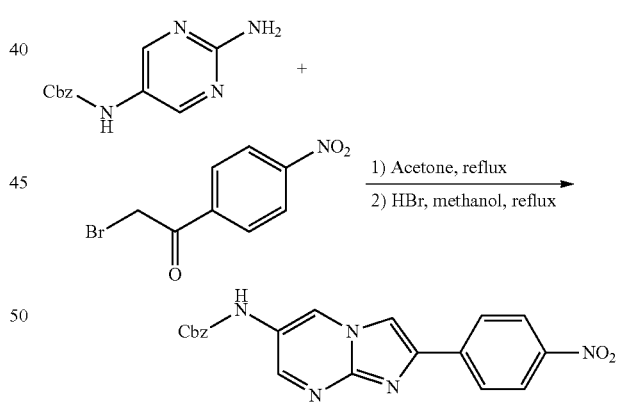

A solution of the product from step 1 above (244 mg, 1.00 mmol) and 2-bromo-1-(4-nitrophenyl)ethanone (244 mg, 1 mmol) in 40 mL of acetone was heated to reflux and stirred for 6 hours. Then, the mixture was cooled to RT and filtered, and the filtrate was then dissolved in 30 ml MeOH, and 0.5 ml HBr was added, the mixture was heated to reflux for another 3 hours; after that, the mixture was concentrated in vacuo to give the product as a pale yellow powder (120 mg). MS (ESI) m/e (M+H): 390.

Step 3

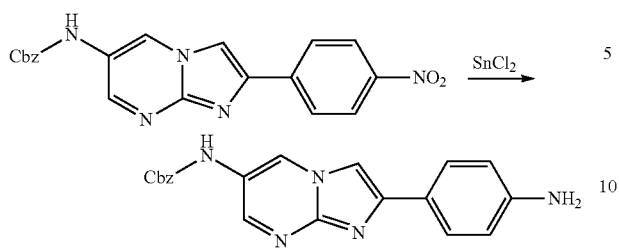

To the product from step 2 above (50 mg, 0.128 mmol) was dissolved in 10 mL CH₃OH was added SnCl₂ (144 mg, 0.64 mmol). The reaction mixture was stirred at RT for 30 minutes and then heated to reflux for 3 hours. MeOH was removed in vacuo, and the residue was purified (DCM/MeOH=50:1) to afford the desired compound (35 mg). MS (ESI) m/e (M+H⁺): 360.

Step 4

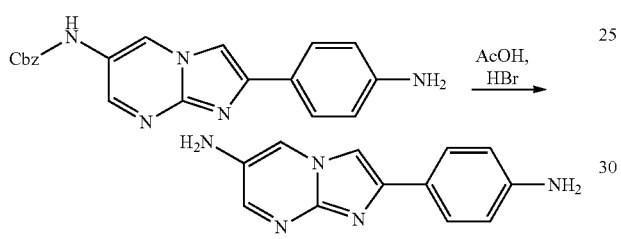

The compound from step 3 (35 mg, 0.1 mmol) was dissolved in 5 ml of HOAc, then HBr (1.5 ml) was added. The reaction mixture was heated to reflux and stirred for 6 hours, cooled and concentrated. The residue was extracted with EtOAc (2×), washed with aq. NaHCO₃ and water (30 mL) and brine (30 mL), dried over anhydrous NaSo₄. Concentration afforded the desired compound as a brown solid (16 mg). MS (ESI) m/e (M+H⁺): 226.

Step 5

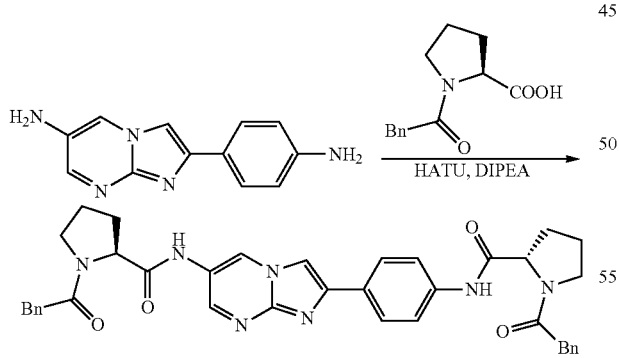

A mixture of the diamine product from step 4 above (16 mg, 0.071 mmol), N-phenylacetyl-L-proline (40 mg, 0.170 mmol), DIPEA (36.9 mg, 0.02 mmol) in CH₃CN (5 mL) was stirred at RT for 10 minutes, then HATU (54 mg, 0.142 mmol) was added. The mixture was stirred at RT overnight then the mixture was concentrated, and the residue was purified to give compound (15 mg). MS (ESI) m/e (M+H⁺): 657. ¹H NMR (MeOD) δ: 9.45 (s, 1H), 8.31 (s, 1H), 8.05 (s, 1H), 7.61~7.48 (m, 4H), 7.34~7.21 (m, 10H), 4.60~4.52 (m, 2H), 3.83~3.69 (m, 8H), 2.24~1.97 (m, 8H).

Example 38

(2S)-1-(phenylacetyl)-N-{4-[6-({[(2S)-1-(phenylacetyl)pyrrolidin-2-yl]carbonyl}amino)imidazo[1,2-a]pyridin-2-yl]phenyl}pyrrolidine-2-carboxamide

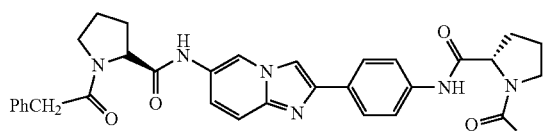

Step 1

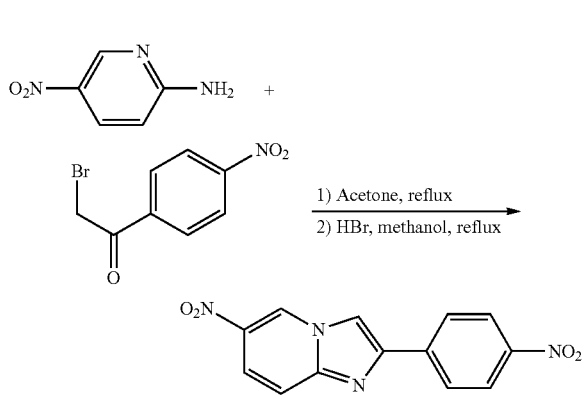

The mixture containing 2-amino-5-nitropyridine (1.39 g, 10 mmol) and p-nitro-alpha-bromoacetophenone (2.42 g, 10 mmol) in 100 mL of acetone was heated at reflux for 12 hours. The solid was collected by filtration and then dissolved in 20 mL of MeOH and treated with a trace amount of HBr. The mixture was stirred at reflux for 1 hour, cooled and the solid was collected by filtration to give the desired (1.4 g). MS (m/z): 285 (M+H)⁺.

Step 2

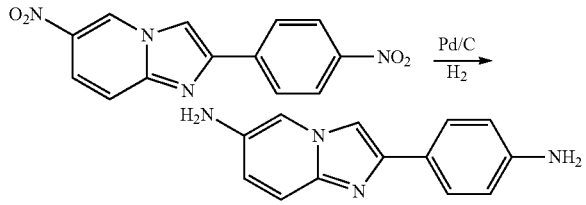

To a suspension of the product from step 1 above (0.7 g, 2.5 mmol) in MeOH (50 mL) was added 0.1 g of Pd/C (20%), and the suspension was stirred under 25 psi of H₂ at RT. After filtration, the filtrate was concentrated in vacuo to give the desired compound. MS (m/z): 225 (M+H)⁺.

Step 3

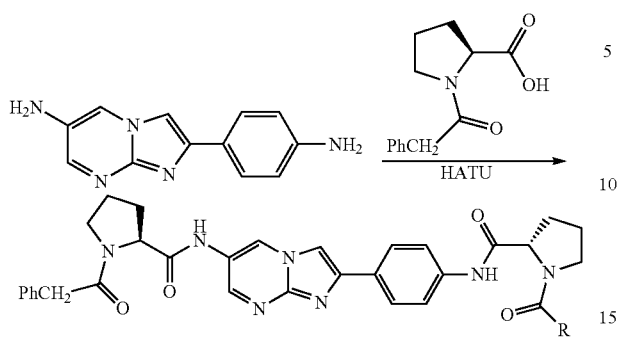

The mixture of the diamine from step 2 above (225 mg, 1 mmol), N-phenylacetylproline (1 mmol), DIPEA (5 mmol) and HATU (380 mg, 1 mmol) in 10 mL of MeCN was stirred at RT for 1 hour. The reaction mixture was concentrated, and the residue was purified by column chromatography to give the desired compound. $^1$H NMR (MeOD) δ: 9.3 (s, 1H), 8.2 (s, 1H), 7.5-7.1 (m, 16H), 4.6 (m, 1H), 4.5 (m, 1H), 3.8 (m, 8H), 2.3-1.8 (m, 8H).

Example 39

(2S,2'S)—N,N'-1H,1'H-2,2'-biindole-5,5'-diylbis[1-(phenylacetyl)pyrrolidine-2-carboxamide]

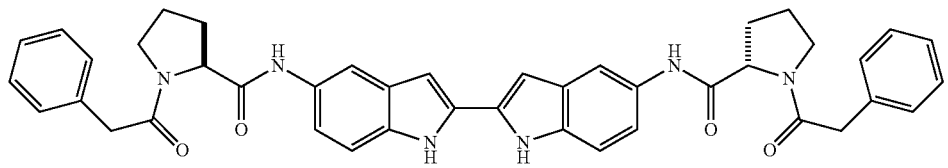 [SMILES: O=C(Nc1ccc2[nH]c(-c3cc4cc(NC(=O)[C@@H]5CCCN5C(=O)Cc5ccccc5)ccc4[nH]3)cc2c1)[C@@H]1CCCN1C(=O)Cc1ccccc1]

Step 1

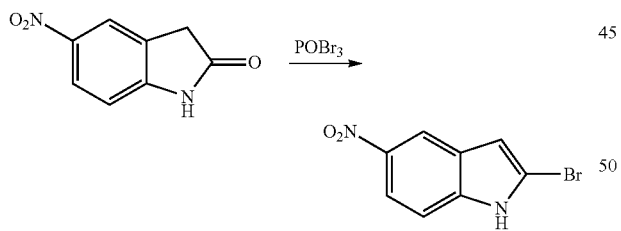

To a suspension of the lactam (10.0 g, 56 mmol) in 200 ml of 1,2-dichloroethane, was added POBr$_3$ (15.3 g, 53.2 mmol) at RT. The resulting mixture was heated at reflux temperature in a 90° C. oil bath for 0.5 hour (the reaction formed a copious amount of precipitate, and an oil bath was preferred over a heating mantle, as it provided gentle heating and avoided a darkening of the precipitate). The reaction was cooled just below reflux temperature, and imidazole (4.57 g, 62 mmol) was added in one portion. The resulting gummy suspension was heated at reflux temperature in an oil bath for another 2 hours. The reaction was cooled to RT, and 100 mL of ice-water was added. Solid NaHCO$_3$ (ca. 50 g) was added to the mixture until no further gas was evolved. The suspension was extracted with DCM (4×), and the combined DCM extracts were washed with 300 mL of brine. The DCM extracts were filtered through silica gel and concentrated to dryness to afford a crude product. The crude product was recrystallized from chloroform to give 5.41 g of the desired compound as a white solid. The filtrate was concentrated to dryness, and the residue was purified by flash column chromatography (30% EtOAc/Hex) to give an additional 2.6 g of desired product. MS (ESI) m/e (M+H$^+$): 242.

Step 2

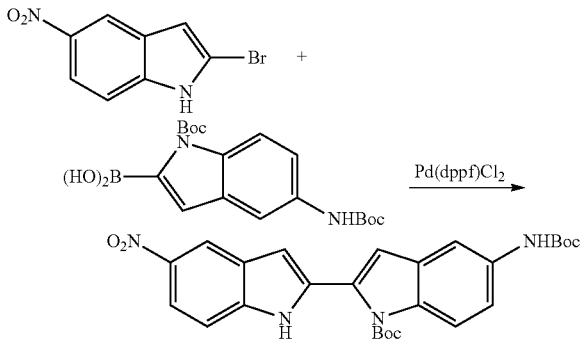

The mixture of compound from step 1 above (602.6 mg, 2.5 mmol), the indole boronic acid (1.034 g, 2.75 mmol), Pd(dppf)Cl$_2$ (183 mg, 0.25 mmol), Na$_2$CO$_3$ (530 mg, 5.0 mmol) in 5 mL dioxane-H$_2$O (5:1) was heated to reflux under N$_2$ atmosphere overnight. When reaction was complete the mixture was poured into water and extracted with DCM. The organic phase was dried over Na$_2$SO$_4$, concentrated, and the residue was purified to give the desired product. MS (ESI) m/e (M+H$^+$): 493.

Step 3

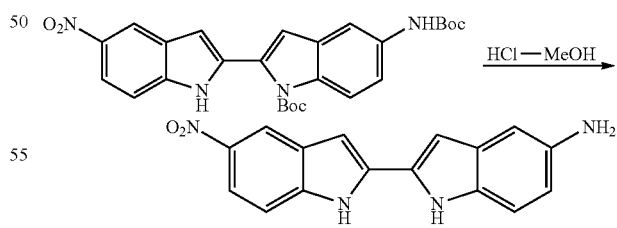

The product from step 2 (600 mg, 1.3 mmol) was added into HCl (30 ml, 3M in MeOH). Then the mixture stirred at RT for 2-3 hours. When reaction was complete, the mixture was concentrated to give the crude product (400 mg). MS (ESI) m/e (M+H$^+$): 293.

Step 4

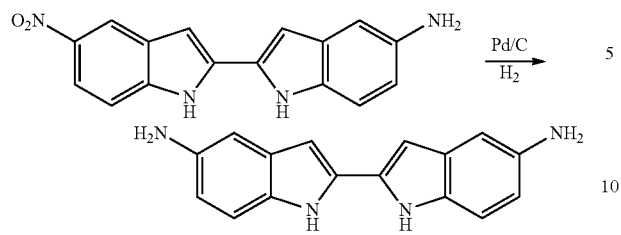

The product from step 3 (400 mg, 1.36 mmol) was dissolved in EtOAc and treated with Pd/C (100 mg, 20%). Then the mixture was stirred at RT overnight under $H_2$ atmosphere. When the reaction was complete, the Pd/C was filtered off, and the resulting solution was concentrated to give the crude product (300 mg). MS (ESI) m/e (M+H$^+$): 263.

Step 5

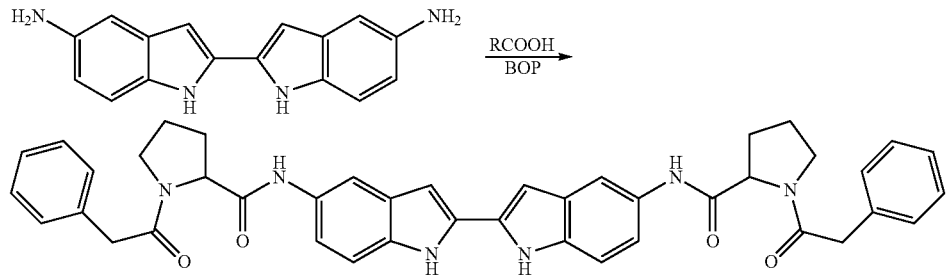

A solution containing (131 mg, 0.5 mmol) of the product from step 4, RCOOH (256.608 mg, 1.1 mmol), DIPEA (390 mg, 1.5 mmol) in $CH_3CN$ (2 mL) was stirred at RT for 5 minutes, then HATU (418 mg, 1.1 mmol) was added into the mixture. The mixture was stirred at RT overnight. When reaction was complete, the mixture was concentrated, and the residue was purified to give the desired product. $^1$H NMR (MeOD) δ: 7.15-7.75 (m, 18H), 4.51-4.59 (m, 2H), 3.56-3.80 (m, 10H), 2.37 (s, 3H), 1.97-2.30 (m, 8H). MS (ESI) m/e (M+H$^+$): 693.

Example 40 di-tert-butyl (1H,1'H-2,2'-biindole-5,5'-diylbis{carbamoyl(2S)pyrrolidine-2,1-diyl[(1R)-2-oxo-1-phenylethane-2,1-diyl]})biscarbamate

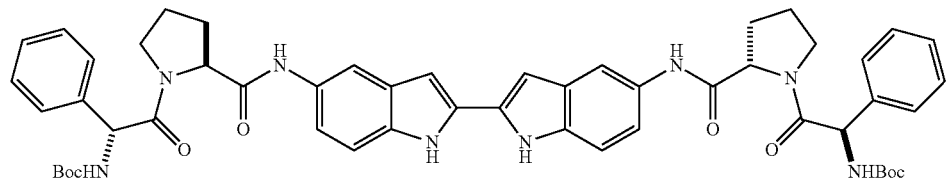 [SMILES: CC(C)(C)OC(=O)N[C@@H](C(=O)N1CCC[C@H]1C(=O)Nc1ccc2[nH]c(-c3cc4cc(NC(=O)[C@@H]5CCCN5C(=O)[C@H](NC(=O)OC(C)(C)C)c5ccccc5)ccc4[nH]3)cc2c1)c1ccccc1]

This compound was prepared using the similar method as Example 39, step 5 using N-Boc-R-Phg-L-Pro-OH. $^1$H NMR (MeOD) δ: 6.78-7.78 (m, 18H), 5.49 (m, 2H), 4.55-4.58 (m, 2H), 3.94-3.97 (m, 3H), 2.37 (s, 3H), 1.87-2.14 (m, 8H), 1.40 (s, 18H). MS (ESI) m/e (M+H$^+$): 924.

Example 41 tert-butyl {(1R)-2-oxo-1-phenyl-2-[(2S)-2-({2-[4-({[(2S)-1-(phenylacetyl)pyrrolidin-2-yl]carbonyl}amino)phenyl]-1H-indol-5-yl}carbamoyl)pyrrolidin-1-yl]ethyl}carbamate

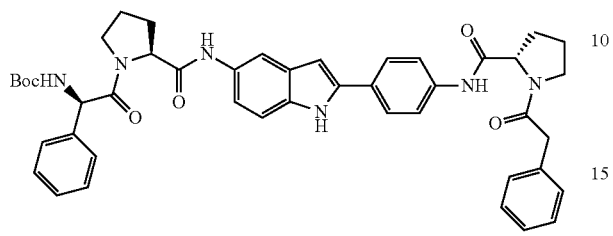

Step 1

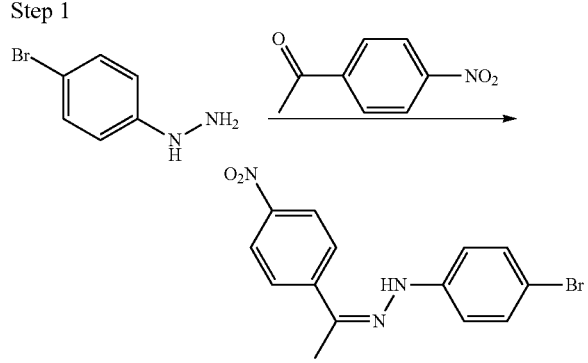

To a solution of 4-bromophenylhydrazine (2.5 g, 13.4 mmol) in acetic acid (19.5 mL) and EtOH (14.5 mL), 4-nitroacetophenone (1.66 g, 10.0 mmol) was added. The reaction was refluxed for 5 hours, and water (35 mL) was added. The resulting mixture was stirred for another 1 hour, and the resulting solid was filtered, washed with water to afford 3.1 g of the desired compound. $^1$H NMR (MeOD) δ: 8.21-8.23 (d, J=8.0 Hz, 2H), 8.01-8.03 (d, J=8.0 Hz, 2H), 7.34-7.36 (d, J=8.0 Hz, 2H), 7.20-7.22 (d, J=8.0 Hz, 2H), 2.03 (s, 3H).

Step 2

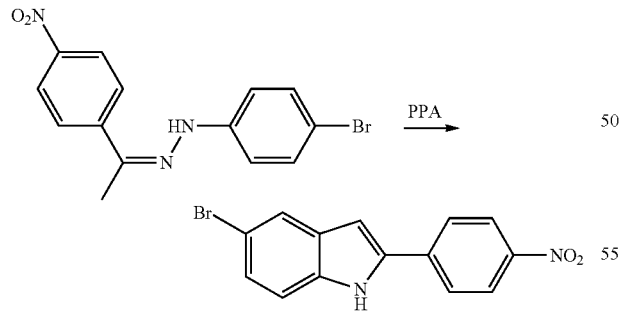

The product from step 1 above (2.0 g, 6.0 mmol) was added into PPA (20 mL), and the mixture was stirred at 80° C. for 1 hour before it was cooled in ice-bath, diluted with water/EtOAc (6020 mL) and stirred for another 1 hour. The mixture was extracted with EtOAc and washed to yield the target. $^1$H NMR (MeOD) δ: 8.28-8.30 (d, J=8.0 Hz, 2H), 7.97-7.99 (d, J=8.0 Hz, 2H), 7.72 (s, 1H), 7.33-7.35 (d, J=8.0 Hz, 1H), 7.24-7.26 (d, J=8.0 Hz, 1H), 7.02 (s, 1H).

Step 3

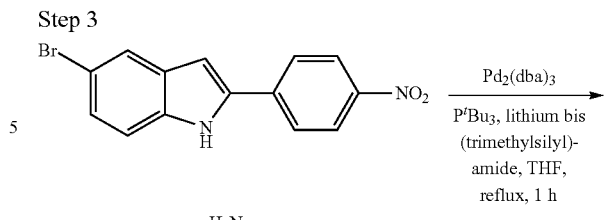

An oven-dried argon-cooled round-bottom flask was charged with the indole from step 2 (2.0 g, 6.31 mmol) and 0.05 equivalents of Pd$_2$(dba)$_3$ in THF (100 mL). A solution of tri-tert-butyl phosphine (10 wt %) in hexane (1.93 mL, 0.63 mmol) was added followed by lithium hexamethyldisilazane (1.0 M in THF) (18.9 mL, 18.9 mmol). The dark solution was heated to reflux overnight then cooled to RT. This mixture was poured into ice-cold aq 1.0 M HCl (70 mL) and stirred vigorously. Hexane was added, and stirring was continued for 30 minutes. The precipitate was filtered, washed with 20 mL of cold water and then 20 mL of THF:Hexanes (5:95) solution. The precipitate was washed with 200 mL of MeOH, and the filtrate was concentrated to give 1.5 g of the desired compound. MS m/z: 254 (M+1).

Step 4

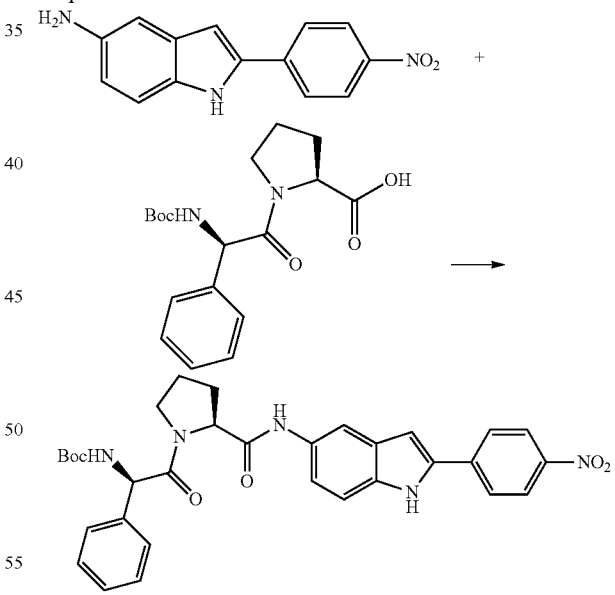

To a solution of the product from step 3 above (1 g, 3.9 mmol) in acetonitrile (20 mL) was added R-N-Boc-Phg-S-Pro-OH (1.4 g, 3.9 mmol), HATU (3 g, 7.8 mmol) and DIPEA (1 g, 7.8 mmol). The mixture was stirred at RT overnight. The solvent was distilled, and the residue was dissolved in EtOAc and washed with water. The organic layer was dried and concentrated in vacuo, and the residue was purified by column chromatography to give the desired compound (1.8 g). MS (ESI) m/e (M+H$^+$): 584.

Step 5

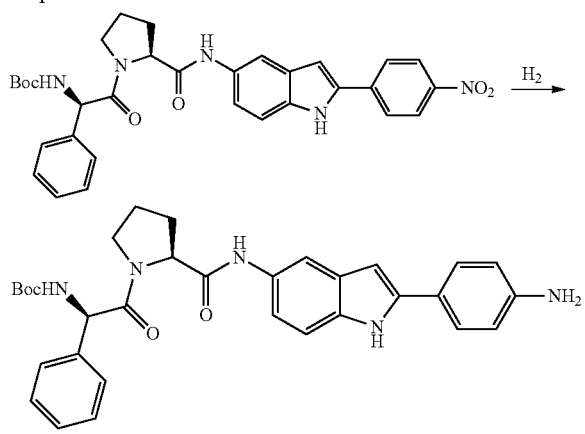

To a solution of compound from step 4 (300 mg, 0.51 mmol) in MeOH (10 mL) was added Pd/C (50 mg, 0.28 mmol). The mixture was stirred under H$_2$ atmosphere at RT for 1 hour. The catalyst was filtered off, and the filtrate was concentrated in vacuo to give the desired compound (230 mg) as a yellow oil, which was used directly in next step. MS (ESI) m/e (M+H)$^+$: 554.

Step 6

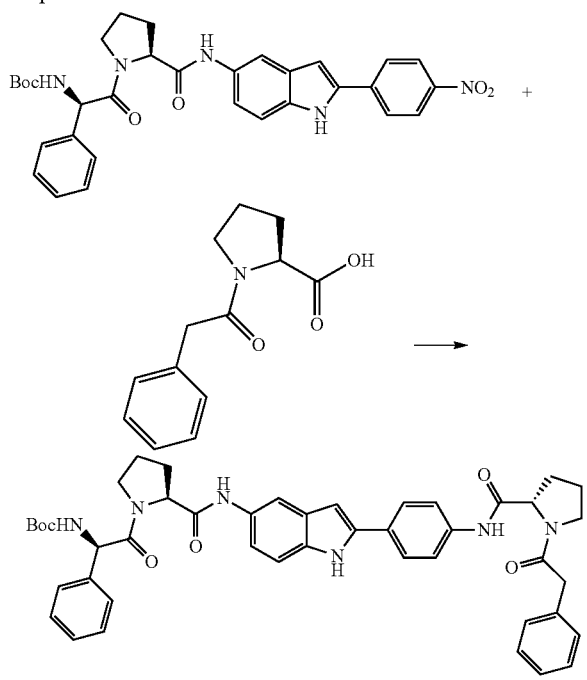

To a solution of the compound from step 5 (100 mg, 0.18 mmol) in acetonitrile (3 mL) was added compound N-pheny- lacetyl-L-proline (42 mg, 0.18 mmol), HATU (140 mg, 0.36 mmol) and DIPEA (46 mg, 0.36 mmol). The mixture was stirred at RT overnight then concentrated, and the residue was purified by RPLC to give (60 mg). $^1$H NMR (CDCl$_3$) δ: 9.62 (s, 1H), 9.08 (s, 1H), 7.84 (s, 1H), 7.45-7.09 (m, 15H), 6.52 (s, 1H), 5.67 (s, 1H), 5.49 (m, 1H), 4.72-4.51 (m, 2H), 3.82-3.48 (m, 5H), 3.20 (m, 1H), 2.15-1.72 (m, 8H), 1.43 (s, 9H). MS (ESI) m/e (M+H$^+$): 769.

Example 42

(2S)-1-(phenylacetyl)-N-{2-[5-({[(2S)-1-(pheny-lacetyl)pyrrolidin-2-yl]carbonyl}amino)-1H-indol-2-yl]pyrimidin-5-yl}pyrrolidine-2-carboxamide

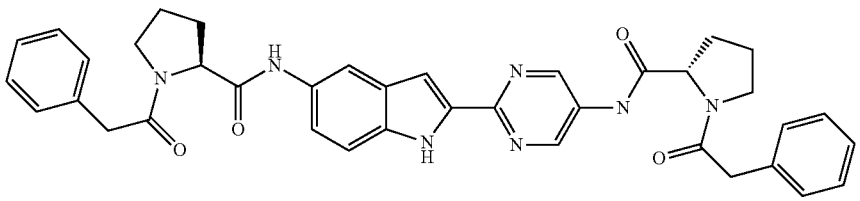 [SMILES: O=C(Nc1cnc(-c2cc3cc(NC(=O)[C@@H]4CCCN4C(=O)Cc4ccccc4)ccc3[nH]2)nc1)[C@@H]1CCCN1C(=O)Cc1ccccc1]

Step 1

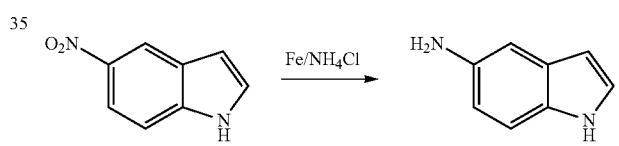

A mixture of 5-nitroindole (5 g, 30.9 mmol), Fe (8.6 g, 154 mmol), NH$_4$Cl (16.5 g, 309 mmol), EtOH (80 mL) and water (20 mL) was refluxed under N$_2$ protection for 2 hours. The mixture was cooled to RT and filtered. The filtrate was concentrated and dissolved in water. The mixture was basified with Na$_2$CO$_3$ and extracted with CH$_2$Cl$_2$ two times. The combined organic phases were combined, dried over Na$_2$SO$_4$ and filtered. The filtrate was concentrated to yield the product (3.6 g). MS (ESI) m/e (M+H$^+$): 133. $^1$H NMR (DMSO) δ: 10.55 (s, 1H), 7.12-7.06 (m, 2H), 6.68 (d, J=2.0 Hz, 1H), 6.48 (dd, J=8.4 Hz, 2.0 Hz, 1H), 6.12 (t, J=2.0 Hz, 1H), 4.39 (s, 2H).

Step 2

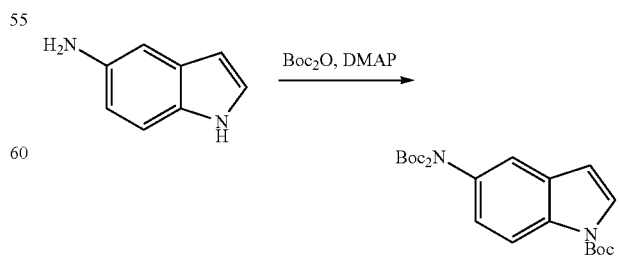

A mixture of 5-aminoindole (20 g, 76 mmol), DMAP (9.2 g, 38 mmol) THF (250 mL) and CH$_3$CN (100 mL) was cooled to 0° C. Boc$_2$O (132 g, 304 mmol) was slowly added to the mixture. The reaction mixture was allowed to warm to RT and stirred over the weekend. The mixture was poured into water and exacted with CH$_2$Cl$_2$ three times. The organic phase was combined, dried over Na$_2$SO$_4$ and filtered. The filtrate was concentrated, dissolved in CH$_2$Cl$_2$ and poured into PE and filtered. The solid was purified by column chromatography (PE/EA=20/1) to yield the product (23 g). $^1$H NMR (CDCl$_3$): δ 8.05 (d, J=8.0 Hz, 1H), 7.56 (d, J=3.2 Hz, 1H), 7.28 (d, J=2.4 Hz, 1H), 7.03 (dd, J=8.8 Hz, 1.6 Hz, 1H), 1.63 (s, 9H), 1.36 (s, 18H).
Step 3

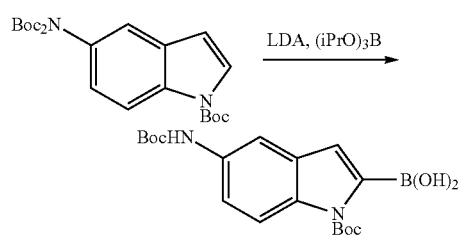

A mixture of the product from step 2 above (5.0 g, 11.6 mmol), (iPrO)$_3$B (17.5 mL, 92.8 mmol) and dry THF (100 mL) was cooled to 0° C. LDA (prepared from nBuLi and iPr$_2$NH in THF, about 116 mmol) was slowly added to the mixture at 0° C. The mixture was allowed to warm to RT and stirred for 2 hours. The mixture was quenched by the addition of 1N HCl to pH=3 and extracted with CH$_2$Cl$_2$ three times. The combined organic phases were combined, dried over Na$_2$SO$_4$ and filtered. The filtrate was concentrated and purified by column chromatography (PE/CH$_2$Cl$_2$=1/1 to pure CH$_2$Cl$_2$ to CH$_2$Cl$_2$/acetone=10/1 to pure acetone) to afford the product (2.8 g). $^1$H NMR (DMSO) δ: 9.22 (s, 1H), 8.10 (s, 2H), 7.84 (d, J=9.2 Hz, 1H), 7.65 (s, 1H), 7.20 (dd, J=9.2 Hz, 2.0 Hz, 1H), 6.48 (d, 1H), 1.51 (s, 9H), 1.41 (s, 9H).
Step 4

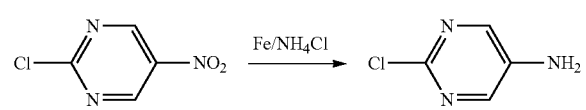

A mixture of the pyrimidine compound (0.3 g, 2 mmol), Fe powder (560 mg, 10 mmol), NH$_4$Cl (1.07 g, 20 mmol), EtOH (8 mL) and water (2 mL) was refluxed under N$_2$ overnight. The mixture was cooled to RT and filtered. The filtrate was concentrated and dissolved in water. The mixture was basified with Na$_2$CO$_3$ and extracted with CH$_2$Cl$_2$ two times. The combined organic phases were dried over Na$_2$SO$_4$ and filtered. The filtrate was concentrated to yield the product (120 mg). MS (ESI) m/e (M+H$^+$): 130. $^1$H NMR (DMSO) δ: 7.99 (s, 2H), 5.73 (s, 2H).
Step 5

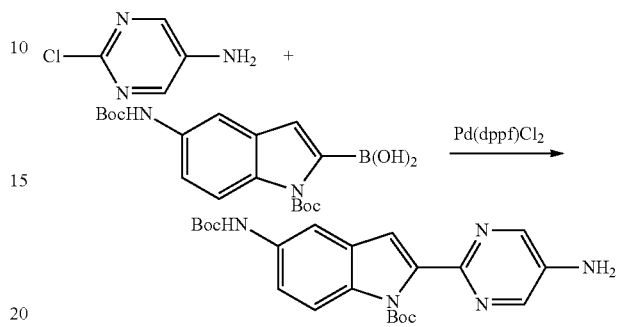

A mixture of the pyrimidine from step 4 (100 mg, 0.77 mmol), indole boronic acid from step 3 (290 mg, 0.77 mmol), Pd(dppf)Cl$_2$ (56 mg, 0.077 mmol), Na$_2$CO$_3$ (244 mg, 2.3 mmol), THF (20 mL) and H$_2$O (2 mL) was refluxed under N$_2$ overnight. The mixture was poured into water and extracted with CH$_2$Cl$_2$. The organic phase was combined, dried over Na$_2$SO$_4$ and filtered. The filtrate was purified by prep TLC (CH$_2$Cl$_2$/MeOH=20/1) to afford the product. MS (ESI) m/e (M+H$^+$): 426.
Step 6

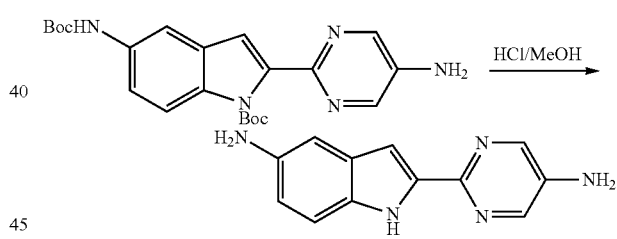

A mixture of compound from step 5 above was added to a solution HCl in MeOH (4M) cooled with ice bath. The mixture was allowed to warm to RT and stirred overnight. The mixture was concentrated, dissolved in water, washed by CH$_2$Cl$_2$ and concentrated. The residue was directly used in the next step without further purification. MS (ESI) m/e (M+H$^+$): 226
Step 7

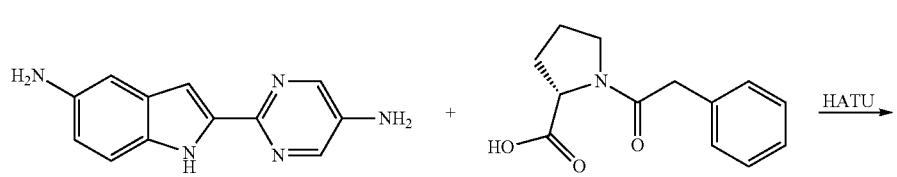

-continued

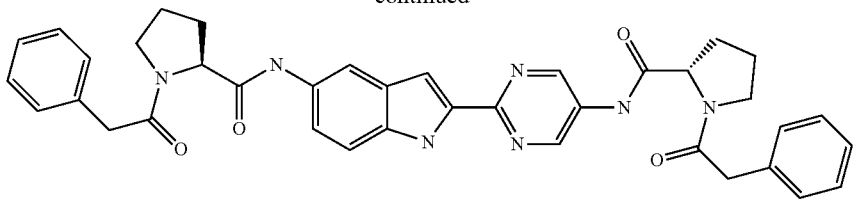

The product of step 6 above (0.22 mmol), N-phenylacetyl-L-proline (51 mg, 0.22 mmol), DIPEA (100 mg), and DMF (3 mL) was added HATU (84 mg, 0.22 mmol), and the mixture was stirred at RT overnight. The mixture was purified by RPLC to afford the product. MS (ESI) m/e (M+H$^+$): 656. $^1$H NMR (CDCl$_3$) δ: 10.42 (s, 1H), 10.01 (s, 1H), 9.77 (s, 1H), 8.32 (s, 1H), 7.34-7.27 (m, 11H), 7.05-7.00 (m, 2H), 6.58 (d, J=8.0 Hz, 1H), 4.63-4.53 (m, 2H), 3.84-3.58 (m, 8H), 2.30-1.94 (m, 8H).

Examples 43-87

Compounds of Examples 43-87 were prepared in a similar manner as described in either Example 41 or Example 42.

| Example | Structure | MW | Name |
|---|---|---|---|
| 43 | 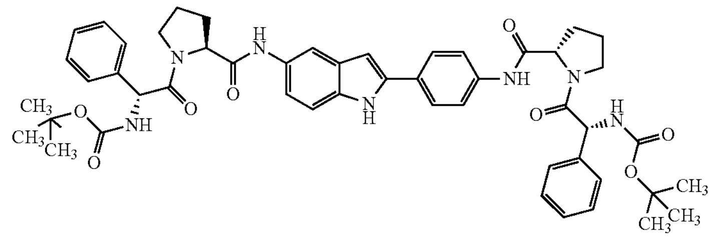 | 884.054 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-1H-indol-2-yl]phenyl}carbamoyl)pyrrolidin-1-yl]-2-oxo-1-phenylethyl}carbamate |
| 44 | 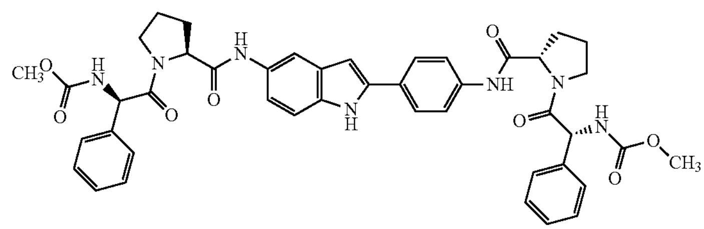 | 799.891 | methyl {(1R)-2-[(2S)-2-({4-[5-({[(2S)-1-{(2R)-2-[(methoxycarbonyl)amino]-2-phenylacetyl}pyrrolidin-2-yl]carbonyl}amino)-1H-indol-2-yl]phenyl}carbamoyl)pyrrolidin-1-yl]-2-oxo-1-phenylethyl}carbamate |
| 45 | 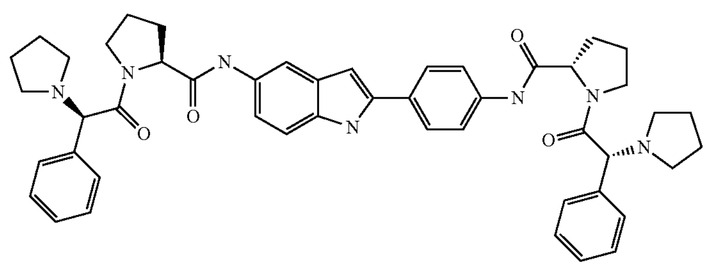 [SMILES: O=C(Nc1ccc(-c2cc3cc(NC(=O)[C@@H]4CCCN4C(=O)[C@@H](c4ccccc4)N4CCCC4)ccc3[nH]2)cc1)[C@@H]1CCCN1C(=O)[C@@H](c1ccccc1)N1CCCC1] | 792.002 | (2S)-1-[(2R)-2-phenyl-2-(pyrrolidin-1-yl)acetyl]-N-(4-{5-[({(2S)-1-[(2R)-2-phenyl-2-(pyrrolidin-1-yl)acetyl]pyrrolidin-2-yl}carbonyl)amino]-1H-indol-2-yl}phenyl)pyrrolidine-2-carboxamide |
| 46 | 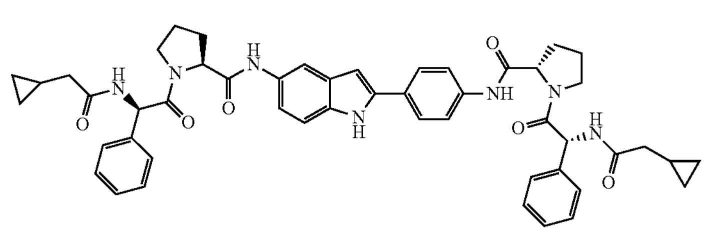 [SMILES: O=C(CC1CC1)N[C@@H](C(=O)N1CCC[C@H]1C(=O)Nc1ccc(-c2cc3cc(NC(=O)[C@@H]4CCCN4C(=O)[C@H](NC(=O)CC4CC4)c4ccccc4)ccc3[nH]2)cc1)c1ccccc1] | 848.023 | (2S)-1-{(2R)-2-[(cyclopropylacetyl)amino]-2-phenylacetyl}-N-{4-[5-({[(2S)-1-{(2R)-2-[(cyclopropylacetyl)amino]-2-phenylacetyl}pyrrolidin-2-yl]carbonyl}amino)-1H-indol-2-yl]phenyl}pyrrolidine-2-carboxamide |
| 47 | 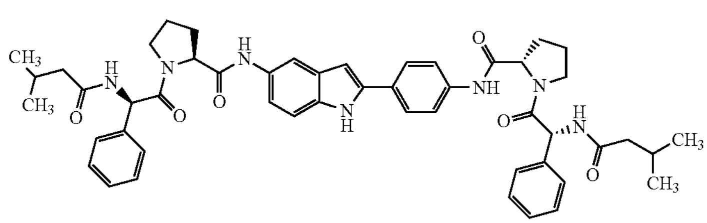 [SMILES: CC(C)CC(=O)N[C@@H](C(=O)N1CCC[C@H]1C(=O)Nc1ccc(-c2cc3cc(NC(=O)[C@@H]4CCCN4C(=O)[C@H](NC(=O)CC(C)C)c4ccccc4)ccc3[nH]2)cc1)c1ccccc1] | 852.055 | (2S)-1-{(2R)-2-[(3-methylbutanoyl)amino]-2-phenylacetyl}-N-{4-[5-({[(2S)-1-{(2R)-2-[(3-methylbutanoyl)amino]-2-phenylacetyl}pyrrolidin-2-yl]carbonyl}amino)-1H-indol-2-yl]phenyl}pyrrolidine-2-carboxamide |

-continued

| Example | Structure | MW | Name |
|---|---|---|---|
| 48 | 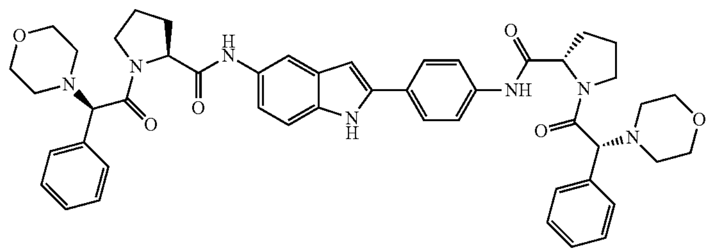 [SMILES: O=C(Nc1ccc(-c2cc3cc(NC(=O)[C@@H]4CCCN4C(=O)[C@@H](c4ccccc4)N4CCOCC4)ccc3[nH]2)cc1)[C@@H]1CCCN1C(=O)[C@@H](c1ccccc1)N1CCOCC1] | 824.001 | (2S)-1-[(2R)-2-(morpholin-4-yl)-2-phenylacetyl]-N-(4-{5-[({(2S)-1-[(2R)-2-(morpholin-4-yl)-2-phenylacetyl]pyrrolidin-2-yl}carbonyl)amino]-1H-indol-2-yl}phenyl)pyrrolidine-2-carboxamide |
| 49 | 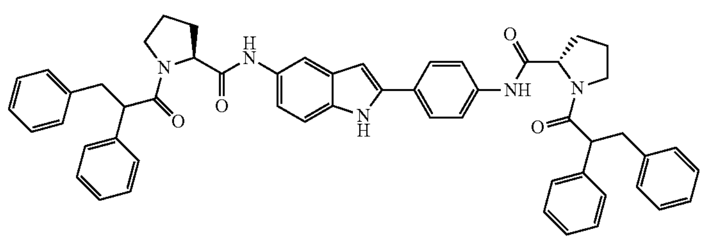 [SMILES: O=C(Nc1ccc(-c2cc3cc(NC(=O)[C@@H]4CCCN4C(=O)C(Cc4ccccc4)c4ccccc4)ccc3[nH]2)cc1)[C@@H]1CCCN1C(=O)C(Cc1ccccc1)c1ccccc1] | 834.04 | (2S)-1-(2,3-diphenylpropanoyl)-N-{4-[5-({[(2S)-1-(2,3-diphenylpropanoyl)pyrrolidin-2-yl]carbonyl}amino)-1H-indol-2-yl]phenyl}pyrrolidine-2-carboxamide |
| 50 | 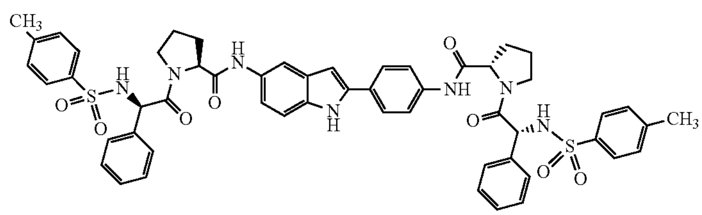 | 992.195 | (2S)-1-(2R)-2-{[(4-methylphenyl)sulfonyl]amino}-2-phenylacetyl]-N-(4-{5-[({(2S)-1-[(2R)-2-{[(4-methylphenyl)sulfonyl]amino}-2-phenylacetyl]pyrrolidin-2-yl}carbonyl)amino]-1H-indol-2-yl}phenyl)pyrrolidine-2-carboxamide |
| 51 | 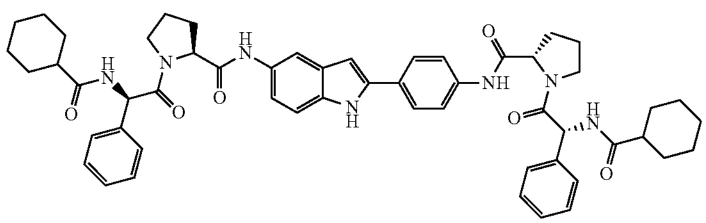 [SMILES: O=C(N[C@@H](C(=O)N1CCC[C@H]1C(=O)Nc1ccc(-c2cc3cc(NC(=O)[C@@H]4CCCN4C(=O)[C@H](NC(=O)C4CCCCC4)c4ccccc4)ccc3[nH]2)cc1)c1ccccc1)C1CCCCC1] | 904.132 | (2S)-1-{(2R)-2-[(cyclohexylcarbonyl)amino]-2-phenylacetyl}-N-{4-[5-({[(2S)-1-{(2R)-2-[(cyclohexylcarbonyl)amino]-2-phenylacetyl}pyrrolidin-2-yl]carbonyl}amino)-1H-indol-2-yl]phenyl}pyrrolidine-2-carboxamide |
| 52 | 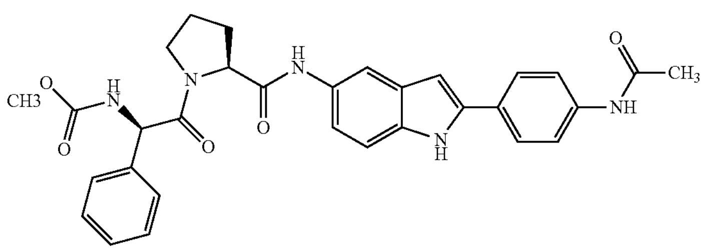 | 553.623 | methyl {(1R)-2-[(2S)-2-({2-[4-(acetylamino)phenyl]-1H-indol-5-yl}carbamoyl)pyrrolidin-1-yl]-2-oxo-1-phenylethyl}carbamate |
| 53 | 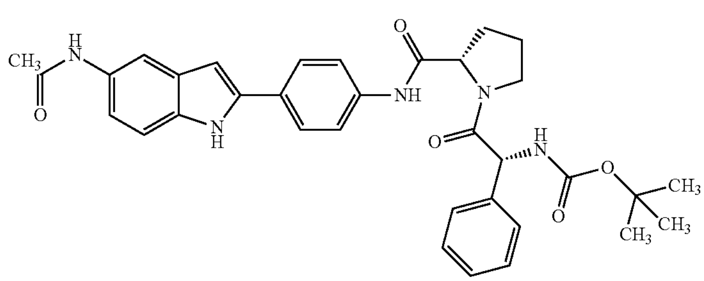 | 595.704 | tert-butyl {(1R)-2-[(2S)-2-({4-[5-(acetylamino)-1H-indol-2-yl]phenyl}carbamoyl)pyrrolidin-1-yl]-2-oxo-1-phenylethyl}carbamate |

| Example | Structure | MW | Name |
|---|---|---|---|
| 54 | 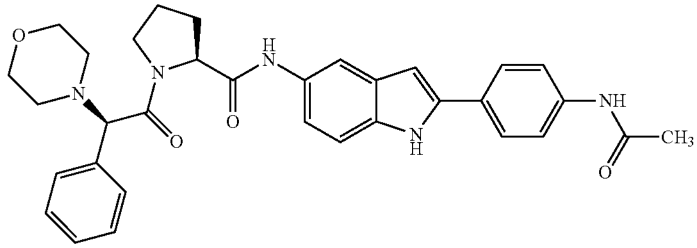 [SMILES: CC(=O)Nc1ccc(-c2cc3cc(NC(=O)[C@@H]4CCCN4C(=O)[C@@H](c4ccccc4)N4CCOCC4)ccc3[nH]2)cc1] | 565.678 | N-{2-[4-(acetylamino)phenyl]-1H-indol-5-yl}-1-[(2R)-2-(morpholin-4-yl)-2-phenylacetyl]-L-prolinamide |
| 55 | 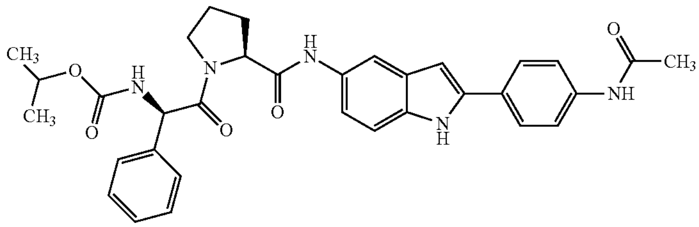 [SMILES: CC(=O)Nc1ccc(-c2cc3cc(NC(=O)[C@@H]4CCCN4C(=O)[C@H](NC(=O)OC(C)C)c4ccccc4)ccc3[nH]2)cc1] | 581.677 | propan-2-yl {(1R)-2-[(2S)-2-({2-[4-(acetylamino)phenyl]-1H-indol-5-yl}carbamoyl)pyrrolidin-1-yl]-2-oxo-1-phenylethyl}carbamate |
| 56 | 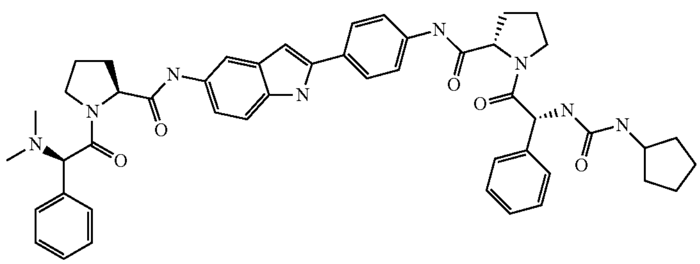 [SMILES: CN(C)[C@@H](C(=O)N1CCC[C@H]1C(=O)Nc1ccc2[nH]c(-c3ccc(NC(=O)[C@@H]4CCCN4C(=O)[C@H](NC(=O)NC4CCCC4)c4ccccc4)cc3)cc2c1)c1ccccc1] | 817.953 | (2S)-1-{(2R)-2-[(cyclopentylcarbamoyl)amino]-2-phenylacetyl}-N-(4-{5-[({(2S)-1-[(2R)-2-(dimethylamino)-2-phenylacetyl]pyrrolidin-2-yl}carbonyl)amino]-1H-indol-2-yl}phenyl)pyrrolidine-2-carboxamide |
| 57 | 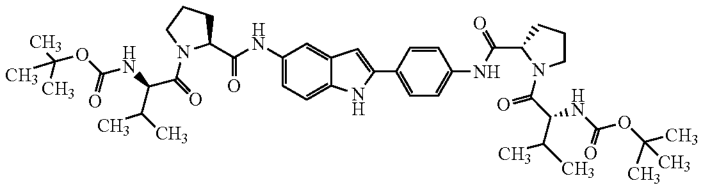 [SMILES: CC(C)[C@@H](NC(=O)OC(C)(C)C)C(=O)N1CCC[C@H]1C(=O)Nc1ccc(-c2cc3cc(NC(=O)[C@@H]4CCCN4C(=O)[C@H](NC(=O)OC(C)(C)C)C(C)C)ccc3[nH]2)cc1] | 816.019 | tert-butyl {(2R)-1-[(2S)-2-({4-[5-({[(2S)-1-{(2R)-2-[(tert-butoxycarbonyl)amino]-3-methylbutanoyl}pyrrolidin-2-yl]carbonyl}amino)-1H-indol-2-yl]phenyl}carbamoyl)pyrrolidin-1-yl]-3-methyl-1-oxobutan-2-yl}carbamate |
| 58 | 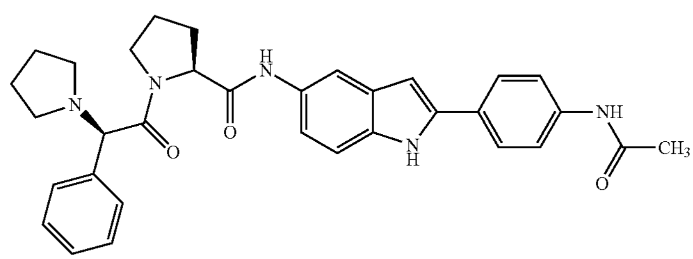 [SMILES: CC(=O)Nc1ccc(-c2cc3cc(NC(=O)[C@@H]4CCCN4C(=O)[C@@H](c4ccccc4)N4CCCC4)ccc3[nH]2)cc1] | 549.679 | N-{2-[4-(acetylamino)phenyl]-1H-indol-5-yl}-1-[(2R)-2-phenyl-2-(pyrrolidin-1-yl)acetyl]-L-prolinamide |
| 59 | 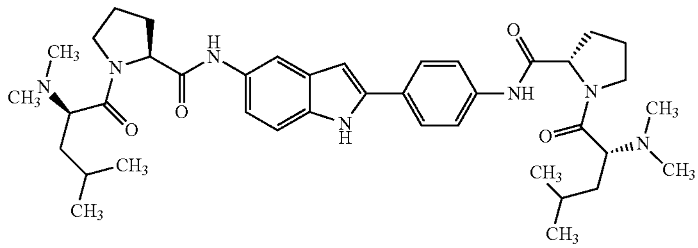 | 699.945 | (2S)-1-[(2R)-2-(dimethylamino)-4-methylpentanoyl]-N-(4-{5-[({(2S)-1-[(2R)-2-(dimethylamino)-4-methylpentanoyl]pyrrolidin-2-yl}carbonyl)amino]-1H-indol-2-yl}phenyl)pyrrolidine-2-carboxamide (non-preferred name) |

| Example | Structure | MW | Name |
|---|---|---|---|
| 60 | 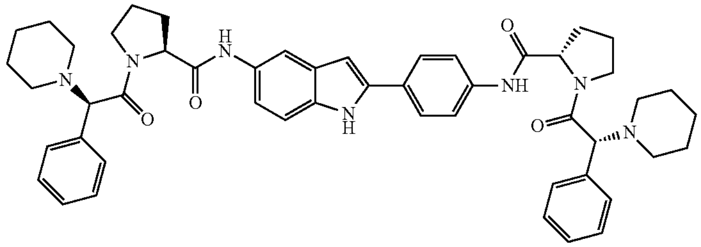 [SMILES: O=C(Nc1ccc(-c2cc3cc(NC(=O)[C@@H]4CCCN4C(=O)[C@@H](c4ccccc4)N4CCCCC4)ccc3[nH]2)cc1)[C@@H]1CCCN1C(=O)[C@@H](c1ccccc1)N1CCCCC1] | 820.056 | (2S)-1-[(2R)-2-phenyl-2-(piperidin-1-yl)acetyl]-N-(4-{5-[({(2S)-1-[(2R)-2-phenyl-2-(piperidin-1-yl)acetyl]pyrrolidin-2-yl}carbonyl)amino]-1H-indol-2-yl}phenyl)pyrrolidine-2-carboxamide |
| 61 | 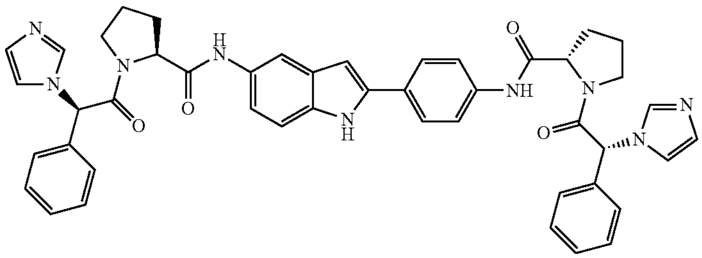 [SMILES: O=C(Nc1ccc(-c2cc3cc(NC(=O)[C@@H]4CCCN4C(=O)[C@@H](c4ccccc4)n4ccnc4)ccc3[nH]2)cc1)[C@@H]1CCCN1C(=O)[C@@H](c1ccccc1)n1ccnc1] | 785.914 | (2S)-1-[(2R)-2-(1H-imidazol-1-yl)-2-phenylacetyl]-N-(4-{5-[({(2S)-1-[(2R)-2-(1H-imidazol-1-yl)-2-phenylacetyl]pyrrolidin-2-yl}carbonyl)amino]-1H-indol-2-yl}phenyl)pyrrolidine-2-carboxamide |
| 62 | 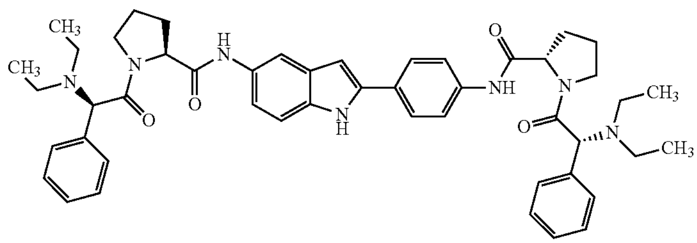 [SMILES: CCN(CC)[C@@H](C(=O)N1CCC[C@H]1C(=O)Nc1ccc(-c2cc3cc(NC(=O)[C@@H]4CCCN4C(=O)[C@@H](c4ccccc4)N(CC)CC)ccc3[nH]2)cc1)c1ccccc1] | 796.034 | (2S)-1-[(2R)-2-(diethylamino)-2-phenylacetyl]-N-(4-{5-[({(2S)-1-[(2R)-2-(diethylamino)-2-phenylacetyl]pyrrolidin-2-yl}carbonyl)amino]-1H-indol-2-yl}phenyl)pyrrolidine-2-carboxamide |
| 63 | 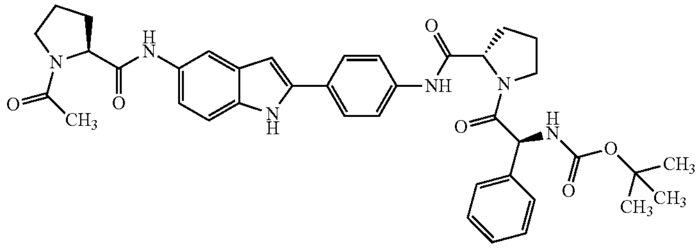 [SMILES: CC(=O)N1CCC[C@H]1C(=O)Nc1ccc2[nH]c(-c3ccc(NC(=O)[C@@H]4CCCN4C(=O)[C@@H](NC(=O)OC(C)(C)C)c4ccccc4)cc3)cc2c1] | 692.822 | tert-butyl {(1S)-2-[(2S)-2-({4-[5-({[(2S)-1-acetylpyrrolidin-2-yl]carbonyl}amino)-1H-indol-2-yl]phenyl}carbamoyl)pyrrolidin-1-yl]-2-oxo-1-phenylethyl}carbamate |
| 64 | 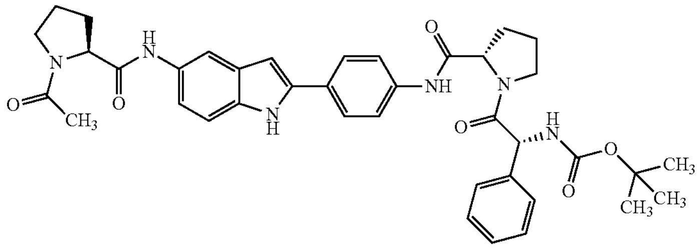 [SMILES: CC(=O)N1CCC[C@H]1C(=O)Nc1ccc2[nH]c(-c3ccc(NC(=O)[C@@H]4CCCN4C(=O)[C@H](NC(=O)OC(C)(C)C)c4ccccc4)cc3)cc2c1] | 692.822 | tert-butyl {(1R)-2-[(2S)-2-({4-[5-({[(2S)-1-acetylpyrrolidin-2-yl]carbonyl}amino)-1H-indol-2-yl]phenyl}carbamoyl)pyrrolidin-1-yl]-2-oxo-1-phenylethyl}carbamate |
| 65 | 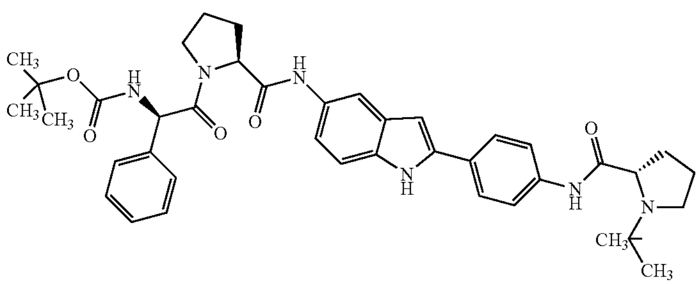 | 692.866 | tert-butyl {(1R)-2-oxo-1-phenyl-2-[(2S)-2-({2-[4-({[(2S)-1-(propan-2-yl)pyrrolidin-2-yl]carbonyl}amino)phenyl]-1H-indol-5-yl}carbamoyl)pyrrolidin-1-yl]ethyl}carbamate |

-continued

| Example | Structure | MW | Name |
|---|---|---|---|
| 66 | 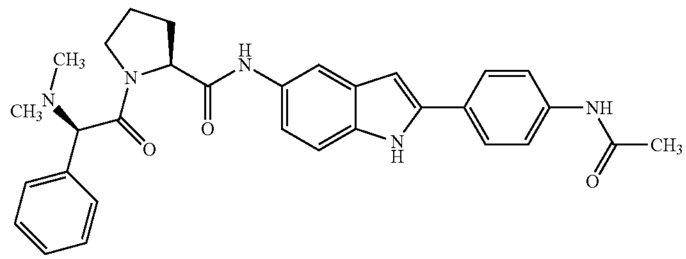 | 523.64 | N-{2-[4-(acetylamino)phenyl]-1H-indol-5-yl}-1-[(2R)-2-(dimethylamino)-2-phenylacetyl]-L-prolinamide |
| 67 | 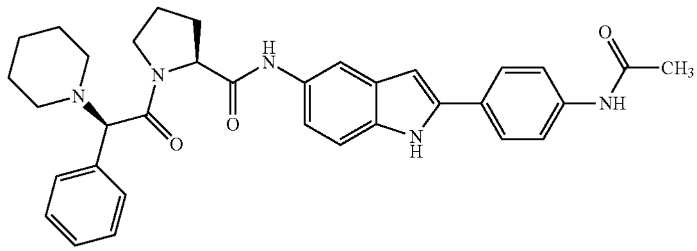 [SMILES: CC(=O)Nc1ccc(-c2cc3cc(NC(=O)[C@@H]4CCCN4C(=O)[C@@H](c4ccccc4)N4CCCCC4)ccc3[nH]2)cc1] | 563.706 | N-{2-[4-(acetylamino)phenyl]-1H-indol-5-yl}-1-[(2R)-2-phenyl-2-(piperidin-1-yl)acetyl]-L-prolinamide |
| 68 | 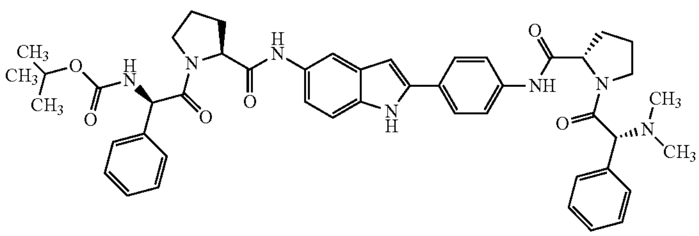 | 811.99 | tert-butyl [(1R)-2-{(2S)-2-[(2-{4-[({(2S)-1-[(2R)-2-(dimethylamino)-2-phenylacetyl]pyrrolidin-2-yl}carbonyl)amino]phenyl}-1H-indol-5-yl)carbamoyl]pyrrolidin-1-yl}-2-oxo-1-phenylethyl]carbamate |
| 69 | 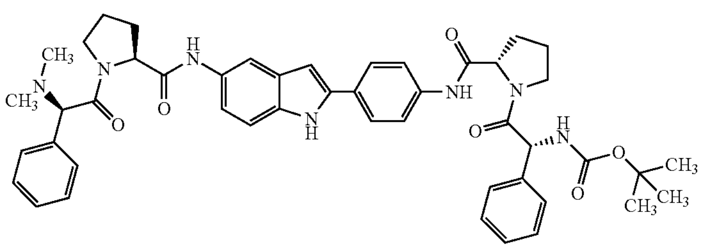 | 811.99 | tert-butyl [(1R)-2-{(2S)-2-[(4-{5-[({(2S)-1-[(2R)-2-(dimethylamino)-2-phenylacetyl]pyrrolidin-2-yl}carbonyl)amino]-1H-indol-2-yl}phenyl)carbamoyl]pyrrolidin-1-yl}-2-oxo-1-phenylethyl]carbamate |
| 70 | 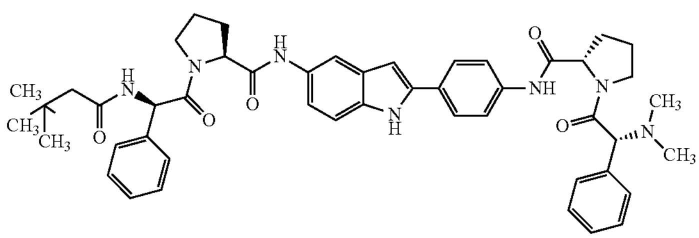 | 810.017 | (2S)-1-[(2R)-2-(dimethylamino)-2-phenylacetyl]-N-{4-[5-({[(2S)-1-{(2R)-2-[(3,3-dimethylbutanoyl)amino]-2-phenylacetyl}pyrrolidin-2-yl]carbonyl}amino)-1H-indol-2-yl]phenyl}pyrrolidine-2-carboxamide |
| 71 | 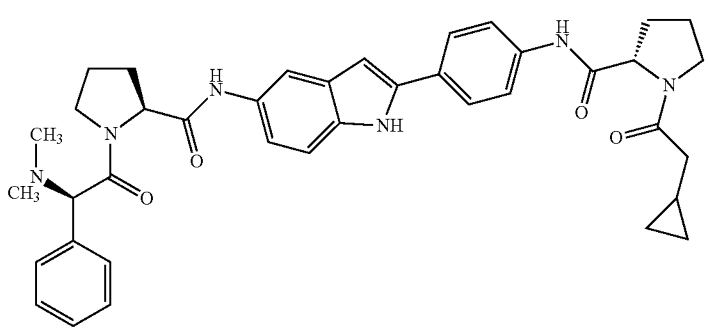 | 660.823 | (2S)-1-(cyclopropylacetyl)-N-(4-{5-[({(2S)-1-[(2R)-2-(dimethylamino)-2-phenylacetyl]pyrrolidin-2-yl}carbonyl)amino]-1H-indol-2-yl}phenyl)pyrrolidine-2-carboxamide |

-continued

| Example | Structure | MW | Name |
|---|---|---|---|
| 72 | 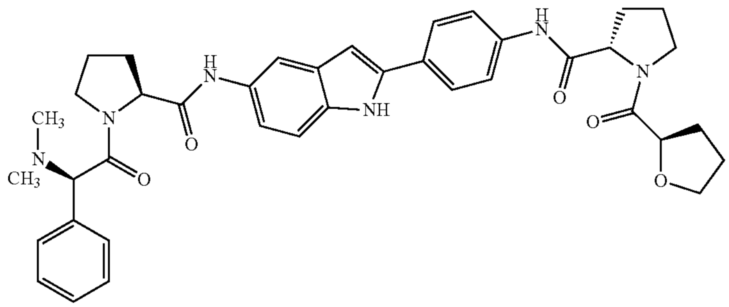 | 676.823 | (2S)-1-[(2R)-2-(dimethylamino)-2-phenylacetyl]-N-(2-{4-[({(2S)-1-[(2R)-tetrahydrofuran-2-ylcarbonyl]pyrrolidin-2-yl}carbonyl)amino]phenyl}-1H-indol-5-yl)pyrrolidine-2-carboxamide |
| 73 | 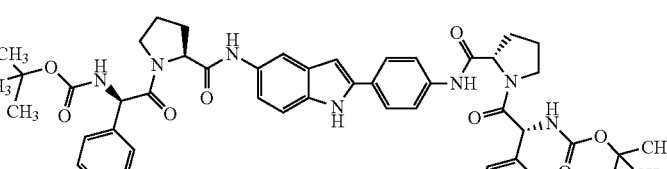 | 920.035 | tert-butyl [(1R)-2-{(2S)-2-[(4-{5-[({(2S)-1-[(2R)-2-[(tert-butoxycarbonyl)amino]-2-(4-fluorophenyl)acetyl]pyrrolidin-2-yl}carbonyl)amino]-1H-indol-2-yl}phenyl)carbamoyl]pyrrolidin-1-yl}-1-(4-fluorophenyl)-2-oxoethyl]carbamate |
| 74 | 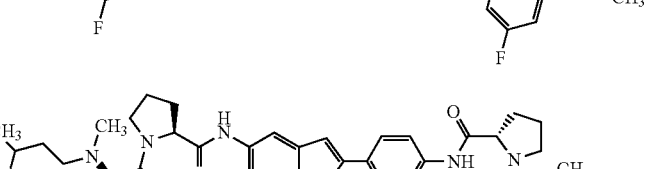 | 852.142 | (2S)-1-{(2R)-2-[methyl(3-methylbutyl)amino]-2-phenylacetyl}-N-{4-[5-({[(2S)-1-{(2R)-2-[methyl(3-methylbutyl)amino]-2-phenylacetyl}pyrrolidin-2-yl]carbonyl}amino)-1H-indol-2-yl]phenyl}pyrrolidine-2-carboxamide |
| 75 | 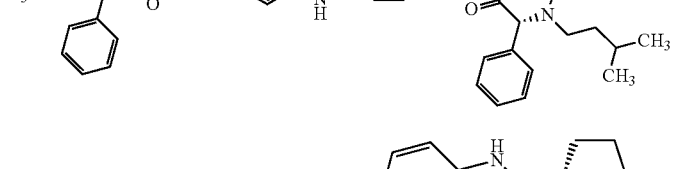 | 613.72 | (2S)-1-[(2S)-tetrahydrofuran-2-ylcarbonyl]-N-(4-{5-[({(2S)-1-[(2S)-tetrahydrofuran-2-ylcarbonyl]pyrrolidin-2-yl}carbonyl)amino]-1H-indol-2-yl}phenyl)pyrrolidine-2-carboxamide |
| 76 | 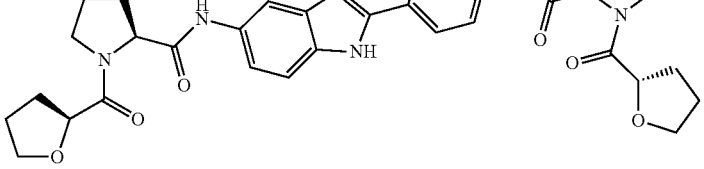 | 777.972 | N-(tert-butoxycarbonyl)-D-valyl-N-{4-[5-({1-[(2R)-2-(dimethylamino)-2-phenylacetyl]-L-prolyl}amino)-1H-indol-2-yl]phenyl}-L-prolinamide |
| 77 | 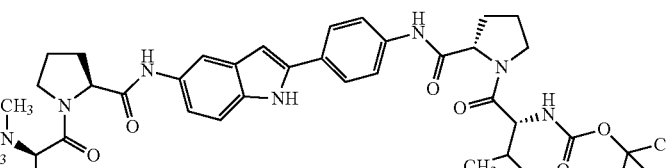 | 673.778 | (2S)-1-[(2R)-2-(dimethylamino)-2-phenylacetyl]-N-{2-[4-({[(2S)-1-(1,3-oxazol-2-ylcarbonyl)pyrrolidin-2-yl]carbonyl}amino)phenyl]-1H-indol-5-yl}pyrrolidine-2-carboxamide |

-continued

| Example | Structure | MW | Name |
|---|---|---|---|
| 78 | 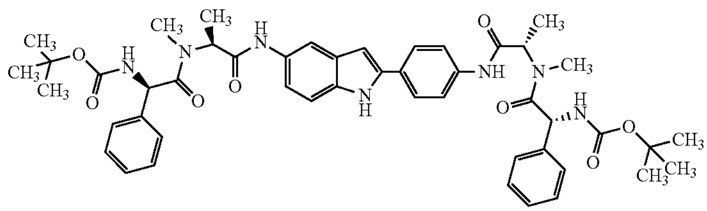 [SMILES: C[C@@H](C(=O)Nc1ccc(-c2cc3cc(NC(=O)[C@H](C)N(C)C(=O)[C@H](NC(=O)OC(C)(C)C)c4ccccc4)ccc3[nH]2)cc1)N(C)C(=O)[C@H](NC(=O)OC(C)(C)C)c1ccccc1] | 860.032 | tert-butyl [(1R)-2-{[(2S)-1-({4-[5-({(2S)-2-[{(2R)-2-[(tert-butoxycarbonyl)amino]-2-phenylacetyl}(methyl)amino]propanoyl}amino)-1H-indol-2-yl]phenyl}amino)-1-oxopropan-2-yl](methyl)amino}-2-oxo-1-phenylethyl]carbamate |
| 79 | 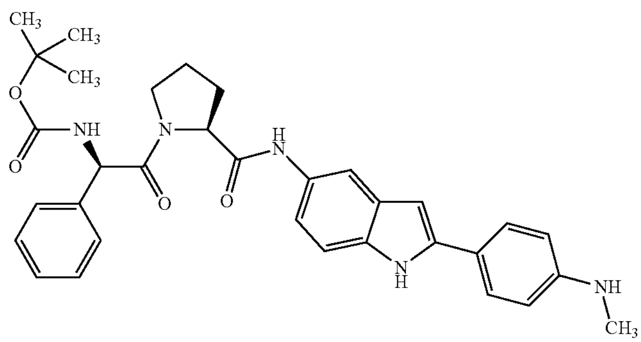 [SMILES: CNc1ccc(-c2cc3cc(NC(=O)[C@@H]4CCCN4C(=O)[C@H](NC(=O)OC(C)(C)C)c4ccccc4)ccc3[nH]2)cc1] | 567.694 | tert-butyl {(1R)-2-[(2S)-2-({2-[4-(methylamino)phenyl]-1H-indol-5-yl}carbamoyl)pyrrolidin-1-yl]-2-oxo-1-phenylethyl}carbamate |
| 80 | 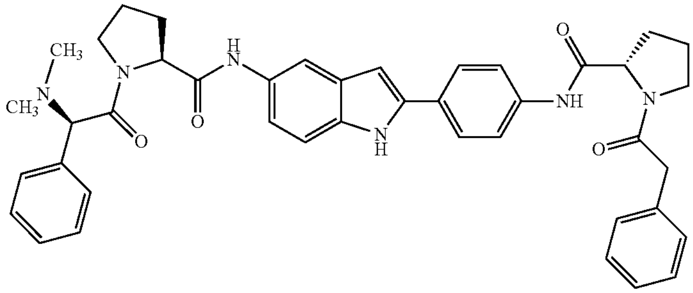 | 696.857 | (2S)-1-[(2R)-2-(dimethylamino)-2-phenylacetyl]-N-{2-[4-({[(2S)-1-(phenylacetyl)pyrrolidin-2-yl]carbonyl}amino)phenyl]-1H-indol-5-yl}pyrrolidine-2-carboxamide |
| 81 | 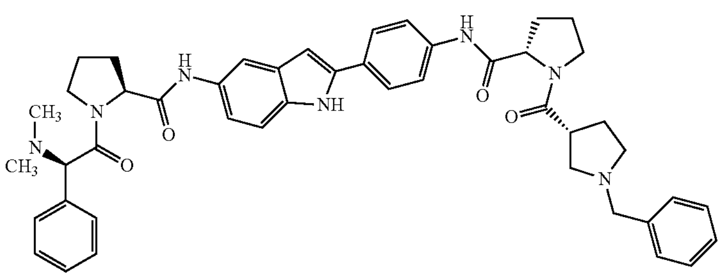 | 765.964 | (2S)-1-{[(3R)-1-benzylpyrrolidin-3-yl]carbonyl}-N-(4-{5-[({(2S)-1-[(2R)-2-(dimethylamino)-2-phenylacetyl]pyrrolidin-2-yl}carbonyl)amino]-1H-indol-2-yl}phenyl)pyrrolidine-2-carboxamide |
| 82 | 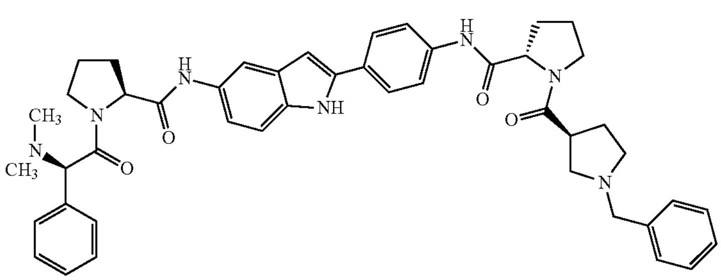 | 765.964 | (2S)-1-{[(3S)-1-benzylpyrrolidin-3-yl]carbonyl}-N-(4-{5-[({(2S)-1-[(2R)-2-(dimethylamino)-2-phenylacetyl]pyrrolidin-2-yl}carbonyl)amino]-1H-indol-2-yl}phenyl)pyrrolidine-2-carboxamide |

-continued

| Example | Structure | MW | Name |
|---|---|---|---|
| 83 | 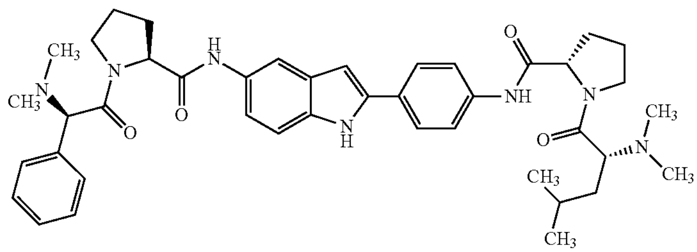 | 719.935 | N,N-dimethyl-D-leucyl-N-{4-[5-({1-[(2R)-2-(dimethylamino)-2-phenylacetyl]-L-prolyl}amino)-1H-indol-2-yl]phenyl}-L-prolinamide |
| 84 | 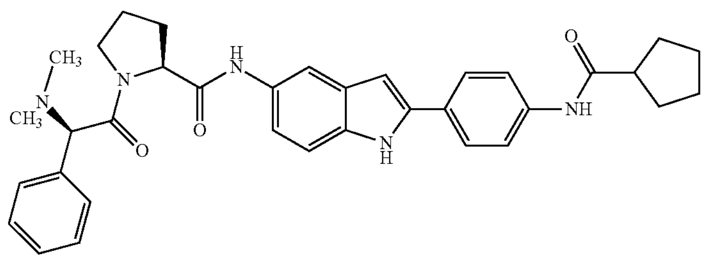 | 577.733 | N-(2-{4-[(cyclopentylcarbonyl)amino]phenyl}-1H-indol-5-yl)-1-[(2R)-2-(dimethylamino)-2-phenylacetyl]-L-prolinamide |
| 85 | 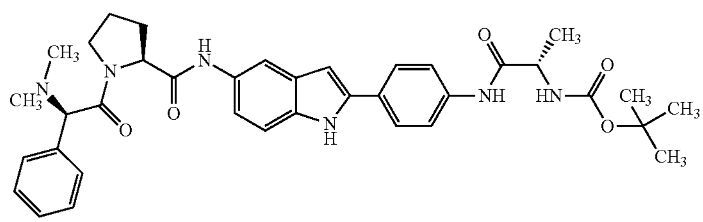 | 652.8 | tert-butyl [(2S)-1-({4-[5-({1-[(2R)-2-(dimethylamino)-2-phenylacetyl]-L-prolyl}amino)-1H-indol-2-yl]phenyl}amino)-1-oxopropan-2-yl]carbamate |
| 86 | 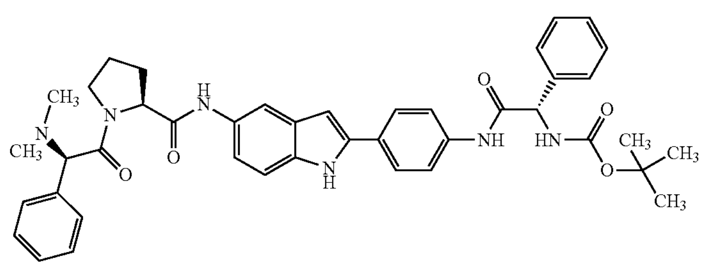 | 714.872 | tert-butyl [(1S)-2-({4-[5-({1-[(2R)-2-(dimethylamino)-2-phenylacetyl]-L-prolyl}amino)-1H-indol-2-yl]phenyl}amino)-2-oxo-1-phenylethyl]carbamate |
| 87 | 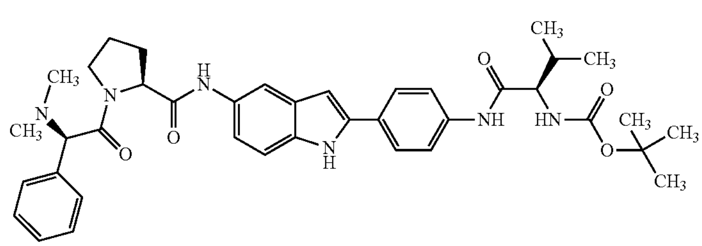 | 680.855 | tert-butyl [(2R)-1-({4-[5-({1-[(2R)-2-(dimethylamino)-2-phenylacetyl]-L-prolyl}amino)-1H-indol-2-yl]phenyl}amino)-3-methyl-1-oxobutan-2-yl]carbamate |

Example 88

(2S,2'S)—N,N'-5,6,7,12-tetrahydrobenzo[6,7]cyclo-hepta[1,2-b]indole-3,9-diylbis[1-(phenylacetyl)pyr-rolidine-2-carboxamide]

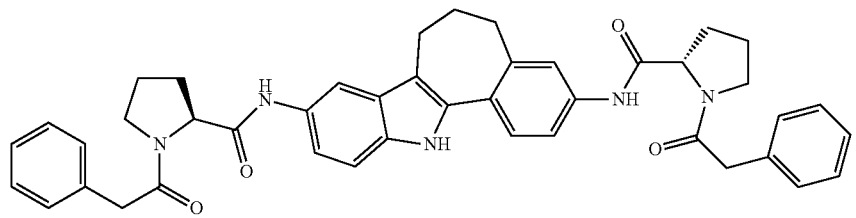 [SMILES: O=C(Nc1ccc2c(c1)CCCc1c-2[nH]c2ccc(NC(=O)[C@@H]3CCCN3C(=O)Cc3ccccc3)cc12)[C@@H]1CCCN1C(=O)Cc1ccccc1]

Step 1

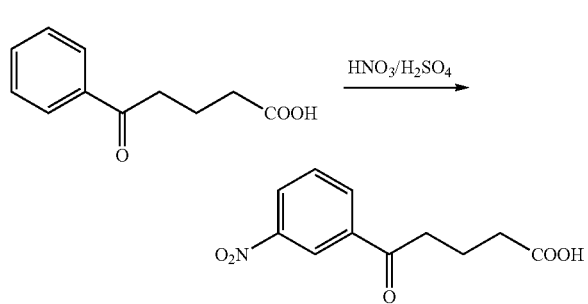

To a mixture of HNO$_3$ (4 mL) and H$_2$SO$_4$ (2 mL) at 0° C. was slowly added the above carboxylic acid (2 g, 10.4 mmol). The mixture was stirred under 0° C. for 30 minutes. The resulting solution was poured into 20 mL of H$_2$O at 0° C., and the precipitate was filtered to give compound (2 g) as a yellow solid. MS (ESI) m/e (M+H$^+$): 238.

Step 2

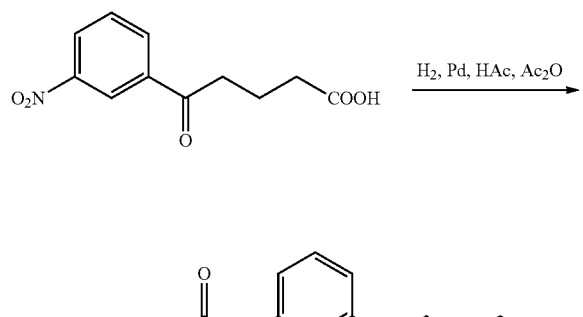

To a mixture of HOAc (10 mL) and Ac$_2$O (3 mL) was added the nitro compound from step 1 (1 g, 4.3 mmol) and Pd/C (100 mg, 0.6 mmol). The mixture was stirred under H$_2$ for 6 hours. The catalyst was filtered, and the filtrate was concentrated in vacuo to give the desired compound (1 g) as a brown solid. MS (ESI) m/e (M+H$^+$): 236.

Step 3

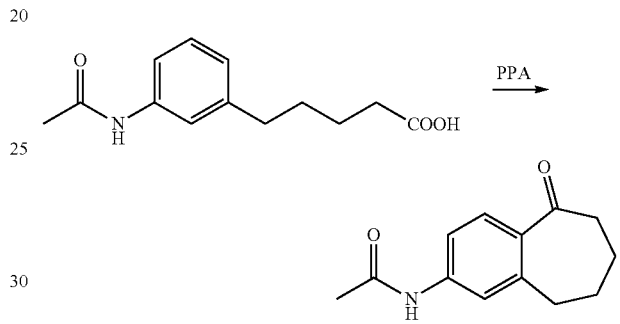

The compound from step 2 above (150 mg, 0.64 mmol) was slowly added to PPA (6 mL) at 100° C. The mixture was stirred for 3 hours. After cooling, the resulting solution was poured into 40 mL mixture of water and ice and extracted with DCM. The organic layer was concentrated to give the cyclic product (70 mg) as a brown solid. MS (ESI) m/e (M+H$^+$): 218.

Step 4

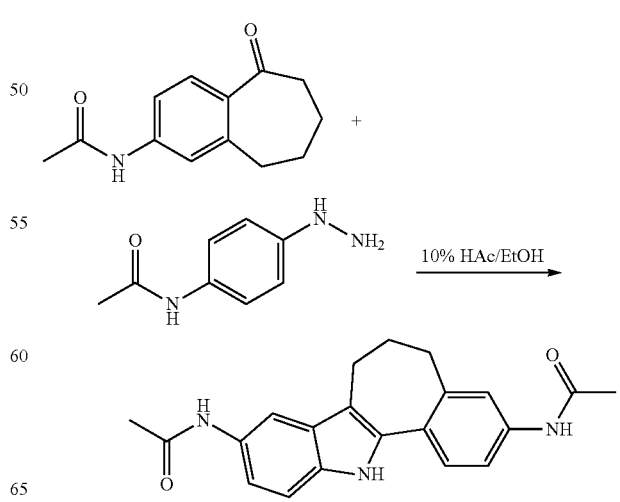

To a solution of the ketone from step 3 (140 mg, 0.65 mmol) in 10% HOAc/EtOH (10 mL) was added 4-acetamidophenylhydrazine (144 mg, 0.72 mmol). The mixture was stirred at reflux for 4 hours. After cooling, the resulting solution was concentrated in vacuo, washed with water and extracted by EtOAc. The organic layer was concentrated in vacuo to give the desired compound (200 mg) as a brown solid. MS (ESI) m/e (M+H$^+$): 348.

Step 5

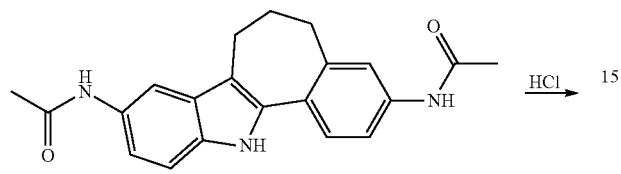

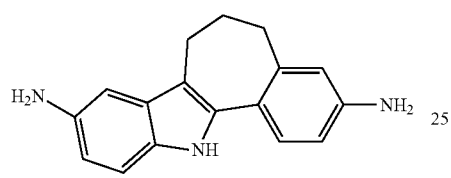

To a solution of the product from step 4 above (200 mg, 0.57 mmol) in EtOH (10 mL) was added 6N HCl (2 mL, 12 mmol). The mixture was stirred at reflux overnight and cooled, and the resulting solution was concentrated then purified by silica gel flash chromatography (petroleum ether/ethyl acetate=5:1) to give the desired compound (150 mg) as a brown solid. MS (ESI) m/e (M+H$^+$): 264.

Step 6

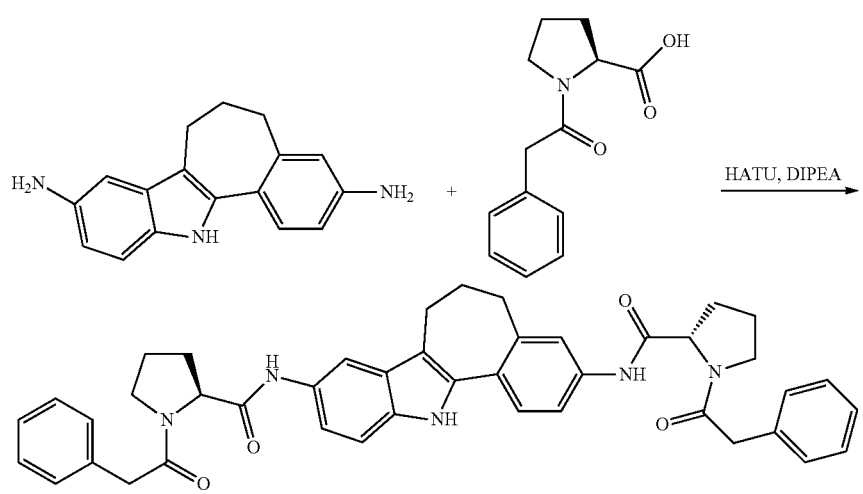

To a solution of the aniline from step 5 (40 mg, 0.15 mmol) in MeCN (5 mL) was added the proline analog (70 mg, 0.3 mol), HATU (250 mg, 0.6 mmol) and DIPEA (80 mg, 0.6 mmol). The mixture was stirred overnight. The resulting solution was purified by pre-HPLC to give the desired compound (10 mg) as a brown solid. $^1$H NMR δ: 7.62-7.20 (m, 16H), 4.58-4.54 (m, 2H), 3.79-3.60 (m, 6H), 2.95 (m, 2H), 2.80 (m, 2H), 2.26-1.94 (m, 8H). MS (ESI) m/e (M+H$^+$): 694.

Examples 89-98

Compounds of Examples 89-98 were prepared in a similar manner as described in Example 88.

| Example | Structure | MW | Name |
|---|---|---|---|
| 89 | 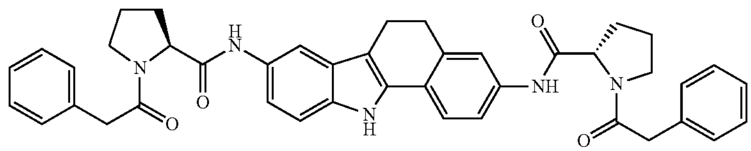 [SMILES: O=C(Nc1ccc2c(c1)CCc1c-2[nH]c2ccc(NC(=O)[C@@H]3CCCN3C(=O)Cc3ccccc3)cc12)[C@@H]1CCCN1C(=O)Cc1ccccc1] | 679.826 | (2S,2'S)-N,N'-6,11-dihydro-5H-benzo[a]carbazole-3,8-diylbis[1-(phenylacetyl)pyrrolidine-2-carboxamide] |
| 90 | 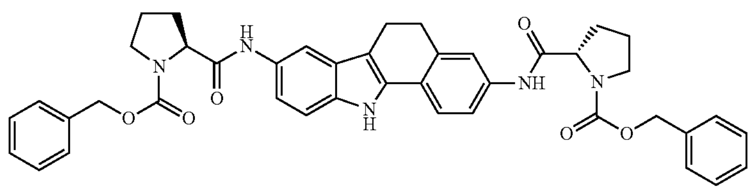 [SMILES: O=C(Nc1ccc2c(c1)CCc1c-2[nH]c2ccc(NC(=O)[C@@H]3CCCN3C(=O)OCc3ccccc3)cc12)[C@@H]1CCCN1C(=O)OCc1ccccc1] | 711.825 | dibenzyl (2S,2'S)-2,2'-(6,11-dihydro-5H-benzo[a]carbazole-3,8-diyldicarbamoyl)dipyrrolidine-1-carboxylate |
| 91 | 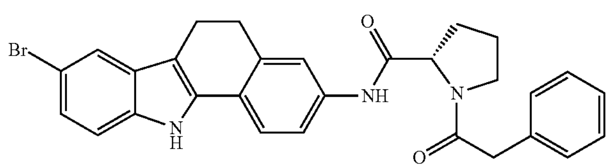 [SMILES: O=C(Nc1ccc2c(c1)CCc1c-2[nH]c2ccc(Br)cc12)[C@@H]1CCCN1C(=O)Cc1ccccc1] | 528.453 | N-(8-bromo-6,11-dihdro-5H-benzo[a]carbazol-3-yl)-1-(phenylacetyl)-L-prolinamide |
| 92 | 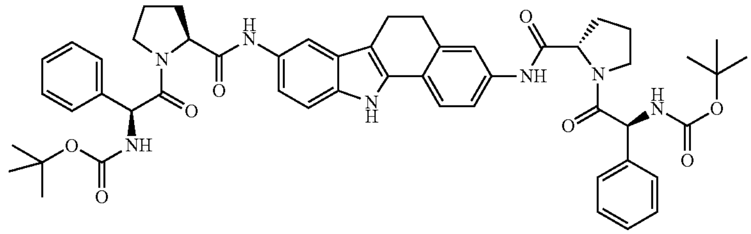 [SMILES: CC(C)(C)OC(=O)N[C@H](C(=O)N1CCC[C@H]1C(=O)Nc1ccc2c(c1)CCc1c-2[nH]c2ccc(NC(=O)[C@@H]3CCCN3C(=O)[C@@H](NC(=O)OC(C)(C)C)c3ccccc3)cc12)c1ccccc1] | 910.092 | di-tert-butyl (6,11-dihydro-5H-benzo[a]carbazole-3,8-diylbis{carbamoyl(2S)pyrrolidine-2,1-diyl[(1S)-2-oxo-1-phenylethane-2,1-diyl]})biscarbamate |
| 93 | 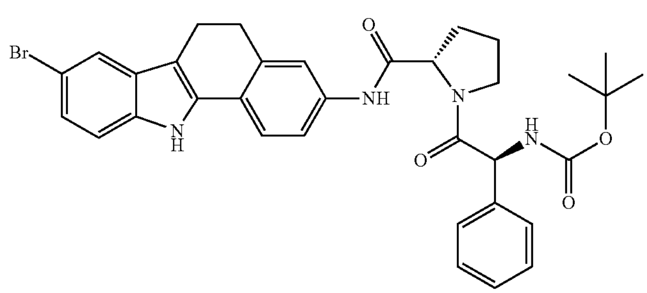 [SMILES: CC(C)(C)OC(=O)N[C@H](C(=O)N1CCC[C@H]1C(=O)Nc1ccc2c(c1)CCc1c-2[nH]c2ccc(Br)cc12)c1ccccc1] | 643.586 | tert-butyl [(1S)-2-[(2S)-2-[(8-bromo-6,11-dihydro-5H-benzo[a]carbazol-3-yl)carbamoyl]pyrrolidin-1-yl}-2-oxo-1-phenylethyl]carbamate |
| 94 | 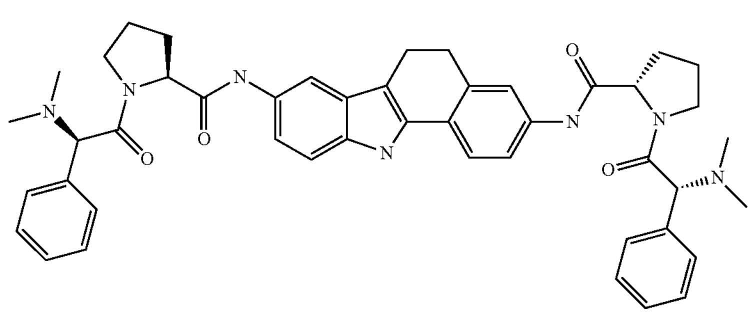 | 765.942 | (2S,2'S)-N,N'-6,11-dihydro-5H-benzo[a]carbazole-3,8-diylbis{1-[(2R)-2-(dimethylamino)-2-phenylacetyl]pyrrolidine-2-carboxamide} |

| Example | Structure | MW | Name |
| --- | --- | --- | --- |
| 95 | 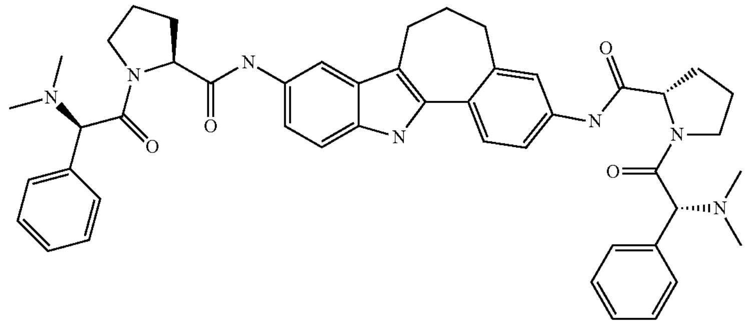 | 779.968 | (2S,2'S)-N,N'-5,6,7,12-tetrahydrobenzo[6,7]cyclohepta[1,2-b]indole-3,9-diylbis{1-[(2R)-2-(dimethylamino)-2-phenylacetyl]pyrrolidine-2-carboxamide} |
| 96 | 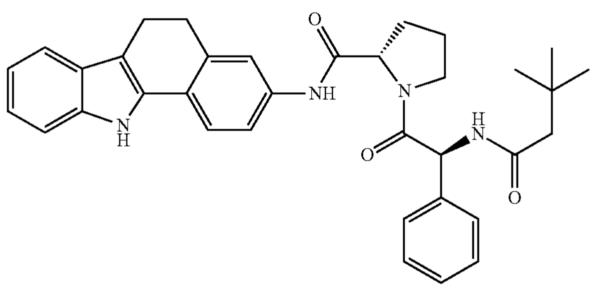 [SMILES: CC(C)(C)CC(=O)N[C@H](C(=O)N1CCC[C@H]1C(=O)Nc1ccc2c(c1)CCc1c-2[nH]c2ccccc12)c1ccccc1] | 562.718 | N-(6,11-dihydro-5H-benzo[a]carbazol-3-yl)-1-[(2S)-2-[(3,3-dimethylbutanoyl)amino]-2-phenylacetyl}-L-prolinamide |
| 97 | 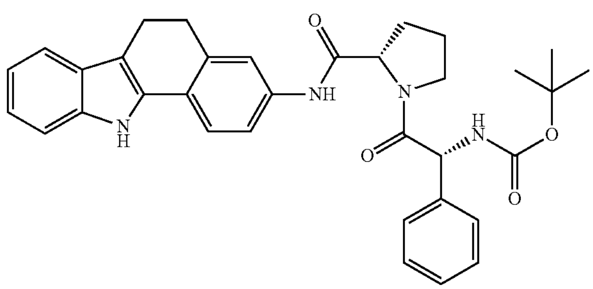 [SMILES: CC(C)(C)OC(=O)N[C@@H](C(=O)N1CCC[C@H]1C(=O)Nc1ccc2c(c1)CCc1c-2[nH]c2ccccc12)c1ccccc1] | 564.69 | tert-butyl {(1R)-2-[(2S)-2-(6,11-dihydro-5H-benzo[a]carbazol-3-ylcarbamoyl)pyrrolidin-1-yl]-2-oxo-1-phenylethyl}carbamate |
| 98 | 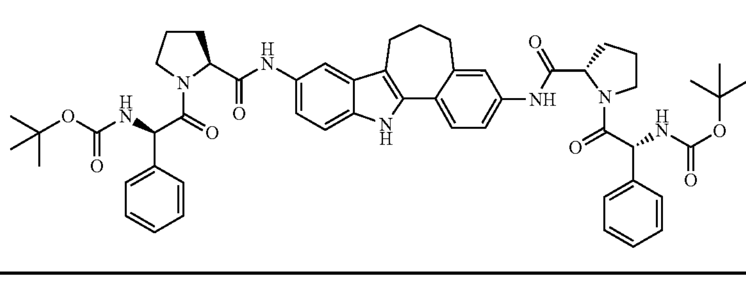 | 924.119 | di-tert-butyl (5,6,7,12-tetrahydrobenzo[6,7]cyclohepta[1,2-b]indole-3,9-diylbis{carbamoyl(2S)pyrrolidine-2,1-diyl[(1R)-2-oxo-1-phenylethane-2,1-diyl]})biscarbamate |

Example 99 tert-butyl {(1R)-2-[(2S)-2-(5-{4-[5-({[(2S)-1-{(2R)-2-[(tert-butoxy carbonyl)amino]-2-phenylacetyl}pyrrolidin-2-yl]carbonyl}amino)-1H-indol-2-yl]phenyl}-1H-imidazol-2-yl)pyrrolidin-1-yl]-2-oxo-1-phenylethyl}carbamate

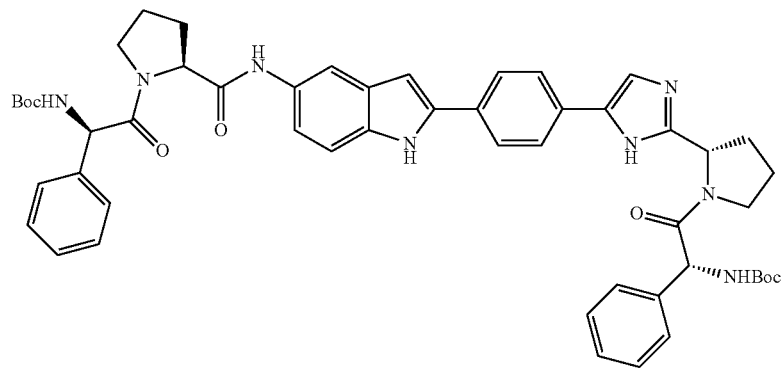 [SMILES: CC(C)(C)OC(=O)N[C@@H](C(=O)N1CCC[C@H]1C(=O)Nc1ccc2[nH]c(-c3ccc(-c4cnc([C@@H]5CCCN5C(=O)[C@H](NC(=O)OC(C)(C)C)c5ccccc5)[nH]4)cc3)cc2c1)c1ccccc1]

Step 1

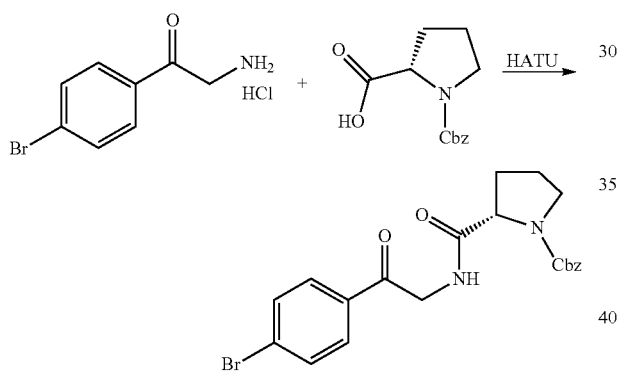

HATU (20 g, 52.3 mmol) was added to a heterogeneous mixture of the amino ketone (12 g, 48.5 mmol) and L-Cbz-Pro (12.4 g, 50 mmol) in MeCN (156 mL). The mixture was cooled in an ice-water bath, and immediately afterward DIPEA (27 mL, 155 mmol) was added dropwise. After the addition of the base, the cooling bath was removed, and the reaction mixture was stirred for an additional 50 minutes. The volatile component was removed, and water (125 mL) was added to the resulting crude solid and stirred for about 1 hour. The off-white solid was filtered and washed with copious water, and dried in vacuo to provide the desired compound as a white solid (20.68 g). MS (ESI) m/e (M+H$^+$): 446.

Step 2

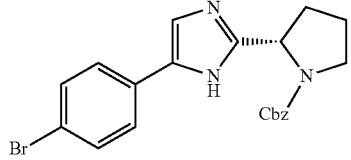

-continued

A mixture of the product from step 1 above (12.8 g, 31.12 mmol) and NH$_4$OAc (12.0 g, 155.7 mmol) in xylenes (155 mL) was heated in a sealed tube at 160° C. for 2 hours. The volatile component was removed in vacuo, and the residue was partitioned carefully between EtOAc and water, whereby enough saturated NaHCO$_3$ solution was added so as to make the pH of the aqueous phase slightly basic after the shaking of the biphasic system. The layers were separated, and the aqueous layer was extracted with an additional EtOAc. The combined organic phase was washed with brine, dried, filtered, and concentrated in vacuo to yield a yellow solid. MS (ESI) m/e (M+H$^+$): 426. $^1$H NMR (CDCl$_3$) δ: 7.31-7.52 (m, 9H), 7.17 (s, 1H), 5.12~5.20 (m, 2H), 5.00~5.01 (m, 1H), 3.50~3.52 (m, 2H), 2.96~2.97 (m, 1H), 1.97~2.17 (m, 3H).

Step 3

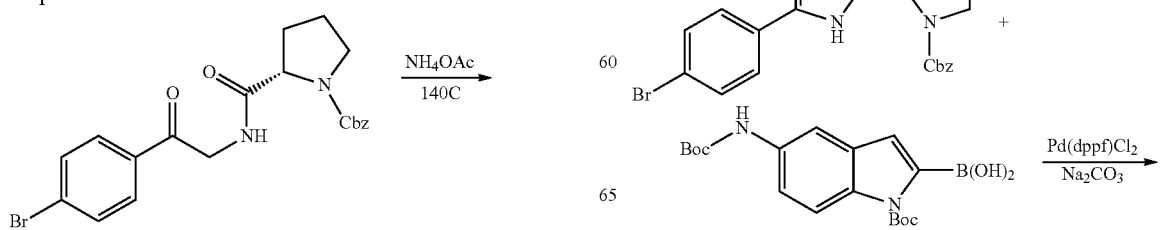

Step 4

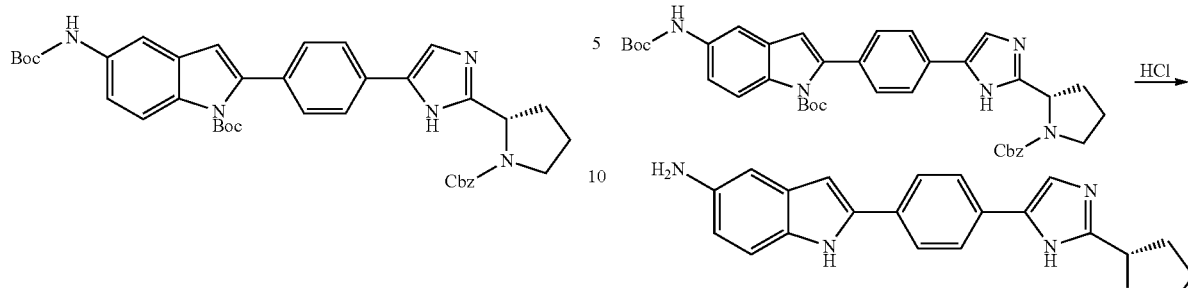

A mixture of the product from step 2 above (327 mg, 0.77 mmol), indole boronic acid from Example 42 (290 mg, 0.77 mmol), Pd(dppf)Cl$_2$ (56 mg, 0.077 mmol), Na$_2$CO$_3$ (244 mg, 2.3 mmol), THF (20 mL) and H$_2$O (2 mL) was refluxed under N$_2$ overnight. The mixture was poured into water and extracted with CH$_2$Cl$_2$. The organic phase was combined, dried over Na$_2$SO$_4$ and filtered to give the desired compound, which was used directly in the next step. MS (ESI) m/e (M+H$^+$): 678.

A solution of the product of step 3 in HCl/CH$_3$OH (5 N) was stirred for 3 hours. Concentration in vacuo afforded the crude product. MS (ESI) m/e (M+H$^+$): 478.

Step 5

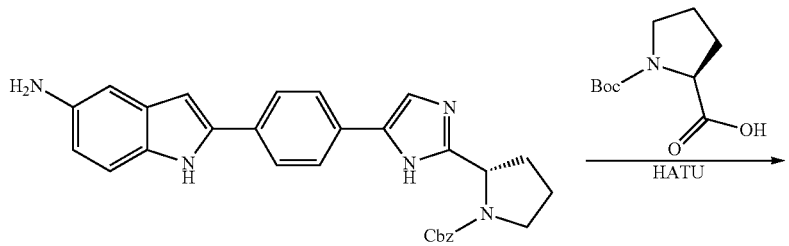

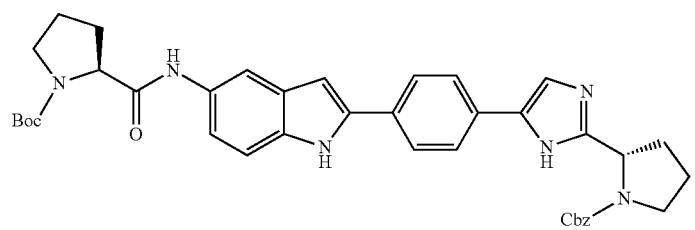

This reaction was carried out using the standard HATU-mediated coupling procedure described in step 1 between Boc-L-Pro-OH and the product from step 4 above. MS (ESI) m/e (M+H$^+$): 808. $^1$H NMR (MeOD) δ: 8.95 (bs, 1H), 6.82~7.56 (m, 17H), 6.50~6.62 (m, 1H), 5.74 (bs, 1H), 5.38~5.39 (m, 1H), 4.91~5.08 (m, 2H), 4.66 (bs, 1H), 3.79 (bs, 1H), 3.40~3.54 (m, 2H), 3.19 (bs, 1H), 1.93~2.25 (m, 4H), 1.75~1.88 (m, 4H), 1.35~1.32 (m, 9H).

Step 6

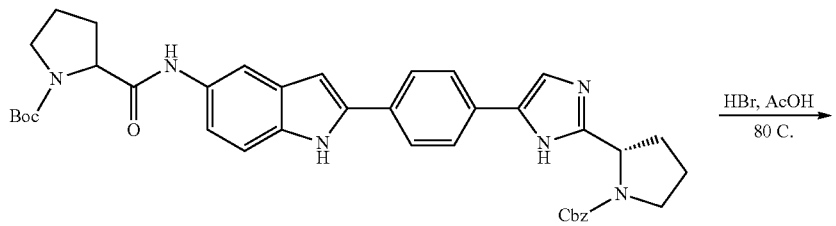

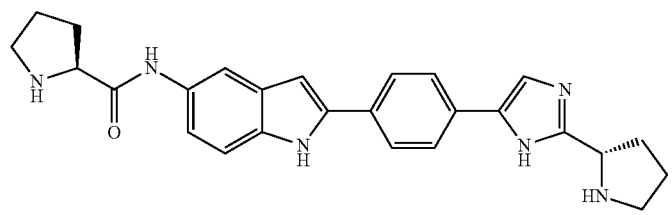

To a solution of the product from step 5 (220 mg, 0.3 mmol) in 20 mL of AcOH was added 3 mL of 48% HBr. The solution was heated to 80° C. for 6 hours. The volatiles were removed in vacuo, and the residue was dissolved in DCM/i-PrOH (3:1), washed with saturated $Na_2CO_3$ and brine, dried and concentrated in vacuo to give a solid, which was used in the next step directly. MS (ESI) m/e (M+H$^+$): 441.

Step 7

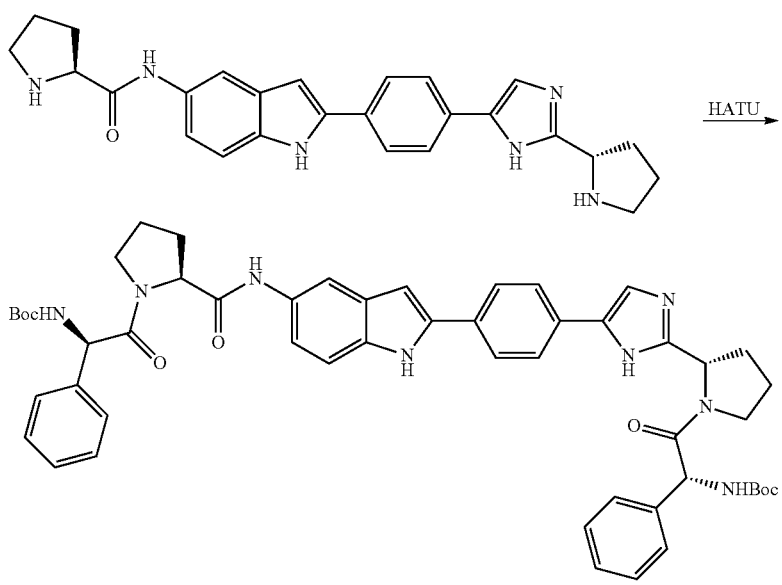

A cooled solution containing HATU (0.6 mmol), the diamine from step 6 above (132 mg, 0.3 mmol) and R-Boc-Pro (129 mg, 0.6 mmol) in MeCN (3 mL), was treated with DIPEA (2.4 mmol), added dropwise over 13 minutes. After the addition of the base was completed, the cooling bath was removed, and the reaction mixture was stirred for an additional 30 minutes. The volatile component was removed in vacuo; water was added to the resulting crude solid and stirred for about 1 hour. The off-white solid was filtered, washed with water, and dried in vacuo to provide the desired compound as a white solid. MS (ESI) m/e (M+H$^+$): 908. $^1$H NMR (MeOD) δ: 7.66~7.84 (m, 6H), 7.28~7.40 (m, 12H), 6.80 (s, 1H), 5.40~5.45 (m, 2H), 5.18~5.20 (m, 1H), 3.70~4.02 (m, 4H), 1.80~2.12 (m, 8H), 1.35~1.37 (m, 18H).

Examples 100-116

Compounds of Examples 100-116 were prepared in a similar manner as described in Example 99.

| Example | Structure | MW | Name |
|---|---|---|---|
| 100 | 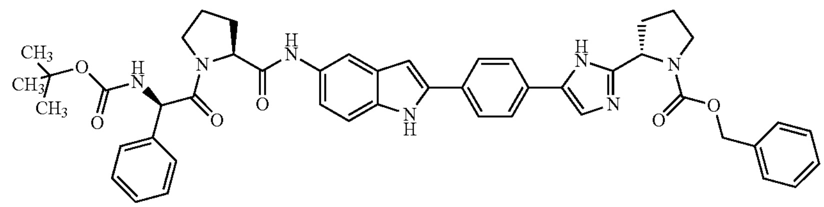 [SMILES: CC(C)(C)OC(=O)N[C@@H](C(=O)N1CCC[C@H]1C(=O)Nc1ccc2[nH]c(-c3ccc(-c4cnc([C@@H]5CCCN5C(=O)OCc5ccccc5)[nH]4)cc3)cc2c1)c1ccccc1] | 807.958 | benzyl (2S)-2-[5-(4-{5-[(1-{(2R)-2-[(tert-butoxycarbonyl)amino]-2-phenylacetyl}-L-prolyl)amino]-1H-indol-2-yl}phenyl)-1H-imidazol-2-yl]pyrrolidine-1-carboxylate |
| 101 | 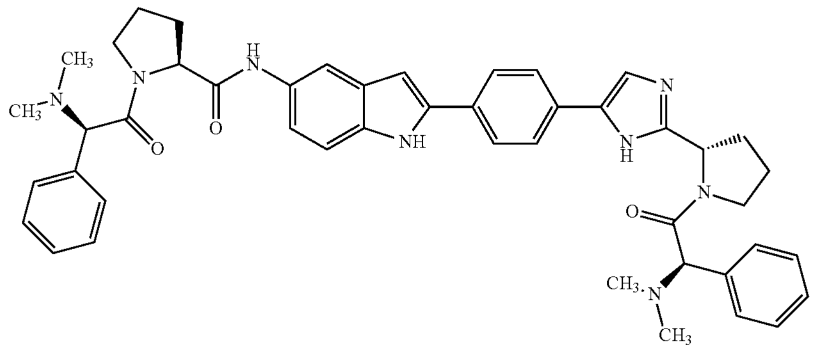 [SMILES: CN(C)[C@@H](C(=O)N1CCC[C@H]1C(=O)Nc1ccc2[nH]c(-c3ccc(-c4cnc([C@@H]5CCCN5C(=O)[C@@H](c5ccccc5)N(C)C)[nH]4)cc3)cc2c1)c1ccccc1] | 762.963 | 1-[(2R)-2-(dimethylamino)-2-phenylacetyl]-N-{2-[4-(2-{(2S)-1-[(2R)-2-(dimethylamino)-2-phenylacetyl]pyrrolidin-2-yl}-1H-imidazol-5-yl)phenyl]-1H-indol-5-yl}-L-prolinamide |
| 102 | 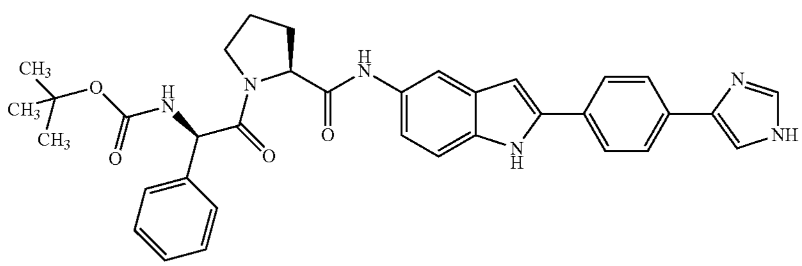 [SMILES: CC(C)(C)OC(=O)N[C@@H](C(=O)N1CCC[C@H]1C(=O)Nc1ccc2[nH]c(-c3ccc(-c4c[nH]cn4)cc3)cc2c1)c1ccccc1] | 604.715 | tert-butyl {(1R)-2-[(2S)-2-({2-[4-(1H-imidazol-4-yl)phenyl]-1H-indol-5-yl}carbamoyl)pyrrolidin-1-yl]-2-oxo-1-phenylethyl}carbamate |
| 103 | 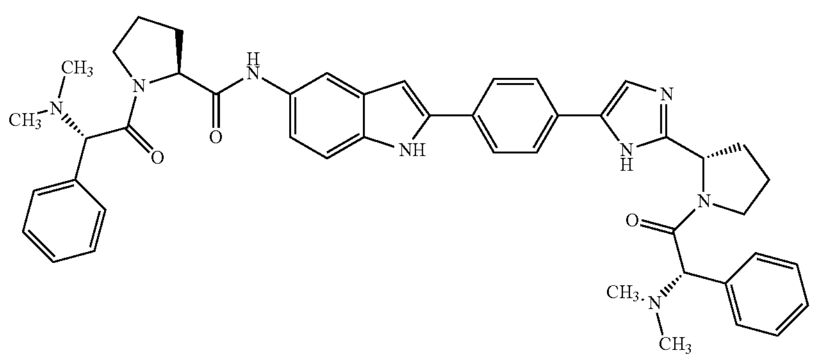 [SMILES: CN(C)[C@H](C(=O)N1CCC[C@H]1C(=O)Nc1ccc2[nH]c(-c3ccc(-c4cnc([C@@H]5CCCN5C(=O)[C@H](c5ccccc5)N(C)C)[nH]4)cc3)cc2c1)c1ccccc1] | 762.963 | 1-[(2S)-2-(dimethylamino)-2-phenylacetyl]-N-{2-[4-(2-{(2S)-1-[(2S)-2-(dimethylamino)-2-phenylacetyl]pyrrolidin-2-yl}-1H-imidazol-5-yl)phenyl]-1H-indol-5-yl}-L-prolinamide |
| 104 | 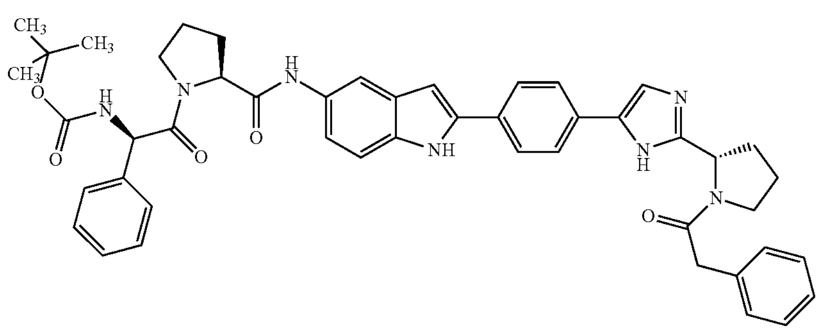 [SMILES: CC(C)(C)OC(=O)N[C@@H](C(=O)N1CCC[C@H]1C(=O)Nc1ccc2[nH]c(-c3ccc(-c4cnc([C@@H]5CCCN5C(=O)Cc5ccccc5)[nH]4)cc3)cc2c1)c1ccccc1] | 791.958 | tert-butyl {(1R)-2-oxo-1-phenyl-2-[(2S)-2-{[2-(4-{2-[(2S)-1-(phenylacetyl)pyrrolidin-2-yl]-1H-imidazol-5-yl}phenyl)-1H-indol-5-yl]carbamoyl}pyrrolidin-1-yl]ethyl}carbamate |

-continued

| Example | Structure | MW | Name |
| --- | --- | --- | --- |
| 105 | 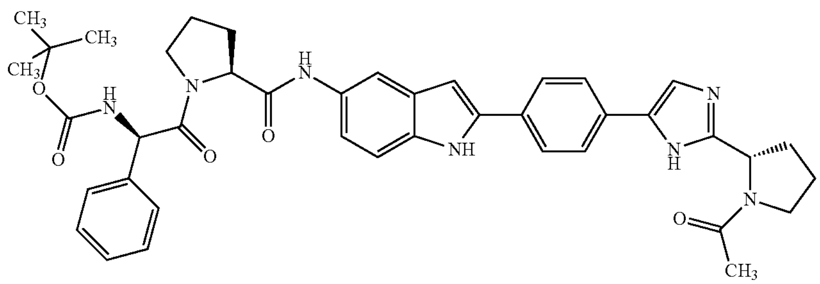 [SMILES: CC(=O)N1CCC[C@H]1c1ncc(-c2ccc(-c3cc4cc(NC(=O)[C@@H]5CCCN5C(=O)[C@H](NC(=O)OC(C)(C)C)c5ccccc5)ccc4[nH]3)cc2)[nH]1] | 715.86 | tert-butyl{(1R)-2-[(2S)-2-{[2-(4-{2-[(2S)-1-acetylpyrrolidin-2-yl]-1H-imidazol-5-yl}phenyl)-1H-indol-5-yl]carbamoyl}pyrrolidin-1-yl]-2-oxo-1-phenylethyl}carbamate |
| 106 | 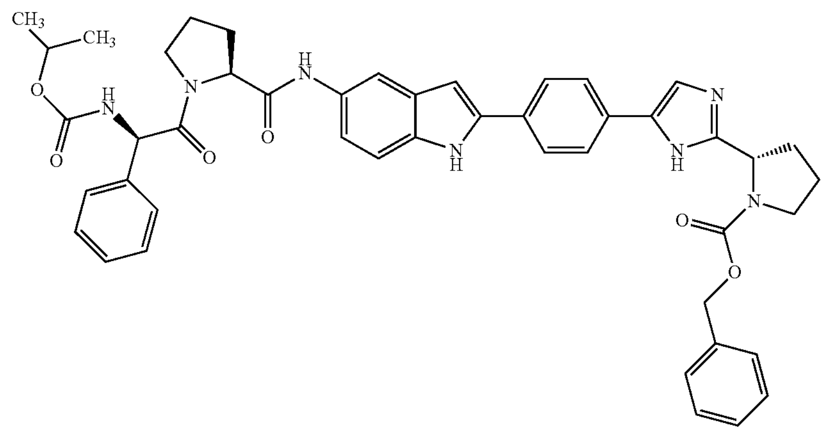 [SMILES: CC(C)OC(=O)N[C@@H](C(=O)N1CCC[C@H]1C(=O)Nc1ccc2[nH]c(-c3ccc(-c4cnc([C@@H]5CCCN5C(=O)OCc5ccccc5)[nH]4)cc3)cc2c1)c1ccccc1] | 793.931 | benzyl (2S)-2-(5-{4-[5-({1[(2R)-2-phenyl-2-{[(propan-2-yloxy)carbonyl]amino}acetyl]-L-prolyl}amino)-1H-indol-2-yl]phenyl}-1H-imidazol-2-yl)pyrrolidine-1-carboxylate |
| 107 | 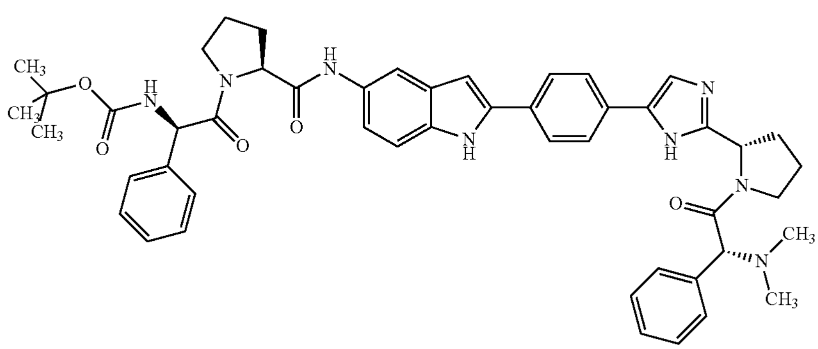 [SMILES: CN(C)[C@@H](C(=O)N1CCC[C@H]1c1ncc(-c2ccc(-c3cc4cc(NC(=O)[C@@H]5CCCN5C(=O)[C@H](NC(=O)OC(C)(C)C)c5ccccc5)ccc4[nH]3)cc2)[nH]1)c1ccccc1] | 835.027 | tert-butyl {(1R)-2-[(2S)-2-({2-[4-(2-{(2S)-1-[(2R)-2-(dimethylamino)-2-phenylacetyl]pyrrolidin-2-yl}-1H-imidazol-5-yl)phenyl]-1H-indol-5-yl}carbamoyl)pyrrolidin-1-yl]-2-oxo-1-phenylethyl}carbamate |
| 108 | 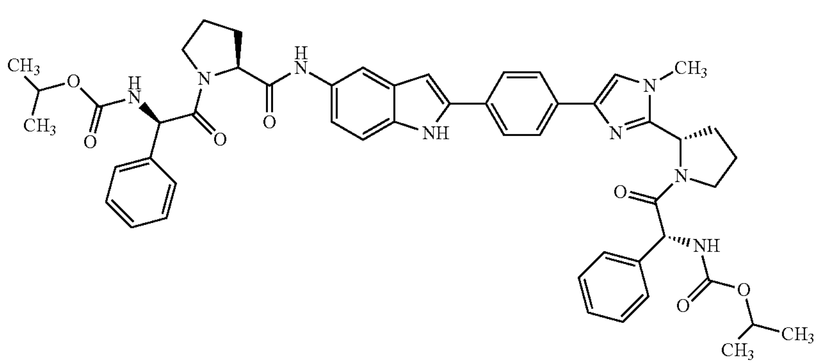 [SMILES: CC(C)OC(=O)N[C@@H](C(=O)N1CCC[C@H]1C(=O)Nc1ccc2[nH]c(-c3ccc(-c4cn(C)c([C@@H]5CCCN5C(=O)[C@H](NC(=O)OC(C)C)c5ccccc5)n4)cc3)cc2c1)c1ccccc1] | 893.064 | propan-2-yl[(1R)-2-{(2S)-2-[1-methyl-4-(4-{5-[({(2S)-1-[(2R)-2-phenyl-2-{[(propan-2-yloxy)carbonyl]amino}acetyl]pyrrolidin-2-yl}carbonyl)amino]-1H-indol-2-yl}phenyl)-1H-imidazol-2-yl]pyrrolidin-1-yl}-2-oxo-1-phenylethyl]carbamate |

| Example | Structure | MW | Name |
|---|---|---|---|
| 109 | 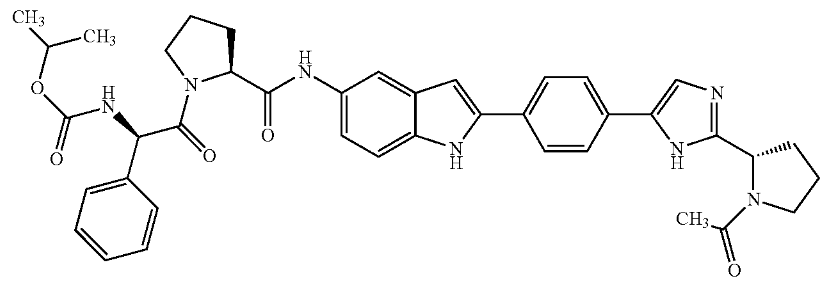 [SMILES: CC(=O)N1CCC[C@H]1c1ncc(-c2ccc(-c3cc4cc(NC(=O)[C@@H]5CCCN5C(=O)[C@H](NC(=O)OC(C)C)c5ccccc5)ccc4[nH]3)cc2)[nH]1] | 701.833 | propan-2-yl {(1R)-2-[(2S)-2-{[2-(4-{2-[(2S)-1-acetylpyrrolidin-2-yl]-1H-imidazol-5-yl}phenyl)-1H-indol-5-yl]carbamoyl}pyrrolidin-1-yl]-2-oxo-1-phenylethyl}carbamate |
| 110 | 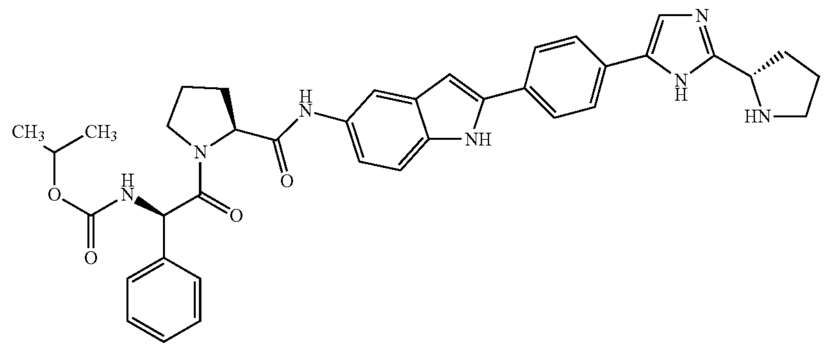 [SMILES: CC(C)OC(=O)N[C@@H](C(=O)N1CCC[C@H]1C(=O)Nc1ccc2[nH]c(-c3ccc(-c4cnc([C@@H]5CCCN5)[nH]4)cc3)cc2c1)c1ccccc1] | 659.795 | propan-2-yl {(1R)-2-oxo-1-phenyl-2-[(2S)-2-{[2-(4-{2-[(2S)-pyrrolidin-2-yl]-1H-imidazol-5-yl}phenyl)-1H-indol-5-yl]carbamoyl}pyrrolidin-1-yl]ethyl}carbamate |
| 111 | 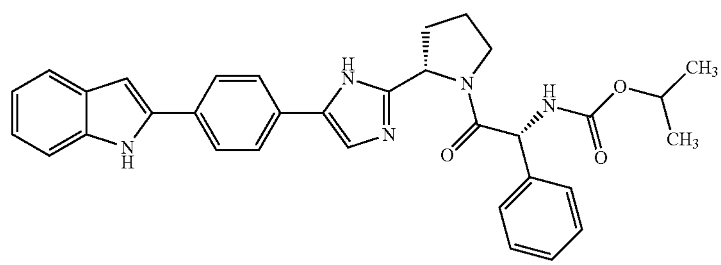 [SMILES: CC(C)OC(=O)N[C@@H](C(=O)N1CCC[C@H]1c1ncc(-c2ccc(-c3cc4ccccc4[nH]3)cc2)[nH]1)c1ccccc1] | 547.663 | propan-2-yl {(1R)-2-[(2S)-2-{5-[4-(1H-indol-2-yl)phenyl]-1H-imidazol-2-yl}pyrrolidin-1-yl]-2-oxo-1-phenylethyl}carbamate |
| 112 | 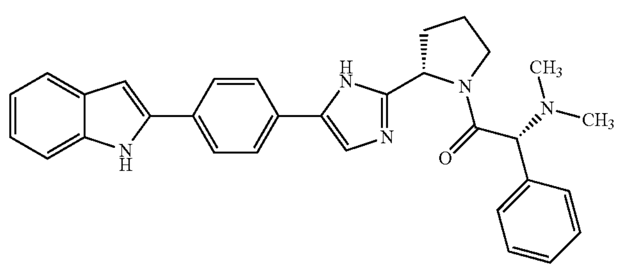 [SMILES: CN(C)[C@@H](C(=O)N1CCC[C@H]1c1ncc(-c2ccc(-c3cc4ccccc4[nH]3)cc2)[nH]1)c1ccccc1] | 489.626 | (2R)-2-(dimethylamino)-1-[(2S)-2-{5-[4-(1H-indol-2-yl)phenyl]-1H-imidazol-2-yl}pyrrolidin-1-yl]-2-phenylethanone |
| 113 | 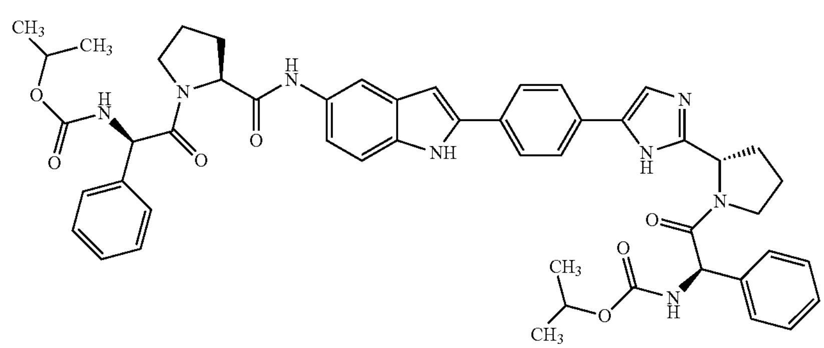 [SMILES: CC(C)OC(=O)N[C@@H](C(=O)N1CCC[C@H]1C(=O)Nc1ccc2[nH]c(-c3ccc(-c4cnc([C@@H]5CCCN5C(=O)[C@H](NC(=O)OC(C)C)c5ccccc5)[nH]4)cc3)cc2c1)c1ccccc1] | 879.037 | propan-2-yl[(1R)-2-oxo-1-phenyl-2-{(2S)-2-[5-(4-{5-[({(2S)-1-[(2R)-2-phenyl-2-{[(propan-2-yloxy)carbonyl]amino}acetyl]pyrrolidin-2-yl}carbonyl)amino]-1H-indol-2-yl}phenyl)-1H-imidazol-2-yl]pyrrolidin-1-yl}ethyl]carbamate |

-continued

| Example | Structure | MW | Name |
|---|---|---|---|
| 114 | 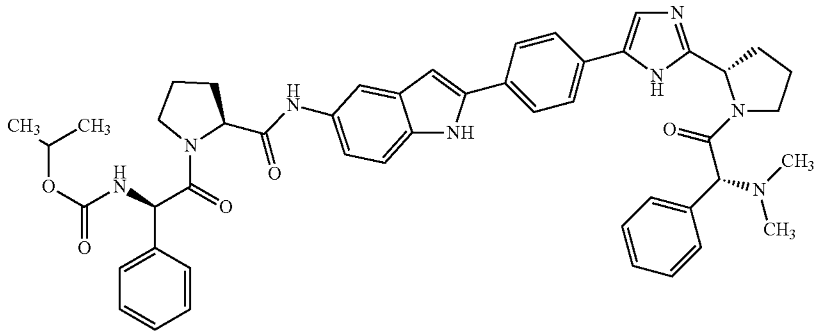 [SMILES: CC(C)OC(=O)N[C@@H](C(=O)N1CCC[C@H]1C(=O)Nc1ccc2[nH]c(-c3ccc(-c4cnc([C@@H]5CCCN5C(=O)[C@@H](c5ccccc5)N(C)C)[nH]4)cc3)cc2c1)c1ccccc1] | 821 | propan-2-yl {(1R)-2-[(2S)-2-({2-[4-(2-{(2S)-1-[(2R)-2-(dimethylamino)-2-phenylacetyl]pyrrolidin-2-yl}-1H-imidazol-5-yl)phenyl]-1H-indol-5-yl{carbamoyl)pyrrolidin-1-yl]-2-oxo-1-phenylethyl}carbamate |
| 115 | 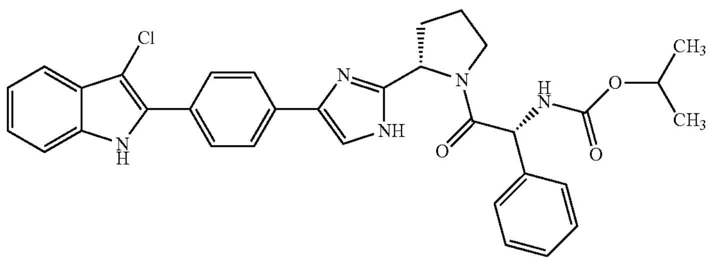 [SMILES: CC(C)OC(=O)N[C@@H](C(=O)N1CCC[C@H]1c1nc(-c2ccc(-c3[nH]c4ccccc4c3Cl)cc2)c[nH]1)c1ccccc1] | 582.108 | propan-2-yl {(1R)-2-[(2S)-2-{4-[4-(3-chloro-1H-indol-2-yl)phenyl]-1H-imidazol-2-yl}pyrrolidin-1-yl]-2-oxo-1-phenylethyl}carbamate |
| 116 | 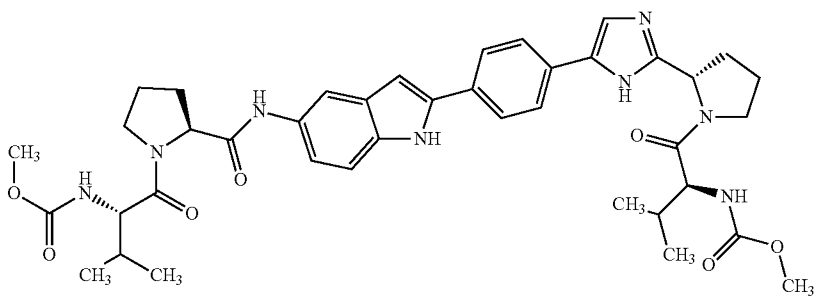 [SMILES: COC(=O)N[C@H](C(=O)N1CCC[C@H]1C(=O)Nc1ccc2[nH]c(-c3ccc(-c4cnc([C@@H]5CCCN5C(=O)[C@@H](NC(=O)OC)C(C)C)[nH]4)cc3)cc2c1)C(C)C] | 754.894 | N-(methoxycarbonyl)-L-valyl-N-{2-[4-(2-{(2S)-1-[N-(methoxycarbonyl)-L-valyl]pyrrolidin-2-yl}-1H-imidazol-5-yl)phenyl]-1H-indol-5-yl}-L-prolinamide |

Example 117

Propan-2-yl [(1R)-2-oxo-1-phenyl-2-{(2S)-2-[3-(4-{5-[({(2S)-1-[(2R)-2-phenyl-2-{[(propan-2-yloxy)carbonyl]amino}acetyl]pyrrolidin-2-yl}carbonyl)amino]-1H-indol-2-yl}phenyl)-1H-pyrazol-5-yl]pyrrolidin-1-yl}ethyl]carbamate

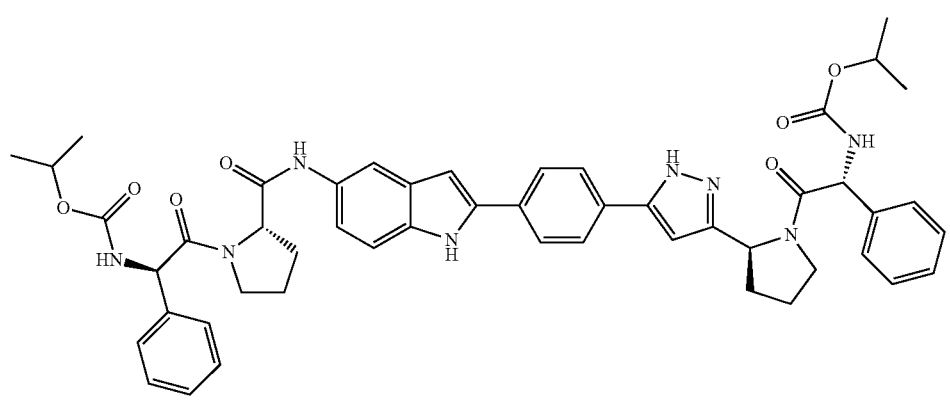 [SMILES: CC(C)OC(=O)N[C@@H](C(=O)N1CCC[C@H]1C(=O)Nc1ccc2[nH]c(-c3ccc(-c4cc([C@@H]5CCCN5C(=O)[C@H](NC(=O)OC(C)C)c5ccccc5)n[nH]4)cc3)cc2c1)c1ccccc1]

Step 1

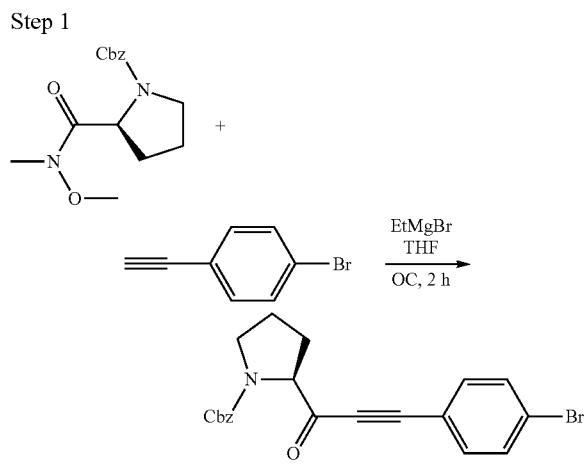

A solution of 4-bromophenylacetylene (5.0 g, 27.6 mmol) in THF (100 mL) at 0° C. was treated a solution of EtMgBr (3M in THF, 9.84 mL, 29.5 mmol). After 10 minutes, the cooling bath was removed, and the mixture was allowed to stir at RT for 3 hours. The reaction mixture was then cooled to 0° C. and added to the Weinreb amide of Z-proline (6.10 g, 20.9 mmol) in THF (50 mL). The reaction mixture was warmed to RT for 48 hours. The reaction mixture was quenched with saturated NH$_4$Cl and diluted with EtOAc/H$_2$O. The aqueous phase was back-extracted with EtOAc (2×), and the combined organic layers were washed (H$_2$O, brine), dried (Na$_2$SO$_4$), and filtered. The solvent was removed, and the residue was purified by silica gel (PE:EA=10:1-4:1) to give the product (7.0 g) as a cream-colored solid. $^1$H NMR (CDCl$_3$) δ: 7.37~7.47 (m, 2H), 7.10~7.30 (m, 7H), 4.98~5.32 (m, 2H), 4.32~4.47 (m, 1H), 3.45~3.61 (m, 2H), 2.15~2.27 (m, 1H), 2.03~2.12 (m, 1H), 1.76~193 (m, 2H). MS (ESI) m/e (M+H$^+$): 413.

Step 2

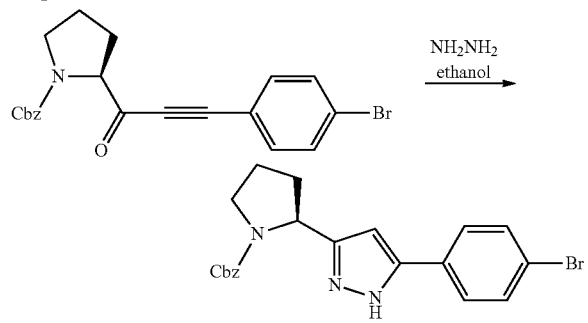

A mixture of the product from step 1 (7.0 g, 17 mmol) and hydrazine hydrate (85%, 1.6 mL) in EtOH (50 mL) was heated at 80° C. for 16 hours. The reaction mixture was cooled and concentrated to afford the desired product (6.7 g). MS (ESI) m/e (M+H$^+$): 426.

Step 3

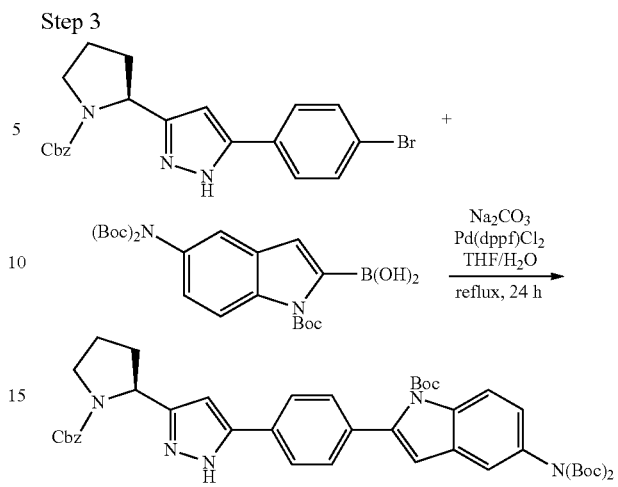

A mixture of the product from step 2 above (0.77 mmol), indole boronic acid from Example 42 (290 mg, 0.77 mmol), Pd(dppf)Cl$_2$ (56 mg, 0.077 mmol), Na$_2$CO$_3$ (244 mg, 2.3 mmol), THF (20 mL) and H$_2$O (2 mL) was refluxed under N$_2$ overnight. The mixture was poured into water and extracted with CH$_2$Cl$_2$, dried over Na$_2$SO$_4$ and filtered to give the desired compound, which was used directly in the next step. MS (ESI) m/e (M+H$^+$): 678.

Step 4

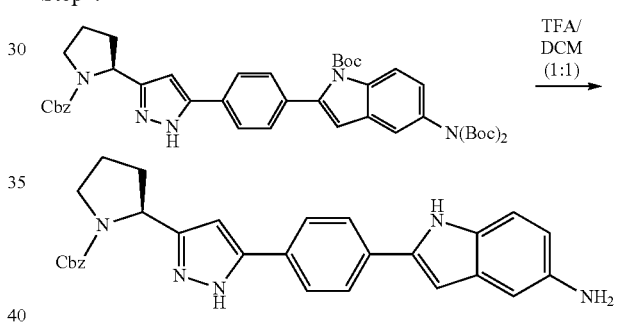

A solution of the product from step 3 above (339 mg, 0.5 mmol) was dissolved in 3 mL of DCM and cooled to 0° C. After the addition of 3 mL of TFA, the reaction mixture was warmed to RT and stirred for 3 hours. Removal of the solvent left the desired product as an oil, which was used directly in the next reaction. MS (ESI) m/e (M+H$^+$): 378.

Step 5

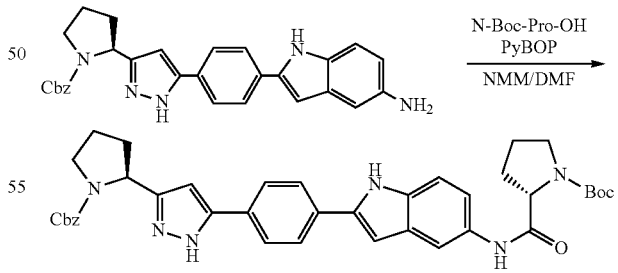

A solution containing PyBOP (0.3 mmol), the amine from step 4 above (132 mg, 0.3 mmol) and N-Boc-L-Pro-OH (62 mg, 0.3 mmol) in DMF (2 mL) was treated with N-methylmorpholine (1.2 mmol). The reaction mixture was stirred for 3 hours, diluted with EtOAc and washed with water (5×). The organic phase was dried and concentrated then chromatographed by RPLC to afford the desired compound. MS (ESI) m/e (M+H$^+$): 675.

Step 6

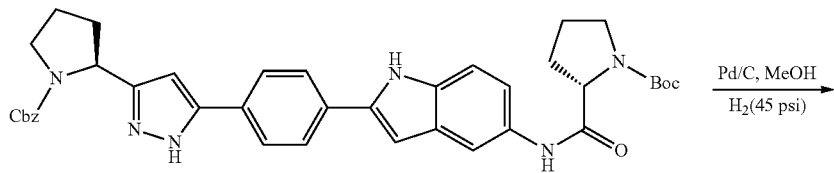

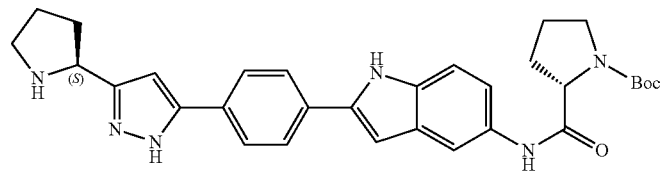

The product from step 5 (100 mg, 0.15 mmol) was dissolved in MeOH and treated with 20 mg of 20% Pd(OH)$_2$ then hydrogenated at 45 psi for 4 hours. The catalyst was removed by filtration through CELITE, and the filtrate was evaporated to leave the desired product. MS (ESI) m/e (M+H$^+$): 541.

Step 7

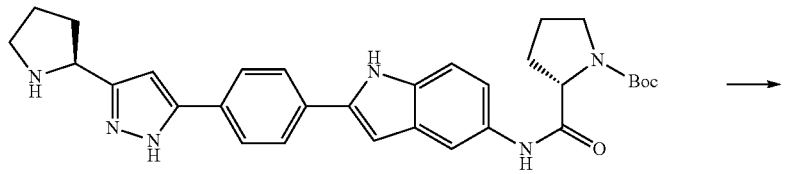

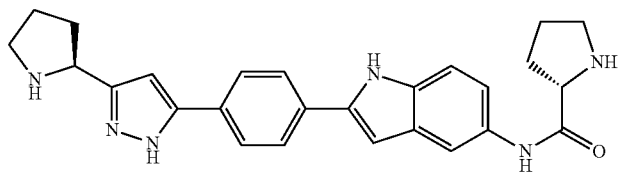

A solution of the product from step 6 above was dissolved in 2 mL of DCM and 2 mL of TFA. The reaction mixture was stirred for 3 hours before the solvent was evaporated to give the desired product as an oil, which was used directly in the next reaction. MS (ESI) m/e (M+H$^+$): 441.

Step 8

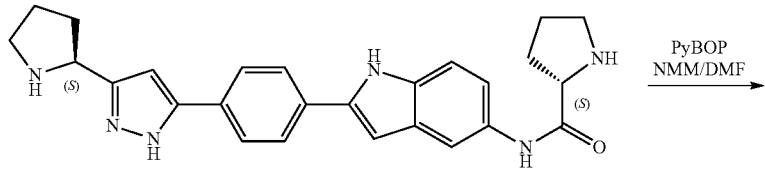

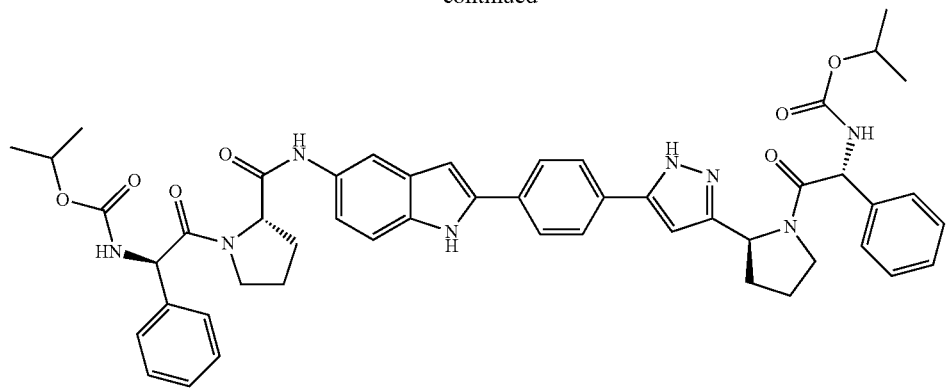

A solution containing PyBOP (0.6 mmol), the diamine from step 7 above (132 mg, 0.3 mmol) and R-i-Proc-Phg-OH (125 mg, 0.6 mmol) in DMF (5 mL) was treated with N-methylmorpholine (2.4 mmol). The reaction mixture was stirred for 3 hours, diluted with 20 mL of EtOAc and washed with water (5×). The organic phase was dried and concentrated then chromatographed by RPLC to afford the desired compound. $^1$H NMR (MeOD) δ: 7.70~7.80 (m, 4H), 7.05~7.55 (m, 14H), 6.80~7.00 (m, 1H), 5.10~5.50 (m, 3H), 4.40~4.65 (m, 2H), 3.25~4.00 (m, 4H), 1.70~2.40 (m, 9H), 1.05~1.20 (m, 12H). MS (ESI) m/e (M+H$^+$): 880.

Example 118

Propan-2-yl [(1R)-2-oxo-1-phenyl-2-{(2S)-2-[5-(4-{5-[({(2S)-1-[(2R)-2-phenyl-2-{[(propan-2-yloxy)carbonyl]amino}acetyl]pyrrolidin-2-yl}carbonyl)amino]-1H-indol-2-yl}phenyl)-1,3-thiazol-2-yl]pyrrolidin-1-yl}ethyl]carbamate

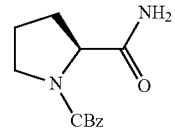

Ethyl chloroformate (12 mL, 125 mmol) in 180 mL of THF was added drop-wise to a cooled solution (−5° C.) of compound Z-Pro-OH (13.8 g, 55.5 mmol), TEA (7.71 mL, 55.5 mmol). The resulting slurry was stirred for 20 minutes at −5° C. before saturated NH$_4$OH (15 mL) was added. The solution was stirred at RT for 18 hours, volatiles were removed, and the residue was taken up in EtOAc (180 mL). The undissolved white precipitate was filtered off and rinsed with EtOAc (100 mL). The organic layers were dried over Na$_2$SO$_4$ and concentrated in vacuo to give the desired product (13.5 g) as off-white amorphous solid. MS (ESI) m/e (M+H$^+$): 249.

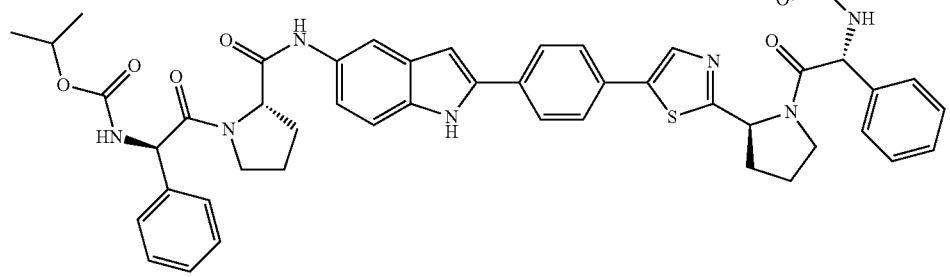

Step 1

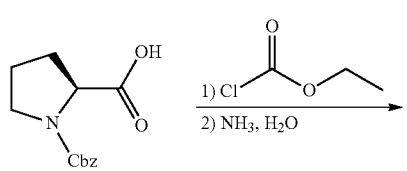

Step 2

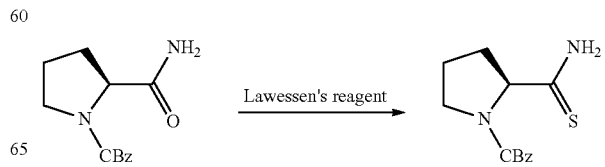

Lawesson's reagent (16.1 g, 39.9 mmol) was added to a stirred slurry of the amide (18 g, 72.6 mmol) in PhMe (200 mL) at RT. The reaction mixture was heated to 100° C. for 3 hours before the solvent was removed. The residue was purified by flash SiO$_2$ chromatography (DCM/MeOH=1:0-20:1) to afford the product (18 g). MS (ESI) m/e (M+H$^+$): 265.

Step 3

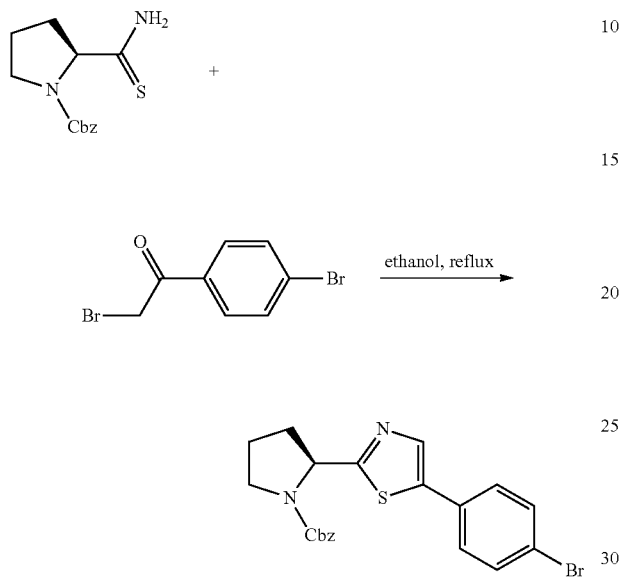

A mixture of the thioamide from step 2 (10.0 g, 37.8 mmol) and the bromoacetophenone (10.0 g, 35.9 mmol) in EtOH (100 mL) was heated at 90° C. for 150 minutes. The reaction mixture was cooled and concentrated, and the residue was purified by SiO$_2$ chromatography to afford the product (11 g). MS (ESI) m/e (M+H$^+$): 444.

Step 4

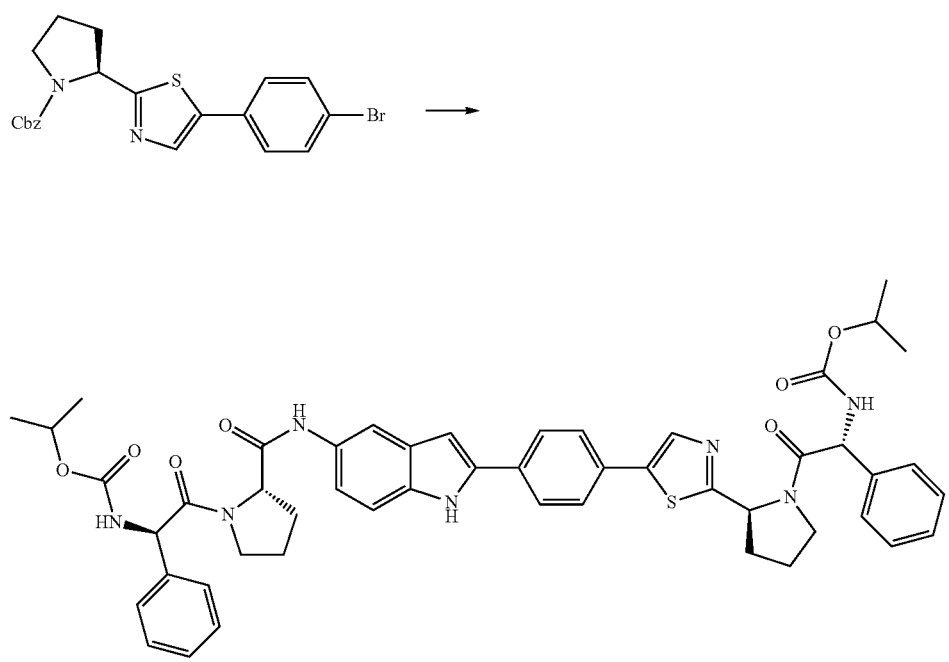

The product from step 3 above can be converted to the final compounds using the same procedure as described in Example 117, steps 4-8. $^1$H NMR (MeOD) δ: 7.00~8.10 (m, 19H), 5.40~5.60 (m, 3H), 4.50~4.70 (m, 1H), 3.45~4.10 (m, 4H), 3.35~3.40 (m, 1H), 1.80~2.6 (m, 9H), 1.05~1.30 (m, 12H). MS (ESI) m/e (M+H$^+$): 897.

Example 119 propan-2-yl [(1R)-2-oxo-1-phenyl-2-{(2S)-2-[2-(4-{5-[({(2S)-1-[(2R)-2-phenyl-2-{[(propan-2-yloxy)carbonyl]amino}acetyl]pyrrolidin-2-yl}carbonyl)amino]-1H-indol-2-yl}phenyl)-1H-imidazol-5-yl]pyrrolidin-1-yl}ethyl]carbamate

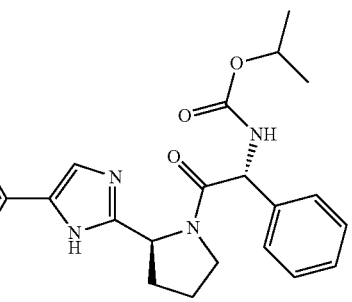

Step 1

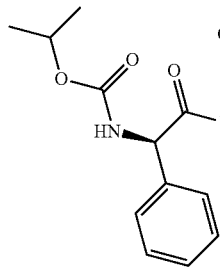

To a solution of 4-bromobenzonitrile (1.82 g, 10 mmol) in anhydrous THF (50 mL) was added LiHMDS (2N, 15 mmol) under N$_2$ atmosphere at RT, and the mixture was stirred for 1 hour. After quenching with 1N HCl, the reaction mixture was heated at reflux for 5 minutes. The precipitate was collected by filtration and then dried in vacuo to give the desired compound (1.9 g). $^1$H NMR (DMSO) δ: 7.74 (d, 2H, J=8.2 Hz), 7.62 (d, 2H, J=8.2 Hz) 6.43 (br, 3H).

Step 2

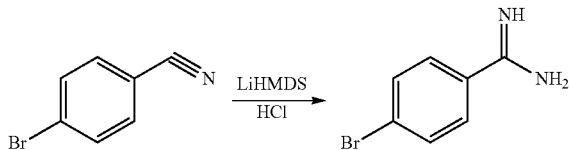 [SMILES: N#Cc1ccc(Br)cc1 ; Cl ; N=C(N)c1ccc(Br)cc1]

To a solution of Cbz-Pro-OH (2.9986 g, 12.0 mmol) in THF (100 mL) was added TEA (1.7 mL, 12.2 mmol). The solution was cooled to −25° C. and ethyl chloroformate (1.6 mL, 12.3 mmol) was added. The resulting solution was stirred at RT for 1 hour. The precipitate was removed by filtration, and the filtrate was used in next step without purification. A solution of 0.5 M diazomethane was added to the above reaction mixture. The sample was stirred at −10° C. for 1 hour. The reaction mixture was concentrated to one half of its original volume and washed once with saturated NaHCO$_3$ (50 mL). The organic layer was dried over MgSO$_4$ and filtered. The crude material was adsorbed onto silica gel and purified by flash chromatography (40 g SiO$_2$, 0-50% ethyl acetate in hexanes) to give the diazoketone (2.29 g). $^1$H NMR (CDCl$_3$) δ: 7.32 (m, 5H) 5.13 (m, 2H), 4.61 (m, 1H), 3.81, 4.03, 4.17 (s, AB quartet, 2H, J=4.0 Hz), 3.58 (m, 2H), 1.88-2.09, 2.17-2.38 (2, br m, 4H).

To a solution of the N-carbobenzyloxy-L-proline diazoketone (1.0 g, 3.6 mmol) in anhydrous diethyl ether (10 mL) was added a saturated solution of HBr in diethyl ether until N$_2$ evolution ceased. The solution was stirred for about 1 hour at about 25° C., then washed with saturated NaHCO$_3$, water and brine. The crude material was purified by silica gel column chromatography and eluted with 40% ethyl acetate in pentane to obtain the bromoketone (0.49 g) as clear oil. $^1$H NMR (CDCl$_3$; mixture of cis-trans amide rotamers) δ: 7.35 (m, 5H), 5.28 (t, 1H), 5.17 (m, 2H), 4.32 (m, 1H), 3.58 (m, 2H), 1.84-2.30 (br m, 4H).

Step 3

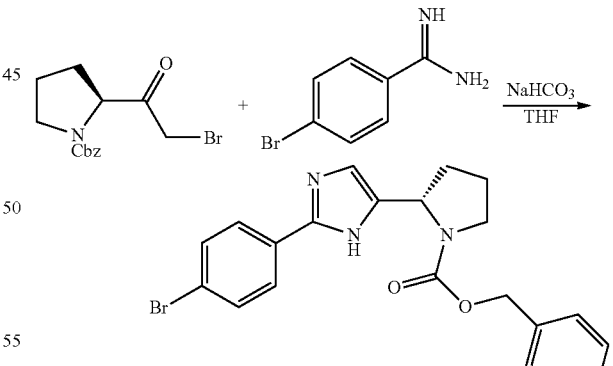

To a mixture of bromoketone (3.25 g, 10 mmol) and the amidine (1.97 g, 10 mol) in THF (100 mL) was added NaHCO$_3$ (1.7 g, 20 mmol), and the suspension was stirred at reflux for 12 hours. The reaction was cooled, concentrated and chromatographed to give compound 7 (0.425 g). MS (ESI) m/e (M+H$^+$): 426, 428.

Step 4

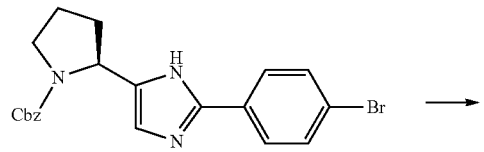

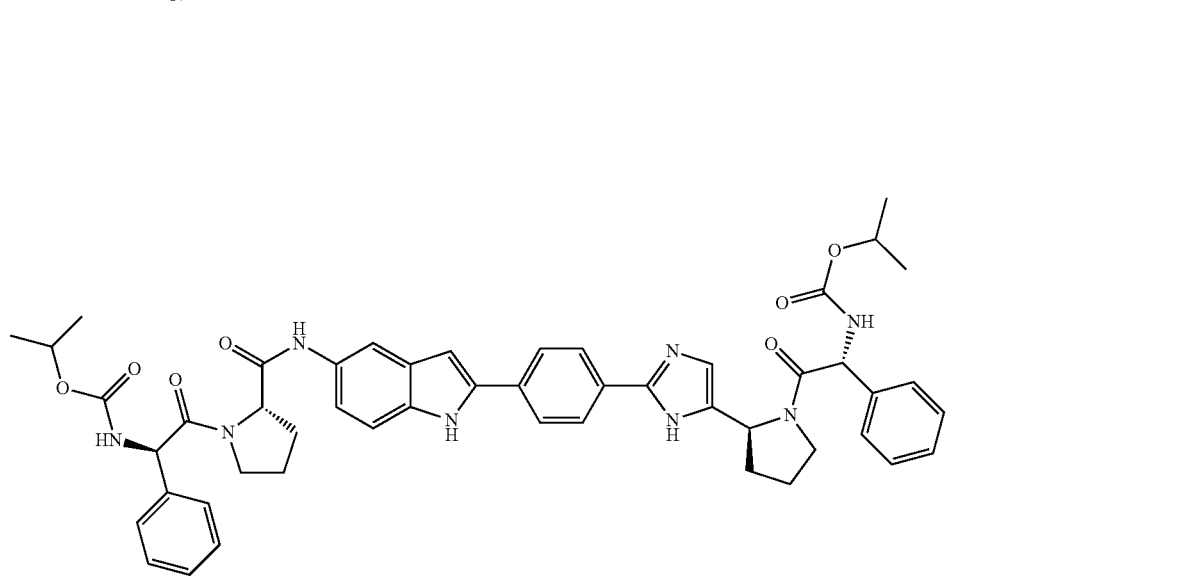

The product from step 3 above can be converted to the final compounds using the same procedure as described in Example 117, steps 4-8. $^1$H NMR (MeOD) δ: 7.7-8.0 (m, 5H), 7.3-7.5 (m, 10H), 6.9-7.1 (m, 3H), 6.8 (d, J=4.8 Hz, 10H), 5.4-5.6 (m, 2H), 5.2-5.3 (m, 1H), 4.8 (s, 2H), 4.5-4.7 (m, 10H), 4.0 (d, J=2.4 Hz, 1H), 3.7 (d, J=4.84 Hz, 1H), 3.1-3.3 (m, 1H), 2.3-2.5 (m, 1H), 1.8-2.2 (m, 1H), 1.1-1.4 (m, 12H). MS (ESI) m/e (M+H$^+$): 880.

Example 120

1-[(2R)-2-phenyl-2-{[(propan-2-yloxy)carbonyl]amino}acetyl]-N-{4-[5-(2-{(2S)-1-[(2R)-2-phenyl-2-{[(propan-2-yloxy)carbonyl]amino}acetyl]pyrrolidin-2-yl}-1H-imidazol-5-yl)-1-benzofuran-2-yl]phenyl}-L-prolinamide

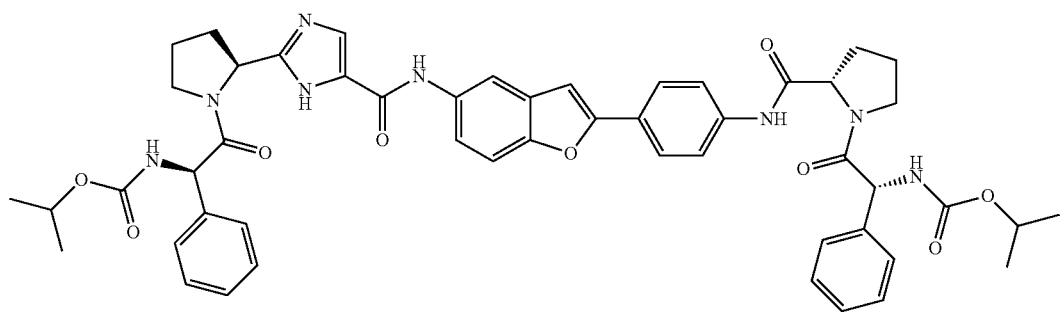 [SMILES: CC(C)OC(=O)N[C@@H](C(=O)N1CCC[C@H]1C(=O)Nc1ccc(-c2cc3cc(NC(=O)c4cnc([C@@H]5CCCN5C(=O)[C@H](NC(=O)OC(C)C)c5ccccc5)[nH]4)ccc3o2)cc1)c1ccccc1]

Step 1

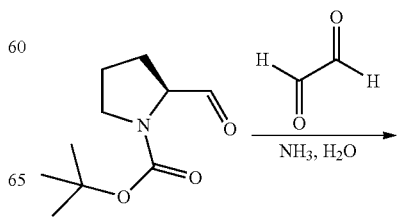

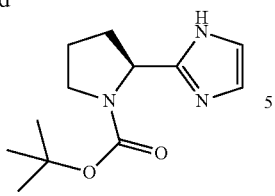

Glyoxal (2.0 mL of 40% in water) was added dropwise to a MeOH solution of NH₄OH (32 mL) and (S)-Boc-prolinal (8.564 g, 42.98 mmol), then the whole was stirred at ambient temperature for 19 hours. The volatile component was removed in vacuo, and the residue was purified by a flash chromatography (silica gel, ethyl acetate) followed by a recrystallization (ethyl acetate) to provide compound as a white fluffy solid (4.43 g). ¹H NMR (DMSO) δ: 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39-1.15 (s, 9H).

Step 2

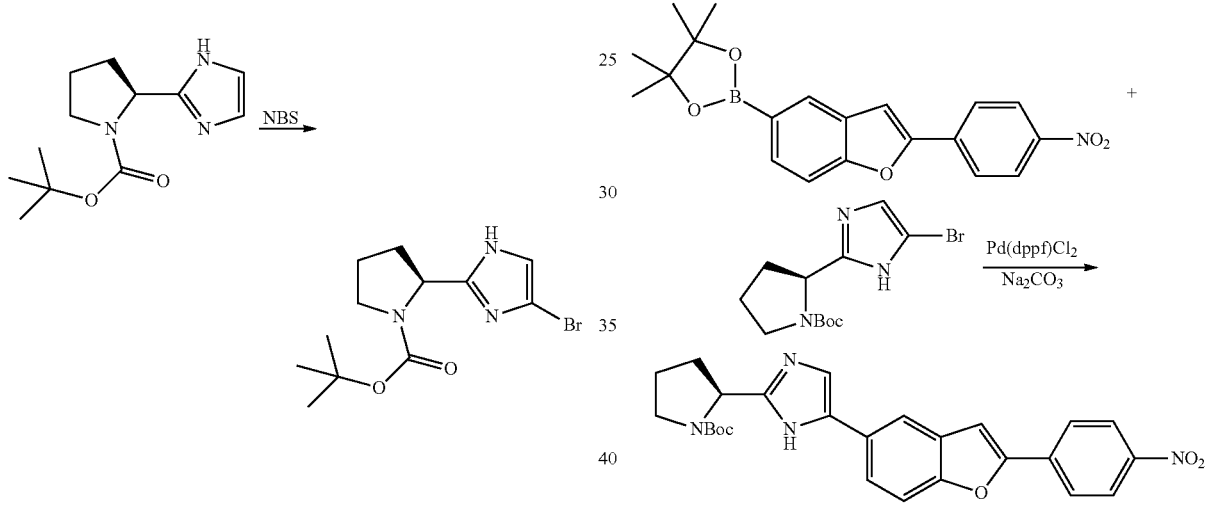

NBS (838.4 mg, 4.71 mmol) was added in batches over 15 minutes to a cooled (ice/water) CH₂Cl₂ (20 mL) solution of imidazole (1.06 g, 4.50 mmol). The reaction mixture was stirred for 75 minutes and concentrated. The crude material was purified by RPLC to separate the mono bromide from its dibromo analog and the starting material. The HPLC elute was neutralized with excess NH₃MeOH, and the volatile component was removed in vacuo. The residue was partitioned between CH₂Cl₂ and water, and the aqueous layer was extracted with water. The combined organic phase was dried (MgSO₄), filtered, and concentrated to provide compound as a white solid (374 mg). ¹H NMR (DMSO) δ: 12.12 (br s, 1H), 7.10 (m, 1H), 4.70 (m, 1H), 3.31 (m, 1H; overlapped with water signal), 2.25-1.73 (m, 4H), 1.39-1.17 (s, 3.8H+5.2H).

Step 3

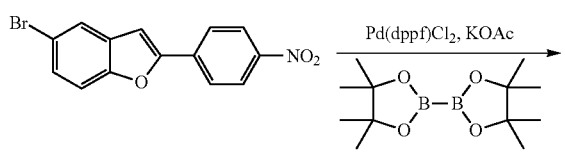

To a mixture of the benzofuran from Example 19, step 1 (15 g, 0.05 mol), bis(pinacolato)diboron (25.4 g, 0.1 mol), Pd(dppf)Cl₂ (1 g), KOAc (0.1 mol) in dioxane (500 mL) was stirred at reflux under N₂ atmosphere for 2 hours. Concentration of the reaction mixture left a residue that was chromatographed to give the desired compound (12 g). ¹H NMR (DMSO) δ: 8.28 (d, J=8.8 Hz, 2H), 8.10 (s, 1H), 7.95 (d, J=8.8 Hz, 2H), 7.72 (d, J=8.8 Hz, 1H), 7.43 (d, J=8.8 Hz, 1H), 7.05 (s, 1H).

Step 4

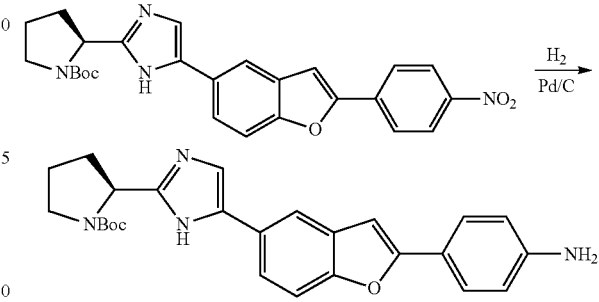

This reaction was conducted in a similar manner to that described in Example 117. MS (ESI) m/e (M+H⁺): 475.

Step 5

The product from step 4 (475 mg, 1.0 mmol) was dissolved in EtOH and treated with 20 mg of 10% Pd/C then hydrogenated over 5 hours. The catalyst was removed by filtration through CELITE, and the filtrate was evaporated to leave the desired product. MS (ESI) m/e (M+H⁺): 445.

Step 6

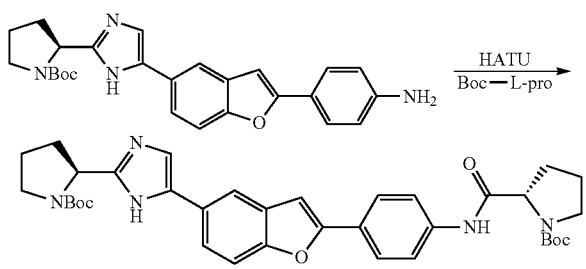

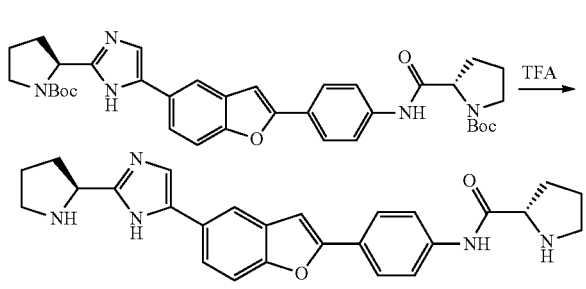

A solution containing HATU (1.0 mmol), the amine from step 5 above (445 mg, 1.0 mmol) and N-Boc-L-Pro-OH (215 mg, 1.0 mmol) in MeCN (10 mL) was treated with DIPEA (1.2 mmol). The reaction mixture was stirred for 3 hours, diluted with EtOAc and washed with water (5×). The organic phase was dried and concentrated then chromatographed by silica gel chromatography (EtOAc) to afford the desired compound. MS (ESI) m/e (M+H⁺): 642.

Step 7

A solution of the product from step 6 above was dissolved in 2 mL of DCM and 2 mL of TFA. The reaction mixture was stirred for 3 hours before the solvent was evaporated to give the desired product as an oil, which was used directly in the next reaction. MS (ESI) m/e (M+H⁺): 442.

Step 8

A solution containing BOP reagent (222 mg, 0.5 mmol), the diamine from step 7 above (112 mg, 0.25 mmol) and R-i-Proc-Phg-OH (125 mg, 0.6 mmol) in DMF (5 mL) was treated with N-methylmorpholine (2.4 mmol). The reaction mixture was stirred for 3 hours, diluted with 20 mL of EtOAc and washed with water (5×). The organic phase was dried and concentrated, then chromatographed by RPLC to afford the desired compound. $^1$H NMR (MeOD) δ: 6.8-7.9 (m, 19H), 5.1-5.5 (m, 3H), 4.5 (m, 1H), 3.5-4.04 (m, 2H), 1.6-2.5 (m, 9H), 0.9-1.3 (m, 12H). MS (ESI) m/e (M+H⁺): 880.

Example 121 propan-2-yl {(1R)-2-[(2S)-2-(5-{2-[4-(acetylamino)phenyl]-1H-indol-5-yl}-1,3,4-oxadiazol-2-yl)pyrrolidin-1-yl]-2-oxo-1-phenylethyl}carbamate

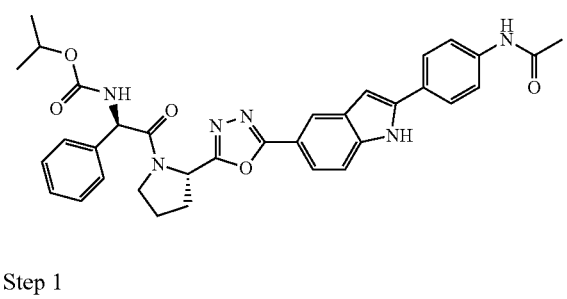

Step 1

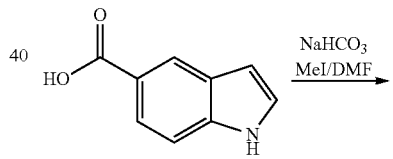

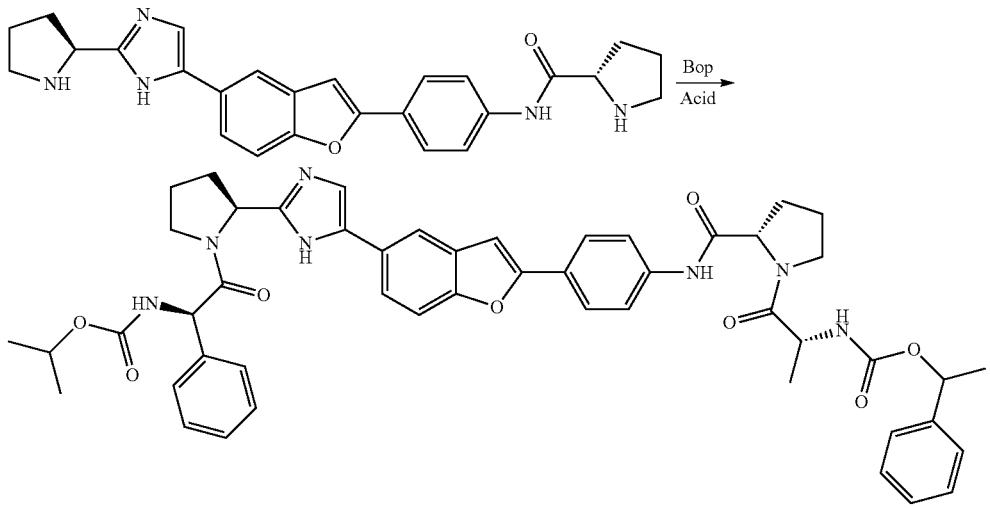

-continued

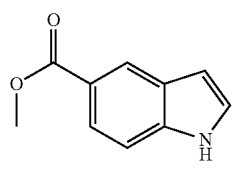

A mixture of 5-carboxyindole (32.2 g, 0.2 mol), NaHCO₃ (53.36 g, 0.64 mol), methyl iodide (122.22 g, 0.86 mol) in 60 mL of DMF were stirred at RT for 2 days. Water and EtOAc are added, and the organic layer was washed with bicarbonate solution, dried and concentrated to obtain 5-(methoxycarbonyl)indole. $^1$H NMR (DMSO) δ: 11.44 (s, 1H), 8.22 (s, 1H), 7.68 (d, J=8.4 Hz, 1H), 7.37~7.47 (m, 2H), 6.56 (d, J=2.0 Hz, 1H), 3.80 (s, 3H). MS (ESI) m/e (M+H⁺): 176.

Step 2

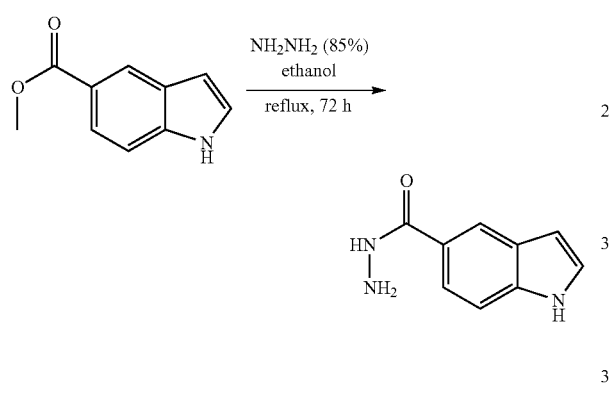

A mixture of the ester (28 g, 0.16 mmol) and NH₂NH₂ (85%, 50 mL) in ethanol (200 mL) was heated at reflux for 48 hours. The reaction mixture was concentrated, and the residue was purified by column chromatography (5% MeOH DCM) to give compound (25 g). $^1$H NMR (DMSO) δ: 11.27 (s, 1H), 9.54 (s, 1H), 8.06 (s, 1H), 7.57 (d, J=8.8 Hz, 1H), 7.37 (d, J=8.8 Hz, 2H), 4.42 (s, 1H), 6.48 (s, 2H), 3.32 (s, 1H). MS (ESI) m/e (M+H⁺): 176.

Step 3

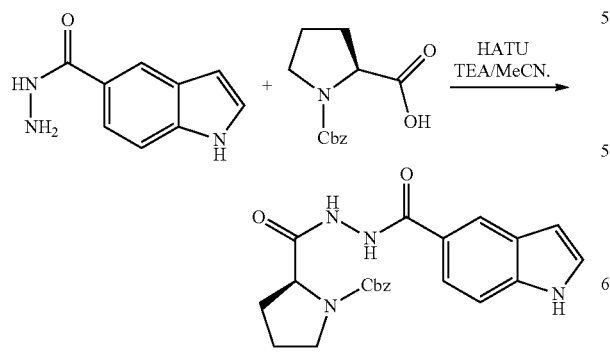

The product from step 3 above was coupled using a standard HATU amide bond forming procedure. MS (ESI) m/e (M+H⁺): 407.

Step 4

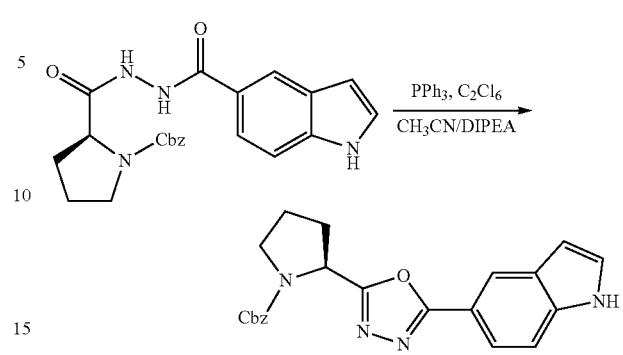

To a suspension of the product from step 3 above (100 g, 0.25 mol), PPh₃ (98.4 g, 0.375 mol) and DIPEA (96.7 g, 0.75 mol) in CH₃CN (500 mL) at RT was added C₂Cl₆ (82.8 g, 0.35 mol). The reaction was stirred at RT for 1.5 hours, and the solvent was removed, and the residue was portioned with EtOAc/H₂O. The layers were separated, the aqueous phase was re-extracted with EtOAc (2×), and the combined organic layers were removed in vacuo, and the residue purified by column chromatography (5% MeOH/DCM) to give compound 4 (55 g). MS (ESI) m/e (M+H⁺): 389

Step 5

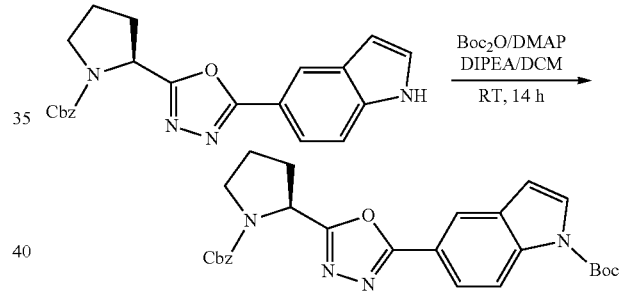

Di-tert-butyl dicarbonate (30.7 g, 142 mmol) was added drop wise to a solution of indole (55.0 g, 142 mmol), DMAP (2.0 g) and DIPEA (18.3 g, 142 mmol) in 50 mL of DCM at 0° C. The reaction was allowed to stir to RT overnight before it was concentrated, and the residue purified by prep TLC (PE/EA=2:1). MS (ESI) m/e (M+H⁺): 489.

Step 6

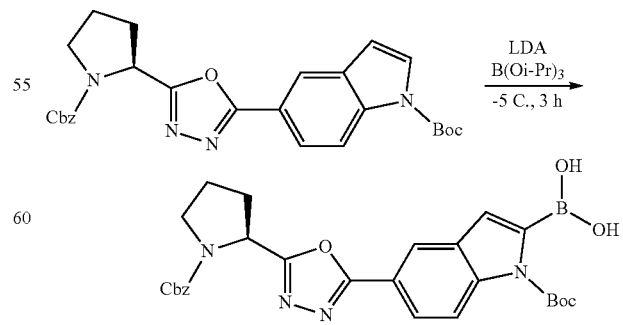

A mixture of compound indole from step 5 (977 mg, 2 mmol), (iPrO)₃B (3.0 g, 16 mmol) and dry THF (100 mL) was cooled to 0° C. LDA (prepared from n-BuLi and iPr₂NH in THF, about 8 mmol) was slowly added and the mixture was allowed to warm to RT over 2 hours. The mixture was quenched by 1N HCl to pH=3 and extracted with CH₂Cl₂ three times. The combined organic phases were combined, dried over Na₂SO₄ and filtered. The filtrate was concentrated and purified by column chromatography (PE/DCM=1/1 to pure CH₂Cl₂ to CH₂Cl₂/acetone=10/1 to pure acetone) to afford the product 8 (0.5 g).

Step 7

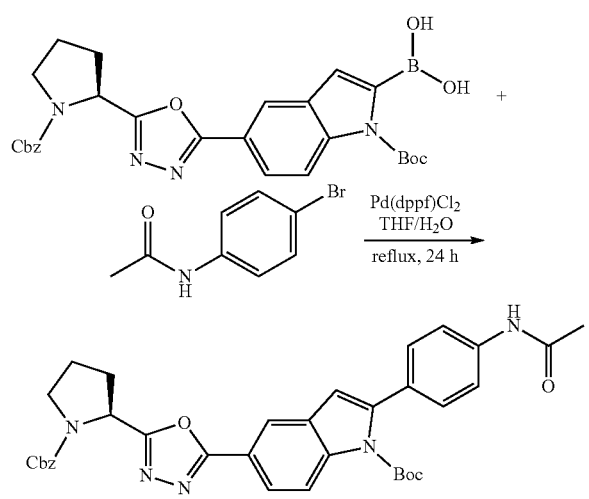

A mixture of the product from step 6 (0.38 mmol), indole boronic acid from Example 42 (145 mg, 0.38 mmol), Pd(dppf)Cl₂ (28 mg, 0.038 mmol), Na₂CO₃ (122 mg, 1.15 mmol), THF (10 mL) and H₂O (1 mL) was refluxed under N₂ overnight. The mixture was poured into water and extracted with CH₂Cl₂. The organic phase was combined, dried over Na₂SO₄ and filtered to give the desired compound, which was used directly in the next step. MS (ESI) m/e (M+H⁺): 622.

Step 8

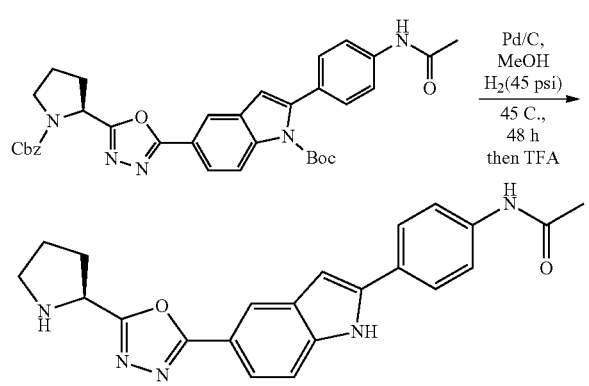

The product from step 7 (0.15 mmol) was dissolved in MeOH and treated with 20 mg of 20% Pd(OH)₂ then hydrogenated at 45 psi for 4 hours. The catalyst was removed by filtration through CELITE, and the filtrate was evaporated then dissolved in 1 mL of DCM then treated with 1 mL of TFA. After stirring for 2 hours, the mixture was evaporated and the residue was used directly in the next reaction without further purification. MS (ESI) m/e (M+H⁺): 488.

Step 9

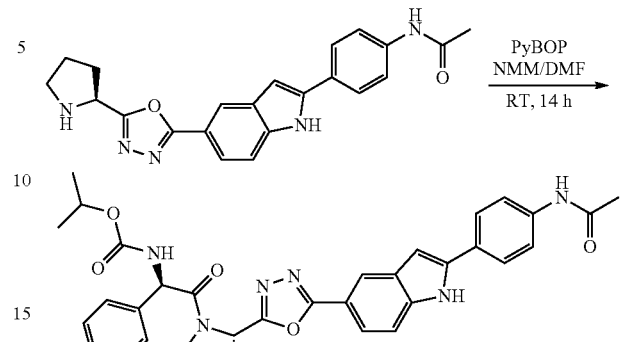

A solution containing PyBOP (44 mg, 0.1 mmol), the amine from step 8 above (49 mg, 0.1 mmol) and R-i-Proc-Phg-OH (21 mg, 0.1 mmol) in DMF (1 mL) was treated with N-methylmorpholine (0.6 mmol). The reaction mixture was stirred for 3 hours, diluted with EtOAc and washed with water (five times). The organic phase was dried and concentrated, then chromatographed by RPLC to afford the desired compound. ¹H NMR (MeOD): δ7.90~8.35 (m, 1H), 7.70~7.85 (m, 2H), 7.60~7.70 (m, 2H), 7.20~7.52 (m, 7H), 6.55~7.20 (m, 1H), 5.50~5.60 (m, 1H), 5.30~5.50 (m, 1H), 4.75~4.85 (m, 1H), 3.70~4.10 (m, 1H), 3.35~3.50 (m, 1H), 1.95~2.50 (m, 7H), 1.10~1.30 (m, 6H). MS (ESI) m/e (M+H⁺): 607.

Example 122

(2S)-1-(phenylacetyl)-N-{3-[5-({[(2S)-1-(phenylacetyl)pyrrolidin-2-yl]carbonyl}amino)-1H-indol-2-yl]phenyl}pyrrolidine-2-carboxamide

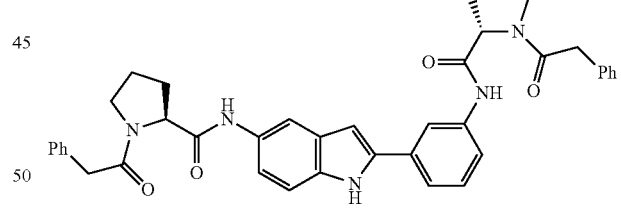

Step 1

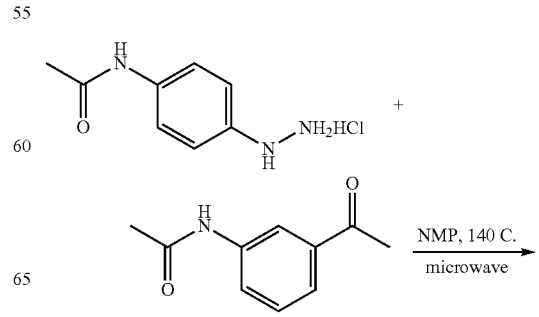

-continued

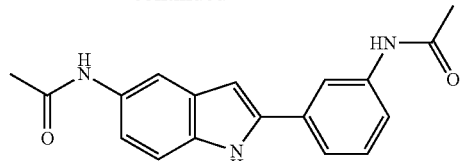

A solution of the hydrazine (1 g, 5 mmol) and 3-acetylacetanilide (0.88 g, 5 mmol) in NMP (5 ml) was heated at 150° C. under microwave for 10 minutes. The solution was poured into water and extracted with EtOAc three times. The organic layer was washed with water, dried over sodium sulfate and then concentrated in vacuo. The residue was purified by RPLC to give the desired compound. MS (m/z): 308 (M+H)+.

Step 2

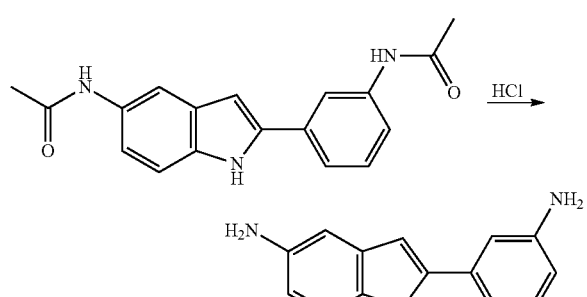

To aqueous HCl (4N, 5 mL) was added the product from step 1 above (300 mg, 1 mmol), and the mixture was heated at reflux for 1 hour. The reaction mixture was cooled and concentrated, and the residue was purified by RPLC to give compound (200 mg). MS (m/z): 224 (M+H)+.

Step 3

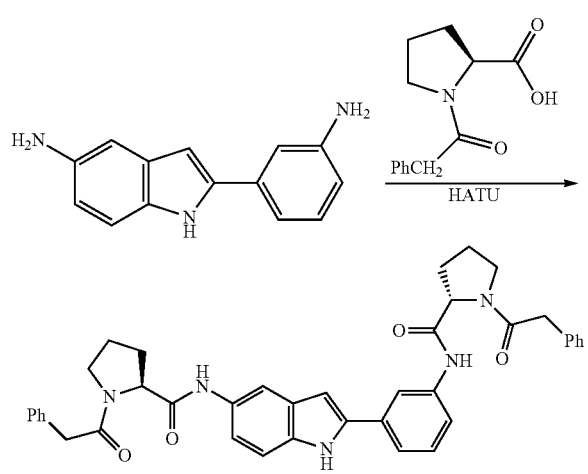

To a solution of the compound from step 2 above (35 mg, 0.148 mmol) in MeCN (5 mL) were added N-phenylacetyl-L-proline (15 mg, 0.0673 mmol), DIPEA (26 mg, 0.202 mmol) and HATU (56 mg, 0.148 mmol). The reaction was stirred overnight and concentrated, and the residue was purified by RPLC to give the desired product (15 mg). MS (ESI) m/e (M+H+): 654. ¹H NMR (MeOD) δ: 8.0 (m, 1H), 7.7 (m, 1H), 7.6-7.1 (m, 14H), 6.7 (m, 1H), 4.6 (m, 2H), 3.9-3.5 (m, 9H), 2.4-1.7 (m, 8H).

Example 123

(2S)-1-(phenylacetyl)-N-{4-[6-({[(2S)-1-(phenylacetyl)pyrrolidin-2-yl]carbonyl}amino)-1H-indol-2-yl]phenyl}pyrrolidine-2-carboxamide

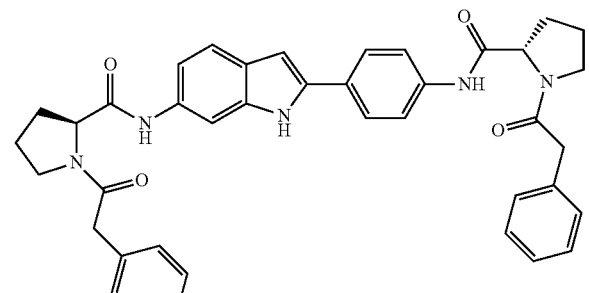

Step 1

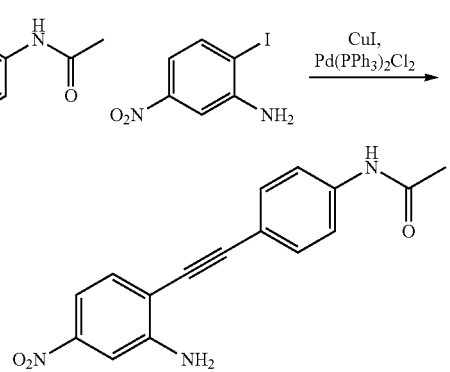

To a stirred solution of 4-ethynylaniline (1 g, 8.5 mmol) in DCM (60 ml) was added acetyl chloride (0.8 g, 10 mmol) and TEA (1.7 g, 17 mmol). The mixture was stirred for 3 hours. The resulting solution was washed with water, 1 N HCl and brine. The organic layer was concentrated in vacuo to give the desired product (900 mg), which was used in next step without purification. MS (ESI) m/e (M+H+): 160.

Step 2

To a stirred solution of 4-ethynylacetanilide (800 mg, 3.1 mmol) in anhydrous THF (6 ml) was added compound 2 (0.5 g, 3.1 mmol), PdCl$_2$(PPh)$_3$ (33 mg, 0.05 mmol), CuI (10 mg, 0.05 mmol) and TEA (2 mL). The mixture was protected from light and stirred at RT overnight. The resulting solution was concentrated in vacuo, and the residue was washed with DCM to give the desired compound (300 mg) as a yellow solid. MS (ESI) m/e (M+H$^+$): 296.

Step 3

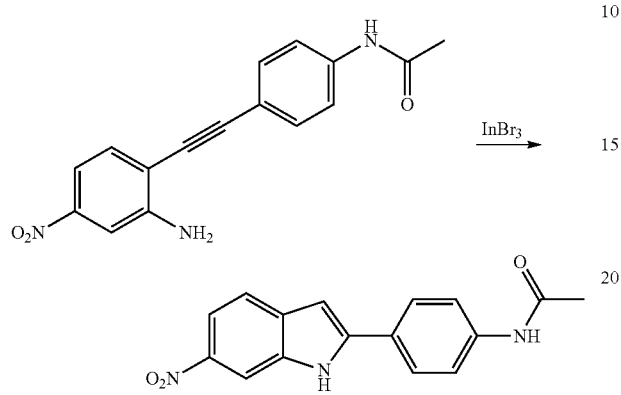

To a stirred solution of compound from step 2 above (200 mg, 0.68 mmol) in toluene (2 ml) was added InBr$_3$ (2 mg, 0.004 mmol). The mixture was stirred at reflux for 3 hours. The resulting solution was washed with water and extracted with EtOAc. The combined organic layers were dried over sodium sulfate, concentrated in vacuo to give the desired indole (170 mg) as a brown solid. MS (ESI) m/e (M+H$^+$): 296.

Step 4

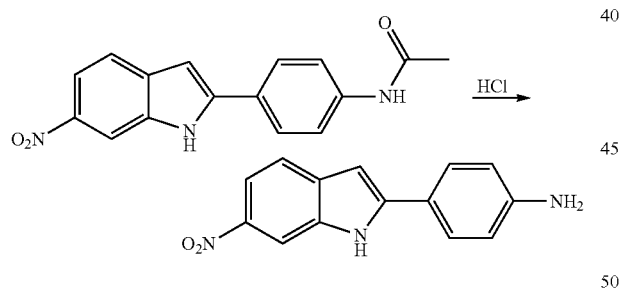

To a stirred solution of the product from step 3 above (100 mg, 0.34 mmol) in EtOH (5 ml) was added 3N HCl (1 mg). The mixture was stirred at reflux overnight. The resulting solution was concentrated in vacuo to give the desired aniline (80 mg) as a brown solid. MS (ESI) m/e (M+H$^+$): 254.

Step 5

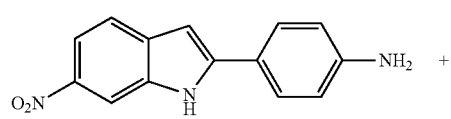

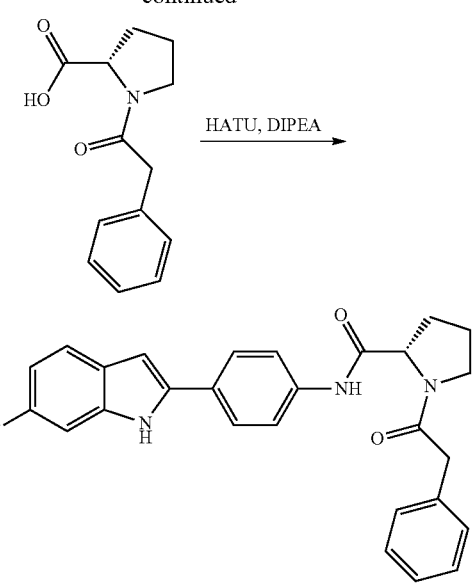

To a solution of the aniline from step 4 (50 mg, 0.2 mmol) in acetonitrile (5 mL) was added N-phenylacetyl-L-proline (56 mg, 0.2 mol), HATU (167 mg, 0.4 mmol) and DIPEA (100 mg, 0.8 mmol). The mixture was stirred overnight. The resulting solution was purified by RPLC to give the desired compound (40 mg) as a brown solid. MS (ESI) m/e (M+H$^+$): 469.

Step 6

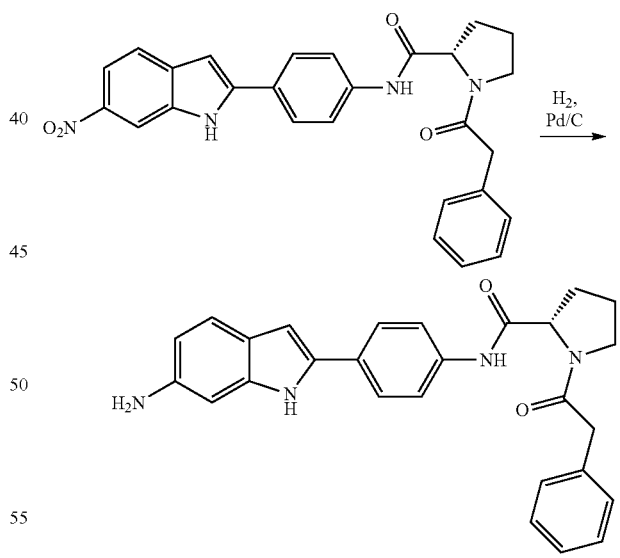

To a solution of the nitro compound (40 mg, 0.08 mmol) in THF (2 mL) was added Pd/C (20 mg, 0.1 mmol). The mixture was stirred under H$_2$ atmosphere for 1 hour. After replacement of H$_2$ with N$_2$, the Pd/C was filtered off, and the filtrate was evaporated in vacuo to give the desired aminoindole (40 mg) as a brown solid. MS (ESI) m/e (M+H$^+$): 439.

Step 7

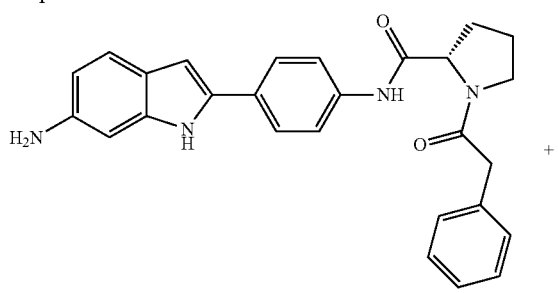

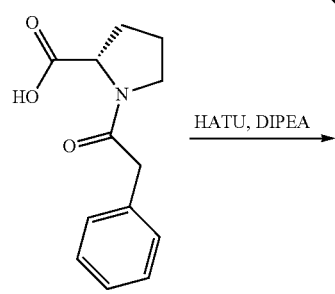

HATU, DIPEA →

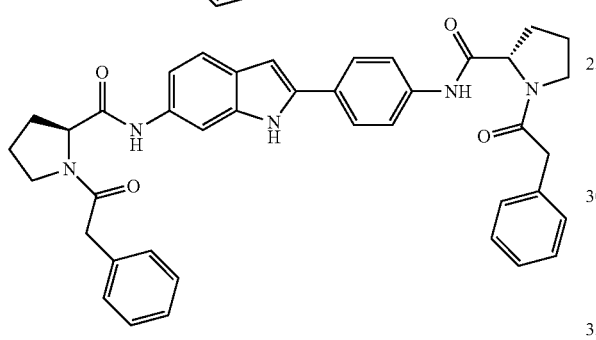

To a solution of the product from step 6 above (40 mg, 0.1 mmol) in acetonitrile (5 mL) was added N-phenylacetyl-L-proline (23 mg, 0.1 mmol), HATU (70 mg, 0.2 mmol) and DIPEA (25 mg, 0.2 mmol). The mixture was stirred overnight. The resulting solution was purified by RPLC to give the desired compound (15 mg) as a brown solid. $^1$H NMR (MeOD) δ: 7.81 (m, 1H), 7.70 (d, J=8.6 Hz, 2H), 7.60 (d, J=8.4 Hz, 2H), 7.39 (m, 1H), 7.30-7.28 (m, 10H), 6.96 (m, 1H), 6.69 (s, 1H), 4.63-4.50 (m, 2H), 3.78-3.60 (m, 8H), 2.23-1.92 (m, 8H). MS (ESI) m/e (M+H$^+$): 654.

Example 124

(2S)-1-(phenylacetyl)-N-{3-[6-({[(2S)-1-(phenylacetyl)pyrrolidin-2-yl]carbonyl}amino)-1H-indol-2-yl]phenyl}pyrrolidine-2-carboxamide

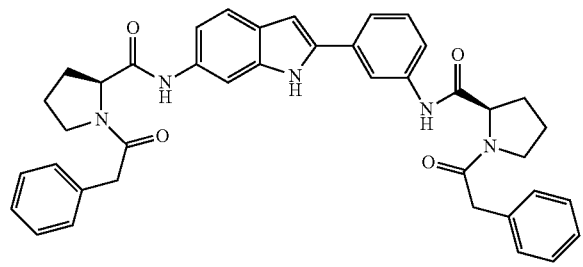 [SMILES: O=C(Nc1cccc(-c2cc3ccc(NC(=O)[C@@H]4CCCN4C(=O)Cc4ccccc4)cc3[nH]2)c1)[C@H]1CCCN1C(=O)Cc1ccccc1]

Step 1

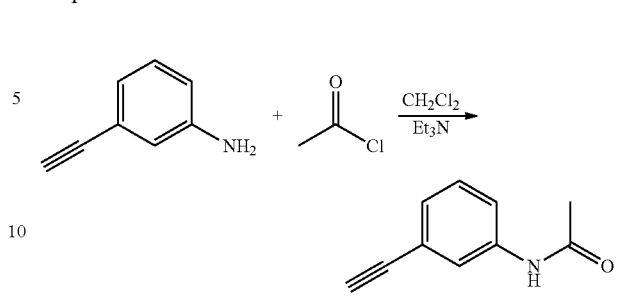

To a solution of 3-ethynylaniline (1.17 g, 10 mmol) and 1.5 ml Et$_3$N in 40 mL DCM was added dropwise acetyl chloride (1 g, 13 mmol). The reaction mixture was stirred at RT for 1 hour. After that, the solvents were evaporated, and the residue was extracted with EtOAc (100 mL), washed with water (50 mL) and brine (50 mL), dried over anhydrous NaSO$_4$, and concentrated in vacuo to afford 3-ethynylacetanilide (1.5 g). MS (ESI) m/e (M+H$^+$): 160.

Step 2

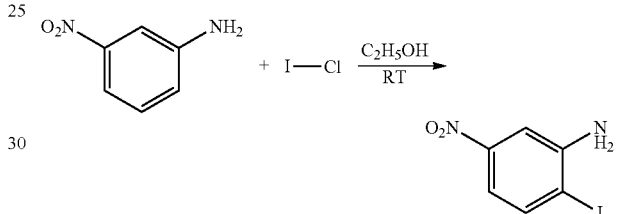

3-nitroaniline (6.9 g, 0.05 mmol) was dissolved in 150 ml ethanol, iodine chloride (8.1 g, 0.05 mmol) added with dropwise. The reaction mixture was stirred at RT for 4 hours. After that, the solvents were evaporated, and the residue was extracted with EtOAc (100 mL), washed with water (50 mL) and brine (50 mL), dried over anhydrous NaSO$_4$. After concentrated in vacuo, the residue was purified by column chromatography (PE/EtOAc=40:1→20:1) to afford the desired product (8.9 g). MS (ESI) m/e (M+H$^+$): 265.

Step 3

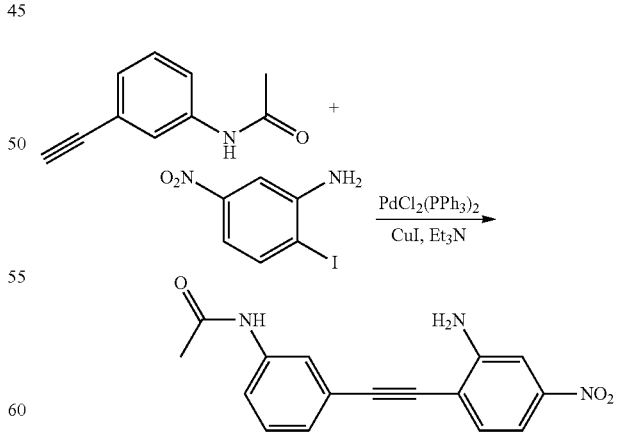

3-Ethynylacetanilide (480 mg, 3 mmol) and 2-iodo-5-intronaniline (800 mg, 3 mmol) were dissolved in anhydrous THF (30 mL), PdCl$_2$(PPh$_3$)$_2$ (105 mg, 0.15 mmol) and CuI (28.5 mg, 0.15 mmol) Et$_3$N (1 ml) was added sequentially. The reaction mixture was protected by N$_2$ and stirred at RT for overnight. After that, the solvents were evaporated, and the residue was extracted with EtOAc (50×2 mL), washed with water (40 mL) and brine (30 mL), dried over anhydrous NaSO₄. After concentrated in vacuo, the residue was purified by column chromatography (DCM/MeOH=50:1→20:1) to afford the desired product (620 mg). MS (ESI) m/e (M+H⁺): 296.
Step 4

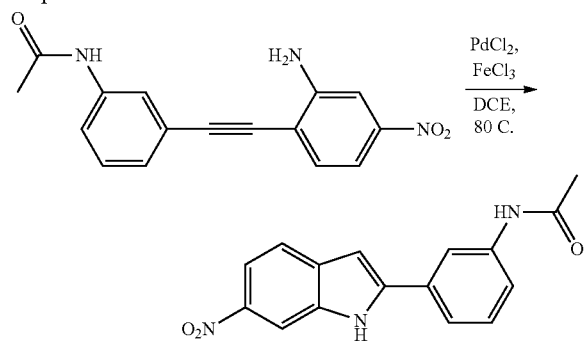

To a solution of the product from step 3 (295 mg, 1.0 mol) in DCE (15 mL) was added PdCl₂ (9 mg, 0.05 mmol) and FeCl₃ (8 mg, 0.05 mmol). The reaction mixture was heated at 80° C. for 2 hours. The reaction was cooled, and the solvents were evaporated, and the residue was extracted with EtOAc (2×), washed with water (30 mL) and brine (30 mL), dried over anhydrous Na₂SO₄. After concentrated in vacuo, the residue was purified by Prep-TLC (DCM/MeOH=50:1) to afford the desired product (240 mg). MS (ESI) m/e (M+H⁺): 296. ¹H NMR (DMSO) δ: 0.12 (s, 1H), 8.25 (d, J=8.0 Hz, 2H), 7.45-7.94 (m, 6H), 7.03 (s, 1H), 2.10 (s, 3H).
Step 5

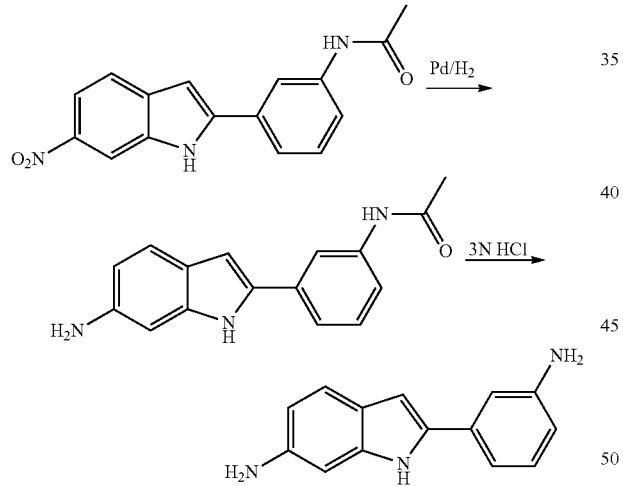

A suspension of the product from step 4 (200 mg, 0.67 mmol), Pd/C (10 mg, 0.034 mmol) in 40 mL EtOH was under H₂ protection and stirred for 1 hour. The mixture was then filtered, and the filtrate was then concentrated to give the product (160 mg). The residue was dissolved in 20 ml 3N HCl, the mixture was stirred at 80° C. for 1 hour. It was cooled to RT, concentrated in vacuo and the residue was purified to give desired compound (120 mg) as a brown solid. MS (m/z) (M+H⁺): 224
Step 6

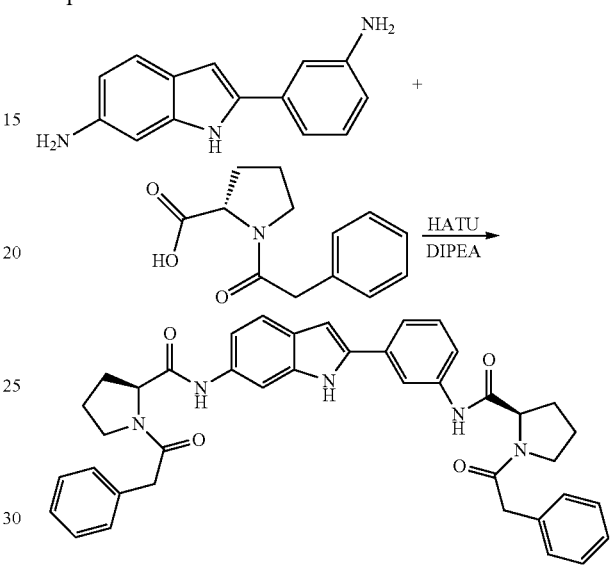

The mixture of compound 10 (50 mg, 0.224 mmol), N-phenylacetyl-L-proline (110 mg, 0.45 mmol), DIPEA (88 mg, 0.7 mmol) in CH₃CN (5 mL) was stirred at RT for 5 minutes, then HATU (82 mg, 0.54 mmol) was added to it. The mixture was stirred at RT overnight. When reaction completed, the mixture was concentrated in vacuo, the residue was purified by chromatography on silica gel to give the desired target (70 mg). MS (ESI) m/e (M+H⁺): 654 ¹H NMR (MeOD): δ 7.95 (d, J=8.0 Hz, 2H), 7.86~7.21 (m, 13H), 6.98 (d, J=8.0 Hz, 1H), 6.72 (s, 1H), 4.57 (m, 2H), 3.53 (m, 3H), 2.02~2.31 (m, 8H).

Example 125 tert-butyl [(1R)-2-{(2S)-2-[(2-{2-[(2S)-1{(2R)-2-[(tert-butoxycarbonyl)amino]-2-phenylacetyl}pyrrolidin-2-yl]-1H-benzimidazol-5-yl}-1H-indol-5-yl)carbamoyl]pyrrolidin-1-yl}-2-oxo-1-phenylethyl]carbamate

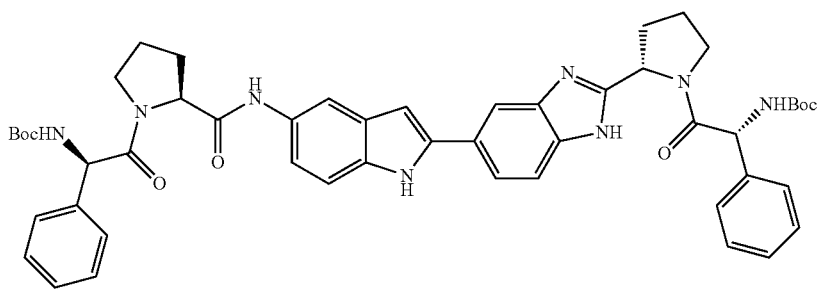 [SMILES: CC(C)(C)OC(=O)N[C@@H](C(=O)N1CCC[C@H]1C(=O)Nc1ccc2[nH]c(-c3ccc4[nH]c([C@@H]5CCCN5C(=O)[C@H](NC(=O)OC(C)(C)C)c5ccccc5)nc4c3)cc2c1)c1ccccc1]

Step 1

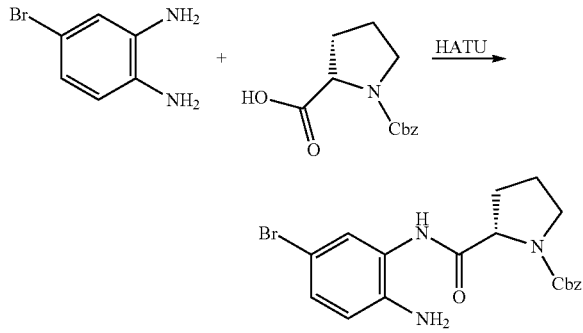

The mixture of 4-bromo-1,2-phenylenediamine (3.1 g, 16 mmol), L-proline (4.3 g, 16 mmol), DIPEA (3 ml) in MeCN (100 mL) was stirred at RT for 5 minutes, then HATU (6 g, 17 mmol) was added. The mixture was stirred at RT overnight. When reaction completed, the mixture was concentrated, the residue was washed with water (100 mL) and extracted with EtOAc (three times), washed with brine (50 mL), dried over anhydrous $Na_2SO_4$. The residue purified by was purified by column chromatography (DCM/MeOH=100:1→50:1) to afford the desired compound (5.0 g). MS (ESI) m/e (M+H$^+$): (418,420).

Step 2

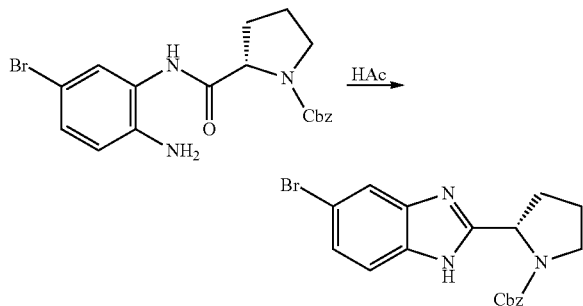

The product from step 1 (5 g, 7.2 mmol) was dissolved in 50 mL acetic acid. The reaction mixture was stirred at 100° C. for 4 hours. The mixture was cooled, and the acetic acid was removed in vacuo. The residue was purified by column chromatography (DCM/MeOH=150:1→100:1) to afford the desired compound (3.8 g). MS (ESI) m/e (M+H$^+$): (400,402).

Step 3

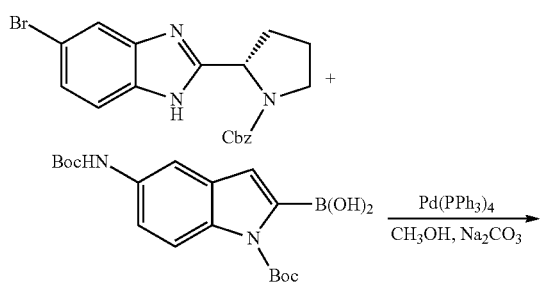

-continued

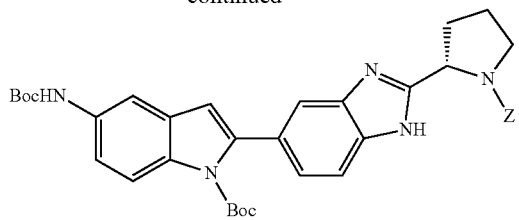

A suspension of the product from step 3 (1.2 g, 3 mmol), 1,5-bis-Boc-5-aminoindole-2-boronic acid (1.2 g, 3 mmol), Pd(PPh$_3$)$_4$ (240 mg), Na$_2$CO$_3$ (1 g, 9 mmol) and H$_2$O (3 mL) in 30 mL of THF under N$_2$ protection was reacted with refluxed at 75° C. overnight. The mixture was filtered, and the filtrate was washed with 50 mL of water and extracted with 100 ml EtOAc and dried over anhydrous Na$_2$SO$_4$. Removal of the solvent and column chromatography (CH$_2$Cl$_2$/MeOH=250:1→200:1) afforded the desired compound (500 mg). MS (ESI) m/e (M+H+): 652

Step 4

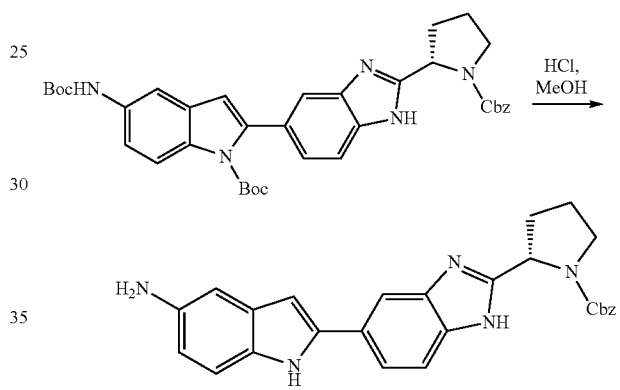

The product from step 3 (500 mg, 0.9 mmol) was stirred in MeOH/HCl (20 mL) for 16 hours. The solvent was removed under reduced pressure and the residue was dried at high vacuum. MS (ESI) m/e (M+H$^+$): 452.

Step 5

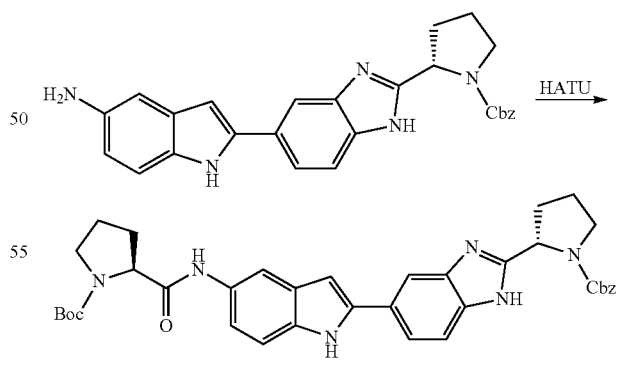

The mixture of aniline from step 4 (450 mg, 1 mmol), (S)—N-Boc proline (215 mg 1 mmol), DIPEA (0.4 mL) in CH$_3$CN (10 mL) was stirred at RT for 10 minutes, then HATU (400 mg, 1.1 mmol) was added. The mixture was stirred at RT overnight, concentrated, and the residue was purified by column chromatography (CH$_2$Cl$_2$ MeOH=250:1200:1). MS (ESI) m/e (M+H$^+$): 649.

Step 6

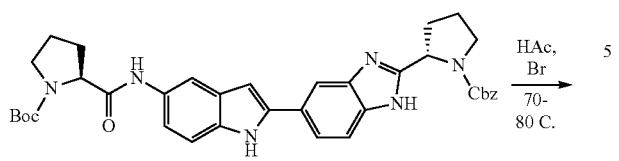

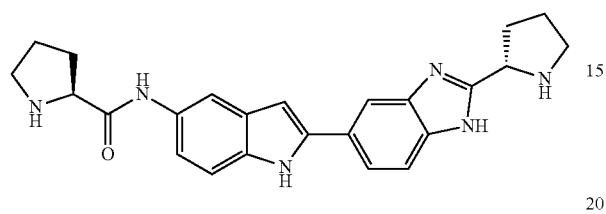

The product from step 5 (290 mg, 0.45 mmol) was dissolved in 5 mL of acetic acid and HBr (1 mL) was added. The reaction mixture was heated to 70-80° C. and stirred for 4 hours. The mixture was cooled to RT and concentrated in vacuo. The residue was extracted with EtOAc (2×), washed with aq NaHCO$_3$ and water (30 mL) and brine (30 mL), dried over anhydrous sodium sulfate. Evaporation of the solvent afforded the desired compound as brown solid (160 mg). MS (ESI) m/e (M+H$^+$): 415.

Step 7

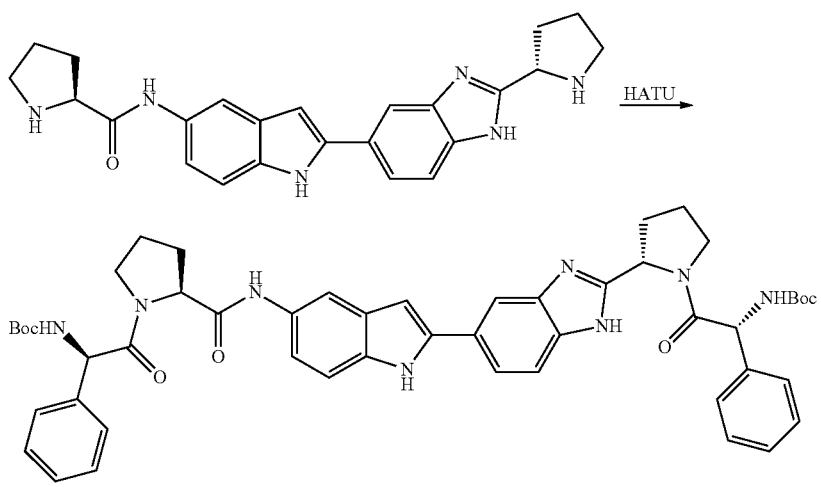

A mixture of the product from step 6 (100 mg, 0.24 mmol), (R)—N-Boc-Phg (120 mg, 0.48 mmol), DIPEA (0.4 mL) in CH$_3$CN (10 mL) was stirred at RT for 10 minutes, then HATU (200 mg, 0.5 mmol) was added. The mixture was stirred at RT overnight then concentrated, and the residue was purified by RPLC to afford the desired compound (54 mg). MS (ESI) m/e (M+H$^+$): 882. $^1$H NMR (MeOD) δ: 7.96~7.69 (m, 4H), 7.49~6.84 (m, 13H), 5.50~5.40 (m, 2H), 4.06~3.94 (m, 2H), 2.27~1.88 (m, 8H), 1.37 (s, 18H).

Example 126

(2S)—N-{4-[3-bromo-5-({[(2S)-1-(phenylacetyl)pyrrolidin-2-yl]carbonyl}amino)-1H-indol-2-yl]phenyl}-1-(phenylacetyl)pyrrolidine-2-carboxamide

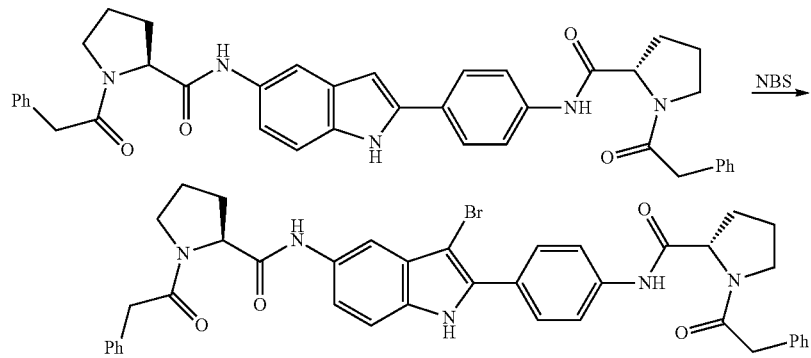

To a solution of the indole (1 equiv) in 5 mL of THF was added NBS (278 mg, 1 mmol) at RT, and the mixture was stirred for 1 hour. Concentration of the solvent and purification of the residue by RPLC afforded the targeted halogenated compounds. $^1$H NMR (MeOD) δ: 7.9-7.5 (m, 5H), 7.4-7.0 (m, 12H), 5.2-4.9 (m, 2H), 4.4 (m, 2H), 3.8-3.5 (m, 6H), 2.5-1.8 (m, 8H).

Example 127 tert-butyl {(1S)-2-[(2S)-2-({2-[4-(acetylamino)phenyl]-3-fluoro-1H-indol-5-yl}carbamoyl)pyrrolidin-1-yl]-2-oxo-1-phenylethyl}carbamate

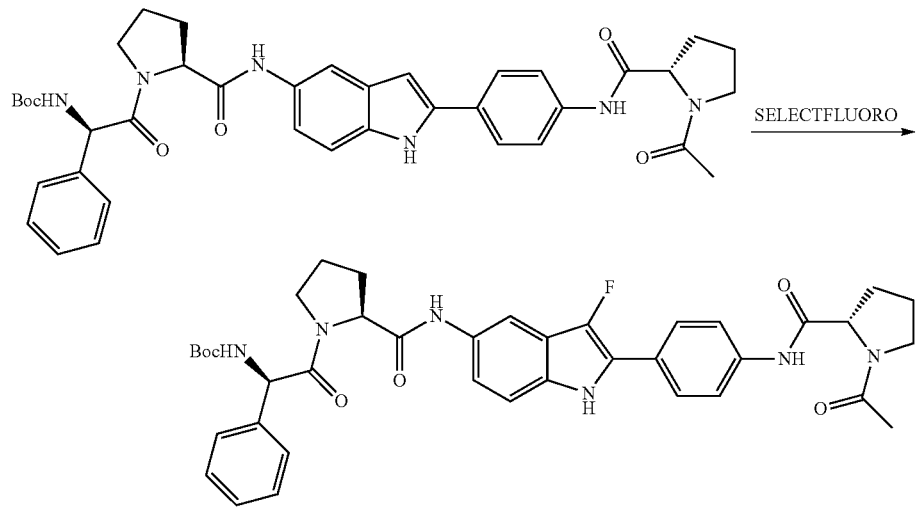

To a solution of the indole (1 equiv.) in acetonitrile/DMSO (5 ml, 1:1) was added SELECTFLUORO (1 equiv.) at 0° C. The mixture was stirred at RT for 33 hours before it was concentrated, and the residue purified with RPLC. $^1$H NMR (MeOD) δ: 7.9-7.c8 (m, 3H), 7.8-7.7 (m, 2H), 7.5-7.3 (m, 6H), 7.3 (m, 1H), 5.5 (s, 1H), 4.6-4.5 (m, 2H), 4.0-3.9 (m, 1H), 3.8 (m, 1H), 3.7 (m, 1H), 2.4-2.3 (m, 1H), 2.2-2.1 (m, 7H), 2.1-2.0 (m, 3H), 2.0-1.9 (m, 1H), 1.4 (m, 9H). MS (m/z): 711 (M+H)$^+$.

Examples 128-154

Compounds of Examples 128-154 can be prepared by direct halogenation of the indole or benzofuran compounds in a similar manner as described in either Example 126 or Example 127.

| Example | Structure | MW | Name |
|---|---|---|---|
| 128 | 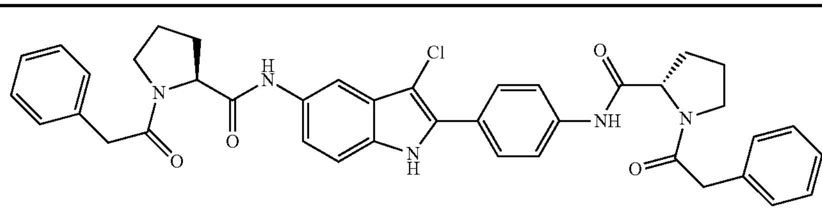 | 688.233 | (2S)-N-{4-[3-chloro-5-({[(2S)-1-(phenylacetyl)pyrrolidin-2-yl]carbonyl}amino)-1H-indol-2-yl]phenyl}-1-(phenylacetyl)pyrrolidine-2-carboxamide |
| 129 | 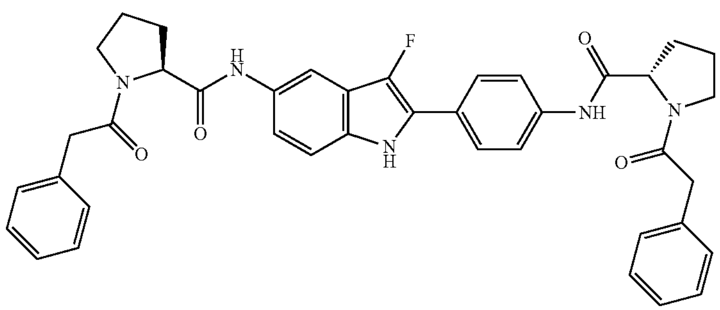 [SMILES: O=C(Nc1ccc(-c2[nH]c3ccc(NC(=O)[C@@H]4CCCN4C(=O)Cc4ccccc4)cc3c2F)cc1)[C@@H]1CCCN1C(=O)Cc1ccccc1] | 671.778 | (2S)-N-{4-[3-fluoro-5-({[(2S)-1-(phenylacetyl)pyrrolidin-2-yl]carbonyl}amino)-1H-indol-2-yl]phenyl}-1-(phenylacetyl)pyrrolidine-2-carboxamide |
| 130 | 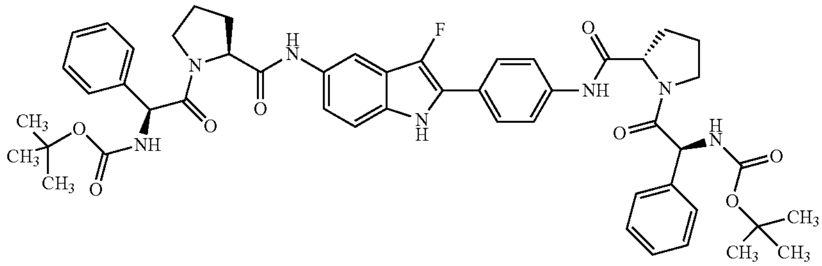 [SMILES: CC(C)(C)OC(=O)N[C@H](C(=O)N1CCC[C@H]1C(=O)Nc1ccc(-c2[nH]c3ccc(NC(=O)[C@@H]4CCCN4C(=O)[C@@H](NC(=O)OC(C)(C)C)c4ccccc4)cc3c2F)cc1)c1ccccc1] | 902.044 | tert-butyl {(1S)-2-[(2S)-2-({4-[5-({[(2S)-1-{(2S)-2-[(tert-butoxycarbonyl)amino]-2-phenylacetyl}pyrrolidin-2-yl]carbonyl}amino)-3-fluoro-1H-indol-2-yl]phenyl}carbamoyl)pyrrolidin-1-yl]-2-oxo-1-phenylethyl}carbamate |
| 131 | 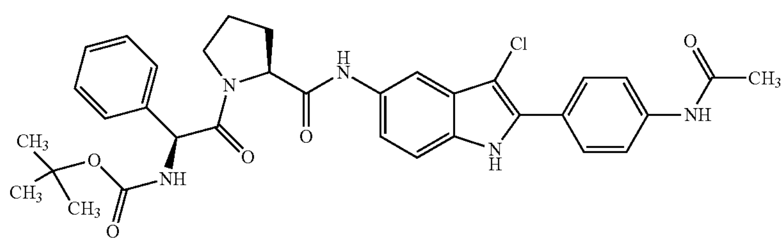 [SMILES: CC(=O)Nc1ccc(-c2[nH]c3ccc(NC(=O)[C@@H]4CCCN4C(=O)[C@@H](NC(=O)OC(C)(C)C)c4ccccc4)cc3c2Cl)cc1] | 630.15 | tert-butyl {(1S)-2-[(2S)-2-({2-[4-(acetylamino)phenyl]-3-chloro-1H-indol-5-yl}carbamoyl)pyrrolidin-1-yl]-2-oxo-1-phenylethyl}carbamate |
| 132 | 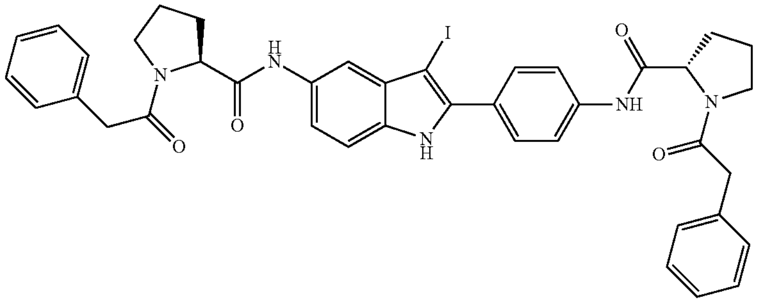 [SMILES: O=C(Nc1ccc(-c2[nH]c3ccc(NC(=O)[C@@H]4CCCN4C(=O)Cc4ccccc4)cc3c2I)cc1)[C@@H]1CCCN1C(=O)Cc1ccccc1] | 779.684 | (2S)-N-{4-[3-iodo-5-({[(2S)-1-(phenylacetyl)pyrrolidin-2-yl]carbonyl}amino)-1H-indol-2-yl]phenyl}-1-(phenylacetyl)pyrrolidine-2-carboxamide |

-continued

| Example | Structure | MW | Name |
|---|---|---|---|
| 133 | 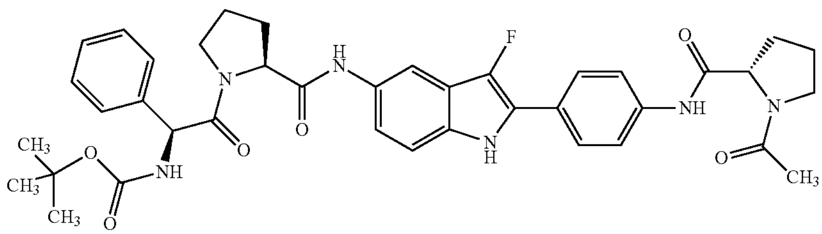 [SMILES: CC(=O)N1CCC[C@H]1C(=O)Nc1ccc(-c2[nH]c3ccc(NC(=O)[C@@H]4CCCN4C(=O)[C@@H](NC(=O)OC(C)(C)C)c4ccccc4)cc3c2F)cc1] | 710.813 | tert-butyl {(1S)-2-[(2S)-2-({2-[4-({[(2S)-1-acetylpyrrolidin-2-yl]carbonyl}amino)phenyl]-3-fluoro-1H-indol-5-yl}carbamoyl)pyrrolidin-1-yl]-2-oxo-1-phenylethyl}carbamate |
| 134 | 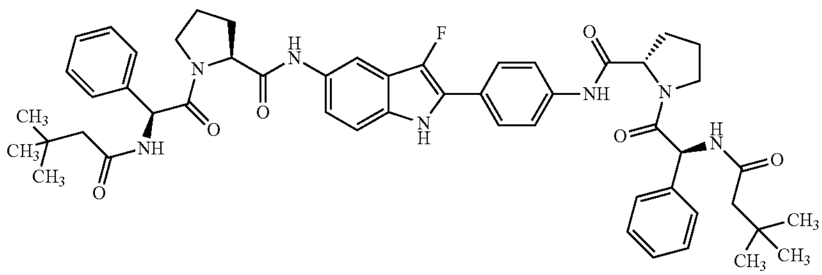 [SMILES: CC(C)(C)CC(=O)N[C@H](C(=O)N1CCC[C@H]1C(=O)Nc1ccc(-c2[nH]c3ccc(NC(=O)[C@@H]4CCCN4C(=O)[C@@H](NC(=O)CC(C)(C)C)c4ccccc4)cc3c2F)cc1)c1ccccc1] | 898.1 | (2S)-1-{(2S)-2-[(3,3-dimethylbutanoyl)amino]-2-phenylacetyl}-N-{4-[5-({[(2S)-1-{(2S)-2-[(3,3-dimethylbutanoyl)amino]-2-phenylacetyl}pyrrolidin-2-yl]carbonyl}amino)-3-fluoro-1H-indol-2-yl]phenyl}pyrrolidine-2-carboxamide |
| 135 | 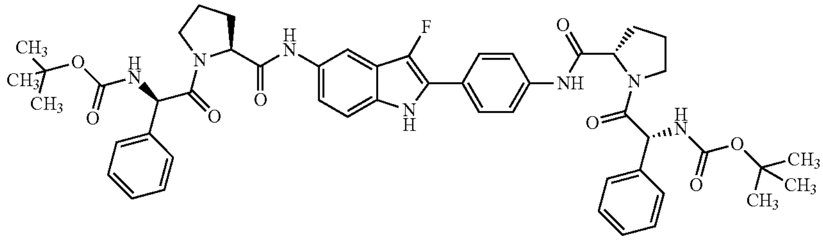 [SMILES: CC(C)(C)OC(=O)N[C@@H](C(=O)N1CCC[C@H]1C(=O)Nc1ccc(-c2[nH]c3ccc(NC(=O)[C@@H]4CCCN4C(=O)[C@H](NC(=O)OC(C)(C)C)c4ccccc4)cc3c2F)cc1)c1ccccc1] | 902.044 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-3-fluoro-1H-indol-2-yl]phenyl}carbamoyl)pyrrolidin-1-yl]-2-oxo-1-phenylethyl}carbamate |
| 136 | 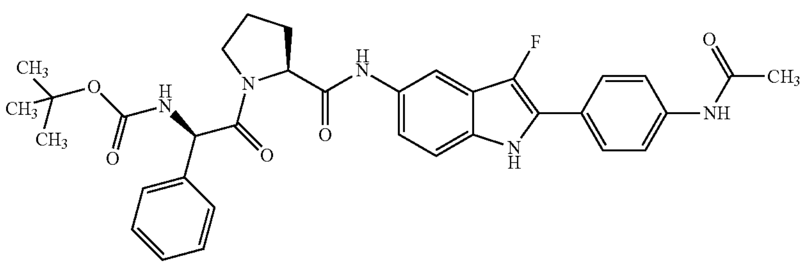 [SMILES: CC(=O)Nc1ccc(-c2[nH]c3ccc(NC(=O)[C@@H]4CCCN4C(=O)[C@H](NC(=O)OC(C)(C)C)c4ccccc4)cc3c2F)cc1] | 613.695 | tert-butyl {(1R)-2-[(2S)-2-({2-[4-(acetylamino)phenyl]-3-fluoro-1H-indol-5-yl}carbamoyl)pyrrolidin-1-yl]-2-oxo-1-phenylethyl}carbamate |
| 137 | 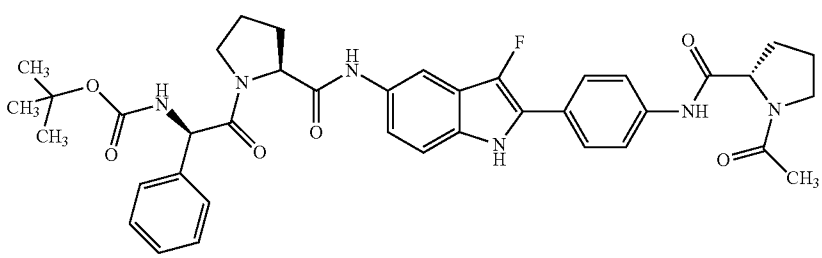 [SMILES: CC(=O)N1CCC[C@H]1C(=O)Nc1ccc(-c2[nH]c3ccc(NC(=O)[C@@H]4CCCN4C(=O)[C@H](NC(=O)OC(C)(C)C)c4ccccc4)cc3c2F)cc1] | 710.813 | tert-butyl {(1R)-2-[(2S)-2-({2-[4-({[(2S)-1-acetylpyrrolidin-2-yl]carbonyl}amino)phenyl]-3-fluoro-1H-indol-5-yl}carbamoyl)pyrrolidin-1-yl]-2-oxo-1-phenylethyl}carbamate |
| 138 | 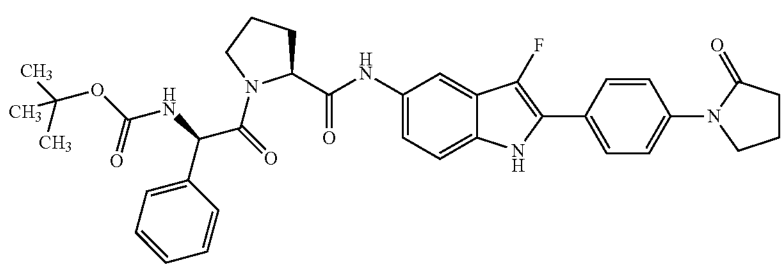 [SMILES: CC(C)(C)OC(=O)N[C@@H](C(=O)N1CCC[C@H]1C(=O)Nc1ccc2[nH]c(-c3ccc(N4CCCC4=O)cc3)c(F)c2c1)c1ccccc1] | 639.733 | tert-butyl {(1R)-2-[(2S)-2-({3-fluoro-2-[4-(2-oxopyrrolidin-1-yl)phenyl]-1H-indol-5-yl}carbamoyl)pyrrolidin-1-yl]-2-oxo-1-phenylethyl}carbamate |

-continued

| Example | Structure | MW | Name |
|---|---|---|---|
| 139 | 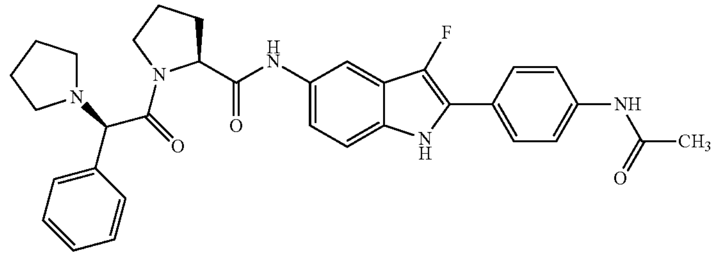 [SMILES: CC(=O)Nc1ccc(-c2[nH]c3ccc(NC(=O)[C@@H]4CCCN4C(=O)[C@@H](c4ccccc4)N4CCCC4)cc3c2F)cc1] | 567.669 | N-{2-[4-(acetylamino)phenyl]-3-fluoro-1H-indol-5-yl}-1-[(2R)-2-phenyl-2-(pyrrolidin-1-yl)acetyl]-L-prolinamide |
| 140 | 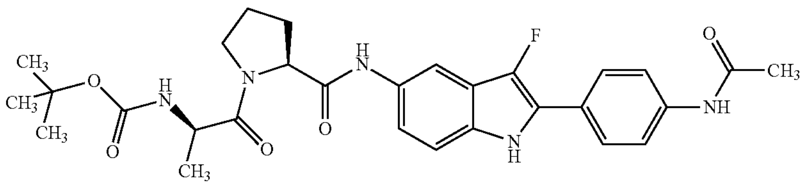 [SMILES: CC(=O)Nc1ccc(-c2[nH]c3ccc(NC(=O)[C@@H]4CCCN4C(=O)[C@@H](C)NC(=O)OC(C)(C)C)cc3c2F)cc1] | 551.623 | N-(tert-butoxycarbonyl)-D-alanyl-N-{2-[4-(acetylamino)phenyl]-3-fluoro-1H-indol-5-yl}-L-prolinamide |
| 141 | 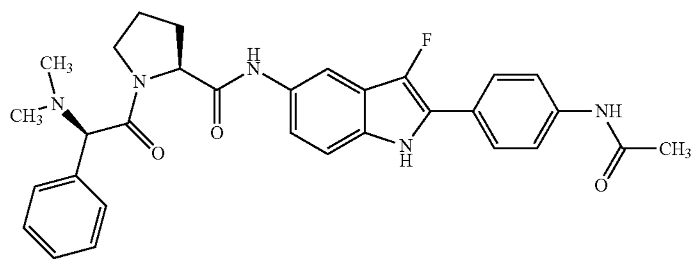 [SMILES: CC(=O)Nc1ccc(-c2[nH]c3ccc(NC(=O)[C@@H]4CCCN4C(=O)[C@@H](c4ccccc4)N(C)C)cc3c2F)cc1] | 541.631 | N-{2-[4-(acetylamino)phenyl]-3-fluoro-1H-indol-5-yl}-1-[(2R)-2-(dimethylamino)-2-phenylacetyl]-L-prolinamide |
| 142 | 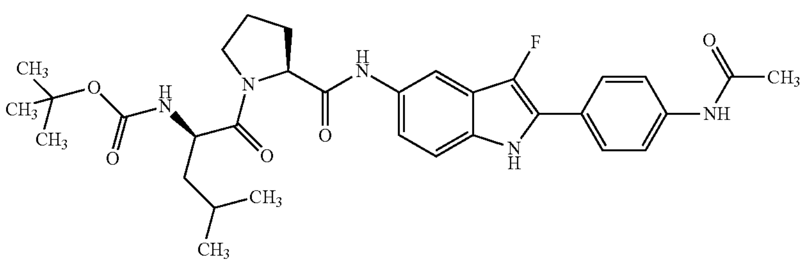 [SMILES: CC(=O)Nc1ccc(-c2[nH]c3ccc(NC(=O)[C@@H]4CCCN4C(=O)[C@@H](CC(C)C)NC(=O)OC(C)(C)C)cc3c2F)cc1] | 593.705 | N-(tert-butoxycarbonyl)-D-leucyl-N-{2-[4-(acetylamino)phenyl]-3-fluoro-1H-indol-5-yl}-L-prolinamide |
| 143 | 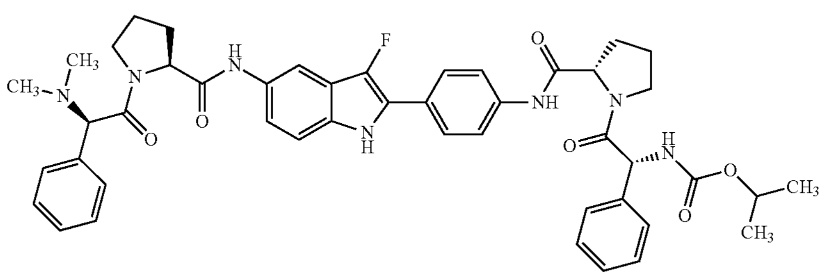 [SMILES: CC(C)OC(=O)N[C@@H](C(=O)N1CCC[C@H]1C(=O)Nc1ccc(-c2[nH]c3ccc(NC(=O)[C@@H]4CCCN4C(=O)[C@@H](c4ccccc4)N(C)C)cc3c2F)cc1)c1ccccc1] | 815.953 | propan-2-yl[(1R)-2-{(2S)-2-[(4-{5-[({(2S)-1-[(2R)-2-(dimethylamino)-2-phenylacetyl]pyrrolidin-2-yl}carbonyl)amino]-3-fluoro-1H-indol-2-yl}phenyl)carbamoyl]pyrrolidin-1-yl}-2-oxo-1-phenylethyl]carbamate) |
| 144 | 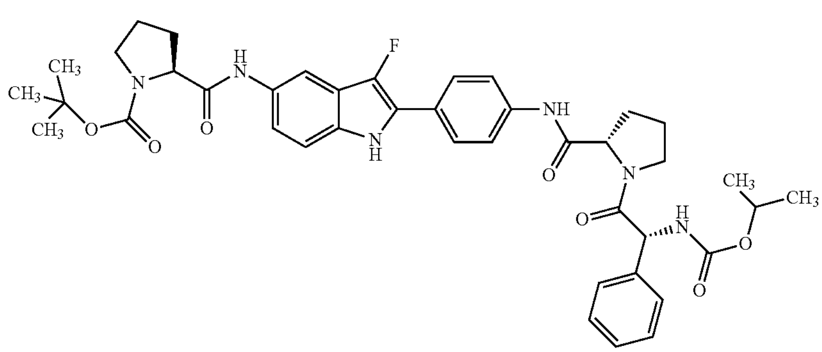 [SMILES: CC(C)OC(=O)N[C@@H](C(=O)N1CCC[C@H]1C(=O)Nc1ccc(-c2[nH]c3ccc(NC(=O)[C@@H]4CCCN4C(=O)OC(C)(C)C)cc3c2F)cc1)c1ccccc1] | 754.866 | tert-butyl (2S)-2-[(3-fluoro-2-{4-[({(2S)-1-[(2R)-2-phenyl-2-{[(propan-2-yloxy)carbonyl]amino}acetyl]pyrrolidin-2-yl}carbonyl)amino]phenyl}-1H-indol-5-yl)carbamoyl]pyrrolidine-1-carboxylate |

-continued

| Example | Structure | MW | Name |
|---|---|---|---|
| 145 | 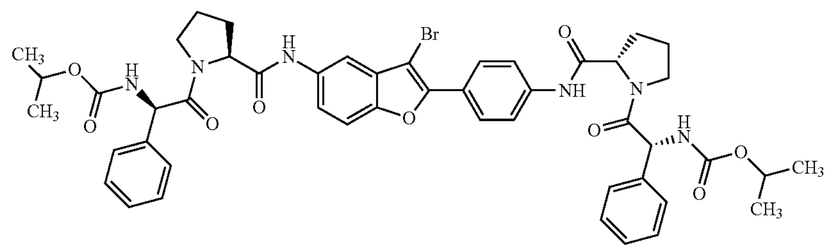 [SMILES: CC(C)OC(=O)N[C@@H](C(=O)N1CCC[C@H]1C(=O)Nc1ccc(-c2oc3ccc(NC(=O)[C@@H]4CCCN4C(=O)[C@H](NC(=O)OC(C)C)c4ccccc4)cc3c2Br)cc1)c1ccccc1] | 935.88 | propan-2-yl [(1R)-2-{(2S)-2-[(4-{3-bromo-5-[({(2S)-1-[(2R)-2-phenyl-2-{[(propan-2-yloxy)carbonyl]amino}acetyl]pyrrolidin-2-yl}carbonyl)amino]-1-benzofuran-2-yl}phenyl)carbamoyl]pyrrolidin-1-yl}-2-oxo-1-phenylethyl]carbamate |
| 146 | 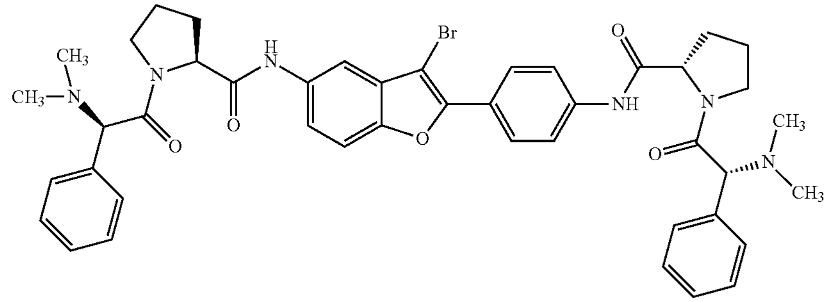 | 819.806 | (2S)-N-(4-{3-bromo-5-[({(2S)-1-[(2R)-2-(dimethylamino)-2-phenylacetyl]pyrrolidin-2-yl}carbonyl)amino]-1-benzofuran-2-yl}phenyl)-1-[(2R)-2-(dimethylamino)-2-phenylacetyl]pyrrolidine-2-carboxamide |
| 147 | 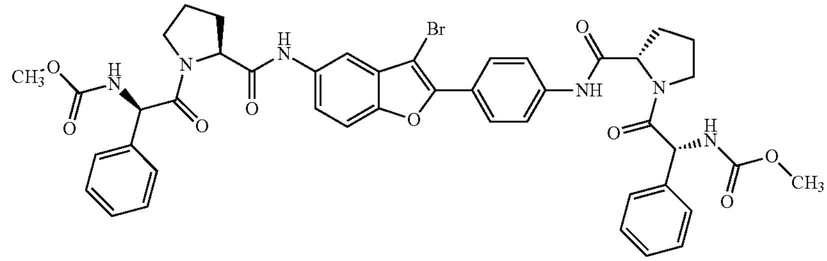 | 879.772 | methyl {(1R)-2-[(2S)-2-({4-[3-bromo-5-({[(2S)-1-{(2R)-2-[(methoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate |
| 148 | 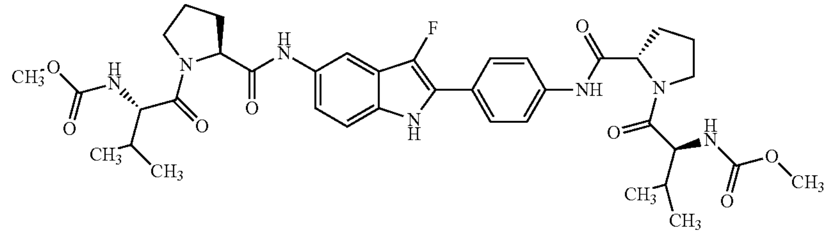 | 749.847 | methyl {(2S)-1-[(2S)-2-({4-[3-fluoro-5-({[(2S)-1-{(2S)-2-[(methoxycarbonyl)amino]-3-methylbutanoyl}pyrrolidin-2-yl]carbonyl}amino)-1H-indol-2-yl]phenyl}carbamoyl)pyrrolidin-1-yl]-3-methyl-1-oxobutan-2-yl}carbamate |
| 149 | 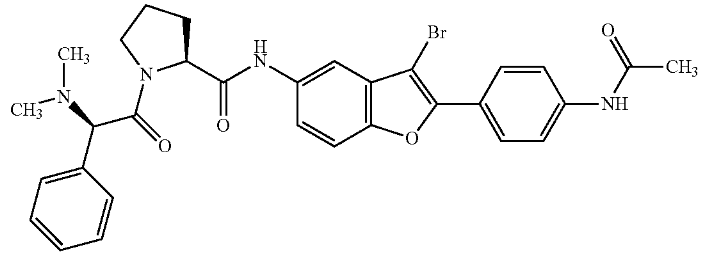 [SMILES: CC(=O)Nc1ccc(-c2oc3ccc(NC(=O)[C@@H]4CCCN4C(=O)[C@@H](c4ccccc4)N(C)C)cc3c2Br)cc1] | 603.521 | N-{2-[4-(acetylamino)phenyl]-3-bromo-1-benzofuran-5-yl}-1-[(2R)-2-(dimethylamino)-2-phenylacetyl]-L-prolinamide |

-continued

| Example | Structure | MW | Name |
| --- | --- | --- | --- |
| 150 | 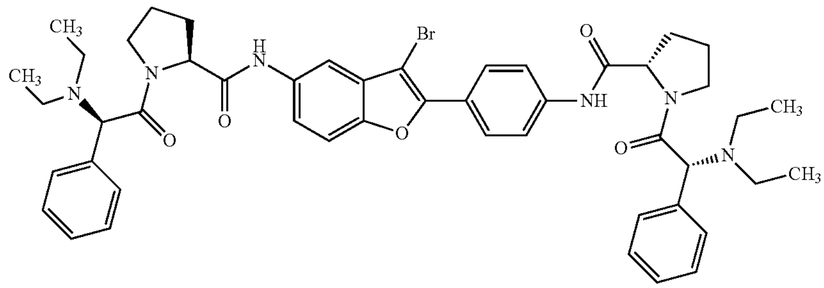 [SMILES: CCN(CC)[C@@H](C(=O)N1CCC[C@H]1C(=O)Nc1ccc(-c2oc3ccc(NC(=O)[C@@H]4CCCN4C(=O)[C@@H](c4ccccc4)N(CC)CC)cc3c2Br)cc1)c1ccccc1] | 875.915 | (2S)-N-(4-{3-bromo-5-[({(2S)-1-[(2R)-2-(diethylamino)-2-phenylacetyl]pyrrolidin-2-yl}carbonyl)amino]-1-benzofuran-2-yl}phenyl)-1-[(2R)-2-(diethylamine)-2-phenylacetyl]pyrrolidine-2-carboxamide |
| 151 | 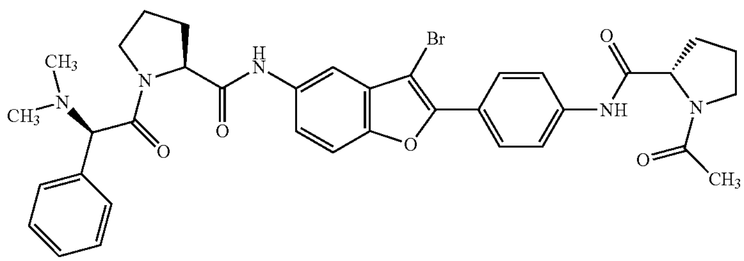 [SMILES: CC(=O)N1CCC[C@H]1C(=O)Nc1ccc(-c2oc3ccc(NC(=O)[C@@H]4CCCN4C(=O)[C@@H](c4ccccc4)N(C)C)cc3c2Br)cc1] | 700.639 | (2S)-1-acetyl-N-(4-{3-bromo-5-[({(2S)-1-[(2R)-2-(dimethylamino)-2-phenylacetyl]pyrrolidin-2-yl}carbonyl)amino]-1-benzofuran-2-yl}phenyl)pyrrolidine-2-carboxamide |
| 152 | 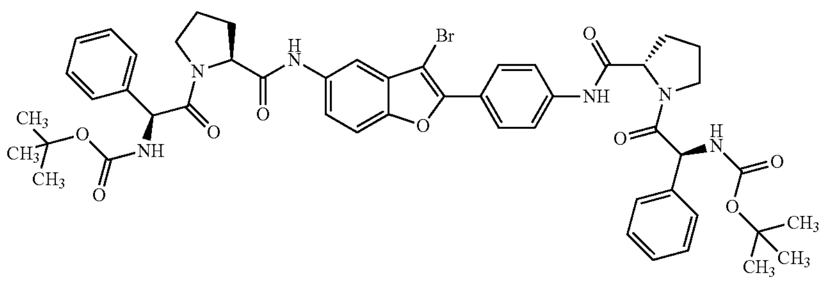 [SMILES: CC(C)(C)OC(=O)N[C@H](C(=O)N1CCC[C@H]1C(=O)Nc1ccc(-c2oc3ccc(NC(=O)[C@@H]4CCCN4C(=O)[C@@H](NC(=O)OC(C)(C)C)c4ccccc4)cc3c2Br)cc1)c1ccccc1] | 963.935 | tert-butyl {(1S)-2-[(2S)-2-({4-[3-bromo-5-({[(2S)-1-{(2S)-2-[(tert-butoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate) |
| 153 | 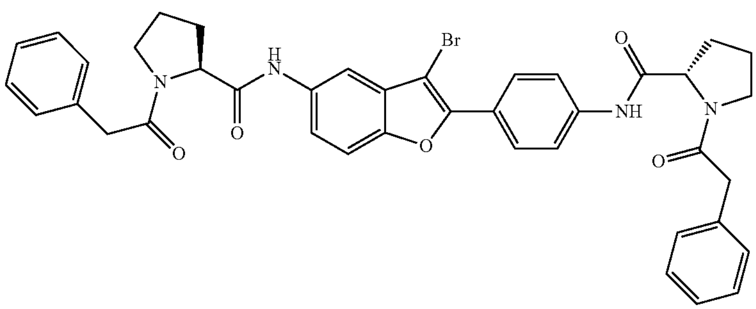 [SMILES: O=C(Nc1ccc(-c2oc3ccc(NC(=O)[C@@H]4CCCN4C(=O)Cc4ccccc4)cc3c2Br)cc1)[C@@H]1CCCN1C(=O)Cc1ccccc1] | 733.669 | (2S)-N-{4-[3-bromo-5-({[(2S)-1-(phenylacetyl)pyrrolidin-2-yl]carbonyl}amino)-1-benzofuran-2-yl]phenyl}-1-(phenylacetyl)pyrrolidine-2-carboxamide |
| 154 | 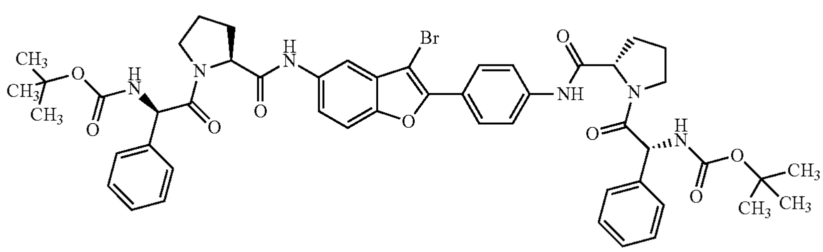 [SMILES: CC(C)(C)OC(=O)N[C@@H](C(=O)N1CCC[C@H]1C(=O)Nc1ccc(-c2oc3ccc(NC(=O)[C@@H]4CCCN4C(=O)[C@H](NC(=O)OC(C)(C)C)c4ccccc4)cc3c2Br)cc1)c1ccccc1] | 963.935 | tert-butyl {(1R)-2-[(2S)-2-({4-[3-bromo-5-({[(2S)-1-{(2R)-2-[(tert-butoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate |

Example 155

(2S)—N-{4-[3-cyano-5-({[(2S)-1-(phenylacetyl)pyrrolidin-2-yl]carbonyl}amino)-1H-indol-2-yl]phenyl}-1-(phenylacetyl)pyrrolidine-2-carboxamide

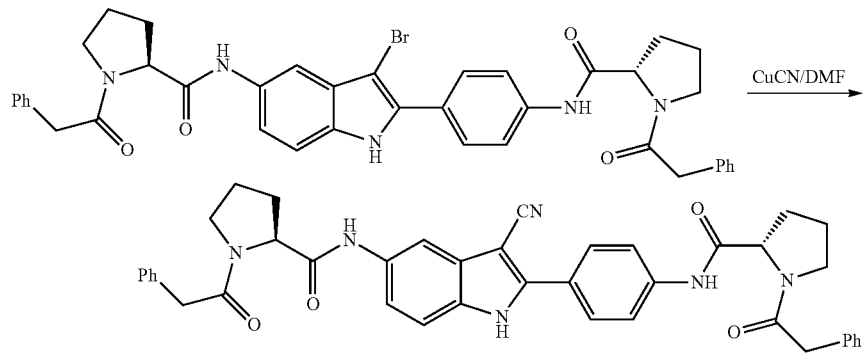

A mixture of the bromo compound from Example 126 (150 mg, 0.2 mmol), CuCN (50 mg, 0.6 mmol) and DMF (3 mL) was refluxed under $N_2$ protection overnight. The mixture was purified by RPLC to afford the product. MS (ESI) m/e (M+H$^+$): 679. $^1$H NMR (CDCl$_3$) δ: 7.73-7.70 (m, 4H), 7.38-7.29 (m, 4H), 7.21-7.04 (m, 6H), 4.63-4.60 (m, 1H), 4.49-4.47 (m, 1H), 3.81-3.59 (m, 4H), 2.48-1.97 (m, 8H).

Example 156

(2S)—N-{4-[3-(2,2-dimethylpropanoyl)-5-({[(2S)-1-(phenylacetyl)pyrrolidin-2-yl]carbonyl}amino)-1H-indol-2-yl]phenyl}-1-(phenylacetyl)pyrrolidine-2-carboxamide

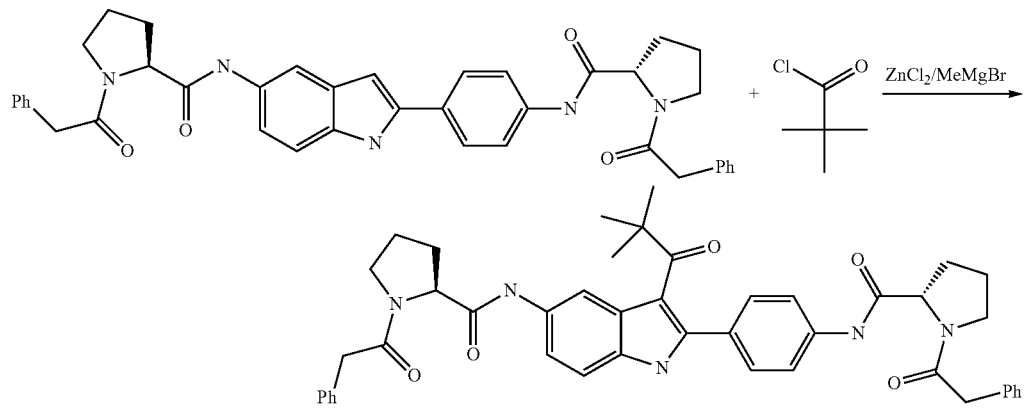

To a stirred solution of the indole (50 mg, 0.076 mmol) in CH$_2$Cl$_2$ (5 mL) was added anhydrous ZnCl$_2$ (54 mg, 0.4 mmol) then MeMgBr (3.0 M in Et$_2$O, 0.4 mL, 0.4 mmol). The resulting suspension was stirred for 10 minutes at RT and then cooled to 0° C. at an ice bath. A solution of pivaloyl chloride (14 mg) in CH$_2$Cl$_2$ (0.2 mL) was added to the mixture. The reaction mixture was allowed to warm to RT and stirred overnight. The reaction mixture was quenched by saturated aqueous NH$_4$Cl and exacted with CH$_2$Cl$_2$ 3 times. The organic layers were combined, dried over anhydrous Na$_2$SO$_4$ and filtered. The filtrate was concentrated and purified by RPLC to yield the product. MS (ESI) m/e (M+H$^+$): 738. $^1$H NMR (MeOD) δ: 7.69-7.63 (m, 3H), 7.44-7.41 (m, 2H), 7.31-7.21 (m, 12H), 4.55-4.52 (m, 2H), 3.76-3.59 (m, 8H), 2.26-1.94 (m, 8H).

Example 157

5-({[(2S)-1-(phenylacetyl)pyrrolidin-2-yl]carbonyl}amino)-2-[4-({[(2S)-1-(phenylacetyl)pyrrolidin-2-yl]carbonyl}amino)phenyl]-1H-indole-3-carboxamide

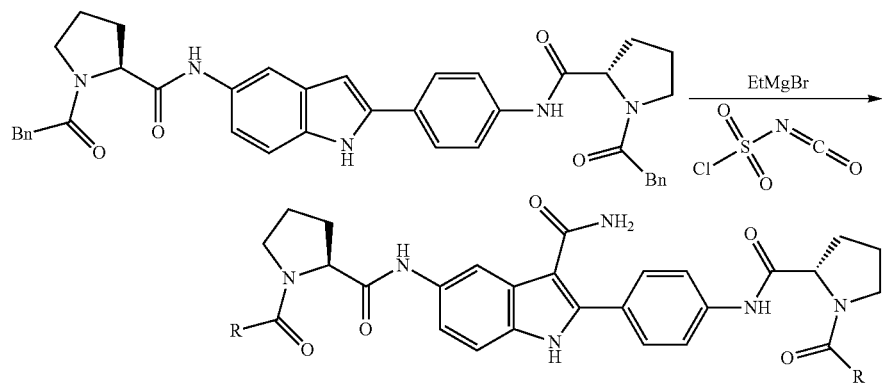

To a solution of the indole (653 mg, 1 mmol) in THF 10 (mL) was added EtMgBr (2 mL, 6 mmol), and the mixture was stirred at RT for 30 minutes. Thereto was added chlorosulfonyl isocyanate (140 mg, 1 mmol), and the mixture was stirred at RT for 20 minutes. Then, DMF (146 mg, 2 mmol) was added to the above mixture, and the stirring continued for 20 minutes. After adding aqueous NaOH (2N, 1 mL), the resulting solution was heated at reflux for 5 minutes. Concentration in vacuo, the residue was purified with RPLC to give (67 mg). $^1$H NMR (MeOD) δ: 8.0 (s, 1H), 7.6 (m, 4H), 7.1-7.4 (m, 12H), 4.5 (m, 4H), 3.5-3.7 (m, 8H), 2.5-2.0 (m, 6H).

Example 158 tert-butyl {(1R)-2-[(2S)-2-*({4-[5-({[(2S)-1-{(2R)-2-[(tert-butoxycarbonyl)amino]-2-phenylacetyl}pyrrolidin-2-yl]carbonyl}amino)-3-(cyclopropylcarbamoyl)-1H-indol-2-yl]phenyl}carbamoyl)pyrrolidin-1-yl]-2-oxo-1-phenylethyl}carbamate

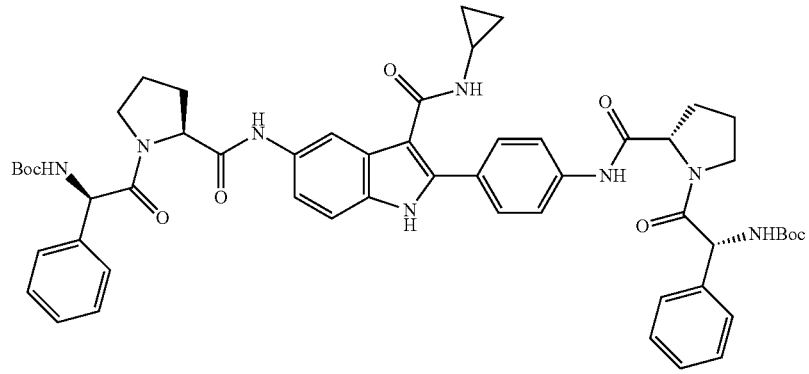 [SMILES: CC(C)(C)OC(=O)N[C@@H](C(=O)N1CCC[C@H]1C(=O)Nc1ccc(-c2[nH]c3ccc(NC(=O)[C@@H]4CCCN4C(=O)[C@H](NC(=O)OC(C)(C)C)c4ccccc4)cc3c2C(=O)NC2CC2)cc1)c1ccccc1]

Step 1

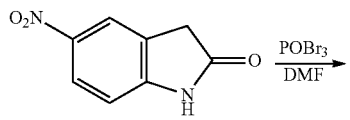

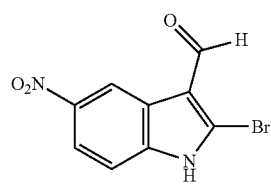

To a solution of POBr₃ (113.2 g, 0.4 mol) in DCE (1 L) was added DMF (14.6 g, 0.2 mol) dropwise under ice bath, and the mixture was stirred at RT for 30 minutes. Thereto was added nitro compound (17.8 g, 0.1 mol), and the mixture was stirred at reflux for 4 hours. The precipitate was collected by filtration and then washed with water and MeOH. The solid was dried in vacuo to give the desired compound (13.5 g). ¹H NMR (DMSO) δ: 13.6 (s, 1H), 9.8 (s, 1H), 8.8 (s, 1H), 8.1 (d, J=9.2 Hz, 1H), 7.6 (d, J=9.2 Hz, 1H).

Step 2

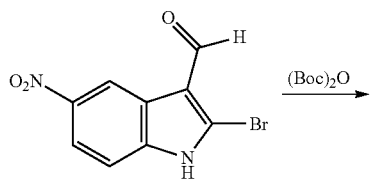

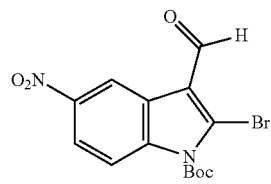

To a solution of the aldehyde from step 1 (13.5 g, 0.05 mol) in DCM (100 mL) was added DMAP (0.6 g, 0.005 mol), TEA (10.1 g, 0.1 mol) and (Boc)₂O (21.8 g, 0.1 mol), and the mixture was stirred at RT overnight. The mixture was concentrated, and the residue was purified by column chromatography to give the desired compound (14.7 g). ¹H NMR (CDCl₃) δ: 9.8 (s, 1H), 8.8 (s, 1H), 8.1 (d, J=9.2 Hz, 1H), 7.6 (d, J=9.2 Hz, 1H), 1.4 (s, 9H).

Step 3

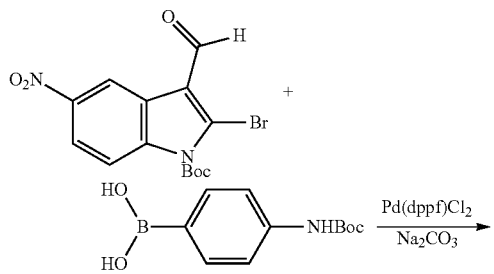

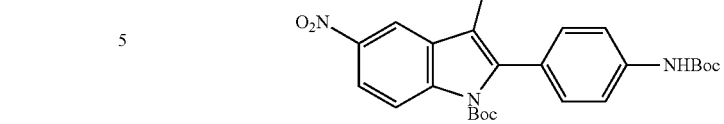

The Suzuki coupling procedure was the same as described in Example 117, step 3. MS (m/z): 482 (M+H)⁺.

Step 4

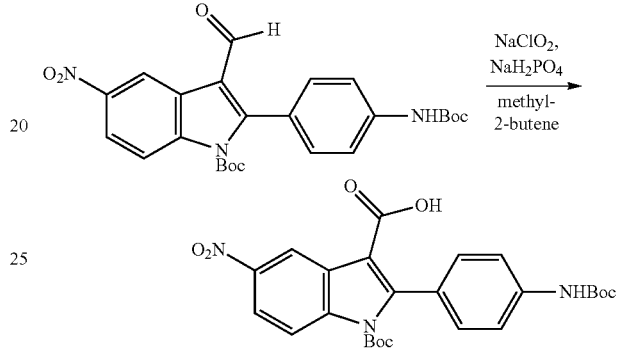

To a solution of compound from step 3 (2.4 g, 5 mmol) in pH 3.5 phosphate buffer (24 mL) and t-BuOH (30 mL) was added 2-methyl-2-butene (10 mL) and sodium chlorate (0.89 g, 10 mmol). The reaction was stirred at RT for 16 hours and then extracted with DCM (3×). The combined organic extracts were washed with brine, dried over anhydrous MgSO₄, and concentrated in vacuo to give the desired carboxylic acid (2.3 g). MS (m/z): 498 (M+H)⁺.

Step 5

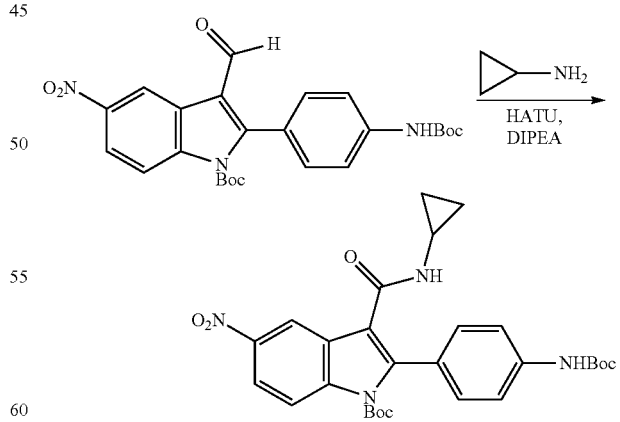

The mixture of compound from step 4 (1 mmol), cyclopropyl amine (1 mmol), HATU (1 mmol) and DIPEA (5 mmol) in DCM was stirred at RT overnight. Concentration and purification of the residue by RPLC gave the desired compound (0.8 mmol). MS (m/z): 538 (M+H)⁺.

Step 6

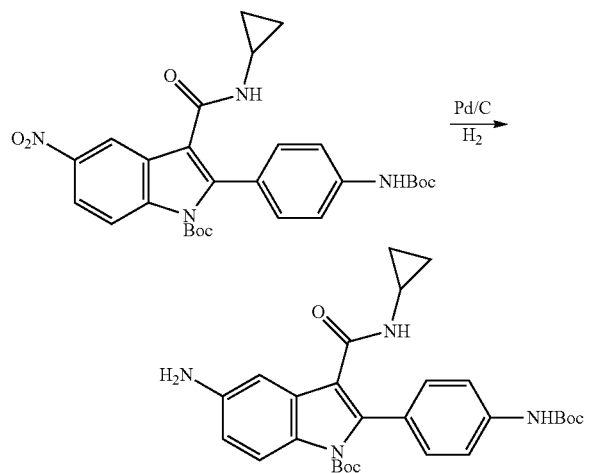

Step 7

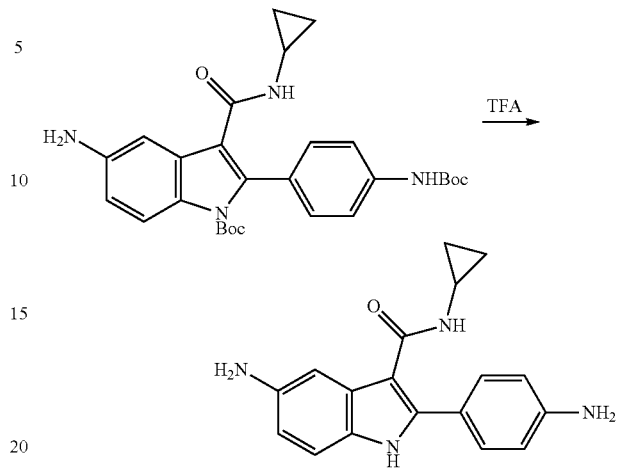

To a solution of the amide from step 5 (0.8 mmol) in MeOH (10 mL) was added Pd/C (100 mg) and the mixture was stirred under H₂ at RT for 1 hour. The Pd/C was removed by filtration, and the filtrate was concentrated to give the desired compound (0.7 mmol). MS (m/z): 507 (M+H)⁺.

To a solution of compound from step 6 (0.7 mmol) in DCM (5 mL) was added TFA (2 mL), and the mixture was stirred at RT overnight. The solution was concentrated, and the residue was used in next step without purification. MS (m/z): 307 (M+H)⁺.

Step 8

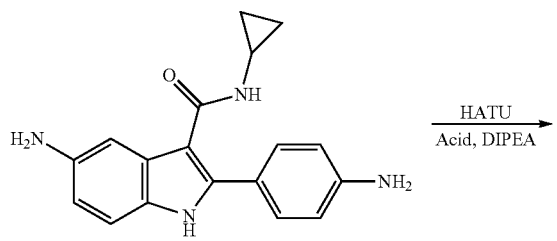

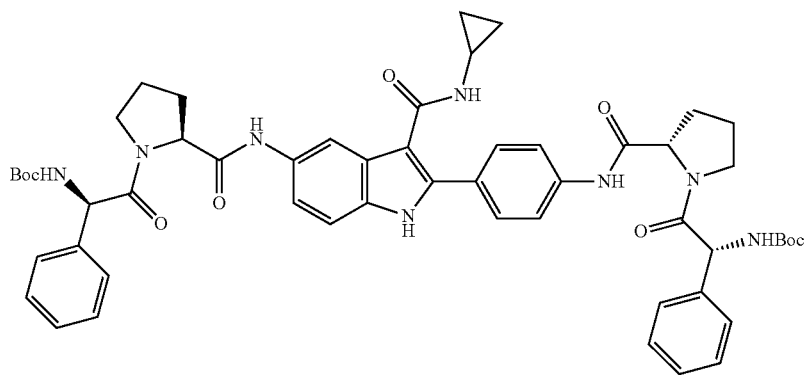

The coupling procedure was the same as used in Example 72, step 7. ¹H NMR (MeOD) δ: 6.9-7.9 (m, 17H), 5.2-5.5 (m, 2H), 4.4-4.5 (m, 2H), 3.5-3.9 (m, 3H), 2.7-2.8 (m, 1H), 1.7-2.2 (m, 8H), 1.4 (s, 18H), 1.2 (m, 1H), 0.4-0.8 (m, 4H). MS (m/z): 967 (M+H)⁺.

Example 159 tert-butyl {(1R)-2-[(2S)-2-({4-[5-({[(2S)-1-{(2R)-2-[(tert-butoxy-carbonyl)amino]-2-phenylacetyl}pyrrolidin-2-yl]carbonyl}amino)-3-(4-methoxyphenyl)-1H-indol-2-yl]phenyl}carbamoyl)pyrrolidin-1-yl]-2-oxo-1-phenylethyl}carbamate

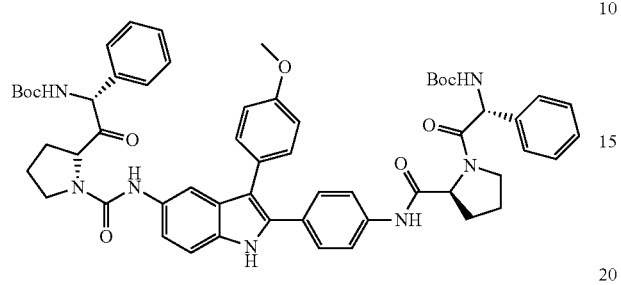

Step 1

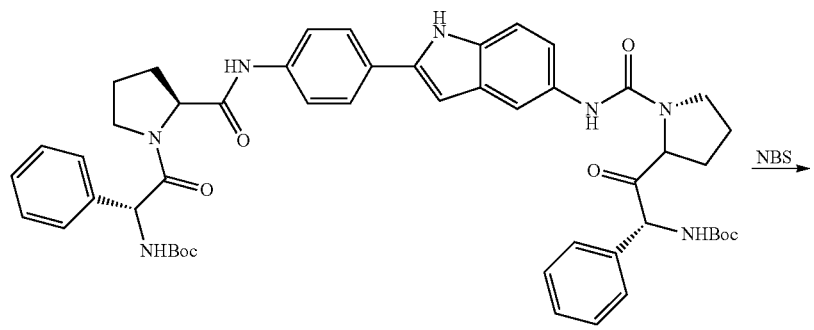

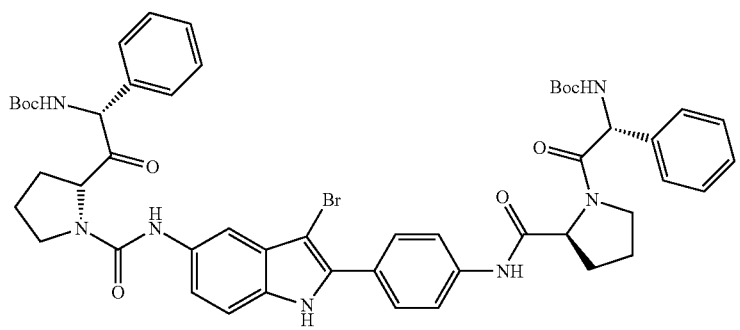

NBS (103 mg, 0.5769 mmol) was added in portions to the solution of the indole (510 mg, 0.5769 mmol) in 20 mL of THF, the mixture was stirred at RT for 1 hour, then concentrated. The residue was purified by Prep-HPLC to afford the desired compound (500 mg). MS (ESI) m/e (M+H$^+$): 962.

Step 2

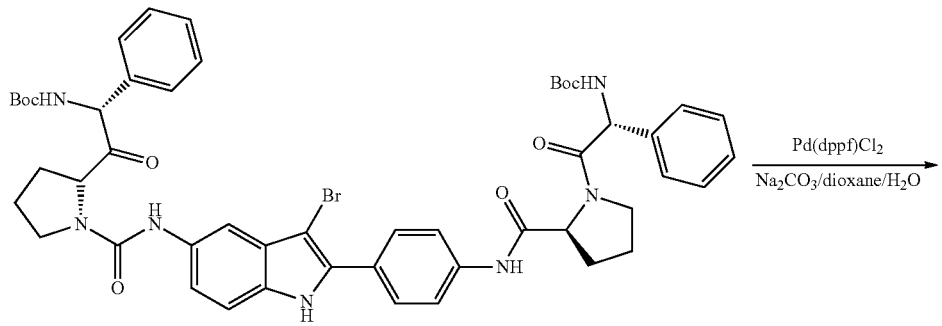

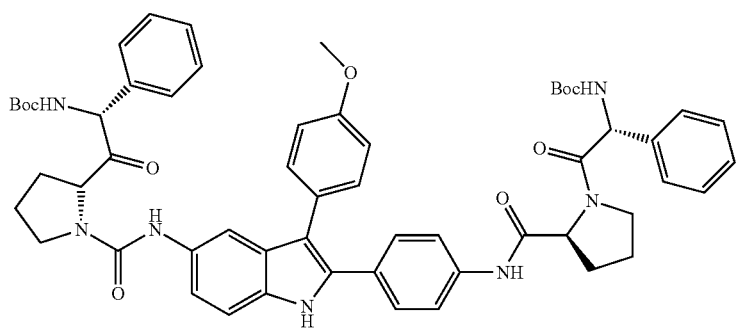

The mixture of the product from step 1 above (100 mg, 0.104 mmol), 4-methoxy-phenylboronic acid (24 mg, 0.1558 mmol), Pd(dppf)Cl$_2$ (7.6 mg, 0.0104 mmol), Na$_2$CO$_3$ (3.3 mg, 0.0312 mmol) in 10 mL of dioxane and 2 mL of water was heated to reflux under N$_2$ atmosphere overnight. The mixture was cooled and concentrated, then the residue was purified by RPLC to give the desired product (30 mg). $^1$H NMR (MeOD) δ: 7.71~7.54 (m, 3H), 7.42~7.26 (m, 16H), 6.96~6.92 (m, 3H), 5.45 (s, 2H), 4.53~4.50 (m, 2H), 3.92~3.81 (m, 5H), 2.08~1.84 (m, 8H), 1.42~1.32 (m, 18H). MS (ESI) m/e (M+H$^+$): 991.

Examples 160-177

Compounds of Examples 160-177 were prepared in a similar manner as described in Examples 155-159.

| Example | Structure | MW | Name |
|---|---|---|---|
| 160 | 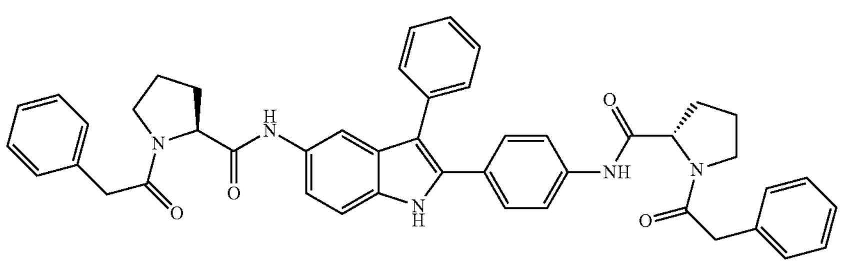 [SMILES: O=C(Nc1ccc(-c2[nH]c3ccc(NC(=O)[C@@H]4CCCN4C(=O)Cc4ccccc4)cc3c2-c2ccccc2)cc1)[C@@H]1CCCN1C(=O)Cc1ccccc1] | 729.887 | (2S)-1-(phenylacetyl)-N-{4-[3-phenyl-5-({[(2S)-1-(phenylacetyl)pyrrolidin-2-yl]carbonyl}amino)-1H-indol-2-yl]phenyl}pyrrolidine-2-carboxamide |
| 161 | 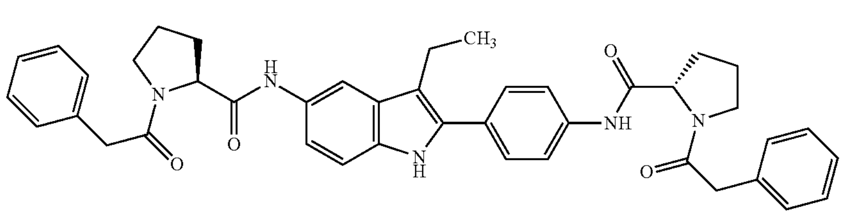 [SMILES: CCc1c(-c2ccc(NC(=O)[C@@H]3CCCN3C(=O)Cc3ccccc3)cc2)[nH]c2ccc(NC(=O)[C@@H]3CCCN3C(=O)Cc3ccccc3)cc12] | 681.842 | (2S)-N-{4-[3-ethyl-5-({[(2S)-1-(phenylacetyl)pyrrolidin-2-yl]carbonyl}amino)-1H-indol-2-yl]phenyl}-1-(phenylacetyl)pyrrolidine-2-carboxamide |

| Example | Structure | MW | Name |
|---|---|---|---|
| 162 | 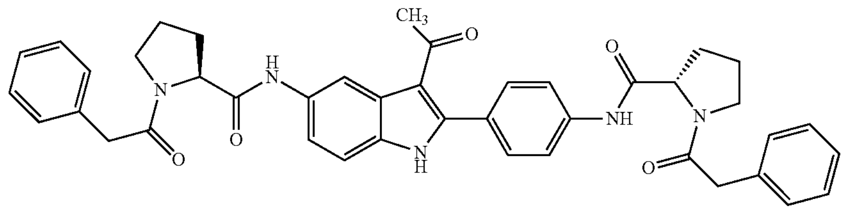 [SMILES: CC(=O)c1c(-c2ccc(NC(=O)[C@@H]3CCCN3C(=O)Cc3ccccc3)cc2)[nH]c2ccc(NC(=O)[C@@H]3CCCN3C(=O)Cc3ccccc3)cc12] | 695.826 | (2S)-N-{4-[3-acetyl-5-({[(2S)-1-(phenylacetyl)pyrrolidin-2-yl]carbonyl}amino)-1H-indol-2-yl]phenyl}-1-(phenylacetyl)pyrrolidine-2-carboxamide |
| 163 | 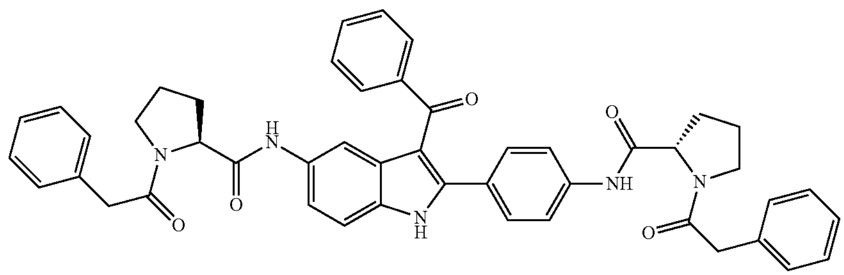 [SMILES: O=C(c1ccccc1)c1c(-c2ccc(NC(=O)[C@@H]3CCCN3C(=O)Cc3ccccc3)cc2)[nH]c2ccc(NC(=O)[C@@H]3CCCN3C(=O)Cc3ccccc3)cc12] | 757.897 | (2S)-1-(phenylacetyl)-N-{4-[5-({[(2S)-1-(phenylacetyl)pyrrolidin-2-yl]carbonyl}amino)-3-(phenylcarbonyl)-1H-indol-2-yl]phenyl}pyrrolidine-2-carboxamide |
| 164 | 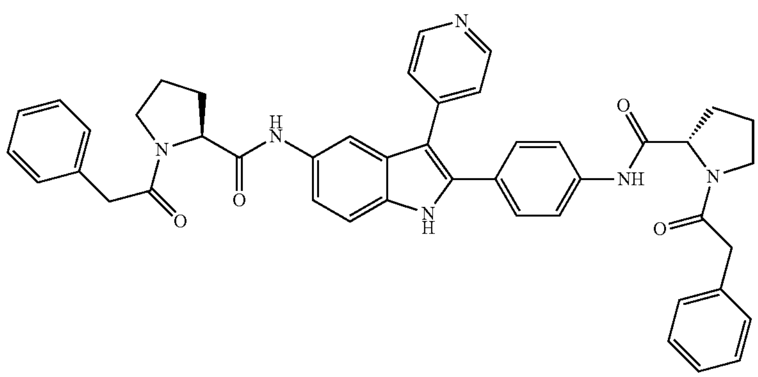 [SMILES: O=C(Nc1ccc(-c2[nH]c3ccc(NC(=O)[C@@H]4CCCN4C(=O)Cc4ccccc4)cc3c2-c2ccncc2)cc1)[C@@H]1CCCN1C(=O)Cc1ccccc1] | 730.874 | (2S)-1-(phenylacetyl)-N-{2-[4-({[(2S)-1-(phenylacetyl)pyrrolidin-2-yl]carbonyl}amino)phenyl]-3-(pyridin-4-yl)-1H-indol-5-yl}pyrrolidine-2-carboxamide |
| 165 | 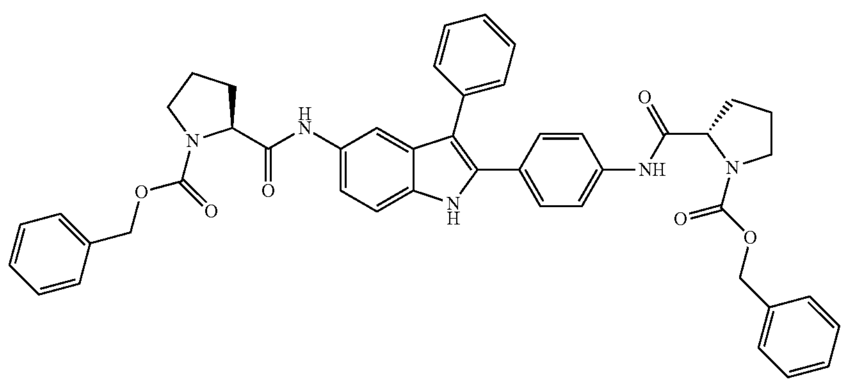 [SMILES: O=C(Nc1ccc(-c2[nH]c3ccc(NC(=O)[C@@H]4CCCN4C(=O)OCc4ccccc4)cc3c2-c2ccccc2)cc1)[C@@H]1CCCN1C(=O)OCc1ccccc1] | 761.886 | benzyl (2S)-2-[(4-{5-[({(2S)-1-[(benzyloxy)carbonyl]pyrrolidin-2-yl}carbonyl)amino]-3-phenyl-1H-indol-2-yl}phenyl)carbamoyl]pyrrolidine-1-carboxylate |
| 166 | 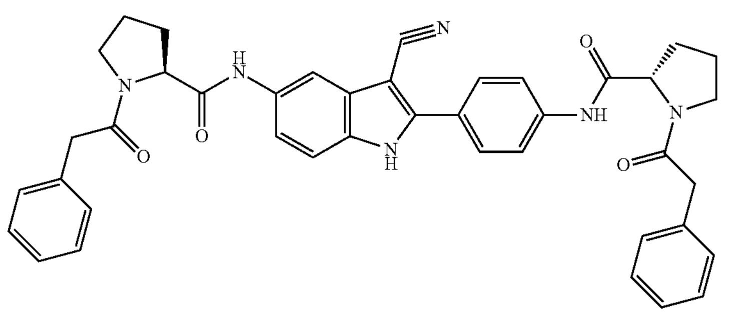 [SMILES: N#Cc1c(-c2ccc(NC(=O)[C@@H]3CCCN3C(=O)Cc3ccccc3)cc2)[nH]c2ccc(NC(=O)[C@@H]3CCCN3C(=O)Cc3ccccc3)cc12] | 678.798 | (2S)-N-{4-[3-cyano-5-({[(2S)-1-(phenylacetyl)pyrrolidin-2-yl]carbonyl}amino)-1H-indol-2-yl]phenyl}-1-(phenylacetyl)pyrrolidine-2-carboxamide |

| Example | Structure | MW | Name |
|---|---|---|---|
| 167 | 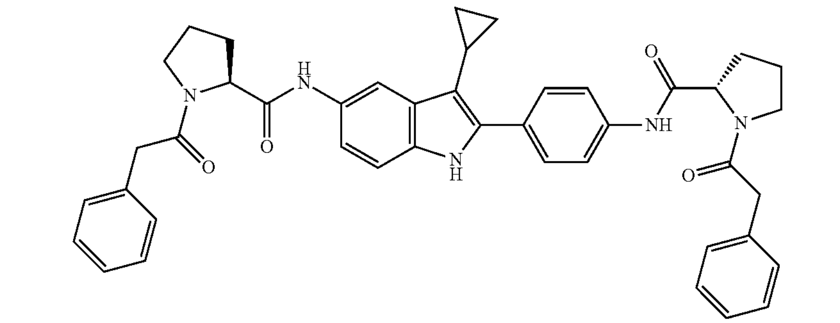 [SMILES: O=C(Nc1ccc(-c2[nH]c3ccc(NC(=O)[C@@H]4CCCN4C(=O)Cc4ccccc4)cc3c2C2CC2)cc1)[C@@H]1CCCN1C(=O)Cc1ccccc1] | 693.853 | (2S)-N-{4-[3-cyclopropyl-5-({[(2S)-1-(phenylacetyl)pyrrolidin-2-yl]carbonyl}amino)-1H-indol-2-yl]phenyl}-1-(phenylacetyl)pyrrolidine-2-carboxamide |
| 168 | 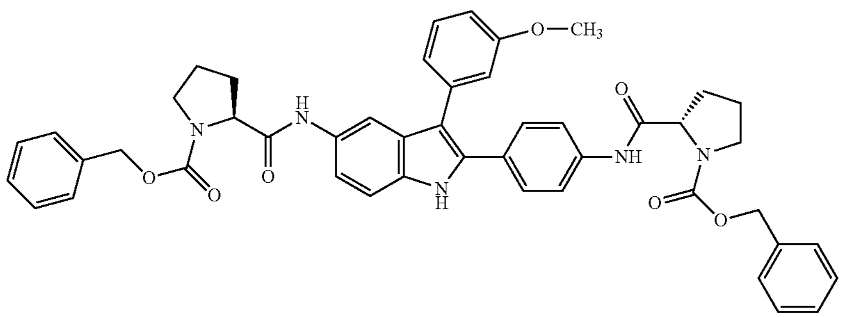 [SMILES: COc1cccc(-c2c(-c3ccc(NC(=O)[C@@H]4CCCN4C(=O)OCc4ccccc4)cc3)[nH]c3ccc(NC(=O)[C@@H]4CCCN4C(=O)OCc4ccccc4)cc23)c1] | 791.912 | benzyl (2S)-2-[(4-{5-[({(2S)-1-[(benzyloxy)carbonyl]pyrrolidin-2-yl}carbonyl)amino]-3-(3-methoxyphenyl)-1H-indol-2-yl}phenyl)carbamoyl]pyrrolidine-1-carboxylate |
| 169 | 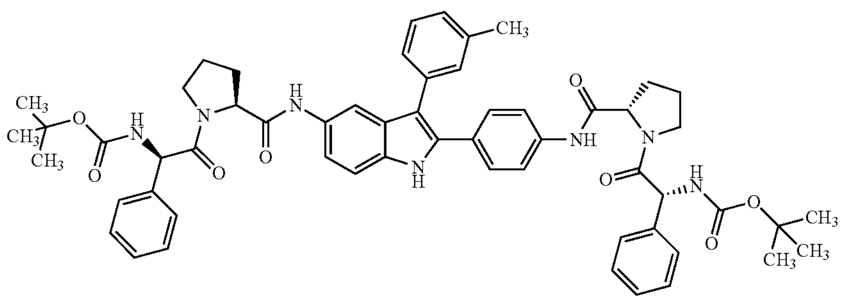 [SMILES: Cc1cccc(-c2c(-c3ccc(NC(=O)[C@@H]4CCCN4C(=O)[C@H](NC(=O)OC(C)(C)C)c4ccccc4)cc3)[nH]c3ccc(NC(=O)[C@@H]4CCCN4C(=O)[C@H](NC(=O)OC(C)(C)C)c4ccccc4)cc23)c1] | 974.18 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-3-(3-methylphenyl)-1H-indol-2-yl]phenyl}carbamoyl)pyrrolidin-1-yl]-2-oxo-1-phenylethyl}carbamate |
| 170 | 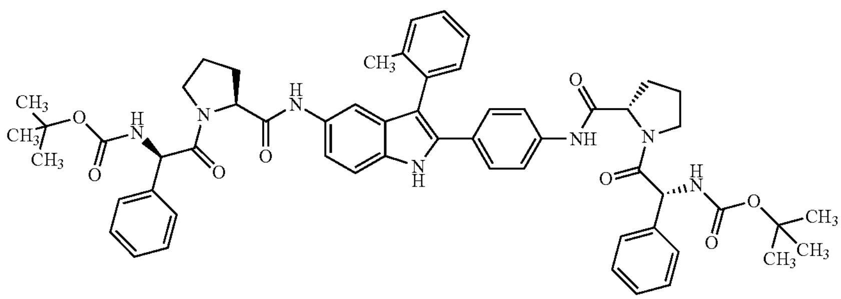 [SMILES: Cc1ccccc1-c1c(-c2ccc(NC(=O)[C@@H]3CCCN3C(=O)[C@H](NC(=O)OC(C)(C)C)c3ccccc3)cc2)[nH]c2ccc(NC(=O)[C@@H]3CCCN3C(=O)[C@H](NC(=O)OC(C)(C)C)c3ccccc3)cc12] | 974.18 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-3-(2-methylphenyl)-1H-indol-2-yl]phenyl}carbamoyl)pyrrolidin-1-yl]-2-oxo-1-phenylethyl}carbamate |
| 171 | 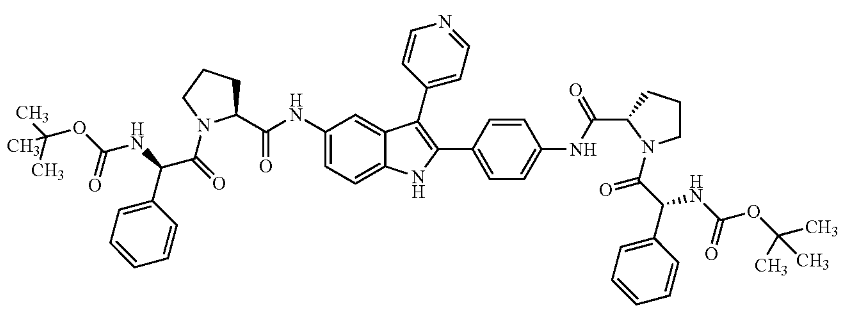 [SMILES: CC(C)(C)OC(=O)N[C@@H](C(=O)N1CCC[C@H]1C(=O)Nc1ccc(-c2[nH]c3ccc(NC(=O)[C@@H]4CCCN4C(=O)[C@H](NC(=O)OC(C)(C)C)c4ccccc4)cc3c2-c2ccncc2)cc1)c1ccccc1] | 961.14 | tert-butyl {(1R)-2-[(2S)-2-({2-[4-({[(2S)-1-{(2R)-2-[(tert-butoxycarbonyl)amino]-2-phenylacetyl}pyrrolidin-2-yl]carbonyl}amino)phenyl]-3-(pyridin-4-yl)-1H-indol-5-yl}carbamoyl)pyrrolidin-1-yl]-2-oxo-1-phenylethyl}carbamate |

| Example | Structure | MW | Name |
|---|---|---|---|
| 172 | 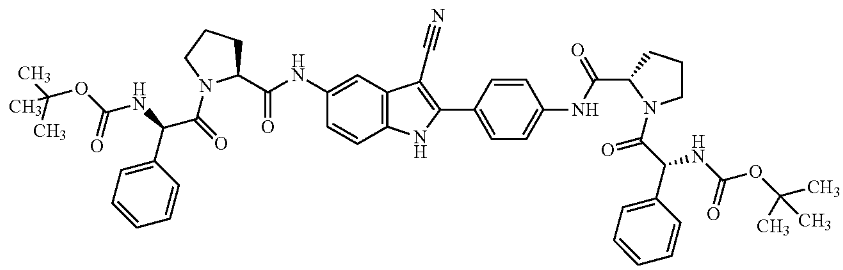 [SMILES: CC(C)(C)OC(=O)N[C@@H](C(=O)N1CCC[C@H]1C(=O)Nc1ccc(-c2[nH]c3ccc(NC(=O)[C@@H]4CCCN4C(=O)[C@H](NC(=O)OC(C)(C)C)c4ccccc4)cc3c2C#N)cc1)c1ccccc1] | 909.064 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-3-cyano-1H-indol-2-yl]phenyl}carbamoyl)pyrrolidin-1-yl]-2-oxo-1-phenylethyl}carbamate |
| 173 | 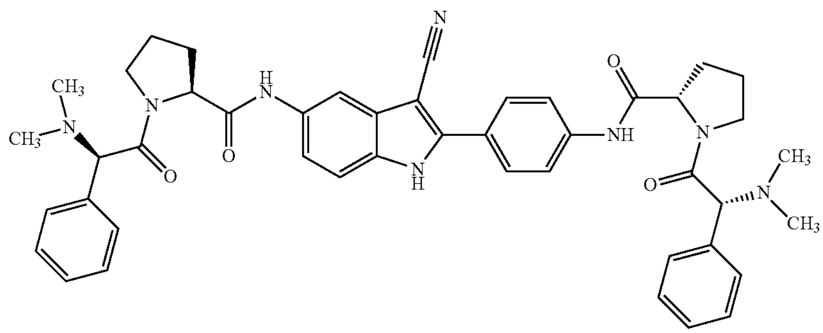 [SMILES: CN(C)[C@@H](C(=O)N1CCC[C@H]1C(=O)Nc1ccc(-c2[nH]c3ccc(NC(=O)[C@@H]4CCCN4C(=O)[C@@H](c4ccccc4)N(C)C)cc3c2C#N)cc1)c1ccccc1] | 764.936 | (2S)-N-(4-{3-cyano-5-[({(2S)-1-[(2R)-2-(dimethylamino)-2-phenylacetyl]pyrrolidin-2-yl}carbonyl)amino]-1H-indol-2-yl}phenyl)-1-[(2R)-2-(dimethylamino)-2-phenylacetyl]pyrrolidine-2-carboxamide |
| 174 | 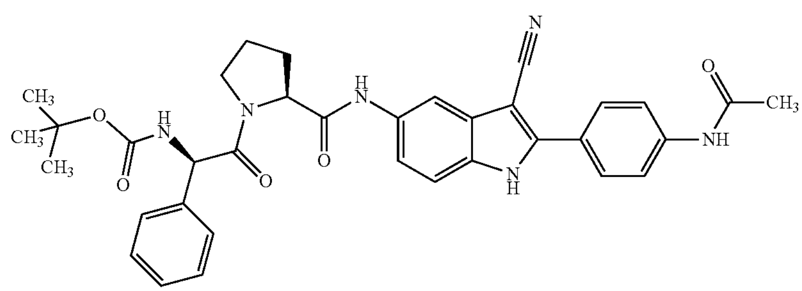 [SMILES: CC(=O)Nc1ccc(-c2[nH]c3ccc(NC(=O)[C@@H]4CCCN4C(=O)[C@H](NC(=O)OC(C)(C)C)c4ccccc4)cc3c2C#N)cc1] | 620.714 | tert-butyl {(1R)-2-[(2S)-2-({2-[4-(acetylamino)phenyl]-3-cyano-1H-indol-5-yl}carbamoyl)pyrrolidin-1-yl]-2-oxo-1-phenylethyl}carbamate |
| 175 | 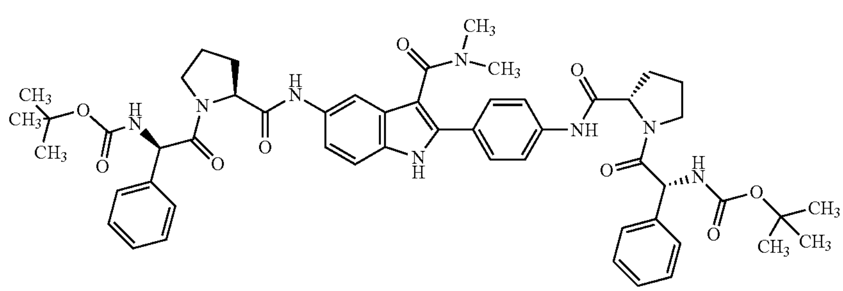 [SMILES: CN(C)C(=O)c1c(-c2ccc(NC(=O)[C@@H]3CCCN3C(=O)[C@H](NC(=O)OC(C)(C)C)c3ccccc3)cc2)[nH]c2ccc(NC(=O)[C@@H]3CCCN3C(=O)[C@H](NC(=O)OC(C)(C)C)c3ccccc3)cc12] | 955.133 | tert-butyl {(1R)-2-[(2S)-2-({4-[5-({[(2S)-1-{(2R)-2-[(tert-butoxycarbonyl)amino]-2-phenylacetyl}pyrrolidin-2-yl]carbonyl}amino)-3-(dimethylcarbamoyl)-1H-indol-2-yl]phenyl}carbamoyl)pyrrolidin-1-yl]-2-oxo-1-phenylethyl}carbamate |
| 176 | 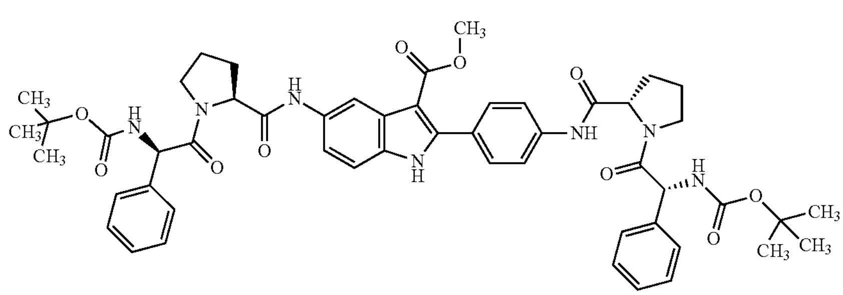 [SMILES: COC(=O)c1c(-c2ccc(NC(=O)[C@@H]3CCCN3C(=O)[C@H](NC(=O)OC(C)(C)C)c3ccccc3)cc2)[nH]c2ccc(NC(=O)[C@@H]3CCCN3C(=O)[C@H](NC(=O)OC(C)(C)C)c3ccccc3)cc12] | 942.091 | methyl 5-({[(2S)-1-{(2R)-2-[(tert-butoxycarbonyl)amino]-2-phenylacetyl}pyrrolidin-2-yl]carbonyl}amino)-2-[4-({[(2S)-1-{(2R)-2-[(tert-butoxycarbonyl)amino]-2-phenylacetyl}pyrrolidin-2-yl]carbonyl}amino)phenyl]-1H-indole-3-carboxylate |

| Example | Structure | MW | Name |
|---|---|---|---|
| 177 | 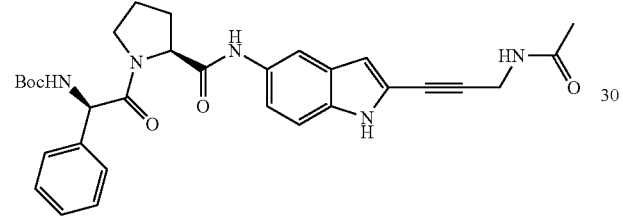 | 928.064 | 5-({[(2S)-1-{(2R)-2-[(tert-butoxycarbonyl)amino]-2-phenylacetyl}pyrrolidin-2-yl]carbonyl}amino)-2-[4-({[(2S)-1-{(2R)-2-[(tert-butoxycarbonyl)amino]-2-phenylacetyl}pyrrolidin-2-yl]carbonyl}amino)phenyl]-1H-indole-3-carboxylic acid |

Example 178 tert-butyl {(1R)-2-[(2S)-2-({2-[3-(acetylamino)prop-1-yn-1-yl]-1H-indol-5-yl}carbamoyl)pyrrolidin-1-yl]-2-oxo-1-phenylethyl}carbamate

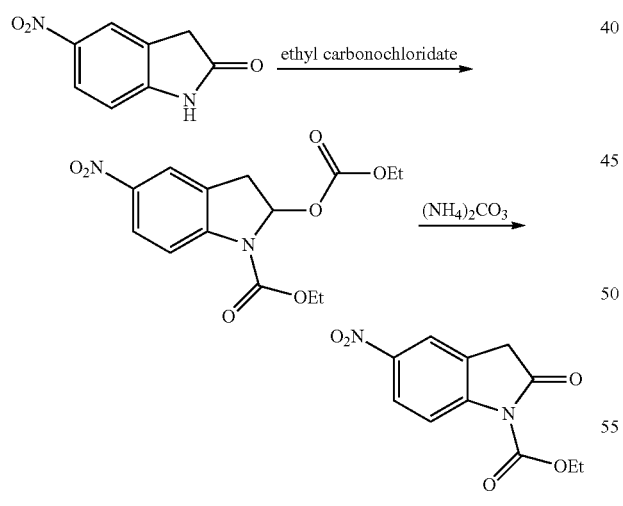

Step 1

Ethyl carbonochloridate (3 mL) was added to the nitro lactam (2.0 g, 11.2 mmol), and the mixture was stirred for 3 hours before being concentrated to give the crude product. MS (ESI) m/e (M+H+): 325. The crude product was dissolved in DMF (25 mL), then (NH$_4$)$_2$CO$_3$ (1.5 g) was added, and the mixture was stirred overnight. The mixture was evaporated and the residue was poured into ice-water and extracted with DCM, and the organics were dried. The solvent was removed, and the residue was purified by chromatography on silica gel to give the desired compound as a white solid. MS (ESI) m/e (M+H$^+$): 251.

Step 2

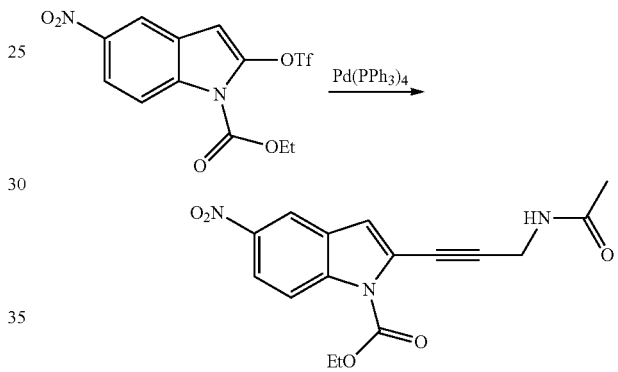

The mixture of the triflate (382 mg, 1.0 mmol), N-(prop-2-ynyl)acetamide (97 mg, 1.0 mmol), Et$_3$N (3 mL) in CH$_3$CN (3 mL) was stirred at RT for 3 hours. The mixture was concentrated, and the residue was purified by chromatography on silica gel to give compound target compound (254 mg). MS (ESI) m/e (M+H$^+$): 330.

Step 3

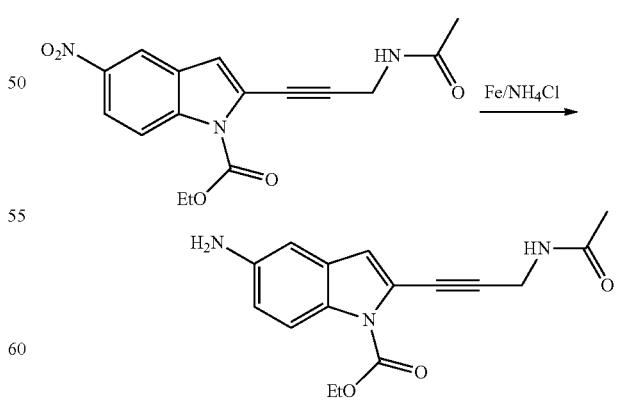

A solution of the nitro compound from step 2 above (165 mg, 0.50 mmol) in absolute EtOH (3 mL) was added Fe power (280 mg, 2.5 mmol) and NH$_4$Cl (535 mg, 5.0 mmol). The mixture was stirred at 70° C. for 2 hours, cooled and poured into ice/water (50 ml). The mixture was extracted with EtOAc (200 ml), and the organic phase was combined and washed with brine, dried and concentrated to yield the crude product (150 mg). MS (ESI) m/z: (M+H) 300.
Step 4

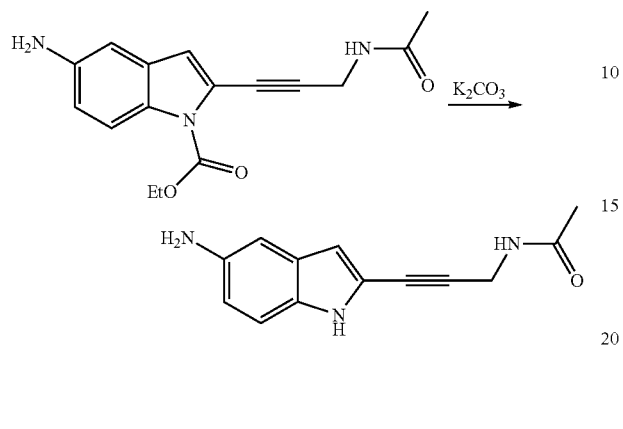

To a solution of the aniline from step 3 (150 mg, 0.50 mmo) in absolute EtOH (3 mL) was added K₂CO₃ (138 mg, 1.0 mmol), and the mixture was stirred at RT for 12 hours. The reaction mixture was poured into water (10 mL), extracted with EtOAc (20 mL), and the organic phases were combined and washed with brine, dried over MgSO₄ and concentrated to yield the crude product (113 mg). MS (ESI) m/z: (M+H+) 228.
Step 5

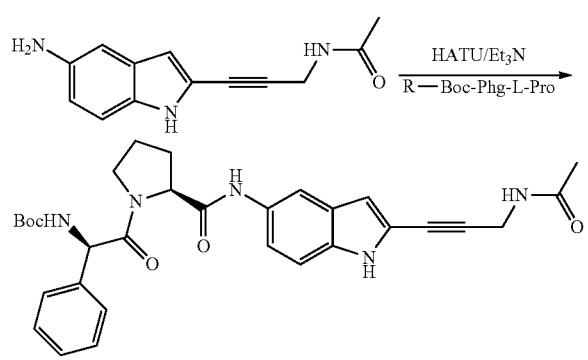

The mixture of the indole (113 mg, 0.5 mmol), R-Boc-Phg-L-Pro-OH (175 mg, 0.5 mmol), DIPEA (115 mg, 1.0 mmol) in MeCN (2 mL) was stirred at RT for 5 minutes, then HATU (190 mg, 0.5 mmol) was added into the mixture. The mixture was stirred at RT overnight then concentrated. The residue was purified by RPLC to give the desired compound (110 mg). ¹H NMR (MeOD) δ: 1.37 (s, 9H), 1.96~2.14 (m, 7H), 3.92~3.94 (m, 2H), 4.51~4.54 (m, 1H), 5.41 (s, 1H), 6.56 (s, 1H), 7.20~7.43 (m, 7H), 7.72 (s, 1H). MS (ESI) m/z: (M+H+) 576.

Example 179

N-{4-[5-(furan-3-yl)-1H-indol-2-yl]phenyl}-1-(phenylacetyl)-L-prolinamide

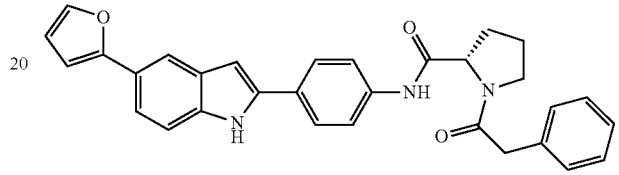

Step 1

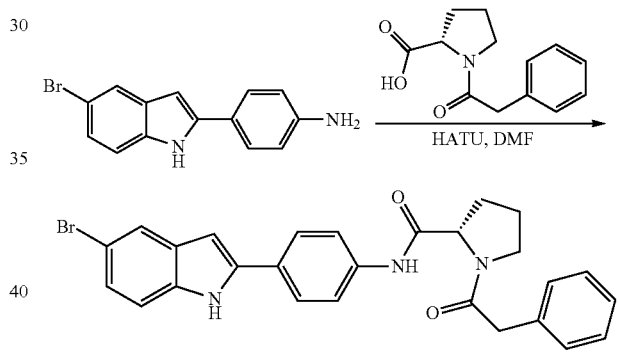

The mixture of the indole from Example 41 (1.6 mg, 5.575 mmol), 1-phenylacetyl pyrrolidine-2-carboxylic acid (1.3 g, 5.575 mmol), DIPEA (1.45 g, 11.15 mmol) in DMF (50 mL) was stirred at RT for 30 minutes, then HATU (2.54 g, 6.689 mmol) was added. The mixture was stirred at RT overnight, concentrated in vacuo, and the residue was purified by chromatography on silica gel to give the desired product (2.3 g). MS (ESI) m/e (M+H⁺): 504.
Step 2

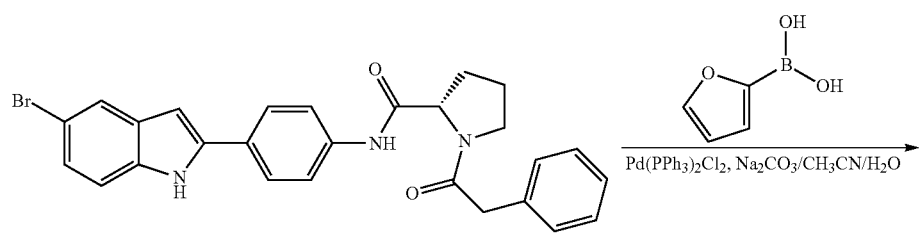

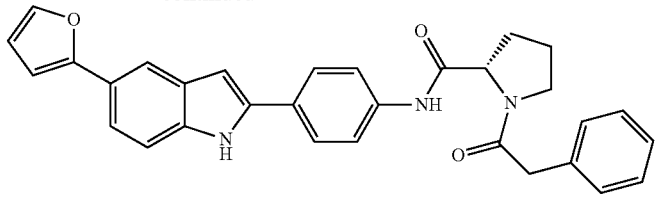 [SMILES: O=C(Nc1ccc(-c2cc3cc(-c4ccco4)ccc3[nH]2)cc1)[C@@H]1CCCN1C(=O)Cc1ccccc1]

A suspension of the product from step 1 above (18 mg, 0.03583 mmol), furan-2-boronic acid (6 mg, 0.05374 mmol), Pd(PPh$_3$)$_2$Cl$_2$ (1.4 mg), Na$_2$CO$_3$ (7.6 mg, 0.07166 mmol) and H$_2$O (0.15 mL) in 0.5 mL of acetonitrile under N$_2$ protection was heated at 150° C. for 10 minutes in a microwave reactor. The mixture was cooled, filtered and washed with 10 mL of DCM. The solvents were removed, and the residue was purified by HPLC to give the desired product. $^1$H NMR (MeOD) δ: 7.79~7.74 (m, 3H), 7.67~7.62 (m, 3H), 7.50 (s, 1H), 7.37~7.22 (m, 6H), 6.78~6.75 (m, 2H), 4.57~4.55 (m, 1H), 3.78~3.61 (m, 4H), 2.24~1.99 (m, 4H).

Examples 180-189b

Compounds of Examples 180-189b were prepared in a similar manner as described in Example 179.

| Example | Structure | MW | Name |
|---|---|---|---|
| 180 | 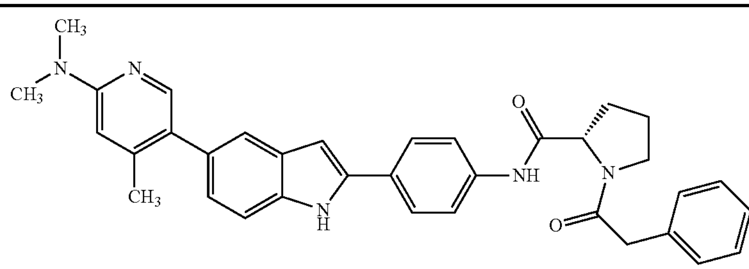 | 557.701 | N-(4-{5-[6-(dimethylamino)-4-methylpyridin-3-yl]-1H-indol-2-yl}phenyl)-1-(phenylacetyl)-L-prolinamide |
| 181 | 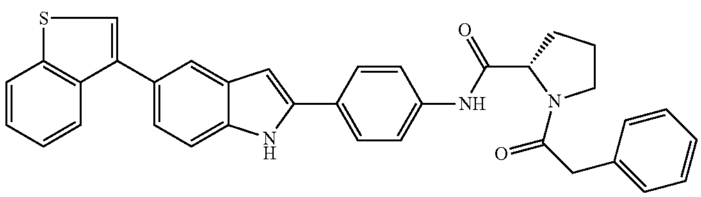 [SMILES: O=C(Nc1ccc(-c2cc3cc(-c4csc5ccccc45)ccc3[nH]2)cc1)[C@@H]1CCCN1C(=O)Cc1ccccc1] | 555.704 | N-{4-[5-(1-benzothiophen-3-yl)-1H-indol-2-yl]phenyl}-1-(phenylacetyl)-L-prolinamide |
| 182 | 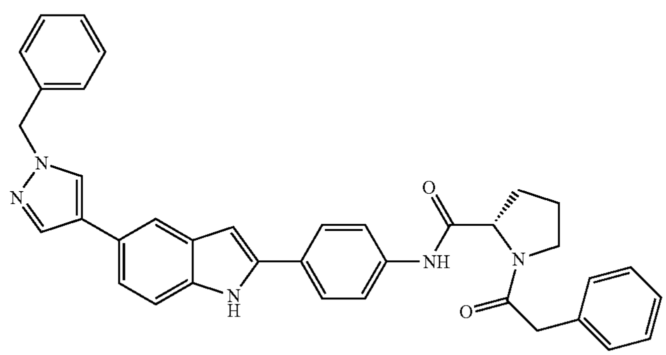 [SMILES: O=C(Nc1ccc(-c2cc3cc(-c4cnn(Cc5ccccc5)c4)ccc3[nH]2)cc1)[C@@H]1CCCN1C(=O)Cc1ccccc1] | 579.708 | N-{4-[5-(1-benzyl-1H-pyrazol-4-yl)-1H-indol-2-yl]phenyl}-1-(phenylacetyl)-L-prolinamide |
| 183 | 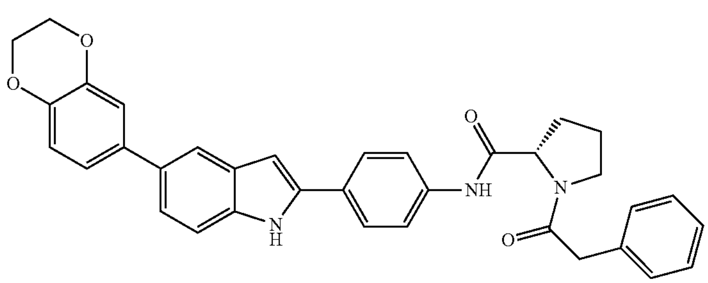 [SMILES: O=C(Nc1ccc(-c2cc3cc(-c4ccc5c(c4)OCCO5)ccc3[nH]2)cc1)[C@@H]1CCCN1C(=O)Cc1ccccc1] | 557.655 | N-{4-[5-(2,3-dihydro-1,4-benzodioxin-6-yl)-1H-indol-2-yl]phenyl}-1-(phenylacetyl)-L-prolinamide |

-continued

| Example | Structure | MW | Name |
|---|---|---|---|
| 184 | 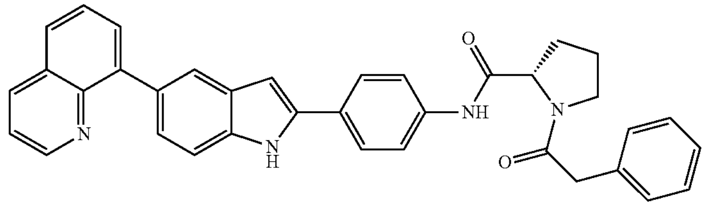 [SMILES: O=C(Nc1ccc(-c2cc3cc(-c4cccc5cccnc45)ccc3[nH]2)cc1)[C@@H]1CCCN1C(=O)Cc1ccccc1] | 550.666 | 1-(phenylacetyl)-N-{4-[5-(quinolin-8-yl)-1H-indol-2-yl]phenyl}-L-prolinamide |
| 185 | 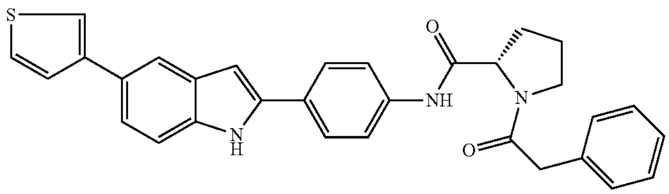 [SMILES: O=C(Nc1ccc(-c2cc3cc(-c4ccsc4)ccc3[nH]2)cc1)[C@@H]1CCCN1C(=O)Cc1ccccc1] | 505.644 | 1-(phenylacetyl)-N-{4-[5-(thiophen-3-yl)-1H-indol-2-yl]phenyl}-L-prolinamide |
| 186 | 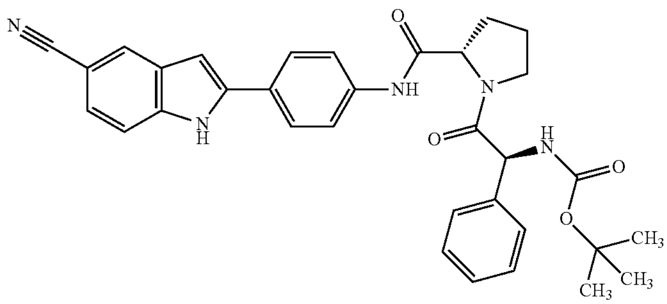 [SMILES: CC(C)(C)OC(=O)N[C@H](C(=O)N1CCC[C@H]1C(=O)Nc1ccc(-c2cc3cc(C#N)ccc3[nH]2)cc1)c1ccccc1] | 563.662 | tert-butyl {(1S)-2-[(2S)-2-{[4-(5-cyano-1H-indol-2-yl)phenyl]carbamoyl}pyrrolidin-1-yl]-2-oxo-1-phenylethyl}carbamate |
| 187 | 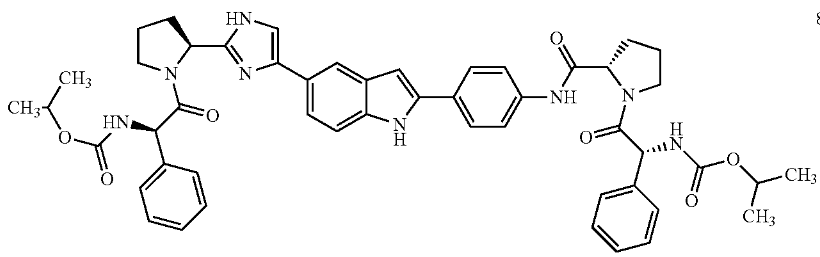 [SMILES: CC(C)OC(=O)N[C@@H](C(=O)N1CCC[C@H]1C(=O)Nc1ccc(-c2cc3cc(-c4c[nH]c([C@@H]5CCCN5C(=O)[C@H](NC(=O)OC(C)C)c5ccccc5)n4)ccc3[nH]2)cc1)c1ccccc1] | 879.037 | propan-2-yl [(1R)-2-oxo-1-phenyl-2-{(2S)-2-[4-(2-{4-[({(2S)-1-[(2R)-2-phenyl-2-{[(propan-2-yloxy)carbonyl]amino}acetyl]pyrrolidin-2-yl}carbonyl)amino]phenyl}-1H-indol-5-yl)-1H-imidazol-2-yl]pyrrolidin-1-yl}ethyl]carbamate |
| 188 | 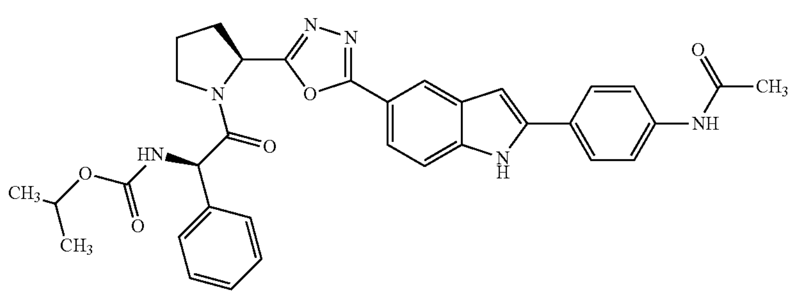 [SMILES: CC(=O)Nc1ccc(-c2cc3cc(-c4nnc([C@@H]5CCCN5C(=O)[C@H](NC(=O)OC(C)C)c5ccccc5)o4)ccc3[nH]2)cc1] | 606.687 | propan-2-yl {(1R)-2-[(2S)-2-(5-{2-[4-(acetylamino)phenyl]-1H-indol-5-yl}-1,3,4-oxadiazol-2-yl)pyrrolidin-1-yl]-2-oxo-1-phenylethyl}carbamate |
| 189 | 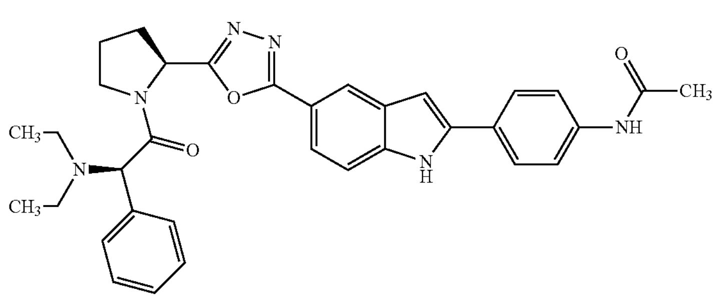 [SMILES: CCN(CC)[C@@H](C(=O)N1CCC[C@H]1c1nnc(-c2ccc3[nH]c(-c4ccc(NC(C)=O)cc4)cc3c2)o1)c1ccccc1] | 576.704 | N-{4-[5-(5-{(2S)-1-[(2R)-2-(diethylamino)-2-phenylacetyl]pyrrolidin-2-yl}-1,3,4-oxadiazol-2-yl)-1H-indol-2-yl]phenyl}acetamide |

-continued

| Example | Structure | MW | Name |
|---|---|---|---|
| 189a | 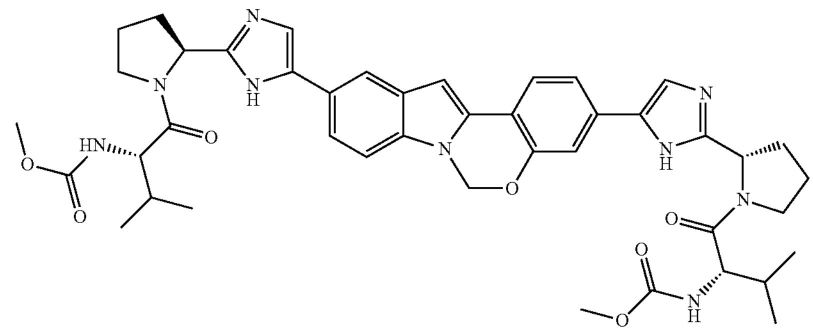 | 806.9 | methyl[(2S)-1-{(2S)-2-[5-(10-{2-[(2S)-1-{(2S)-2-[(methoxycarbonyl)amino]-3-methylbutanoyl}pyrrolidin-2-yl]-1H-imidazol-5-yl}indolo[1,2-c][1,3]benzoxazin-3-yl)-1H-imidazol-2-yl]pyrrolidin-1-yl}-3-methyl-1-oxobutan-2-yl]carbamate |
| 189b | 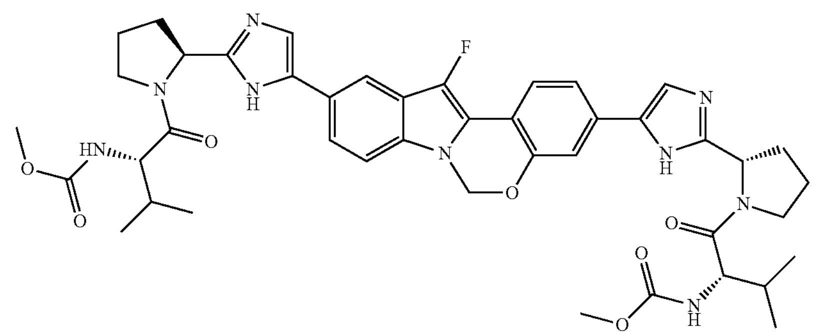 [SMILES: COC(=O)N[C@H](C(=O)N1CCC[C@H]1c1ncc(-c2ccc3c(c2)OCn2c-3c(F)c3cc(-c4cnc([C@@H]5CCCN5C(=O)[C@@H](NC(=O)OC)C(C)C)[nH]4)ccc32)[nH]1)C(C)C] | 824.9 | methyl [(2S)-1-{(2S)-2-[5-(12-fluoro-10-{2-[(2S)-1-{(2S)-2-[(methoxycarbonyl)amino]-3-methylbutanoyl}pyrrolidin-2-yl]-1H-imidazol-5-yl}indolo[1,2-c][1,3]benzoxazin-3-yl)-1H-imidazol-2-yl]pyrrolidin-1-yl}-3-methyl-1-oxobutan-2-yl]carbamate |

Example 189b (Alternative Procedure: Methyl[(2S)-1{(2S)-2-[5-(12-fluoro-10-{2-[(2S)-1-{(2s)-2-[(methoxycarbonyl)amino]-3-methylbutanoyl}pyrrolidin-2-yl]-1H-imidazol-5-yl}indolo[1,2-c][1,3]benzoxazin-3-yl)-1H-imidazol-2-yl]pyrrolidin-1-yl}-3-methyl-1-oxobutan-2-yl]carbamate

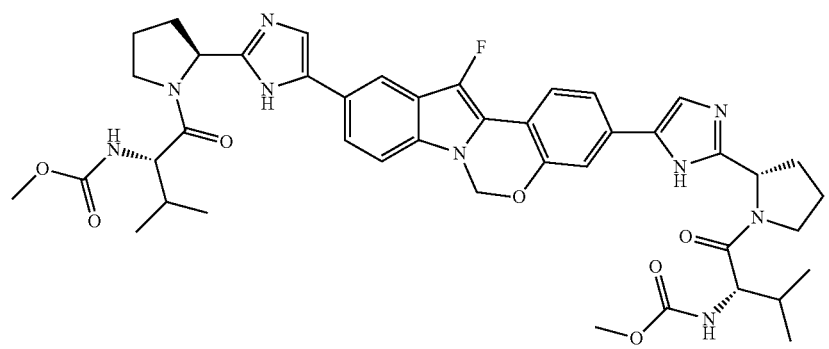 [SMILES: COC(=O)N[C@H](C(=O)N1CCC[C@H]1c1ncc(-c2ccc3c(c2)OCn2c-3c(F)c3cc(-c4cnc([C@@H]5CCCN5C(=O)[C@@H](NC(=O)OC)C(C)C)[nH]4)ccc32)[nH]1)C(C)C]

Step 1

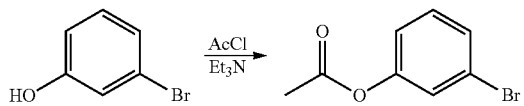

To a solution of compound 3-bromophenol (51 g, 0.3 mol) and Et₃N (36 g, 0.36 mol) in 500 mL of DCM was added dropwise acetyl chloride (26 g, 0.33 mol) in an ice-water bath. The mixture was stirred at RT for 30 minutes. The mixture was washed with 1 N HCl, saturated Na₂CO₃ and brine, dried over Na₂SO₄ and concentrated in vacuo to give a oil (62 g).

Step 2

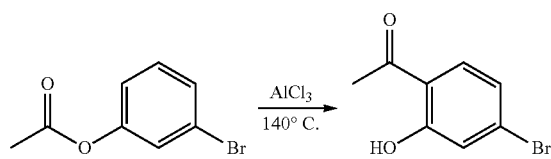

AlCl₃ (40 g, 0.3 mol) was slowly added to the product from step 1 (21.5 g, 0.1 mol) in an ice-water bath. The mixture was stirred at 140° C. for 2 hours. After cooling to 60-70° C., the mixture was slowly poured into an ice water. The resulting solution was extracted with DCM. The combined organic phases were washed with brine, dried over Na₂SO₄ and concentrated in vacuo. The residue was purified by column chromatography to give the desired compound (14 g). MS (ESI) m/e (M+H⁺): 214.

Step 3

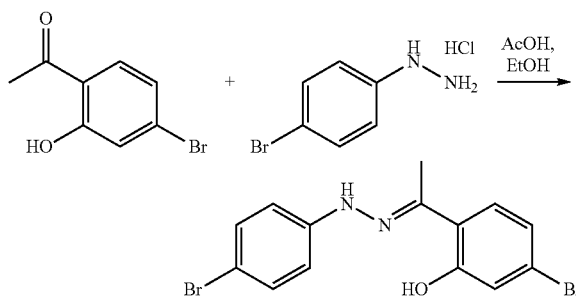

A mixture of the ketone obtained in step 2 (4.2 g, 20 mmol) and 4-bromophenyl hydrazine hydrochloride (4.4 g, 20 mmol) in AcOH and EtOH (1:10, 100 mL) was heated to reflux for 6 hours. The solvent was removed in vacuo to give a solid, which was used in the next step without further purification (9.2 g crude). MS (ESI) m/e (M+H⁺): 383.

Step 4

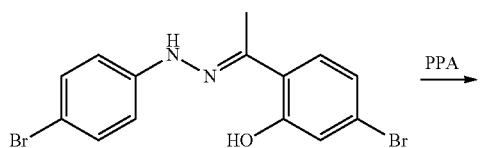

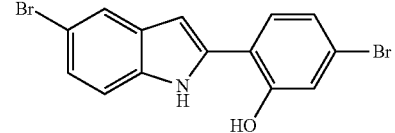

A mixture of product from step 3 (9.2 g) in PPA was heated to 80° C. for 2 hours. After cooling to RT, the mixture was poured into ice water. The resulting solution was extracted with DCM. The combined organic phases were washed with brine, dried over Na₂SO₄, and concentrated in vacuo. The residue was purified by column chromatography to give the desired indole (4.8 g). MS (ESI) m/e (M+H⁺): 368.

Step 5

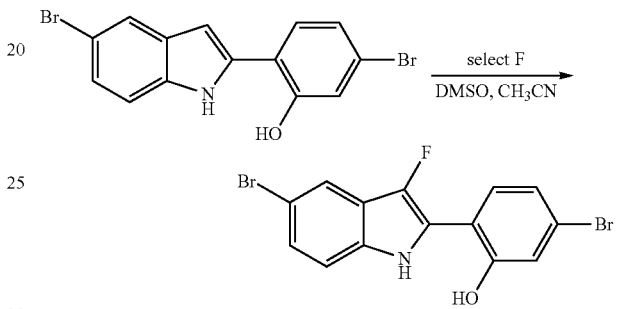

To a mixture of the indole from step 4 (6 g, 16.3 mmol) in DMSO/CH₃CN (1:1, 24 mL) was added SELECTFLUOR® (5.8 g, 16.3 mmol) in portion at RT. The mixture was stirred for an additional 1 hour at RT, and the mixture was purified by HPLC to give a solid (1.0 g). MS (ESI) m/e (M+H⁺): 386.

Step 6

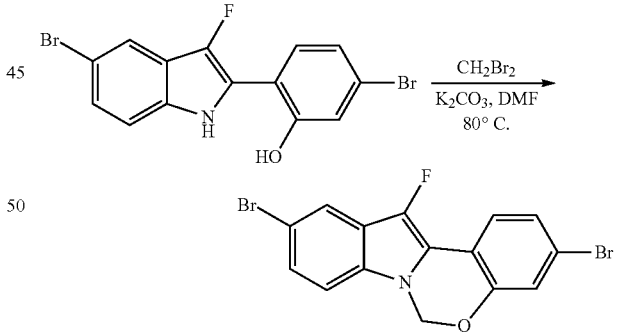

A mixture of the compound from step 5 (650 mg, 1.63 mmol), CH₂Br₂ (1.5 g, 8.62 mmol) and K₂CO₃ (1.2 g, 8.7 mmol) in DMF (32.5 mL) was stirred for 5 hours at 80° C. Then the mixture was evaporated in vacuo. The residue was diluted with EA and water. The organic layer was separated, dried over Na₂SO₄ and concentrated in vacuo to give a solid, which was directly used to next step without further purification (610 mg). MS (ESI) m/e (M+H⁺): 396.

Step 7

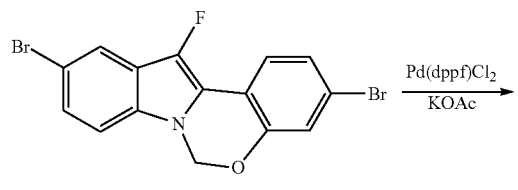

Step 8

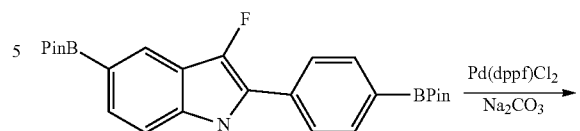

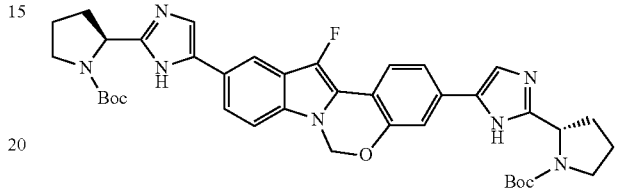

To a solution of the product from step 6 (1 mmol) in 1,4-dioxane was added bis pinacol borate (1.1 mmol) and Pd(dppf)Cl₂ (0.02 mmol) and KOAc (2 mmol). The reaction mixture was stirred under N₂ and heated to 110° C. for 3 hours. After that, the solvent was removed under vacuum, and the residue was purified by column chromatography to afford the product. MS (ESI) m/e (M+H⁺): 492.

A suspension of the boronate from above (2 mmol), tert-butyl 2-(2-bromo-1H-imidazol-5-yl)pyrrolidine-1-carboxylate (2.4 mmol), Pd(dppf) Cl₂ (200 mg), Na₂CO₃ (3 mmol) and in THF/H₂O (10:1, 33 mL) was refluxed at 75° C. overnight under N₂ protection. The mixture was cooled and filtered, and the filtrate was washed with water (50 mL) and extracted with EtOAc (100 mL), washed with brine and dried over anhydrous sodium sulfate. After concentrated in vacuo, the residue was purified by column chromatography to afford the desired compound. MS (ESI) m/e (M+H⁺): 710.

Step 9

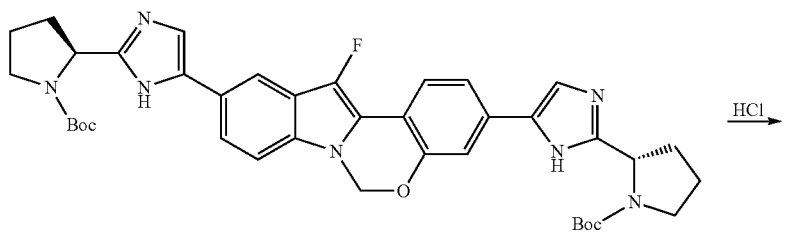

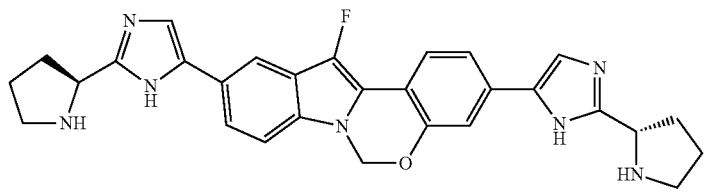

The protected proline from above (1.3 mmol) was added to HCl/CH₃OH (10 mL, 3M). The mixture was stirred at RT for 2-3 hours before the mixture was concentrated to give the crude product, which was used in the next step without further purification. MS (ESI) m/e (M+H⁺): 510

Step 10

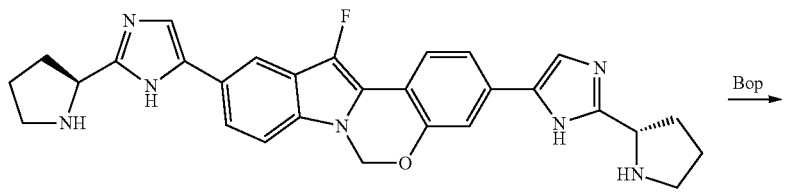

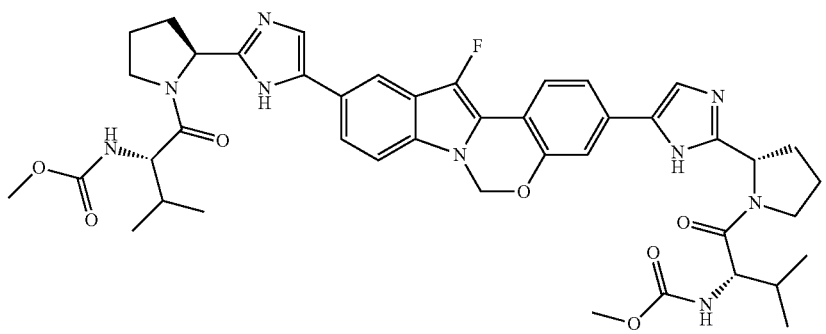

To a mixture of the crude product from step 9 (1.0 mmol), (S)-2-(methoxycarbonylamino)-3-methylbutanoic acid (2.0 mmol) and DIPEA (8 mmol) in CH$_3$CN (10 mL) was added BOP (2.2 mmol). The resulting mixture was stirred at RT. After LCMS showed the starting material to be consumed, the mixture was filtered, and the filtrate was purified by HPLC to give the desired compound as a white solid. MS (ESI) m/e (M+H$^+$): 825. $^1$H NMR (MeOD): δ 7.83-7.85 (m, 3H), 7.72 (s, 1H), 7.53 (s, 2H), 7.46-7.48 (m, 1H), 7.42 (s, 1H), 5.92 (s, 2H), 5.20-5.22 (m, 2H), 4.20-4.23 (m, 2H), 4.06-4.09 (m, 2H), 3.86-3.88 (m, 2H), 3.61 (s, 6H), 2.50-2.52 (m, 2H), 1.96-2.20 (m, 8H), 0.90-0.98 (m, 12H).

Example 190

(2S)-1-[(2R)-2-(dimethylamino)-2-phenylacetyl]-N-(2-{5-[({(2S)-1-[(2R)-2-(dimethylamino)-2-phenylacetyl]pyrrolidin-2-yl}carbonyl)amino]-1,3-benzoxazol-2-yl}-1H-indol-5-yl)pyrrolidine-2-carboxamide Step 1

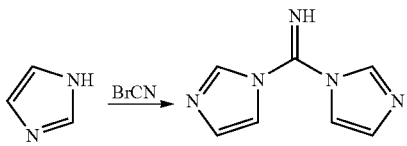

To a solution of imidazole (13.6 g, 0.2 mol) in 1 L of DCM was added BrCN (7.4 g, 66 mmol), and the mixture was heated at reflux for 30 minutes. The mixture was cooled to RT, and the white precipitate removed by filtration, and the filtrate concentrated to 100 mL then cooled to 0° C. for 2 days. The crystallized solid was filtered and washed with cold DCM, then dried in vacuo to give the desired product (8.8 g) as a white solid.

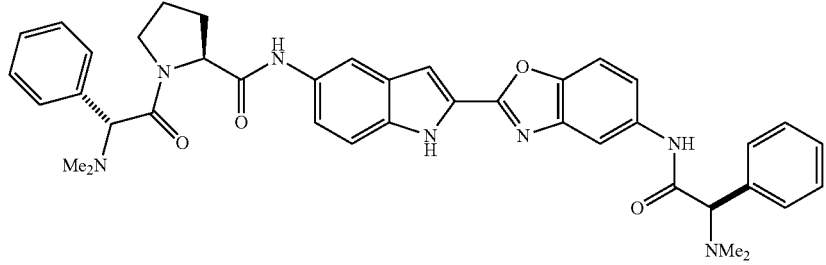 [SMILES: CN(C)[C@@H](C(=O)Nc1ccc2oc(-c3cc4cc(NC(=O)[C@@H]5CCCN5C(=O)[C@@H](c5ccccc5)N(C)C)ccc4[nH]3)nc2c1)c1ccccc1]

Step 2

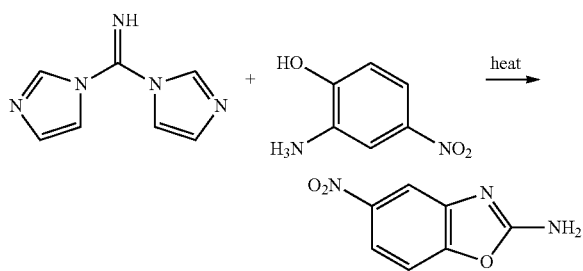

A solution containing the product from step 1 (8.36 g, 54.2 mmol) and 2-amino-4-nitrophenol (8.74 g, 54.2 mmol) in anhydrous THF (200 mL) was allowed to reflux under $N_2$ for 14 hours. The mixture was cooled to RT, filtered, and the precipitate was washed with THF (cold) then dried in vacuo to afford the desired product (9.0 g), as a yellow solid. MS (ESI) m/e (M+H$^+$): 180. $^1$H NMR (DMSO) δ: 7.85~7.96(m, 3H), 7.52(d, J=8.8 Hz, 1H).

Step 3

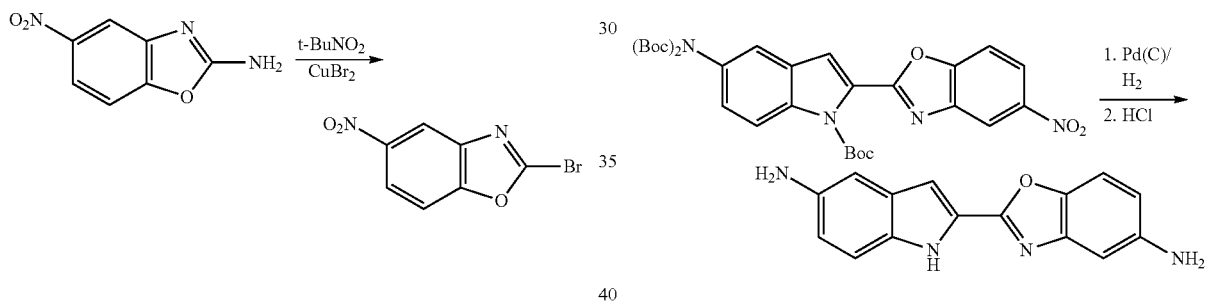

To a suspension of the product from step 2 (3.58 g, 20 mmol) in acetonitrile (300 mL) was added CuBr$_2$ (8.96 g, 40 mmol). The solution became dark green and t-butyl nitrite (4.12 g, 40 mmol) was added RT over 5 minutes, whereupon the mixture heated at 45° C. for 2 hours. The reaction mixture was poured into water (800 mL) and DCM (800 mL), and the phases were separated. The aqueous phase was extracted with DCM (3×800 mL), dried with Na$_2$SO$_4$ and evaporated to afford the crude product. Purification by column chromatography afforded the desired product. MS (ESI) m/e (M+H$^+$): 243/245. $^1$H NMR (DMSO) δ: 8.71 (s, 1H), 8.42(d, J=9.2 Hz, 1H), 8.10 (d, J=9.2 Hz, 1H).

Step 4

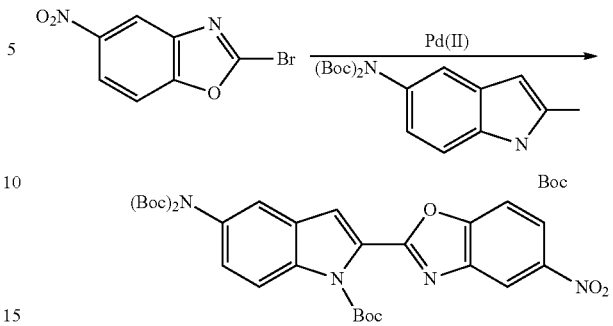

The mixture of compound from step 3 above (603 mg, 2.5 mmol), the indole boronic acid from Example 42 (1.0 g, 2.75 mmol), Pd(dppf)Cl$_2$ (183 mg, 0.25 mmol), Na$_2$CO$_3$ (530 mg, 5.0 mmol) in 5 mL dioxane-H$_2$O (5:1) was heated to reflux under N$_2$ atmosphere overnight. When reaction was complete, the mixture was poured into water and extracted with DCM. The organic phase was dried over Na$_2$SO$_4$ and concentrated, and the residue was purified to give compound the desired product. MS (ESI) m/e (M+H$^+$): 596.

Step 5

The product from step 4 (596 mg, 1.0 mmol) was dissolved in EtOAc and treated with Pd/C (100 mg, 20%). Then, the mixture was stirred at RT overnight under H$_2$ atmosphere. When the reaction was complete, the Pd/C was filtered off, and the resulting solution was concentrated to give the crude product MS (ESI) m/e (M+H$^+$): 565. This material was covered with 5 mL of 3M HCl, and the mixture was stirred at RT for 2 hours. Evaporation of the solvent afforded the desired product, which was used directly without further purification. MS (ESI) m/e (M+H$^+$): 265.

Step 6

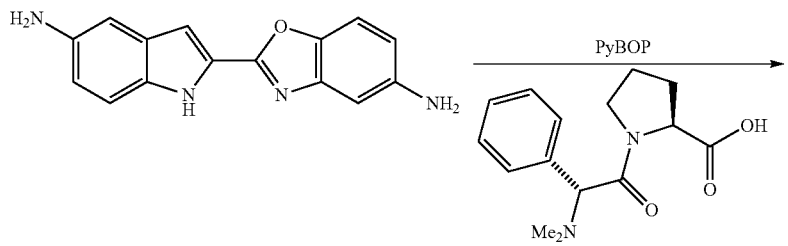

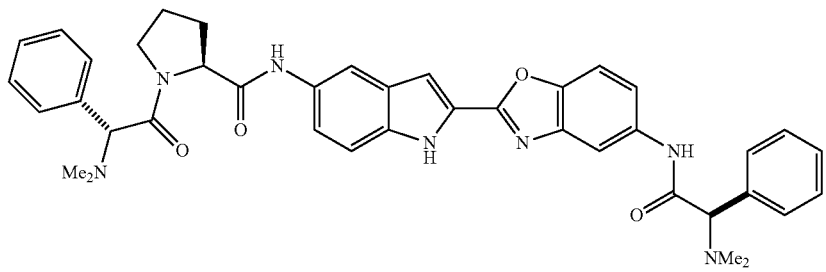
The compound was coupled using the procedure similar to that which was described in Example 40 starting from 265 mg (1.0 mmol) of the product from step 5. $^1$H NMR (MeOD) δ: 8.12(s, 1H), 7.97(d, J=2 Hz, 1H), 7.30~7.70 (m, 15H), 5.30~5.35 (m, 2H), 4.51~4.60 (m, 2H), 3.85~3.95(m, 2H), 3.15~3.25(m, 2H), 3.06(s, 3H), 2.54(s, 6H), 1.80~2.30(m, 8H). MS (ESI) m/e (M+H$^+$): 781.
Example 191
1-[(2R)-2-(diethylamino)-2-phenylacetyl]-N-{2-[4-(5-{(2S)-1-[(2R)-2-(diethylamino)-2-phenylacetyl] pyrrolidin-2-yl}-1,3,4-oxadiazol-2-yl)phenyl]-1H-indol-5-yl}-L-prolinamide
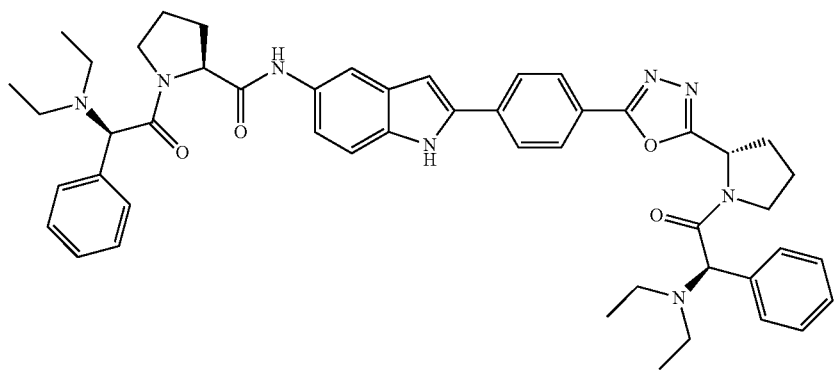
Step 1
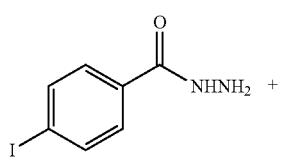
-continued
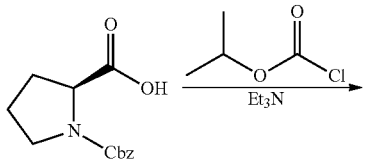

-continued

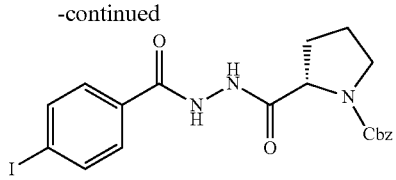

To a solution of N-Cbz-L-Pro (14.9 g, 0.06 mol) and TEA (8.08 g, 0.08 mol) in 100 mL of DCM added dropwise isopropyl chloroformate (8.05 g, 0.066 mol) at 0° C. After addition, the solution was continued to stir for 1 hour before the hydrazide (13.0 g, 0.05 mol) was added, and the mixture was continued to stir for another 1 hour. The solvent was evaporated in vacuo, and the residue was recrystallized from EtOH to give a white solid (22.1 g). $^1$H NMR (DMSO) δ: 10.47 (s, 1H), 10.03 (s, 1H), 7.86 (d, J=8.0 Hz, 2H), 7.62 (d, J=8.0 Hz, 2H), 7.31~7.61 (m, 5H), 4.91~5.14 (m, 2 H), 4.26~4.35 (m, 1 H), 3.30~3.4 (m, 2 H), 1.95~2.19 (s, 4 H). MS (ESI) m/e (M+H$^+$): 494.

Step 2

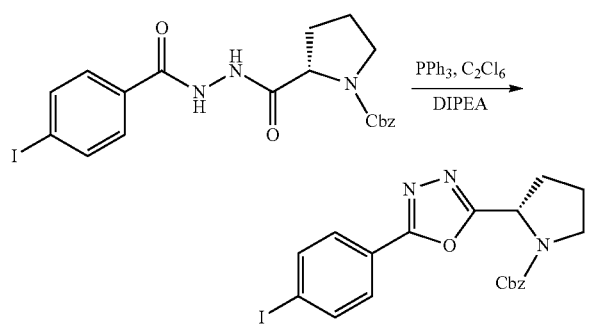

To a solution of the product from step 1 (2.1 g, 4.26 mmol), DIPEA (2.3 mL, 17.7 mmol) and PPh$_3$ (1.71 g, 6.5 mmol) in 20 mL of MeCN was added hexchloroethane (1.41 g, 5.97 mmol), and the mixture was stirred at RT for 1.5 hours. The solvent was evaporated, and the residue was purified by chromatography to give a white solid (1.75 g). MS (ESI) m/e (M+H$^+$): 494.

Step 3

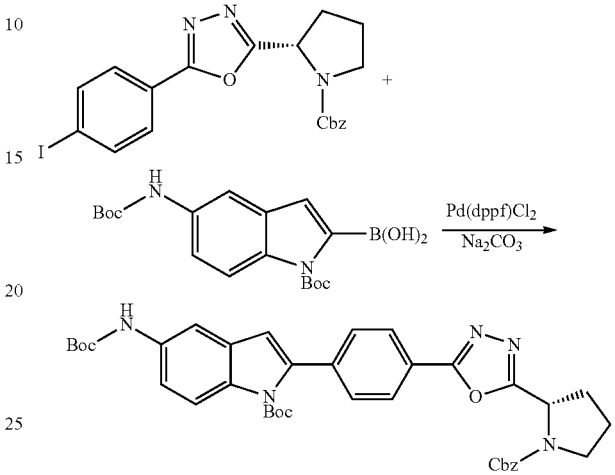

A mixture of the product from step 2 above (494 mg, 1.0 mmol), indole boronic acid from Example 42 (377 mg, 1.0 mmol), Pd(dppf)Cl$_2$ (73 mg, 0.10 mmol), Na$_2$CO$_3$ (318 mg, 3.0 mmol), THF (25 mL) and H$_2$O (5 mL) was refluxed under N$_2$ overnight. The mixture was poured into water and extracted with CH$_2$Cl$_2$. The organic phase was combined, dried over Na$_2$SO$_4$ and filtered to give the desired compound, which was used directly in the next step. MS (ESI) m/e (M+H$^+$): 680.

Step 4

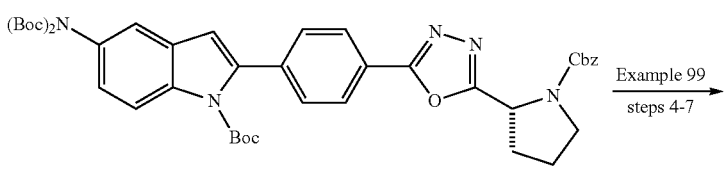

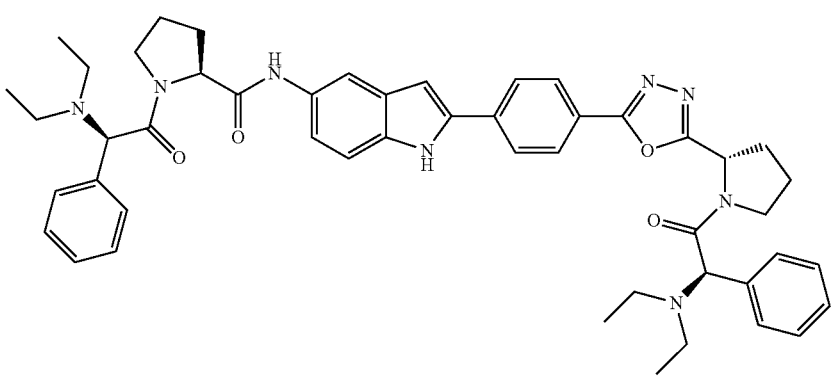 [SMILES: CCN(CC)[C@@H](C(=O)N1CCC[C@H]1C(=O)Nc1ccc2[nH]c(-c3ccc(-c4nnc([C@@H]5CCCN5C(=O)[C@@H](c5ccccc5)N(CC)CC)o4)cc3)cc2c1)c1ccccc1]

Following the procedure described in Example 99, steps 4-7, the oxadiazole from step 3 above was converted to the desired product. $^1$H NMR (MeOD) δ: 8.09 (d, J=8.8 Hz, 2H), 7.99 (d, J=8.8 Hz, 2H), 7.83 (s, 1H), 7.66~7.68 (m, 4H), 7.55~7.58 (m, 6H), 7.38~7.40 (m, 1H), 7.22~7.24 (m, 1H), 6.98 (s, 1H), 5.39 (s, 1H), 5.37~5.39 (m, 2H), 4.52~4.54 (m, 1H), 4.12~4.14 (m, 1H), 3.94~3.96 (m, 1H), 3.10~3.41 (m, 8H), 2.72~2.76 (m, 2H), 1.84~2.24 (m, 8H), 1.34~1.41 (m, 6H), 1.16~1.19 (m, 6H). MS (ESI) m/e (M+H$^+$): 821.

Example 192

Methyl {(2S)-1-[(2S)-2-{5-[4-(5-{2-[(2S)-1-{(2S)-2-[(methoxy-carbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate Step 1

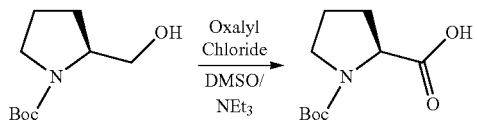 [SMILES: CC(C)(C)OC(=O)N1CCC[C@H]1CO ; CC(C)(C)OC(=O)N1CCC[C@H]1C(=O)O]

A 2 L, 3-necked round bottomed flask equipped with an overhead stir and a N$_2$ inlet was charged with a solution of oxalyl chloride (130 mL, 0.26 mol) in DCM (250 mL). The solution was cooled to −78° C., and a solution of DMSO (20 mL, 0.28 mol) in DCM (30 mL) was added dropwise. After 30 minutes, a solution of (S)—N-Boc-prolinol (40 g, 0.20 mol) in DCM (200 mL) was added dropwise. After 30 minutes, TEA (140 mL, 1.00 mol) was added to the solution, and the flask was transferred to an ice/water bath and stirred for another 30 minutes. The reaction mixture was diluted with DCM (200 mL) and washed successively with H$_2$O, 1M HCl, saturated NaHCO$_3$, and brine. The DCM layer was dried over Na$_2$SO$_4$, filtered, and concentrated to afford crude (S)-2-formyl-pyrrolidine-1-carboxylic acid tert-butyl ester (40 g) as an oil, which was used without further purification.

Step 2

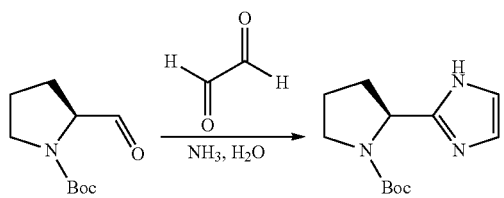

Glyoxal (2.0 mL of 40% in water) was added dropwise over 11 minutes to a methanol solution of NH$_4$OH (32 mL) and (S)-Boc-prolinal (8.564 g, 42.98 mmol) and stirred at ambient temperature for 19 hours. The volatile components were removed in vacuo, and the residue was purified by a flash silica gel chromatography (EtOAc) followed by a recrystallization (EtOAc) to provide the desired compound as a white fluffy solid (4.43 g). $^1$H NMR (DMSO) δ: 11.68, 11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39-1.15 (s, 9H). MS (ESI) m/e (M+H$^+$): 238.

Step 3

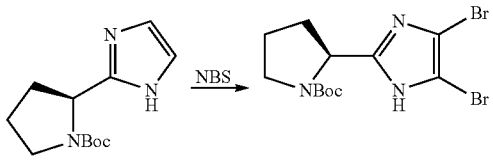

To a suspension of the compound from step 2 (140 g, 0.59 mol) in THF (2000 ml) was added NBS (200 g, 1.1 mol). The mixture was stirred at RT under N$_2$ protection overnight before the solvent was removed, and the residue was purified by chromatography on silica gel to give 230 g of the desired dibromo compound. MS (ESI) m/e (M+H$^+$): 396.

Step 4

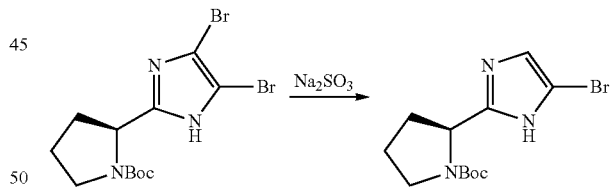

To a suspension of compound from step 3 (230 g, 0.58 mol) in EtOH/H$_2$O (3000 ml) was added Na$_2$SO$_3$ (733 g, 5.8 mol). The resulting mixture was stirred under reflux overnight. After cooling to RT, the mixture was extracted by DCM and concentrated under vacuum. The resulting residue was purified by chromatography on silica gel to give the desired bromo imidazole target. MS (ESI) m/e (M+H$^+$): 317.

Step 5

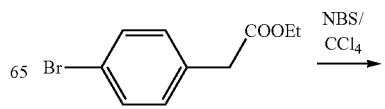

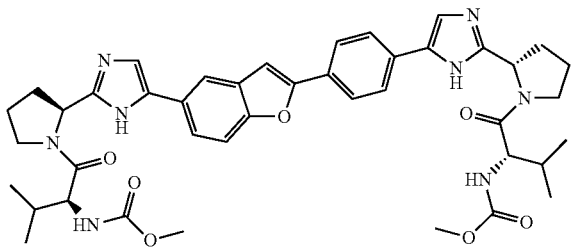

-continued

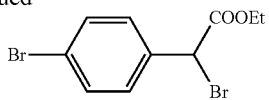

To a stirred solution of ethyl 4-bromophenylacetate (50 g, 205.8 mmol) in CCl$_4$ (500 mL) was added NBS (38 g, 214.7 mmol), then 48% aqueous HBr (4 drops). After the addition, the solution was stirred overnight at 80° C. under argon. Then the reaction was cooled to RT, filtered, and concentrated. The resulting oil was directly used the next step.
Step 6

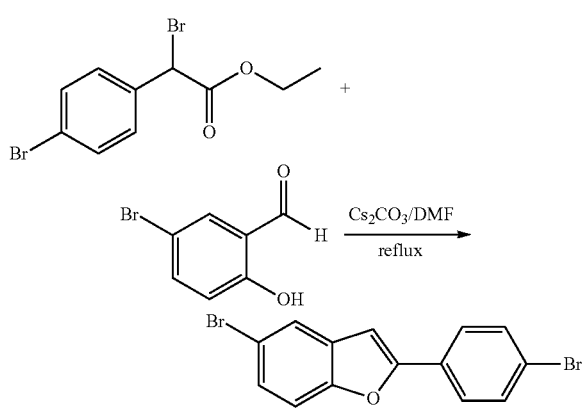

To a solution of the compound from step 5 (2 g, 6.2 mmol) in DMF (20 mL) was added 5-bromosalicylaldehyde (1.21 g, 6.0 mmol) and Cs$_2$CO$_3$ (2 g, 12.3 mmol) under N$_2$ protection. The resulting suspension was stirred for 5 hours at 160° C., then cooled and treated with water. The resulting precipitate was filtered, and the filtrate cake was dried in vacuo to give the desired compound, which was used directly in next step.
Step 7

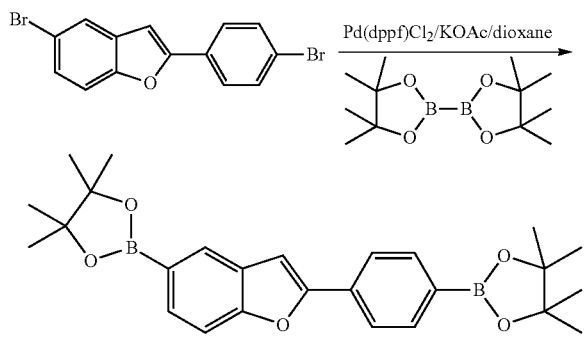

A suspension of the product from step 6 above (4.43 g, 12.58 mmol), bis(pincolato)diboron (8.31 g, 32.72 mmol), AcOK (3.72 g, 37.7 mmol) and Pd(dppf)Cl$_2$ (921 mg, 1.26 mmol) in dioxane (100 mL) was heated to reflux for 4 hours under N$_2$. The mixture was concentrated, the residue was partitioned between H$_2$O and DCM, and the aqueous phase was extracted with DCM. The combined organic layers were washed with brine, dried over Na$_2$SO$_4$, concentrated. The residue was purified by chromatography on silica gel to afford the desired compound (5 g).
Step 8

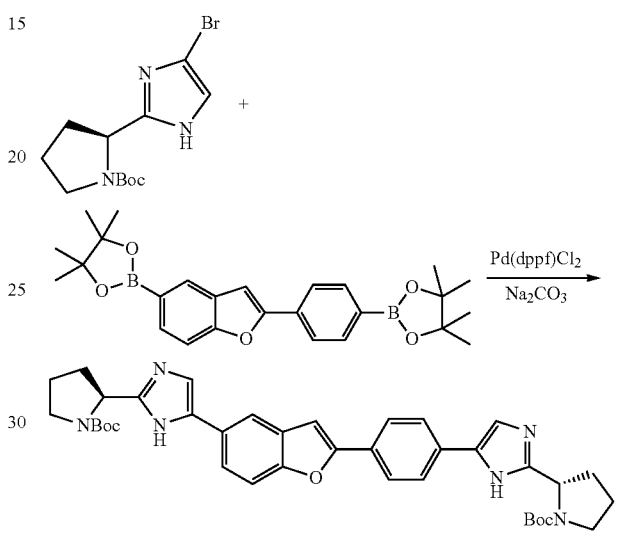

A suspension of the product from step 4 (5 mmol), the boronate ester from step 7 (2 mmol), Pd(dppf)Cl$_2$ (146 mg, 0.2 mmol), and Na$_2$CO$_3$ (636 mg, 6 mmol) were refluxed in THF/H$_2$O (10:1, 33 mL) overnight under N$_2$ protection. The mixture was cooled and filtered, and the filtrate was washed with water (50 mL) then extracted with EtOAc (100 mL), washed with brine and dried over anhydrous sodium sulfate. The solution was concentrated and the resulting residue was purified by column chromatography (PE/EA=8:1→5:1) to afford the desired compound. MS (ESI) m/z (M+H)$^+$: 641.
Step 9

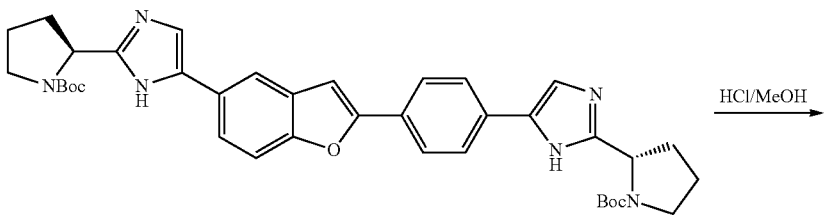

-continued

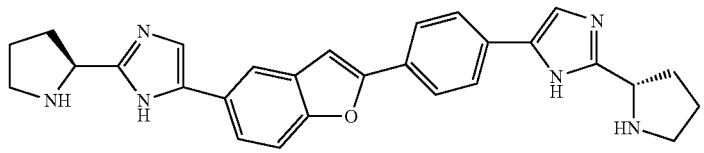

The product from step 8 (1.3 mmol) was added into 3M HCl/CH$_3$OH (20 mL) and the mixture was stirred at RT for 2 to 3 hours. The mixture was concentrated, and the crude product was used directly in the next step without further purification. MS (ESI) m/z (M+H)$^+$: 441.

Step 10

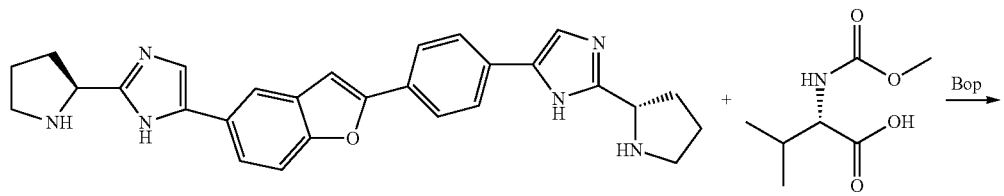

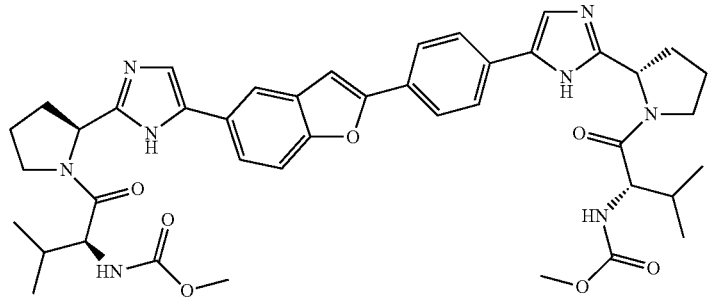

To a mixture of the product from step 9 (1 mmol), N-Moc-L-valine (2.1 mmol) and DIPEA (0.4 mL) in DMF (3 mL) was added BOP reagent (2.2 mmol). The resulting mixture was stirred at RT for 16 hours. The solution was subjected directly to RPLC to afford the desired compound. $^1$H NMR (MeOD) δ: 7.7-8.1 (m, 10 H), 7.4 (m, 1 H), 5.3 (m, 2 H), 4.3 (m, 2 H), 4.1 (d, J=4.8 Hz, 2 H), 3.9 (m, 2 H), 3.7 (m, 6 H), 2.6 (d, J=4.8 Hz, 2 H), 2.0-2.4 (m, 8 H), 1.3-1.4 (m, 2 H), 0.9-1.0 (m, 12 H). MS (ESI) m/z (M+H)$^+$: 780.

Examples 193-202

Compounds of Examples 193-202 were prepared in a similar manner as described in Example 192.

| Example | Structure | ¹H NMR | M + 1 | Name |
|---|---|---|---|---|
| 193 | 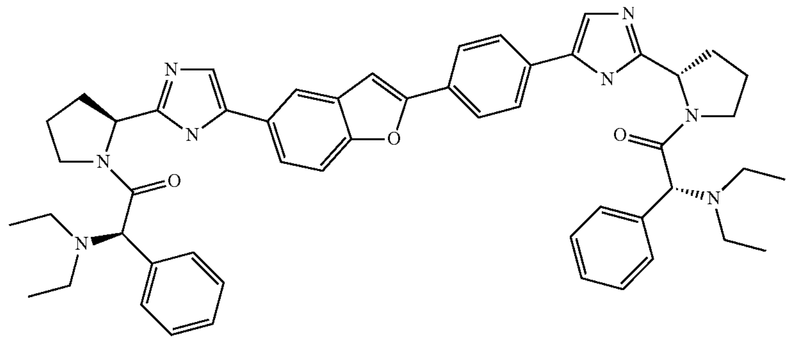 [SMILES: CCN(CC)[C@@H](C(=O)N1CCC[C@H]1c1ncc(-c2ccc(-c3cc4cc(-c5cnc([C@@H]6CCCN6C(=O)[C@@H](c6ccccc6)N(CC)CC)[nH]5)ccc4o3)cc2)[nH]1)c1ccccc1] | (MeOD) δ: 7.2-8.1 (m, 20 H), 5.2-5.6 (m, 4 H), 3.9-4.2 (m, 2 H), 3.1 (m, 2 H), 2.6 (m, 8 H), 1.9-2.5 (m, 8 H), 1.0-1.5 (m, 12 H). | 844 | (2R)-2-(diethylamino)-1-[(2S)-2-(5-{4-[5-(2-{(2S)-1-[(2R)-2-(diethylamino)-2-phenylacetyl]pyrrolidin-2-yl}-1H-imidazol-5-yl)-1-benzofuran-2-yl]phenyl}-1H-imidazol-2-yl)pyrrolidin-1-yl]-2-phenylethanone |
| 194 | 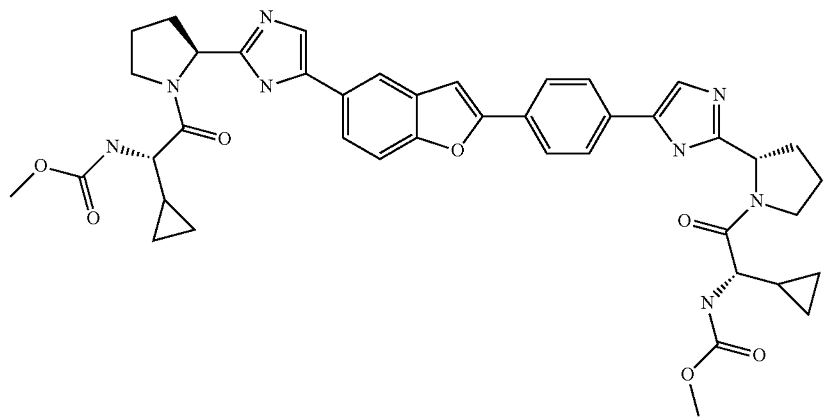 [SMILES: COC(=O)N[C@H](C(=O)N1CCC[C@H]1c1ncc(-c2ccc(-c3cc4cc(-c5cnc([C@@H]6CCCN6C(=O)[C@@H](NC(=O)OC)C6CC6)[nH]5)ccc4o3)cc2)[nH]1)C1CC1] | (MeOD) δ: 8.0-8.1 (m, 3 H), 7.7-7.9 (m, 6 H), 7.4 (d, J = 2.4 Hz, 1 H), 5.3 (d, J = 5.6 Hz, 2 H), 4.1 (m, 2 H), 3.9 (m, 4 H), 3.7 (m, 6 H), 2.5-2.6 (m, 2 H), 2.1-2.3 (m, 6 H), 1.1-1.2 (m, 2 H), 0.4-0.6 (m, 9 H). | 775 | Methyl {(1S)-1-cyclopropyl-2-[(2S)-2-{5-[4-(5-{2-[(2S)-1-{(2S)-2-cyclopropyl-2-[(methoxycarbonyl)amino]acetyl}pyrrolidin-2-yl]-1H-imidazol-5-yl}-1-benzofuran-2-yl)phenyl]-1H-imidazol-2-yl}pyrrolidin-1-yl]-2-oxoethyl}carbamate |

| Example | Structure | ¹H NMR | M + 1 | Name |
|---|---|---|---|---|
| 195 | 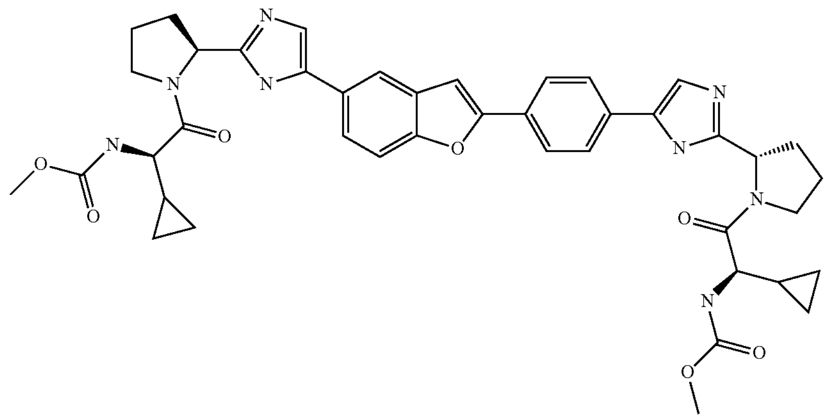 [SMILES: COC(=O)N[C@@H](C(=O)N1CCC[C@H]1c1ncc(-c2ccc(-c3cc4cc(-c5cnc([C@@H]6CCCN6C(=O)[C@H](NC(=O)OC)C6CC6)[nH]5)ccc4o3)cc2)[nH]1)C1CC1] | (MeOD) δ: 7.7-8.1 (m, 9 H), 7.4 (m, 16 H), 5.3-5.4 (m, 2 H) 3.5-4.1 (m, 12 H), 2.6 (d, J = 4.8 Hz, 26 H), 2.2 (d, J = 4.8 Hz, 6 H), 1.1-1.2 (m, 2 H), 0.4-0.7 (m, 8 H). | 775 | Methyl {(1R)-1-cyclopropyl-2-[(2S)-2-{5-[4-(5-{2-[(2S)-1-{(2R)-2-cyclopropyl-2-[(methoxycarbonyl)amino]acetyl}pyrrolidin-2-yl]-1H-imidazol-5-yl]-1-benzofuran-2-yl}phenyl]-1H-imidazol-2-yl}pyrrolidin-1-yl]-2-oxoethyl}carbamate |
| 196 | 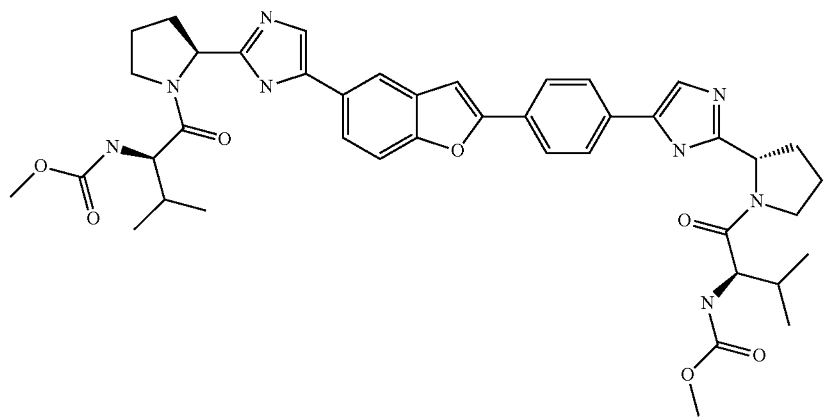 [SMILES: COC(=O)N[C@@H](C(=O)N1CCC[C@H]1c1ncc(-c2ccc(-c3cc4cc(-c5cnc([C@@H]6CCCN6C(=O)[C@H](NC(=O)OC)C(C)C)[nH]5)ccc4o3)cc2)[nH]1)C(C)C] | (MeOD) δ: 7.8-7.9 (m, 5 H), 7.1-7.6 (m, 5 H), 5.6-5.7 (m, 1 H), 5.2 (d, J = 4.8 Hz, 1 H), 4.0-4.2 (m, 3 H), 3.6-3.8 (m, 8 H), 2.0-2.5 (m, 10 H), 1.6 (d, J = 4.8 Hz, 1 H), 1.3 (m, 1 H), 0.8-1.1 (m, 11 H), 0.4 (m, 26 H). | 780 | Methyl {(2R)-1-[(2S)-2-{5-[2-(4-{2-[(2S)-1-{(2R)-2-[(methoxycarbonyl)amino]-3-methylbutanoyl}pyrrolidin-2-yl]-1H-imidazol-5-yl}phenyl)-1-benzofuran-5-yl]-1H-imidazol-2-yl}pyrrolidin-1-yl]-3-methyl-1-oxobutan-2-yl}carbamate |

| Example | Structure | ¹H NMR | M + 1 | Name |
|---|---|---|---|---|
| 197 | 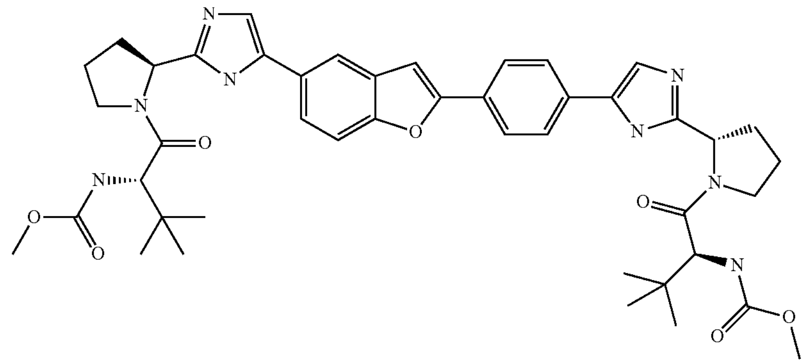 | (MeOD), δ 8.10 (d, J = 4 Hz, 2 H), 8.01 (s, 1 H), 7.94 (s, 1 H), 7.87 (d, J = 2 Hz, 2 H), 7.84 (m, 1 H), 7.73 (d, J = 4 Hz, 1 H), 7.44 (m, 1 H), 5.25 (m, 2 H), 4.33 (m, 1 H), 4.16 (m, 2 H), 3.89 (m, 2 H), 3.67 (s, 6 H), 2.58 (m, 2 H), 2.20 (m, 6 H), 0.97 (m, 18 H) | 806 | Methyl {(2S)-1-[(2S)-2-{5-[4-(5-{2-[(2S)-1-{(2S)-2-[(methoxycarbonyl)amino]-3,3-dimethylbutanoyl}pyrrolidin-2-yl]-1H-imidazol-5-yl}-1-benzofuran-2-yl)phenyl]-1H-imidazol-2-yl}pyrrolidin-1-yl]-3,3-dimethyl-1-oxobutan-2-yl}carbamate |
| 198 | 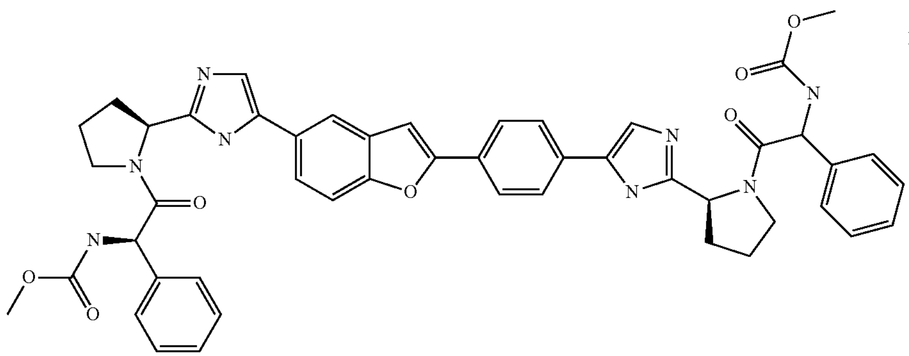 [SMILES: COC(=O)NC(C(=O)N1CCC[C@H]1c1ncc(-c2ccc(-c3cc4cc(-c5cnc([C@@H]6CCCN6C(=O)[C@H](NC(=O)OC)c6ccccc6)[nH]5)ccc4o3)cc2)[nH]1)c1ccccc1] | (MeOD) δ: 7.6-8.1 (m, 9 H), 7.3-7.5 (m, 11 H), 7.2 (m, 1 H), 5.4-5.5 (m, 2 H), 5.3 (m, 2 H), 4.1 (d, J = 4.8 Hz, 2 H), 3.7 (d, J = 2.4 Hz, 6 H), 1.9-2.4 (m, 8 H) | 848 | Methyl {(1R)-2-[(2S)-2-{5-[4-(5-{2-[(2S)-1-{(2R)-2-[(methoxycarbonyl)amino]-2-phenylacetyl}pyrrolidin-2-yl]-1H-imidazol-4-yl}-1-benzofuran-2-yl)phenyl]-1H-imidazol-2-yl}pyrrolidin-1-yl]-2-oxo-1-phenylethyl}carbamate |

| Example | Structure | ¹H NMR | M + 1 | Name |
|---|---|---|---|---|
| 199 | 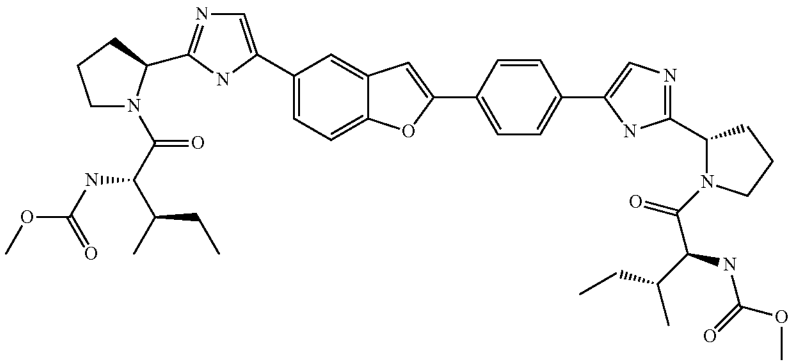 | (MeOD) δ 8.08 (d, J = 4 Hz, 2 H), 8.04 (s, 1 H), 7.89 (d, 3 H), 7.78 (m, 1 H), 7.77 (m, 2 H), 7.42 (m, 1 H), 5.34 (t, J = 4 Hz, 2 H), 4.42 (d, J = 4Hz, 2 H), 4.10 (s, 2 H), 3.82 (m, 2 H), 3.79 (m, 3 H), 3.64 (s, 3 H), 2.57 (m, 2 H), 2.20 (m, 6 H), 1.88 (m, 2 H), 1.48 (m, 2 H), 1.32 (m, 2 H), 0.97 (m, 12 H). | 806 | Methyl {(2S,3R)-1-[(2S)-2-(5-{2-[4-(2-{(2S)-1-[N-(methoxycarbonyl)-L-alloisoleucyl]pyrrolidin-2-yl}-1H-imidazol-5-yl)phenyl]-1-benzofuran-5-yl}-1H-imidazol-2-yl)pyrrolidin-1-yl]-3-methyl-1-oxopentan-2-yl}carbamate |
| 200 | 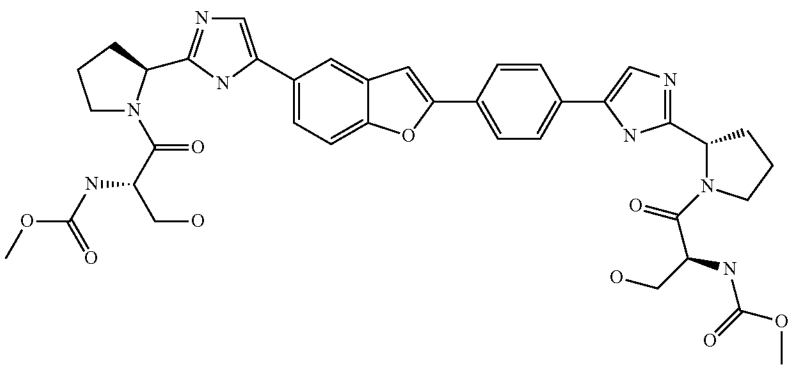 | (MeOD) δ: 7.6-8.1 (m, 9 H), 7.4 (m, 6 H), 5.4 (m, 2 H), 4.6 (m, 2 H), 3.5-4.1 (m, 13 H), 2.5-2.7 (m, 6 H), 2.3 (m, 5 H). | 755 | Methyl {(2S)-3-hydroxy-1-[(2S)-2-{5-[4-(5-{2-[(2S)-1-{(2S)-3-hydroxy-2-[(methoxycarbonyl)amino]propanoyl}pyrrolidin-2-yl]-1H-imidazol-5-yl}-1-benzofuran-2-yl)phenyl]-1H-imidazol-2-yl}pyrrolidin-1-yl]-1-oxopropan-2-yl}carbamate |

| Example | Structure | ¹H NMR | M + 1 | Name |
|---|---|---|---|---|
| 201 | 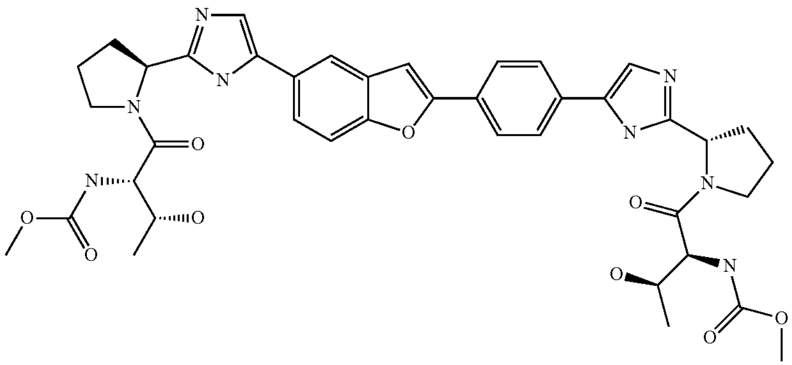 | (MeOD), δ 8.04 (d, J = 4 Hz, 2 H), 7.97 (s, 1 H), 7.84 (d, J = 2 Hz, 2 H), 7.81 (m, 1 H), 7.76 (m, 1 H), 7.64 (d, J = 4 Hz, 2 H), 7.38 (m, 1 H), 5.29 (m, 2 H), 4.49 (m, 2 H), 4.15 (m, 2 H) 3.97 (m, 1 H), 3.92 (m, 1 H), 3.66 (m, 6 H), 2.63 (m, 1 H), 2.60 (m, 1 H), 2.54 (m, 2 H), 2.16-2.22 (m, 6 H), 1.16 (d, J = 2 Hz, 6 H). | 783 | Methyl {(2S,3R)-3-hydroxy-1-[(2S)-2-{5-[4-(5-{2-[(2S,3R)-3-hydroxy-2-[(methoxycarbonyl)amino]butanoyl]pyrrolidin-2-yl}-1H-imidazol-5-yl]-1-benzofuran-2-yl)phenyl]-1H-imidazol-2-yl}pyrrolidin-1-yl]-1-oxobutan-2-yl}carbamate |
| 202 | 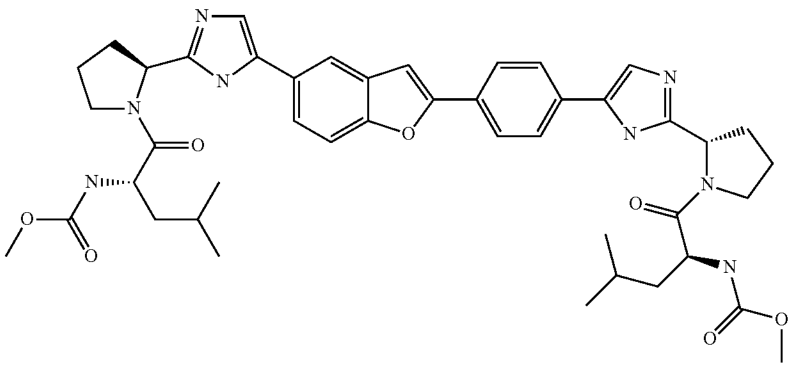 | (MeOD), δ 8.05 (d, J = 4 Hz, 2 H), 7.97 (s, 1 H), 7.84 (d, J = 2 Hz, 2 H), 7.81 (d, J = 2 Hz, 2 H), 7.76 (m, 1 H), 7.64 (d, J = 4 Hz, 2 H), 7.39 (m, 1 H), 5.25 (m, 2 H), 4.45 (m, 2 H), 4.03 (m, 2 H), 3.84 (m, 2 H), 3.85 (m, 2 H), 3.64 (s, 6 H), 2.55 (m, 2 H), 2.22 (m, 6 H), 1.70 (m, 2 H), 1.51 (m, 4 H), 0.98 (m, 12 H) | 806 | Methyl {(2S)-1-[(2S)-2-{5-[4-(5-{2-[(2S)-1-{(2S)-2-[(methoxycarbonyl)amino]-4-methylpentanoyl]pyrrolidin-2-yl]-1H-imidazol-5-yl]-1-benzofuran-2-yl)phenyl]-1H-imidazol-2-yl}pyrrolidin-1-yl]-4-methyl-1-oxopentan-2-yl}carbamate |

Example 203

Methyl {(2S)-1-[(2S)-2-{5-[3-fluoro-4-(5-{2-[(2S)-1-{(2S)-2-[(methoxycarbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate

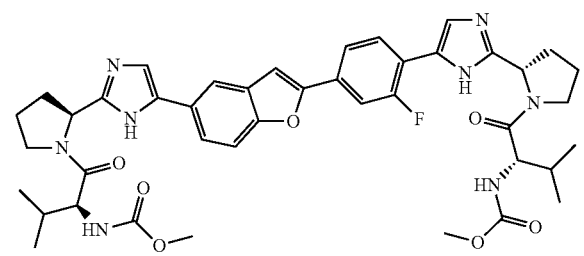 [SMILES: COC(=O)N[C@H](C(=O)N1CCC[C@H]1c1ncc(-c2ccc3oc(-c4ccc(-c5cnc([C@@H]6CCCN6C(=O)[C@@H](NC(=O)OC)C(C)C)[nH]5)c(F)c4)cc3c2)[nH]1)C(C)C]

Step 1

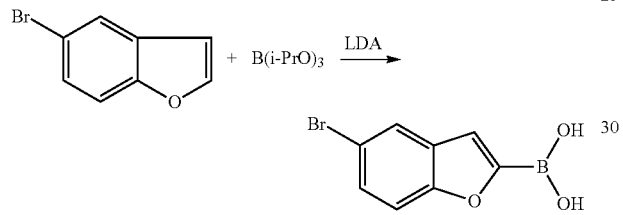

To a solution of 5-bromobenzofuran (3.9 g, 20 mmol) in dry THF (30 mL) cooled to −78° C. under $N_2$-protected LDA (prepared from n-BuLi and iPr$_2$NH in THF (~30 mmol)) was slowly added. The mixture was stirred at the same temperature for 30 minutes, then triisopropylborate (5.64 g, 30 mmol) was added to the mixture. The mixture was allowed to warm to RT and stirred for 2 hours. The mixture was then quenched with 1N HCl to pH=3 and extracted with EtOAc. The combined organic phases were combined, dried and filtered. The filtrate was concentrated to afford the desired product (4.3 g). MS (ESI) m/e (M+H$^+$): 241.

Step 2

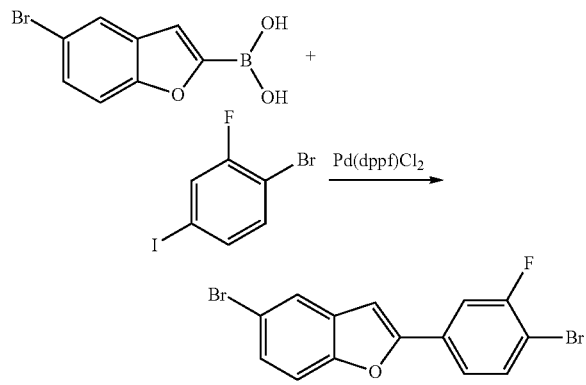

A suspension of the boronic acid from step 1 (1.44 mg, 6.0 mmol), 2-fluoro-4-iodobromobenzene (1.8 g, 6.0 mmol), Pd(dppf)Cl$_2$ (600 mg), Na$_2$CO$_3$ (954 mg, 9.0 mmol) and in THF/H$_2$O (9:1, 100 mL) was refluxed at 75° C. overnight under N$_2$ protection. The mixture was cooled and filtered. The filtrate was washed with water (150 mL) and extracted with EtOAc (200 mL), washed with brine and dried over anhydrous sodium sulfate. The solution was evaporated and the residue was purified by column chromatography (PE/EA=8:1→5:1) to afford the desired compound. MS (ESI) m/e (M+H$^+$): 370.

Step 3

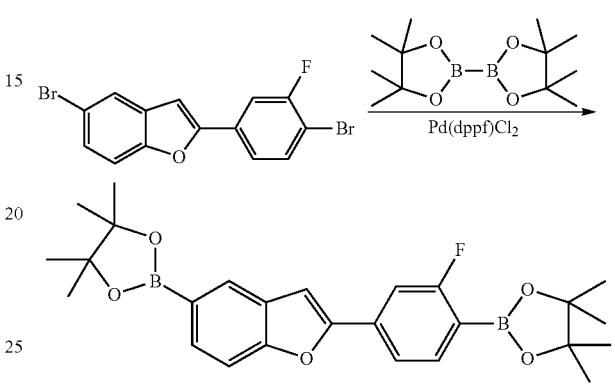

To a solution of the product from step 2 (1.85 g, 5 mmol), bis(pinacolato)diboron (2.54 g, 10 mmol) and Pd(dppf)Cl$_2$ (80 mg) and KOAc (0.98 g, 10 mmol) were dissolved in 1,4-dioxane (30 mL), and the reaction mixture was heated at 110° C. for 16 hours. The solvent was evaporated, and the residue was purified by column chromatography with silica gel elution with PE to afford the desired product as white solid (1.95 g). MS (ESI) m/e (M+H$^+$): 465.

Step 4

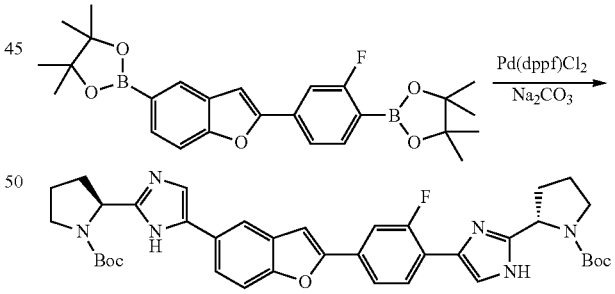

A suspension of the bromoimidazole from Example 192 (5 mmol), the boronate ester from step 3 (2 mmol), Pd(dppf)Cl$_2$ (146 mg, 0.2 mmol) and Na$_2$CO$_3$ (636 mg, 6 mmol) was refluxed in THF/H$_2$O (10:1, 33 mL) overnight under N$_2$ protection. The mixture was cooled and filtered, and the filtrate was washed with water (50 mL) and extracted with EtOAc (100 mL), washed with brine and dried over anhydrous sodium sulfate. The solution was concentrated, and the resulting residue was purified by column chromatography (PE/EtOAc=8:1) to afford the desired compound. MS (ESI) m/e (M+H$^+$): 683.

Step 5

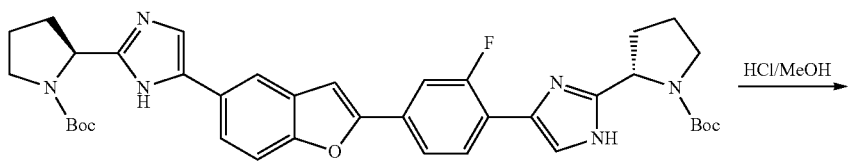

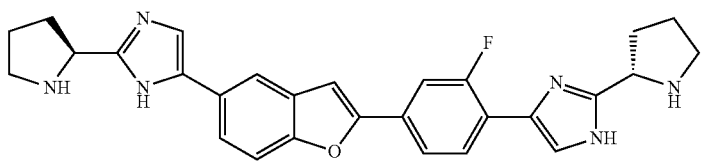

The product from step 4 (682 mg, 1.0 mmol) was treated with 3M HCl/CH₃OH (10 mL) and the mixture was stirred at RT for 3 hours. The reaction mixture was concentrated, and the crude product was used directly in the next step without further purification. MS (ESI) m/e (M+H$^+$): 483.

Step 6

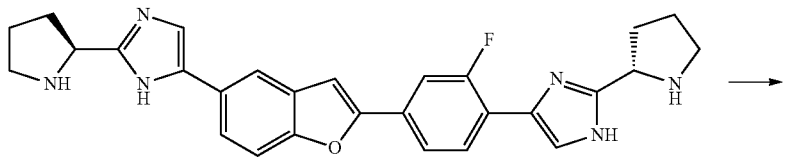

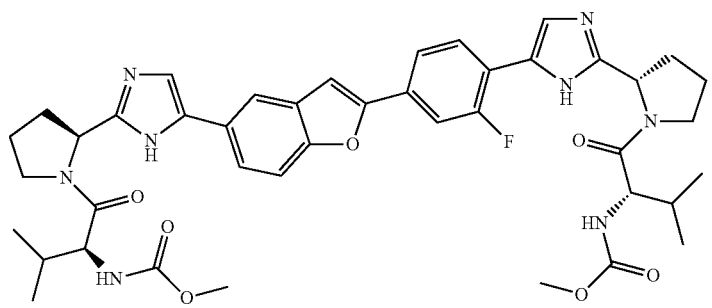

To a mixture of the product from step 5 (482 mg, 1.0 mmol), N-Moc-L-valine (2.1 mmol) and DIPEA (0.4 mL) in DMF (3 mL) was added BOP reagent (977 mg, 2.2 mmol). The resulting mixture was stirred at RT for 16 hours. The solution was subjected directly to RPLC to afford the desired compound as white solid (40 mg). $^1$H NMR (MeOD) δ: 7.99 (s, 1 H), 7.89-7.80 (m, 5 H), 7.72-7.67 (m, 2 H), 7.47 (s, 1 H), 5.27-5.22 (m, 2 H), 4.22 (d, 2 H), 4.09 (d, 2 H), 3.89-3.84 (m, 2 H), 3.64 (s, 6 H), 2.55-2.02 (m, 10 H), 0.92 (d, 6 H), 0.88 (d, 6 H). MS (ESI) m/e (M+H$^+$): 797.

Examples 204-212

Compounds of Examples 204-212 were prepared in a similar manner as described in Example 203.

| Example | Structure | M + 1 | Name |
| --- | --- | --- | --- |
| 204 | 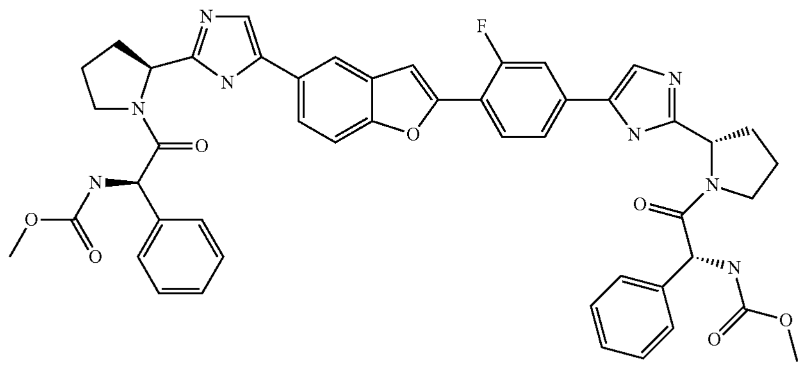 | 866 | Methyl {(1R)-2-[(2S)-2-{5-[3-fluoro-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-2-oxo-1-phenylethyl}carbamate |
| 205 | 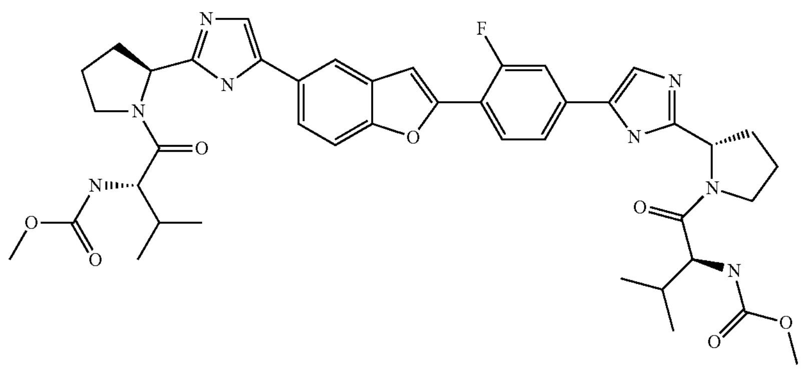 | 797 | Methyl {(2S)-1-[(2S)-2-{5-[3-fluoro-4-(5-{2-[(2S)-1-{(2S)-2-[(methoxycarbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate |
| 206 | 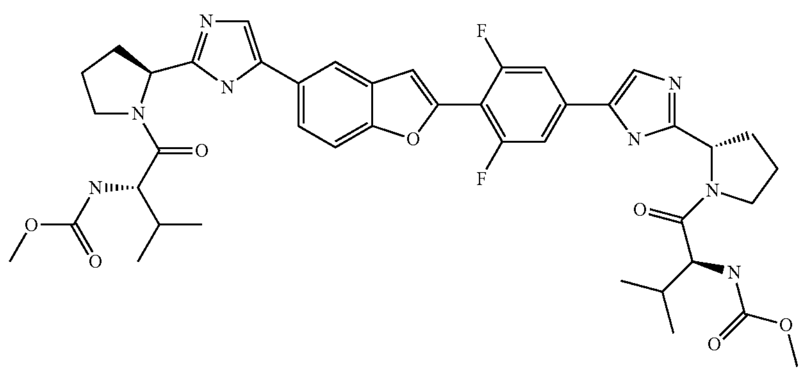 | 816 | Methyl {(2S)-1-[(2S)-2-{5-[2-(2,6-difluoro-4-{2-[(2S)-1-{(2S)-2-[(methoxycarbonyl)amino]-3-methylbutanoyl}pyrrolidin-2-yl]-1H-imidazol-5-yl}phenyl)-1-benzofuran-5-yl]-1H-imidazol-2-yl}pyrrolidin-1-yl]-3-methyl-1-oxobutan-2-yl}carbamate |
| 207 | 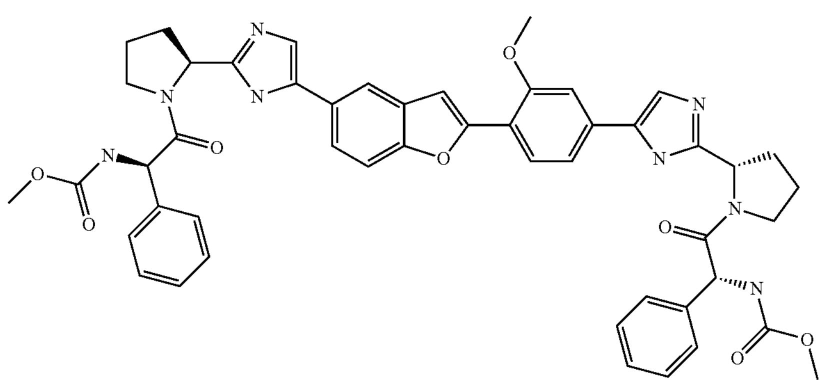 | 878 | Methyl {(1R)-2-[(2S)-2-{5-[3-methoxy-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-2-oxo-1-phenylethyl}carbamate |

-continued

| Example | Structure | M + 1 | Name |
|---|---|---|---|
| 208 | 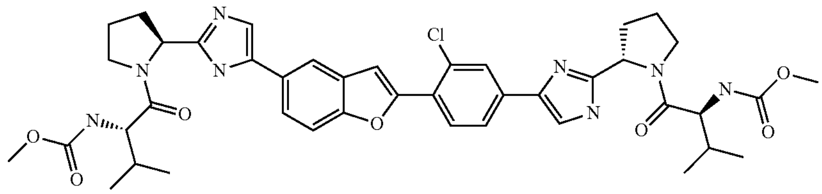 | 814 | Methyl {(2S)-1-[(2S)-2-{5-[2-(2-chloro-4-{2-[(2S)-1-{(2S)-2-[(methoxycarbonyl)amino]-3-methylbutanoyl}pyrrolidin-2-yl]-1H-imidazol-4-yl}phenyl)-1-benzofuran-5-yl]-1H-imidazol-2-yl}pyrrolidin-1-yl]-3-methyl-1-oxobutan-2-yl}carbamate |
| 209 | 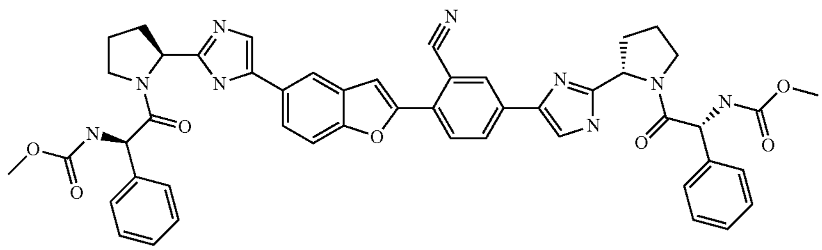 | 873 | Methyl {(1R)-2-[(2S)-2-{4-[3-cyano-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-2-oxo-1-phenylethyl}carbamate |
| 210 | 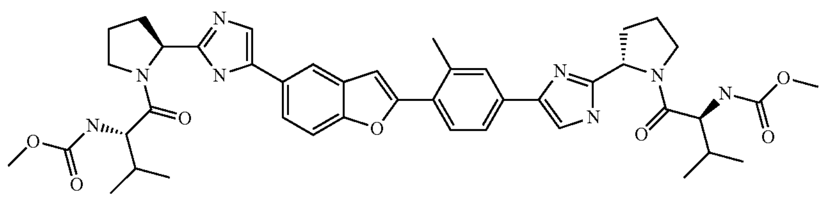 | 794 | Methyl {(2S)-1-[(2S)-2-{5-[2-(4-{2-[(2S)-1-{(2S)-2-[(methoxycarbonyl)amino]-3-methylbutanoyl}pyrrolidin-2-yl]-1H-imidazol-4-yl}-2-methylphenyl)-1-benzofuran-5-yl]-1H-imidazol-2-yl}pyrrolidin-1-yl]-3-methyl-1-oxobutan-2-yl}carbamate |
| 211 | 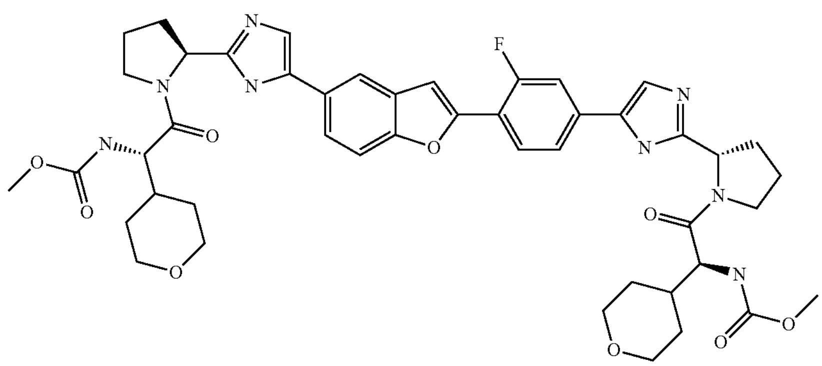 | | Methyl[(1S)-2-[(2S)-2-(5-{3-fluoro-4-[5-(2-{(2S)-1-[(2S)-2-[(methoxycarbonyl)amino]-2-(tetrahydro-2H-pyran-4-yl)acetyl]pyrrolidin-2-yl}-1H-imidazol-5-yl)-1-benzofuran-2-yl]phenyl}-1H-imidazol-2-yl)pyrrolidin-1-yl]-2-oxo-1-(tetrahydro-2H-pyran-4-yl)ethyl]carbamate |
| 212 | 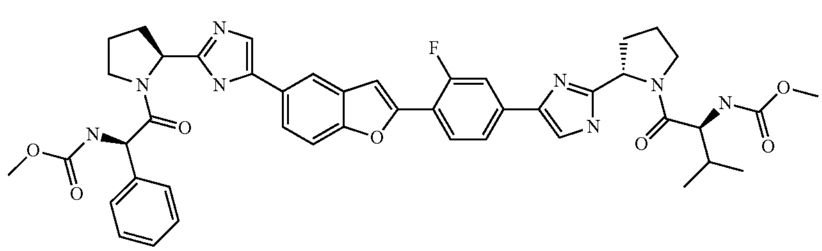 | 832 | Methyl {(2S)-1-[(2S)-2-{4-[3-fluoro-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate |

Example 213

Methyl {(1R)-2-[(2S)-2-{5-[4-(5-{2-[(2S)-1-{(2R)-2-[(methoxy-carbonyl)amino]-2-phenylacetyl}pyrrolidin-2-yl]-1H-imidazol-5-yl}-1,3-benzoxazol-2-yl)phenyl]-1H-imidazol-2-yl}pyrrolidin-1-yl]-2-oxo-1-phenylethyl}carbamate

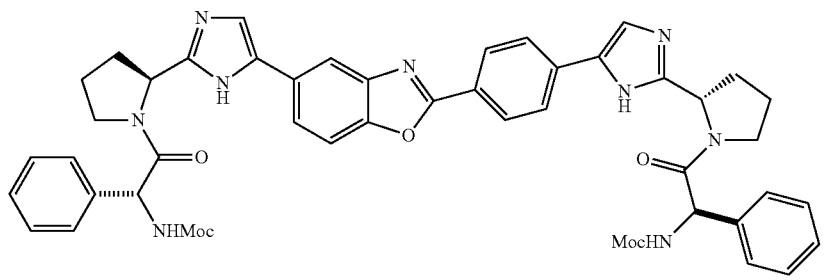

Step 1

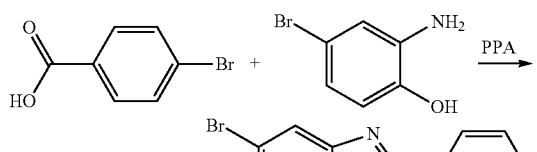

4-Bromobenzoic acid (20 g, 0.1 mol) and 2-amino-4-bromophenol (18.8 g, 0.1 mol) were added into polyphosphoric acid (250 mL), and the mixture was stirred at 140° C. for 90 minutes. After cooling in an ice-bath, the reaction mixture was diluted with water (4000 mL) and neutralized with NaOH. The resulting solid was filtered off and dried to afford the desired benzoxazole. MS (ESI) m/e (M+H$^+$): 354.

Step 2

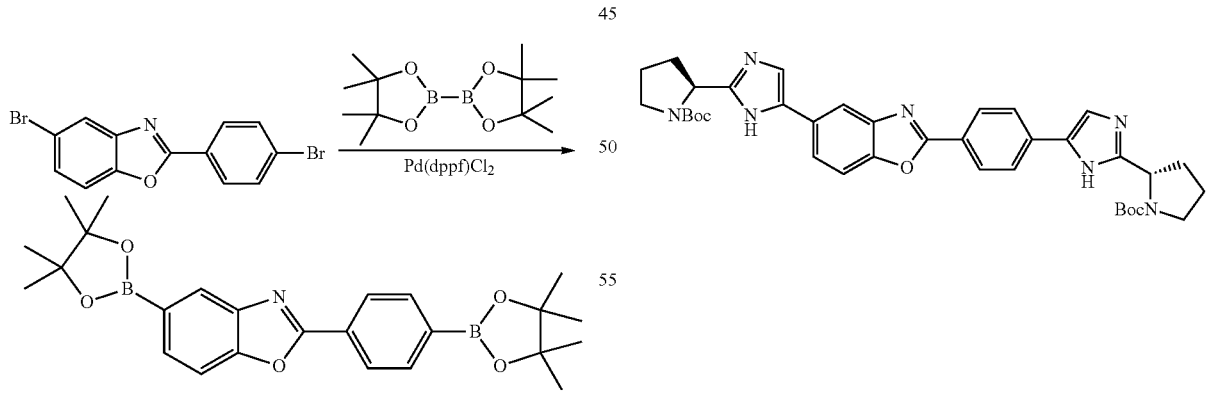

A suspension of the product from step 1 above (10.6 g, 30 mmol), bis(pinacolato)diboron (30.3 g, 120 mmol), KOAc (7.6 g, 78 mmol) and Pd(dppf)Cl$_2$ (1.1 g, 1.5 mmol) in dioxane (300 ml) was stirred at 100° C. under N$_2$ protection overnight. The reaction mixture was cooled and concentrated, then chromatographed on silica gel gave the product compound. MS (ESI) m/e (M+H$^+$): 366.

Step 3

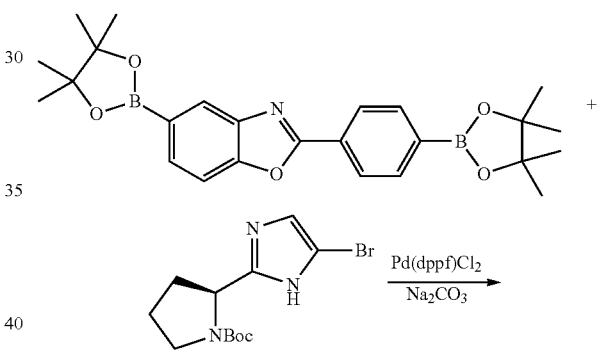

A suspension of the product from step 2 (1.2 g, 2.6 mmol), bromoimidazole from Example 192 (2 g, 6.3 mmol), Na$_2$CO$_3$ (1.3 g, 12 mmol) and Pd(dppf)Cl$_2$ (220 mg, 0.3 mmol) in THF/H$_2$O (36 ml) was stirred at 100° C. under N$_2$ protection overnight. The reaction mixture was concentrated and purified by chromatography on silica gel to give the desired compound. MS (ESI) m/e (M+H$^+$): 666.

Step 4

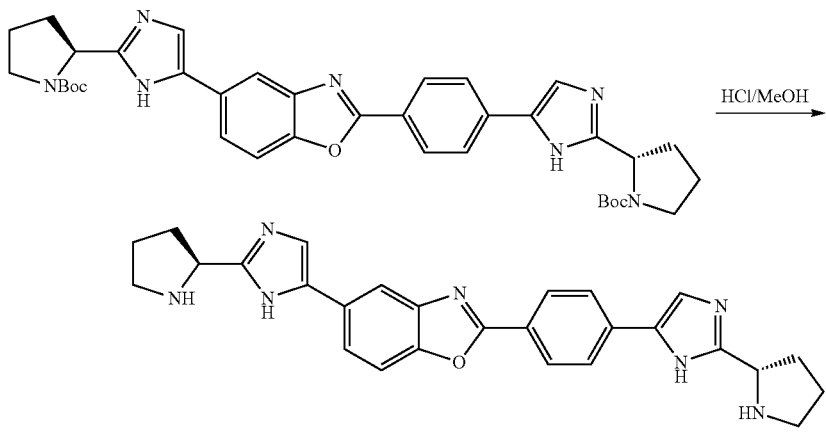

A solution of the product from step 3 (400 mg, 0.6 mmol) in HCl/MeOH (20 ml) was stirred at ambient temperature for 3 hours, then concentrated and dried under high vacuum to give to desired product. MS (ESI) m/e (M+H$^+$): 466.

Step 5

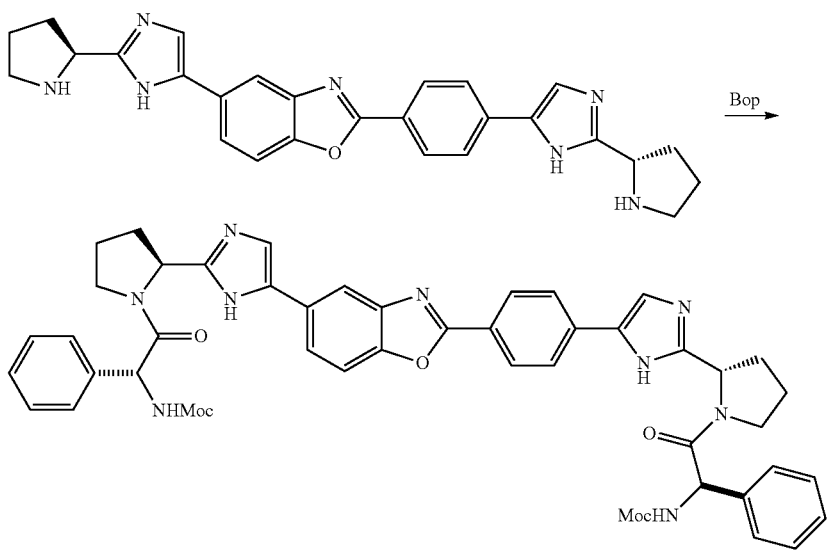

To a mixture of the product from step 4 (233 mg, 0.5 mmol), N-Moc-D-Phg (1.1 mmol) and DIPEA (0.2 mL) in DMF (3 mL) was added BOP reagent (488 mg, 1.1 mmol). The resulting mixture was stirred at RT for 16 hours before the solution was subjected directly to RPLC to afford the desired compound. $^1$H NMR (MeOD) δ: 8.4 (d, J=8.4 Hz, 2 H), 8.2 (s, 1 H), 8.0 (m, 3 H), 7.9 (m, 3 H), 7.5-7.4 (m, 10 H), 5.5 (s, 2 H), 5.3 (m, 2 H), 4.1-4.0 (m, 2 H), 3.6 (d, J=2.8 Hz, 6 H), 3.3 (m, 1 H), 3.3-3.1 (m, 1 H), 2.5-2.3 (m, 2 H), 2.2-2.1 (m, 4 H), 2.0 (m, 2 H). MS (ESI) m/e (M+H$^+$): 780.

Examples 214-215

Compounds of Examples 214-215 were prepared in a similar manner as described in Example 213.

| Example | Structure | ¹H NMR | M + 1 | Name |
|---|---|---|---|---|
| 214 | 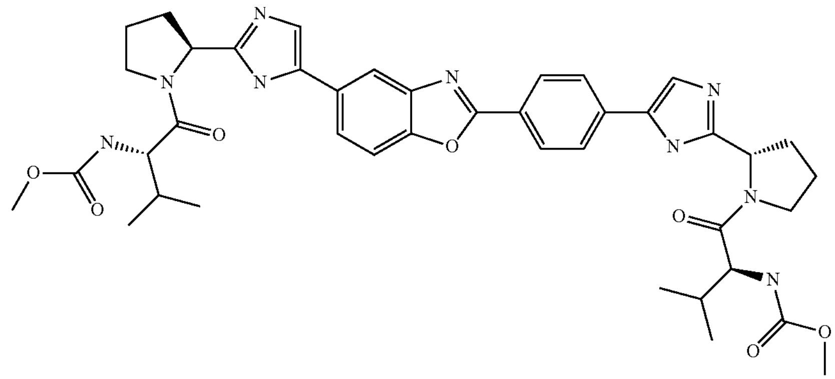 | (MeOD) δ: 8.4 (d, J = 8.4 Hz, 2 H), 8.1 (s, 1 H), 7.9 (m, 3 H), 7.8 (m, 2 H), 7.7 (m, 1 H), 5.3 (m, 2 H), 4.2 (m, 2 H), 4.1-4.0 (m, 2 H), 3.9-3.8 (m, 2 H), 3.6 (s, 2 H), 2.6 (m, 2 H), 2.3 (m, 2 H), 2.2 (m, 4 H), 2.0 (m, 2 H), 0.9 (m, 12 H). | 848 | Methyl {(2S)-1-[(2S)-2-{5-[2-(4-{2-[(2S)-1-{(2S)-2-[(methoxycarbonyl)amino]-3-methylbutanoyl}pyrrolidin-2-yl]-1H-imidazol-5-yl}-1,3-benzoxazol-5-yl]-1H-imidazol-2-yl}pyrrolidin-1-yl]-3-methyl-1-oxobutan-2-yl}carbamate |
| 215 | 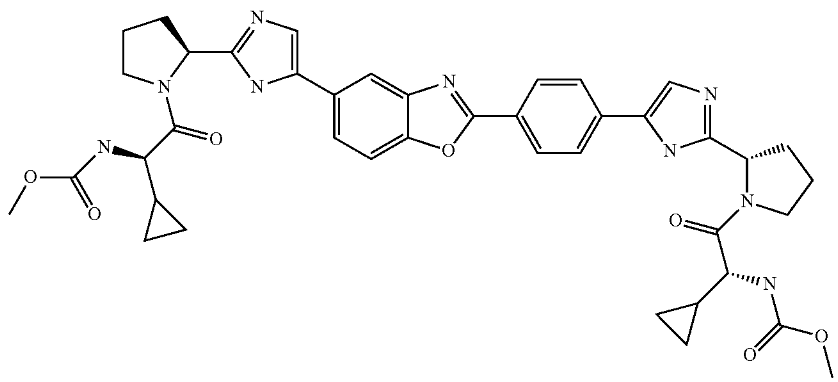 | (MeOD) δ: 8.4 (d, J = 6.8 Hz, 2 H), 8.2-8.1 (s, 1 H), 8.0 (m, 3 H), 7.9-7.8 (m, 3 H), 5.3 (m, 2 H), 4.1-4.0 (m, 2 H), 4.0 (m, 2 H), 3.9-3.8 (m, 2 H), 3.7 (m, 6 H), 2.6 (m, 2 H), 2.4-2.1 (m, 6 H), 1.3-1.1 (m, 2 H), 0.7-0.6 (m, 3 H), 0.6-0.5 (m, 3 H), 0.4 (m, 2 H). | 776 | Methyl {(1R)-1-cyclopropyl-2-[(2S)-2-{5-[4-(5-{2-[(2S)-1-{(2R)-2-cyclopropyl-2-[(methoxycarbonyl)amino]acetyl}pyrrolidin-2-yl]-1H-imidazol-5-yl}-1,3-benzoxazol-2-yl)phenyl]-1H-imidazol-2-yl}pyrrolidin-1-yl]-2-oxoethyl}carbamate |

Examples 216-227

Compounds of Examples 216-227 were prepared in a similar manner as described in Example 189b (Alternative Procedure).

| Example | Structure | M + 1 | Name |
|---|---|---|---|
| 216 | 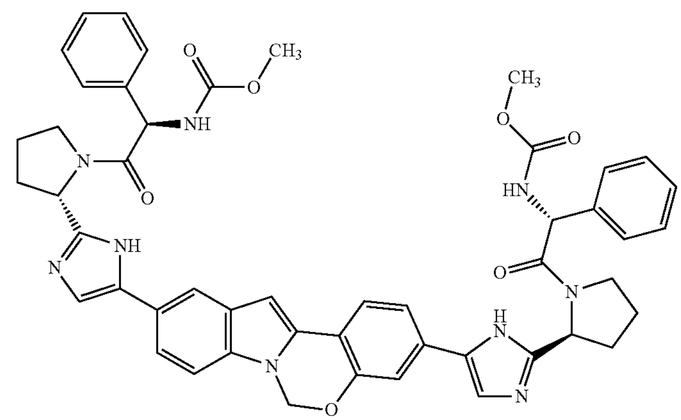 [SMILES: COC(=O)N[C@@H](C(=O)N1CCC[C@H]1c1ncc(-c2ccc3c(c2)OCn2c-3cc3cc(-c4cnc([C@@H]5CCCN5C(=O)[C@H](NC(=O)OC)c5ccccc5)[nH]4)ccc32)[nH]1)c1ccccc1] | 875 | dimethyl (indolo[1,2-c][1,3]benzoxazine-3,10-diylbis{1H-imidazole-5,2-diyl(2S)pyrrolidine-2,1-diyl[(1R)-2-oxo-1-phenylethane-2,1-diyl]})biscarbamate |
| 217 | 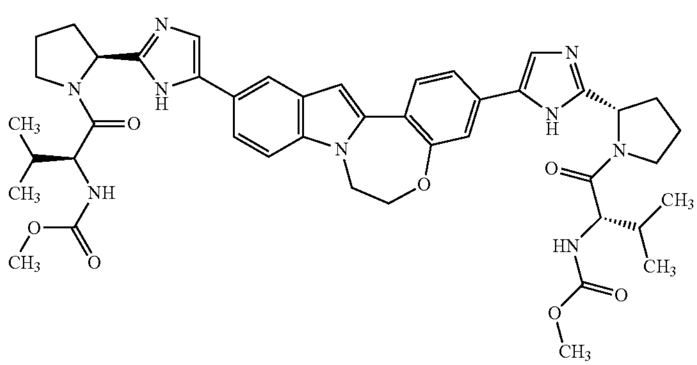 [SMILES: COC(=O)N[C@H](C(=O)N1CCC[C@H]1c1ncc(-c2ccc3c(c2)OCCn2c-3cc3cc(-c4cnc([C@@H]5CCCN5C(=O)[C@@H](NC(=O)OC)C(C)C)[nH]4)ccc32)[nH]1)C(C)C] | 821 | methyl [(2S)-1-{(2S)-2-[5-(11-{2-[(2S)-1-{(2S)-2-[(methoxycarbonyl)amino]-3-methylbutanoyl}pyrrolidin-2-yl]-1H-imidazol-5-yl}-6,7-dihydroindolo[1,2-d][1,4]benzoxazepin-3-yl)-1H-imidazol-2-yl]pyrrolidin-1-yl}-3-methyl-1-oxobutan-2-yl]carbamate |
| 218 | 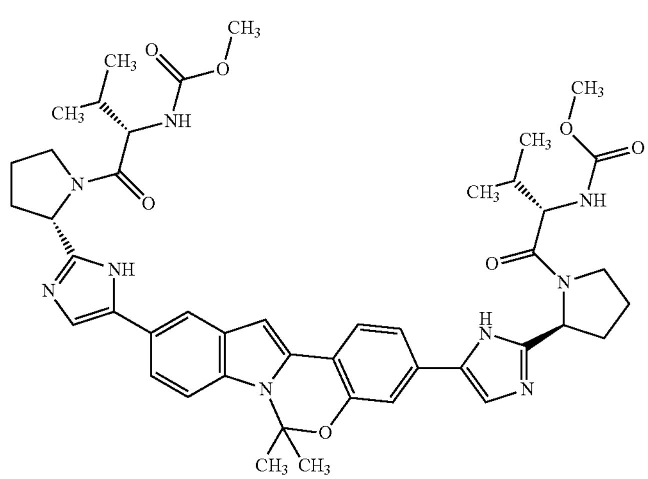 [SMILES: COC(=O)N[C@H](C(=O)N1CCC[C@H]1c1ncc(-c2ccc3c(c2)OC(C)(C)n2c-3cc3cc(-c4cnc([C@@H]5CCCN5C(=O)[C@@H](NC(=O)OC)C(C)C)[nH]4)ccc32)[nH]1)C(C)C] | 835 | methyl [(2S)-1-{(2S)-2-[5-(3-{2-[(2S)-1-{(2S)-2-[(methoxycarbonyl)amino]-3-methylbutanoyl}pyrrolidin-2-yl]-1H-imidazol-5-yl}-6,6-dimethylindolo[1,2-c][1,3]benzoxazin-10-yl)-1H-imidazol-2-yl]pyrrolidin-1-yl}-3-methyl-1-oxobutan-2-yl]carbamate |

| Example | Structure | M + 1 | Name |
|---|---|---|---|
| 219 | 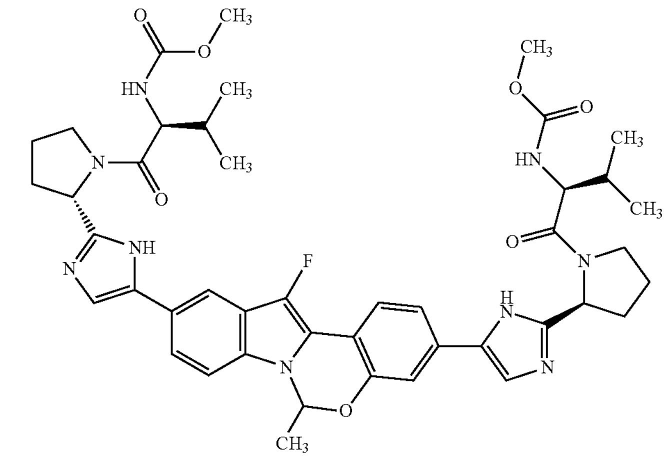 [SMILES: COC(=O)N[C@H](C(=O)N1CCC[C@H]1c1ncc(-c2ccc3c(c2)OC(C)n2c-3c(F)c3cc(-c4cnc([C@@H]5CCCN5C(=O)[C@@H](NC(=O)OC)C(C)C)[nH]4)ccc32)[nH]1)C(C)C] | 839 | methyl [(2S)-1-{(2S)-2-[5-(12-fluoro-10-{2-[(2S)-1-{(2S)-2-[(methoxycarbonyl)amino]-3-methylbutanoyl}pyrrolidin-2-yl]-1H-imidazol-5-yl}-6-methylindolo[1,2-c][1,3]benzoxazin-3-yl)-1H-imidazol-2-yl]pyrrolidin-1-yl}-3-methyl-1-oxobutan-2-yl]carbamate |
| 220 | 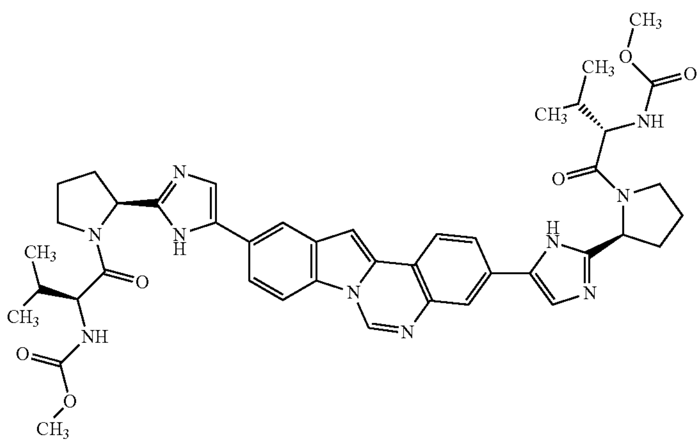 [SMILES: COC(=O)N[C@H](C(=O)N1CCC[C@H]1c1ncc(-c2ccc3c(c2)cc2c4ccc(-c5cnc([C@@H]6CCCN6C(=O)[C@@H](NC(=O)OC)C(C)C)[nH]5)cc4ncn32)[nH]1)C(C)C] | 804 | methyl [(2S)-1-{(2S)-2-[5-(3-{2-[(2S)-1-{(2S)-2-[(methoxycarbonyl)amino]-3-methylbutanoyl}pyrrolidin-2-yl]-1H-imidazol-5-yl}indolo[1,2-c]quinazolin-10-yl)-1H-imidazol-2-yl]pyrrolidin-1-yl}-3-methyl-1-oxobutan-2-yl]carbamate |
| 221 | 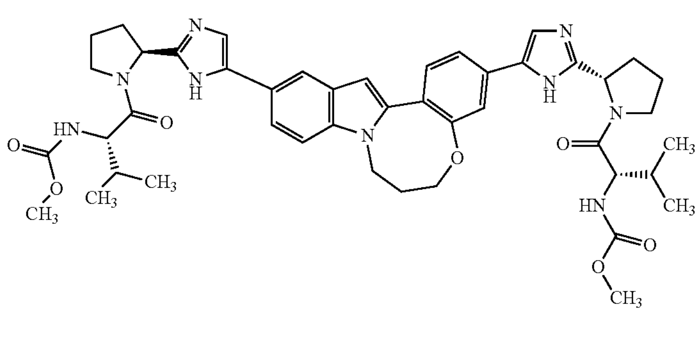 [SMILES: COC(=O)N[C@H](C(=O)N1CCC[C@H]1c1ncc(-c2ccc3c(c2)OCCCn2c-3cc3cc(-c4cnc([C@@H]5CCCN5C(=O)[C@@H](NC(=O)OC)C(C)C)[nH]4)ccc32)[nH]1)C(C)C] | 835 | methyl [(2S)-1-{(2S)-2-[5-(12-{2-[(2S)-1-{(2S)-2-[(methoxycarbonyl)amino]-3-methylbutanoyl}pyrrolidin-2-yl]-1H-imidazol-5-yl}-7,8-dihydro-6H-indolo[1,2-e][1,5]benzoxazocin-3-yl)-1H-imidazol-2-yl]pyrrolidin-1-yl}-3-methyl-1-oxobutan-2-yl]carbamate |

313
314

-continued

| Example | Structure | M + 1 | Name |
|---------|-----------|-------|------|
| 222 | 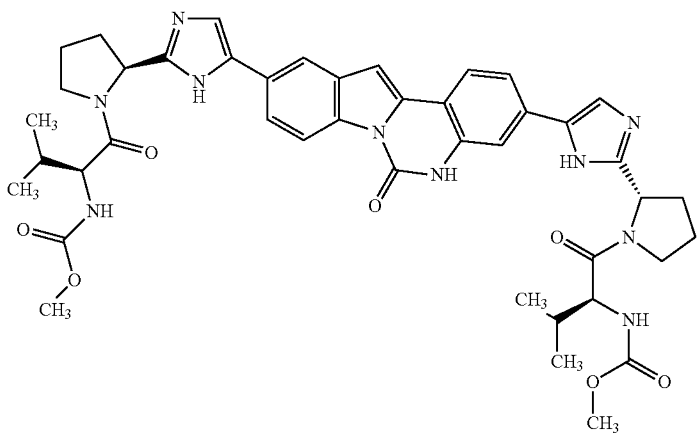 [SMILES: COC(=O)N[C@H](C(=O)N1CCC[C@H]1c1ncc(-c2ccc3c(c2)cc2c4ccc(-c5cnc([C@@H]6CCCN6C(=O)[C@@H](NC(=O)OC)C(C)C)[nH]5)cc4[nH]c(=O)n32)[nH]1)C(C)C] | 820 | methyl [(2S)-1-{(2S)-2-[5-(3-{2-[(2S)-1-{(2S)-2-[(methoxycarbonyl)amino]-3-methylbutanoyl}pyrrolidin-2-yl]-1H-imidazol-5-yl}-6-oxo-5,6-dihydroindolo[1,2-c]quinazolin-10-yl)-1H-imidazol-2-yl]pyrrolidin-1-yl}-3-methyl-1-oxobutan-2-yl]carbamate |
| 223 | 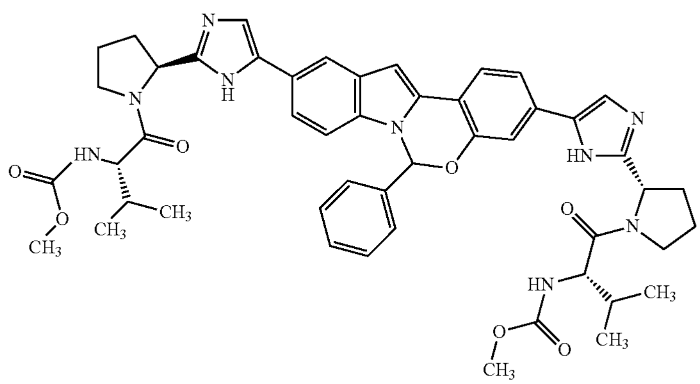 [SMILES: COC(=O)N[C@H](C(=O)N1CCC[C@H]1c1ncc(-c2ccc3c(c2)OC(c2ccccc2)n2c-3cc3cc(-c4cnc([C@@H]5CCCN5C(=O)[C@@H](NC(=O)OC)C(C)C)[nH]4)ccc32)[nH]1)C(C)C] | 883 | methyl [(2S)-1-{(2S)-2-[5-(10-{2-[(2S)-1-{(2S)-2-[(methoxycarbonyl)amino]-3-methylbutanoyl}pyrrolidin-2-yl]-1H-imidazol-5-yl}-6-phenylindolo[1,2-c][1,3]benzoxazin-3-yl)-1H-imidazol-2-yl]pyrrolidin-1-yl}-3-methyl-1-oxobutan-2-yl]carbamate |
| 224 | 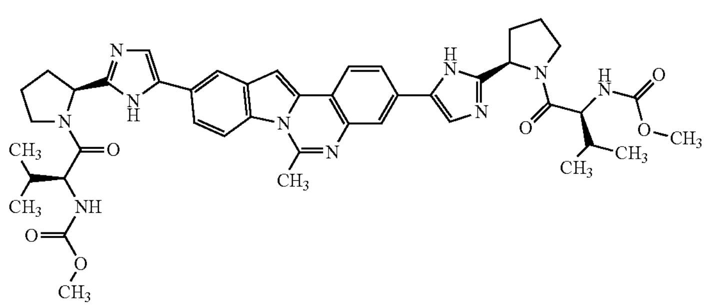 [SMILES: COC(=O)N[C@H](C(=O)N1CCC[C@@H]1c1ncc(-c2ccc3c(c2)nc(C)n2c4ccc(-c5cnc([C@@H]6CCCN6C(=O)[C@@H](NC(=O)OC)C(C)C)[nH]5)cc4cc32)[nH]1)C(C)C] | 818 | methyl [(2S)-1-{(2S)-2-[5-(3-{2-[(2S)-1-{(2S)-2-[(methoxycarbonyl)amino]-3-methylbutanoyl}pyrrolidin-2-yl]-1H-imidazol-5-yl}-6-methylindolo[1,2-c]quinazolin-10-yl)-1H-imidazol-2-yl]pyrrolidin-1-yl}-3-methyl-1-oxobutan-2-yl]carbamate |
| 225 | 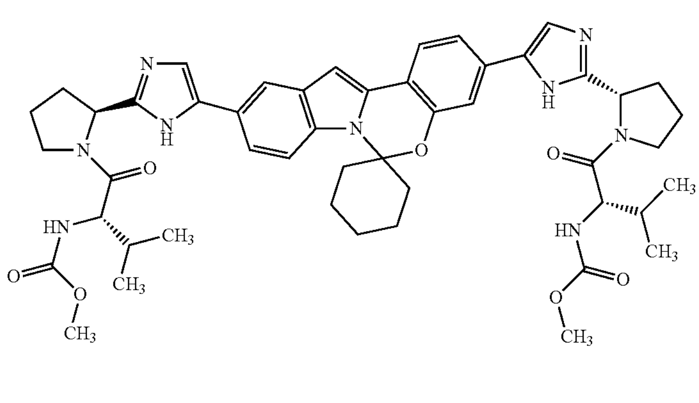 [SMILES: COC(=O)N[C@H](C(=O)N1CCC[C@H]1c1ncc(-c2ccc3c(c2)OC2(CCCCC2)n2c-3cc3cc(-c4cnc([C@@H]5CCCN5C(=O)[C@@H](NC(=O)OC)C(C)C)[nH]4)ccc32)[nH]1)C(C)C] | 875.1 | methyl [(2S)-1-{(2S)-2-[5-(10'-{2-[(2S)-1-{(2S)-2-[(methoxycarbonyl)amino]-3-methylbutanoyl}pyrrolidin-2-yl]-1H-imidazol-5-yl}spiro[cyclohexane-1,6'-indolo[1,2-c][1,3]benzoxazin]-3'-yl)-1H-imidazol-2-yl]pyrrolidin-1-yl}-3-methyl-1-oxobutan-2-yl]carbamate |

-continued

| Example | Structure | M + 1 | Name |
|---|---|---|---|
| 226 | 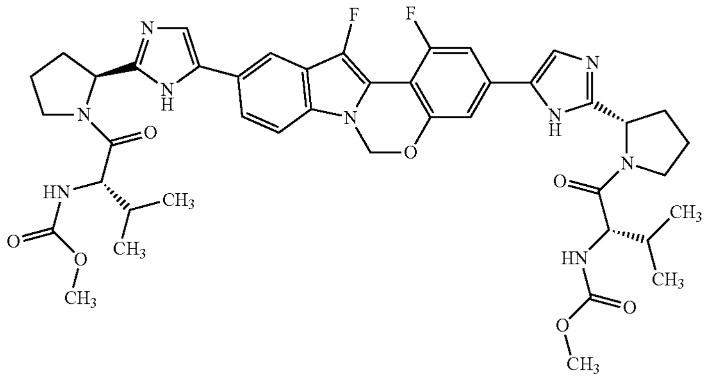 [SMILES: COC(=O)N[C@H](C(=O)N1CCC[C@H]1c1ncc(-c2cc(F)c3c(c2)OCn2c-3c(F)c3cc(-c4cnc([C@@H]5CCCN5C(=O)[C@@H](NC(=O)OC)C(C)C)[nH]4)ccc32)[nH]1)C(C)C] | 842 | methyl [(2S)-1-{(2S)-2-[5-(1,12-difluoro-10-{2-[(2S)-1-{(2S)-2-[(methoxycarbonyl)amino]-3-methylbutanoyl}pyrrolidin-2-yl]-1H-imidazol-5-yl}indolo[1,2-c][1,3]benzoxazin-3-yl)-1H-imidazol-2-yl]pyrrolidin-1-yl}-3-methyl-1-oxobutan-2-yl]carbamate |
| 227 | 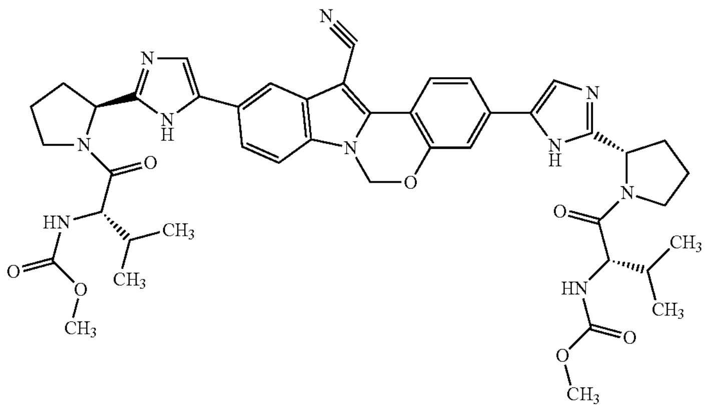 [SMILES: COC(=O)N[C@H](C(=O)N1CCC[C@H]1c1ncc(-c2ccc3c(c2)OCn2c-3c(C#N)c3cc(-c4cnc([C@@H]5CCCN5C(=O)[C@@H](NC(=O)OC)C(C)C)[nH]4)ccc32)[nH]1)C(C)C] | 832 | methyl [(2S)-1-{(2S)-2-[5-(12-cyano-10-{2-[(2S)-1-{(2S)-2-[(methoxycarbonyl)amino]-3-methylbutanoyl}pyrrolidin-2-yl]-1H-imidazol-5-yl}indolo[1,2-c][1,3]benzoxazin-3-yl)-1H-imidazol-2-yl]pyrrolidin-1-yl}-3-methyl-1-oxobutan-2-yl]carbamate |

Example 228

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278(14) J. BIOLOGICAL CHEMISTRY 11979 (2003). However, the underlying principles are common to all of these determinations, and are outlined below.

Stable neomycin phosphotransferase encoding replicon-harboring cell lines were used, so all cell lines were maintained under G418 selection prior to the assay. In some cases, the cell lines encoded a luciferase:Neor fusion and could be assayed either directly by determination of RNA copy number, or indirectly through measurement of the luciferase activity.

To initiate an assay, replicon cells were plated in the presence of a dilution series of test compound in the absence of G418. Typically, the assays were performed in a 96-well plate format for manual operation, or a 384-well plate in an automated assay. Replicon cells and compound were incubated for 24 to 72 hours. At the end of the assay, cells are washed free of media and compound and then lysed. Luciferase activity was measured using a conventional luciferase assay. $EC_{50}$ determinations were calculated as a percent of a DMSO control by fitting the data to a four parameter fit function.

The activity table below provides representative data illustrating observed activity against genotype 1b.

| Activity Table | |
|---|---|
| Example | $EC_{50}$ (nM) |
| 2 | 9 |
| 6 | 200 |
| 14 | 10 |
| 15 | 0.045 |
| 19 | 25 |
| 26 | 0.063 |
| 30 | 26 |
| 39 | 0.24 |
| 40 | 0.026 |
| 41 | 0.05 |
| 42 | 14 |
| 45 | 0.02 |
| 49 | 0.072 |
| 58 | 0.97 |
| 60 | 0.13 |
| 62 | 0.067 |
| 72 | 0.17 |
| 94 | 0.006 |
| 95 | 0.01 |
| 96 | 0.015 |
| 99 | 0.038 |
| 100 | 0.031 |
| 101 | 0.5 |
| 102 | 8.3 |

-continued

Activity Table

| Example | EC$_{50}$ (nM) |
|---|---|
| 103 | 5.7 |
| 105 | 0.08 |
| 107 | 0.04 |
| 116 | 0.065 |
| 119 | 0.013 |
| 125 | 0.016 |
| 129 | 0.7 |
| 130 | 0.05 |
| 131 | 17 |
| 137 | 0.009 |
| 138 | 8.5 |
| 144 | 0.036 |
| 155 | 0.9 |
| 158 | 0.5 |
| 159 | 0.002 |
| 169 | 0.004 |
| 178 | 317 |
| 186 | 0.015 |
| 189a | 0.15 |
| 189b | 0.001 |
| 190 | 0.067 |
| 191 | 0.02 |
| 192 | 0.002 |
| 193 | 0.05 |
| 203 | 0.004 |
| 213 | 0.009 |

It will be appreciated that various of the above-discussed and other features and functions, or alternatives thereof, may be desirably combined into many other different systems or applications. It will also be appreciated that various presently unforeseen or unanticipated alternatives, modifications, variations or improvements therein, also intended to be encompassed by the following claims, may be subsequently made by those skilled in the art.

What is claimed is:

1. A compound having structural formula (I):

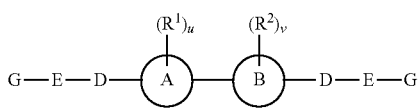

(I)

and/or a pharmaceutically acceptable salt thereof, wherein:

is

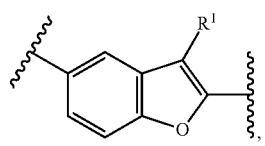

which is substituted by u substituents $R^1$, each $R^1$ is independently chosen from the group consisting of hydrogen, halogen, —OR$^{3a}$, —CN, —(CH$_2$)$_{0-6}$C(O)R$^3$, —CO$_2$R$^{3a}$, —C(O)N(R$^{3a}$)$_2$, —SR$^{3a}$, —S(O)R$^{3a}$, —S(O)$_2$R$^{3a}$, —(CH$_2$)$_{0-6}$N(R$^{3a}$)$_2$, —N(R$^{3a}$)SO$_2$R$^{3a}$, —N(R$^{3a}$)CO$_2$R$^3$a, —N(R$^{3a}$)C(O)R$^3$, —N(R$^{3a}$)COR$^{3a}$, —N(R$^{3a}$)C(O)N(R$^{3a}$), C$_{1-6}$alkyl, C$_{3-8}$carbocycle containing from 0 to 3 heteroatoms chosen from N, O and S, and phenyl, and the C$_{1-6}$alkyl, C$_{3-8}$carbocycle and phenyl are substituted by from 0 to 3 substitutents independently chosen from the group consisting of hydrogen, halogen, —OR$^{3a}$, —CN, —CO$_2$R$^{3a}$, —C(O)N(R$^{3a}$)$_2$, —N(R$^{3a}$)$_2$, —N(R$^{3a}$)CO$_2$R$^{3a}$, —SR$^{3a}$, —S(O)R$^{3a}$, —S(O)$_2$R$^{3a}$, —N(R$^{3a}$)SO$_2$R$^{3a}$, —N(R$^{3a}$)CO$_2$R$^{3a}$, —N(R$^{3a}$)C(O)N(R$^{3a}$), C$_{1-6}$alkyl, —O—C$_{1-6}$alkyl, —S—C$_{1-6}$alkyl, and C$_{3-8}$cycloalkyl, u is from 0 to 4, each $R^3$ is independently chosen from the group consisting of hydrogen, C$_{1-6}$alkyl, —OH, —O—C$_{1-6}$alkyl and C$_{3-8}$cycloalkyl, and each $R^{3a}$ is independently chosen from the group consisting of hydrogen, C$_{1-6}$alkyl and C$_{3-8}$cycloalkyl;

is phenyl, which is substituted by v substituents $R^2$, each $R^2$ is independently chosen from the group consisting of hydrogen, halogen, —OR$^{4a}$, —CN, —CO$_2$R$^{4a}$, —C(O)R$^{4a}$, —C(O)N(R$^{4a}$)$_2$ —N(R$^{4a}$)$_2$, —N(R$^{4a}$)COR$^4$, —N(R$^{4a}$)CO$_2$R$^{4a}$, —N(R$^{4a}$)C(O)N(R$^{4a}$), —N(R$^{4a}$)SO$_2$R$^{4a}$, —SR$^{4a}$, —S(O)R$^{4a}$, —S(O)$_2$R$^{4a}$, C$_{1-6}$alkyl substituted by from 0 to 4 $R^4$ and C$_{3-8}$cycloalkyl substituted by from 0 to 4 $R^4$, v is from 0 to 4, each $R^4$ is independently chosen from the group consisting of hydrogen, —OH, C$_{1-6}$alkyl and C$_{3-8}$cycloalkyl;

each $R^{4a}$ is independently chosen from the group consisting of hydrogen, C$_{1-6}$alkyl and C$_{3-8}$cycloalkyl;

each D is independently a 5- or 6-membered aryl ring system D' containing from 0 to 4 heteroatoms independently chosen from the group consisting of N, O and S, and substituted on C or N atoms by from 0 to 2 substituents $R^5$, each $R^5$ is independently chosen from the group consisting of hydrogen, halogen, —OR$^6$, —CN, —CO$_2$R$^6$, —C(O)N(R$^6$)$_2$, —N(R$^6$)$_2$, —N(R$^6$)COR$^6$, —SR$^6$, —S(O)R$^6$, —S(O$_2$)R$^6$, —N(R$^6$)SO$_2$R$^6$, —NCO$_2$R$^6$, —NC(O)N(R$^6$)$_2$, C$_{1-6}$alkyl substituted by from 0 to 3 $R^6$ and C$_{3-8}$cycloalkyl substituted by from 0 to 3 $R^6$, and each $R^6$ is independently chosen from the group consisting of hydrogen, C$_{1-6}$alkyl and C$_{3-8}$cycloalkyl;

each E is a pyrrolidinyl derivative chosen from the group consisting of:

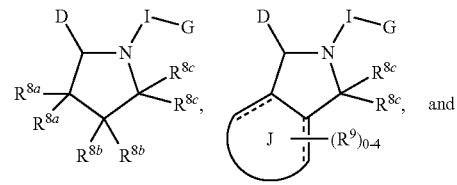

-continued

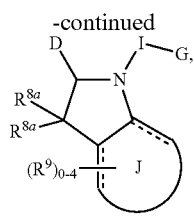

I is a bivalent group chosen from —C(O)—, —CO₂— and —C(O)N(R⁷)—,

J is a fused ring system chosen from the group consisting of 3- to 7-membered carbocycles and 5- or 6-membered aryl rings containing from 0 to 4 heteroatoms independently chosen from the group consisting of N, O and S, and substituted on C or N atoms by substituents $R^9$, each $R^{8a}$ is independently chosen from the group consisting of hydrogen, halogen, —OH, —OC$_{1-6}$alkyl and C$_{1-6}$alkyl, or two $R^{8a}$ may be taken together to form oxo, each $R^{8b}$ is independently chosen from the group consisting of hydrogen, halogen, —OH, —OC$_{1-6}$alkyl and C$_{1-6}$alkyl, or two $R^{8b}$ may be taken together to form oxo, each $R^{8c}$ is independently chosen from the group consisting of hydrogen and C$_{1-6}$alkyl, or any two groups selected from $R^{8a}$, $R^{8b}$ and $R^{8c}$ may be taken together to form a spiro-bicyclic or bridged bicyclic ring;

each $R^9$ is independently chosen from the group consisting of hydrogen, halogen, C$_{1-6}$alkyl, —O—C$_{1-6}$alkyl, —S—C$_{1-6}$alkyl, —NH—C$_{1-6}$alkyl and —NHC(O)—C$_{1-6}$alkyl; and each G is independently chosen from the group consisting of:
  (a) hydrogen,
  (b) —OR$^{10a}$,
  (c) —CN,
  (d) —CO₂R$^{10a}$,
  (e) —C(O)N(R$^{10}$)₂,
  (f) —SR$^{10a}$,
  (g) —S(O)R$^{10a}$,
  (h) —S(O₂)R$^{10a}$,
  (i) —N(R$^{10}$)₂,
  (j) —N(R$^{10}$)SO₂R$^{10a}$,
  (k) —NCO₂R$^{10a}$,
  (l) —NC(O)N(R$^{10}$)₂,
  (m) C$_{1-6}$alkyl having 0 to 4 substituents R$^{11}$,
    each R$^{11}$ is independently chosen from the group consisting of:
    (i) —OH,
    (ii) —N(R$^{10}$)₂,
    (iii) =NR$^{10}$,
    (iv) —O—C$_{1-6}$alkyl,
    (v) —C(O)R$^{10}$,
    (vi) —S—C$_{1-6}$alkyl,
    (vii) —SO₂—C$_{1-6}$alkyl,
    (viii) 3- to 8-membered carbocycles containing from 0 to 3 heteroatoms independently chosen from the group consisting of N, O and S, and having from 0 to 3 substituents R$^{12}$ on N or C atoms, and each R$^{12}$ is independently selected from the group consisting of hydrogen, halogen, C$_{1-6}$alkyl having from 0 to 3 substituents chosen from R$^{10}$, —O—C$_{1-6}$alkyl, —S—C$_{1-6}$alkyl,
    —OR$^{10a}$, —CN, —C(O)R$^{10}$, —CO₂R$^{10a}$, —C(O)N(R$^{10}$)₂, —SR$^{10a}$, —S(O)R$^{10a}$, —S(O₂)R$^{10a}$, —N(R$^{10}$)SO₂R$^{10a}$, —NCO₂R$^{10a}$, —NC(O)N(R$^{10}$)₂ and —N(R$^{10}$)₂, or two R$^{12}$ are taken together to form oxo, and
    (ix) 5- or 6-membered aryl containing from 0 to 3 heteroatoms independently chosen from the group consisting of N, O and S, and having from 0 to 3 substitutents R$^{13}$ on N or C atoms, and each R$^{13}$ is independently selected from the group consisting of hydrogen, halogen, C$_{1-6}$alkyl, —O—C$_{1-6}$alkyl and 3- to 8-membered carbocycles containing from 0 to 3 heteroatoms independently chosen from the group consisting of N, O and S,
  (n) 3- to 8-membered carbocycles containing from 0 to 3 heteroatoms independently chosen from the group consisting of N, O and S, and having from 0 to 3 substitutents R$^{10}$ on N or C atoms; and
  (o) aryl ring systems G' chosen from the group consisting of:
    (i) 5- to 7-membered monocyclic ring systems and
    (ii) 8- to 10-membered bicyclic ring systems,
    and the aryl ring systems G' containing from 0 to 4 heteroatoms independently chosen from the group consisting of N, O and S, and substituted on C or N atoms by 0 to 3 substitutents R$^{10}$;

each R$^{10}$ is independently chosen from the group consisting of
  (i) hydrogen,
  (ii) —CN,
  (iii) C$_{1-6}$alkyl,
  (iv) —O—C$_{0-6}$alkyl,
  (v) —S—C$_{0-6}$alkyl,
  (vi) C$_{1-6}$alkyl-O—R$^{14}$,
  (vii) —C(O)R$^{14}$,
  (viii) —CO₂R$^{14}$,
  (ix) —SO₂R$^{14}$,
  (x) —N(R$^{14}$)₂,
  (xi) —N(R$^{14}$)SO₂R$^{14}$,
  (xii) —NCO₂R$^{14}$,
  (xiii) —NC(O)N(R$^{14}$)₂, and
  (xiv) 3- to 8-membered carbocycles containing from 0 to 3 heteroatoms independently chosen from the group consisting of N, O and S,
or two R$^{10}$ may be taken together to form oxo;

each R$^{10a}$ is independently chosen from the group consisting of
  (i) hydrogen,
  (ii) —CN,
  (iii) C$_{1-6}$alkyl,
  (iv) C$_{1-6}$alkyl-O—R$^{14}$,
  (v) —C(O)R$^{14}$,
  (vi) —CO₂R$^{14}$,
  (vii) —SO₂R$^{14}$,
  (x) —N(R$^{14}$)₂,
  (xi) —N(R$^{14}$)SO₂R$^{14}$,
  (xii) —NCO₂R$^{14}$,
  (xiii) —NC(O)N(R$^{14}$)₂, and
  (xiv) 3- to 8-membered carbocycles containing from 0 to 3 heteroatoms independently chosen from the group consisting of N, O and S,
and two R$^{10}$ or R$^{10a}$ groups can be taken together with the N to which they are attached to form a ring, which may be substituted by from 0 to 3 substituents R$^{14}$, and each $R^{14}$ is independently chosen from the group consisting of hydrogen, $C_{1-6}$alkyl, $C_{3-8}$cycloalkyl, —$(CH_2)_{0-3}C_{3-8}$cycloalkyl and phenyl.

2. The compound according to claim 1, wherein each $R^1$ is chosen from the group consisting of hydrogen, fluorine and —CN.

3. The compound according to claim 1, wherein
v is from 0 to 4,
each $R^2$ is independently chosen from the group consisting of hydrogen, halogen, —$OR^{4a}$, —CN, —$CO_2R^{4a}$, —$C(O)N(R^{4a})_2$, —$N(R^{4a})_2$, —$N(R^{4a})CO_2R^{4a}$, —$SR^{4a}$, —$S(O)R^{4a}$, —$S(O_2)R^{4a}$, —$N(R^{4a})SO_2R^{4a}$, —$N(R^{4a})CO_2R^{4a}$, —$N(R^{4a})C(O)N(R^{4a})$, $C_{1-6}$alkyl substituted by from 0 to 4 $R^4$ and $C_{3-8}$cycloalkyl substituted by from 0 to 4 $R^4$,
each $R^4$ is independently chosen from the group consisting of hydrogen, —OH, $C_{1-6}$alkyl and $C_{3-8}$cycloalkyl, and each $R^{4a}$ is independently chosen from the group consisting of hydrogen, $C_{1-6}$alkyl and $C_{3-8}$cycloalkyl.

4. The compound according to claim 1, wherein each D is independently chosen from the group consisting of

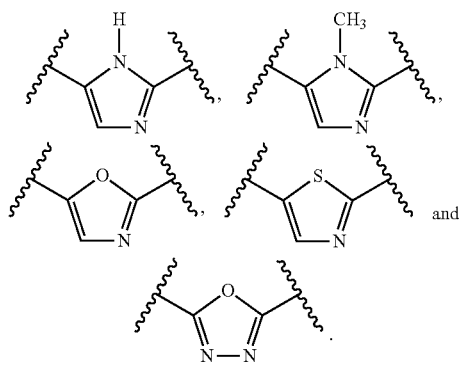

5. The compound according to claim 1, wherein each E is independently chosen from the group consisting of

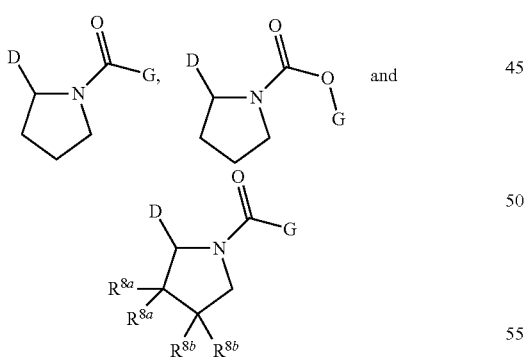

where one of $R^{8a}$ and $R^{8b}$ is —OH or fluorine.

6. The compound according to claim 1, wherein each G is independently chosen from the group consisting of
 (a) hydrogen,
 (b) —CN,
 (c) $C_{1-5}$alkyl having 1 to 3 substituents $R^{11}$,
  each $R^{11}$ is independently chosen from the group consisting of —OH, —$NH_2$, —$NCH_3H$, —$N(CH_3)_2$, —$N(CH_2CH_3)_2$, =NH, =$NCH_3$, —C(O)H, —C(O)OH, —$C(O)CH_3$, —$C(O)OCH_3$, —NHC(O)H, —NHC(O)OH, —$NHC(O)CH_3$, —$NHC(O)OCH_3$, cyclopropyl, cyclobutyl, cyclopentyl, cyclohexyl, pyranyl, pyrrolidinyl, piperidinyl, oxacyclopentyl, and oxacyclohexyl, phenyl, pyridinyl, pyrimidinyl and pyrrolyl, where
  the cyclopropyl, cyclobutyl, cyclopentyl, cyclohexyl, pyranyl, pyrrolidinyl, piperidinyl, oxacyclopentyl and oxacyclohexyl are substituted by from 0 to 2 substitutents $R^{12}$ on N or C atoms, and each $R^{12}$ is independently selected from the group consisting of hydrogen, halogen, carboxy, $C_{1-6}$alkyl, —O—$C_{1-6}$alkyl and —S—$C_{1-6}$alkyl; and
  the phenyl, pyridinyl, pyrimidinyl and pyrrolyl are substituted by from 0 to 3 substitutents $R^{13}$ on N or C atoms, and each $R^{13}$ is independently selected from the group consisting of hydrogen, halogen, $C_{1-6}$alkyl and 3- to 8-membered cycloalkyl containing from 0 to 3 heteroatoms independently chosen from the group consisting of N, O and S,
 (d) cyclopropyl, cyclobutyl, cyclopentyl, cyclohexyl, pyranyl, pyrrolidinyl, piperidinyl, oxacyclopentyl and oxacyclohexyl having from 0 to 3 substitutents $R^{10}$ on N or C atoms, said $R^{10}$ independently selected from the group consisting of hydrogen, halogen, carboxy, $C_{1-6}$alkyl, —O—$C_{1-6}$alkyl, —S—$C_{1-6}$alkyl, phenyl and benzyl, and
 (e) aryl ring systems G' chosen from the group consisting of: phenyl, pyridinyl and 9-membered bicyclic ring systems containing from 0 to 2 heteroatoms independently chosen from the group consisting of N and O.

7. The compound according to claim 1, wherein said

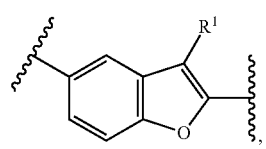

is where said is substituted by from 0 to 3 additional $R^1$;
v is from 0 to 2;
each $R^2$ is independently chosen from the group consisting of fluorine, chlorine, —OH, —$CH_3$, —$OCH_3$ and —CN;
each D is independently chosen from the group consisting of

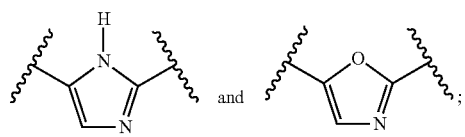 [SMILES: *c1cnc(*)[nH]1 ; *c1cnc(*)o1] and each E is independently chosen from the group consisting of

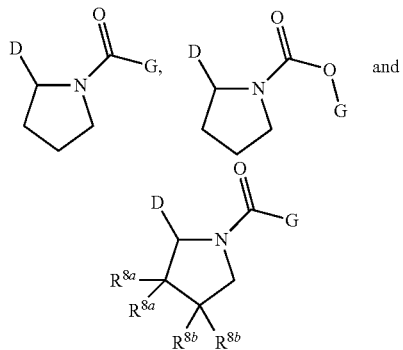

where one of $R^{8a}$ and $R^{8b}$ is —OH or fluorine; and each G is independently chosen from the group consisting of $C_{1-4}$alkyl having 1 to 2 substituents $R^{11}$, wherein each $R^{11}$ is independently chosen from the group consisting of —OH, —NH$_2$, —NCH$_3$H, —N(CH$_3$)$_2$, —N(CH$_2$CH$_3$)$_2$, —C(O)OCH$_3$, cyclopropyl, cyclobutyl, cyclopentyl, cyclohexyl, pyranyl, pyrrolidinyl, piperidinyl, oxacyclopentyl, oxacyclohexyl, phenyl, pyridinyl, pyrimidinyl and pyrrolyl.

8. The compound according to according to claim 1, wherein the compound having structural formula (I) is a compound having structural formula (Ib):

(Ib)

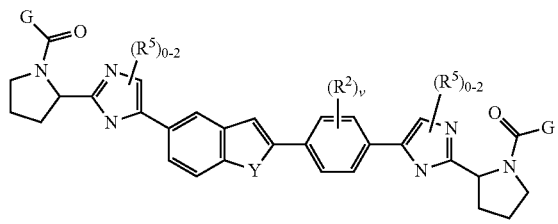

or a pharmaceutically acceptable salt thereof, wherein said

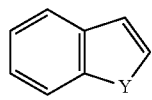

is substituted by u substituents $R^1$, and Y is O.

9. The compound according to according to claim 8, wherein said

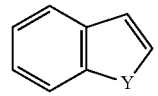

is substituted by u substituents $R^1$, Y is O, and both instances of G are

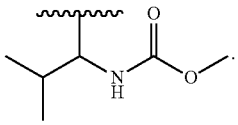 [SMILES: *C(NC(=O)OC)C(C)C]

10. The compound according to according to claim 1, wherein the compound having structural formula (I) is a compound having structural formula (Ib):

(Ib)

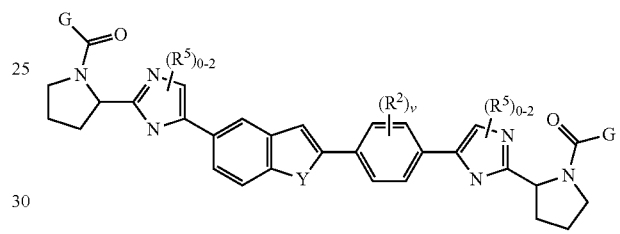

or a pharmaceutically acceptable salt thereof, wherein said

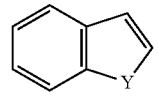

is substituted by u substituents $R^1$, Y is O, and both instances of G are

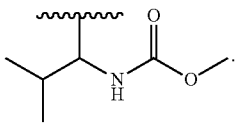 [SMILES: *C(NC(=O)OC)C(C)C]

11. A compound according to claim 1, chosen from the group consisting of:
propan-2-yl[(1R)-2-{(2S)-2-[(4-{3-bromo-5-[({(2S)-1-[(2R)-2-phenyl-2-{[(propan-2-yloxy)carbamonyl]amino}acetyl]pyrrolidin-2-yl}carbonyl)amino]-1-benzofuran-2-yl}phenyl)carbamoyl]pyrrolidin-1-yl}-2-oxo-1-phenylethyl]carbamate;
(2S)-N-(4-{3-bromo-5-[({(2S)-1-[(2R)-2-(dimethylamino)-2-phenylacetyl]pyrrolidin-2-yl}carbonyl)amino]-1-benzofuran-2-yl}phenyl)-1-[(2R)-2-(dimethylamino)-2-phenylacetyl]pyrrolidine-2-carboxamide;
methyl{(1R)-2-[(2S)-2-({4-[3-bromo-5-({[(2S)-1-{(2R)-2-[(methoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate;

methyl{(2S)-1-[(2S)-2-({4-[3-fluoro-5-({[(2S)-1-{(2S)-2-[(methoxycarbonyl)amino]-3-methylbutanoyl}pyrrolidin-2-yl]carbonyl}amino)-1H-indol-2-yl]phenyl}carbamoyl)pyrrolidin-1-yl]-3-methyl-1-oxobutan-2-yl}carbamate;

N-{2-[4-(acetylamino)phenyl]-3-bromo-1-benzofuran-5-yl}-1-[(2R)-2-(dimethylamino)-2-phenylacetyl]-L-prolinamide;

tert-butyl {(1S)-2-[(2S)-2-({4-[3-bromo-5-({[(2S)-1-{(2S)-2-[(tert-butoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate);

(2S)-N-{4-[3-bromo-5-({[(2S)-1-phenylacetyl)pyrrolidin-2-yl]carbonyl}amino)-1-benzofuran-2-yl]phenyl}-1-(phenylacetyl)pyrrolidine-2-carboxamide;

tert-butyl{(1R)-2-[(2S)-2-({4-[3-bromo-5-({[(2S)-1-{(2R)-2-[(tert-butoxycarbonyl)amino]-2-phenylacetyl}pyrrolidin-2-yl]carbonyl}amino)-1-benzofuran-2-yl]phenyl}carbamoyl)pyrrolidin-1-yl]-2-oxo-1-phenylethyl}carbamate;

methyl{(2S)-1-[(2S)-2-{5-[4-(5-{2-[(2S)-1-{(2S)-2-[(methoxy-carbonyl)amino]-3-methylbutanoyl}pyrrolidin-2-yl]-1H-imidazol-5-yl]-1-benzofuran-2-yl]phenyl]-1H-imidazol-2-yl}pyrrolidin-1-yl]-3-methyl-1-oxobutan-2-yl}carbamate;

(2R)-2-(diethylamino)-1-[(2S)-2-(5-{4-[5-(2-{(2S)-1-[(2R)-2-(diethylamino)-2-phenylacetyl]pyrrolidin-2-yl}-1H-imidazol-5-yl)-1-benzofuran-2-yl]phenyl}-1H-imidazol-2-yl)pyrrolidin-1-yl]-2-phenylethanone;

methyl{(1S)-1-cyclopropyl-2-[(2S)-2-{5-[4-(5-{2-[(2S)-1-{(2S)-2-cyclopropyl-2-[(methoxycarbonyl)amino]acetyl}pyrrolidin-2-yl]-1H-imidazol-5-yl}-1-benzofuran-2-yl)phenyl]-1H-imidazol-2-yl}pyrrolidin-1-yl]-2-oxoethyl}carbamate;

methyl{(1R)-1-cyclopropyl-2-[(2S)-2-{5-[4-(5-{2-[(2S)-1-{(2R)-2-cyclopropyl-2-[(methoxycarbonyl)amino]acetyl}pyrrolidin-2-yl]-1H-imidazol-5-yl}-1-benzofuran-2-yl)phenyl]-1H-imidazol-2-yl}pyrrolidin-1-yl]-2-oxoethyl}carbamate;

methyl{(2R)-1[(2S)-2-{5-[2-(4-{2-[(2S)-1-{(2R)-2-[(methoxycarbonyl)amino]-3-methylbutanoyl}pyrrolidin-2-yl]-1H-imidazol-5-yl}phenyl)-1-benzofuran-5-yl]-1H-imidazol-2-yl}pyrrolidin-1-yl]-3-methyl-1-oxobutan-2-yl}carbamate;

methyl{(2S)-1-[(2S)-2-{5-[4-(5-{2-[(2S)-1-{(2S)-2-[(methoxycarbonyl)amino]-3,3-dimethylbutanoyl}pyrrolidin-2-yl]-1H-imidazol-5-yl}-1-benzofuran-2-yl)phenyl]-1H-imidazol-2-yl}pyrrolidin-1-yl]-3 ,3-dimethyl-1-oxobutan-2-yl}carbamate;

methyl{(1R)-2-[(2S)-2-{5-[4-(5-{2-[(2S)-1-{(2R)-2-[(methoxycarbonyl)amino]-2-phenylacetyl}pyrrolidin-2-yl]-1H-imidazol-4-yl}-1-benzofuran-2-yl)phenyl]-1H-imidazol-2-yl}pyrrolidin-1-yl]-2-oxo-1-phenylethyl}carbamate;

methyl{(2S,3R)-1-[(2S)-2-(5-{2-[4-(2-{(2S)-1-[N-(methoxycarbonyl)-L-alloisoleucyl]pyrrolidin-2-yl}-1H-imidazol-5-yl)phenyl]-1-benzofuran-5-yl}-1H-imidazol-2-yl)pyrrolidin-1-yl]-3-methyl-1-oxopentan-2-yl}carbamate;

methyl{(2S)-3-hydroxy-1-[(2S)-2-{5-[4-(5-{2-[(2S)-1-{(2S)-3-hydroxy-2-[(methoxycarbonyl)amino]propanoyl}pyrrolidin-2-yl]-1H-imidazol-5-yl}-1-benzofuran-2-yl)phenyl]-1H-imidazol-2-yl}pyrrolidin-1-yl]-1-oxopropan-2-yl}carbamate;

methyl{(2S,3R)-3-hydroxy-1-[(2S)-2-{5-[4-(5-{2-[(2S)-1-{(2S,3R)-3-hydroxy-2-[(methoxycarbonyl)amino]butanoyl}pyrrolidin-2-yl]-1H-imidazol-5-yl}-1-benzofuran-2-yl)phenyl]-1H-imidazol-2-yl}pyrrolidin-1-yl]-1-oxobutan-2-yl}carbamate;

methyl{(2S)-1-[(2S)-2-{5-[4-(5-{2-[(2S)-1-{(2S)-2-[(methoxycarbonyl)amino]-4-methylpentanoyl}pyrrolidin-2-yl]-1H-imidazol-5-yl}-1-benzofuran-2-yl)phenyl]-1H-imidazol-2-yl}pyrrolidin-1-yl]-4-methyl-1-oxopentan-2-yl}carbamate;

methyl{(2S)-1-[(2S)-2-{5-[3-fluoro-4-(5-{2-[(2S)-1-{(2S)-2-[(methoxycarbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate;

methyl{(1R)-2-[(2S)-2-{5-[3-fluoro-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-2-oxo-1-phenylethyl}carbamate;

methyl{(2S)-1-[(2S)-2-{5-[3-fluoro-4-(5-{2-[(2S)-1-{(2S)-2-[(methoxycarbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate;

methyl{(2S)-1-[(2S)-2-{5-[2-(2,6-difluoro-4-{2-[(2S)-1-{(2S)-2-[(methoxycarbonyl)amino]-3-methylbutanoyl}pyrrolidin-2-yl]-1H-imidazol-5-yl}phenyl)-1-benzofuran-5-yl]-1H-imidazol-2-yl}pyrrolidin-1-yl]-3-methyl-1-oxobutan-2-yl}carbamate;

methyl{(1R)-2-[(2S)-2-{5-[3-methoxy-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-2-oxo-1-phenylethyl}carbamate;

methyl{(2S)-1-[(2S)-2-{5-[2-(2-chloro-4-{2-[(2S)-1-{(2S)-2-[(methoxycarbonyl)amino]-3-methylbutanoyl}pyrrolidin-2-yl]-1H-imidazol-4-yl}phenyl)-1-benzofuran-5-yl]-1H-imidazol-2-yl}pyrrolidin-1-yl]-3-methyl-1-oxobutan-2-yl}carbamate;

methyl{(1R)-2-[(2S)-2-{4-[3-cyano-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-2-oxo-1-phenylethyl}carbamate;

methyl{(2S)-1-[(2S)-2-{5-[2-(4-{2-[(2S)-1-{(2S)-2-[(methoxycarbonyl)amino]-3-methylbutanoyl}pyrrolidin-2-yl]-1H-imidazol-4-yl}-2-methylphenyl)-1-benzofuran-5-yl]-1H-imidazol-2-yl}pyrrolidin-1-yl]-3-methyl-1-oxobutan-2-yl}carbamate;

methyl{(1S)-2-[(2S)-2-(5-{3-fluoro-4-[5-(2-{(2S)-1-[(2S)-2-[(methoxycarbonyl)amino]-2-(tetrahydro-2H-pyran-4-yl)acetyl]pyrrolidin-2-yl}-1H-imidazol-5-yl)-1-benzofuran-2-yl]phenyl}-1H-imidazol-2-yl)pyrrolidin-1-yl]-2-oxo -1-(tetrahydro-2H-pyran-4-yl)ethyl]carbamate; and methyl{(2S)-1-[(2S)-2-{4-[3-fluoro-4-(5-{2-[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate.

12. A compound according to claim 1, chosen from the group consisting of:

methyl{(2S)-1-[(2S)-2-{5-[4-(5-{2-[(2S)-1-{(2S)-2-[(methoxy-carbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate;

methyl{(2R)-1-[(2S)-2-{5-[2-(4-{2-[(2S)-1-{(2R)-2-[(methoxycarbonyl)amino]-3-methylbutanoyl}pyrrolidin-2-yl]-1H-imidazol-5-yl}phenyl)-1-benzofuran-5-yl]-1H-imidazol-2-yl}pyrrolidin-1-yl]-3-methyl-1-oxobutan-2-yl}carbamate;

methyl{(2S)-1-[(2S)-2-{5-[4-(5-{2-[(2S)-1-{(2S)-2-[(methoxycarbonyl)amino]-4-methylpentanoyl}pyrrolidin-2-yl]-1H-imidazol-5-yl}-1-benzofuran-2-yl)phenyl]-1H-imidazol-2-yl}pyrrolidin-1-yl]-4-methyl-1-oxopentan-2-yl}carbamate;

methyl{(2S)-1-[(2S)-2-{5-[3-fluoro-4-(5-{2-[(2S)-1-{(2S)-2-[(methoxycarbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate;

methyl{(2S)-1-[(2S)-2-{5-[3-fluoro-4-(5-{2-[(2S)-1-{(2S)-2-[(methoxycarbonyl)amino]-3-methylbutanoyl}pyrrolidin-2-yl]-1H-imidazol-5-yl}-1-benzofuran-2-yl)phenyl]-1H-imidazol-2-yl}pyrrolidin-1-yl]-3-methyl-1-oxobutan-2-yl}carbamate;

methyl{(2S)-1-[(2S)-2-{5-[2-(2,6-difluoro-4-{2-[(2S)-1-{(2S)-2-[(methoxycarbonyl)amino]-3-methylbutanoyl}pyrrolidin-2-yl]-1H-imidazol-5-yl}phenyl)-1-benzofuran-5-yl]-1H-imidazol-2-yl}pyrrolidin-1-yl]-3-methyl-1-oxobutan-2-yl}carbamate;

methyl{(2S)-1-[(2S)-2-{5-[2-(2-chloro-4-{2-[(2S)-1-{(2S)-2-[(methoxycarbonyl)amino]-3-methylbutanoyl}pyrrolidin-2-yl]-1H-imidazol-4-yl}phenyl)-1-benzofuran-5-yl]-1H-imidazol-2-yl}pyrrolidin-1-yl]-3-methyl-1-oxobutan-2-yl}carbamate;

methyl{(1R)-2-[(2S)-2-{4-[3-cyano-4-(5-{2[(2S)-1-{(2R)-2-[(methoxycarbonyl)amino]-2-phenylacetyl}pyrrolidin-2-yl]-1H-imidazol-5-yl}-1-benzofuran-2-yl)phenyl]-1H-imidazol-2-yl}pyrrolidin-1-yl]-2-oxo-1-phenylethyl}carbamate; and methyl{(2S)-1-[(2S)-2-{5-[2-(4-{2-[(2S)-1-{(2S)-2-[(methoxycarbonyl)amino]-3-methylbutanoyl}pyrrolidin-2-yl]-1H-imidazol-4-yl}-2-methylphenyl)-1-benzofuran-5-yl]-1H-imidazol-2-yl}pyrrolidin-1-yl]-3-methyl-1-oxobutan-2-yl}carbamate; and pharmaceutically acceptable salts thereof.

13. A pharmaceutical composition comprising an effective amount of the compound according to claim 1, and a pharmaceutically acceptable carrier.

14. The pharmaceutical composition according to claim 13, further comprising a second therapeutic agent selected from the group consisting of HCV antiviral agents, immunomodulators, and anti-infective agents.

15. The pharmaceutical composition according to claim 13, further comprising a second therapeutic agent selected from the group consisting of HCV protease inhibitors and HCV NS5B polymerase inhibitors.

16. A method of treating a patient infected with HCV comprising the step of administering an amount of the compound according to claim 1 effective to treat infection by HCV in a subject in need thereof.

* * * * *